US012398379B2

(12) United States Patent
Perez-Garcia et al.

(10) Patent No.: US 12,398,379 B2
(45) **Date of Patent: *Aug. 26, 2025**

(54) COMPOSITIONS AND METHODS FOR TREATING ORNITHINE TRANSCARBAMYLASE DEFICIENCY

(71) Applicant: ARCTURUS THERAPEUTICS, INC., San Diego, CA (US)

(72) Inventors: Carlos G. Perez-Garcia, San Diego, CA (US); Kiyoshi Tachikawa, San Diego, CA (US); Daiki Matsuda, San Diego, CA (US); Padmanabh Chivukula, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,977

(22) Filed: May 18, 2023

(65) Prior Publication Data

US 2024/0002815 A1 Jan. 4, 2024

Related U.S. Application Data

(63) Continuation of application No. 16/705,102, filed on Dec. 5, 2019, now Pat. No. 11,685,906.

(60) Provisional application No. 62/776,302, filed on Dec. 6, 2018.

(51) Int. Cl.

| | |
|---|---|
| ***C07H 21/02*** | (2006.01) |
| ***A61P 9/00*** | (2006.01) |
| ***C07H 21/04*** | (2006.01) |
| ***C12N 9/10*** | (2006.01) |
| *A61K 48/00* | (2006.01) |

(52) U.S. Cl.

CPC .............. *C12N 9/1018* (2013.01); *A61P 9/00* (2018.01); *C12Y 201/03003* (2013.01); *A61K 48/00* (2013.01)

(58) Field of Classification Search

CPC ............................................. C12Y 201/03003

See application file for complete search history.

(56) References Cited

U.S. PATENT DOCUMENTS

| | | | |
|---|---|---|---|
| 8,058,069 | B2 | 11/2011 | Yaworski et al. |
| 8,093,367 | B2 | 1/2012 | Kore et al. |
| 8,158,601 | B2 | 4/2012 | Chen et al. |
| 8,278,036 | B2 | 10/2012 | Kariko et al. |
| 8,304,529 | B2 | 11/2012 | Kore et al. |
| 8,492,359 | B2 | 7/2013 | Yaworski et al. |
| 8,691,966 | B2 | 4/2014 | Kariko et al. |
| 8,748,089 | B2 | 6/2014 | Kariko et al. |
| 8,822,668 | B2 | 9/2014 | Yaworski et al. |
| 9,006,191 | B2 | 4/2015 | Maclachlan et al. |
| 9,006,417 | B2 | 4/2015 | Yaworski et al. |
| 9,364,435 | B2 | 6/2016 | Yaworski et al. |
| 9,404,127 | B2 | 8/2016 | Yaworski et al. |
| 9,428,535 | B2 | 8/2016 | De Fougerolles et al. |
| 9,518,272 | B2 | 12/2016 | Yaworski et al. |
| 9,572,874 | B2 | 2/2017 | Fotin-Mleczek et al. |
| 9,750,824 | B2 | 9/2017 | Kariko et al. |
| 9,751,925 | B2 | 9/2017 | Hoge et al. |
| 9,890,365 | B2 | 2/2018 | Wang et al. |
| 9,896,413 | B2 | 2/2018 | Payne et al. |
| 10,072,057 | B2 | 9/2018 | Hoge et al. |
| 10,143,758 | B2 | 12/2018 | Guild et al. |
| 10,167,454 | B2 | 1/2019 | Wang et al. |
| 10,188,748 | B2 | 1/2019 | Von Der Mulbe et al. |
| 10,201,620 | B2 | 2/2019 | Meis et al. |
| 10,232,055 | B2 | 3/2019 | Kariko et al. |
| 10,238,754 | B2 | 3/2019 | Guild et al. |
| 10,487,105 | B2 | 11/2019 | Chivukula et al. |
| 10,501,512 | B2 | 12/2019 | De Fougerolles et al. |
| 10,526,284 | B2 | 1/2020 | Payne et al. |
| 10,568,972 | B2 | 2/2020 | Von Der Mulbe et al. |
| 11,685,906 | B2 | 6/2023 | Perez-Garcia et al. |
| 11,859,215 | B2 | 1/2024 | Zhuo et al. |
| 2005/0147993 | A1 | 7/2005 | Khan |
| 2007/0196334 | A1 | 8/2007 | Khan |
| 2011/0256175 | A1 | 10/2011 | Hope et al. |
| 2012/0027803 | A1 | 2/2012 | Manoharan et al. |
| 2012/0128760 | A1 | 5/2012 | Manoharan et al. |

(Continued)

FOREIGN PATENT DOCUMENTS

| | | | |
|---|---|---|---|
| SG | 11201903460 | A | 5/2019 |
| WO | 9207065 | A1 | 4/1992 |

(Continued)

OTHER PUBLICATIONS

Extended European Search Report issued in European Application No. 21763861.8, mailed on Mar. 18, 2024, 10 pages.
(1978) Federation of Experimental Biologists Society Letter, 96:1-11.
European Search Report from corresponding European Application No. 19893199.0, mailed on Jul. 29, 2022, 2 Pages.
International Preliminary Report on Patentability received for PCT Application No. PCT/US2019/064786, mailed on Oct. 13, 2020, 29 pages.
International Search Report and Written Opinion issued in International Application No. PCT/US2021/020634, mailed on May 27, 2021, 11 pages.

(Continued)

*Primary Examiner* — Amy Rose Hudson
(74) *Attorney, Agent, or Firm* — Greenberg Traurig, LLP

(57) ABSTRACT

The present disclosure provides a modified human OTC protein having improved properties for the treatment of OTC deficiency in a patient. Preferably, the protein of the disclosure is produced from a codon optimized mRNA suitable for administration to a patient suffering from OTC deficiency wherein upon administration of the mRNA to the patient, the protein of the disclosure is expressed in the patient in therapeutically effective amounts to treat OTC deficiency. The present disclosure also provides codon optimized mRNA sequences encoding wild type human OTC comprising a 5' UTR derived from a gene expressed by *Arabidopsis thaliana* for use in treating OTC deficiency in a patient.

20 Claims, 15 Drawing Sheets

Specification includes a Sequence Listing.

(56) References Cited

U.S. PATENT DOCUMENTS

| | | | |
|---|---|---|---|
| 2014/0090108 | A1 | 3/2014 | Garabagi et al. |
| 2015/0064235 | A1 | 3/2015 | Bancel et al. |
| 2015/0104476 | A1 | 4/2015 | Von Der Mülbe et al. |
| 2016/0089451 | A1 | 3/2016 | Armstrong |
| 2016/0136301 | A1 | 5/2016 | Von Der Mülbe et al. |
| 2016/0161403 | A1 | 6/2016 | Sugimoto |
| 2016/0354493 | A1 | 12/2016 | Roy et al. |
| 2017/0056528 | A1 | 3/2017 | De Fougerolles et al. |
| 2017/0130216 | A1 | 5/2017 | Armstrong |
| 2017/0252461 | A1 | 9/2017 | Chakraborty et al. |
| 2017/0362627 | A1 | 12/2017 | Reynders et al. |
| 2018/0135030 | A1 | 5/2018 | Wang et al. |
| 2018/0169268 | A1 | 6/2018 | Payne et al. |
| 2018/0222863 | A1 | 8/2018 | Payne et al. |
| 2018/0273576 | A1 | 9/2018 | Hogrefe et al. |
| 2018/0327471 | A1 | 11/2018 | Limphong et al. |
| 2018/0353618 | A1 | 12/2018 | Burkhardt et al. |
| 2019/0002906 | A1 | 1/2019 | Limphong et al. |
| 2019/0192688 | A1 | 6/2019 | Askew et al. |
| 2019/0307897 | A1 | 10/2019 | Angel et al. |
| 2020/0181584 | A1 | 6/2020 | Perez-Garcia et al. |
| 2020/0297634 | A1 | 9/2020 | Karmali et al. |
| 2021/0284974 | A1 | 9/2021 | Chivukula et al. |

FOREIGN PATENT DOCUMENTS

| | | | |
|---|---|---|---|
| WO | 9315187 | A1 | 8/1993 |
| WO | 2009086558 | A1 | 7/2009 |
| WO | 2009127060 | A1 | 10/2009 |
| WO | 2010048536 | A2 | 4/2010 |
| WO | 2010054406 | A1 | 5/2010 |
| WO | 2010088537 | A2 | 8/2010 |
| WO | 2010129709 | A1 | 11/2010 |
| WO | 2011025242 | A2 | 3/2011 |
| WO | 2011068810 | A1 | 6/2011 |
| WO | 2011153493 | A2 | 12/2011 |
| WO | 2014170896 | A2 | 10/2014 |
| WO | 2015017519 | A1 | 2/2015 |
| WO | 2015051169 | A2 | 4/2015 |
| WO | 2015061491 | A1 | 4/2015 |
| WO | 2015074085 | A1 | 5/2015 |
| WO | 2015138348 | A1 | 9/2015 |
| WO | 2015138357 | A2 | 9/2015 |
| WO | 2016070166 | A2 | 5/2016 |
| WO | 2016081029 | A1 | 5/2016 |
| WO | 2016118697 | A1 | 7/2016 |
| WO | 2017023817 | A1 | 2/2017 |
| WO | 2017117530 | A1 | 7/2017 |
| WO | 2017218524 | A1 | 12/2017 |
| WO | 2018078053 | A1 | 5/2018 |
| WO | 2018089846 | A1 | 5/2018 |
| WO | 2018118102 | A1 | 6/2018 |
| WO | 2018119163 | A1 | 6/2018 |
| WO | 2018127382 | A1 | 7/2018 |
| WO | 2018222890 | A1 | 12/2018 |
| WO | 2018222926 | A1 | 12/2018 |
| WO | 2019104152 | A1 | 5/2019 |
| WO | 2020118115 | A1 | 6/2020 |
| WO | 2021178510 | A1 | 9/2021 |

OTHER PUBLICATIONS

International Search Report and Written Opinion received for PCT Application No. PCT/US2019/64786, mailed on Apr. 16, 2020, 15 pages.
(1985) Remington's Pharmaceutical Sciences, Mack Publishing Company, 17th edition, 4 pages.
Altschul et al. (Oct. 5, 1990) "Basic Local Alignment Search Tool", Journal of Molecular Biology, 215(3):403-410.
Berge et al. (1977) "Pharmaceutical Salts", Journal of Pharmaceutical Sciences, 66(1):1-19.
Bochicchio et al. (2014) "Liposomes as siRNA Delivery Vectors", Current Drug Metabolism, 15(9):882-892.
Both et al. (Mar. 1, 1975) "Methylation-Dependent Translation of Viral Messenger RNAs In Vitro", Proceedings of the National Academy of Sciences, 72(3):1189-1193.
Bouloy et al. (Jul. 1, 1980) "Both The 7-Methyl and the 2'-O-Methyl Groups in The Cap Of mRNA Strongly Influence Its Ability to Act as Primer for Influenza Virus RNA Transcription", Proceedings of the National Academy of Sciences, 77(7):3952-3956.
Burgin et al. (Nov. 12, 1996) "Chemically Modified Hammerhead Ribozymes with Improved Catalytic Rates", Biochemistry, 35(45):14090-14097.
Carrillo et al. (Oct. 1988) "The Multiple Sequence Alignment Problem in Biology", SIAM Journal on Applied Mathematics, 48(5):1073-1082.
Cunningham et al. (2011) " Induction and Prevention of Severe Hyperammonemia in the spfash Mouse Model of Ornithine Transcarbamylase Deficiency Using shRNA and rAAV-mediated Gene Delivery", Molecular Therapy, 19(5):854-859.
Dabkowska et al. (Mar. 7, 2012) "The Effect of Neutral Helper Lipids on The Structure of Cationic Lipid Monolayers", Journal of the Royal Society Interface, 9(68):548-561.
Dam et al. (Mar. 6, 1998) "Garlic (Allium Sativum) Lectins Bind to High Mannose Oligosaccharide Chains", Journal of Biological Chemistry, 273(10):5528-5535.
Database Genbank (Feb. 8, 2018) "Human Ornithine Transcarbamylase Protein", GSP:BES38683, 1 page.
Database Genbank (Aug. 12, 2020) "Sequence 2 from U.S. Pat. No. 10,626,382", 1 page.
Devereux et al. (Jan. 11, 1984) "A Comprehensive Set of Sequence Analysis Programs for the VAX", Nucleic Acids Research, 12(1):387-395.
Furuichi et al. (Mar. 1, 1977) "5'-Terminal Structure and mRNA Stability", Nature, 266:235-239.
Gingras et al. (1999) "elF4 Initiation Factors: Effectors Of mRNA Recruitment to Ribosomes and Regulators of Translation", Annual Review of Biochemistry, 68:913-963.
Gordon, Neil (May 2003) "Ornithine Transcarbamylase Deficiency: A Urea Cycle Defect", European Journal of Paediatric Neurology, 7(3):115-121.
Gustafsson et al. (Jul. 2004) "Codon Bias and Heterologous Protein Expression", Trends in Biotechnology, 22(7):346-353.
Hata et al. (1986) "Isolation and Characterization of the Human Ornithinc Transcarbamylase Gene: Structure of the 5'-End Region", Journal of Biochemistry, 100:717-725.
Horwich et al. (Jun. 8, 1984) "Structure and Expression of a Complementary DNA for the Nuclear Coded Precursor of Human Mitochondrial Ornithine Transcarbamylase", Science, 224(4653):1068-1074.
Horwich et al. (Feb. 14, 1986) "Targeting of Pre-Ornithine Transcarbamylase to Mitochondria: Definition of Critical Regions and Residues in The Leader Peptide", Cell, 44(3):451-459.
Huang et al. (Aug. 15, 2011) "In Vivo Delivery of RNAi with Lipid-Based Nanoparticles", Annual Review of Biomedical Engineering, 13:507-530.
Ishikawa et al. (Sep. 27, 2009) "Preparation of Eukaryotic mRNA having Differently Methylated Adenosine at the 5'-Terminus and the Effect of the Methyl Group in Translation", Nucleic Acids Symposium, 53(1):129-130.
Jemielity et al. (2003) "Novel "Anti-Reverse" Cap Analogs with Superior Translational Properties", RNA, 9(9):1108-1122.
Jokerst et al. (Jun. 2011) "Nanoparticle PEGylation for Imaging and Therapy", Nanomedicine (Lond), 6(4):715-728.
Kawabata et al. (1995) "The Fate of Plasmid DNA After Intravenous Injection in Mice: Involvement of Scavenger Receptors in Its Hepatic Uptake", Pharmaceutical Research, 12:825-830.
Kozak, Marilyn (Nov. 1990) "Downstream Secondary Structure Facilitates Recognition of Initiator Codons by Eukaryotic Ribosomes", Proceedings of the National Academy of Sciences, 87(21):8301-8305.
Kozak, Marilyn (Jul. 1988) "Leader Length and Secondary Structure Modulate mRNA Function Under Conditions of Stress", Molecular and Cellular Biology, 8(7):2737-2744.

(56) References Cited

OTHER PUBLICATIONS

Kozak, Marilyn (Oct. 25, 1991) "Structural Features in Eukaryotic mRNAs That Modulate the Initiation of Translation", Journal of Biological Chemistry, 266(30):19867-19870.
Kozak, Marilyn (Feb. 1989) "The Scanning Model for Translation: An Update", Journal of Cell Biology, 108(2):229-241.
Kwok et al. (2015) "A Stable RNA G-Quadruplex within the 5'-UTR of *Arabidopsis thaliana* ATR mRNA Inhibits Translation", Biochemical Journal, 467(1):91-102.
Lasic, Dan D. (Jul. 1, 1998) "Novel Applications of Liposomes", Trends in Biotechnology, 16(7):307-321.
Li et al. (Aug. 3, 2010) "Stealth Nanoparticles: High Density but Sheddable PEG is a Key for Tumor Targeting", Journal of Controlled Release, 145(3):178-181.
Lichter-Koneki et al. (2016) "Ornithine Transcarbamylase Deficiency, GeneReviews® [Internet]", University of Washington, Seattle, 28 pages.
Limbach et al. (Jun. 25, 1994) "Summary: The Modified Nucleosides of RNA", Nucleic Acids Research, 22(12):2183-2196.
Lin et al. (Jan. 2014) "Lipid-Based Nanoparticles in the Systemic Delivery of siRNA", Nanomedicine, 9(1):105-120.
Lindgren et al. (Nov. 9, 1984) "Human Ornithine Transcarbamylase Locus Mapped to Band Xp21.1 Near the Duchenne Muscular Dystrophy Locus", Science, 226(4675)698-700.
Love et al. (Feb. 2, 2010) "Lipid-Like Materials for Low-Dose, In Vivo Gene Silencing", Proceedings of the National Academy of Sciences, 107(5):1864-1869.
Muthukrishnan et al. (May 1, 1975) "5'-Terminal 7-Methylguanosine in Eukaryotic mRNA is Required for Translation", Nature, 255:33-37.
Myers et al. (Mar. 1988) "Optimal Alignments in Linear Space", Computer Applications in the Biosciences., 4(1):11-17.
Patil et al. (Jan. 2014) "Novel Methods for Liposome Preparation", Chemistry and Physics of Lipids, 177:8-18.
Prieve et al. (2018) "Targeted mRNA therapy for Ornithine Transcarbamylase Deficiency", Molecular Therapy, 26(3):801-813.
Rhoads R.E. (Oct. 22, 1999) "Signal Transduction Pathways That Regulate Eukaryotic Protein Synthesis", Journal of Biological Chemistry, 274(43):30337-30340.
Rodriguez-Gascon et al. (Apr. 10, 2014) "Development of Nucleic Acid Vaccines: Use of Self-Amplifying RNA In Lipid Nanoparticles", International Journal of Nanomedicine, 9:1833-1843.
Sablad et al. (2019) "mRNA Therapy for Ornithine Transcarbamlyse Deficiency", Poster presented at 41st Annual Meeting for the Society for Inherited Metabolic Disorders, 1 page.
Shatkin A.J. (Feb. 1985) "mRNA Cap Binding Proteins: Essential Factors for Initiating Translation", Cell, 40(2):223-224.
Shatkin A.J. (Dec. 1976) "Capping of Eucaryotic mRNAs", Cell, 9(4 PT 2):645-653.
Sonenberg Nahum (1988) "Cap-Binding Proteins of Eukaryotic Messenger RNA: Functions in Initiation and Control of Translation", Progress in Nucleic Acid Research and Molecular Biology, 35:173-207.
Taverniti et al. (Jan. 9, 2015) "Elimination of Cap Structures Generated by mRNA Decay Involves the New Scavenger mRNA Decapping Enzyme Aph1/FHIT Together with DcpS", Nucleic Acids Research, 43(1):482-492.
Villalobos et al. (Jun. 6, 2006) "Gene Designer: A Synthetic Biology Tool for Constructing Artificial DNA Segments", BMC Bioinformatics, 7:285 (8 pages).

3A

3B

4A

4B

SEQUENCE LISTING

```
Sequence total quantity: 253
SEQ ID NO: 1           moltype = RNA  length = 1065
FEATURE                Location/Qualifiers
source                 1..1065
                       mol_type = genomic RNA
                       organism = Homo sapiens
SEQUENCE: 1
atgctgttta atctgaggat cctgttaaac aatgcagctt ttagaaatgg tcacaacttc  60
atggttcgaa attttcggtg tggacaacca ctacaaaata aagtgcagct gaagggccgt  120
gaccttctca ctctaaaaaa ctttaccgga gaagaaatta aatatatgct atggctatca  180
gcagatctga aatttaggat aaaacagaaa ggagagtatt tgcctttatt gcaagggaag  240
tccttaggca tgatttttga gaaaagaagt actcgaacaa gattgtctac agaaacaggc  300
tttgcacttc tgggaggaca tccttgtttt cttaccacac aagatattca tttgggtgtg  360
aatgaaagtc tcacggacac ggcccgtgta ttgtctagca tggcagatgc agtattggct  420
cgagtgtata aacaatcaga tttggacacc ctggctaaag aagcatccat cccaattatc  480
aatgggctgt cagatttgta ccatcctatc cagatcctgg ctgattacct cacgctccag  540
gaacactata gctctctgaa aggtcttacc ctcagctgga tcggggatgg gaacaatatc  600
ctgcactcca tcatgatgag cgcagcgaaa ttcggaatgc accttcaggc agctactcca  660
aagggttatg agccggatgc tagtgtaacc aagttggcag agcagtatgc caaagagaat  720
ggtaccaagc tgttgctgac aaatgatcca ttggaagcag cgcatggagg caatgtatta  780
attacagaca cttggataag catgggacaa gaagaggaga agaaaaagcg gctccaggct  840
ttccaaggtt accaggttac aatgaagact gctaaagttg ctgcctctga ctggacattt  900
ttacactgct tgcccagaaa gccagaagaa gtggatgatg aagtctttta ttctcctcga  960
tcactagtgt tcccagaggc agaaaacaga aagtggacaa tcatggctgt catggtgtcc  1020
ctgctgacag attactcacc tcagctccag aagcctaaat tttga                 1065

SEQ ID NO: 2           moltype = DNA  length = 1065
FEATURE                Location/Qualifiers
source                 1..1065
                       mol_type = genomic DNA
                       organism = Homo sapiens
SEQUENCE: 2
atgctgttta atctgaggat cctgttaaac aatgcagctt ttagaaatgg tcacaacttc  60
atggttcgaa attttcggtg tggacaacca ctacaaaata aagtgcagct gaagggccgt  120
gaccttctca ctctaaaaaa ctttaccgga gaagaaatta aatatatgct atggctatca  180
gcagatctga aatttaggat aaaacagaaa ggagagtatt tgcctttatt gcaagggaag  240
tccttaggca tgatttttga gaaaagaagt actcgaacaa gattgtctac agaaacaggc  300
tttgcacttc tgggaggaca tccttgtttt cttaccacac aagatattca tttgggtgtg  360
aatgaaagtc tcacggacac ggcccgtgta ttgtctagca tggcagatgc agtattggct  420
cgagtgtata aacaatcaga tttggacacc ctggctaaag aagcatccat cccaattatc  480
aatgggctgt cagatttgta ccatcctatc cagatcctgg ctgattacct cacgctccag  540
gaacactata gctctctgaa aggtcttacc ctcagctgga tcggggatgg gaacaatatc  600
ctgcactcca tcatgatgag cgcagcgaaa ttcggaatgc accttcaggc agctactcca  660
aagggttatg agccggatgc tagtgtaacc aagttggcag agcagtatgc caaagagaat  720
ggtaccaagc tgttgctgac aaatgatcca ttggaagcag cgcatggagg caatgtatta  780
attacagaca cttggataag catgggacaa gaagaggaga agaaaaagcg gctccaggct  840
ttccaaggtt accaggttac aatgaagact gctaaagttg ctgcctctga ctggacattt  900
ttacactgct tgcccagaaa gccagaagaa gtggatgatg aagtctttta ttctcctcga  960
tcactagtgt tcccagaggc agaaaacaga aagtggacaa tcatggctgt catggtgtcc  1020
ctgctgacag attactcacc tcagctccag aagcctaaat tttga                 1065

SEQ ID NO: 3           moltype = AA  length = 353
FEATURE                Location/Qualifiers
source                 1..353
                       mol_type = protein
                       organism = Homo sapiens
SEQUENCE: 3
MLFNLRILLN NAAFRNGHNF MVRNFRCGQP LQNKVQLKGR DLLTLKNFTG EEIKYMLWLS  60
ADLKFRIKQK GEYLPLLQGK SLGMIFEKRS TRTRLSTETG FALLGGHPCF LTTQDIHLGV  120
```

-continued

```
NESLTDTARV LSSMADAVLA RVYKQSDLDT LAKEASIPIF GLSDLYHPIQ ILADYLTLQE  180
HYSSLKGLTL SWIGDGNNIL HSIMMSAAKF GMHLQAATPK GYEPDASVTK LAEQYAKENG  240
TKLLLTNDPL EAAHGGNVLI TDTWISMGQE EEKKKRLQAF QGYQVTMKTA KVAASDWTFL  300
HCLPRKPEEV DDEVFYSPRS LVFPEAENRK WTIMAVMVSL LTDYSPQLQK PKF         353

SEQ ID NO: 4            moltype = AA  length = 355
FEATURE                 Location/Qualifiers
REGION                  1..355
                        note = Synthetic construct
source                  1..355
                        mol_type = protein
                        organism = synthetic construct
SEQUENCE: 4
MLVFNLRILL NNAAFRNGHN FMVRNFRCGQ PLQNRVQLKG RDLLTLKNFT GEEIRYMLWL  60
SADLKFRIKQ KGEYLPLLQG KSLGMIFEKR STRTRLSTET GFALLGGHPC FLTTQDIHLG  120
VNESLTDTAR VLSSMADAVL ARVYKQSDLD TLAKEASIPI INGLSDLYHP IQILADYLTL  180
QEHYSSLKGL TLSWIGDGNN ILHSIMMSAA KFGMHLQAAT PKGYEPDASV TKLAEQYAKE  240
NGTKLLLTND PLEAAHGGNV LITDTWISMG QEEEKKKRLQ AFQGYQVTMK TAKVAASDWT  300
FLHCLPRKPE EVDDEVFYSP RSLVFPEAEN RKWTIMAVMV SLLTDYSPQL QKPKF        355

SEQ ID NO: 5            moltype = RNA  length = 129
FEATURE                 Location/Qualifiers
misc_feature            1..129
                        note = Synthetic construct
source                  1..129
                        mol_type = other RNA
                        organism = synthetic construct
SEQUENCE: 5
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatag                                                          129

SEQ ID NO: 6            moltype = RNA  length = 28
FEATURE                 Location/Qualifiers
misc_feature            1..28
                        note = Synthetic construct
source                  1..28
                        mol_type = other RNA
                        organism = synthetic construct
SEQUENCE: 6
attattacat caaaacaaaa agccgcca                                     28

SEQ ID NO: 7            moltype = RNA  length = 245
FEATURE                 Location/Qualifiers
misc_feature            1..245
                        note = Synthetic construct
source                  1..245
                        mol_type = other RNA
                        organism = synthetic construct
SEQUENCE: 7
cttaaggggg cgctgcctac ggaggtggca gccatctcct tctcggcatc aagcttacca  60
tggtgcccca ggccctgctc ttggtcccgc tgctggtgtt ccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctac                                                              245

SEQ ID NO: 8            moltype = RNA  length = 177
FEATURE                 Location/Qualifiers
misc_feature            1..177
                        note = Synthetic construct
source                  1..177
                        mol_type = other RNA
                        organism = synthetic construct
SEQUENCE: 8
tgagtgtcgt acagcctcca ggcccccccc tcccgggaga gccatagtgg tctgcggaac  60
cggtgagtac accggaattg ccgggaagac tgggtccttt cttggataaa cccactctat  120
gcccggccat ttgggcgtgc ccccgcaaga ctgctagccg agtagtgttg ggttgcg     177

SEQ ID NO: 9            moltype = RNA  length = 89
FEATURE                 Location/Qualifiers
misc_feature            1..89
                        note = Synthetic construct
source                  1..89
                        mol_type = other RNA
                        organism = synthetic construct
SEQUENCE: 9
aattattggt taaagaagta tattagtgct aatttccctc cgtttgtcct agcttttctc  60
ttctgtcaac cccacacgcc tttggcaca                                    89
```

-continued

```
SEQ ID NO: 10          moltype = RNA  length = 569
FEATURE                Location/Qualifiers
misc_feature           1..569
                       note = Synthetic construct
source                 1..569
                       mol_type = other RNA
                       organism = synthetic construct
SEQUENCE: 10
ctccctcccc ccccctaac gttactggcc gaagccgctt ggaataaggc cggtgtgcgt  60
ttgtctatat gttattttcc accatattgc cgtcttttgg caatgtgagg gcccggaaac  120
ctggccctgt cttcttgacg agcattccta ggggtctttc ccctctcgcc aaaggaatgc  180
aaggtctgtt gaatgtcgtg aaggaagcag ttcctctgga agcttcttga agacaaacaa  240
cgtctgtagc gaccctttgc aggcagcgga accccccacc tggcgacagg tgcctctgcg  300
gccaaaagcc acgtgtataa gatacacctg caaaggcggc acaaccccag tgccacgttg  360
tgagttggat agttgtggaa agagtcaaat ggctctcctc aagcgtattc aacaaggggc  420
tgaaggatgc ccagaaggta ccccattgta tgggatctga tctggggcct cggtgcacat  480
gctttacgtg tgtttagtcg aggttaaaaa acgtctaggc cccccgaacc acggggacgt  540
ggttttcctt tgaaaaacac gatgataat                                   569

SEQ ID NO: 11          moltype = RNA  length = 44
FEATURE                Location/Qualifiers
misc_feature           1..44
                       note = Synthetic construct
source                 1..44
                       mol_type = other RNA
                       organism = synthetic construct
SEQUENCE: 11
gtcagctttc aaactctttg tttcttgttt gttgattgag aata                  44

SEQ ID NO: 12          moltype = RNA  length = 54
FEATURE                Location/Qualifiers
misc_feature           1..54
                       note = Synthetic construct
source                 1..54
                       mol_type = other RNA
                       organism = synthetic construct
SEQUENCE: 12
ctctcgcctg agaaaaaaaa tccacgaacc aatttctcag caaccagcag cacg       54

SEQ ID NO: 13          moltype = RNA  length = 52
FEATURE                Location/Qualifiers
misc_feature           1..52
                       note = Synthetic construct
source                 1..52
                       mol_type = other RNA
                       organism = synthetic construct
SEQUENCE: 13
acctgtgagg gttcgaagga agtagcagtg tttttgttc ctagaggaag ag          52

SEQ ID NO: 14          moltype = RNA  length = 71
FEATURE                Location/Qualifiers
misc_feature           1..71
                       note = Synthetic construct
source                 1..71
                       mol_type = other RNA
                       organism = synthetic construct
SEQUENCE: 14
acacagaaac attcgcaaaa acaaaatccc agtatcaaaa ttcttctctt tttttcatat  60
ttcgcaaaga c                                                      71

SEQ ID NO: 15          moltype = RNA  length = 52
FEATURE                Location/Qualifiers
misc_feature           1..52
                       note = Synthetic construct
source                 1..52
                       mol_type = other RNA
                       organism = synthetic construct
SEQUENCE: 15
cagaaaaatt tgctacattg tttcacaaac ttcaaatatt attcatttat tt          52

SEQ ID NO: 16          moltype = RNA  length = 158
FEATURE                Location/Qualifiers
misc_feature           1..158
                       note = Synthetic construct
source                 1..158
                       mol_type = other RNA
                       organism = synthetic construct
```

```
SEQUENCE: 16
ctagtgactg actaggatct ggttaccact aaaccagcct caagaacacc cgaatggagt    60
ctctaagcta cataatacca acttacactt acaaaatgtt gtcccccaaa atgtagccat   120
tcgtatctgc tcctaataaa aagaaagttt cttcacat                           158

SEQ ID NO: 17          moltype = RNA  length = 166
FEATURE                Location/Qualifiers
misc_feature           1..166
                       note = Synthetic construct
source                 1..166
                       mol_type = other RNA
                       organism = synthetic construct
SEQUENCE: 17
tgcaaggctg gccggaagcc cttgcctgaa agcaagattt cagcctggaa gagggcaaag    60
tggacgggag tggacaggag tggatgcgat aagatgtggt ttgaagctga tgggtgccag   120
ccctgcattg ctgagtcaat caataaagag ctttcttttg acccat                  166

SEQ ID NO: 18          moltype = RNA  length = 143
FEATURE                Location/Qualifiers
misc_feature           1..143
                       note = Synthetic construct
source                 1..143
                       mol_type = other RNA
                       organism = synthetic construct
SEQUENCE: 18
acgccgaagc ctgcagccat gcgaccccac gccaccccgt gcctcctgcc tccgcgcagc    60
ctgcagcggg agaccctgtc cccgcccag ccgtcctcct ggggtggacc ctagtttaat   120
aaagattcac caagtttcac gca                                           143

SEQ ID NO: 19          moltype = RNA  length = 220
FEATURE                Location/Qualifiers
misc_feature           1..220
                       note = Synthetic construct
source                 1..220
                       mol_type = other RNA
                       organism = synthetic construct
SEQUENCE: 19
tagagcggca aaccctagct acactccata gctagtttct tttttttttg tttttttttt    60
tttttttttt tttttttttt tttttttttc ctttcttttc cttcttttt tcctcttttc   120
ttggtggctc catcttagcc ctagtcacgg ctagctgtga aaggtccgtg agccgcatga   180
ctgcagagag tgccgtaact ggtctctctg cagatcatgt                         220

SEQ ID NO: 20          moltype = RNA  length = 170
FEATURE                Location/Qualifiers
misc_feature           1..170
                       note = Synthetic construct
source                 1..170
                       mol_type = other RNA
                       organism = synthetic construct
SEQUENCE: 20
acacatcaca accacaacct tctcaggcta ccctgagaaa aaaagacatg aagactcagg    60
actcatcttt tctgttggtg taaaatcaac accctaagga acacaaattt ctttaaacat   120
ttgacttctt gtctctgtgc tgcaattaat aaaaaatgga aagaatctac               170

SEQ ID NO: 21          moltype = RNA  length = 110
FEATURE                Location/Qualifiers
misc_feature           1..110
                       note = Synthetic construct
source                 1..110
                       mol_type = other RNA
                       organism = synthetic construct
SEQUENCE: 21
gctggagcct cggtagccgt tcctcctgcc cgctgggcct cccaacgggc cctcctcccc    60
tccttgcacc ggcccttcct ggtctttgaa taaagtctga gtgggcagca               110

SEQ ID NO: 22          moltype = RNA  length = 123
FEATURE                Location/Qualifiers
misc_feature           1..123
                       note = Synthetic construct
source                 1..123
                       mol_type = other RNA
                       organism = synthetic construct
SEQUENCE: 22
tagtgcagtc actggcacaa cgcgttgccc ggtaagccaa tcgggtatac acggtcgtca    60
tactgcagac agggttcttc tactttgcaa gatagtctag agtagtaaaa taaatagtat   120
aag                                                                 123
```

SEQ ID NO: 23 moltype = length =
SEQUENCE: 23
000

SEQ ID NO: 24 moltype = length =
SEQUENCE: 24
000

SEQ ID NO: 25 moltype = length =
SEQUENCE: 25
000

SEQ ID NO: 26 moltype = RNA length = 1368
FEATURE Location/Qualifiers
misc_feature 1..1368
note = Synthetic construct
source 1..1368
mol_type = other RNA
organism = synthetic construct
SEQUENCE: 26
tcaacacaac atatacaaaa caaacgaatc tcaagcaatc aagcattcta cttctattgc 60
agcaatttaa atcatttctt ttaaagcaaa agcaattttc tgaaaatttt caccatttac 120
gaacgatagc caccatgctg tttaatctga ggatcctgtt aaacaatgca gcttttagaa 180
atggtcacaa cttcatggtt cgaaattttc ggtgtggaca accactacaa aataaagtgc 240
agctgaaggg ccgtgacctt ctcactctaa aaaactttac cggagaagaa attaaatata 300
tgctatggct atcagcagat ctgaaattta ggataaaaca gaaaggagag tatttgcctt 360
tattgcaagg gaagtcctta ggcatgattt ttgagaaaag aagtactcga acaagattgt 420
ctacagaaac aggctttgca cttctgggag gacatccttg ttttcttacc acacaagata 480
ttcatttggg tgtgaatgaa agtctcacgg acacggcccg tgtattgtct agcatggcag 540
atgcagtatt ggctcgagtg tataaacaat cagatttgga caccctggct aaagaagcat 600
ccatcccaat tatcaatggg ctgtcagatt tgtaccatcc tatccagatc ctggctgatt 660
acctcacgct ccaggaacac tatagctctc tgaaaggtct taccctcagc tggatcgggg 720
atgggaacaa tatcctgcac tccatcatga tgagcgcagc gaaattcgga atgcaccttc 780
aggcagctac tccaaagggt tatgagccgg atgctagtgt aaccaagttg gcagagcagt 840
atgccaaaga gaatggtacc aagctgttgc tgacaaatga tccattggaa gcagcgcatg 900
gaggcaatgt attaattaca gacacttgga taagcatggg acaagaagag gagaagaaaa 960
agcggctcca ggctttccaa ggttaccagg ttacaatgaa gactgctaaa gttgctgcct 1020
ctgactggac atttttacac tgcttgccca gaaagccaga agaagtggat gatgaagtct 1080
tttattctcc tcgatcacta gtgttcccag aggcagaaaa cagaaagtgg acaatcatgg 1140
ctgtcatggt gtccctgctg acagattact cacctcagct ccagaagcct aaattttgac 1200
tcgagctagt gactgactag gatctggtta ccactaaacc agcctcaaga acacccgaat 1260
ggagtctcta agctacataa taccaactta cacttacaaa atgttgtccc ccaaaatgta 1320
gccattcgta tctgctccta ataaaaagaa agtttcttca cattctag 1368

SEQ ID NO: 27 moltype = RNA length = 1368
FEATURE Location/Qualifiers
misc_feature 1..1368
note = Synthetic construct
source 1..1368
mol_type = other RNA
organism = synthetic construct
SEQUENCE: 27
tcaacacaac atatacaaaa caaacgaatc tcaagcaatc aagcattcta cttctattgc 60
agcaatttaa atcatttctt ttaaagcaaa agcaattttc tgaaaatttt caccatttac 120
gaacgatagc caccatgctc tttaatctgc gcatcttact gaacaacgcc gcattccgga 180
acggtcacaa cttcatggtc cgcaatttcc gctgtggcca gccgcttcaa aacaaggtcc 240
agctgaaggg acgggatctg ctgacactga agaacttcac cggagaagag atcaagtaca 300
tgctgtggct cagcgcagac ttgaagttcc ggatcaagca gaagggagaa tacttgcccc 360
tgctgcaagg aaagtcgctg ggaatgattt ttgagaagcg gtcaactcgc accagactct 420
ccaccgaaac tggtttcgca ctgcttggcg ggcacccttg cttcctgacg actcaggaca 480
tccacctcgg cgtgaacgaa tcgctaaccg ataccgccag agtgctttct tccatggccg 540
acgcggtgct ggccagggtg tacaagcagt ccgacctcga taccttggca aaggaggctt 600
ccattcccat catcaacggc ctgagcgacc tgtaccaccc aatccaaatc ctggctgact 660
acctgaccct gcaagagcac tacagcagcc tgaagggtct gaccctgtca tggattggcg 720
atggaaacaa tattctgcac tccatcatga tgtccgccgc gaagttcgga atgcatctgc 780
aagccgccac tccaaaagga tacgaaccgg atgcgtccgt gaccaagttg gcggaacagt 840
acgcgaagga gaacggaacc aagcttctgc tgactaacga ccccctcgag gctgcgcatg 900
ggggcaacgt gctgattacc gacacctgga tctccatggg gcaggaggaa gagaagaaga 960
agagactgca ggcattccag gggtaccagg tcaccatgaa aaccgcaaaa gtggcagctt 1020
cggactggac tttcctgcat tgcctgccga ggaagccgga ggaagtcgac gacgaagtgt 1080
tctactcgcc tcggtccctg gtgttccccg aggccgaaaa ccggaagtgg accatcatgg 1140
ccgtgatggt gtccttgctg actgactata gcccgcagct gcagaagcct aagttctagc 1200
tcgagctagt gactgactag gatctggtta ccactaaacc agcctcaaga acacccgaat 1260
ggagtctcta agctacataa taccaactta cacttacaaa atgttgtccc ccaaaatgta 1320
gccattcgta tctgctccta ataaaaagaa agtttcttca cattctag 1368

SEQ ID NO: 28 moltype = RNA length = 1368
FEATURE Location/Qualifiers

-continued

```
misc_feature           1..1368
                       note = Synthetic construct
source                 1..1368
                       mol_type = other RNA
                       organism = synthetic construct
SEQUENCE: 28
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg tttaacctac gtattttgct caacaatgca gcctttagaa  180
acggacataa ctttatggtt cgaaactttc gctgcgggca gccactgcag aacaaggtcc  240
agctgaaagg gagagatttg ctcacgctga agaactttac tggcgaagaa atcaagtata  300
tgctgtggtt gtccgcggac ctcaagtttc ggattaagca gaaaggggag tatctgccac  360
tgctgcaagg aaagagcctc ggcatgatct tcgagaagcg gagcactcgg accaggctga  420
gtaccgaaac tggcttcgca ttgttgggtg gacatccatg ttttctgaca acgcaggaca  480
ttcatctggg cgtgaacgag agtctgacgg acacagctcg cgttctgtcc tctatggctg  540
atgcggtgtt ggcccgggtc tataagcagt ccgatttgga caccttggct aaggaagcta  600
gcataccgat tatcaatggg ctgtccgacc tgtatcaccc tattcaaatc ctggccgact  660
acctcacact gcaagaacac tatagctcat tgaagggact gaccctgagc tggatagggg  720
acggaaacaa catcctacat agcattatga tgtccgctgc caagtttggc atgcatcttc  780
aagccgccac gccaaagggt tatgagcccg acgcgtcagt gacaaagctg gccgagcagt  840
acgctaagga gaatggtacc aaattactgc tgactaatga tccactggag gctgcacatg  900
gcggcaatgt actgatcacc gacacatgga tctcgatggg ccaggaggaa gaaaagaaga  960
agaggcttca ggccttccaa ggctaccagg tcaccatgaa aacagctaag gttgcagcat  1020
ctgattggac ctttctgcac tgtctgccaa ggaagcccga agaggtggac gatgaagtat  1080
tctatagccc acggagtttg gtgttccctg aggctgaaaa taggaagtgg acaattatgg  1140
ccgtaatggt gtccctgtta accgactact ctccgcaact gcagaaacct aagttttagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 29          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 29
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg tttaacttaa ggatcctgct gaacaacgcc gcttttcgta  180
acggtcataa ctttatggtc cggaacttta gatgtggcca gccgctgcag aacaaggttc  240
agctgaaggg gagggatctg ctgaccttga agaactttac cggcgaagag atcaagtaca  300
tgttgtggct gagcgccgat ctgaagttta ggattaagca gaagggggag tatttgccac  360
tgctgcaagg aaaatccttg gggatgatct tcgagaagcg ctccactaga acccggctaa  420
gcacagaaac cggcttcgca cttctgggtg gacatccctg ttttctgacg acgcaggata  480
tacacctggg cgtgaatgag agtctgacgg acacagctag ggtgttgagc agcatggccg  540
atgcagtact ggcccgcgtt tataagcaga gcgacttgga cacactggcc aaggaagcgt  600
caattccgat tatcaatggg ctgtcagacc tgtatcatcc cattcaaatc ttggctgact  660
atctgaccct gcaagaacat tacagctccc tgaagggcct cacgttgtcc tggattggcg  720
acggaaacaa cattctgcat tcgatcatga tgagcgctgc taagtttggc atgcacctcc  780
aagccgctac acctaaggga tatgagcctg atgccagcgt aaccaagctg gccgaacagt  840
acgcgaagga gaatggcacg aaactgctgt tgacaaatga cccactggag gcagctcacg  900
gtggcaacgt gctgatcacc gacacgtgga tatctatggg acaggaagaa gagaagaaga  960
agcggctgca ggcattccaa gggtatcagg tcaccatgaa aacggccaag gttgctgcat  1020
ccgactggac atttctgcat tgcttgcccc gcaaaccaga agaagtagac gacgaagtct  1080
tttattcccc acggtcgctg gtgttccccg aggcggagaa tcgaaagtgg acgattatgg  1140
ccgtgatggt gtccctgctg actgattact ctccccaact gcaaaagcct aagttttagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 30          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 30
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacctga ggatcctcct gaacaacgcc gcctttcgca  180
atggtcacaa ctttatggtc cggaacttca gatgcggcca gccgctgcag aacaaggtcc  240
agctgaaggg acgggatctg ctgactctga agaacttcac cggagaagag atcaagtaca  300
tgctgtggct gtcggccgac ctgaagttca ggatcaagca gaagggagaa tacctcccgc  360
tgctgcaagg aaagtccctg ggcatgattt tcgagaagcg ctcgaccaga actcggttgt  420
ccaccgaaac cgggtttgcg ctgctgggcg gacatccttg cttcctgacg actcaggata  480
ttcacctggg agtgaacgag tcgctgaccg acaccgccag agtgctgagc tcgatggccg  540
```

```
acgccgtgtt ggcacgcgtg tacaagcagt ccgatctgga taccctggcc aaagaagctt  600
ccatcccgat cattaacggg ctgagcgacc tctaccaccc cattcaaatc ctggccgact  660
acctgactct gcaagaacac tacagctcgc tgaaggggtt gactctgtcc tggatcggcg  720
acggaaacaa catcctgcac tccatcatga tgtcggccgc aaagttcggc atgcatttgc  780
aagccgccac cccaaagggc tacgaaccag acgcgagcgt caccaagctg gccgaacagt  840
acgcgaagga aaatggtact aagctgctgc tgaccaacga cccattggaa gctgcccatg  900
gtggaaacgt gctgatcacc gacacctgga tctcgatggg ccaggaagag gagaagaaga  960
agcggctgca ggcgttccag gggtatcagg tcaccatgaa aacagccaaa gtggcagcgt  1020
cagactggac cttcctccac tgtctgcctc gcaagccaga ggaggtggac gacgaggtgt  1080
tctactcccc tcggtccctc gtgttccctg aggctgagaa ccggaagtgg accattatgg  1140
ccgtgatggt gtcactcctg actgattact ccccgcaact gcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

```
SEQ ID NO: 31           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 31
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg tttaacctga ggatcctatt gaacaatgct gcttttcgta  180
atggccataa ctttatggtt cggaacttta gatgcgggca gccactgcag aacaaggtcc  240
agttgaaagg ccgcgatctg ttgacattga agaactttac cggcgaagag attaagtata  300
tgctgtggct gtctgctgac ctcaagtttc gaatcaagca gaagggcgaa tatctccccc  360
tgctgcaagg aaagtctctc ggcatgatct ttgagaagcg gagtacccga acacggctga  420
gcaccgaaac gggcttcgca ctgctggggg gccatccctg ttttctgaca acgcaggaca  480
tccacttggg ggttaacgaa tcattgactg ataccgcccg cgtactgtca tccatggccg  540
acgctgtgct ggctagggtg tacaagcagt cagatctgga tacactggcc aaggaagcta  600
gcataccaat catcaatgga ctgagtgacc tttatcaccc gattcaaata ctagccgatt  660
atctgaccct gcaagagcat tactcctcgc tgaaaggcct cacgctgtcc tggatcggcg  720
acggcaacaa cattctgcat agtattatga tgtctgctgc caaattcggc atgcatctgc  780
aagctgctac gccgaagggt tatgaacccg acgcgtcagt tacgaagctc gctgagcagt  840
atgcaaagga gaatggcaca aagctgttgc ttaccaacga tcccctggaa gctgctcatg  900
gcggcaatgt gctgattact gacacctgga tttcaatggg ccaggaggag gagaagaaga  960
agaggttaca ggcttttcaa ggttaccaag tcacgatgaa aaccgctaag gtcgcagcca  1020
gcgactggac attcctgcac tgtctgccaa gaaagccgga agaagtggac gacgaggtgt  1080
tctattcccc gcggtctttg gtgtttccgg aggccgaaaa caggaaatgg accattatgg  1140
ccgtgatggt atcgttgctg acggactaca gccctcagtt gcaaaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

```
SEQ ID NO: 32           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 32
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctc tttaacctcc gcatcctcct caacaacgcc gccttccgga  180
atgggcataa cttcatggtc cggaacttca gatgcggcca gcccctgcaa aacaaggtcc  240
agttgaaggg acgggacctc cttacgctga agaactttac cggagaagag attaagtaca  300
tgctgtggtt gtccgctgac ctcaagttcc gcattaagca gaagggagaa tatctgccgc  360
tgctgcaagg aaagagcctg ggcatgatct tcgaaaagcg ctccactaga acccggctgt  420
cgactgagac tggattcgcc ttgctcggtg gacacccgtg cttcctgacg acccaggaca  480
tccacctggg agtgaacgag tcacttacgg ataccgcgag ggtgctgtcc tcaatggccg  540
acgcagtgct cgcgcgcgtg tacaagcagt cagatctgga taccctggcc aaggaagcca  600
gcattcccat catcaacgga ctgagcgacc tttaccaccc aatccagatc ctcgccgact  660
acttaaccct gcaagagcac tacagctccc tgaagggact gactctgtcc tggatcgggg  720
atggaaacaa catcctgcac tccatcatga tgtctgccgc taagtttggg atgcatctgc  780
aagccgcaac ccctaaggga tacgagcccg acgcctcggt gaccaaactt gcggaacagt  840
acgccaagga aaacggtacc aagctgctgc tgaccaacga ccctctggaa gcggcccacg  900
gaggaaatgt gctgattacc gacacctgga tttcgatggg ccaggaggag gagaagaaga  960
agagactgca ggcgttccag ggatatcagg tcaccatgaa aaccgccaag gtcgccgcca  1020
gcgactggac cttcctgcac tgtctccctc ggaaaccgga agaagtggat gacgaggtgt  1080
tctactcccc gcgctcgctg gtgttcccgg aggctgaaaa caggaagtgg acaatcatgg  1140
ccgtgatggt gtccctgttg accgactact ccccacaact gcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

-continued

```
SEQ ID NO: 33          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 33
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctgc gcatcctcct gaacaacgcc gccttccgca  180
atggacacaa ctttatggtc cgcaacttcc gctgtgggca gccgctgcag aacaaggtcc  240
agctcaaggg gagagatctc ctgaccctga agaacttcac tggagaggag atcaagtaca  300
tgctgtggct gtccgccgac ctgaaatttc ggattaagca gaagggcgaa tacctcccac  360
tgctgcaagg aaagtctttg ggcatgatct tcgaaaagag aagcacccgg acccggttga  420
gcaccgaaac tgggttcgcg ctcctcggtg gacacccgtg cttcctgacc acccaagata  480
ttcatctggg tgtcaacgaa agcctgaccg acaccgccag ggtgctgtca tccatggctg  540
acgcagtgct cgcccgggtg tacaagcagt cagacctgga caccctcgcc aaggaagctt  600
cgatccctat catcaacgga ctttccgacc tgtaccaccc catccaaatt ctggccgact  660
acctgactct gcaagaacac tatagctcgc tgaaaggact tactctgtcc tggatcgggg  720
acggcaacaa cattctccat tccatcatga tgtccgctgc caagttcgga atgcaccttc  780
aagcagcgac tcccaaggga tacgaacctg atgcctccgt gactaagctg gcagagcagt  840
acgccaagga gaacggtaca aagctgctgc tcacgaacga ccccctggag gcggcccacg  900
gcggaaacgt gctgattacc gatacctgga tctcaatggg ccaggaagag gagaagaaga  960
agcggctcca ggcgtttcaa ggctaccagg tcaccatgaa aaccgcgaag gtcgccgcct  1020
ccgactggac tttcttgcac tgcctgccgc ggaagcccga ggaagtggat gacgaagtgt  1080
tctactcgcc gagatcgttg gtgttccctg aggccgaaaa caggaagtgg accatcatgg  1140
ccgtgatggt gtccctgctg actgattaca gcccacagct gcagaagcct aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag             1368

SEQ ID NO: 34          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 34
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag             1368

SEQ ID NO: 35          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 35
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacctga gaatcctcct gaacaacgcc gccttccgca  180
atggtcataa cttcatggtc cgcaactttc gctgcggaca gcctctccaa aacaaggtcc  240
agctcaaggg gcgcgacctc ctcacactga agaacttcac tggagaagaa atcaagtaca  300
tgctgtggct gagcgccgat ctgaagttcc ggatcaagca gaagggagag taccttcctc  360
tgctgcaagg gaagtccttg ggaatgattt tcgagaagcg gtccacccgg accaggctga  420
```

```
gcactgaaac tggcttcgcc ctgctgggag gccacccttg tttcctgacc actcaggaca  480
tccacctggg cgtgaacgag tccctgaccg atactgccag agtgctgtcc tccatggccg  540
acgccgtgct cgcccgggtg tacaagcagt cagacctcga tacgctggcc aaggaagcct  600
ccattcccat tatcaatggt ctgtcggacc tctaccatcc aatccaaatc ctcgccgact  660
acctgactct gcaagaacac tacagctcac tcaagggcct caccctctcc tggatcggcg  720
acggaaacaa catccttcac tcgattatga tgtcggccgc gaagttcggg atgcacctcc  780
aagctgccac tccaaaaggc tacgagccgg atgcctcagt gactaagttg gcggaacagt  840
atgcgaagga gaacggtacc aagctcctgc tgactaacga cccgctggag gccgcccacg  900
ggggaaacgt gctcatcacc gatacttgga tttccatggg acaggaggaa gagaagaaga  960
agcggttgca ggcatttcag ggctaccagg tcaccatgaa aactgccaaa gtcgccgcca  1020
gcgactggac cttcctgcac tgcctgcccc gcaagcctga agaagtggac gacgaggtgt  1080
tctactctcc ccggtccctc gtgttccctg aggccgaaaa caggaagtgg accatcatgg  1140
ctgtgatggt gtccctcctg accgactaca gccctcagct ccaaaaaccc aagttttagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 36          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 36
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacctga gaatcctctt gaacaatgct gcttttcgga  180
atggccacaa ctttatggtt cggaacttcc gttgcggcca gcctttacaa aacaaggtcc  240
agctgaaggg ccgggatttg ctcacactga agaactttac tggggaggag attaagtata  300
tgctgtggct gtccgctgac ctgaagttta ggatcaagca gaagggcgaa tatctgccgc  360
tgctgcaagg gaaaagtctg ggcatgattt ttgaaaagcg ctctacccgg accagactgt  420
ctacggaaac aggctttgcc ctgctgggcg gccacccctg ttttctgaca acgcaggaca  480
tccatctggg cgtgaacgaa tcactgaccg atactgctcg ggtactcagt tctatggctg  540
acgcagtgct ggctagggtg tacaagcaga gcgacttgga cacactggct aaggaggcca  600
gcatccccat tatcaatggc ctgtctgatt tgtaccatcc cattcaaatc ctggctgatt  660
atctgacact acaagagcat tactcaagtc tgaagggttt gactctctcc tggatcggcg  720
acggcaacaa cattttacat tccattatga tgagtgctgc taagtttggc atgcatttgc  780
aagctgctac cccaaagggc tatgaacctg acgctagcgt aaccaagttg gccgaacagt  840
atgctaaaga gaatggcacc aagctgctcc tgacgaatga ccccctggaa gctgctcatg  900
gcggaaacgt acttataact gatacatgga ttagcatggg ccaggaagag gagaagaaga  960
agagactgca ggccttccaa ggctatcagg tcaccatgaa aactgccaag gttgcagcta  1020
gcgactggac cttcctgcac tgtttgccga ggaaacccga ggaggtggac gatgaagtct  1080
tttattctcc ccgctccttg gtgtttcccg aggctgaaaa tcgaaagtgg acgataatgg  1140
cagtgatggt gtccctactg accgactatt ctccacaact gcagaagcct aaattctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 37          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 37
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctga ggatcctgct gaacaacgct gcttttcgca  180
acggtcataa ctttatggtt cgcaattttc gttgtggcca gccgctgcag aacaaggttc  240
agctgaaggg cagagatctg ctgactctga agaacttcac tggggaagaa atcaagtata  300
tgttatggct gtccgcggat ctgaaatttc gaatcaagca gaagggcgaa tatcttcccc  360
tgctgcaagg gaaatccttg ggcatgattt ttgagaagag gagcactagg actagattgt  420
caacagaaac aggctttgct ttgttgggcg gacatccctg ctttctgacg acacaggata  480
tccacctcgg cgtaaacgag tccctcaccg acactgctag ggtactgagc agcatggccg  540
acgctgtgct agcccgggtt tacaagcagt cagacctgga caccccttgcc aaggaagctt  600
ctattccaat tatcaacggc ctgagtgacc tgtatcaccc tattcaaata ctcgccgact  660
atttgacgct tcaagaacat tacagcagcc tcaagggctt aaccttgagt tggataggcg  720
acggcaacaa tatcctgcat tccattatga tgtctgccgc taagtttggc atgcatctac  780
aagccgcaac acccaagggc tatgaacccg acgctagcgt gaccaagctg gccgagcagt  840
atgctaagga aaatggcaca aagctccttc ttaccaacga tcccctggag gctgctcacg  900
gcggcaacgt gctgattacc gatacatgga ttagcatggg ccaggaggag gagaaaaaga  960
agcggctcca ggcttttcaa ggctatcagg tcaccatgaa aactgcaaag gtcgctgcct  1020
ccgactggac tttcctgcat tgtctacccc gcaagcctga ggaagtggac gatgaggtgt  1080
tctactcccc acggagtctg gtgttcccgg aagcagagaa tcggaagtgg accatcatgg  1140
ctgtcatggt gtcgctcttg actgactatt ctccccaact gcaaaaaccc aagttttagc  1200
tcgagctagt gactgactag gatctggtta ccactaaacc agcctcaaga acacccgaat  1260
```

```
ggagtctcta agctacataa taccaactta cacttacaaa atgttgtccc ccaaaatgta  1320
gccattcgta tctgctccta ataaaaagaa agtttcttca cattctag              1368

SEQ ID NO: 38           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 38
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgtta ttcaaccttc gtatcctgct aaacaatgct gcttttcgca  180
atggccataa ctttatggtt cgcaacttta gatgcggcca gccgctgcag aacaaggttc  240
agctgaaggg ccgggacttg ctgacgctga aaaactttac cggggaagag attaagtata  300
tgctgtggct aagcgctgat ctgaagttta ggatcaagca gaagggcgaa tatctgccac  360
tgctgcaagg gaagagtctt ggcatgattt ttgaaaagcg gtctaccaga acccggctgt  420
cgaccgagac aggttttgct ctgctggggg gccatccctg ttttctgaca actcaggaca  480
ttcacctggg cgtgaatgag tccctgaccg atactgctag ggtgttgagt agcatggccg  540
acgctgtact cgctcgagtg tataagcagt ctgatctgga cactctggct aaggaagctt  600
ccattcctat tatcaacggc ttgagcgacc tgtaccaccc cattcaaatc ctcgctgatt  660
acttgacttt gcaagaacat tacagcagct tgaagggctt aacactgagc tggataggcg  720
acggaaacaa catcttgcat tccataatga tgtccgccgc taagttcggg atgcacctcc  780
aagcagccac acccaagggc tatgaaccgg atgcttccgt gacaaaactg gctgagcagt  840
atgctaagga gaatggcacg aaactgctgc tcaccaacga cccattggaa gctgcacatg  900
gtggcaacgt actgatcact gacacttgga tctcaatggg ccaggaggaa gagaagaaga  960
aaaggctgca ggcatttcag ggataccaag tcactatgaa aactgccaag gtcgctgcct  1020
ccgactggac attcctgcat tgtctgccac ggaagcctga ggaagtcgat gacgaagtgt  1080
tctatagccc acgaagcttg gtgtttcccg aggctgagaa taggaagtgg accattatgg  1140
ctgttatggt gtccctgctc accgactatt cccctcaact gcaaaaaccc aagttttagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 39           moltype = RNA  length = 1365
FEATURE                 Location/Qualifiers
misc_feature            1..1365
                        note = Synthetic construct
source                  1..1365
                        mol_type = other RNA
                        organism = synthetic construct
SEQUENCE: 39
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catgcttttt aatctccgca tcctccttaa caacgccgcg tttagaaacg  180
gccacaactt catggtccgg aacttcagat gtggccagcc gcttcaaaac aaggtccagc  240
tgaagggccg ggatcttctg accctgaaga actttactgg cgaagagatc aagtacatgc  300
tctggctctc cgcggacttg aagttccgca ttaagcagaa gggggaatac cttccgctgc  360
ttcaaggaaa gagcctcggc atgatctttg agaagcgctc aaccaggacc cgcctttcta  420
ctgaaactgg gttcgcgctg ctcggtggcc acccctgctt cctgacgacc caggacatcc  480
acctcggagt gaacgaatcc ctcaccgata ccgcccgggt gttatcgagc atggcagatg  540
ccgtgctggc cagggtgtac aaacagtccg atctggacac tctggccaag gaggcgtcaa  600
ttcccatcat caacggcctg agcgacctgt accacccaat ccaaatcctg gctgactacc  660
tgaccctgca agagcactac agcagcctga agggtctgac cctgtcatgg attggcgatg  720
gaaacaatat tctgcactcc atcatgatgt ccgccgcgaa gttcggaatg catctgcaag  780
ccgccacgcc aaaaggatac gaaccggatg cgtccgtgac gaagttggcg gaacagtacg  840
cgaaggagaa cggaaccaag cttctgctga ctaacgaccc cctcgaggct gcgcatgggg  900
gcaacgtgct gattaccgac acctggatct ccatggggca ggaggaagag aagaagaaga  960
gactgcaggc attccagggg taccaggtca ccatgaaaac cgcaaaagtg gcagcttcgg  1020
actggacttt cctgcattgc ctgccgagga agccggagga agtcgacgac gaagtgttct  1080
actcgcctcg gtccctggtg ttccccgagg ccgaaaaccg gaagtggacc atcatggccg  1140
tgatggtgtc cttgctgact gactatagcc cgcagctgca gaagcctaag ttctagctcg  1200
agctagtgac tgactaggat ctggttacca ctaaaccagc ctcaagaaca cccgaatgga  1260
gtctctaagc tacataatac caacttacac ttacaaaatg ttgtccccca aaatgtagcc  1320
attcgtatct gctcctaata aaaagaaagt ttcttcacat tctag                 1365

SEQ ID NO: 40           moltype = RNA  length = 1365
FEATURE                 Location/Qualifiers
misc_feature            1..1365
                        note = Synthetic construct
source                  1..1365
                        mol_type = other RNA
                        organism = synthetic construct
SEQUENCE: 40
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catgcttttc aacctgagaa tcctcttgaa caatgctgct tttcggaatg  180
gccacaactt tatggttcgg aacttccgtt gcggccagcc tttacaaaac aaggtccagc  240
```

```
tgaagggccg ggatttgctc acactgaaga actttactgg agaagagatc aagtacatgc  300
tgtggctgtc ggccgacctg aagttcagga tcaagcagaa gggagaatac cttccgctgc  360
ttcaaggaaa gagcctcggc atgatctttg agaagcgctc aaccaggacc cgcctttcta  420
ctgaaactgg gttcgcgctg ctcggtggcc acccctgctt cctgacgacc caggacatcc  480
acctcggagt gaacgaatcc ctcaccgata ccgcccgggt gttatcgagc atggcagatg  540
ccgtgctggc cagggtgtac aaacagtccg atctcgatac cttggcaaag gaggcttcca  600
ttcccatcat caacggcctg agcgacctgt accacccaat ccaaatcctg gctgactacc  660
tgaccctgca agagcactac agcagcctga agggtctgac cctgtcatgg attggcgatg  720
gaaacaatat tctgcactcc atcatgatgt ccgccgcgaa gttcggaatg catctgcaag  780
ccgccactcc aaaaggatac gaaccggatg cgtccgtgac caagttggcg gaacagtacg  840
cgaaggagaa cggaaccaag cttctgctga ctaacgaccc cctcgaggct gcgcatgggg  900
gcaacgtgct gattaccgac acctggatct ccatggggca ggaggaagag aagaagaaga  960
gactgcaggc attccagggg taccaggtca ccatgaaaac cgcaaaagtg gcagcttcgg  1020
actggacttt cctgcattgc ctgccgagga agccggagga agtcgacgac gaagtgttct  1080
actcgcctcg gtccctggtg ttccccgagg ccgaaaaccg gaagtggacc atcatggccg  1140
tgatggtgtc cttgctgact gactatagcc cgcagctgca gaagcctaag ttctagctcg  1200
agctagtgac tgactaggat ctggttacca ctaaaccagc ctcaagaaca cccgaatgga  1260
gtctctaagc tacataatac caacttacac ttacaaaatg ttgtccccca aaatgtagcc  1320
attcgtatct gctcctaata aaaagaaagt ttcttcacat tctag                 1365

SEQ ID NO: 41          moltype = RNA  length = 1365
FEATURE                Location/Qualifiers
misc_feature           1..1365
                       note = Synthetic construct
source                 1..1365
                       mol_type = other RNA
                       organism = synthetic construct
SEQUENCE: 41
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catgcttttc aacctgagaa tcctcttgaa caatgctgct tttcggaatg  180
gccacaactt tatggttcgg aacttccgtt gcggccagcc tttacaaaac aaggtccagc  240
tgaagggccg ggatttgctc acactaaaga actttactgg agaagagatc aagtacatgc  300
tatggctgtc ggccgacctg aagttccgta tcaagcagaa gggagaatac cttccgctgc  360
ttcaaggaaa gagcctcggc atgatctttg agaagcgctc aaccaggacc cgcctttcta  420
ctgaaactgg gttcgcgctg ctcggtggcc acccctgctt cctgacgacc caggacatcc  480
acctcggagt gaacgaatcc ctcaccgata ccgcccgggt gttatcgagc atggcagatg  540
ccgtgctggc cagggtgtac aaacagtccg atctcgatac cttggcaaag gaggcttcca  600
ttcccatcat caacggcctg agcgacctgt accacccaat ccaaatcctg gctgactacc  660
tgaccctgca agagcactac agcagcctga agggtctgac cctgtcatgg attggcgatg  720
gaaacaatat tctgcactcc atcatgatgt ccgccgcgaa gttcggaatg catctgcaag  780
ccgccactcc aaaaggatac gaaccggatg catccgtgac caagttggcg gaacagtacg  840
cgaaggagaa cggaaccaag ctcctgctga ctaacgaccc gctcgaggct gcgcatgggg  900
gtaacgtgct gattacggac acctggatct ccatggggca ggaggaagag aagaagaaga  960
gactgcaggc attccagggg taccaggtca ccatgaaaac cgcaaaagtg gcagcttcgg  1020
actggacttt cctgcattgc ctgccgagga agccggagga agtcgacgac gaagtgttct  1080
actcgcctcg gtccctggtg ttccccgagg ccgaaaaccg gaagtggacc atcatggccg  1140
tgatggtgtc cttgctgact gactatagcc cgcagctgca gaagcctaag ttctagctcg  1200
agctagtgac tgactaggat ctggttacca ctaaaccagc ctcaagaaca cccgaatgga  1260
gtctctaagc tacataatac caacttacac ttacaaaatg ttgtccccca aaatgtagcc  1320
attcgtatct gctcctaata aaaagaaagt ttcttcacat tctag                 1365

SEQ ID NO: 42          moltype = RNA  length = 1365
FEATURE                Location/Qualifiers
misc_feature           1..1365
                       note = Synthetic construct
source                 1..1365
                       mol_type = other RNA
                       organism = synthetic construct
SEQUENCE: 42
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catgcttttc aacctgagaa tcctcttgaa caatgctgct tttcggaatg  180
gccacaactt tatggttcgg aacttccgtt gcggccagcc tttacaaaac aaggtccagc  240
tgaagggccg ggatttgctc acactaaaga actttactgg agaagagatc aagtacatgc  300
tatggctgtc ggccgacctg aagttccgta tcaagcagaa gggagaatac cttccgctgc  360
ttcaaggaaa gagcctcggc atgatctttg agaagcgctc aaccaggacc cgcctttcta  420
ctgaaactgg gttcgcgctg ctcggtggcc acccctgctt cctgacgacc caggacatcc  480
acctcggagt gaacgaatcc ctcaccgata ccgcccgggt gttatcgagc atggcagatg  540
ccgtgctggc cagggtgtac aaacagtccg atctcgatac cttggcaaag gaggcttcca  600
ttcccatcat caacggcctg agcgacctgt accacccaat ccaaatcctg gctgactacc  660
tgaccctgca agagcactac agcagcctga agggtctgac cctgtcatgg attggcgatg  720
gaaacaatat tctgcactcc atcatgatgt ccgccgcgaa gttcggaatg catctgcaag  780
ccgccactcc aaaaggatac gaaccggatg cgtccgtgac caagttggcg gaacagtacg  840
cgaaggagaa cggaaccaag cttctgctga ctaacgaccc cctcgaggct gcgcatgggg  900
gcaacgtgct gattaccgac acctggatct ccatggggca ggaggaagag aagaagaaga  960
gactgcaggc attccagggg taccaggtca ccatgaaaac cgcaaaagtg gcagcttcgg  1020
actggacttt cctgcattgc ctgccgagga agccggagga agtcgacgac gaagtgttct  1080
actcgcctcg gtccctggtg ttccccgagg ccgaaaaccg gaagtggacc atcatggccg  1140
```

```
tgatggtgtc cttgctgact gactatagcc cgcagctgca gaagcctaag ttctagctcg  1200
agctagtgac tgactaggat ctggttacca ctaaaccagc ctcaagaaca cccgaatgga  1260
gtctctaagc tacataatac caacttacac ttacaaaatg ttgtccccca aaatgtagcc  1320
attcgtatct gctcctaata aaaagaaagt ttcttcacat tctag                  1365

SEQ ID NO: 43           moltype = RNA  length = 1371
FEATURE                 Location/Qualifiers
misc_feature            1..1371
                        note = Synthetic construct
source                  1..1371
                        mol_type = other RNA
                        organism = synthetic construct
SEQUENCE: 43
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctgc gaatcctgct gaacaacgcc gcttttcgga  180
acgggcacaa ctttatggtg aggaactttc gctgcggaca gcccctccag aataaggtcc  240
agctgaaggg cagggacctg ctgaccctga aaaatttcac aggggaggaa atcaagtata  300
tgctgtggct gtcagctgat ctgaagttcc ggatcaagca gaagggcgaa tatctgcctc  360
tgctccaggg caaaagcctg ggatgatct tcgaaaagcg cagtactcgg accagactgt  420
caaccgagac tggattcgct ctgctgggag gacacccttg ttttctgacc actcaggaca  480
ttcacctggg agtgaacgag tccctgaccg acactgctcg cgtcctgagc tctatggccg  540
acgctgtgct ggctcgagtc tacaaacagt ccgacctgga taccctggcc aaggaagctt  600
ctatcccaat tattaacggc ctgtcagacc tgtatcaccc catccagatt ctggccgatt  660
acctgaccct ccaggagcac tattctagtc tgaaagggct gacactgagt tggattgggg  720
acggaaacaa tatcctgcac tctattatga tgtcagccgc caagtttgga atgcacctcc  780
aggctgcaac ccccaaaggc tacgaacccg atgcctcagt gacaaagctg gctgaacagt  840
acgccaaaga gaacggcact aagctgctgc tgaccaacga ccctctggag gccgctcacg  900
gaggcaacgt gctgatcacc gatacctgga ttagtatggg acaggaggaa gagaagaaga  960
agcggctcca ggccttccag ggctaccagg tgacaatgaa aaccgctaag gtcgcagcca  1020
gcgattggac ctttctgcac tgcctgccca gaaagcccga agaggtggac gacgaggtct  1080
tctactctcc cagaagcctg gtgtttcccg aagctgagaa taggaagtgg acaattatgg  1140
cagtgatggt cagcctgctg actgattatt cacctcagct ccagaaacca aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 44           moltype = RNA  length = 1371
FEATURE                 Location/Qualifiers
misc_feature            1..1371
                        note = Synthetic construct
source                  1..1371
                        mol_type = other RNA
                        organism = synthetic construct
SEQUENCE: 44
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctgc gcatcctgct gaacaacgcc gccttccgca  180
acggccacaa cttcatggtg cgcaacttcc gctgcggcca gcccctgcag aacaaggtgc  240
agctgaaggg ccgcgacctg ctgaccctga agaacttcac cggcgaggag atcaagtaca  300
tgctgtggct gagcgccgac ctgaagttcc gcatcaagca gaagggcgag tacctgcccc  360
tgctgcaggg caagagcctg ggcatgatct tcgagaagcg cagcacccgc acccgcctga  420
gcaccgagac aggcctggcc ctgctgggcg gccacccctg cttcctgacc acccaggaca  480
tccacctggg cgtgaacgag agcctgaccg acaccgcccg cgtgctgagc agcatggccg  540
acgccgtgct ggcccgcgtg tacaagcaga gcgacctgga caccctggcc aaggaggcca  600
gcatccccat catcaacggc ctgagcgacc tgtaccaccc catccagatc ctggccgact  660
acctgaccct gcaggagcac tacagcagcc tgaagggcct gaccctgagc tggatcggcg  720
acggcaacaa catcctgcac agcatcatga tgagcgccgc caagttcggc atgcacctgc  780
aggccgccac ccccaagggc tacgagcccg acgccagcgt gaccaagctg gccgagcagt  840
acgccaagga gaacggcacc aagctgctgc tgaccaacga cccccctggag gccgcccacg  900
gcggcaacgt gctgatcacc gacacctgga tcagcatggg ccaggaggag gagaagaaga  960
agcgcctgca ggccttccag ggctaccagg tgaccatgaa gaccgccaag gtggccgcca  1020
gcgactggac cttcctgcac tgcctgcccc gcaagcccga ggaggtggac gacgaggtgt  1080
tctacagccc ccgcagcctg gtgttccccg aggccgagaa ccgcaagtgg accatcatgg  1140
ccgtgatggt gagcctgctg accgactaca gcccccagct gcagaagccc aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 45           moltype = RNA  length = 1371
FEATURE                 Location/Qualifiers
misc_feature            1..1371
                        note = Synthetic construct
source                  1..1371
                        mol_type = other RNA
                        organism = synthetic construct
SEQUENCE: 45
tcaacacaac atatacaaaa caaacgaatc tcaagcaatc aagcattcta cttctattgc  60
agcaatttaa atcatttctt ttaaagcaaa agcaattttc tgaaaatttt caccatttac  120
```

```
gaacgatagc caccatgctg ttcaacctgc gaatcctgct gaacaacgcc gcttttcgga  180
acgggcacaa ctttatggtg aggaactttc gctgcggaca gcccctccag aataaggtcc  240
agctgaaggg cagggacctg ctgaccctga aaaatttcac aggggaggaa atcaagtata  300
tgctgtggct gtcagctgat ctgaagttcc ggatcaagca gaagggcgaa tatctgcctc  360
tgctccaggg caaaagcctg ggatgatct tcgaaaagcg cagtactcgg accagactgt  420
caaccgagac tggattcgct ctgctgggag gacacccttg ttttctgacc actcaggaca  480
ttcacctggg agtgaacgag tccctgaccg acactgctcg cgtcctgagc tctatggccg  540
acgctgtgct agctcgagtc tacaaacagt ccgacctgga taccctggcc aaggaagctt  600
ctatcccaat tattaacggc ctgtcagacc tgtatcaccc catccagatt ctggccgatt  660
acctgaccct ccaggagcac tattctagtc tgaaagggct gacactgagt tggattgggg  720
acggaaacaa tatcctgcac tctattatga tgtcagccgc caagtttgga atgcacctcc  780
aggctgcaac cccaaaaggc tacgaacccg atgcctcagt gacaaagctg gctgaacagt  840
acgccaaaga gaacggcact aagctgctgc tgaccaacga ccctctggag gccgctcacg  900
gaggcaacgt gctgatcacc gatacctgga ttagtatggg acaggaggaa gagaagaaga  960
agcggctcca ggccttccag ggctaccagg tgacaatgaa aaccgctaag gtcgcagcca  1020
gcgattggac ctttctgcac tgcctgccca gaaagcccga agaggtggac gacgaggtct  1080
tctactctcc cagaagcctg gtgtttcccg aagctgagaa taggaagtgg acaattatgg  1140
cagtgatggt cagcctgctg actgattatt cacctcagct ccagaaacca aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

```
SEQ ID NO: 46           moltype = RNA  length = 1371
FEATURE                 Location/Qualifiers
misc_feature            1..1371
                        note = Synthetic construct
source                  1..1371
                        mol_type = other RNA
                        organism = synthetic construct
SEQUENCE: 46
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctgc gaatcctgct gaacaatgcc gcttttcgga  180
acgggcacaa tttcatggtg aggaactttc gctgcggaca gcccctccag aacaaggtcc  240
agctgaaggg cagggacctg ctgaccctga aaaatttcac aggggaggaa atcaagtaca  300
tgctgtggct gtcagccgat ctgaagttcc ggatcaagca gaagggcgaa tatctgcctc  360
tgctccaggg caaaagcctg ggatgatct tcgaaaagcg cagtactcgg accagactgt  420
caacagagac tggattcgca ctgctgggag gacacccatg ttttctgacc acacaggaca  480
ttcatctggg agtgaacgag tccctgaccg acacagcacg cgtcctgagc tccatggctg  540
atgcagtgct ggctcgagtc tacaaacagt ctgacctgga taccctggcc aaggaagctt  600
ctatcccaat cattaatggc ctgagtgacc tgtatcaccc catccagatt ctggccgatt  660
acctgaccct ccaggagcat tattctagtc tgaaagggct gacactgagc tggattgggg  720
acggaaacaa tatcctgcac tccattatga tgagcgccgc caagtttgga atgcacctcc  780
aggctgcaac cccaaaaggc tacgaacccg atgcctccgt gacaaagctg gcagaacagt  840
atgccaaaga gaacggcact aagctgctgc tgaccaatga ccctctggag gccgctcacg  900
gaggcaacgt gctgatcact gatacctgga ttagtatggg acaggaggaa gagaagaaga  960
agcggctcca ggccttccag ggctaccagg tgacaatgaa aactgctaag gtcgcagcca  1020
gcgactggac ctttctgcat tgcctgccca gaaagcctga agaggtggac gatgaggtct  1080
tctactcacc cagaagcctg gtgtttcctg aagctgagaa taggaagtgg acaatcatgg  1140
cagtgatggt cagcctgctg actgattatt cccctcagct ccagaaacca aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

```
SEQ ID NO: 47           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 47
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaaccttc gcattctcct caacaacgcc gcgtttagaa  180
acggacacaa cttcatggtc cgcaacttcc gctgcggaca gccgctgcag aacaaggtcc  240
agctcaaggg tcgggatctc ctgacgctga agaactttac cggcgaagag attaagtaca  300
tgctgtggct gtccgccgac cttaagttcc ggatcaagca gaagggcgaa taccttcccc  360
tgctgcaagg aaagtccctg ggcatgatct tcgagaagcg cagtaccaga accagactct  420
ccactgaaac cgggttcgcg ctgcttggcg gccacccgtg tttcctcact acgcaagaca  480
tccatcttgg cgtgaacgag tcccttaccg acaccgccag ggtgctgtca agcatggccg  540
acgccgtcct tgcgcgcgtg tacaagcagt cagaccttga tactctggcc aaggaagcct  600
ccatccctat tatcaacggc ctatccgacc tttaccaccc gatccagatc ctcgctgact  660
acctgaccct gcaagaacac tacagcagcc tcaagggact gactctgtcc tggatcggcg  720
acgggaacaa catcctgcac tcaatcatga tgagcgcagc caagttcggc atgcatctcc  780
aagccgctac acccaagggt tatgaaccgg acgcctctgt gaccaagttg gcagaacagt  840
acgccaagga gaacggtact aagctccttt taaccaacga ccccctcgaa gcagcccatg  900
gcgggaatgt gctcattacc gatacctgga tttcgatggg ccaggaggag gagaagaaga  960
agcggctgca ggcgttccag ggctaccagg tcaccatgaa aactgccaaa gtggccgcct  1020
```

```
cggattggac ctttctccac tgcctgcctc ggaagcctga ggaggtggac gacgaagtgt  1080
tctactcccc acggtccctc gtgttccccg aggccgaaaa taggaagtgg accatcatgg  1140
ccgtgatggt gtccctcttg accgattaca gcccgcagct tcagaagcct aaattctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 48          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 48
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatcttc gcatcctgtt gaacaacgcc gccttccgca  180
atggtcacaa cttcatggtc cggaacttca gatgtggaca gcctctccaa aacaaggtcc  240
agctgaaggg aagggacctc ttaaccctca aaaactttac tggagaggag atcaagtaca  300
tgctgtggct tagcgccgac cttaagttcc ggatcaagca gaagggagag tacctcccgc  360
tgctgcaagg aaagagtctt ggaatgatct tcgagaagcg gtccaccaga actcgcctct  420
ccactgaaac cggattcgca ctcctgggtg gacacccgtg ctttctgacc acccaagaca  480
tccacctcgg agtgaacgag agcctcacgg acaccgcgag agtgctgtca tccatggccg  540
acgccgtgct tgcacgggtc tacaagcagt ccgatctgga cactcttgcc aaggaagcct  600
ccattcctat cattaacggt ctgtcggatc tgtaccaccc gattcagatc cttgcggact  660
acctcacact tcaagaacac tattcaagcc taaagggtct gaccctgtcc tggatcggag  720
atggaaacaa cattctccat tccatcatga tgagcgctgc caagttcgga atgcatctcc  780
aagcagcgac tcctaagggt tacgagccgg acgcctcagt gactaagctg gccgagcagt  840
acgccaagga gaacggtacc aaactgttgc ttactaacga cccgcttgaa gcggcccatg  900
gaggaaacgt gctgattacc gacacctgga tttcgatggg acaggaagag gagaagaaga  960
agcggctcca ggcgttccag ggataccagg tcaccatgaa aacggccaaa gtggccgcta  1020
gcgattggac ctttctgcac tgcctcccgc gcaagcctga agaagtggac gacgaagtgt  1080
tctactcccc tcgctctctt gtgttcccgg aagccgaaaa caggaagtgg accatcatgg  1140
ccgtgatggt gtccctcctg accgattaca gcccgcagct gcagaagcct aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 49          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 49
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct caacaacgcc gcgtttagaa  180
acggccacaa cttcatggtc cggaacttca gatgtggcca gccgcttcag aacaaggtcc  240
agctcaaggg ccgggatctt ctgaccctga agaactttac tggcgaagaa atcaagtaca  300
tgctctggct ctccgccgac ttgaagttcc gcattaagca gaagggggaa taccttccgc  360
tgctgcaagg aaagtcgctc ggcatgatct ttgagaagcg ctcaacccgc accaggctgt  420
ccactgaaac cgggttcgcg ctgcttggtg gccacccctg cttcctgacc acccaagaca  480
ttcacctcgg agtgaacgaa tcgctcactg atactgcccg ggtgctgtcg tcgatggccg  540
atgcagtgct ggccagggtg tacaaacagt ccgatctgga cactctggcc aaggaggcgt  600
ccatccctat tatcaacggc ctttccgacc tctaccaccc gattcagatc cttgccgatt  660
acctcaccct gcaagaacac tactcgtcac tgaagggtct gaccttgtcc tggatcggcg  720
acggcaacaa catcctccat tccattatga tgtccgccgc caaattcggc atgcatcttc  780
aagccgcaac ccctaagggt tacgagccgg acgcttccgt gaccaagctc gccgagcagt  840
acgctaagga gaacggaacc aagcttctgc tgactaacga ccccctagag gcagcccacg  900
ggggcaacgt gcttattact gacacctgga tctccatggg acaggaagaa gagaagaaga  960
agcggttaca ggcgttccag ggctatcagg tcaccatgaa aaccgccaag gtcgctgcct  1020
cggactggac cttcctgcat tgcctgcctc gcaagcccga agaagtggac gacgaggtgt  1080
tctactcgcc acggtccctt gtgttccctg aggccgagaa tagaaagtgg accattatgg  1140
ccgtgatggt gtcccttctc accgactact cgccgcaact gcagaaaccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 50          moltype = RNA  length = 1368
FEATURE                Location/Qualifiers
misc_feature           1..1368
                       note = Synthetic construct
source                 1..1368
                       mol_type = other RNA
                       organism = synthetic construct
```

```
SEQUENCE: 50
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatcttc gcatcctcct caacaacgcc gccttccgga  180
acggtcacaa cttcatggtc cggaacttcc gctgcggcca gccgctccaa aacaaagtgc  240
agcttaaggg ccgcgatctc ctgaccctga agaacttcac cggagaggaa atcaagtaca  300
tgctgtggct ctcggcggac ctgaagttta ggattaagca gaagggggag tatctgccgc  360
tgctccaagg gaagtccctt ggcatgatct tcgaaaagag gtccacccgg actcggctca  420
gcaccgaaac aggttttgca cttctggggg gccacccgtg cttcctgacg acccaggaca  480
tccatctggg tgtcaacgag agtttgaccg acactgccag agtgctgtca tccatggcgg  540
acgcggtgct cgcgagagtg tacaagcagt ccgatcttga caccctggca aaagaggctt  600
caatcccgat cattaacgga ctctcggatc tgtaccaccc tatccaaatc ttggccgact  660
acctgaccct gcaagaacac tacagctccc tgaagggcct gactctttcc tggattggcg  720
atggaaacaa cattctccat tctattatga tgtccgccgc caagttcggc atgcaccttc  780
aagccgccac cccgaagggc tacgaacctg acgcctccgt gactaagcta gccgaacagt  840
acgctaagga gaacggcact aagcttctcc ttaccaacga tccgctggag gcggcccatg  900
gcggaaatgt gcttatcacc gacacctgga ttagcatggg gcaggaagaa gagaagaaga  960
aacggctcca ggcattccag ggctaccagg tcaccatgaa aactgccaag gtcgccgcta  1020
gcgactggac cttcctccac tgtctgcctc gcaagcctga agaagtggac gacgaggtgt  1080
tctactcccc gcgctccctc gtgtttcctg aggccgagaa cagaaagtgg accatcatgg  1140
ccgtgatggt gtcattactt acggactaca gcccgcagct gcagaagccg aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 51          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 51
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt tttaacttga gaatccttct gaacaacgcc gctttccgca  180
acggtcataa cttcatggtc cggaacttca gatgtggcca gcccctccaa aacaaagtgc  240
agctgaaggg ccgggacctt cttacgctga agaatttcac cggcgaagaa atcaagtaca  300
tgctctggct gtccgccgat cttaagttcc gcattaagca gaagggggaa tacctcccgc  360
tgctgcaagg gaagtcgctg ggcatgattt ttgagaagcg gtcaactcgc acccgcctgt  420
ccactgaaac tggattcgca ctgctcggtg gccatccctg cttcctgacc acccaagaca  480
tccacctcgg cgtgaacgag tccctgactg acaccgcccg ggtcttatcc tcgatggccg  540
atgctgtgct tgcgagggtg tacaagcagt ccgacctcga cacactcgcg aaggaggcct  600
ccatccccat catcaacggc ctgtccgacc tttaccaccc aattcagatc ctcgccgatt  660
acctgaccct gcaagagcac tactcgtcgc tcaaggggct taccctctcg tggattggcg  720
acggcaacaa catccttcac tccatcatga tgtcggcagc gaagttcggc atgcatctgc  780
aagccgccac gcctaagggt tatgaaccgg atgcctcagt gaccaagctc gccgaacagt  840
acgcgaaaga gaatggaacc aagctacttc tgaccaacga ccccctggag gccgctcacg  900
gcggcaacgt cctcattacc gatacttgga tttcgatggg acaggaagag gaaaagaaga  960
agagactgca ggcgttccag ggataccagg tcaccatgaa aactgccaaa gtggcagcct  1020
ccgactggac cttccttcac tgcctgccga ggaagcctga agaggtggac gacgaggtgt  1080
tctactcccc gcgctccttg gtgtttcctg aggccgaaaa ccggaagtgg actatcatgg  1140
ccgtgatggt gtccctcctc accgactact cgccgcaact gcagaagcct aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 52          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 52
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgtta ttcaacctta gaattctcct taacaacgcc gccttccgga  180
atgggcataa ctttatggtc cgcaatttcc gctgtggaca gcctctgcaa aacaaggtcc  240
agctcaaggg ccgggatctg ctgactctca agaacttcac tggggaagaa atcaagtaca  300
tgctctggct gagcgccgac ctcaagttcc gcatcaagca gaagggagag tacctcccgc  360
tgctccaagg gaagtccctg ggcatgatct tcgagaagag atccacccgc accagacttt  420
ccactgagac tggcttcgcc ttgctgggag gccacccatg cttcctgacg acccaggaca  480
ttcaccttgg cgtgaacgag tccctgactg acaccgcaag ggtgttgtcc tcgatggccg  540
acgccgtgct tgcccgggtg tacaagcaga gcgatcttga caccctggct aaggaagctt  600
ccattcccat catcaacggt ctgagcgacc tgtaccaccc gattcagatc ctggcggact  660
acctaaccct gcaagagcac tatagctccc tgaagggcct cacactttca tggatcggcg  720
acggcaacaa catcctgcac tctattatga tgagcgctgc caaattcggc atgcacctcc  780
aagccgccac gcctaaaggc tacgagcccg acgcctcggt gaccaagctt gcggagcagt  840
```

```
acgcgaagga aaacggcacc aagctgcttc tcaccaacga tcctctggaa gcggcccatg  900
gtggcaacgt gctcattacc gacacttgga tctccatggg acaggaggag gaaaagaaga  960
agcggctcca ggcgtttcag ggttaccagg tcaccatgaa aaccgccaag gtcgcagcct  1020
ccgactggac cttccttcat tgccttccgc gcaagcccga agaagtggac gatgaagtgt  1080
tttactcacc tcggtcactc gtgttcccgg aagcagagaa caggaaatgg accattatgg  1140
ccgtgatggt gtccctgctc accgattaca gtccgcaact gcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 53           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 53
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcaaatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gcctaagggt tacgaacccg acgcttccgt gactaagctc gccgagcagt  840
acgctaagga gaacggaacc aagctgctgc tgactaacga cccgctagaa gcagcccacg  900
ggggcaacgt gcttattact gacacctgga tctccatggg ccaggaggaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcacttctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 54           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 54
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agcttaaggg ccgggatctc ctcaccctta aaaacttcac cggcgaagag atcaagtaca  300
tgctctggct ctccgcggac cttaagttcc gcattaagca gaagggggaa taccttccgc  360
tgcttcaagg aaagagcctc ggcatgatct ttgagaagcg ctcaaccagg accaggcttt  420
ctactgaaac tgggttcgcg cttctcggcg gtcatccctg cttcctcacg acccaagaca  480
tccacctcgg agtgaacgaa tccctcacgg atactgcccg cgtgctttcg agcatggcag  540
acgccgtgct cgcccgggtg tacaaacagt ccgatctcga cactctcgcc aaggaggcgt  600
caattcctat tatcaacggt cttagtgacc tttaccaccc gatccagatc ctcgccgatt  660
acctcacact ccaagaacac tacagctccc ttaagggtct taccctctcc tggatcggcg  720
acggcaacaa cattctccac tccatcatga tgtccgccgc aaagttcggc atgcatcttc  780
aagccgccac cccgaagggc tacgagcctg atgcttccgt gactaagctc gccgagcagt  840
acgctaagga gaacggaacc aagcttcttc tcactaacga cccactcgaa gcagcccatg  900
ggggcaacgt gcttatcact gacacctgga tctccatggg ccaggaagaa gagaagaaga  960
agcggctcca ggcgttccag ggatatcagg tcaccatgaa aaccgccaag gtcgctgcct  1020
ccgactggac ctttctccac tgcctccctc gcaaacctga agaagtggac gacgaggtgt  1080
tctactcgcc ccggagcctc gtgttccccg aggccgagaa tagaaagtgg accattatgg  1140
ccgtgatggt gtcactcctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 55           moltype = RNA  length = 1368
FEATURE                 Location/Qualifiers
misc_feature            1..1368
                        note = Synthetic construct
```

```
source                  1..1368
                        mol_type = other RNA
                        organism = synthetic construct
SEQUENCE: 55
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggacataa cttcatggtc cggaacttca gatgtggaca gccgcttcaa aacaaggtcc  240
agctgaaggg tcgggatctt ctgaccctga agaactttac cggagaagag atcaagtaca  300
tgctctggct ctccgcggac ttgaagttcc gcattaagca gaagggagaa tacctcccgc  360
tgcttcaagg aaagagcctc ggaatgattt ttgagaagcg ctcaaccagg acccgccttt  420
ctactgaaac tggattcgcg ctgctgggtg gacaccctcg cttcctgacg acccaggaca  480
tccacctcgg agtgaacgaa tccctcactg ataccgcccg ggtgttatcg agcatggcag  540
atgccgtgct ggccagggtg tacaaacagt ccgatctgga cactctggcc aaggaggcgt  600
caattcctat catcaacgga cttagtgacc tctaccatcc gattcaaatc ctggccgact  660
acctcaccct gcaagaacac tacagctccc tgaagggtct gacattgtcc tggatcggag  720
atggaaacaa cattctccac tccatcatga tgtccgccgc aaaattcgga atgcatcttc  780
aagccgccac gcctaagggt tacgaacccg acgcttccgt gactaagctc gccgagcagt  840
acgctaagga gaacggtacc aagcttctcc tgaccaacga cccactagaa gcagcccacg  900
gtggaaacgt gcttattact gacacttgga tctccatggg acaggaggaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc gcggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 56           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 56
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacctcc gcattctcct caacaacgct gccttccgga  180
atggacataa cttcatggtc cggaacttca gatgcggaca gccgcttcag aacaaggtcc  240
agcttaaggg gagagatctc cttaccctca aaaacttcac tggcgaagaa atcaagtaca  300
tgctctggct tagtgcggat ctcaagttcc gcatcaagca gaagggagaa tacctcccgc  360
tccttcaagg aaagagcctc ggcatgattt ttgagaagag gtccaccaga actcgccttt  420
caaccgagac tgggttcgcc ctgcttggcg gtcacccctg cttcctcact acccaagaca  480
tccacctcgg cgtgaacgag agccttaccg acaccgcccg cgtgctctcc tcaatggccg  540
acgctgtgct cgcccgggtg tacaagcagt ccgaccttga tactctcgcc aaggaggcct  600
ccatcccaat tatcaacggg ctctctgatc tctaccaccc tatccaaatc ctcgcggact  660
acctcaccct ccaagagcac tatagctcgc tcaagggcct cacccttttcc tggattggcg  720
acggcaacaa cattcttcac tcgatcatga tgtccgccgc caagttcggc atgcatctcc  780
aagccgcgac ccccaagggc tacgagcctg acgcatccgt gaccaagctc gccgagcagt  840
acgcgaagga aaatggcacc aagcttcttc tcaccaacga ccccccttgag gccgctcatg  900
gcggcaacgt gctcatcact gacacttgga tcagcatggg ccaggaggag gaaaagaaga  960
agcgccttca ggcattccag ggttaccagg tcaccatgaa aaccgccaaa gtggccgcct  1020
ccgactggac ctttcttcac tgtctcccgc ggaagcctga agaagtggat gacgaagtgt  1080
tttactcccc tcggtcactc gtgttcccgg aagcagaaaa caggaagtgg accattatgg  1140
cggtcatggt gtccctcctc accgactaca gcccgcagct tcagaaaccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 57           moltype = RNA  length = 1368
FEATURE                 Location/Qualifiers
misc_feature            1..1368
                        note = Synthetic construct
source                  1..1368
                        mol_type = other RNA
                        organism = synthetic construct
SEQUENCE: 57
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgca gcgtttagaa  180
acggtcacaa cttcatggtc cggaacttcc gctgtggaca gccgcttcaa aacaaggtcc  240
agctgaaggg tcgggacctt ctgaccctga agaactttac tggagaagag atcaagtaca  300
tgctttggct gtccgcggac ttgaagttcc gcattaagca gaagggagaa taccttccgc  360
tgctccaagg aaagagcctg ggaatgatct ttgagaagcg ctcaaccagg acccgccttt  420
ctactgaaac tggattcgcg ctgctgggtg gtcacccttg cttcctgacg acccaggaca  480
ttcacctcgg agtgaacgag tccctcactg ataccgccag agtgttatcg agcatggcag  540
atgccgtgct ggctagggtg tacaaacagt ccgatctgga caccctggcc aaggaggcat  600
caattcctat tatcaacgga cttagtgacc tctaccatcc gattcaaatc ctggccgatt  660
```

```
acctcaccct gcaagaacac tacagctccc tgaagggtct gacattgtcc tggatcggag  720
atggaaacaa cattctccat tccatcatga tgtccgcggc caagttcgga atgcatctcc  780
aagccgccac gccgaaagga tacgagccgg acgcttccgt gactaagctc gccgagcagt  840
acgctaagga gaacggaacc aagcttctgc tgactaacga cccgctagaa gccgcccacg  900
gtggaaacgt gcttattact gacacctgga tctccatggg acaggaagaa gagaaaaaga  960
agcggctgca ggcgttccag ggatatcagg tcaccatgaa aaccgccaag gtcgccgcct  1020
ccgactggac cttccttcac tgcctgcctc ggaagcctga agaagtggac gacgaggtgt  1080
tctactcgcc gcggagcctc gtgttccctg aggccgagaa tagaaagtgg accatcatgg  1140
ccgtgatggt gtcactcctc accgactaca gcccgcagct tcagaagcct aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 58          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 58
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcattctcct caacaacgca gcctttagaa  180
acggccacaa cttcatggtc cggaacttca gatgtggcca gccgcttcag aacaaggtcc  240
agctcaaggg ccgggacctc ctcaccctca aaaactttac cggcgaagag atcaagtaca  300
tgctctggct ttcggccgac cttaagttcc gcatcaagca gaagggggaa taccttccgc  360
tgcttcaagg aaagtccctc ggcatgatct ttgaaaagcg ctcgaccagg acccgccttt  420
ccactgaaac cgggttcgcg cttctcggtg gccaccccctg cttcctcacc acccaagaca  480
ttcacctcgg agtgaacgaa tcccttaccg ataccgcaag agtgctttcg tcgatggccg  540
atgccgtgct tgcgcgggtg tacaagcagt cagatctcga cactctcgcc aaggaggcgt  600
ccattcctat tatcaacggc ctttccgacc tttaccaccc gattcagatc ctcgccgatt  660
acctcaccct gcaagagcac tactcgtcac tcaagggtct taccctctcc tggatcggcg  720
acggaaacaa catcctccat tcgatcatga tgtccgccgc caaattcggc atgcacctcc  780
aagccgcgac cccgaagggt tacgagcccg acgcttccgt gaccaagctc gccgaacagt  840
acgctaagga aaacggcacc aagctcctcc tcactaacga ccctctcgaa gcagcccatg  900
ggggcaacgt gctcattact gacacttgga tctcgatggg ccaggaagag gagaaaaaga  960
agcggcttca ggcgttccag ggatatcagg tcaccatgaa aaccgccaag gtcgctgcct  1020
cggactggac cttccttcac tgccttccgc gcaagcctga agaggtggac gatgaggtgt  1080
tctactcccc acggtccctt gtgttccccg aggccgagaa taggaagtgg accatcatgg  1140
ccgtgatggt gtcgctcctc actgactact ccccgcaact tcagaagcct aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 59          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 59
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg tttaatctga gaatacttct aaacaacgcc gccttccgga  180
atggccataa ctttatggtt cggaatttcc gctgcggcca gccgctgcag aacaaggtcc  240
agctgaaggg aagagacttg ctgaccctca agaacttcac cggagaagaa atcaagtata  300
tgctgtggct gtccgccgac ctgaaattcc gcatcaagca gaagggcgaa tatctgccgc  360
tgttgcaagg gaagtccctg gggatgatct tcgagaagag gtccaccaga acacggcttt  420
caaccgaaac cgggtttgca ctgctgggtg gacacccctg ttttctgacc actcaagata  480
tccacctggg cgtgaacgag tcccttaccg acactgctag ggtgttgtcc agcatggccg  540
atgccgtcct ggctcgcgtg tacaagcagt ccgacctgga taccctggca aaggaagcgt  600
ccattcccat tatcaacggg ctgtccgacc tgtaccatcc gattcaaatc ctggcggact  660
acctgactct gcaagagcat tacagcagct tgaaggggct tactctctcg tggatcggcg  720
acgggaacaa catcctgcac tccatcatga tgtccgccgc caagttcggg atgcatttgc  780
aagctgcgac cccgaaaggt tacgagcccg atgctagcgt aactaagctt gccgaacagt  840
acgccaaaga gaatggtaca aaactgcttc tgactaacga cccgctggaa gcagcccacg  900
gcgggaacgt gctgataacc gacacctgga tttcaatggg gcaggaggaa gagaagaaga  960
agcgactgca ggcgttccaa ggctatcagg ttaccatgaa aaccgccaaa gtggcagcca  1020
gcgattggac tttcctgcac tgtctgccgc ggaagcccga ggaagttgat gacgaagtat  1080
tctactcacc ccggagcctc gtgttccccg aggccgaaaa ccggaagtgg actattatgg  1140
ccgtgatggt gtcgctgttg accgactaca gcccgcaact gcagaagccg aagttttagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 60          moltype = RNA  length = 1368
FEATURE                Location/Qualifiers
```

```
misc_feature           1..1368
                       note = Synthetic construct
source                 1..1368
                       mol_type = other RNA
                       organism = synthetic construct
SEQUENCE: 60
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacctga ggatcctttt gaacaacgcc gcctttcgca  180
acggccacaa ctttatggtc cgcaatttcc gctgcgggca gccgctgcag aacaaggtcc  240
agctgaaggg ccgggatctg ctgaccctga agaacttcac cggggaggaa atcaagtaca  300
tgctttggct ctccgccgat ctgaagttca gaatcaagca gaagggagag tacctcccgt  360
tgctgcaagg aaagtcactc ggaatgattt tcgaaaagag aagcactagg acccgcctct  420
caactgaaac cgggttcgcg ctgctcgggg gccatccgtg tttcctgact acccaagaca  480
tccacctggg agtgaacgag tcgctgaccg acaccgcacg cgtgctgtca tccatggcgg  540
acgcagtgct tgcccgggtg tacaagcagt cggacctgga cactcttgcc aaggaggcat  600
caatccccat cattaacgga ctgtccgatc tctaccaccc gattcagatc ctggctgact  660
acctaaccct gcaagagcac tactcaagcc tgaaggggct gaccctgtcg tggatcgggg  720
acggcaacaa cattctgcac tccatcatga tgtcggcggc taagttcggg atgcatttgc  780
aagcggcaac tccgaagggt tatgaacccg acgcctccgt gaccaagctg gccgaacagt  840
acgccaagga aaacggaacc aagttgctgc tgactaatga tcccctggag gcggcccacg  900
gggggaacgt gctgataacc gatacctgga tctccatggg gcaggaagaa gagaagaaaa  960
agcggctgca ggcattccag ggataccagg tcaccatgaa aaccgcaaaa gtggcagcca  1020
gcgactggac tttcctccat tgcctgccgc gaaagccgga ggaggtcgat gacgaggtgt  1080
tctactcccc gcggtcgctg gtgttcccgg aggcggaaaa ccggaagtgg accattatgg  1140
ccgtgatggt gtcactcctg actgactaca gcccgcaact gcagaagccg aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 61          moltype = RNA  length = 1496
FEATURE                Location/Qualifiers
misc_feature           1..1496
                       note = Synthetic construct
source                 1..1496
                       mol_type = other RNA
                       organism = synthetic construct
SEQUENCE: 61
cttaaggggg cgctgcctac ggaggtggca gccatctcct tctcggcatc aagcttacca  60
tggtgcccca ggccctgctc ttggtcccgc tgctggtgtt ccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctacatgct tttcaatctc cgcatcctcc ttaacaacgc cgcgtttaga aacggccaca  300
acttcatggt ccggaacttc agatgtggcc agccgcttca aaacaaggtc cagctgaagg  360
gccgggatct tctgaccctg aagaacttta ctggcgaaga gatcaagtac atgctctggc  420
tctccgcgga cttgaagttc cgcattaagc agaaggggga ataccttccg ctgcttcaag  480
gaaagagcct cggcatgatc tttgagaagc gctcaaccag gacccgcctt tctactgaaa  540
ctgggttcgc gctgctcggt ggccacccct gcttcctgac gacccaggac atccacctcg  600
gagtgaacga atccctcacc gataccgccc gggtgttatc gagcatggca gatgccgtgc  660
tggccagggt gtacaaacag tccgatctgg acactctggc caaggaggcg tcaattccta  720
ttatcaacgg ccttagtgac ctctaccatc cgattcagat cctggccgat tacctcaccc  780
tgcaagaaca ctacagctcc ctgaagggtc tgacattgtc ctggatcggc gacggcaaca  840
acattctcca ttccatcatg atgtccgccg caaaattcgg catgcatctt caagccgcca  900
cgccgaaggg ttacgagccc gacgcttccg tgactaagct cgccgagcag tacgctaagg  960
agaacggaac caagcttctg ctgactaacg acccactaga agcagcccac gggggcaacg  1020
tgcttattac tgacacctgg atctccatgg gccaggaaga agagaaaaag aagcggctgc  1080
aggcgttcca gggatatcag gtcaccatga aaaccgccaa ggtcgctgcc tccgactgga  1140
ccttcctgca ctgcctgcct cgcaagcctg aagaagtgga cgacgaggtg ttctactcgc  1200
cacggagcct cgtgttcccc gaggccgaga atagaaagtg gaccatcatg gccgtgatgg  1260
tgtcactgct caccgactac agcccgcagc ttcagaagcc caagttctag ataagtgaat  1320
gcaaggctgg ccggaagccc ttgcctgaaa gcaagatttc agcctggaag agggcaaagt  1380
ggacgggagt ggacaggagt ggatgcgata agatgtggtt tgaagctgat gggtgccagc  1440
cctgcattgc tgagtcaatc aataaagagc tttcttttga cccattctag atctag      1496

SEQ ID NO: 62          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 62
aggaaactta agattattac atcaaaacaa aaagccgcca atgctgttca acctgcgcat  60
cctgctgaac aacgccgcct tccgcaacgg ccacaacttc atggtgcgca acttccgctg  120
cggccagccc ctgcagaaca aggtgcagct gaagggccgc gacctgctga ccctgaagaa  180
cttcaccggc gaggagatca agtacatgct gtggctgagc gccgacctga agttccgcat  240
caagcagaag ggcgagtacc tgcccctgct gcagggcaag agcctgggca tgatcttcga  300
gaagcgcagc acccgcaccc gcctgagcac cgagacaggc ctggccctgc tgggcggcca  360
cccctgcttc ctgaccaccc aggacatcca cctgggcgtg aacgagagcc tgaccgacac  420
```

```
cgcccgcgtg ctgagcagca tggccgacgc cgtgctggcc cgcgtgtaca agcagagcga  480
cctggacacc ctggccaagg aggccagcat ccccatcatc aacggcctga gcgacctgta  540
ccaccccatc cagatcctgg ccgactacct gaccctgcag gagcactaca gcagcctgaa  600
gggcctgacc ctgagctgga tcggcgacgg caacaacatc ctgcacagca tcatgatgag  660
cgccgccaag ttcggcatgc acctgcaggc cgccaccccc aagggctacg agcccgacgc  720
cagcgtgacc aagctggccg agcagtacgc caaggagaac ggcaccaagc tgctgctgac  780
caacgacccc ctggaggccg cccacggcgg caacgtgctg atcaccgaca cctggatcag  840
catgggccag gaggaggaga agaagaagcg cctgcaggcc ttccagggct accaggtgac  900
catgaagacc gccaaggtgg ccgccagcga ctggaccttc ctgcactgcc tgccccgcaa  960
gcccgaggag gtggacgacg aggtgttcta cagcccccgc agcctggtgt tccccgaggc  1020
cgagaaccgc aagtggacca tcatggccgt gatggtgagc ctgctgaccg actacagccc  1080
ccagctgcag aagcccaagt tctgaacgcc gaagcctgca gccatgcgac cccacgccac  1140
cccgtgcctc ctgcctccgc gcagcctgca gcgggagacc ctgtccccgc cccagccgtc  1200
ctcctggggt ggaccctagt ttaataaaga ttcaccaagt ttcacgcaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaa              1368

SEQ ID NO: 63          moltype = RNA  length = 1495
FEATURE                Location/Qualifiers
misc_feature           1..1495
                       note = Synthetic construct
source                 1..1495
                       mol_type = other RNA
                       organism = synthetic construct
SEQUENCE: 63
cttaaggggg cgctgcctac ggaggtggca gccatctcct tctcggcatc aagcttacca  60
tggtgcccca ggccctgctc ttggtcccgc tgctggtgtt cccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctacatgct gttcaacctg cgcatcctgc tgaacaacgc cgccttccgc aacggccaca  300
acttcatggt gcgcaacttc cgctgcggcc agcccctgca gaacaaggtg cagctgaagg  360
gccgcgacct gctgaccctg aagaacttca ccggcgagga gatcaagtac atgctgtggc  420
tgagcgccga cctgaagttc cgcatcaagc agaagggcga gtacctgccc ctgctgcagg  480
gcaagagcct gggcatgatc ttcgagaagc gcagcacccg cacccgcctg agcaccgaga  540
caggcctggc cctgctgggc ggccacccct gcttcctgac cacccaggac atccacctgg  600
gcgtgaacga gagcctgacc gacaccgccc gcgtgctgag cagcatggcc gacgccgtgc  660
tggcccgcgt gtacaagcag agcgacctgg acaccctggc caaggaggcc agcatcccca  720
tcatcaacgg cctgagcgac ctgtaccacc ccatccagat cctggccgac tacctgaccc  780
tgcaggagca ctacagcagc ctgaagggcc tgaccctgag ctggatcggc gacggcaaca  840
acatcctgca cagcatcatg atgagcgccg ccaagttcgg catgcacctg caggccgcca  900
cccccaaggg ctacgagccc gacgccagcg tgaccaagct ggccgagcag tacgccaagg  960
agaacggcac caagctgctg ctgaccaacg acccccctgga ggccgcccac ggcggcaacg  1020
tgctgatcac cgacacctgg atcagcatgg gccaggagga ggagaagaag aagcgcctgc  1080
aggccttcca gggctaccag gtgaccatga agaccgccaa ggtggccgcc agcgactgga  1140
ccttcctgca ctgcctgccc cgcaagcccg aggaggtgga cgacgaggtg ttctacagcc  1200
cccgcagcct ggtgttcccc gaggccgaga accgcaagtg gaccatcatg gccgtgatgg  1260
tgagcctgct gaccgactac agcccccagc tgcagaagcc caagttctga ataagtgatg  1320
caaggctggc cggaagccct tgcctgaaag caagatttca gcctggaaga gggcaaagtg  1380
gacgggagtg gacaggagtg gatgcgataa gatgtggttt gaagctgatg ggtgccagcc  1440
ctgcattgct gagtcaatca ataaagagct ttcttttgac ccattctaga tctag        1495

SEQ ID NO: 64          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 64
aggaaactta agattattac atcaaaacaa aaagccgcca atgcttttca atctccgcat  60
cctccttaac aacgccgcgt ttagaaacgg ccacaacttc atggtccgga acttcagatg  120
tggccagccg cttcaaaaca aggtccagct gaagggccgg gatcttctga ccctgaagaa  180
ctttactggc gaagagatca agtacatgct ctggctctcc gcggacttga agttccgcat  240
taagcagaag ggggaatacc ttccgctgct tcaaggaaag agcctcggca tgatctttga  300
gaagcgctca accaggaccc gcctttctac tgaaactggg ttcgcgctgc tcggtggcca  360
cccctgcttc ctgacgaccc aggacatcca cctcggagtg aacgaatccc tcaccgatac  420
cgcccgggtg ttatcgagca tggcagatgc cgtgctggcc agggtgtaca aacagtccga  480
tctggacact ctggccaagg aggcgtcaat tcctattatc aacggcctta gtgacctcta  540
ccatccgatt cagatcctgg ccgattacct caccctgcaa gaacactaca gctccctgaa  600
gggtctgaca ttgtcctgga tcggcgacgg caacaacatt ctccattcca tcatgatgtc  660
cgccgcaaaa ttcggcatgc atcttcaagc cgccacgccg aagggttacg agcccgacgc  720
ttccgtgact aagctcgccg agcagtacgc taaggagaac ggaaccaagc ttctgctgac  780
taacgaccca ctagaagcag cccacggggg caacgtgctt attactgaca cctggatctc  840
catgggccag gaagaagaga aaaagaagcg gctgcaggcg ttccagggat atcaggtcac  900
catgaaaacc gccaaggtcg ctgcctccga ctggaccttc ctgcactgcc tgcctcgcaa  960
gcctgaagaa gtggacgacg aggtgttcta ctcgccacgg agcctcgtgt tccccgaggc  1020
cgagaataga aagtggacca tcatggccgt gatggtgtca ctgctcaccg actacagccc  1080
gcagcttcag aagcccaagt tctagacgcc gaagcctgca gccatgcgac cccacgccac  1140
cccgtgcctc ctgcctccgc gcagcctgca gcgggagacc ctgtccccgc cccagccgtc  1200
```

-continued

```
ctcctggggt ggaccctagt ttaataaaga ttcaccaagt ttcacgcaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaa               1368

SEQ ID NO: 65          moltype = RNA  length = 1495
FEATURE                Location/Qualifiers
misc_feature           1..1495
                       note = Synthetic construct
source                 1..1495
                       mol_type = other RNA
                       organism = synthetic construct
SEQUENCE: 65
cttaaggggg cgctgcctac ggaggtggca gccatctcct tctcggcatc aagcttacca  60
tggtgcccca ggccctgctc ttggtcccgc tgctggtgtt ccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctacatgct tttcaacctg agaatcctct tgaacaatgc tgcttttcgg aatggccaca  300
actttatggt tcggaacttc cgttgcggcc agcctttaca aaacaaggtc cagctgaagg  360
gccgggattt gctcacacta aagaacttta ctggagaaga gatcaagtac atgctatggc  420
tgtcggccga cctgaagttc cgtatcaagc agaagggaga ataccttccg ctgcttcaag  480
gaaagagcct cggcatgatc tttgagaagc gctcaaccag gacccgcctt tctactgaaa  540
ctgggttcgc gctgctcggt ggccacccct gcttcctgac gacccaggac atccacctcg  600
gagtgaacga atccctcacc gataccgccc gggtgttatc gagcatggca gatgccgtgc  660
tggccagggt gtacaaacag tccgatctcg ataccttggc aaaggaggct tccattccca  720
tcatcaacgg cctgagcgac ctgtaccacc caatccaaat cctggctgac tacctgaccc  780
tgcaagagca ctacagcagc ctgaagggtc tgaccctgtc atggattggc gatggaaaca  840
atattctgca ctccatcatg atgtccgccg cgaagttcgg aatgcatctg caagccgcca  900
ctccaaaagg atacgaaccg gatgcatccg tgaccaagtt ggcggaacag tacgcgaagg  960
agaacggaac caagctcctg ctgactaacg acccgctcga ggctgcgcat gggggtaacg  1020
tgctgattac ggacacctgg atctccatgg ggcaggagga agagaagaag aagagactgc  1080
aggcattcca ggggtaccag gtcaccatga aaaccgcaaa agtggcagct tcggactgga  1140
ctttcctgca ttgcctgccg aggaagccgg aggaagtcga cgacgaagtg ttctactcgc  1200
ctcggtccct ggtgttcccc gaggccgaaa accggaagtg gaccatcatg gccgtgatgg  1260
tgtccttgct gactgactat agcccgcagc tgcagaagcc taagttctag ataagtgatg  1320
caaggctggc cggaagccct tgcctgaaag caagatttca gcctggaaga gggcaaagtg  1380
gacgggagtg gacaggagtg gatgcgataa gatgtggttt gaagctgatg ggtgccagcc  1440
ctgcattgct gagtcaatca ataaagagct ttcttttgac ccattctaga tctag       1495

SEQ ID NO: 66          moltype = RNA  length = 1475
FEATURE                Location/Qualifiers
misc_feature           1..1475
                       note = Synthetic construct
source                 1..1475
                       mol_type = other RNA
                       organism = synthetic construct
SEQUENCE: 66
tgagtgtcgt acagcctcca ggcccccccc tcccgggaga gccatagtgg tctgcggaac  60
cggtgagtac accggaattg ccgggaagac tgggtccttt cttggataaa cccactctat  120
gcccggccat ttgggcgtgc ccccgcaaga ctgctagccg agtagtgttg ggttgcgatg  180
ctgttcaacc tgcgcatcct gctgaacaac gccgccttcc gcaacggcca caacttcatg  240
gtgcgcaact tccgctgcgg ccagcccctg cagaacaagg tgcagctgaa gggccgcgac  300
ctgctgaccc tgaagaactt caccggcgag gagatcaagt acatgctgtg gctgagcgcc  360
gacctgaagt tccgcatcaa gcagaagggc gagtacctgc ccctgctgca gggcaagagc  420
ctgggcatga tcttcgagaa gcgcagcacc cgcacccgcc tgagcaccga gacaggcctg  480
gccctgctgg gcggccaccc ctgcttcctg accacccagg acatccacct gggcgtgaac  540
gagagcctga ccgacaccgc ccgcgtgctg agcagcatgg ccgacgccgt gctggcccgc  600
gtgtacaagc agagcgacct ggacaccctg gccaaggagg ccagcatccc catcatcaac  660
ggcctgagcg acctgtacca ccccatccag atcctggccg actacctgac cctgcaggag  720
cactacagca gcctgaaggg cctgaccctg agctggatcg gcgacggcaa caacatcctg  780
cacagcatca tgatgagcgc cgccaagttc ggcatgcacc tgcaggccgc cacccccaag  840
ggctacgagc ccgacgccag cgtgaccaag ctggccgagc agtacgccaa ggagaacggc  900
accaagctgc tgctgaccaa cgacccccctg gaggccgccc acggcggcaa cgtgctgatc  960
accgacacct ggatcagcat gggccaggag gaggagaaga agaagcgcct gcaggccttc  1020
cagggctacc aggtgaccat gaagaccgcc aaggtggccg ccagcgactg gaccttcctg  1080
cactgcctgc cccgcaagcc cgaggaggtg gacgacgagg tgttctacag cccccgcagc  1140
ctggtgttcc ccgaggccga gaaccgcaag tggaccatca tggccgtgat ggtgagcctg  1200
ctgaccgact acagccccca gctgcagaag cccaagttct gaataagtga tagagcggca  1260
aaccctagct acactccata gctagtttct tttttttttg ttttttttttt ttttttttt  1320
ttttttttt tttttttttc ctttcttttc cttcttttt tcctcttttc ttggtggctc  1380
catcttagcc ctagtcacgg ctagctgtga aaggtccgtg agccgcatga ctgcagagag  1440
tgccgtaact ggcctctctg cagatcatgt tctag                             1475

SEQ ID NO: 67          moltype = RNA  length = 1335
FEATURE                Location/Qualifiers
misc_feature           1..1335
                       note = Synthetic construct
source                 1..1335
                       mol_type = other RNA
                       organism = synthetic construct
```

```
SEQUENCE: 67
aggaaactta agattattac atcaaaacaa aaagccgcca atgcttttca atctccgcat  60
cctccttaac aacgccgcgt ttagaaacgg ccacaacttc atggtccgga acttcagatg  120
tggccagccg cttcaaaaca aggtccagct gaagggccgg gatcttctga ccctgaagaa  180
ctttactggc gaagagatca agtacatgct ctggctctcc gcggacttga agttccgcat  240
taagcagaag ggggaatacc ttccgctgct tcaaggaaag agcctcggca tgatctttga  300
gaagcgctca accaggaccc gcctttctac tgaaactggg ttcgcgctgc tcggtggcca  360
cccctgcttc ctgacgaccc aggacatcca cctcggagtg aacgaatccc tcaccgatac  420
cgcccgggtg ttatcgagca tggcagatgc cgtgctggcc agggtgtaca aacagtccga  480
tctggacact ctggccaagg aggcgtcaat tcctattatc aacggcctta gtgacctcta  540
ccatccgatt cagatcctgg ccgattacct caccctgcaa gaacactaca gctccctgaa  600
gggtctgaca ttgtcctgga tcggcgacgg caacaacatt ctccattcca tcatgatgtc  660
cgccgcaaaa ttcggcatgc atcttcaagc cgccacgccg aagggttacg agcccgacgc  720
ttccgtgact aagctcgccg agcagtacgc taaggagaac ggaaccaagc ttctgctgac  780
taacgaccca ctagaagcag cccacggggg caacgtgctt attactgaca cctggatctc  840
catgggccag gaagaagaga aaaagaagcg gctgcaggcg ttccagggat atcaggtcac  900
catgaaaacc gccaaggtcg ctgcctccga ctggaccttc ctgcactgcc tgcctcgcaa  960
gcctgaagaa gtggacgacg aggtgttcta ctcgccacgg agcctcgtgt tccccgaggc  1020
cgagaataga aagtggacca tcatggccgt gatggtgtca ctgctcaccg actacagccc  1080
gcagcttcag aagcccaagt tctaggctgg agcctcggta gccgttcctc ctgcccgctg  1140
ggcctcccaa cgggccctcc tcccctcctt gcaccggccc ttcctggtct ttgaataaag  1200
tctgagtggg cagcaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaa                                                   1335

SEQ ID NO: 68          moltype = RNA  length = 1335
FEATURE                Location/Qualifiers
misc_feature           1..1335
                       note = Synthetic construct
source                 1..1335
                       mol_type = other RNA
                       organism = synthetic construct
SEQUENCE: 68
aggaaactta agattattac atcaaaacaa aaagccgcca atgctgttca acctgcgcat  60
cctgctgaac aacgccgcct tccgcaacgg ccacaacttc atggtgcgca acttccgctg  120
cggccagccc ctgcagaaca aggtgcagct gaagggccgc gacctgctga ccctgaagaa  180
cttcaccggc gaggagatca agtacatgct gtggctgagc gccgacctga agttccgcat  240
caagcagaag ggcgagtacc tgcccctgct gcagggcaag agcctgggca tgatcttcga  300
gaagcgcagc acccgcaccc gcctgagcac cgagacaggc ctggccctgc tgggcggcca  360
cccctgcttc ctgaccaccc aggacatcca cctgggcgtg aacgagagcc tgaccgacac  420
cgcccgcgtg ctgagcagca tggccgacgc cgtgctggcc cgcgtgtaca agcagagcga  480
cctggacacc ctggccaagg aggccagcat ccccatcatc aacggcctga gcgacctgta  540
ccaccccatc cagatcctgg ccgactacct gaccctgcag gagcactaca gcagcctgaa  600
gggcctgacc ctgagctgga tcggcgacgg caacaacatc ctgcacagca tcatgatgag  660
cgccgccaag ttcggcatgc acctgcaggc cgccaccccc aagggctacg agcccgacgc  720
cagcgtgacc aagctggccg agcagtacgc caaggagaac ggcaccaagc tgctgctgac  780
caacgacccc ctggaggccg cccacggcgg caacgtgctg atcaccgaca cctggatcag  840
catgggccag gaggaggaga agaagaagcg cctgcaggcc ttccagggct accaggtgac  900
catgaagacc gccaaggtgg ccgccagcga ctggaccttc ctgcactgcc tgccccgcaa  960
gcccgaggag gtggacgacg aggtgttcta cagcccccgc agcctggtgt tccccgaggc  1020
cgagaaccgc aagtggacca tcatggccgt gatggtgagc ctgctgaccg actacagccc  1080
ccagctgcag aagcccaagt tctgagctgg agcctcggta gccgttcctc ctgcccgctg  1140
ggcctcccaa cgggccctcc tcccctcctt gcaccggccc ttcctggtct ttgaataaag  1200
tctgagtggg cagcaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaa                                                   1335

SEQ ID NO: 69          moltype = RNA  length = 1335
FEATURE                Location/Qualifiers
misc_feature           1..1335
                       note = Synthetic construct
source                 1..1335
                       mol_type = other RNA
                       organism = synthetic construct
SEQUENCE: 69
aggaaactta agattattac atcaaaacaa aaagccgcca atgcttttca acctgagaat  60
cctcttgaac aatgctgctt ttcggaatgg ccacaacttt atggttcgga acttccgttg  120
cggccagcct ttacaaaaca aggtccagct gaagggccgg gatttgctca cactaaagaa  180
ctttactgga gaagagatca agtacatgct atggctgtcg gccgacctga agttccgtat  240
caagcagaag ggagaatacc ttccgctgct tcaaggaaag agcctcggca tgatctttga  300
gaagcgctca accaggaccc gcctttctac tgaaactggg ttcgcgctgc tcggtggcca  360
cccctgcttc ctgacgaccc aggacatcca cctcggagtg aacgaatccc tcaccgatac  420
cgcccgggtg ttatcgagca tggcagatgc cgtgctggcc agggtgtaca aacagtccga  480
tctcgatacc ttggcaaagg aggcttccat tcccatcatc aacggcctga gcgacctgta  540
ccacccaatc caaatcctgg ctgactacct gaccctgcaa gagcactaca gcagcctgaa  600
gggtctgacc ctgtcatgga ttggcgatgg aaacaatatt ctgcactcca tcatgatgtc  660
cgccgcgaag ttcggaatgc atctgcaagc cgccactcca aaaggatacg aaccggatgc  720
atccgtgacc aagttggcgg aacagtacgc gaaggagaac ggaaccaagc tcctgctgac  780
taacgacccg ctcgaggctg cgcatggggg taacgtgctg attacggaca cctggatctc  840
```

-continued

```
catggggcag gaggaagaga agaagaagag actgcaggca ttccaggggt accaggtcac  900
catgaaaacc gcaaaagtgg cagcttcgga ctggactttc ctgcattgcc tgccgaggaa  960
gccggaggaa gtcgacgacg aagtgttcta ctcgcctcgg tccctggtgt tccccgaggc  1020
cgaaaaccgg aagtggacca tcatggccgt gatggtgtcc ttgctgactg actatagccc  1080
gcagctgcag aagcctaagt tctaggctgg agcctcggta gccgttcctc ctgcccgctg  1140
ggcctcccaa cgggccctcc tcccctcctt gcaccggccc ttcctggtct ttgaataaag  1200
tctgagtggg cagcaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaa                                                   1335

SEQ ID NO: 70          moltype = RNA  length = 1346
FEATURE                Location/Qualifiers
misc_feature           1..1346
                       note = Synthetic construct
source                 1..1346
                       mol_type = other RNA
                       organism = synthetic construct
SEQUENCE: 70
aggaaactta agaattattg gttaaagaag tatattagtg ctaatttccc tccgtttgtc  60
ctagcttttc tcttctgtca accccacacg cctttggcac aatgcttttc aatctccgca  120
tcctccttaa caacgccgcg tttagaaacg gccacaactt catggtccgg aacttcagat  180
gtggccagcc gcttcaaaac aaggtccagc tgaagggccg ggatcttctg accctgaaga  240
actttactgg cgaagagatc aagtacatgc tctggctctc cgcggacttg aagttccgca  300
ttaagcagaa gggggaatac cttccgctgc ttcaaggaaa gagcctcggc atgatctttg  360
agaagcgctc aaccaggacc cgcctttcta ctgaaactgg gttcgcgctg ctcggtggcc  420
acccctgctt cctgacgacc caggacatcc acctcggagt gaacgaatcc ctcaccgata  480
ccgcccgggt gttatcgagc atggcagatg ccgtgctggc cagggtgtac aaacagtccg  540
atctggacac tctggccaag gaggcgtcaa ttcctattat caacggcctt agtgacctct  600
accatccgat tcagatcctg gccgattacc tcaccctgca agaacactac agctccctga  660
agggtctgac attgtcctgg atcggcgacg gcaacaacat tctccattcc atcatgatgt  720
ccgccgcaaa attcggcatg catcttcaag ccgccacgcc gaagggttac gagcccgacg  780
cttccgtgac taagctcgcc gagcagtacg ctaaggagaa cggaaccaag cttctgctga  840
ctaacgaccc actagaagca gcccacgggg gcaacgtgct tattactgac acctggatct  900
ccatgggcca ggaagaagag aaaaagaagc ggctgcaggc gttccaggga tatcaggtca  960
ccatgaaaac cgccaaggtc gctgcctccg actggacctt cctgcactgc ctgcctcgca  1020
agcctgaaga agtggacgac gaggtgttct actcgccacg gagcctcgtg ttccccgagg  1080
ccgagaatag aaagtggacc atcatggccg tgatggtgtc actgctcacc gactacagcc  1140
cgcagcttca gaagcccaag ttctagctcg agacacatca caaccacaac cttctcaggc  1200
taccctgaga aaaaaagaca tgaagactca ggactcatct tttctgttgg tgtaaaatca  1260
acaccctaag gaacacaaat ttctttaaac atttgacttc ttgtctctgt gctgcaatta  1320
ataaaaaatg gaaagaatct atctag                                      1346

SEQ ID NO: 71          moltype = RNA  length = 1346
FEATURE                Location/Qualifiers
misc_feature           1..1346
                       note = Synthetic construct
source                 1..1346
                       mol_type = other RNA
                       organism = synthetic construct
SEQUENCE: 71
aggaaactta agaattattg gttaaagaag tatattagtg ctaatttccc tccgtttgtc  60
ctagcttttc tcttctgtca accccacacg cctttggcac aatgctgttc aacctgcgca  120
tcctgctgaa caacgccgcc ttccgcaacg gccacaactt catggtgcgc aacttccgct  180
gcggccagcc cctgcagaac aaggtgcagc tgaagggccg cgacctgctg accctgaaga  240
acttcaccgg cgaggagatc aagtacatgc tgtggctgag cgccgacctg aagttccgca  300
tcaagcagaa gggcgagtac ctgcccctgc tgcagggcaa gagcctgggc atgatcttcg  360
agaagcgcag cacccgcacc cgcctgagca ccgagacagg cctggccctg ctgggcggcc  420
acccctgctt cctgaccacc caggacatcc acctgggcgt gaacgagagc ctgaccgaca  480
ccgcccgcgt gctgagcagc atggccgacg ccgtgctggc ccgcgtgtac aagcagagcg  540
acctggacac cctggccaag gaggccagca tccccatcat caacggcctg agcgacctgt  600
accaccccat ccagatcctg gccgactacc tgaccctgca ggagcactac agcagcctga  660
agggcctgac cctgagctgg atcggcgacg gcaacaacat cctgcacagc atcatgatga  720
gcgccgccaa gttcggcatg cacctgcagg ccgccacccc caagggctac gagcccgacg  780
ccagcgtgac caagctggcc gagcagtacg ccaaggagaa cggcaccaag ctgctgctga  840
ccaacgaccc cctggaggcc gcccacggcg gcaacgtgct gatcaccgac acctggatca  900
gcatgggcca ggaggaggag aagaagaagc gcctgcaggc cttccagggc taccaggtga  960
ccatgaagac cgccaaggtg gccgccagcg actggacctt cctgcactgc ctgccccgca  1020
agcccgagga ggtggacgac gaggtgttct acagcccccg cagcctggtg ttccccgagg  1080
ccgagaaccg caagtggacc atcatggccg tgatggtgag cctgctgacc gactacagcc  1140
cccagctgca gaagcccaag ttctgactcg agacacatca caaccacaac cttctcaggc  1200
taccctgaga aaaaaagaca tgaagactca ggactcatct tttctgttgg tgtaaaatca  1260
acaccctaag gaacacaaat ttctttaaac atttgacttc ttgtctctgt gctgcaatta  1320
ataaaaaatg gaaagaatct atctag                                      1346

SEQ ID NO: 72          moltype = RNA  length = 1346
FEATURE                Location/Qualifiers
misc_feature           1..1346
                       note = Synthetic construct
```

```
source                  1..1346
                        mol_type = other RNA
                        organism = synthetic construct
SEQUENCE: 72
aggaaactta agaattattg gttaaagaag tatattagtg ctaatttccc tccgtttgtc  60
ctagcttttc tcttctgtca accccacacg cctttggcac aatgcttttc aacctgagaa  120
tcctcttgaa caatgctgct tttcggaatg gccacaactt tatggttcgg aacttccgtt  180
gcggccagcc tttacaaaac aaggtccagc tgaagggccg ggatttgctc acactaaaga  240
actttactgg agaagagatc aagtacatgc tatggctgtc ggccgacctg aagttccgta  300
tcaagcagaa gggagaatac cttccgctgc ttcaaggaaa gagcctcggc atgatctttg  360
agaagcgctc aaccaggacc cgcctttcta ctgaaactgg gttcgcgctg ctcggtggcc  420
acccctgctt cctgacgacc caggacatcc acctcggagt gaacgaatcc ctcaccgata  480
ccgcccgggt gttatcgagc atggcagatg ccgtgctggc cagggtgtac aaacagtccg  540
atctcgatac cttggcaaag gaggcttcca ttcccatcat caacggcctg agcgacctgt  600
accacccaat ccaaatcctg gctgactacc tgaccctgca agagcactac agcagcctga  660
agggtctgac cctgtcatgg attggcgatg gaaacaatat tctgcactcc atcatgatgt  720
ccgccgcgaa gttcggaatg catctgcaag ccgccactcc aaaaggatac gaaccggatg  780
catccgtgac caagttggcg gaacagtacg cgaaggagaa cggaaccaag ctcctgctga  840
ctaacgaccc gctcgaggct gcgcatgggg gtaacgtgct gattacggac acctggatct  900
ccatggggca ggaggaagag aagaagaaga gactgcaggc attccagggg taccaggtca  960
ccatgaaaac cgcaaaagtg gcagcttcgg actggacttt cctgcattgc ctgccgagga  1020
agccggagga agtcgacgac gaagtgttct actcgcctcg gtccctggtg ttccccgagg  1080
ccgaaaaccg gaagtggacc atcatggccg tgatggtgtc cttgctgact gactatagcc  1140
cgcagctgca gaagcctaag ttctagctcg agacacatca caaccacaac cttctcaggc  1200
taccctgaga aaaaaagaca tgaagactca ggactcatct tttctgttgg tgtaaaatca  1260
acaccctaag gaacacaaat ttctttaaac atttgacttc ttgtctctgt gctgcaatta  1320
ataaaaaatg gaaagaatct atctag                                        1346

SEQ ID NO: 73           moltype = RNA  length = 1222
FEATURE                 Location/Qualifiers
misc_feature            1..1222
                        note = Synthetic construct
source                  1..1222
                        mol_type = other RNA
                        organism = synthetic construct
SEQUENCE: 73
attattacat caaaacaaaa agccgccacc atgctgttca acctgcgcat cctgctgaac  60
aacgccgcct tccgcaacgg ccacaacttc atggtgcgca acttccgctg cggccagccc  120
ctgcagaaca aggtgcagct gaagggccgc gacctgctga ccctgaagaa cttcaccggc  180
gaggagatca agtacatgct gtggctgagc gccgacctga agttccgcat caagcagaag  240
ggcgagtacc tgcccctgct gcagggcaag agcctgggca tgatcttcga gaagcgcagc  300
acccgcaccc gcctgagcac cgagacaggc ttcgccctgc tgggcggcca cccctgcttc  360
ctgaccaccc aggacatcca cctgggcgtg aacgagagcc tgaccgacac cgcccgcgtg  420
ctgagcagca tggccgacgc cgtgctggcc cgcgtgtaca agcagagcga cctggacacc  480
ctggccaagg aggccagcat ccccatcatc aacggcctga gcgacctgta ccaccccatc  540
cagatcctgg ccgactacct gaccctgcag gagcactaca gcagcctgaa gggcctgacc  600
ctgagctgga tcggcgacgg caacaacatc ctgcacagca tcatgatgag cgccgccaag  660
ttcggcatgc acctgcaggc cgccaccccc aagggctacg agcccgacgc cagcgtgacc  720
aagctggccg agcagtacgc caaggagaac ggcaccaagc tgctgctgac caacgacccc  780
ctggaggccg cccacggcgg caacgtgctg atcaccgaca cctggatcag catgggccag  840
gaggaggaga agaagaagcg cctgcaggcc ttccagggct accaggtgac catgaagacc  900
gccaaggtgg ccgccagcga ctggaccttc ctgcactgcc tgccccgcaa gcccgaggag  960
gtggacgacg aggtgttcta cagcccccgc agcctggtgt tccccgaggc cgagaaccgc  1020
aagtggacca tcatggccgt gatggtgagc ctgctgaccg actacagccc ccagctgcag  1080
aagcccaagt tctgaggtct ctagtaatga gctggagcct cggtagccgt tcctcctgcc  1140
cgctgggcct cccaacgggc cctcctcccc tccttgcacc ggcccttcct ggtctttgaa  1200
taaagtctga gtgggcatct ag                                            1222

SEQ ID NO: 74           moltype = RNA  length = 1346
FEATURE                 Location/Qualifiers
misc_feature            1..1346
                        note = Synthetic construct
source                  1..1346
                        mol_type = other RNA
                        organism = synthetic construct
SEQUENCE: 74
aggaaactta agaattattg gttaaagaag tatattagtg ctaatttccc tccgtttgtc  60
ctagcttttc tcttctgtca accccacacg cctttggcac aatgctgttc aacctgcgca  120
tcctgctgaa caacgccgcc ttccgcaacg gccacaactt catggtgcgc aacttccgct  180
gcggccagcc cctgcagaac aaggtgcagc tgaagggccg cgacctgctg accctgaaga  240
acttcaccgg cgaggagatc aagtacatgc tgtggctgag cgccgacctg aagttccgca  300
tcaagcagaa gggcgagtac ctgcccctgc tgcagggcaa gagcctgggc atgatcttcg  360
agaagcgcag cacccgcacc cgcctgagca ccgagacagg cttcgccctg ctgggcggcc  420
acccctgctt cctgaccacc caggacatcc acctgggcgt gaacgagagc ctgaccgaca  480
ccgcccgcgt gctgagcagc atggccgacg ccgtgctggc ccgcgtgtac aagcagagcg  540
acctggacac cctggccaag gaggccagca tccccatcat caacggcctg agcgacctgt  600
accaccccat ccagatcctg gccgactacc tgaccctgca ggagcactac agcagcctga  660
agggcctgac cctgagctgg atcggcgacg gcaacaacat cctgcacagc atcatgatga  720
gcgccgccaa gttcggcatg cacctgcagg ccgccacccc caagggctac gagcccgacg  780
```

```
ccagcgtgac caagctggcc gagcagtacg ccaaggagaa cggcaccaag ctgctgctga  840
ccaacgaccc cctggaggcc gcccacggcg gcaacgtgct gatcaccgac acctggatca  900
gcatgggcca ggaggaggag aagaagaagc gcctgcaggc cttccagggc taccaggtga  960
ccatgaagac cgccaaggtg gccgccagcg actggacctt cctgcactgc ctgccccgca  1020
agcccgagga ggtggacgac gaggtgttct acagcccccg cagcctggtg ttccccgagg  1080
ccgagaaccg caagtggacc atcatggccg tgatggtgag cctgctgacc gactacagcc  1140
cccagctgca gaagcccaag ttctgactcg agacacatca caaccacaac cttctcaggc  1200
taccctgaga aaaaaagaca tgaagactca ggactcatct tttctgttgg tgtaaaatca  1260
acaccctaag gaacacaaat ttctttaaac atttgacttc ttgtctctgt gctgcaatta  1320
ataaaaaatg gaaagaatct atctag                                      1346

SEQ ID NO: 75          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 75
aggaaactta agattattac atcaaaacaa aaagccgcca atgctgttca acctgcgcat  60
cctgctgaac aacgccgcct tccgcaacgg ccacaacttc atggtgcgca acttccgctg  120
cggccagccc ctgcagaaca aggtgcagct gaagggccgc gacctgctga ccctgaagaa  180
cttcaccggc gaggagatca agtacatgct gtggctgagc gccgacctga agttccgcat  240
caagcagaag ggcgagtacc tgcccctgct gcagggcaag agcctgggca tgatcttcga  300
gaagcgcagc acccgcaccc gcctgagcac cgagacaggc ttcgccctgc tgggcggcca  360
cccctgcttc ctgaccaccc aggacatcca cctgggcgtg aacgagagcc tgaccgacac  420
cgcccgcgtg ctgagcagca tggccgacgc cgtgctggcc cgcgtgtaca agcagagcga  480
cctggacacc ctggccaagg aggccagcat ccccatcatc aacggcctga gcgacctgta  540
ccaccccatc cagatcctgg ccgactacct gaccctgcag gagcactaca gcagcctgaa  600
gggcctgacc ctgagctgga tcggcgacgg caacaacatc ctgcacagca tcatgatgag  660
cgccgccaag ttcggcatgc acctgcaggc cgccaccccc aagggctacg agcccgacgc  720
cagcgtgacc aagctggccg agcagtacgc caaggagaac ggcaccaagc tgctgctgac  780
caacgacccc ctggaggccg cccacggcgg caacgtgctg atcaccgaca cctggatcag  840
catgggccag gaggaggaga agaagaagcg cctgcaggcc ttccagggct accaggtgac  900
catgaagacc gccaaggtgg ccgccagcga ctggaccttc ctgcactgcc tgccccgcaa  960
gcccgaggag gtggacgacg aggtgttcta cagcccccgc agcctggtgt tccccgaggc  1020
cgagaaccgc aagtggacca tcatggccgt gatggtgagc ctgctgaccg actacagccc  1080
ccagctgcag aagcccaagt tctgaacgcc gaagcctgca gccatgcgac cccacgccac  1140
cccgtgcctc ctgcctccgc gcagcctgca gcgggagacc ctgtccccgc cccagccgtc  1200
ctcctggggt ggaccctagt ttaataaaga ttcaccaagt ttcacgcaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaa              1368

SEQ ID NO: 76          moltype = RNA  length = 1496
FEATURE                Location/Qualifiers
misc_feature           1..1496
                       note = Synthetic construct
source                 1..1496
                       mol_type = other RNA
                       organism = synthetic construct
SEQUENCE: 76
cttaaggggg cgctgcctac ggaggtggca gccatctcct tctcggcatc aagcttacca  60
tggtgcccca ggccctgctc ttggtcccgc tgctggtgtt ccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctacatgct gttcaacctg cgcatcctgc tgaacaacgc cgccttccgc aacggccaca  300
acttcatggt gcgcaacttc cgctgcggcc agcccctgca gaacaaggtg cagctgaagg  360
gccgcgacct gctgaccctg aagaacttca ccggcgagga gatcaagtac atgctgtggc  420
tgagcgccga cctgaagttc cgcatcaagc agaagggcga gtacctgccc ctgctgcagg  480
gcaagagcct gggcatgatc ttcgagaagc gcagcacccg cacccgcctg agcaccgaga  540
caggcttcgc cctgctgggc ggccacccct gcttcctgac cacccaggac atccacctgg  600
gcgtgaacga gagcctgacc gacaccgccc gcgtgctgag cagcatggcc gacgccgtgc  660
tggcccgcgt gtacaagcag agcgacctgg acaccctggc caaggaggcc agcatcccca  720
tcatcaacgg cctgagcgac ctgtaccacc ccatccagat cctggccgac tacctgaccc  780
tgcaggagca ctacagcagc ctgaagggcc tgaccctgag ctggatcggc gacggcaaca  840
acatcctgca cagcatcatg atgagcgccg ccaagttcgg catgcacctg caggccgcca  900
cccccaaggg ctacgagccc gacgccagcg tgaccaagct ggccgagcag tacgccaagg  960
agaacggcac caagctgctg ctgaccaacg acccccctgga ggccgcccac ggcggcaacg  1020
tgctgatcac cgacacctgg atcagcatgg gccaggagga ggagaagaag aagcgcctgc  1080
aggccttcca gggctaccag gtgaccatga agaccgccaa ggtggccgcc agcgactgga  1140
ccttcctgca ctgcctgccc cgcaagcccg aggaggtgga cgacgaggtg ttctacagcc  1200
cccgcagcct ggtgttcccc gaggccgaga accgcaagtg gaccatcatg gccgtgatgg  1260
tgagcctgct gaccgactac agcccccagc tgcagaagcc caagttctga ataagtgaat  1320
gcaaggctgg ccggaagccc ttgcctgaaa gcaagatttc agcctggaag agggcaaagt  1380
ggacgggagt ggacaggagt ggatgcgata agatgtggtt tgaagctgat gggtgccagc  1440
cctgcattgc tgagtcaatc aataaagagc tttcttttga cccattctag atctag      1496

SEQ ID NO: 77          moltype = RNA  length = 1380
FEATURE                Location/Qualifiers
```

```
misc_feature            1..1380
                        note = Synthetic construct
source                  1..1380
                        mol_type = other RNA
                        organism = synthetic construct
SEQUENCE: 77
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgggc gtcttcaacc tgcggatcct gctgaacaac gccgccttcc  180
ggaacggcca caacttcatg gtccgcaact tcagatgcgg ccagcccctg cagaacaagg  240
tgcagctgaa gggccgggac ctgctgaccc tgaagaactt caccggcgaa gagatcaagt  300
acatgctgtg gctgagcgcc gacctgaagt tccggatcaa gcagaagggc gagtacctgc  360
ccctgctgca aggcaagagc ctgggcatga tcttcgagaa gcggagcacc cggacccggc  420
tgagcaccga gacaggcttt gccctgctgg gaggccaccc ctgctttctg accacccagg  480
acatccacct gggcgtgaac gagagcctga ccgacaccgc cagagtgctg agcagcatgg  540
ccgacgccgt gctggcccgg gtgtacaagc agagcgacct ggacaccctg gccaaagagg  600
ccagcatccc catcatcaac ggcctgagcg acctgtacca ccccatccag atcctggccg  660
actacctgac cctgcaggaa cactacagct ccctgaaggg cctgaccctg agctggatcg  720
gcgacggcaa caacatcctg cacagcatca tgatgagcgc cgccaagttc ggcatgcatc  780
tgcaggccgc cacccccaag ggctacgagc ctgatgccag cgtgaccaag ctggccgagc  840
agtacgccaa agagaacggc accaagctgc tgctgaccaa cgacccccctg gaagccgccc  900
acggcggcaa cgtgctgatc accgacacct ggatcagcat gggccaggaa gaggaaaaga  960
agaagcggct gcaggccttc cagggctacc aggtcacaat gaagaccgcc aaggtggccg  1020
ccagcgactg gaccttcctg cactgcctgc cccggaagcc cgaagaggtg gacgacgagg  1080
tgttctacag cccccggtcc ctggtgttcc ccgaggccga gaaccggaag tggaccatta  1140
tggccgtgat ggtgtccctg ctgaccgact actcccccca gctgcagaag cccaagttct  1200
agataagtga actcgagcta gtgactgact aggatctggt taccactaaa ccagcctcaa  1260
gaacacccga atggagtctc taagctacat aataccaact tacacttaca aaatgttgtc  1320
ccccaaaatg tagccattcg tatctgctcc taataaaaag aaagtttctt cacattctag  1380

SEQ ID NO: 78           moltype = RNA  length = 1380
FEATURE                 Location/Qualifiers
misc_feature            1..1380
                        note = Synthetic construct
source                  1..1380
                        mol_type = other RNA
                        organism = synthetic construct
SEQUENCE: 78
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgggc gtcttcaacc tgcggatcct gctgaacaac gccgccttcc  180
ggaacggcca caacttcatg gtccgcaact tcagatgcgg ccagcccctg cagaacaggg  240
tgcagctgaa gggccgggac ctgctgaccc tgaagaactt caccggcgaa gagatcaggt  300
acatgctgtg gctgagcgcc gacctgaagt tccggatcaa gcagaagggc gagtacctgc  360
ccctgctgca aggcaagagc ctgggcatga tcttcgagaa gcggagcacc cggacccggc  420
tgagcaccga gacaggcttt gccctgctgg gaggccaccc ctgctttctg accacccagg  480
acatccacct gggcgtgaac gagagcctga ccgacaccgc cagagtgctg agcagcatgg  540
ccgacgccgt gctggcccgg gtgtacaagc agagcgacct ggacaccctg gccaaagagg  600
ccagcatccc catcatcaac ggcctgagcg acctgtacca ccccatccag atcctggccg  660
actacctgac cctgcaggaa cactacagct ccctgaaggg cctgaccctg agctggatcg  720
gcgacggcaa caacatcctg cacagcatca tgatgagcgc cgccaagttc ggcatgcatc  780
tgcaggccgc cacccccaag ggctacgagc ctgatgccag cgtgaccaag ctggccgagc  840
agtacgccaa agagaacggc accaagctgc tgctgaccaa cgacccccctg gaagccgccc  900
acggcggcaa cgtgctgatc accgacacct ggatcagcat gggccaggaa gaggaaaaga  960
agaagcggct gcaggccttc cagggctacc aggtcacaat gaagaccgcc aaggtggccg  1020
ccagcgactg gaccttcctg cactgcctgc cccggaagcc cgaagaggtg gacgacgagg  1080
tgttctacag cccccggtcc ctggtgttcc ccgaggccga gaaccggaag tggaccatta  1140
tggccgtgat ggtgtccctg ctgaccgact actcccccca gctgcagaag cccaagttct  1200
agataagtga actcgagcta gtgactgact aggatctggt taccactaaa ccagcctcaa  1260
gaacacccga atggagtctc taagctacat aataccaact tacacttaca aaatgttgtc  1320
ccccaaaatg tagccattcg tatctgctcc taataaaaag aaagtttctt cacattctag  1380

SEQ ID NO: 79           moltype = RNA  length = 1380
FEATURE                 Location/Qualifiers
misc_feature            1..1380
                        note = Synthetic construct
source                  1..1380
                        mol_type = other RNA
                        organism = synthetic construct
SEQUENCE: 79
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcttcaacc tgcggatcct gctgaacaac gccgccttcc  180
ggaacggcca caacttcatg gtccgcaact tcagatgcgg ccagcccctg cagaacaggg  240
tgcagctgaa gggccgggac ctgctgaccc tgaagaactt caccggcgaa gagatcaggt  300
acatgctgtg gctgagcgcc gacctgaagt tccggatcaa gcagaagggc gagtacctgc  360
ccctgctgca aggcaagagc ctgggcatga tcttcgagaa gcggagcacc cggacccggc  420
tgagcaccga gacaggcttt gccctgctgg gaggccaccc ctgctttctg accacccagg  480
acatccacct gggcgtgaac gagagcctga ccgacaccgc cagagtgctg agcagcatgg  540
```

```
ccgacgccgt gctggcccgg gtgtacaagc agagcgacct ggacaccctg gccaaagagg  600
ccagcatccc catcatcaac ggcctgagcg acctgtacca ccccatccag atcctggccg  660
actacctgac cctgcaggaa cactacagct ccctgaaggg cctgaccctg agctggatcg  720
gcgacggcaa caacatcctg cacagcatca tgatgagcgc cgccaagttc ggcatgcatc  780
tgcaggccgc caccccccaag ggctacgagc ctgatgccag cgtgaccaag ctggccgagc  840
agtacgccaa agagaacggc accaagctgc tgctgaccaa cgacccccctg gaagccgccc  900
acggcggcaa cgtgctgatc accgacacct ggatcagcat gggccaggaa gaggaaaaga  960
agaagcggct gcaggccttc cagggctacc aggtcacaat gaagaccgcc aaggtggccg  1020
ccagcgactg gaccttcctg cactgcctgc cccggaagcc cgaagaggtg gacgacgagg  1080
tgttctacag cccccggtcc ctggtgttcc ccgaggccga gaaccggaag tggaccatta  1140
tggccgtgat ggtgtccctg ctgaccgact actcccccca gctgcagaag cccaagttct  1200
agataagtga actcgagcta gtgactgact aggatctggt taccactaaa ccagcctcaa  1260
gaacacccga atggagtctc taagctacat aataccaact tacacttaca aaatgttgtc  1320
ccccaaaatg tagccattcg tatctgctcc taataaaaag aaagtttctt cacattctag  1380

SEQ ID NO: 80          moltype = RNA  length = 1377
FEATURE                Location/Qualifiers
misc_feature           1..1377
                       note = Synthetic construct
source                 1..1377
                       mol_type = other RNA
                       organism = synthetic construct
SEQUENCE: 80
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctga ggatcctgct gaacaacgca gctttcagga  180
acggccacaa cttcatggtg aggaacttcc ggtgcggcca gcccctgcag aacaaggtgc  240
agctgaaggg cagggacctg ctgaccctga agaacttcac cggagaggag atcaagtaca  300
tgctgtggct gagcgcagac ctgaagttca ggatcaagca gaagggagag tacctgcccc  360
tgctgcaggg gaagtccctg ggcatgatct tcgagaagag gagtaccagg accaggctga  420
gcaccgaaac cggcttcgcc ctgctgggag gacaccccctg cttcctgacc acccaggaca  480
tccacctggg cgtgaacgag agtctgaccg acaccgccag ggtgctgtct agcatggccg  540
acgccgtgct ggccagggtg tacaagcagt cagacctgga caccctggct aaggaggcca  600
gcatccccat catcaacggc ctgagcgacc tgtaccaccc catccagatc ctggctgact  660
acctgaccct gcaggagcac tacagctctc tgaagggcct gaccctgagc tggatcggcg  720
acgggaacaa catcctgcac agcatcatga tgagcgccgc caagttcggc atgcacctgc  780
aggccgctac ccccaagggt tacgagcccg acgccagcgt gaccaagctg gcagagcagt  840
acgccaagga gaacggcacc aagctgctgc tgaccaacga ccccctggag gccgcccacg  900
gaggcaacgt gctgatcacc gacacctgga tcagcatggg acaggaggag gagaagaaga  960
agcggctgca ggctttccag ggttaccagg tgaccatgaa gaccgccaag gtggctgcca  1020
gcgactggac cttcctgcac tgcctgccca ggaagcccga ggaggtggac gacgaggtgt  1080
tctactctcc caggagcctg gtgttccccg aggccgagaa caggaagtgg accatcatgg  1140
ctgtgatggt gtccctgctg accgactaca gcccccagct gcagaagccc aagttctgaa  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377

SEQ ID NO: 81          moltype = RNA  length = 1377
FEATURE                Location/Qualifiers
misc_feature           1..1377
                       note = Synthetic construct
source                 1..1377
                       mol_type = other RNA
                       organism = synthetic construct
SEQUENCE: 81
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctga ggatcctgct gaacaacgca gctttcagga  180
acggccacaa cttcatggtg aggaacttcc ggtgcggcca gcccctgcag aacaaggtgc  240
agctgaaggg cagggacctg ctgaccctga agaacttcac cggagaggag atcaagtaca  300
tgctgtggct gagcgcagac ctgaagttca ggatcaagca gaagggagag tacctgcccc  360
tgctgcaggg gaagtccctg ggcatgatct tcgagaagag gagtaccagg accaggctga  420
gcaccgaaac cggcttcgcc ctgctgggag gacacccctg cttcctgacg acccaggaca  480
tccacctcgg agtgaacgaa tccctcaccg ataccgcccg ggtgttatca agcatggcag  540
atgccgtgct ggccagggtg tacaaacagt ccgatctgga cactctggct aaggaggcca  600
gcatccccat catcaacggc ctgagcgacc tgtaccaccc catccagatc ctggctgact  660
acctgaccct gcaggagcac tacagctctc tgaagggcct gaccctgagc tggatcggcg  720
acgggaacaa catcctgcac tccatcatga tgtccgccgc gaagttcgga atgcatctgc  780
aagccgccac gccaaaagga tacgaaccgg atgcgcccgt gacaaagttg gcggaacagt  840
acgctaagga gaacggaacc aagctgctgc tgaccaacga ccccctggag gccgcccacg  900
gaggcaacgt gctgatcacc gacacctgga tcagcatggg acaggaggag gagaagaaga  960
agcggctgca ggctttccag ggttaccagg tgaccatgaa gaccgccaag gtggctgcca  1020
gcgactggac cttcctgcac tgcctgccca ggaagcccga ggaggtggac gacgaggtgt  1080
tctactctcc caggagcctg gtgttccccg aggccgagaa caggaagtgg accatcatgg  1140
ctgtgatggt gtccctgctg accgactaca gcccccagct gcagaagccc aagttctgaa  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377
```

-continued

```
SEQ ID NO: 82          moltype = RNA  length = 1477
FEATURE                Location/Qualifiers
misc_feature           1..1477
                       note = Synthetic construct
source                 1..1477
                       mol_type = other RNA
                       organism = synthetic construct
SEQUENCE: 82
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctgc gcatcctgct gaacaacgcc gccttccgca  180
acggccacaa cttcatggtg cgcaacttcc gctgcggcca gcccctgcag aacaaggtgc  240
agctgaaggg ccgcgacctg ctgaccctga agaacttcac cggcgaggag atcaagtaca  300
tgctgtggct gagcgccgac ctgaagttcc gcatcaagca gaagggcgag tacctgcccc  360
tgctgcaggg caagagcctg ggcatgatct tcgagaagcg cagcacccgc acccgcctga  420
gcaccgagac aggcttcgcc ctgctgggcg gccacccctg cttcctgacc acccaggaca  480
tccacctggg cgtgaacgag agcctgaccg acaccgcccg cgtgctgagc agcatggccg  540
acgccgtgct ggcccgcgtg tacaagcaga gcgacctgga caccctggcc aaggaggcca  600
gcatccccat catcaacggc ctgagcgacc tgtaccaccc catccagatc ctggccgact  660
acctgaccct gcaggagcac tacagcagcc tgaagggcct gaccctgagc tggatcggcg  720
acggcaacaa catcctgcac agcatcatga tgagcgccgc caagttcggc atgcacctgc  780
aggccgccac ccccaagggc tacgagcccg acgccagcgt gaccaagctg gccgagcagt  840
acgccaagga gaacggcacc aagctgctgc tgaccaacga cccccctggag gccgcccacg  900
gcggcaacgt gctgatcacc gacacctgga tcagcatggg ccaggaggag gagaagaaga  960
agcgcctgca ggccttccag ggctaccagg tgaccatgaa gaccgccaag gtggccgcca  1020
gcgactggac cttcctgcac tgcctgcccc gcaagcccga ggaggtggac gacgaggtgt  1080
tctacagccc ccgcagcctg gtgttccccg aggccgagaa ccgcaagtgg accatcatgg  1140
ccgtgatggt gagcctgctg accgactaca gcccccagct gcagaagccc aagttctgaa  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttctcac attctagaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaa                           1477

SEQ ID NO: 83          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 83
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tcaacctgcg catcctgctg aacaacgccg  180
ccttccgcaa cggccacaac ttcatggtgc gcaacttccg ctgcggccag cccctgcaga  240
acaaggtgca gctgaagggc cgcgacctgc tgaccctgaa gaacttcacc ggcgaggaga  300
tcaagtacat gctgtggctg agcgccgacc tgaagttccg catcaagcag aagggcgagt  360
acctgcccct gctgcagggc aagagcctgg gcatgatctt cgagaagcgc agcacccgca  420
cccgcctgag caccgagaca ggcttcgccc tgctgggcgg ccacccctgc ttcctgacca  480
cccaggacat ccacctgggc gtgaacgaga gcctgaccga caccgcccgc gtgctgagca  540
gcatggccga cgccgtgctg gcccgcgtgt acaagcagag cgacctggac accctggcca  600
aggaggccag catccccatc atcaacggcc tgagcgacct gtaccacccc atccagatcc  660
tggccgacta cctgaccctg caggagcact acagcagcct gaagggcctg accctgagct  720
ggatcggcga cggcaacaac atcctgcaca gcatcatgat gagcgccgcc aagttcggca  780
tgcacctgca ggccgccacc cccaagggct acgagcccga cgccagcgtg accaagctgg  840
ccgagcagta cgccaaggag aacggcacca agctgctgct gaccaacgac cccctggagg  900
ccgcccacgg cggcaacgtg ctgatcaccg acacctggat cagcatgggc caggaggagg  960
agaagaagaa gcgcctgcag gccttccagg gctaccaggt gaccatgaag accgccaagg  1020
tggccgccag cgactggacc ttcctgcact gcctgccccg caagcccgag gaggtggacg  1080
acgaggtgtt ctacagcccc cgcagcctgg tgttccccga ggccgagaac cgcaagtgga  1140
ccatcatggc cgtgatggtg agcctgctga ccgactacag cccccagctg cagaagccca  1200
agttctgact agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 84          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 84
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaacttga gaatcctgct gaacaacgcc gcctttcgca  180
acggtcacaa ttttatggtc agaaacttca gatgcggaca gcccctccaa aacaaggtcc  240
agctgaaggg ccgcgatctc ctcaccctga agaacttcac gggggaggag atcaagtaca  300
```

-continued

```
tgctgtggct ctccgctgac ctgaagttca ggatcaagca gaagggagaa tatctgccgc  360
tgctgcaagg gaagtccctg gggatgattt tcgagaagcg gagcacccgg actcggctct  420
ccactgaaac tggtttcgcc cttctgggcg gtcacccctg cttcctgacc actcaagaca  480
ttcacctcgg agtgaacgag tccttgactg acaccgcccg ggtgctgtcg agcatggcag  540
acgccgtgct agcccgcgtg tacaagcagt cagacctcga taccctggcc aaggaggctt  600
cgatcccgat catcaacggg ttgtccgacc tgtaccaccc gattcagatt ctcgccgact  660
acctcaccct gcaagagcat tacagctccc tgaaggggct taccctgtcc tggattggcg  720
acggaaacaa catcctgcac tccattatga tgtcggcggc caagttcggc atgcacctcc  780
aagccgcgac ccctaagggt tacgaaccag acgcgtcagt gactaagctg gccgaacagt  840
acgcaaagga aaatggcacg aagctgctcc tgaccaacga tccgttggaa gccgcccatg  900
gcggaaatgt gctcatcacc gacacctgga tctcgatggg acaggaggaa gagaagaaga  960
agcggctgca ggcgttccag ggctaccagg tcaccatgaa aactgccaag gtggccgcca  1020
gcgactggac cttcctgcac tgccttccgc gcaagcctga ggaggtggac gatgaagtgt  1080
tctactctcc acggtccctg gtgttccccg aggcggagaa ccgcaaatgg accatcatgg  1140
ctgtgatggt cagcctgctg accgattaca gccctcagtt gcaaaagccg aagttttgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

```
SEQ ID NO: 85          moltype = RNA  length = 1471
FEATURE                Location/Qualifiers
misc_feature           1..1471
                       note = Synthetic construct
source                 1..1471
                       mol_type = other RNA
                       organism = synthetic construct
SEQUENCE: 85
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg ttcaacctcc gcatcctcct caacaacgcc gcattcagaa  180
acgggcacaa cttcatggtc agaaacttcc gctgcgggca acccctacaa aacaaggtcc  240
agctcaaggg gcgggacctc ctgaccctga agaacttcac cggcgaagag atcaagtaca  300
tgctgtggct ctccgccgac ctgaagttcc gcatcaagca gaagggagag tacctcccgc  360
tgctgcaagg gaagtcgctg gggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta gaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa a                                 1471
```

```
SEQ ID NO: 86          moltype = RNA  length = 1771
FEATURE                Location/Qualifiers
misc_feature           1..1771
                       note = Synthetic construct
source                 1..1771
                       mol_type = other RNA
                       organism = synthetic construct
SEQUENCE: 86
ctccctcccc uccccctaac gttactggcc gaagccgctt ggaataaggc cggtgtgcgt  60
ttgtctatat gttattttcc accatattgc cgtcttttgg caatgtgagg gcccggaaac  120
ctggccctgt cttcttgacg agcattccta ggggtctttc ccctctcgcc aaaggaatgc  180
aaggtctgtt gaatgtcgtg aaggaagcag ttcctctgga agcttcttga agacaaacaa  240
cgtctgtagc gacccttttgc aggcagcgga accccccacc tggcgacagg tgcctctgcg  300
gccaaaagcc acgtgtataa gatacacctg caaaggcggc acaaccccag tgccacgttg  360
tgagttggat agttgtggaa agagtcaaat ggctctcctc aagcgtattc aacaaggggc  420
tgaaggatgc ccagaaggta ccccattgta tgggatctga tctggggcct cggtgcacat  480
gctttacgtg tgtttagtcg aggttaaaaa acgtctaggc cccccgaacc acggggacgt  540
ggttttcctt tgaaaaacac gatgataata tgcttttcaa tctccgcatc ctccttaaca  600
acgccgcgtt tagaaacggc cacaacttca tggtccggaa cttcagatgt ggccagccgc  660
ttcaaaacaa ggtccagctg aagggccggg atcttctgac cctgaagaac tttactggcg  720
aagagatcaa gtacatgctc tggctctccg cggacttgaa gttccgcatt aagcagaagg  780
gggaatacct tccgctgctt caaggaaaga gcctcggcat gatctttgag aagcgctcaa  840
ccaggacccg cctttctact gaaactgggt tcgcgctgct cggtggccac ccctgcttcc  900
tgacgaccca ggacatccac ctcggagtga acgaatccct caccgatacc gcccgggtgt  960
tatcgagcat ggcagatgcc gtgctggcca gggtgtacaa acagtccgat ctggacactc  1020
tggccaagga ggcgtcaatt cctattatca acggccttag tgacctctac catccgattc  1080
```

```
agatcctggc cgattacctc accctgcaag aacactacag ctccctgaag ggtctgacat  1140
tgtcctggat cggcgacggc aacaacattc tccattccat catgatgtcc gccgcaaaat  1200
tcggcatgca tcttcaagcc gccacgccga agggttacga gcccgacgct tccgtgacta  1260
agctcgccga gcagtacgct aaggagaacg gaaccaagct tctgctgact aacgacccac  1320
tagaagcagc ccacgggggc aacgtgctta ttactgacac ctggatctcc atgggccagg  1380
aagaagagaa aaagaagcgg ctgcaggcgt tccagggata tcaggtcacc atgaaaaccg  1440
ccaaggtcgc tgcctccgac tggaccttcc tgcactgcct gcctcgcaag cctgaagaag  1500
tggacgacga ggtgttctac tcgccacgga gcctcgtgtt ccccgaggcc gagaatagaa  1560
agtggaccat catggccgtg atggtgtcac tgctcaccga ctacagcccg cagcttcaga  1620
agcccaagtt ctgaataagt agatagtgca gtcactggca caacgcgttg cccggtaagc  1680
caatcgggta tacacggtcg tcatactgca gacagggttc ttctactttg caagatagtc  1740
tagagtagta aaataaatag tataagtcta g                                 1771
```

```
SEQ ID NO: 87          moltype = RNA  length = 1771
FEATURE                Location/Qualifiers
misc_feature           1..1771
                       note = Synthetic construct
source                 1..1771
                       mol_type = other RNA
                       organism = synthetic construct
SEQUENCE: 87
ctccctcccc ccccccctaac gttactggcc gaagccgctt ggaataaggc cggtgtgcgt  60
ttgtctatat gttattttcc accatattgc cgtcttttgg caatgtgagg gcccggaaac  120
ctggccctgt cttcttgacg agcattccta ggggtctttc ccctctcgcc aaaggaatgc  180
aaggtctgtt gaatgtcgtg aaggaagcag ttcctctgga agcttcttga agacaaacaa  240
cgtctgtagc gaccctttgc aggcagcgga acccccccacc tggcgacagg tgcctctgcg  300
gccaaaagcc acgtgtataa gatacacctg caaaggcggc acaaccccag tgccacgttg  360
tgagttggat agttgtggaa agagtcaaat ggctctcctc aagcgtattc aacaaggggc  420
tgaaggatgc ccagaaggta ccccattgta tgggatctga tctggggcct cggtgcacat  480
gctttacgtg tgtttagtcg aggttaaaaa acgtctaggc cccccgaacc acggggacgt  540
ggttttcctt tgaaaaacac gatgataata tgcttttcaa cctgagaatc ctcttgaaca  600
atgctgcttt tcggaatggc cacaacttta tggttcggaa cttccgttgc ggccagcctt  660
tacaaaacaa ggtccagctg aagggccggg atttgctcac actaaagaac tttactggag  720
aagagatcaa gtacatgcta tggctgtcgg ccgacctgaa gttccgtatc aagcagaagg  780
gagaatacct tccgctgctt caaggaaaga gcctcggcat gatctttgag aagcgctcaa  840
ccaggacccg cctttctact gaaactgggt tcgcgctgct cggtggccac ccctgcttcc  900
tgacgaccca ggacatccac ctcggagtga acgaatccct caccgatacc gcccgggtgt  960
tatcgagcat ggcagatgcc gtgctggcca gggtgtacaa acagtccgat ctcgatacct  1020
tggcaaagga ggcttccatt cccatcatca acggcctgag cgacctgtac cacccaatcc  1080
aaatcctggc tgactacctg accctgcaag agcactacag cagcctgaag ggtctgaccc  1140
tgtcatggat tggcgatgga aacaatattc tgcactccat catgatgtcc gccgcgaagt  1200
tcggaatgca tctgcaagcc gccactccaa aaggatacga accggatgca tccgtgacca  1260
agttggcgga acagtacgcg aaggagaacg gaaccaagct cctgctgact aacgacccgc  1320
tcgaggctgc gcatgggggt aacgtgctga ttacggacac ctggatctcc atggggcagg  1380
aggaagagaa gaagaagaga ctgcaggcat tccaggggta ccaggtcacc atgaaaaccg  1440
caaaagtggc agcttcggac tggactttcc tgcattgcct gccgaggaag ccggaggaag  1500
tcgacgacga agtgttctac tcgcctcggt ccctggtgtt ccccgaggcc gaaaaccgga  1560
agtggaccat catggccgtg atggtgtcct tgctgactga ctatagcccg cagctgcaga  1620
agcctaagtt ctgaataagt agatagtgca gtcactggca caacgcgttg cccggtaagc  1680
caatcgggta tacacggtcg tcatactgca gacagggttc ttctactttg caagatagtc  1740
tagagtagta aaataaatag tataagtcta g                                 1771
```

```
SEQ ID NO: 88          moltype = RNA  length = 1771
FEATURE                Location/Qualifiers
misc_feature           1..1771
                       note = Synthetic construct
source                 1..1771
                       mol_type = other RNA
                       organism = synthetic construct
SEQUENCE: 88
ctccctcccc ccccccctaac gttactggcc gaagccgctt ggaataaggc cggtgtgcgt  60
ttgtctatat gttattttcc accatattgc cgtcttttgg caatgtgagg gcccggaaac  120
ctggccctgt cttcttgacg agcattccta ggggtctttc ccctctcgcc aaaggaatgc  180
aaggtctgtt gaatgtcgtg aaggaagcag ttcctctgga agcttcttga agacaaacaa  240
cgtctgtagc gaccctttgc aggcagcgga acccccccacc tggcgacagg tgcctctgcg  300
gccaaaagcc acgtgtataa gatacacctg caaaggcggc acaaccccag tgccacgttg  360
tgagttggat agttgtggaa agagtcaaat ggctctcctc aagcgtattc aacaaggggc  420
tgaaggatgc ccagaaggta ccccattgta tgggatctga tctggggcct cggtgcacat  480
gctttacgtg tgtttagtcg aggttaaaaa acgtctaggc cccccgaacc acggggacgt  540
ggttttcctt tgaaaaacac gatgataata tgctgttcaa cctgcgcatc ctgctgaaca  600
acgccgcctt ccgcaacggc cacaacttca tggtgcgcaa cttccgctgc ggccagcccc  660
tgcagaacaa ggtgcagctg aagggccgcg acctgctgac cctgaagaac ttcaccggcg  720
aggagatcaa gtacatgctg tggctgagcg ccgacctgaa gttccgcatc aagcagaagg  780
gcgagtacct gcccctgctg cagggcaaga gcctgggcat gatcttcgag aagcgcagca  840
cccgcacccg cctgagcacc gagacaggcc tggccctgct gggcggccac ccctgcttcc  900
tgaccaccca ggacatccac ctgggcgtga acgagagcct gaccgacacc gcccgcgtgc  960
tgagcagcat ggccgacgcc gtgctggccc gcgtgtacaa gcagagcgac ctggacaccc  1020
tggccaagga ggccagcatc cccatcatca acggcctgag cgacctgtac caccccatcc  1080
agatcctggc cgactacctg accctgcagg agcactacag cagcctgaag ggcctgaccc  1140
```

```
tgagctggat cggcgacggc aacaacatcc tgcacagcat catgatgagc gccgccaagt  1200
tcggcatgca cctgcaggcc gccacccca agggctacga gcccgacgcc agcgtgacca  1260
agctggccga gcagtacgcc aaggagaacg gcaccaagct gctgctgacc aacgaccccc  1320
tggaggccgc ccacggcggc aacgtgctga tcaccgacac ctggatcagc atgggccagg  1380
aggaggagaa gaagaagcgc ctgcaggcct tccagggcta ccaggtgacc atgaagaccg  1440
ccaaggtggc cgccagcgac tggaccttcc tgcactgcct gccccgcaag cccgaggagg  1500
tggacgacga ggtgttctac agcccccgca gcctggtgtt ccccgaggcc gagaaccgca  1560
agtggaccat catggccgtg atggtgagcc tgctgaccga ctacagcccc cagctgcaga  1620
agcccaagtt ctgaataagt agatagtgca gtcactggca caacgcgttg cccggtaagc  1680
caatcgggta tacacggtcg tcatactgca gacagggttc ttctactttg caagatagtc  1740
tagagtagta aaataaatag tataagtcta g                                1771
```

```
SEQ ID NO: 89          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 89
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

```
SEQ ID NO: 90          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 90
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

```
SEQ ID NO: 91          moltype = RNA  length = 1368
FEATURE                Location/Qualifiers
```

```
misc_feature           1..1368
                       note = Synthetic construct
source                 1..1368
                       mol_type = other RNA
                       organism = synthetic construct
SEQUENCE: 91
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 92          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 92
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368

SEQ ID NO: 93          moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 93
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt ttcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
```

-continued

```
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag              1368
```

```
SEQ ID NO: 94          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 94
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatggtg ttcaacctcc gcatcctcct caacaacgcc gcattcagaa  180
acgggcacaa cttcatggtc agaaacttcc gctgcgggca acccctacaa aacaaggtcc  240
agctcaaggg gcgggacctc ctgaccctga agaacttcac cggcgaagag atcaagtaca  300
tgctgtggct ctccgccgac ctgaagttcc gcatcaagca gaagggagag tacctcccgc  360
tgctgcaagg gaagtcgctg ggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

```
SEQ ID NO: 95          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 95
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatggtg ttcaacctcc gcatcctcct caacaacgcc gcattcagaa  180
acgggcacaa cttcatggtc agaaacttcc gctgcgggca acccctacaa aaccgggtcc  240
agctcaaggg gcgggacctc ctgaccctga agaacttcac cggcgaagag atcaagtaca  300
tgctgtggct ctccgccgac ctgaagttcc gcatcaagca gaagggagag tacctcccgc  360
tgctgcaagg gaagtcgctg ggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

-continued

```
SEQ ID NO: 96          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 96
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatggtg ttcaacctcc gcatcctcct caacaacgcc gcattcagaa  180
acgggcacaa cttcatggtc agaaacttcc gctgcgggca acccctacaa aaccgggtcc  240
agctcaaggg gcgggacctc ctgaccctga agaacttcac cggcgaagag atccggtaca  300
tgctgtggct ctccgccgac ctgaagttcc gcatcaagca gaagggagag tacctcccgc  360
tgctgcaagg gaagtcgctg ggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 97          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 97
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcaacctcc gcatcctcct caacaacgcc gcattcagaa  180
acgggcacaa cttcatggtc agaaacttcc gctgcgggca acccctacaa aacaaggtcc  240
agctcaaggg gcgggacctc ctgaccctga agaacttcac cggcgaagag atcaagtaca  300
tgctgtggct ctccgccgac ctgaagttcc gcatcaagca gaagggagag tacctcccgc  360
tgctgcaagg gaagtcgctg ggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 98          moltype = RNA  length = 1471
FEATURE                Location/Qualifiers
misc_feature           1..1471
                       note = Synthetic construct
source                 1..1471
                       mol_type = other RNA
                       organism = synthetic construct
SEQUENCE: 98
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcaacctcc gcatcctcct caacaacgcc gcattcagaa  180
acgggcacaa cttcatggtc agaaacttcc gctgcgggca acccctacaa aaccgggtcc  240
agctcaaggg gcgggacctc ctgaccctga agaacttcac cggcgaagag atcaagtaca  300
tgctgtggct ctccgccgac ctgaagttcc gcatcaagca gaagggagag tacctcccgc  360
tgctgcaagg gaagtcgctg ggatgatct tcgagaagcg gtcaaccaga acccggctgt  420
```

```
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta gaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa a                                 1471
```

```
SEQ ID NO: 99          moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 99
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcaacctcc gcatcctcct caacaacgcc gcattcagaa  180
acgggcacaa cttcatggtc agaaacttcc gctgcgggca acccctacaa aaccgggtcc  240
agctcaaggg gcgggacctc ctgaccctga agaacttcac cggcgaagag atccggtaca  300
tgctgtggct ctccgccgac ctgaagttcc gcatcaagca gaagggagag tacctcccgc  360
tgctgcaagg gaagtcgctg gggatgatct tcgagaagcg gtcaaccaga acccggctgt  420
caaccgaaac cgggttcgca ctgctggggg gacacccgtg cttcctgacc acccaagaca  480
tccacctggg agtgaacgaa tcgctgaccg acaccgcccg cgtgctgagc tcaatggcgg  540
acgccgtgct ggcccgcgtg tacaagcagt ccgacctgga caccctggcc aaggaagcgt  600
ccatcccgat catcaacgga ctgtccgacc tgtaccaccc gatccagatc ctggcagact  660
acctgaccct gcaagaacac tacagctccc tgaagggcct gaccctgtca tggatcgggg  720
acgggaacaa catcctgcac tccataatga tgtcagccgc caagttcgga atgcacctcc  780
aagccgcaac cccgaagggc tacgaaccgg acgcatcagt gaccaaactg gccgagcagt  840
acgccaagga aaacggcacc aagctcctgc tgaccaacga cccgctggag gccgcacacg  900
gggggaacgt gctgatcacc gacacctgga tctccatggg acaggaggag gaaaagaaga  960
agcggctgca ggcgttccag gggtaccagg tcaccatgaa aaccgcgaag gtcgcggcat  1020
cagactggac cttcctgcac tgcctgcccc ggaagccgga agaggtggac gacgaggtgt  1080
tctactcgcc gcgctcgctg gtgttccccg aggcggagaa caggaagtgg accatcatgg  1140
cggtgatggt cagcctcctg accgactact cgccgcagct gcagaagccg aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371
```

```
SEQ ID NO: 100         moltype = RNA  length = 1471
FEATURE                Location/Qualifiers
misc_feature           1..1471
                       note = Synthetic construct
source                 1..1471
                       mol_type = other RNA
                       organism = synthetic construct
SEQUENCE: 100
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcaacctgc gcatcctgct gaacaacgcc gccttccgca  180
acggccacaa cttcatggtg cgcaacttcc gctgcggcca gcccctgcag aacaaggtgc  240
agctgaaggg ccgcgacctg ctgaccctga agaacttcac cggcgaggag atcaagtaca  300
tgctgtggct gagcgccgac ctgaagttcc gcatcaagca gaagggcgag tacctgcccc  360
tgctgcaggg caagagcctg ggcatgatct tcgagaagcg cagcacccgc acccgcctga  420
gcaccgagac aggcttcgcc ctgctgggcg gccacccctg cttcctgacc acccaggaca  480
tccacctggg cgtgaacgag agcctgaccg acaccgcccg cgtgctgagc agcatggccg  540
acgccgtgct ggcccgcgtg tacaagcaga gcgacctgga caccctggcc aaggaggcca  600
gcatccccat catcaacggc ctgagcgacc tgtaccaccc catccagatc ctggccgact  660
acctgaccct gcaggagcac tacagcagcc tgaagggcct gaccctgagc tggatcggcg  720
acggcaacaa catcctgcac agcatcatga tgagcgccgc caagttcggc atgcacctgc  780
aggccgccac ccccaagggc tacgagcccg acgccagcgt gaccaagctg gccgagcagt  840
acgccaagga gaacggcacc aagctgctgc tgaccaacga ccccctggag gccgcccacg  900
gcggcaacgt gctgatcacc gacacctgga tcagcatggg ccaggaggag gagaagaaga  960
agcgcctgca ggccttccag ggctaccagg tgaccatgaa gaccgccaag gtggccgcca  1020
gcgactggac cttcctgcac tgcctgcccc gcaagcccga ggaggtggac gacgaggtgt  1080
tctacagccc ccgcagcctg gtgttccccg aggccgagaa ccgcaagtgg accatcatgg  1140
ccgtgatggt gagcctgctg accgactaca gcccccagct gcagaagccc aagttctgat  1200
```

```
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta gaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa a                                 1471

SEQ ID NO: 101         moltype = RNA  length = 1371
FEATURE                Location/Qualifiers
misc_feature           1..1371
                       note = Synthetic construct
source                 1..1371
                       mol_type = other RNA
                       organism = synthetic construct
SEQUENCE: 101
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctg gtcaacctgc gcatcctgct gaacaacgcc gccttccgca  180
acggccacaa cttcatggtg cgcaacttcc gctgcggcca gcccctgcag aaccgggtgc  240
agctgaaggg ccgcgacctg ctgaccctga agaacttcac cggcgaggag atcaagtaca  300
tgctgtggct gagcgccgac ctgaagttcc gcatcaagca gaagggcgag tacctgcccc  360
tgctgcaggg caagagcctg ggcatgatct tcgagaagcg cagcacccgc acccgcctga  420
gcaccgagac aggcttcgcc ctgctgggcg gccacccctg cttcctgacc acccaggaca  480
tccacctggg cgtgaacgag agcctgaccg acaccgcccg cgtgctgagc agcatggccg  540
acgccgtgct ggcccgcgtg tacaagcaga gcgacctgga caccctggcc aaggaggcca  600
gcatccccat catcaacggc ctgagcgacc tgtaccaccc catccagatc ctggccgact  660
acctgaccct gcaggagcac tacagcagcc tgaagggcct gaccctgagc tggatcggcg  720
acggcaacaa catcctgcac agcatcatga tgagcgccgc caagttcggc atgcacctgc  780
aggccgccac ccccaagggc tacgagcccg acgccagcgt gaccaagctg gccgagcagt  840
acgccaagga gaacggcacc aagctgctgc tgaccaacga cccccctggag gccgcccacg  900
gcggcaacgt gctgatcacc gacacctgga tcagcatggg ccaggaggag gagaagaaga  960
agcgcctgca ggccttccag ggctaccagg tgaccatgaa gaccgccaag gtggccgcca  1020
gcgactggac cttcctgcac tgcctgcccc gcaagcccga ggaggtggac gacgaggtgt  1080
tctacagccc ccgcagcctg gtgttccccg aggccgagaa ccgcaagtgg accatcatgg  1140
ccgtgatggt gagcctgctg accgactaca gcccccagct gcagaagccc aagttctgat  1200
aactcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta g           1371

SEQ ID NO: 102         moltype = RNA  length = 1368
FEATURE                Location/Qualifiers
misc_feature           1..1368
                       note = Synthetic construct
source                 1..1368
                       mol_type = other RNA
                       organism = synthetic construct
SEQUENCE: 102
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgctt gtcaatctcc gcatcctcct taacaacgcc gcgtttagaa  180
acggccacaa cttcatggtc cggaacttca gatgtggcca gccgcttcaa aacaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctagc  1200
tcgagctagt gactgactag gatctggtta ccactaaacc agcctcaaga acacccgaat  1260
ggagtctcta agctacataa taccaactta cacttacaaa atgttgtccc ccaaaatgta  1320
gccattcgta tctgctccta ataaaaagaa agtttcttca cattctag               1368

SEQ ID NO: 103         moltype = RNA  length = 1368
FEATURE                Location/Qualifiers
misc_feature           1..1368
                       note = Synthetic construct
source                 1..1368
                       mol_type = other RNA
                       organism = synthetic construct
```

SEQUENCE: 103
tcaacacaac atatacaaaa caaacgaatc tcaagcaatc aagcattcta cttctattgc 60
agcaatttaa atcatttctt ttaaagcaaa agcaattttc tgaaaatttt caccatttac 120
gaacgatagc caccatgctt gtcaatctcc gcatcctcct taacaacgcc gcgtttagaa 180
acggccacaa cttcatggtc cggaacttca gatgtggcca gccgcttcaa aaccgggtcc 240
agctgaaggg ccgggatctt ctgaccctga agaactttac tggcgaagag atcaagtaca 300
tgctctggct ctccgcggac ttgaagttcc gcattaagca gaagggggaa taccttccgc 360
tgcttcaagg aaagagcctc ggcatgatct ttgagaagcg ctcaaccagg acccgccttt 420
ctactgaaac tgggttcgcg ctgctcggtg gccacccctg cttcctgacg acccaggaca 480
tccacctcgg agtgaacgaa tccctcaccg ataccgcccg ggtgttatcg agcatggcag 540
atgccgtgct ggccagggtg tacaaacagt ccgatctgga cactctggcc aaggaggcgt 600
caattcctat tatcaacggc cttagtgacc tctaccatcc gattcagatc ctggccgatt 660
acctcaccct gcaagaacac tacagctccc tgaagggtct gacattgtcc tggatcggcg 720
acggcaacaa cattctccat tccatcatga tgtccgccgc aaaattcggc atgcatcttc 780
aagccgccac gccgaagggt tacgagcccg acgcttccgt gactaagctc gccgagcagt 840
acgctaagga gaacggaacc aagcttctgc tgactaacga cccactagaa gcagcccacg 900
ggggcaacgt gcttattact gacacctgga tctccatggg ccaggaagaa gagaaaaaga 960
agcggctgca ggcgttccag ggatatcagg tcaccatgaa aaccgccaag gtcgctgcct 1020
ccgactggac cttcctgcac tgcctgcctc gcaagcctga agaagtggac gacgaggtgt 1080
tctactcgcc acggagcctc gtgttccccg aggccgagaa tagaaagtgg accatcatgg 1140
ccgtgatggt gtcactgctc accgactaca gcccgcagct tcagaagccc aagttctagc 1200
tcgagctagt gactgactag gatctggtta ccactaaacc agcctcaaga acacccgaat 1260
ggagtctcta agctacataa taccaactta cacttacaaa atgttgtccc ccaaaatgta 1320
gccattcgta tctgctccta ataaaaagaa agtttcttca cattctag 1368

SEQ ID NO: 104 moltype = RNA length = 1371
FEATURE Location/Qualifiers
misc_feature 1..1371
note = Synthetic construct
source 1..1371
mol_type = other RNA
organism = synthetic construct
SEQUENCE: 104
tcaacacaac atatacaaaa caaacgaatc tcaagcaatc aagcattcta cttctattgc 60
agcaatttaa atcatttctt ttaaagcaaa agcaattttc tgaaaatttt caccatttac 120
gaacgatagc caccatgggc cttgtcaatc tccgcatcct ccttaacaac gccgcgttta 180
gaaacggcca caacttcatg gtccggaact tcagatgtgg ccagccgctt caaaacaagg 240
tccagctgaa gggccgggat cttctgaccc tgaagaactt tactggcgaa gagatcaagt 300
acatgctctg gctctccgcg gacttgaagt tccgcattaa gcagaagggg gaataccttc 360
cgctgcttca aggaaagagc ctcggcatga tctttgagaa gcgctcaacc aggacccgcc 420
tttctactga aactgggttc gcgctgctcg gtggccaccc ctgcttcctg acgacccagg 480
acatccacct cggagtgaac gaatccctca ccgataccgc ccgggtgtta tcgagcatgg 540
cagatgccgt gctggccagg gtgtacaaac agtccgatct ggacactctg gccaaggagg 600
cgtcaattcc tattatcaac ggccttagtg acctctacca tccgattcag atcctggccg 660
attacctcac cctgcaagaa cactacagct ccctgaaggg tctgacattg tcctggatcg 720
gcgacggcaa caacattctc cattccatca tgatgtccgc cgcaaaattc ggcatgcatc 780
ttcaagccgc cacgccgaag ggttacgagc ccgacgcttc cgtgactaag ctcgccgagc 840
agtacgctaa ggagaacgga accaagcttc tgctgactaa cgacccacta gaagcagccc 900
acgggggcaa cgtgcttatt actgacacct ggatctccat gggccaggaa gaagagaaaa 960
agaagcggct gcaggcgttc cagggatatc aggtcaccat gaaaaccgcc aaggtcgctg 1020
cctccgactg gaccttcctg cactgcctgc ctcgcaagcc tgaagaagtg gacgacgagg 1080
tgttctactc gccacggagc ctcgtgttcc ccgaggccga gaatagaaag tggaccatca 1140
tggccgtgat ggtgtcactg ctcaccgact acagcccgca gcttcagaag cccaagttct 1200
agctcgagct agtgactgac taggatctgg ttaccactaa accagcctca agaacacccg 1260
aatggagtct ctaagctaca taataccaac ttacacttac aaaatgttgt cccccaaaat 1320
gtagccattc gtatctgctc ctaataaaaa gaaagtttct tcacattcta g 1371

SEQ ID NO: 105 moltype = RNA length = 1485
FEATURE Location/Qualifiers
misc_feature 1..1485
note = Synthetic construct
source 1..1485
mol_type = other RNA
organism = synthetic construct
SEQUENCE: 105
tcaacacaac atatacaaaa caaacgaatc tcaagcaatc aagcattcta cttctattgc 60
agcaatttaa atcatttctt ttaaagcaaa agcaattttc tgaaaatttt caccatttac 120
gaacgatagc caccatgggc cttgtcaatc tccgcatcct ccttaacaac gccgcgttta 180
gaaacggcca caacttcatg gtccggaact tcagatgtgg ccagccgctt caaaaccggg 240
tccagctgaa gggccgggat cttctgaccc tgaagaactt tactggcgaa gagatcaagt 300
acatgctctg gctctccgcg gacttgaagt tccgcattaa gcagaagggg gaataccttc 360
cgctgcttca aggaaagagc ctcggcatga tctttgagaa gcgctcaacc aggacccgcc 420
tttctactga aactgggttc gcgctgctcg gtggccaccc ctgcttcctg acgacccagg 480
acatccacct cggagtgaac gaatccctca ccgataccgc ccgggtgtta tcgagcatgg 540
cagatgccgt gctggccagg gtgtacaaac agtccgatct ggacactctg gccaaggagg 600
cgtcaattcc tattatcaac ggccttagtg acctctacca tccgattcag atcctggccg 660
attacctcac cctgcaagaa cactacagct ccctgaaggg tctgacattg tcctggatcg 720
gcgacggcaa caacattctc cattccatca tgatgtccgc cgcaaaattc ggcatgcatc 780
ttcaagccgc cacgccgaag ggttacgagc ccgacgcttc cgtgactaag ctcgccgagc 840

```
agtacgctaa ggagaacgga accaagcttc tgctgactaa cgacccacta gaagcagccc  900
acgggggcaa cgtgcttatt actgacacct ggatctccat gggccaggaa gaagagaaaa  960
agaagcggct gcaggcgttc cagggatatc aggtcaccat gaaaaccgcc aaggtcgctg  1020
cctccgactg gaccttcctg cactgcctgc ctcgcaagcc tgaagaagtg gacgacgagg  1080
tgttctactc gccacggagc ctcgtgttcc ccgaggccga gaatagaaag tggaccatca  1140
tggccgtgat ggtgtcactg ctcaccgact acagcccgca gcttcagaag cccaagttct  1200
agctcgagct agtgactgac taggatctgg ttaccactaa accagcctca agaacacccg  1260
aatggagtct ctaagctaca taataccaac ttacacttac aaaatgttgt cccccaaaat  1320
gtagccattc gtatctgctc ctaataaaaa gaaagtttct tcacattcta gaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaa                  1485

SEQ ID NO: 106          moltype = RNA  length = 1374
FEATURE                 Location/Qualifiers
misc_feature            1..1374
                        note = Synthetic construct
source                  1..1374
                        mol_type = other RNA
                        organism = synthetic construct
SEQUENCE: 106
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgggc ggacttgtca atctccgcat cctccttaac aacgccgcgt  180
ttagaaacgg ccacaacttc atggtccgga acttcagatg tggccagccg cttcaaaaca  240
aggtccagct gaagggccgg gatcttctga ccctgaagaa ctttactggc gaagagatca  300
agtacatgct ctggctctcc gcggacttga agttccgcat taagcagaag gggggaatacc  360
ttccgctgct tcaaggaaag agcctcggca tgatctttga gaagcgctca accaggaccc  420
gcctttctac tgaaactggg ttcgcgctgc tcggtggcca cccctgcttc ctgacgaccc  480
aggacatcca cctcggagtg aacgaatccc tcaccgatac cgcccgggtg ttatcgagca  540
tggcagatgc cgtgctggcc agggtgtaca aacagtccga tctggacact ctggccaagg  600
aggcgtcaat tcctattatc aacggcctta gtgacctcta ccatccgatt cagatcctgg  660
ccgattacct caccctgcaa gaacactaca gctccctgaa gggtctgaca ttgtcctgga  720
tcggcgacgg caacaacatt ctccattcca tcatgatgtc cgccgcaaaa ttcggcatgc  780
atcttcaagc cgccacgccg aagggttacg agcccgacgc ttccgtgact aagctcgccg  840
agcagtacgc taaggagaac ggaaccaagc ttctgctgac taacgaccca ctagaagcag  900
cccacggggg caacgtgctt attactgaca cctggatctc catgggccag gaagaagaga  960
aaaagaagcg gctgcaggcg ttccagggat atcaggtcac catgaaaacc gccaaggtcg  1020
ctgcctccga ctggaccttc ctgcactgcc tgcctcgcaa gcctgaagaa gtggacgacg  1080
aggtgttcta ctcgccacgg agcctcgtgt tccccgaggc cgagaataga aagtggacca  1140
tcatggccgt gatggtgtca ctgctcaccg actacagccc gcagcttcag aagcccaagt  1200
tctagctcga gctagtgact gactaggatc tggttaccac taaaccagcc tcaagaacac  1260
ccgaatggag tctctaagct acataatacc aacttacact tacaaaatgt tgtcccccaa  1320
aatgtagcca ttcgtatctg ctcctaataa aaagaaagtt tcttcacatt ctag        1374

SEQ ID NO: 107          moltype = RNA  length = 1377
FEATURE                 Location/Qualifiers
misc_feature            1..1377
                        note = Synthetic construct
source                  1..1377
                        mol_type = other RNA
                        organism = synthetic construct
SEQUENCE: 107
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt ttcaatctcc gcatcctcct taacaacgcc gcgtttagaa  180
acggccacaa cttcatggtc cggaacttca gatgtggcca gccgcttcaa ggcaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctaga  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377
```

```
SEQ ID NO: 108          moltype = RNA  length = 1377
FEATURE                 Location/Qualifiers
misc_feature            1..1377
                        note = Synthetic construct
source                  1..1377
                        mol_type = other RNA
                        organism = synthetic construct
SEQUENCE: 108
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt ttcaatctcc gcatcctcct taacaacgcc gcgtttagaa  180
acggccacaa cttcatggtc cggaacttca gatgtggcca gccgcttcaa ggccgggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctaga  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377

SEQ ID NO: 109          moltype = RNA  length = 1377
FEATURE                 Location/Qualifiers
misc_feature            1..1377
                        note = Synthetic construct
source                  1..1377
                        mol_type = other RNA
                        organism = synthetic construct
SEQUENCE: 109
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt ttcaatctcc gcatcctcct taacaacgcc gcgtttagaa  180
acggccacaa cttcatggtc cggaacttca gatgtggcca gccgcttcaa ggccgggtcc  240
agctgaaggg ccgggatctt ctgaccctga agaactttac tggcgaagag atcaggtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctaga  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377

SEQ ID NO: 110          moltype = RNA  length = 1377
FEATURE                 Location/Qualifiers
misc_feature            1..1377
                        note = Synthetic construct
source                  1..1377
                        mol_type = other RNA
                        organism = synthetic construct
SEQUENCE: 110
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt gtcaatctcc gcatcctcct taacaacgcc gcgtttagaa  180
acggccacaa cttcatggtc cggaacttca gatgtggcca gccgcttcaa ggcagggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
```

-continued

```
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctaag  1200
tgaatagact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377

SEQ ID NO: 111         moltype = RNA  length = 1496
FEATURE                Location/Qualifiers
misc_feature           1..1496
                       note = Synthetic construct
source                 1..1496
                       mol_type = other RNA
                       organism = synthetic construct
SEQUENCE: 111
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt ttcaatctcc gcatcctcct taacaacgcc gcgtttagaa  180
acggccacaa cttcatggtc cggaacttca gatgtggcca gccgcttcaa gtcaaggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
ccgtgatggt gtcactgctc accgactaca gcccgcagct tcagaagccc aagttctaga  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctagaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaa      1496

SEQ ID NO: 112         moltype = RNA  length = 1377
FEATURE                Location/Qualifiers
misc_feature           1..1377
                       note = Synthetic construct
source                 1..1377
                       mol_type = other RNA
                       organism = synthetic construct
SEQUENCE: 112
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc catggccctt ttcaatctcc gcatcctcct taacaacgcc gcgtttagaa  180
acggccacaa cttcatggtc cggaacttca gatgtggcca gccgcttcaa gtcagggtcc  240
agctgaaggg ccgggatctt ctgaccctga agaactttac tggcgaagag atcaagtaca  300
tgctctggct ctccgcggac ttgaagttcc gcattaagca gaagggggaa taccttccgc  360
tgcttcaagg aaagagcctc ggcatgatct ttgagaagcg ctcaaccagg acccgccttt  420
ctactgaaac tgggttcgcg ctgctcggtg gccacccctg cttcctgacg acccaggaca  480
tccacctcgg agtgaacgaa tccctcaccg ataccgcccg ggtgttatcg agcatggcag  540
atgccgtgct ggccagggtg tacaaacagt ccgatctgga cactctggcc aaggaggcgt  600
caattcctat tatcaacggc cttagtgacc tctaccatcc gattcagatc ctggccgatt  660
acctcaccct gcaagaacac tacagctccc tgaagggtct gacattgtcc tggatcggcg  720
acggcaacaa cattctccat tccatcatga tgtccgccgc aaaattcggc atgcatcttc  780
aagccgccac gccgaagggt tacgagcccg acgcttccgt gactaagctc gccgagcagt  840
acgctaagga gaacggaacc aagcttctgc tgactaacga cccactagaa gcagcccacg  900
ggggcaacgt gcttattact gacacctgga tctccatggg ccaggaagaa gagaaaaaga  960
agcggctgca ggcgttccag ggatatcagg tcaccatgaa aaccgccaag gtcgctgcct  1020
ccgactggac cttcctgcac tgcctgcctc gcaagcctga agaagtggac gacgaggtgt  1080
tctactcgcc acggagcctc gtgttccccg aggccgagaa tagaaagtgg accatcatgg  1140
```

```
ccgtgatggt gtcactgctc accgactaca gcccgcagct tcagaagccc aagttctaga  1200
taagtgaact cgagctagtg actgactagg atctggttac cactaaacca gcctcaagaa  1260
cacccgaatg gagtctctaa gctacataat accaacttac acttacaaaa tgttgtcccc  1320
caaaatgtag ccattcgtat ctgctcctaa taaaaagaaa gtttcttcac attctag     1377

SEQ ID NO: 113         moltype = RNA  length = 1282
FEATURE                Location/Qualifiers
misc_feature           1..1282
                       note = Synthetic construct
source                 1..1282
                       mol_type = other RNA
                       organism = synthetic construct
SEQUENCE: 113
ggcagaaaaa tttgctacat tgtttcacaa acttcaaata ttattcattt atttagatct  60
attattacat caaaacaaaa agccgccacc atgctgttca acctgcgcat cctgctgaac  120
aacgccgcct tccgcaacgg ccacaacttc atggtgcgca acttccgctg cggccagccc  180
ctgcagaaca aggtgcagct gaagggccgc gacctgctga ccctgaagaa cttcaccggc  240
gaggagatca agtacatgct gtggctgagc gccgacctga agttccgcat caagcagaag  300
ggcgagtacc tgcccctgct gcagggcaag agcctgggca tgatcttcga gaagcgcagc  360
acccgcaccc gcctgagcac cgagacaggc ttcgccctgc tgggcggcca cccctgcttc  420
ctgaccaccc aggacatcca cctgggcgtg aacgagagcc tgaccgacac cgcccgcgtg  480
ctgagcagca tggccgacgc cgtgctggcc cgcgtgtaca agcagagcga cctggacacc  540
ctggccaagg aggccagcat ccccatcatc aacggcctga gcgacctgta ccaccccatc  600
cagatcctgg ccgactacct gaccctgcag gagcactaca gcagcctgaa gggcctgacc  660
ctgagctgga tcggcgacgg caacaacatc ctgcacagca tcatgatgag cgccgccaag  720
ttcggcatgc acctgcaggc cgccaccccc aagggctacg agcccgacgc cagcgtgacc  780
aagctggccg agcagtacgc caaggagaac ggcaccaagc tgctgctgac caacgacccc  840
ctggaggccg cccacggcgg caacgtgctg atcaccgaca cctggatcag catgggccag  900
gaggaggaga agaagaagcg cctgcaggcc ttccagggct accaggtgac catgaagacc  960
gccaaggtgg ccgccagcga ctggaccttc ctgcactgcc tgccccgcaa gcccgaggag  1020
gtggacgacg aggtgttcta cagcccccgc agcctggtgt tccccgaggc cgagaaccgc  1080
aagtggacca tcatggccgt gatggtgagc ctgctgaccg actacagccc ccagctgcag  1140
aagcccaagt tctgaggtct ctagtaatga gctggagcct cggtagccgt tcctcctgcc  1200
cgctgggcct cccaacgggc cctcctcccc tccttgcacc ggcccttcct ggtctttgaa  1260
taaagtctga gtgggcatct ag                                          1282

SEQ ID NO: 114         moltype = RNA  length = 1285
FEATURE                Location/Qualifiers
misc_feature           1..1285
                       note = Synthetic construct
source                 1..1285
                       mol_type = other RNA
                       organism = synthetic construct
SEQUENCE: 114
ggcagaaaaa tttgctacat tgtttcacaa acttcaaata ttattcattt atttagatct  60
attattacat caaaacaaaa agccgccacc atgggagtat tcaacctgcg catcctgctg  120
aacaacgccg ccttccgcaa cggccacaac ttcatggtgc gcaacttccg ctgcggccag  180
cccctgcaga acaaggtgca gctgaagggc cgcgacctgc tgaccctgaa gaacttcacc  240
ggcgaggaga tcaagtacat gctgtggctg agcgccgacc tgaagttccg catcaagcag  300
aagggcgagt acctgcccct gctgcagggc aagagcctgg gcatgatctt cgagaagcgc  360
agcacccgca cccgcctgag caccgagaca ggcttcgccc tgctgggcgg ccacccctgc  420
ttcctgacca cccaggacat ccacctgggc gtgaacgaga gcctgaccga caccgcccgc  480
gtgctgagca gcatggccga cgccgtgctg gcccgcgtgt acaagcagag cgacctggac  540
accctggcca aggaggccag catccccatc atcaacggcc tgagcgacct gtaccacccc  600
atccagatcc tggccgacta cctgaccctg caggagcact acagcagcct gaagggcctg  660
accctgagct ggatcggcga cggcaacaac atcctgcaca gcatcatgat gagcgccgcc  720
aagttcggca tgcacctgca ggccgccacc cccaagggct acgagcccga cgccagcgtg  780
accaagctgg ccgagcagta cgccaaggag aacggcacca agctgctgct gaccaacgac  840
cccctggagg ccgcccacgg cggcaacgtg ctgatcaccg acacctggat cagcatgggc  900
caggaggagg agaagaagaa gcgcctgcag gccttccagg gctaccaggt gaccatgaag  960
accgccaagg tggccgccag cgactggacc ttcctgcact gcctgccccg caagcccgag  1020
gaggtggacg acgaggtgtt ctacagcccc cgcagcctgg tgttccccga ggccgagaac  1080
cgcaagtgga ccatcatggc cgtgatggtg agcctgctga ccgactacag cccccagctg  1140
cagaagccca agttctgagg tctctagtaa tgagctggag cctcggtagc cgttcctcct  1200
gcccgctggg cctcccaacg ggccctcctc ccctccttgc accggccctt cctggtcttt  1260
gaataaagtc tgagtgggca tctag                                       1285

SEQ ID NO: 115         moltype = RNA  length = 1285
FEATURE                Location/Qualifiers
misc_feature           1..1285
                       note = Synthetic construct
source                 1..1285
                       mol_type = other RNA
                       organism = synthetic construct
SEQUENCE: 115
ggcagaaaaa tttgctacat tgtttcacaa acttcaaata ttattcattt atttagatct  60
attattacat caaaacaaaa agccgccacc atgggagtat tcaacctgcg catcctgctg  120
aacaacgccg ccttccgcaa cggccacaac ttcatggtgc gcaacttccg ctgcggccag  180
cccctgcaga accgggtgca gctgaagggc cgcgacctgc tgaccctgaa gaacttcacc  240
```

```
ggcgaggaga tccggtacat gctgtggctg agcgccgacc tgaagttccg catcaagcag  300
aagggcgagt acctgcccct gctgcagggc aagagcctgg gcatgatctt cgagaagcgc  360
agcacccgca cccgcctgag caccgagaca ggcttcgccc tgctgggcgg ccacccctgc  420
ttcctgacca cccaggacat ccacctgggc gtgaacgaga gcctgaccga caccgcccgc  480
gtgctgagca gcatggccga cgccgtgctg gcccgcgtgt acaagcagag cgacctggac  540
accctggcca aggaggccag catccccatc atcaacggcc tgagcgacct gtaccacccc  600
atccagatcc tggccgacta cctgaccctg caggagcact acagcagcct gaagggcctg  660
accctgagct ggatcggcga cggcaacaac atcctgcaca gcatcatgat gagcgccgcc  720
aagttcggca tgcacctgca ggccgccacc cccaagggct acgagcccga cgccagcgtg  780
accaagctgg ccgagcagta cgccaaggag aacggcacca agctgctgct gaccaacgac  840
cccctggagg ccgcccacgg cggcaacgtg ctgatcaccg acacctggat cagcatgggc  900
caggaggagg agaagaagaa gcgcctgcag gccttccagg gctaccaggt gaccatgaag  960
accgccaagg tggccgccag cgactggacc ttcctgcact gcctgccccg caagcccgag  1020
gaggtggacg acgaggtgtt ctacagcccc cgcagcctgg tgttccccga ggccgagaac  1080
cgcaagtgga ccatcatggc cgtgatggtg agcctgctga ccgactacag cccccagctg  1140
cagaagccca agttctgagg tctctagtaa tgagctggag cctcggtagc cgttcctcct  1200
gcccgctggg cctcccaacg ggccctcctc ccctccttgc accggccctt cctggtcttt  1260
gaataaagtc tgagtgggca tctag                                        1285
```

```
SEQ ID NO: 116         moltype = RNA  length = 1285
FEATURE                Location/Qualifiers
misc_feature           1..1285
                       note = Synthetic construct
source                 1..1285
                       mol_type = other RNA
                       organism = synthetic construct
SEQUENCE: 116
ggcagaaaaa tttgctacat tgtttcacaa acttcaaata ttattcattt atttagatct  60
attattacat caaaacaaaa agccgccacc atgctggtat tcaacctgcg catcctgctg  120
aacaacgccg ccttccgcaa cggccacaac ttcatggtgc gcaacttccg ctgcggccag  180
cccctgcaga accgggtgca gctgaagggc cgcgacctgc tgaccctgaa gaacttcacc  240
ggcgaggaga tccggtacat gctgtggctg agcgccgacc tgaagttccg catcaagcag  300
aagggcgagt acctgcccct gctgcagggc aagagcctgg gcatgatctt cgagaagcgc  360
agcacccgca cccgcctgag caccgagaca ggcttcgccc tgctgggcgg ccacccctgc  420
ttcctgacca cccaggacat ccacctgggc gtgaacgaga gcctgaccga caccgcccgc  480
gtgctgagca gcatggccga cgccgtgctg gcccgcgtgt acaagcagag cgacctggac  540
accctggcca aggaggccag catccccatc atcaacggcc tgagcgacct gtaccacccc  600
atccagatcc tggccgacta cctgaccctg caggagcact acagcagcct gaagggcctg  660
accctgagct ggatcggcga cggcaacaac atcctgcaca gcatcatgat gagcgccgcc  720
aagttcggca tgcacctgca ggccgccacc cccaagggct acgagcccga cgccagcgtg  780
accaagctgg ccgagcagta cgccaaggag aacggcacca agctgctgct gaccaacgac  840
cccctggagg ccgcccacgg cggcaacgtg ctgatcaccg acacctggat cagcatgggc  900
caggaggagg agaagaagaa gcgcctgcag gccttccagg gctaccaggt gaccatgaag  960
accgccaagg tggccgccag cgactggacc ttcctgcact gcctgccccg caagcccgag  1020
gaggtggacg acgaggtgtt ctacagcccc cgcagcctgg tgttccccga ggccgagaac  1080
cgcaagtgga ccatcatggc cgtgatggtg agcctgctga ccgactacag cccccagctg  1140
cagaagccca agttctgagg tctctagtaa tgagctggag cctcggtagc cgttcctcct  1200
gcccgctggg cctcccaacg ggccctcctc ccctccttgc accggccctt cctggtcttt  1260
gaataaagtc tgagtgggca tctag                                        1285
```

```
SEQ ID NO: 117         moltype = RNA  length = 1225
FEATURE                Location/Qualifiers
misc_feature           1..1225
                       note = Synthetic construct
source                 1..1225
                       mol_type = other RNA
                       organism = synthetic construct
SEQUENCE: 117
attattacat caaaacaaaa agccgccacc atgggagtat tcaacctgcg catcctgctg  60
aacaacgccg ccttccgcaa cggccacaac ttcatggtgc gcaacttccg ctgcggccag  120
cccctgcaga acaaggtgca gctgaagggc cgcgacctgc tgaccctgaa gaacttcacc  180
ggcgaggaga tcaagtacat gctgtggctg agcgccgacc tgaagttccg catcaagcag  240
aagggcgagt acctgcccct gctgcagggc aagagcctgg gcatgatctt cgagaagcgc  300
agcacccgca cccgcctgag caccgagaca ggcttcgccc tgctgggcgg ccacccctgc  360
ttcctgacca cccaggacat ccacctgggc gtgaacgaga gcctgaccga caccgcccgc  420
gtgctgagca gcatggccga cgccgtgctg gcccgcgtgt acaagcagag cgacctggac  480
accctggcca aggaggccag catccccatc atcaacggcc tgagcgacct gtaccacccc  540
atccagatcc tggccgacta cctgaccctg caggagcact acagcagcct gaagggcctg  600
accctgagct ggatcggcga cggcaacaac atcctgcaca gcatcatgat gagcgccgcc  660
aagttcggca tgcacctgca ggccgccacc cccaagggct acgagcccga cgccagcgtg  720
accaagctgg ccgagcagta cgccaaggag aacggcacca agctgctgct gaccaacgac  780
cccctggagg ccgcccacgg cggcaacgtg ctgatcaccg acacctggat cagcatgggc  840
caggaggagg agaagaagaa gcgcctgcag gccttccagg gctaccaggt gaccatgaag  900
accgccaagg tggccgccag cgactggacc ttcctgcact gcctgccccg caagcccgag  960
gaggtggacg acgaggtgtt ctacagcccc cgcagcctgg tgttccccga ggccgagaac  1020
cgcaagtgga ccatcatggc cgtgatggtg agcctgctga ccgactacag cccccagctg  1080
cagaagccca agttctgagg tctctagtaa tgagctggag cctcggtagc cgttcctcct  1140
gcccgctggg cctcccaacg ggccctcctc ccctccttgc accggccctt cctggtcttt  1200
gaataaagtc tgagtgggca tctag                                        1225
```

```
SEQ ID NO: 118          moltype = RNA  length = 1225
FEATURE                 Location/Qualifiers
misc_feature            1..1225
                        note = Synthetic construct
source                  1..1225
                        mol_type = other RNA
                        organism = synthetic construct
SEQUENCE: 118
attattacat caaaacaaaa agccgccacc atgggagtat tcaacctgcg catcctgctg  60
aacaacgccg ccttccgcaa cggccacaac ttcatggtgc gcaacttccg ctgcggccag  120
cccctgcaga accgggtgca gctgaagggc cgcgacctgc tgaccctgaa gaacttcacc  180
ggcgaggaga tccggtacat gctgtggctg agcgccgacc tgaagttccg catcaagcag  240
aagggcgagt acctgcccct gctgcagggc aagagcctgg gcatgatctt cgagaagcgc  300
agcacccgca cccgcctgag caccgagaca ggcttcgccc tgctgggcgg ccacccctgc  360
ttcctgacca cccaggacat ccacctgggc gtgaacgaga gcctgaccga caccgcccgc  420
gtgctgagca gcatggccga cgccgtgctg gcccgcgtgt acaagcagag cgacctggac  480
accctggcca aggaggccag catccccatc atcaacggcc tgagcgacct gtaccacccc  540
atccagatcc tggccgacta cctgaccctg caggagcact acagcagcct gaagggcctg  600
accctgagct ggatcggcga cggcaacaac atcctgcaca gcatcatgat gagcgccgcc  660
aagttcggca tgcacctgca ggccgccacc cccaagggct acgagcccga cgccagcgtg  720
accaagctgg ccgagcagta cgccaaggag aacggcacca agctgctgct gaccaacgac  780
cccctggagg ccgcccacgg cggcaacgtg ctgatcaccg acacctggat cagcatgggc  840
caggaggagg agaagaagaa gcgcctgcag gccttccagg gctaccaggt gaccatgaag  900
accgccaagg tggccgccag cgactggacc ttcctgcact gcctgccccg caagcccgag  960
gaggtggacg acgaggtgtt ctacagcccc cgcagcctgg tgttccccga ggccgagaac  1020
cgcaagtgga ccatcatggc cgtgatggtg agcctgctga ccgactacag cccccagctg  1080
cagaagccca agttctgagg tctctagtaa tgagctggag cctcggtagc cgttcctcct  1140
gcccgctggg cctcccaacg ggccctcctc ccctccttgc accggccctt cctggtcttt  1200
gaataaagtc tgagtgggca tctag                                       1225

SEQ ID NO: 119          moltype = RNA  length = 1228
FEATURE                 Location/Qualifiers
misc_feature            1..1228
                        note = Synthetic construct
source                  1..1228
                        mol_type = other RNA
                        organism = synthetic construct
SEQUENCE: 119
attattacat caaaacaaaa agccgccacc atgctggtat tcaacctgcg catcctgctg  60
aacaacgccg ccttccgcaa cggccacaac ttcatggtgc gcaacttccg ctgcggccag  120
cccctgcaga accgggtgca gctgaagggc cgcgacctgc tgaccctgaa gaacttcacc  180
ggcgaggaga tccggtacat gctgtggctg agcgccgacc tgaagttccg catcaagcag  240
aagggcgagt acctgcccct gctgcagggc aagagcctgg gcatgatctt cgagaagcgc  300
agcacccgca cccgcctgag caccgagaca ggcttcgccc tgctgggcgg ccacccctgc  360
ttcctgacca cccaggacat ccacctgggc gtgaacgaga gcctgaccga caccgcccgc  420
gtgctgagca gcatggccga cgccgtgctg gcccgcgtgt acaagcagag cgacctggac  480
accctggcca aggaggccag catccccatc atcaacggcc tgagcgacct gtaccacccc  540
atccagatcc tggccgacta cctgaccctg caggagcact acagcagcct gaagggcctg  600
accctgagct ggatcggcga cggcaacaac atcctgcaca gcatcatgat gagcgccgcc  660
aagttcggca tgcacctgca ggccgccacc cccaagggct acgagcccga cgccagcgtg  720
accaagctgg ccgagcagta cgccaaggag aacggcacca agctgctgct gaccaacgac  780
cccctggagg ccgcccacgg cggcaacgtg ctgatcaccg acacctggat cagcatgggc  840
caggaggagg agaagaagaa gcgcctgcag gccttccagg gctaccaggt gaccatgaag  900
accgccaagg tggccgccag cgactggacc ttcctgcact gcctgccccg caagcccgag  960
gaggtggacg acgaggtgtt ctacagcccc cgcagcctgg tgttccccga ggccgagaac  1020
cgcaagtgga ccatcatggc cgtgatggtg agcctgctga ccgactacag cccccagctg  1080
cagaagccca agttctgagg tctctagtaa tgagctggag cctcggtagc cgttcctcct  1140
gcccgctggg cctcccaacg ggccctcctc ccctccttgc accggccctt cctggtcttt  1200
gaataaagtc tgagtgggca gcatctag                                    1228

SEQ ID NO: 120          moltype = RNA  length = 1376
FEATURE                 Location/Qualifiers
misc_feature            1..1376
                        note = Synthetic construct
source                  1..1376
                        mol_type = other RNA
                        organism = synthetic construct
SEQUENCE: 120
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatagc caccatgttg ttcaacttga ggatcttgtt gaacaacgcc gccttcagga  180
acggacacaa cttcatggta aggaacttca ggtgcggaca gcccttgcag aacaaagtac  240
agttgaaagg aagggacttg ttgacattga aaaacttcac aggagaagaa atcaaataca  300
tgttgtggtt gtcggccgac ttgaaattca ggatcaaaca gaaaggagaa tacttgccct  360
tgttgcaggg aaaatcgttg ggaatgatct tcgaaaaaag gtcgacaagg acaaggttgt  420
cgacagaaac aggattcgcc ttgttgggag gacacccctg cttcttgaca acacaggaca  480
tccacttggg agtaaacgaa tcgttgacag acacagccag ggtattgtcg tcgatggccg  540
acgccgtatt ggccagggta tacaaacagt cggacttgga cacattggcc aaagaagcct  600
```

```
cgatccccat catcaacgga ttgtcggact tgtaccaccc catccagatc ttggccgact  660
acttgacatt gcaggaacac tactcgtcgt tgaaaggatt gacattgtcg tggatcggag  720
acggaaacaa catcttgcac tcgatcatga tgtcggccgc caaattcgga atgcacttgc  780
aggccgccac acccaaagga tacgaacccg acgcctcggt aacaaaattg gccgaacagt  840
acgccaaaga aaacggaaca aaattgttgt tgacaaacga ccccttggaa gccgcccacg  900
gaggaaacgt attgatcaca gacacatgga tctcgatggg acaggaagaa gaaaaaaaaa  960
aaaggttgca ggccttccag ggataccagg taacaatgaa aacagccaaa gtagccgcct  1020
cggactggac attcttgcac tgcttgccca ggaaacccga agaagtagac gacgaagtat  1080
tctactcgcc caggtcgttg gtattccccg aagccgaaaa caggaaatgg acaatcatgg  1140
ccgtaatggt atcgttgttg acagactact cgccccagtt gcagaaaccc aaattctgaa  1200
tagtgaactc gagctagtga ctgactagga tctggttacc actaaaccag cctcaagaac  1260
acccgaatgg agtctctaag ctacataata ccaacttaca cttacaaaat gttgtccccc  1320
aaaatgtagc cattcgtatc tgctcctaat aaaaagaaag tttcttcaca ttctag      1376
```

```
SEQ ID NO: 121         moltype = RNA  length = 1222
FEATURE                Location/Qualifiers
misc_feature           1..1222
                       note = Synthetic construct
source                 1..1222
                       mol_type = other RNA
                       organism = synthetic construct
SEQUENCE: 121
attattacat caaaacaaaa agccgccacc atgctgttca acctgcgcat cctgctgaac  60
aacgccgcct tccgcaacgg ccacaacttc atggtgcgca acttccgctg cggccagccc  120
ctgcagggca aggtgcagct gaagggccgc gacctgctga ccctgaagaa cttcaccggc  180
gaggagatca agtacatgct gtggctgagc gccgacctga agttccgcat caagcagaag  240
ggcgagtacc tgcccctgct gcagggcaag agcctgggca tgatcttcga gaagcgcagc  300
acccgcaccc gcctgagcac cgagacaggc ttcgccctgc tgggcggcca cccctgcttc  360
ctgaccaccc aggacatcca cctgggcgtg aacgagagcc tgaccgacac cgcccgcgtg  420
ctgagcagca tggccgacgc cgtgctggcc cgcgtgtaca agcagagcga cctggacacc  480
ctggccaagg aggccagcat ccccatcatc aacggcctga gcgacctgta ccaccccatc  540
cagatcctgg ccgactacct gaccctgcag gagcactaca gcagcctgaa gggcctgacc  600
ctgagctgga tcggcgacgg caacaacatc ctgcacagca tcatgatgag cgccgccaag  660
ttcggcatgc acctgcaggc cgccaccccc aagggctacg agcccgacgc cagcgtgacc  720
aagctggccg agcagtacgc caaggagaac ggcaccaagc tgctgctgac caacgacccc  780
ctggaggccg cccacggcgg caacgtgctg atcaccgaca cctggatcag catgggccag  840
gaggaggaga agaagaagcg cctgcaggcc ttccagggct accaggtgac catgaagacc  900
gccaaggtgg ccgccagcga ctggaccttc ctgcactgcc tgccccgcaa gcccgaggag  960
gtggacgacg aggtgttcta cagcccccgc agcctggtgt tccccgaggc cgagaaccgc  1020
aagtggacca tcatggccgt gatggtgagc ctgctgaccg actacagccc ccagctgcag  1080
aagcccaagt tctgaggtct ctagtaatga gctggagcct cggtagccgt tcctcctgcc  1140
cgctgggcct cccaacgggc cctcctcccc tccttgcacc ggcccttcct ggtctttgaa  1200
taaagtctga gtgggcatct ag                                          1222
```

```
SEQ ID NO: 122         moltype = RNA  length = 1222
FEATURE                Location/Qualifiers
misc_feature           1..1222
                       note = Synthetic construct
source                 1..1222
                       mol_type = other RNA
                       organism = synthetic construct
SEQUENCE: 122
attattacat caaaacaaaa agccgccacc atgctgttca acctgcgcat cctgctgaac  60
aacgccgcct tccgcaacgg ccacaacttc atggtgcgca acttccgctg cggccagccc  120
ctgcagggcc gggtgcagct gaagggccgc gacctgctga ccctgaagaa cttcaccggc  180
gaggagatca agtacatgct gtggctgagc gccgacctga agttccgcat caagcagaag  240
ggcgagtacc tgcccctgct gcagggcaag agcctgggca tgatcttcga gaagcgcagc  300
acccgcaccc gcctgagcac cgagacaggc ttcgccctgc tgggcggcca cccctgcttc  360
ctgaccaccc aggacatcca cctgggcgtg aacgagagcc tgaccgacac cgcccgcgtg  420
ctgagcagca tggccgacgc cgtgctggcc cgcgtgtaca agcagagcga cctggacacc  480
ctggccaagg aggccagcat ccccatcatc aacggcctga gcgacctgta ccaccccatc  540
cagatcctgg ccgactacct gaccctgcag gagcactaca gcagcctgaa gggcctgacc  600
ctgagctgga tcggcgacgg caacaacatc ctgcacagca tcatgatgag cgccgccaag  660
ttcggcatgc acctgcaggc cgccaccccc aagggctacg agcccgacgc cagcgtgacc  720
aagctggccg agcagtacgc caaggagaac ggcaccaagc tgctgctgac caacgacccc  780
ctggaggccg cccacggcgg caacgtgctg atcaccgaca cctggatcag catgggccag  840
gaggaggaga agaagaagcg cctgcaggcc ttccagggct accaggtgac catgaagacc  900
gccaaggtgg ccgccagcga ctggaccttc ctgcactgcc tgccccgcaa gcccgaggag  960
gtggacgacg aggtgttcta cagcccccgc agcctggtgt tccccgaggc cgagaaccgc  1020
aagtggacca tcatggccgt gatggtgagc ctgctgaccg actacagccc ccagctgcag  1080
aagcccaagt tctgaggtct ctagtaatga gctggagcct cggtagccgt tcctcctgcc  1140
cgctgggcct cccaacgggc cctcctcccc tccttgcacc ggcccttcct ggtctttgaa  1200
taaagtctga gtgggcatct ag                                          1222
```

```
SEQ ID NO: 123         moltype = RNA  length = 1222
FEATURE                Location/Qualifiers
misc_feature           1..1222
                       note = Synthetic construct
```

```
source                 1..1222
                       mol_type = other RNA
                       organism = synthetic construct
SEQUENCE: 123
attattacat caaaacaaaa agccgccacc atgctgttca acctgcgcat cctgctgaac  60
aacgccgcct tccgcaacgg ccacaacttc atggtgcgca acttccgctg cggccagccc  120
ctgcagggcc gggtgcagct gaagggccgc gacctgctga ccctgaagaa cttcaccggc  180
gaggagatcc ggtacatgct gtggctgagc gccgacctga agttccgcat caagcagaag  240
ggcgagtacc tgcccctgct gcagggcaag agcctgggca tgatcttcga gaagcgcagc  300
acccgcaccc gcctgagcac cgagacaggc ttcgccctgc tgggcggcca cccctgcttc  360
ctgaccaccc aggacatcca cctgggcgtg aacgagagcc tgaccgacac cgcccgcgtg  420
ctgagcagca tggccgacgc cgtgctggcc cgcgtgtaca agcagagcga cctggacacc  480
ctggccaagg aggccagcat ccccatcatc aacggcctga gcgacctgta ccaccccatc  540
cagatcctgg ccgactacct gaccctgcag gagcactaca gcagcctgaa gggcctgacc  600
ctgagctgga tcggcgacgg caacaacatc ctgcacagca tcatgatgag cgccgccaag  660
ttcggcatgc acctgcaggc cgccaccccc aagggctacg agcccgacgc cagcgtgacc  720
aagctggccg agcagtacgc caaggagaac ggcaccaagc tgctgctgac caacgacccc  780
ctggaggccg cccacggcgg caacgtgctg atcaccgaca cctggatcag catgggccag  840
gaggaggaga agaagaagcg cctgcaggcc ttccagggct accaggtgac catgaagacc  900
gccaaggtgg ccgccagcga ctggaccttc ctgcactgcc tgccccgcaa gcccgaggag  960
gtggacgacg aggtgttcta cagcccccgc agcctggtgt tccccgaggc cgagaaccgc  1020
aagtggacca tcatggccgt gatggtgagc ctgctgaccg actacagccc ccagctgcag  1080
aagcccaagt tctgaggtct ctagtaatga gctggagcct cggtagccgt tcctcctgcc  1140
cgctgggcct cccaacgggc cctcctcccc tccttgcacc ggcccttcct ggtctttgaa  1200
taaagtctga gtgggcatct ag                                          1222

SEQ ID NO: 124         moltype = RNA  length = 1282
FEATURE                Location/Qualifiers
misc_feature           1..1282
                       note = Synthetic construct
source                 1..1282
                       mol_type = other RNA
                       organism = synthetic construct
SEQUENCE: 124
ggcagaaaaa tttgctacat tgtttcacaa acttcaaata ttattcattt atttagatct  60
attattacat caaaacaaaa agccgccacc atgctgttca acctgcgcat cctgctgaac  120
aacgccgcct tccgcaacgg ccacaacttc atggtgcgca acttccgctg cggccagccc  180
ctgcagggca aggtgcagct gaagggccgc gacctgctga ccctgaagaa cttcaccggc  240
gaggagatca agtacatgct gtggctgagc gccgacctga agttccgcat caagcagaag  300
ggcgagtacc tgcccctgct gcagggcaag agcctgggca tgatcttcga gaagcgcagc  360
acccgcaccc gcctgagcac cgagacaggc ttcgccctgc tgggcggcca cccctgcttc  420
ctgaccaccc aggacatcca cctgggcgtg aacgagagcc tgaccgacac cgcccgcgtg  480
ctgagcagca tggccgacgc cgtgctggcc cgcgtgtaca agcagagcga cctggacacc  540
ctggccaagg aggccagcat ccccatcatc aacggcctga gcgacctgta ccaccccatc  600
cagatcctgg ccgactacct gaccctgcag gagcactaca gcagcctgaa gggcctgacc  660
ctgagctgga tcggcgacgg caacaacatc ctgcacagca tcatgatgag cgccgccaag  720
ttcggcatgc acctgcaggc cgccaccccc aagggctacg agcccgacgc cagcgtgacc  780
aagctggccg agcagtacgc caaggagaac ggcaccaagc tgctgctgac caacgacccc  840
ctggaggccg cccacggcgg caacgtgctg atcaccgaca cctggatcag catgggccag  900
gaggaggaga agaagaagcg cctgcaggcc ttccagggct accaggtgac catgaagacc  960
gccaaggtgg ccgccagcga ctggaccttc ctgcactgcc tgccccgcaa gcccgaggag  1020
gtggacgacg aggtgttcta cagcccccgc agcctggtgt tccccgaggc cgagaaccgc  1080
aagtggacca tcatggccgt gatggtgagc ctgctgaccg actacagccc ccagctgcag  1140
aagcccaagt tctgaggtct ctagtaatga gctggagcct cggtagccgt tcctcctgcc  1200
cgctgggcct cccaacgggc cctcctcccc tccttgcacc ggcccttcct ggtctttgaa  1260
taaagtctga gtgggcatct ag                                          1282

SEQ ID NO: 125         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 125
cacaaagagt aaagaagaac a                                           21

SEQ ID NO: 126         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 126
aacactaaaa gtagaagaaa a                                           21

SEQ ID NO: 127         moltype = RNA  length = 21
FEATURE                Location/Qualifiers
```

```
misc_feature            1..21
                        note = Synthetic construct
source                  1..21
                        mol_type = other RNA
                        organism = synthetic construct
SEQUENCE: 127
ctcagaaaga taagatcagc c                                             21

SEQ ID NO: 128          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 128
atgctgttta atctgaggat cctgttaaac aatgcagctt ttagaaatgg tcacaacttc  60
atggttcgaa attttcggtg tggacaacca ctacaaaata aagtgcagct gaagggccgt  120
gaccttctca ctctaaaaaa ctttaccgga gaagaaatta aatatatgct atggctatca  180
gcagatctga aatttaggat aaaacagaaa ggagagtatt tgcctttatt gcaagggaag  240
tccttaggca tgatttttga gaaaagaagt actcgaacaa gattgtctac agaaacaggc  300
tttgcacttc tgggaggaca tccttgtttt cttaccacac aagatattca tttgggtgtg  360
aatgaaagtc tcacggacac ggcccgtgta ttgtctagca tggcagatgc agtattggct  420
cgagtgtata aacaatcaga tttggacacc ctggctaaag aagcatccat cccaattatc  480
aatgggctgt cagatttgta ccatcctatc cagatcctgg ctgattacct cacgctccag  540
gaacactata gctctctgaa aggtcttacc ctcagctgga tcggggatgg gaacaatatc  600
ctgcactcca tcatgatgag cgcagcgaaa ttcggaatgc accttcaggc agctactcca  660
aagggttatg agccggatgc tagtgtaacc aagttggcag agcagtatgc caaagagaat  720
ggtaccaagc tgttgctgac aaatgatcca ttggaagcag cgcatggagg caatgtatta  780
attacagaca cttggataag catgggacaa gaagaggaga agaaaaagcg gctccaggct  840
ttccaaggtt accaggttac aatgaagact gctaaagttg ctgcctctga ctggacattt  900
ttacactgct tgcccagaaa gccagaagaa gtggatgatg aagtctttta ttctcctcga  960
tcactagtgt tcccagaggc agaaaacaga aagtggacaa tcatggctgt catggtgtcc  1020
ctgctgacag attactcacc tcagctccag aagcctaaat tttga                   1065

SEQ ID NO: 129          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 129
atgctcttta atctgcgcat cttactgaac aacgccgcat tccggaacgg tcacaacttc  60
atggtccgca atttccgctg tggccagccg cttcaaaaca aggtccagct gaagggacgg  120
gatctgctga cactgaagaa cttcaccgga gaagagatca agtacatgct gtggctcagc  180
gcagacttga agttccggat caagcagaag ggagaatact tgcccctgct gcaaggaaag  240
tcgctgggaa tgatttttga gaagcggtca actcgcacca gactctccac cgaaactggt  300
ttcgcactgc ttggcgggca cccttgcttc ctgacgactc aggacatcca cctcggcgtg  360
aacgaatcgc taaccgatac cgccagagtg ctttcttcca tggccgacgc ggtgctggcc  420
agggtgtaca agcagtccga cctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc gtccgtgacc aagttggcgg aacagtacgc gaaggagaac  720
ggaaccaagc ttctgctgac taacgacccc ctcgaggctg cgcatggggg caacgtgctg  780
attaccgaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctag                   1065

SEQ ID NO: 130          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 130
atgctgttta acctacgtat tttgctcaac aatgcagcct ttagaaacgg acataacttt  60
atggttcgaa actttcgctg cgggcagcca ctgcagaaca aggtccagct gaaagggaga  120
gatttgctca cgctgaagaa ctttactggc gaagaaatca agtatatgct gtggttgtcc  180
gcggacctca agtttcggat taagcagaaa ggggagtatc tgccactgct gcaaggaaag  240
agcctcggca tgatcttcga gaagcggagc actcggacca ggctgagtac cgaaactggc  300
ttcgcattgt tgggtggaca tccatgtttt ctgacaacgc aggacattca tctgggcgtg  360
aacgagagtc tgacggacac agctcgcgtt ctgtcctcta tggctgatgc ggtgttggcc  420
cgggtctata agcagtccga tttggacacc ttggctaagg aagctagcat accgattatc  480
aatgggctgt ccgacctgta tcaccctatt caaatcctgg ccgactacct cacactgcaa  540
```

-continued

```
gaacactata gctcattgaa gggactgacc ctgagctgga taggggacgg aaacaacatc  600
ctacatagca ttatgatgtc cgctgccaag tttggcatgc atcttcaagc cgccacgcca  660
aagggttatg agcccgacgc gtcagtgaca aagctggccg agcagtacgc taaggagaat  720
ggtaccaaat tactgctgac taatgatcca ctggaggctg cacatggcgg caatgtactg  780
atcaccgaca catggatctc gatgggccag gaggaagaaa agaagaagag gcttcaggcc  840
ttccaaggct accaggtcac catgaaaaca gctaaggttg cagcatctga ttggaccttt  900
ctgcactgtc tgccaaggaa gcccgaagag gtggacgatg aagtattcta tagcccacgg  960
agtttggtgt tccctgaggc tgaaaatagg aagtggacaa ttatggccgt aatggtgtcc  1020
ctgttaaccg actactctcc gcaactgcag aaacctaagt tttag                  1065
```

```
SEQ ID NO: 131          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 131
atgctgttta acttaaggat cctgctgaac aacgccgctt ttcgtaacgg tcataacttt  60
atggtccgga actttagatg tggccagccg ctgcagaaca aggttcagct gaaggggagg  120
gatctgctga ccttgaagaa ctttaccggc gaagagatca agtacatgtt gtggctgagc  180
gccgatctga agtttaggat taagcagaag ggggagtatt tgccactgct gcaaggaaaa  240
tccttgggga tgatcttcga gaagcgctcc actagaaccc ggctaagcac agaaaccggc  300
ttcgcacttc tgggtggaca tccctgtttt ctgacgacgc aggatataca cctgggcgtg  360
aatgagagtc tgacggacac agctagggtg ttgagcagca tggccgatgc agtactggcc  420
cgcgtttata agcagagcga cttggacaca ctggccaagg aagcgtcaat tccgattatc  480
aatgggctgt cagacctgta tcatcccatt caaatcttgg ctgactatct gaccctgcaa  540
gaacattaca gctccctgaa gggcctcacg ttgtcctgga ttggcgacgg aaacaacatt  600
ctgcattcga tcatgatgag cgctgctaag tttggcatgc acctccaagc cgctacacct  660
aagggatatg agcctgatgc cagcgtaacc aagctggccg aacagtacgc gaaggagaat  720
ggcacgaaac tgctgttgac aaatgaccca ctggaggcag ctcacggtgg caacgtgctg  780
atcaccgaca cgtggatatc tatgggacag gaagaagaga agaagaagcg gctgcaggca  840
ttccaagggt atcaggtcac catgaaaacg gccaaggttg ctgcatccga ctggacattt  900
ctgcattgct tgccccgcaa accagaagaa gtagacgacg aagtctttta ttccccacgg  960
tcgctggtgt tccccgaggc ggagaatcga aagtggacga ttatggccgt gatggtgtcc  1020
ctgctgactg attactctcc ccaactgcaa aagcctaagt tttag                  1065
```

```
SEQ ID NO: 132          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 132
atgcttttca acctgaggat cctcctgaac aacgccgcct ttcgcaatgg tcacaacttt  60
atggtccgga acttcagatg cggccagccg ctgcagaaca aggtccagct gaagggacgg  120
gatctgctga ctctgaagaa cttcaccgga gaagagatca agtacatgct gtggctgtcg  180
gccgacctga agttcaggat caagcagaag ggagaatacc tcccgctgct gcaaggaaag  240
tccctgggca tgattttcga gaagcgctcg accagaactc ggttgtccac cgaaaccggg  300
tttgcgctgc tgggcggaca tccttgcttc ctgacgactc aggatattca cctgggagtg  360
aacgagtcgc tgaccgacac cgccagagtg ctgagctcga tggccgacgc cgtgttggca  420
cgcgtgtaca agcagtccga tctggatacc ctggccaaag aagcttccat cccgatcatt  480
aacgggctga gcgacctcta ccaccccatt caaatcctgg ccgactacct gactctgcaa  540
gaacactaca gctcgctgaa ggggttgact ctgtcctgga tcggcgacgg aaacaacatc  600
ctgcactcca tcatgatgtc ggccgcaaag ttcggcatgc atttgcaagc cgccacccca  660
aagggctacg aaccagacgc gagcgtcacc aagctggccg aacagtacgc gaaggaaaat  720
ggtactaagc tgctgctgac caacgaccca ttggaagctg cccatggtgg aaacgtgctg  780
atcaccgaca cctggatctc gatgggccag gaagaggaga agaagaagcg gctgcaggcg  840
ttccaggggt atcaggtcac catgaaaaca gccaaagtgg cagcgtcaga ctggaccttc  900
ctccactgtc tgcctcgcaa gccagaggag gtggacgacg aggtgttcta ctcccctcgg  960
tccctcgtgt tccctgaggc tgagaaccgg aagtggacca ttatggccgt gatggtgtca  1020
ctcctgactg attactcccc gcaactgcag aagcccaagt tctag                  1065
```

```
SEQ ID NO: 133          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 133
atgctgttta acctgaggat cctattgaac aatgctgctt ttcgtaatgg ccataacttt  60
atggttcgga actttagatg cgggcagcca ctgcagaaca aggtccagtt gaaaggccgc  120
gatctgttga cattgaagaa ctttaccggc gaagagatta agtatatgct gtggctgtct  180
gctgacctca agtttcgaat caagcagaag ggcgaatatc tccccctgct gcaaggaaag  240
tctctcggca tgatctttga gaagcggagt acccgaacac ggctgagcac cgaaacgggc  300
ttcgcactgc tggggggcca tccctgtttt ctgacaacgc aggacatcca cttggggg tt  360
aacgaatcat tgactgatac cgcccgcgta ctgtcatcca tggccgacgc tgtgctggct  420
```

```
agggtgtaca agcagtcaga tctggataca ctggccaagg aagctagcat accaatcatc  480
aatggactga gtgacctttta tcacccgatt caaatactag ccgattatct gaccctgcaa  540
gagcattact cctcgctgaa aggcctcacg ctgtcctgga tcggcgacgg caacaacatt  600
ctgcatagta ttatgatgtc tgctgccaaa ttcggcatgc atctgcaagc tgctacgccg  660
aagggttatg aacccgacgc gtcagttacg aagctcgctg agcagtatgc aaaggagaat  720
ggcacaaagc tgttgcttac caacgatccc ctggaagctg ctcatggcgg caatgtgctg  780
attactgaca cctggatttc aatgggccag gaggaggaga agaagaagag gttacaggct  840
tttcaaggtt accaagtcac gatgaaaacc gctaaggtcg cagccagcga ctggacattc  900
ctgcactgtc tgccaagaaa gccggaagaa gtggacgacg aggtgttcta ttccccgcgg  960
tctttggtgt ttccggaggc cgaaaacagg aaatggacca ttatggccgt gatggtatcg  1020
ttgctgacgg actacagccc tcagttgcaa aagcccaagt tctag                 1065

SEQ ID NO: 134         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 134
atgctcttta acctccgcat cctcctcaac aacgccgcct tccggaatgg gcataacttc  60
atggtccgga acttcagatg cggccagccc ctgcaaaaca aggtccagtt gaagggacgg  120
gacctcctta cgctgaagaa ctttaccgga gaagagatta agtacatgct gtggttgtcc  180
gctgacctca agttccgcat taagcagaag ggagaatatc tgccgctgct gcaaggaaag  240
agcctgggca tgatcttcga aaagcgctcc actagaaccc ggctgtcgac tgagactgga  300
ttcgccttgc tcggtggaca cccgtgcttc ctgacgaccc aggacatcca cctgggagtg  360
aacgagtcac ttacggatac cgcgagggtg ctgtcctcaa tggccgacgc agtgctcgcg  420
cgcgtgtaca agcagtcaga tctggatacc ctggccaagg aagccagcat tcccatcatc  480
aacggactga gcgaccttta ccacccaatc cagatcctcg ccgactactt aaccctgcaa  540
gagcactaca gctccctgaa gggactgact ctgtcctgga tcggggatgg aaacaacatc  600
ctgcactcca tcatgatgtc tgccgctaag tttgggatgc atctgcaagc cgcaacccct  660
aagggatacg agcccgacgc ctcggtgacc aaacttgcgg aacagtacgc caaggaaaac  720
ggtaccaagc tgctgctgac caacgaccct ctggaagcgg cccacggagg aaatgtgctg  780
attaccgaca cctggatttc gatgggccag gaggaggaga agaagaagag actgcaggcg  840
ttccagggat atcaggtcac catgaaaacc gccaaggtcg ccgccagcga ctggaccttc  900
ctgcactgtc tccctcggaa accggaagaa gtggatgacg aggtgttcta ctccccgcgc  960
tcgctggtgt tcccggaggc tgaaaacagg aagtggacaa tcatggccgt gatggtgtcc  1020
ctgttgaccg actactcccc acaactgcag aagcccaagt tctag                 1065

SEQ ID NO: 135         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 135
atgcttttca atctgcgcat cctcctgaac aacgccgcct tccgcaatgg acacaacttt  60
atggtccgca acttccgctg tgggcagccg ctgcagaaca aggtccagct caaggggaga  120
gatctcctga ccctgaagaa cttcactgga gaggagatca agtacatgct gtggctgtcc  180
gccgacctga aatttcggat taagcagaag ggcgaatacc tcccactgct gcaaggaaag  240
tctttgggca tgatcttcga aaagagaagc acccggaccc ggttgagcac cgaaactggg  300
ttcgcgctcc tcggtggaca cccgtgcttc ctgaccaccc aagatattca tctgggtgtc  360
aacgaaagcc tgaccgacac cgccagggtg ctgtcatcca tggctgacgc agtgctcgcc  420
cgggtgtaca agcagtcaga cctggacacc ctcgccaagg aagcttcgat ccctatcatc  480
aacggacttt ccgacctgta ccacccccatc caaattctgg ccgactacct gactctgcaa  540
gaacactata gctcgctgaa aggacttact ctgtcctgga tcggggacgg caacaacatt  600
ctccattcca tcatgatgtc cgctgccaag ttcggaatgc accttcaagc agcgactccc  660
aagggatacg aacctgatgc ctccgtgact aagctggcag agcagtacgc caaggagaac  720
ggtacaaagc tgctgctcac gaacgacccc ctggaggcgg cccacggcgg aaacgtgctg  780
attaccgata cctggatctc aatgggccag gaagaggaga agaagaagcg gctccaggcg  840
tttcaaggct accaggtcac catgaaaacc gcgaaggtcg ccgcctccga ctggactttc  900
ttgcactgcc tgccgcggaa gcccgaggaa gtggatgacg aagtgttcta ctcgccgaga  960
tcgttggtgt tccctgaggc cgaaaacagg aagtggacca tcatggccgt gatggtgtcc  1020
ctgctgactg attacagccc acagctgcag aagcctaagt tctag                 1065

SEQ ID NO: 136         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 136
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
```

```
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                  1065
```

```
SEQ ID NO: 137          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 137
atgcttttca acctgagaat cctcctgaac aacgccgcct tccgcaatgg tcataacttc  60
atggtccgca actttcgctg cggacagcct ctccaaaaca aggtccagct caaggggcgc  120
gacctcctca cactgaagaa cttcactgga gaagaaatca agtacatgct gtggctgagc  180
gccgatctga agttccggat caagcagaag ggagagtacc ttcctctgct gcaagggaag  240
tccttgggaa tgattttcga gaagcggtcc acccggacca ggctgagcac tgaaactggc  300
ttcgccctgc tgggaggcca cccttgtttc ctgaccactc aggacatcca cctgggcgtg  360
aacgagtccc tgaccgatac tgccagagtg ctgtcctcca tggccgacgc cgtgctcgcc  420
cgggtgtaca agcagtcaga cctcgatacg ctggccaagg aagcctccat tcccattatc  480
aatggtctgt cggacctcta ccatccaatc caaatcctcg ccgactacct gactctgcaa  540
gaacactaca gctcactcaa gggcctcacc ctctcctgga tcggcgacgg aaacaacatc  600
cttcactcga ttatgatgtc ggccgcgaag ttcgggatgc acctccaagc tgccactcca  660
aaaggctacg agccggatgc ctcagtgact aagttggcgg aacagtatgc gaaggagaac  720
ggtaccaagc tcctgctgac taacgacccg ctggaggccg cccacggggg aaacgtgctc  780
atcaccgata cttggatttc catgggacag gaggaagaga agaagaagcg gttgcaggca  840
tttcagggct accaggtcac catgaaaact gccaaagtcg ccgccagcga ctggaccttc  900
ctgcactgcc tgccccgcaa gcctgaagaa gtggacgacg aggtgttcta ctctccccgg  960
tccctcgtgt tccctgaggc cgaaaacagg aagtggacca tcatggctgt gatggtgtcc  1020
ctcctgaccg actacagccc tcagctccaa aaacccaagt tttag                  1065
```

```
SEQ ID NO: 138          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 138
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactgaagaa ctttactggg gaggagatta agtatatgct gtggctgtcc  180
gctgacctga agtttaggat caagcagaag ggcgaatatc tgccgctgct gcaagggaaa  240
agtctgggca tgatttttga aaagcgctct acccggacca gactgtctac ggaaacaggc  300
tttgccctgc tgggcggcca cccctgtttt ctgacaacgc aggacatcca tctgggcgtg  360
aacgaatcac tgaccgatac tgctcgggta ctcagttcta tggctgacgc agtgctggct  420
agggtgtaca agcagagcga cttggacaca ctggctaagg aggccagcat ccccattatc  480
aatggcctgt ctgatttgta ccatcccatt caaatcctgg ctgattatct gacactacaa  540
gagcattact caagtctgaa gggtttgact ctctcctgga tcggcgacgg caacaacatt  600
ttacattcca ttatgatgag tgctgctaag tttggcatgc atttgcaagc tgctacccca  660
aagggctatg aacctgacgc tagcgtaacc aagttggccg aacagtatgc taaagagaat  720
ggcaccaagc tgctcctgac gaatgacccc ctggaagctg ctcatggcgg aaacgtactt  780
ataactgata catggattag catgggccag gaagaggaga agaagaagag actgcaggcc  840
ttccaaggct atcaggtcac catgaaaact gccaaggttg cagctagcga ctggaccttc  900
ctgcactgtt tgccgaggaa acccgaggag gtggacgatg aagtctttta ttctccccgc  960
tccttggtgt ttcccgaggc tgaaaatcga aagtggacga taatggcagt gatggtgtcc  1020
ctactgaccg actattctcc acaactgcag aagcctaaat tctag                  1065
```

```
SEQ ID NO: 139          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 139
atgcttttca atctgaggat cctgctgaac aacgctgctt ttcgcaacgg tcataacttt  60
atggttcgca attttcgttg tggccagccg ctgcagaaca aggttcagct gaagggcaga  120
gatctgctga ctctgaagaa cttcactggg gaagaaatca agtatatgtt atggctgtcc  180
```

```
gcggatctga aatttcgaat caagcagaag ggcgaatatc ttcccctgct gcaagggaaa  240
tccttgggca tgatttttga gaagaggagc actaggacta gattgtcaac agaaacaggc  300
tttgctttgt tgggcggaca tccctgcttt ctgacgacac aggatatcca cctcggcgta  360
aacgagtccc tcaccgacac tgctagggta ctgagcagca tggccgacgc tgtgctagcc  420
cgggtttaca agcagtcaga cctggacacc cttgccaagg aagcttctat tccaattatc  480
aacggcctga gtgacctgta tcaccctatt caaatactcg ccgactattt gacgcttcaa  540
gaacattaca gcagcctcaa gggcttaacc ttgagttgga taggcgacgg caacaatatc  600
ctgcattcca ttatgatgtc tgccgctaag tttggcatgc atctacaagc cgcaacaccc  660
aagggctatg aacccgacgc tagcgtgacc aagctggccg agcagtatgc taaggaaaat  720
ggcacaaagc tccttcttac caacgatccc ctggaggctg ctcacggcgg caacgtgctg  780
attaccgata catggattag catgggccag gaggaggaga aaaagaagcg gctccaggct  840
tttcaaggct atcaggtcac catgaaaact gcaaaggtcg ctgcctccga ctggactttc  900
ctgcattgtc taccccgcaa gcctgaggaa gtggacgatg aggtgttcta ctccccacgg  960
agtctggtgt tcccggaagc agagaatcgg aagtggacca tcatggctgt catggtgtcg  1020
ctcttgactg actattctcc ccaactgcaa aaacccaagt tttag                 1065
```

```
SEQ ID NO: 140          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 140
atgcttttca atctgaggat cctgctgaac aacgctgctt ttcgcaacgg tcataacttt  60
atggttcgca attttcgttg tggccagccg ctgcagaaca aggttcagct gaagggcaga  120
gatctgctga ctctgaagaa cttcactggg gaagaaatca agtatatgtt atggctgtcc  180
gcggatctga aatttcgaat caagcagaag ggcgaatatc ttcccctgct gcaagggaaa  240
tccttgggca tgatttttga gaagaggagc actaggacta gattgtcaac agaaacaggc  300
tttgctttgt tgggcggaca tccctgcttt ctgacgacac aggatatcca cctcggcgta  360
aacgagtccc tcaccgacac tgctagggta ctgagcagca tggccgacgc tgtgctagcc  420
cgggtttaca agcagtcaga cctggacacc cttgccaagg aagcttctat tccaattatc  480
aacggcctga gtgacctgta tcaccctatt caaatactcg ccgactattt gacgcttcaa  540
gaacattaca gcagcctcaa gggcttaacc ttgagttgga taggcgacgg caacaatatc  600
ctgcattcca ttatgatgtc tgccgctaag tttggcatgc atctacaagc cgcaacaccc  660
aagggctatg aacccgacgc tagcgtgacc aagctggccg agcagtatgc taaggaaaat  720
ggcacaaagc tccttcttac caacgatccc ctggaggctg ctcacggcgg caacgtgctg  780
attaccgata catggattag catgggccag gaggaggaga aaaagaagcg gctccaggct  840
tttcaaggct atcaggtcac catgaaaact gcaaaggtcg ctgcctccga ctggactttc  900
ctgcattgtc taccccgcaa gcctgaggaa gtggacgatg aggtgttcta ctccccacgg  960
agtctggtgt tcccggaagc agagaatcgg aagtggacca tcatggctgt catggtgtcg  1020
ctcttgactg actattctcc ccaactgcaa aaacccaagt tttag                 1065
```

```
SEQ ID NO: 141          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 141
atgcttttta atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccacgcca  660
aaaggatacg aaccggatgc gtccgtgacg aagttggcgg aacagtacgc gaaggagaac  720
ggaaccaagc ttctgctgac taacgacccc ctcgaggctg cgcatggggg caacgtgctg  780
attaccgaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctag                 1065
```

```
SEQ ID NO: 142          moltype = DNA  length = 1065
FEATURE                 Location/Qualifiers
misc_feature            1..1065
                        note = Synthetic construct
source                  1..1065
                        mol_type = other DNA
                        organism = synthetic construct
```

```
SEQUENCE: 142
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactgaagaa ctttactgga gaagagatca agtacatgct gtggctgtcg  180
gccgacctga agttcaggat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc gtccgtgacc aagttggcgg aacagtacgc gaaggagaac  720
ggaaccaagc ttctgctgac taacgacccc ctcgaggctg cgcatggggg caacgtgctg  780
attaccgaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctag                  1065

SEQ ID NO: 143         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 143
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc atccgtgacc aagttggcgg aacagtacgc gaaggagaac  720
ggaaccaagc tcctgctgac taacgacccg ctcgaggctg cgcatggggg taacgtgctg  780
attacggaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctag                  1065

SEQ ID NO: 144         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 144
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc gtccgtgacc aagttggcgg aacagtacgc gaaggagaac  720
ggaaccaagc ttctgctgac taacgacccc ctcgaggctg cgcatggggg caacgtgctg  780
attaccgaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctag                  1065

SEQ ID NO: 145         moltype = DNA  length = 1065
FEATURE                Location/Qualifiers
misc_feature           1..1065
                       note = Synthetic construct
```

-continued

```
source                  1..1065
                        mol_type = other DNA
                        organism = synthetic construct
SEQUENCE: 145
atgctgttca acctgcgaat cctgctgaac aacgccgctt ttcggaacgg gcacaacttt  60
atggtgagga actttcgctg cggacagccc ctccagaata aggtccagct gaagggcagg  120
gacctgctga ccctgaaaaa tttcacaggg gaggaaatca agtatatgct gtggctgtca  180
gctgatctga agttccggat caagcagaag ggcgaatatc tgcctctgct ccagggcaaa  240
agcctgggga tgatcttcga aaagcgcagt actcggacca gactgtcaac cgagactgga  300
ttcgctctgc tgggaggaca cccttgtttt ctgaccactc aggacattca cctgggagtg  360
aacgagtccc tgaccgacac tgctcgcgtc ctgagctcta tggccgacgc tgtgctggct  420
cgagtctaca aacagtccga cctggatacc ctggccaagg aagcttctat cccaattatt  480
aacggcctgt cagacctgta tcaccccatc cagattctgg ccgattacct gaccctccag  540
gagcactatt ctagtctgaa agggctgaca ctgagttgga ttggggacgg aaacaatatc  600
ctgcactcta ttatgatgtc agccgccaag tttggaatgc acctccaggc tgcaacccca  660
aaaggctacg aacccgatgc ctcagtgaca aagctggctg aacagtacgc caaagagaac  720
ggcactaagc tgctgctgac caacgaccct ctggaggccg ctcacggagg caacgtgctg  780
atcaccgata cctggattag tatgggacag gaggaagaga agaagaagcg gctccaggcc  840
ttccagggct accaggtgac aatgaaaacc gctaaggtcg cagccagcga ttggaccttt  900
ctgcactgcc tgcccagaaa gcccgaagag gtggacgacg aggtcttcta ctctcccaga  960
agcctggtgt ttcccgaagc tgagaatagg aagtggacaa ttatggcagt gatggtcagc  1020
ctgctgactg attattcacc tcagctccag aaaccaaagt tctga                  1065

SEQ ID NO: 146          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 146
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                  1065

SEQ ID NO: 147          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 147
atgctgttca acctgcgaat cctgctgaac aacgccgctt ttcggaacgg gcacaacttt  60
atggtgagga actttcgctg cggacagccc ctccagaata aggtccagct gaagggcagg  120
gacctgctga ccctgaaaaa tttcacaggg gaggaaatca agtatatgct gtggctgtca  180
gctgatctga agttccggat caagcagaag ggcgaatatc tgcctctgct ccagggcaaa  240
agcctgggga tgatcttcga aaagcgcagt actcggacca gactgtcaac cgagactgga  300
ttcgctctgc tgggaggaca cccttgtttt ctgaccactc aggacattca cctgggagtg  360
aacgagtccc tgaccgacac tgctcgcgtc ctgagctcta tggccgacgc tgtgctagct  420
cgagtctaca aacagtccga cctggatacc ctggccaagg aagcttctat cccaattatt  480
aacggcctgt cagacctgta tcaccccatc cagattctgg ccgattacct gaccctccag  540
gagcactatt ctagtctgaa agggctgaca ctgagttgga ttggggacgg aaacaatatc  600
ctgcactcta ttatgatgtc agccgccaag tttggaatgc acctccaggc tgcaacccca  660
aaaggctacg aacccgatgc ctcagtgaca aagctggctg aacagtacgc caaagagaac  720
ggcactaagc tgctgctgac caacgaccct ctggaggccg ctcacggagg caacgtgctg  780
atcaccgata cctggattag tatgggacag gaggaagaga agaagaagcg gctccaggcc  840
ttccagggct accaggtgac aatgaaaacc gctaaggtcg cagccagcga ttggaccttt  900
ctgcactgcc tgcccagaaa gcccgaagag gtggacgacg aggtcttcta ctctcccaga  960
agcctggtgt ttcccgaagc tgagaatagg aagtggacaa ttatggcagt gatggtcagc  1020
ctgctgactg attattcacc tcagctccag aaaccaaagt tctga                  1065

SEQ ID NO: 148          moltype = DNA  length = 1065
FEATURE                 Location/Qualifiers
```

-continued

```
misc_feature            1..1065
                        note = Synthetic construct
source                  1..1065
                        mol_type = other DNA
                        organism = synthetic construct
SEQUENCE: 148
atgctgttca acctgcgaat cctgctgaac aatgccgctt ttcggaacgg gcacaatttc  60
atggtgagga actttcgctg cggacagccc ctccagaaca aggtccagct gaagggcagg  120
gacctgctga ccctgaaaaa tttcacaggg gaggaaatca agtacatgct gtggctgtca  180
gccgatctga agttccggat caagcagaag ggcgaatatc tgcctctgct ccagggcaaa  240
agcctgggga tgatcttcga aaagcgcagt actcggacca gactgtcaac agagactgga  300
ttcgcactgc tgggaggaca cccatgtttt ctgaccacac aggacattca tctgggagtg  360
aacgagtccc tgaccgacac agcacgcgtc ctgagctcca tggctgatgc agtgctggct  420
cgagtctaca aacagtctga cctggatacc ctggccaagg aagcttctat cccaatcatt  480
aatggcctga gtgacctgta tcaccccatc cagattctgg ccgattacct gaccctccag  540
gagcattatt ctagtctgaa agggctgaca ctgagctgga ttggggacgg aaacaatatc  600
ctgcactcca ttatgatgag cgccgccaag tttggaatgc acctccaggc tgcaacccca  660
aaaggctacg aacccgatgc ctccgtgaca aagctggcag aacagtatgc caaagagaac  720
ggcactaagc tgctgctgac caatgaccct ctggaggccg ctcacggagg caacgtgctg  780
atcactgata cctggattag tatgggacag gaggaagaga agaagaagcg gctccaggcc  840
ttccagggct accaggtgac aatgaaaact gctaaggtcg cagccagcga ctggaccttt  900
ctgcattgcc tgcccagaaa gcctgaagag gtggacgatg aggtcttcta ctcacccaga  960
agcctggtgt ttcctgaagc tgagaatagg aagtggacaa tcatggcagt gatggtcagc  1020
ctgctgactg attattcccc tcagctccag aaaccaaagt tctga                  1065

SEQ ID NO: 149          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 149
atgcttttca accttcgcat tctcctcaac aacgccgcgt ttagaaacgg acacaacttc  60
atggtccgca acttccgctg cggacagccg ctgcagaaca aggtccagct caagggtcgg  120
gatctcctga cgctgaagaa ctttaccggc gaagagatta agtacatgct gtggctgtcc  180
gccgacctta agttccggat caagcagaag ggcgaatacc ttcccctgct gcaaggaaag  240
tccctgggca tgatcttcga gaagcgcagt accagaacca gactctccac tgaaaccggg  300
ttcgcgctgc ttggcggcca cccgtgtttc ctcactacgc aagacatcca tcttggcgtg  360
aacgagtccc ttaccgacac cgccagggtg ctgtcaagca tggccgacgc cgtccttgcg  420
cgcgtgtaca agcagtcaga ccttgatact ctggccaagg aagcctccat ccctattatc  480
aacggcctat ccgaccttta ccacccgatc cagatcctcg ctgactacct gaccctgcaa  540
gaacactaca gcagcctcaa gggactgact ctgtcctgga tcggcgacgg gaacaacatc  600
ctgcactcaa tcatgatgag cgcagccaag ttcggcatgc atctccaagc cgctacaccc  660
aagggttatg aaccggacgc ctctgtgacc aagttggcag aacagtacgc caaggagaac  720
ggtactaagc tccttttaac caacgacccc ctcgaagcag cccatggcgg gaatgtgctc  780
attaccgata cctggatttc gatgggccag gaggaggaga agaagaagcg gctgcaggcg  840
ttccagggct accaggtcac catgaaaact gccaaagtgg ccgcctcgga ttggaccttt  900
ctccactgcc tgcctcggaa gcctgaggag gtggacgacg aagtgttcta ctccccacgg  960
tccctcgtgt tccccgaggc cgaaaatagg aagtggacca tcatggccgt gatggtgtcc  1020
ctcttgaccg attacagccc gcagcttcag aagcctaaat tctag                  1065

SEQ ID NO: 150          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 150
atgcttttca atcttcgcat cctgttgaac aacgccgcct tccgcaatgg tcacaacttc  60
atggtccgga acttcagatg tggacagcct ctccaaaaca aggtccagct gaagggaagg  120
gacctcttaa ccctcaaaaa ctttactgga gaggagatca agtacatgct gtggcttagc  180
gccgacctta agttccggat caagcagaag ggagagtacc tcccgctgct gcaaggaaag  240
agtcttggaa tgatcttcga gaagcggtcc accagaactc gcctctccac tgaaaccgga  300
ttcgcactcc tgggtggaca cccgtgcttt ctgaccaccc aagacatcca cctcggagtg  360
aacgagagcc tcacggacac cgcgagagtg ctgtcatcca tggccgacgc cgtgcttgca  420
cgggtctaca agcagtccga tctggacact cttgccaagg aagcctccat tcctatcatt  480
aacggtctgt cggatctgta ccacccgatt cagatccttg cggactacct cacacttcaa  540
gaacactatt caagcctaaa gggtctgacc ctgtcctgga tcggagatgg aaacaacatt  600
ctccattcca tcatgatgag cgctgccaag ttcggaatgc atctccaagc agcgactcct  660
aagggttacg agccggacgc ctcagtgact aagctggccg agcagtacgc caaggagaac  720
ggtaccaaac tgttgcttac taacgacccg cttgaagcgg cccatggagg aaacgtgctg  780
attaccgaca cctggatttc gatgggacag gaagaggaga agaagaagcg gctccaggcg  840
ttccagggat accaggtcac catgaaaacg gccaaagtgg ccgctagcga ttggaccttt  900
ctgcactgcc tcccgcgcaa gcctgaagaa gtggacgacg aagtgttcta ctcccctcgc  960
tctcttgtgt tcccggaagc cgaaaacagg aagtggacca tcatggccgt gatggtgtcc  1020
ctcctgaccg attacagccc gcagctgcag aagcctaagt tctag                  1065
```

```
SEQ ID NO: 151         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 151
atgcttttca atctccgcat cctcctcaac aacgccgcgt ttagaaacgg ccacaacttc  60
atggtccgga acttcagatg tggccagccg cttcagaaca aggtccagct caagggccgg  120
gatcttctga ccctgaagaa ctttactggc gaagaaatca agtacatgct ctggctctcc  180
gccgacttga agttccgcat taagcagaag ggggaatacc ttccgctgct gcaaggaaag  240
tcgctcggca tgatctttga gaagcgctca acccgcacca ggctgtccac tgaaaccggg  300
ttcgcgctgc ttggtggcca cccctgcttc ctgaccaccc aagacattca cctcggagtg  360
aacgaatcgc tcactgatac tgcccgggtg ctgtcgtcga tggccgatgc agtgctggcc  420
agggtgtaca aacagtccga tctggacact ctggccaagg aggcgtccat ccctattatc  480
aacggccttt ccgacctcta ccacccgatt cagatccttg ccgattacct caccctgcaa  540
gaacactact cgtcactgaa gggtctgacc ttgtcctgga tcggcgacgg caacaacatc  600
ctccattcca ttatgatgtc cgccgccaaa ttcggcatgc atcttcaagc cgcaacccct  660
aagggttacg agccggacgc ttccgtgacc aagctcgccg agcagtacgc taaggagaac  720
ggaaccaagc ttctgctgac taacgacccc ctagaggcag cccacggggg caacgtgctt  780
attactgaca cctggatctc catgggacag gaagaagaga agaagaagcg gttacaggcg  840
ttccagggct atcaggtcac catgaaaacc gccaaggtcg ctgcctcgga ctggaccttc  900
ctgcattgcc tgcctcgcaa gcccgaagaa gtggacgacg aggtgttcta ctcgccacgg  960
tcccttgtgt tccctgaggc cgagaataga aagtggacca ttatggccgt gatggtgtcc  1020
cttctcaccg actactcgcc gcaactgcag aaacccaagt tctag                 1065

SEQ ID NO: 152         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 152
atgcttttca atcttcgcat cctcctcaac aacgccgcct tccggaacgg tcacaacttc  60
atggtccgga acttccgctg cggccagccg ctccaaaaca aagtgcagct taagggccgc  120
gatctcctga ccctgaagaa cttcaccgga gaggaaatca agtacatgct gtggctctcg  180
gcggacctga agtttaggat taagcagaag ggggagtatc tgccgctgct ccaagggaag  240
tcccttggca tgatcttcga aaagaggtcc acccggactc ggctcagcac cgaaacaggt  300
tttgcacttc tggggggcca cccgtgcttc ctgacgaccc aggacatcca tctgggtgtc  360
aacgagagtt tgaccgacac tgccagagtg ctgtcatcca tggcggacgc ggtgctcgcg  420
agagtgtaca agcagtccga tcttgacacc ctggcaaaag aggcttcaat cccgatcatt  480
aacggactct cggatctgta ccaccctatc caaatcttgg ccgactacct gaccctgcaa  540
gaacactaca gctccctgaa gggcctgact ctttcctgga ttggcgatgg aaacaacatt  600
ctccattcta ttatgatgtc cgccgccaag ttcggcatgc accttcaagc cgccaccccg  660
aagggctacg aacctgacgc ctccgtgact aagctagccg aacagtacgc taaggagaac  720
ggcactaagc ttctccttac caacgatccg ctggaggcgg cccatggcgg aaatgtgctt  780
atcaccgaca cctggattag catggggcag gaagaagaga agaagaaacg gctccaggca  840
ttccagggct accaggtcac catgaaaact gccaaggtcg ccgctagcga ctggaccttc  900
ctccactgtc tgcctcgcaa gcctgaagaa gtggacgacg aggtgttcta ctccccgcgc  960
tccctcgtgt ttcctgaggc cgagaacaga aagtggacca tcatggccgt gatggtgtca  1020
ttacttacgg actacagccc gcagctgcag aagccgaagt tctag                 1065

SEQ ID NO: 153         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 153
atgcttttta acttgagaat ccttctgaac aacgccgctt tccgcaacgg tcataacttc  60
atggtccgga acttcagatg tggccagccc ctccaaaaca aagtgcagct gaagggccgg  120
gaccttctta cgctgaagaa tttcaccggc gaagaaatca agtacatgct ctggctgtcc  180
gccgatctta agttccgcat taagcagaag ggggaatacc tcccgctgct gcaagggaag  240
tcgctgggca tgatttttga gaagcggtca actcgcaccc gcctgtccac tgaaactgga  300
ttcgcactgc tcggtggcca tccctgcttc ctgaccaccc aagacatcca cctcggcgtg  360
aacgagtccc tgactgacac cgcccgggtc ttatcctcga tggccgatgc tgtgcttgcg  420
agggtgtaca agcagtccga cctcgacaca ctcgcgaagg aggcctccat ccccatcatc  480
aacggcctgt ccgaccttta ccacccaatt cagatcctcg ccgattacct gaccctgcaa  540
gagcactact cgtcgctcaa ggggcttacc ctctcgtgga ttggcgacgg caacaacatc  600
cttcactcca tcatgatgtc ggcagcgaag ttcggcatgc atctgcaagc cgccacgcct  660
aagggttatg aaccggatgc ctcagtgacc aagctcgccg aacagtacgc gaaagagaat  720
ggaaccaagc tacttctgac caacgacccc ctggaggccg ctcacggcgg caacgtcctc  780
attaccgata cttggatttc gatgggacag gaagaggaaa agaagaagag actgcaggcg  840
ttccagggat accaggtcac catgaaaact gccaaagtgg cagcctccga ctggaccttc  900
```

```
cttcactgcc tgccgaggaa gcctgaagag gtggacgacg aggtgttcta ctccccgcgc  960
tccttggtgt ttcctgaggc cgaaaaccgg aagtggacta tcatggccgt gatggtgtcc  1020
ctcctcaccg actactcgcc gcaactgcag aagcctaagt tctag                  1065

SEQ ID NO: 154          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 154
atgttattca accttagaat tctccttaac aacgccgcct tccggaatgg gcataacttt  60
atggtccgca atttccgctg tggacagcct ctgcaaaaca aggtccagct caagggccgg  120
gatctgctga ctctcaagaa cttcactggg gaagaaatca agtacatgct ctggctgagc  180
gccgacctca agttccgcat caagcagaag ggagagtacc tcccgctgct ccaagggaag  240
tccctgggca tgatcttcga gaagagatcc acccgcacca gactttccac tgagactggc  300
ttcgccttgc tgggaggcca cccatgcttc ctgacgaccc aggacattca ccttggcgtg  360
aacgagtccc tgactgacac cgcaagggtg ttgtcctcga tggccgacgc cgtgcttgcc  420
cgggtgtaca agcagagcga tcttgacacc ctggctaagg aagcttccat tcccatcatc  480
aacggtctga gcgacctgta ccacccgatt cagatcctgg cggactacct aaccctgcaa  540
gagcactata gctccctgaa gggcctcaca ctttcatgga tcggcgacgg caacaacatc  600
ctgcactcta ttatgatgag cgctgccaaa ttcggcatgc acctccaagc cgccacgcct  660
aaaggctacg agcccgacgc ctcggtgacc aagcttgcgg agcagtacgc gaaggaaaac  720
ggcaccaagc tgcttctcac caacgatcct ctggaagcgg cccatggtgg caacgtgctc  780
attaccgaca cttggatctc catgggacag gaggaggaaa agaagaagcg gctccaggcg  840
tttcagggtt accaggtcac catgaaaacc gccaaggtcg cagcctccga ctggaccttc  900
cttcattgcc ttccgcgcaa gcccgaagaa gtggacgatg aagtgtttta ctcacctcgg  960
tcactcgtgt tcccggaagc agagaacagg aaatggacca ttatggccgt gatggtgtcc  1020
ctgctcaccg attacagtcc gcaactgcag aagcccaagt tctag                  1065

SEQ ID NO: 155          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 155
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt caaatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgcct  660
aagggttacg aacccgacgc ttccgtgact aagctcgccg agcagtacgc taaggagaac  720
ggaaccaagc tgctgctgac taacgacccg ctagaagcag cccacggggg caacgtgctt  780
attactgaca cctggatctc catgggccag gaggaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
cttctcaccg actacagccc gcagcttcag aagcccaagt tctag                  1065

SEQ ID NO: 156          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 156
atgcttttca atctccgcat cctccttaac aacgccgcgt ttagaaacgg ccacaacttc  60
atggtccgga acttcagatg tggccagccg cttcaaaaca aggtccagct taagggccgg  120
gatctcctca cccttaaaaa cttcaccggc gaagagatca agtacatgct ctggctctcc  180
gcggacctta agttccgcat taagcagaag gggaatacc ttccgctgct tcaaggaaag  240
agcctcggca tgatctttga gaagcgctca accaggacca ggctttctac tgaaactggg  300
ttcgcgcttc tcggcggtca tccctgcttc ctcacgaccc aagacatcca cctcggagtg  360
aacgaatccc tcacggatac tgcccgcgtg ctttcgagca tggcagacgc cgtgctcgcc  420
cgggtgtaca aacagtccga tctcgacact ctcgccaagg aggcgtcaat tcctattatc  480
aacggtctta gtgaccttta ccacccgatc cagatcctcg ccgattacct cacactccaa  540
gaacactaca gctcccttaa gggtcttacc ctctcctgga tcggcgacgg caacaacatt  600
ctccactcca tcatgatgtc cgccgcaaag ttcggcatgc atcttcaagc cgccaccccg  660
aagggctacg agcctgatgc ttccgtgact aagctcgccg agcagtacgc taaggagaac  720
ggaaccaagc ttcttctcac taacgaccca ctcgaagcag cccatggggg caacgtgctt  780
```

-continued

```
atcactgaca cctggatctc catgggccag gaagaagaga agaagaagcg gctccaggcg  840
ttccagggat atcaggtcac catgaaaacc gccaaggtcg ctgcctccga ctggaccttt  900
ctccactgcc tccctcgcaa acctgaagaa gtggacgacg aggtgttcta ctcgccccgg  960
agcctcgtgt tccccgaggc cgagaataga aagtggacca ttatggccgt gatggtgtca  1020
ctcctcaccg actacagccc gcagcttcag aagcccaagt tctag                  1065

SEQ ID NO: 157          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 157
atgcttttca atctccgcat cctccttaac aacgccgcgt ttagaaacgg acataacttc  60
atggtccgga acttcagatg tggacagccg cttcaaaaca aggtccagct gaagggtcgg  120
gatcttctga ccctgaagaa ctttaccgga gaagagatca agtacatgct ctggctctcc  180
gcggacttga agttccgcat taagcagaag ggagaatacc tcccgctgct tcaaggaaag  240
agcctcggaa tgatttttga gaagcgctca accaggaccc gcctttctac tgaaactgga  300
ttcgcgctgc tgggtggaca cccctgcttc ctgacgaccc aggacatcca cctcggagtg  360
aacgaatccc tcactgatac cgcccgggtg ttatcgagca tggcagatgc cgtgctggcc  420
agggtgtaca aacagtccga tctggacact ctggccaagg aggcgtcaat tcctatcatc  480
aacggactta gtgacctcta ccatccgatt caaatcctgg ccgactacct caccctgcaa  540
gaacactaca gctccctgaa gggtctgaca ttgtcctgga tcggagatgg aaacaacatt  600
ctccactcca tcatgatgtc cgccgcaaaa ttcggaatgc atcttcaagc cgccacgcct  660
aagggttacg aacccgacgc ttccgtgact aagctcgccg agcagtacgc taaggagaac  720
ggtaccaagc ttctcctgac caacgaccca ctagaagcag cccacggtgg aaacgtgctt  780
attactgaca cttggatctc catgggacag gaggaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccgcgg  960
agcctcgtgt tccccgaggc cgagaataga aagtggacca tcatggccgt gatggtgtca  1020
ctgctcaccg actacagccc gcagcttcag aagcccaagt tctag                  1065

SEQ ID NO: 158          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 158
atgcttttca acctccgcat tctcctcaac aacgctgcct tccggaatgg acataacttc  60
atggtccgga acttcagatg cggacagccg cttcagaaca aggtccagct taaggggaga  120
gatctcctta ccctcaaaaa cttcactggc gaagaaatca agtacatgct ctggcttagt  180
gcggatctca agttccgcat caagcagaag ggagaatacc tcccgctcct tcaaggaaag  240
agcctcggca tgatttttga gaagaggtcc accagaactc gcctttcaac cgagactggg  300
ttcgccctgc ttggcggtca cccctgcttc ctcactaccc aagacatcca cctcggcgtg  360
aacgagagcc ttaccgacac cgcccgcgtg ctctcctcaa tggccgacgc tgtgctcgcc  420
cgggtgtaca agcagtccga ccttgatact ctcgccaagg aggcctccat cccaattatc  480
aacgggctct ctgatctcta ccaccctatc caaatcctcg cggactacct caccctccaa  540
gagcactata gctcgctcaa gggcctcacc ctttcctgga ttggcgacgg caacaacatt  600
cttcactcga tcatgatgtc cgccgccaag ttcggcatgc atctccaagc cgcgaccccc  660
aagggctacg agcctgacgc atccgtgacc aagctcgccg agcagtacgc gaaggaaaat  720
ggcaccaagc ttcttctcac caacgacccc cttgaggccg ctcatggcgg caacgtgctc  780
atcactgaca cttggatcag catgggccag gaggaggaaa agaagaagcg ccttcaggca  840
ttccagggtt accaggtcac catgaaaacc gccaaagtgg ccgcctccga ctggaccttt  900
cttcactgtc tcccgcggaa gcctgaagaa gtggatgacg aagtgtttta ctcccctcgg  960
tcactcgtgt tcccggaagc agaaaacagg aagtggacca ttatggcggt catggtgtcc  1020
ctcctcaccg actacagccc gcagcttcag aaacccaagt tctag                  1065

SEQ ID NO: 159          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 159
atgcttttca atctccgcat cctccttaac aacgcagcgt ttagaaacgg tcacaacttc  60
atggtccgga acttccgctg tggacagccg cttcaaaaca aggtccagct gaagggtcgg  120
gaccttctga ccctgaagaa ctttactgga gaagagatca agtacatgct ttggctgtcc  180
gcggacttga agttccgcat taagcagaag ggagaatacc ttccgctgct ccaaggaaag  240
agcctgggaa tgatctttga gaagcgctca accaggaccc gcctttctac tgaaactgga  300
ttcgcgctgc tgggtggtca cccttgcttc ctgacgaccc aggacattca cctcggagtg  360
aacgagtccc tcactgatac cgccagagtg ttatcgagca tggcagatgc cgtgctggct  420
agggtgtaca aacagtccga tctggacacc ctggccaagg aggcatcaat tcctattatc  480
aacggactta gtgacctcta ccatccgatt caaatcctgg ccgattacct caccctgcaa  540
gaacactaca gctccctgaa gggtctgaca ttgtcctgga tcggagatgg aaacaacatt  600
ctccattcca tcatgatgtc cgcggccaag ttcggaatgc atctccaagc cgccacgccg  660
```

```
aaaggatacg agccggacgc ttccgtgact aagctcgccg agcagtacgc taaggagaac  720
ggaaccaagc ttctgctgac taacgacccg ctagaagccg cccacggtgg aaacgtgctt  780
attactgaca cctggatctc catgggacag gaagaagaga aaaagaagcg gctgcaggcg  840
ttccagggat atcaggtcac catgaaaacc gccaaggtcg ccgcctccga ctggaccttc  900
cttcactgcc tgcctcggaa gcctgaagaa gtggacgacg aggtgttcta ctcgccgcgg  960
agcctcgtgt tccctgaggc cgagaataga aagtggacca tcatggccgt gatggtgtca  1020
ctcctcaccg actacagccc gcagcttcag aagcctaagt tctag                 1065

SEQ ID NO: 160          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 160
atgcttttca atctccgcat tctcctcaac aacgcagcct ttagaaacgg ccacaacttc  60
atggtccgga acttcagatg tggccagccg cttcagaaca aggtccagct caagggccgg  120
gacctcctca ccctcaaaaa ctttaccggc gaagagatca agtacatgct ctggctttcg  180
gccgacctta agttccgcat caagcagaag ggggaatacc ttccgctgct tcaaggaaag  240
tccctcggca tgatctttga aaagcgctcg accaggaccc gcctttccac tgaaaccggg  300
ttcgcgcttc tcggtggcca cccctgcttc ctcaccaccc aagacattca cctcggagtg  360
aacgaatccc ttaccgatac cgcaagagtg ctttcgtcga tggccgatgc cgtgcttgcg  420
cgggtgtaca agcagtcaga tctcgacact ctcgccaagg aggcgtccat tcctattatc  480
aacggccttt ccgaccttta ccacccgatt cagatcctcg ccgattacct caccctgcaa  540
gagcactact cgtcactcaa gggtcttacc ctctcctgga tcggcgacgg aaacaacatc  600
ctccattcga tcatgatgtc cgccgccaaa ttcggcatgc acctccaagc cgcgaccccg  660
aagggttacg agcccgacgc ttccgtgacc aagctcgccg aacagtacgc taaggaaaac  720
ggcaccaagc tcctcctcac taacgaccct ctcgaagcag cccatggggg caacgtgctc  780
attactgaca cttggatctc gatgggccag gaagaggaga aaaagaagcg gcttcaggcg  840
ttccagggat atcaggtcac catgaaaacc gccaaggtcg ctgcctcgga ctggaccttc  900
cttcactgcc ttccgcgcaa gcctgaagag gtggacgatg aggtgttcta ctccccacgg  960
tcccttgtgt tccccgaggc cgagaatagg aagtggacca tcatggccgt gatggtgtcg  1020
ctcctcactg actactcccc gcaacttcag aagcctaagt tctag                 1065

SEQ ID NO: 161          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 161
atgctgttta atctgagaat acttctaaac aacgccgcct tccggaatgg ccataacttt  60
atggttcgga atttccgctg cggccagccg ctgcagaaca aggtccagct gaagggaaga  120
gacttgctga ccctcaagaa cttcaccgga gaagaaatca agtatatgct gtggctgtcc  180
gccgacctga aattccgcat caagcagaag ggcgaatatc tgccgctgtt gcaagggaag  240
tccctgggga tgatcttcga gaagaggtcc accagaacac ggctttcaac cgaaaccggg  300
tttgcactgc tgggtggaca cccctgtttt ctgaccactc aagatatcca cctgggcgtg  360
aacgagtccc ttaccgacac tgctagggtg ttgtccagca tggccgatgc cgtcctggct  420
cgcgtgtaca agcagtccga cctggatacc ctggcaaagg aagcgtccat tcccattatc  480
aacgggctgt ccgacctgta ccatccgatt caaatcctgg cggactacct gactctgcaa  540
gagcattaca gcagcttgaa ggggcttact ctctcgtgga tcggcgacgg gaacaacatc  600
ctgcactcca tcatgatgtc cgccgccaag ttcgggatgc atttgcaagc tgcgaccccg  660
aaaggttacg agcccgatgc tagcgtaact aagcttgccg aacagtacgc caaagagaat  720
ggtacaaaac tgcttctgac taacgacccg ctggaagcag cccacggcgg gaacgtgctg  780
ataaccgaca cctggatttc aatggggcag gaggaagaga agaagaagcg actgcaggcg  840
ttccaaggct atcaggttac catgaaaacc gccaaagtgg cagccagcga ttggactttc  900
ctgcactgtc tgccgcggaa gcccgaggaa gttgatgacg aagtattcta ctcaccccgg  960
agcctcgtgt tccccgaggc cgaaaaccgg aagtggacta ttatggccgt gatggtgtcg  1020
ctgttgaccg actacagccc gcaactgcag aagccgaagt tttag                 1065

SEQ ID NO: 162          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 162
atgcttttca acctgaggat ccttttgaac aacgccgcct ttcgcaacgg ccacaacttt  60
atggtccgca atttccgctg cgggcagccg ctgcagaaca aggtccagct gaagggccgg  120
gatctgctga ccctgaagaa cttcaccggg gaggaaatca agtacatgct ttggctctcc  180
gccgatctga agttcagaat caagcagaag ggagagtacc tcccgttgct gcaaggaaag  240
tcactcggaa tgattttcga aaagagaagc actaggaccc gcctctcaac tgaaaccggg  300
ttcgcgctgc tcgggggcca tccgtgtttc ctgactaccc aagacatcca cctgggagtg  360
aacgagtcgc tgaccgacac cgcacgcgtg ctgtcatcca tggcggacgc agtgcttgcc  420
cgggtgtaca agcagtcgga cctggacact cttgccaagg aggcatcaat ccccatcatt  480
aacggactgt ccgatctcta ccacccgatt cagatcctgg ctgactacct aaccctgcaa  540
```

-continued

```
gagcactact caagcctgaa ggggctgacc ctgtcgtgga tcggggacgg caacaacatt  600
ctgcactcca tcatgatgtc ggcggctaag ttcgggatgc atttgcaagc ggcaactccg  660
aagggttatg aacccgacgc ctccgtgacc aagctggccg aacagtacgc caaggaaaac  720
ggaaccaagt tgctgctgac taatgatccc ctggaggcgg cccacggggg gaacgtgctg  780
ataaccgata cctggatctc catggggcag gaagaagaga agaaaaagcg gctgcaggca  840
ttccagggat accaggtcac catgaaaacc gcaaaagtgg cagccagcga ctggactttc  900
ctccattgcc tgccgcgaaa gccggaggag gtcgatgacg aggtgttcta ctccccgcgg  960
tcgctggtgt tcccggaggc ggaaaaccgg aagtggacca ttatggccgt gatggtgtca  1020
ctcctgactg actacagccc gcaactgcag aagccgaagt tctag                 1065
```

```
SEQ ID NO: 163         moltype = DNA  length = 1074
FEATURE                Location/Qualifiers
misc_feature           1..1074
                       note = Synthetic construct
source                 1..1074
                       mol_type = other DNA
                       organism = synthetic construct
SEQUENCE: 163
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctagataag tgaa        1074
```

```
SEQ ID NO: 164         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 164
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tga         1073
```

```
SEQ ID NO: 165         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 165
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
```

```
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tga         1073

SEQ ID NO: 166         moltype = DNA  length = 1074
FEATURE                Location/Qualifiers
misc_feature           1..1074
                       note = Synthetic construct
source                 1..1074
                       mol_type = other DNA
                       organism = synthetic construct
SEQUENCE: 166
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag ggggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctagataag tgaa        1074

SEQ ID NO: 167         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 167
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc atccgtgact aagttggcgg aacagtacgc gaaggagaac  720
ggaaccaagc tcctgctgac taacgacccg ctcgaggctg cgcatggggg taacgtgctg  780
attacggaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctagataag tga         1073

SEQ ID NO: 168         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 168
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
```

-continued

```
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tga         1073
```

```
SEQ ID NO: 169         moltype = DNA  length = 1074
FEATURE                Location/Qualifiers
misc_feature           1..1074
                       note = Synthetic construct
source                 1..1074
                       mol_type = other DNA
                       organism = synthetic construct
SEQUENCE: 169
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctagataag tgaa        1074
```

```
SEQ ID NO: 170         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 170
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tga         1073
```

```
SEQ ID NO: 171         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 171
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
```

-continued

```
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc atccgtgacc aagttggcgg aacagtacgc gaaggagaac  720
ggaaccaagc tcctgctgac taacgacccg ctcgaggctg cgcatggggg taacgtgctg  780
attacggaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctagataag tga         1073

SEQ ID NO: 172          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 172
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctagataag tgaa        1074

SEQ ID NO: 173          moltype = DNA  length = 1073
FEATURE                 Location/Qualifiers
misc_feature            1..1073
                        note = Synthetic construct
source                  1..1073
                        mol_type = other DNA
                        organism = synthetic construct
SEQUENCE: 173
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tga         1073

SEQ ID NO: 174          moltype = DNA  length = 1073
FEATURE                 Location/Qualifiers
misc_feature            1..1073
                        note = Synthetic construct
source                  1..1073
                        mol_type = other DNA
                        organism = synthetic construct
```

```
SEQUENCE: 174
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc atccgtgacc aagttggcgg aacagtacgc gaaggagaac  720
ggaaccaagc tcctgctgac taacgacccg ctcgaggctg cgcatggggg taacgtgctg  780
attacggaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctagataag tga         1073

SEQ ID NO: 175         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 175
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                  1065

SEQ ID NO: 176         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 176
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                  1065

SEQ ID NO: 177         moltype = DNA  length = 1065
FEATURE                Location/Qualifiers
misc_feature           1..1065
                       note = Synthetic construct
```

-continued

```
source                  1..1065
                        mol_type = other DNA
                        organism = synthetic construct
SEQUENCE: 177
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                  1065

SEQ ID NO: 178          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 178
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tgaa        1074

SEQ ID NO: 179          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 179
atgggcgtct tcaacctgcg gatcctgctg aacaacgccg ccttccggaa cggccacaac  60
ttcatggtcc gcaacttcag atgcggccag cccctgcaga acaaggtgca gctgaagggc  120
cgggacctgc tgaccctgaa gaacttcacc ggcgaagaga tcaagtacat gctgtggctg  180
agcgccgacc tgaagttccg gatcaagcag aagggcgagt acctgcccct gctgcaaggc  240
aagagcctgg gcatgatctt cgagaagcgg agcacccgga cccggctgag caccgagaca  300
ggctttgccc tgctgggagg ccacccctgc tttctgacca cccaggacat ccacctgggc  360
gtgaacgaga gcctgaccga caccgccaga gtgctgagca gcatggccga cgccgtgctg  420
gcccgggtgt acaagcagag cgacctggac accctggcca aagaggccag catccccatc  480
atcaacggcc tgagcgacct gtaccacccc atccagatcc tggccgacta cctgaccctg  540
caggaacact acagctccct gaagggcctg accctgagct ggatcggcga cggcaacaac  600
atcctgcaca gcatcatgat gagcgccgcc aagttcggca tgcatctgca ggccgccacc  660
cccaagggct acgagcctga tgccagcgtg accaagctgg ccgagcagta cgccaaagag  720
aacggcacca agctgctgct gaccaacgac cccctggaag ccgcccacgg cggcaacgtg  780
ctgatcaccg acacctggat cagcatgggc caggaagagg aaaagaagaa gcggctgcag  840
gccttccagg gctaccaggt cacaatgaag accgccaagg tggccgccag cgactggacc  900
ttcctgcact gcctgccccg gaagcccgaa gaggtggacg acgaggtgtt ctacagcccc  960
cggtccctgg tgttccccga ggccgagaac cggaagtgga ccattatggc cgtgatggtg  1020
tccctgctga ccgactactc cccccagctg cagaagccca agttctagat aagtgaa     1077

SEQ ID NO: 180          moltype = DNA  length = 1077
FEATURE                 Location/Qualifiers
```

```
misc_feature            1..1077
                        note = Synthetic construct
source                  1..1077
                        mol_type = other DNA
                        organism = synthetic construct
SEQUENCE: 180
atgggcgtct tcaacctgcg gatcctgctg aacaacgccg ccttccggaa cggccacaac  60
ttcatggtcc gcaacttcag atgcggccag cccctgcaga acagggtgca gctgaagggc  120
cgggacctgc tgaccctgaa gaacttcacc ggcgaagaga tcaggtacat gctgtggctg  180
agcgccgacc tgaagttccg gatcaagcag aagggcgagt acctgcccct gctgcaaggc  240
aagagcctgg gcatgatctt cgagaagcgg agcacccgga cccggctgag caccgagaca  300
ggctttgccc tgctgggagg ccacccctgc tttctgacca cccaggacat ccacctgggc  360
gtgaacgaga gcctgaccga caccgccaga gtgctgagca gcatggccga cgccgtgctg  420
gcccgggtgt acaagcagag cgacctggac accctggcca aagaggccag catccccatc  480
atcaacggcc tgagcgacct gtaccacccc atccagatcc tggccgacta cctgaccctg  540
caggaacact acagctccct gaagggcctg accctgagct ggatcggcga cggcaacaac  600
atcctgcaca gcatcatgat gagcgccgcc aagttcggca tgcatctgca ggccgccacc  660
cccaagggct acgagcctga tgccagcgtg accaagctgg ccgagcagta cgccaaagag  720
aacggcacca agctgctgct gaccaacgac cccctggaag ccgcccacgg cggcaacgtg  780
ctgatcaccg acacctggat cagcatgggc caggaagagg aaaagaagaa gcggctgcag  840
gccttccagg gctaccaggt cacaatgaag accgccaagg tggccgccag cgactggacc  900
ttcctgcact gcctgccccg gaagcccgaa gaggtggacg acgaggtgtt ctacagcccc  960
cggtccctgg tgttccccga ggccgagaac cggaagtgga ccattatggc cgtgatggtg  1020
tccctgctga ccgactactc cccccagctg cagaagccca agttctagat aagtgaa     1077

SEQ ID NO: 181          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 181
atgctggtct tcaacctgcg gatcctgctg aacaacgccg ccttccggaa cggccacaac  60
ttcatggtcc gcaacttcag atgcggccag cccctgcaga acagggtgca gctgaagggc  120
cgggacctgc tgaccctgaa gaacttcacc ggcgaagaga tcaggtacat gctgtggctg  180
agcgccgacc tgaagttccg gatcaagcag aagggcgagt acctgcccct gctgcaaggc  240
aagagcctgg gcatgatctt cgagaagcgg agcacccgga cccggctgag caccgagaca  300
ggctttgccc tgctgggagg ccacccctgc tttctgacca cccaggacat ccacctgggc  360
gtgaacgaga gcctgaccga caccgccaga gtgctgagca gcatggccga cgccgtgctg  420
gcccgggtgt acaagcagag cgacctggac accctggcca aagaggccag catccccatc  480
atcaacggcc tgagcgacct gtaccacccc atccagatcc tggccgacta cctgaccctg  540
caggaacact acagctccct gaagggcctg accctgagct ggatcggcga cggcaacaac  600
atcctgcaca gcatcatgat gagcgccgcc aagttcggca tgcatctgca ggccgccacc  660
cccaagggct acgagcctga tgccagcgtg accaagctgg ccgagcagta cgccaaagag  720
aacggcacca agctgctgct gaccaacgac cccctggaag ccgcccacgg cggcaacgtg  780
ctgatcaccg acacctggat cagcatgggc caggaagagg aaaagaagaa gcggctgcag  840
gccttccagg gctaccaggt cacaatgaag accgccaagg tggccgccag cgactggacc  900
ttcctgcact gcctgccccg gaagcccgaa gaggtggacg acgaggtgtt ctacagcccc  960
cggtccctgg tgttccccga ggccgagaac cggaagtgga ccattatggc cgtgatggtg  1020
tccctgctga ccgactactc cccccagctg cagaagccca agttctagat aagtgaa     1077

SEQ ID NO: 182          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 182
atgctgttca acctgaggat cctgctgaac aacgcagctt tcaggaacgg ccacaacttc  60
atggtgagga acttccggtg cggccagccc ctgcagaaca aggtgcagct gaagggcagg  120
gacctgctga ccctgaagaa cttcaccgga gaggagatca agtacatgct gtggctgagc  180
gcagacctga agttcaggat caagcagaag ggagagtacc tgcccctgct gcaggggaag  240
tccctgggca tgatcttcga gaagaggagt accaggacca ggctgagcac cgaaaccggc  300
ttcgccctgc tgggaggaca cccctgcttc ctgaccaccc aggacatcca cctgggcgtg  360
aacgagagtc tgaccgacac cgccagggtg ctgtctagca tggccgacgc cgtgctggcc  420
agggtgtaca agcagtcaga cctggacacc ctggctaagg aggccagcat ccccatcatc  480
aacggcctga gcgacctgta ccaccccatc cagatcctgg ctgactacct gaccctgcag  540
gagcactaca gctctctgaa gggcctgacc ctgagctgga tcggcgacgg gaacaacatc  600
ctgcacagca tcatgatgag cgccgccaag ttcggcatgc acctgcaggc cgctaccccc  660
aagggttacg agcccgacgc cagcgtgacc aagctggcag agcagtacgc caaggagaac  720
ggcaccaagc tgctgctgac caacgacccc ctggaggccg cccacggagg caacgtgctg  780
atcaccgaca cctggatcag catgggacag gaggaggaga agaagaagcg gctgcaggct  840
ttccagggtt accaggtgac catgaagacc gccaaggtgg ctgccagcga ctggaccttc  900
ctgcactgcc tgcccaggaa gcccgaggag gtggacgacg aggtgttcta ctctcccagg  960
agcctggtgt tccccgaggc cgagaacagg aagtggacca tcatggctgt gatggtgtcc  1020
ctgctgaccg actacagccc ccagctgcag aagcccaagt tctgaataag tgaa        1074
```

-continued

```
SEQ ID NO: 183          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 183
atgctgttca acctgaggat cctgctgaac aacgcagctt tcaggaacgg ccacaacttc  60
atggtgagga acttccggtg cggccagccc ctgcagaaca aggtgcagct gaagggcagg  120
gacctgctga ccctgaagaa cttcaccgga gaggagatca agtacatgct gtggctgagc  180
gcagacctga agttcaggat caagcagaag ggagagtacc tgcccctgct gcaggggaag  240
tccctgggca tgatcttcga gaagaggagt accaggacca ggctgagcac cgaaaccggc  300
ttcgccctgc tgggaggaca cccctgcttc ctgacgaccc aggacatcca cctcggagtg  360
aacgaatccc tcaccgatac cgcccgggtg ttatcaagca tggcagatgc cgtgctggcc  420
agggtgtaca aacagtccga tctggacact ctggctaagg aggccagcat ccccatcatc  480
aacggcctga gcgacctgta ccaccccatc cagatcctgg ctgactacct gaccctgcag  540
gagcactaca gctctctgaa gggcctgacc ctgagctgga tcggcgacgg gaacaacatc  600
ctgcactcca tcatgatgtc cgccgcgaag ttcggaatgc atctgcaagc cgccacgcca  660
aaaggatacg aaccggatgc gcccgtgaca aagttggcgg aacagtacgc taaggagaac  720
ggaaccaagc tgctgctgac caacgacccc ctggaggccg cccacggagg caacgtgctg  780
atcaccgaca cctggatcag catgggacag gaggaggaga agaagaagcg gctgcaggct  840
ttccagggtt accaggtgac catgaagacc gccaaggtgg ctgccagcga ctggaccttc  900
ctgcactgcc tgcccaggaa gcccgaggag gtggacgacg aggtgttcta ctctcccagg  960
agcctggtgt tccccgaggc cgagaacagg aagtggacca tcatggctgt gatggtgtcc  1020
ctgctgaccg actacagccc ccagctgcag aagcccaagt tctgaataag tgaa        1074

SEQ ID NO: 184          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 184
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag tgaa        1074

SEQ ID NO: 185          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 185
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
```

```
ctgcactgcc tgccccgcaa gcccgaggag gtggacgacg aggtgttcta cagccccgc  960
agcctggtgt tccccgaggc cgagaaccgc aagtggacca tcatggccgt gatggtgagc  1020
ctgctgaccg actacagccc ccagctgcag aagcccaagt tctgaataag tgaa        1074

SEQ ID NO: 186          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 186
atgcttttca acttgagaat cctgctgaac aacgccgcct ttcgcaacgg tcacaatttt  60
atggtcagaa acttcagatg cggacagccc ctccaaaaca aggtccagct gaagggccgc  120
gatctcctca ccctgaagaa cttcacgggg gaggagatca agtacatgct gtggctctcc  180
gctgacctga agttcaggat caagcagaag ggagaatatc tgccgctgct gcaagggaag  240
tccctgggga tgattttcga gaagcggagc acccggactc ggctctccac tgaaactggt  300
ttcgcccttc tgggcggtca cccctgcttc ctgaccactc aagacattca cctcggagtg  360
aacgagtcct tgactgacac cgcccgggtg ctgtcgagca tggcagacgc cgtgctagcc  420
cgcgtgtaca agcagtcaga cctcgatacc ctggccaagg aggcttcgat cccgatcatc  480
aacgggttgt ccgacctgta ccacccgatt cagattctcg ccgactacct caccctgcaa  540
gagcattaca gctccctgaa ggggcttacc ctgtcctgga ttggcgacgg aaacaacatc  600
ctgcactcca ttatgatgtc ggcggccaag ttcggcatgc acctccaagc cgcgacccct  660
aagggttacg aaccagacgc gtcagtgact aagctggccg aacagtacgc aaaggaaaat  720
ggcacgaagc tgctcctgac caacgatccg ttggaagccg cccatggcgg aaatgtgctc  780
atcaccgaca cctggatctc gatgggacag gaggaagaga agaagaagcg gctgcaggcg  840
ttccagggct accaggtcac catgaaaact gccaaggtgg ccgccagcga ctggaccttc  900
ctgcactgcc ttccgcgcaa gcctgaggag gtggacgatg aagtgttcta ctctccacgg  960
tccctggtgt tccccgaggc ggagaaccgc aaatggacca tcatggctgt gatggtcagc  1020
ctgctgaccg attacagccc tcagttgcaa aagccgaagt tttga                  1065

SEQ ID NO: 187          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 187
atgctgttca acctccgcat cctcctcaac aacgccgcat tcagaaacgg gcacaacttc  60
atggtcagaa acttccgctg cgggcaaccc ctacaaaaca aggtccagct caaggggcgg  120
gacctcctga ccctgaagaa cttcaccggc gaagagatca agtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tgggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                  1065

SEQ ID NO: 188          moltype = DNA  length = 1074
FEATURE                 Location/Qualifiers
misc_feature            1..1074
                        note = Synthetic construct
source                  1..1074
                        mol_type = other DNA
                        organism = synthetic construct
SEQUENCE: 188
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
```

```
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctgaataag taga        1074

SEQ ID NO: 189         moltype = DNA  length = 1074
FEATURE                Location/Qualifiers
misc_feature           1..1074
                       note = Synthetic construct
source                 1..1074
                       mol_type = other DNA
                       organism = synthetic construct
SEQUENCE: 189
atgcttttca acctgagaat cctcttgaac aatgctgctt ttcggaatgg ccacaacttt  60
atggttcgga acttccgttg cggccagcct ttacaaaaca aggtccagct gaagggccgg  120
gatttgctca cactaaagaa ctttactgga gaagagatca agtacatgct atggctgtcg  180
gccgacctga agttccgtat caagcagaag ggagaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctcgatacc ttggcaaagg aggcttccat tcccatcatc  480
aacggcctga gcgacctgta ccacccaatc caaatcctgg ctgactacct gaccctgcaa  540
gagcactaca gcagcctgaa gggtctgacc ctgtcatgga ttggcgatgg aaacaatatt  600
ctgcactcca tcatgatgtc cgccgcgaag ttcggaatgc atctgcaagc cgccactcca  660
aaaggatacg aaccggatgc atccgtgacc aagttggcgg aacagtacgc gaaggagaac  720
ggaaccaagc tcctgctgac taacgacccg ctcgaggctg cgcatggggg taacgtgctg  780
attacggaca cctggatctc catggggcag gaggaagaga agaagaagag actgcaggca  840
ttccaggggt accaggtcac catgaaaacc gcaaaagtgg cagcttcgga ctggactttc  900
ctgcattgcc tgccgaggaa gccggaggaa gtcgacgacg aagtgttcta ctcgcctcgg  960
tccctggtgt tccccgaggc cgaaaaccgg aagtggacca tcatggccgt gatggtgtcc  1020
ttgctgactg actatagccc gcagctgcag aagcctaagt tctgaataag taga        1074

SEQ ID NO: 190         moltype = DNA  length = 1074
FEATURE                Location/Qualifiers
misc_feature           1..1074
                       note = Synthetic construct
source                 1..1074
                       mol_type = other DNA
                       organism = synthetic construct
SEQUENCE: 190
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ctggccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctgaataag taga        1074

SEQ ID NO: 191         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 191
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
```

-continued

```
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                 1065
```

```
SEQ ID NO: 192          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 192
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggga atacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                 1065
```

```
SEQ ID NO: 193          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 193
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggga atacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                 1065
```

```
SEQ ID NO: 194          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 194
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggga atacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
```

```
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                 1065

SEQ ID NO: 195         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 195
atgcttttca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                 1065

SEQ ID NO: 196         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 196
atggtgttca acctccgcat cctcctcaac aacgccgcat tcagaaacgg gcacaacttc  60
atggtcagaa acttccgctg cgggcaaccc ctacaaaaca aggtccagct caaggggcgg  120
gacctcctga ccctgaagaa cttcaccggc gaagagatca agtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 197         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 197
atggtgttca acctccgcat cctcctcaac aacgccgcat tcagaaacgg gcacaacttc  60
atggtcagaa acttccgctg cgggcaaccc ctacaaaacc gggtccagct caaggggcgg  120
gacctcctga ccctgaagaa cttcaccggc gaagagatca agtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tggggggaca cccgtgcttc ctgaccaccc aagacatcca cctgggagtg  360
aacgaatcgc tgaccgacac cgcccgcgtg ctgagctcaa tggcggacgc cgtgctggcc  420
```

```
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 198         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 198
atggtgttca acctccgcat cctcctcaac aacgccgcat tcagaaacgg gcacaacttc  60
atggtcagaa acttccgctg cgggcaaccc ctacaaaacc gggtccagct caaggggcgg  120
gacctcctga ccctgaagaa cttcaccggc gaagagatcc ggtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tgggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 199         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 199
atgctggtca acctccgcat cctcctcaac aacgccgcat tcagaaacgg gcacaacttc  60
atggtcagaa acttccgctg cgggcaaccc ctacaaaaca aggtccagct caaggggcgg  120
gacctcctga ccctgaagaa cttcaccggc gaagagatca agtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tgggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 200         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 200
atgctggtca acctccgcat cctcctcaac aacgccgcat tcagaaacgg gcacaacttc  60
atggtcagaa acttccgctg cgggcaaccc ctacaaaacc gggtccagct caaggggcgg  120
gacctcctga ccctgaagaa cttcaccggc gaagagatca agtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
```

-continued

```
ttcgcactgc tggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 201         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 201
atgctggtca acctccgcat cctcctcaac aacgccgcat tcagaaacgg gcacaacttc  60
atggtcagaa acttccgctg cgggcaaccc ctacaaaacc gggtccagct caaggggcgg  120
gacctcctga ccctgaagaa cttcaccggc gaagagatcc ggtacatgct gtggctctcc  180
gccgacctga agttccgcat caagcagaag ggagagtacc tcccgctgct gcaagggaag  240
tcgctgggga tgatcttcga gaagcggtca accagaaccc ggctgtcaac cgaaaccggg  300
ttcgcactgc tggggggaca cccgtgcttc ctgaccaccc aagacatcca cctgggagtg  360
aacgaatcgc tgaccgacac cgcccgcgtg ctgagctcaa tggcggacgc cgtgctggcc  420
cgcgtgtaca agcagtccga cctggacacc ctggccaagg aagcgtccat cccgatcatc  480
aacggactgt ccgacctgta ccacccgatc cagatcctgg cagactacct gaccctgcaa  540
gaacactaca gctccctgaa gggcctgacc ctgtcatgga tcggggacgg gaacaacatc  600
ctgcactcca taatgatgtc agccgccaag ttcggaatgc acctccaagc cgcaaccccg  660
aagggctacg aaccggacgc atcagtgacc aaactggccg agcagtacgc caaggaaaac  720
ggcaccaagc tcctgctgac caacgacccg ctggaggccg cacacggggg gaacgtgctg  780
atcaccgaca cctggatctc catgggacag gaggaggaaa agaagaagcg gctgcaggcg  840
ttccaggggt accaggtcac catgaaaacc gcgaaggtcg cggcatcaga ctggaccttc  900
ctgcactgcc tgccccggaa gccggaagag gtggacgacg aggtgttcta ctcgccgcgc  960
tcgctggtgt tccccgaggc ggagaacagg aagtggacca tcatggcggt gatggtcagc  1020
ctcctgaccg actactcgcc gcagctgcag aagccgaagt tctga                 1065

SEQ ID NO: 202         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 202
atgctggtca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                 1065

SEQ ID NO: 203         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 203
atgctggtca acctgcgcat cctgctgaac aacgccgcct tccgcaacgg ccacaacttc  60
atggtgcgca acttccgctg cggccagccc ctgcagaacc gggtgcagct gaagggccgc  120
gacctgctga ccctgaagaa cttcaccggc gaggagatca agtacatgct gtggctgagc  180
```

```
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                  1065

SEQ ID NO: 204         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 204
atgcttgtca atctccgcat cctccttaac aacgccgcgt ttagaaacgg ccacaacttc  60
atggtccgga acttcagatg tggccagccg cttcaaaaca aggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                  1065

SEQ ID NO: 205         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 205
atgcttgtca atctccgcat cctccttaac aacgccgcgt ttagaaacgg ccacaacttc  60
atggtccgga acttcagatg tggccagccg cttcaaaacc gggtccagct gaagggccgg  120
gatcttctga ccctgaagaa ctttactggc gaagagatca agtacatgct ctggctctcc  180
gcggacttga agttccgcat taagcagaag gggaatacc ttccgctgct tcaaggaaag  240
agcctcggca tgatctttga gaagcgctca accaggaccc gcctttctac tgaaactggg  300
ttcgcgctgc tcggtggcca cccctgcttc ctgacgaccc aggacatcca cctcggagtg  360
aacgaatccc tcaccgatac cgcccgggtg ttatcgagca tggcagatgc cgtgctggcc  420
agggtgtaca aacagtccga tctggacact ctggccaagg aggcgtcaat tcctattatc  480
aacggcctta gtgacctcta ccatccgatt cagatcctgg ccgattacct caccctgcaa  540
gaacactaca gctccctgaa gggtctgaca ttgtcctgga tcggcgacgg caacaacatt  600
ctccattcca tcatgatgtc cgccgcaaaa ttcggcatgc atcttcaagc cgccacgccg  660
aagggttacg agcccgacgc ttccgtgact aagctcgccg agcagtacgc taaggagaac  720
ggaaccaagc ttctgctgac taacgaccca ctagaagcag cccacggggg caacgtgctt  780
attactgaca cctggatctc catgggccag gaagaagaga aaaagaagcg gctgcaggcg  840
ttccagggat atcaggtcac catgaaaacc gccaaggtcg ctgcctccga ctggaccttc  900
ctgcactgcc tgcctcgcaa gcctgaagaa gtggacgacg aggtgttcta ctcgccacgg  960
agcctcgtgt tccccgaggc cgagaataga aagtggacca tcatggccgt gatggtgtca  1020
ctgctcaccg actacagccc gcagcttcag aagcccaagt tctag                  1065

SEQ ID NO: 206         moltype = DNA  length = 1068
FEATURE                Location/Qualifiers
misc_feature           1..1068
                       note = Synthetic construct
source                 1..1068
                       mol_type = other DNA
                       organism = synthetic construct
```

```
SEQUENCE: 206
atgggccttg tcaatctccg catcctcctt aacaacgccg cgtttagaaa cggccacaac  60
ttcatggtcc ggaacttcag atgtggccag ccgcttcaaa acaaggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctag               1068

SEQ ID NO: 207         moltype = DNA  length = 1068
FEATURE                Location/Qualifiers
misc_feature           1..1068
                       note = Synthetic construct
source                 1..1068
                       mol_type = other DNA
                       organism = synthetic construct
SEQUENCE: 207
atgggccttg tcaatctccg catcctcctt aacaacgccg cgtttagaaa cggccacaac  60
ttcatggtcc ggaacttcag atgtggccag ccgcttcaaa accgggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctag               1068

SEQ ID NO: 208         moltype = DNA  length = 1071
FEATURE                Location/Qualifiers
misc_feature           1..1071
                       note = Synthetic construct
source                 1..1071
                       mol_type = other DNA
                       organism = synthetic construct
SEQUENCE: 208
atgggcggac ttgtcaatct ccgcatcctc cttaacaacg ccgcgtttag aaacggccac  60
aacttcatgg tccggaactt cagatgtggc cagccgcttc aaaacaaggt ccagctgaag  120
ggccgggatc ttctgaccct gaagaacttt actggcgaag agatcaagta catgctctgg  180
ctctccgcgg acttgaagtt ccgcattaag cagaaggggg aataccttcc gctgcttcaa  240
ggaaagagcc tcggcatgat ctttgagaag cgctcaacca ggacccgcct ttctactgaa  300
actgggttcg cgctgctcgg tggccacccc tgcttcctga cgacccagga catccacctc  360
ggagtgaacg aatccctcac cgataccgcc cgggtgttat cgagcatggc agatgccgtg  420
ctggccaggg tgtacaaaca gtccgatctg gacactctgg ccaaggaggc gtcaattcct  480
attatcaacg gccttagtga cctctaccat ccgattcaga tcctggccga ttacctcacc  540
ctgcaagaac actacagctc cctgaagggt ctgacattgt cctggatcgg cgacggcaac  600
aacattctcc attccatcat gatgtccgcc gcaaaattcg gcatgcatct tcaagccgcc  660
acgccgaagg gttacgagcc cgacgcttcc gtgactaagc tcgccgagca gtacgctaag  720
gagaacggaa ccaagcttct gctgactaac gacccactag aagcagccca cgggggcaac  780
gtgcttatta ctgacacctg gatctccatg ggccaggaag aagagaaaaa gaagcggctg  840
caggcgttcc agggatatca ggtcaccatg aaaaccgcca aggtcgctgc ctccgactgg  900
accttcctgc actgcctgcc tcgcaagcct gaagaagtgg acgacgaggt gttctactcg  960
ccacggagcc tcgtgttccc cgaggccgag aatagaaagt ggaccatcat ggccgtgatg  1020
gtgtcactgc tcaccgacta cagcccgcag cttcagaagc ccaagttcta g           1071

SEQ ID NO: 209         moltype = DNA  length = 1077
FEATURE                Location/Qualifiers
misc_feature           1..1077
                       note = Synthetic construct
```

```
source                  1..1077
                        mol_type = other DNA
                        organism = synthetic construct
SEQUENCE: 209
atggcccttt tcaatctccg catcctcctt aacaacgccg cgtttagaaa cggccacaac  60
ttcatggtcc ggaacttcag atgtggccag ccgcttcaag gcaaggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctagat aagtgaa     1077

SEQ ID NO: 210          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 210
atggcccttt tcaatctccg catcctcctt aacaacgccg cgtttagaaa cggccacaac  60
ttcatggtcc ggaacttcag atgtggccag ccgcttcaag gccgggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctagat aagtgaa     1077

SEQ ID NO: 211          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 211
atggcccttt tcaatctccg catcctcctt aacaacgccg cgtttagaaa cggccacaac  60
ttcatggtcc ggaacttcag atgtggccag ccgcttcaag gccgggtcca gctgaagggc  120
cgggatcttc tgaccctgaa gaactttact ggcgaagaga tcaggtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctagat aagtgaa     1077

SEQ ID NO: 212          moltype = DNA  length = 1077
FEATURE                 Location/Qualifiers
```

```
misc_feature            1..1077
                        note = Synthetic construct
source                  1..1077
                        mol_type = other DNA
                        organism = synthetic construct
SEQUENCE: 212
atggcccttg tcaatctccg catcctcctt aacaacgccg cgtttagaaa cggccacaac  60
ttcatggtcc ggaacttcag atgtggccag ccgcttcaag gcagggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctaagt gaataga     1077

SEQ ID NO: 213          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 213
atggcccttt tcaatctccg catcctcctt aacaacgccg cgtttagaaa cggccacaac  60
ttcatggtcc ggaacttcag atgtggccag ccgcttcaag tcaaggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctagat aagtgaa     1077

SEQ ID NO: 214          moltype = DNA  length = 1077
FEATURE                 Location/Qualifiers
misc_feature            1..1077
                        note = Synthetic construct
source                  1..1077
                        mol_type = other DNA
                        organism = synthetic construct
SEQUENCE: 214
atggcccttt tcaatctccg catcctcctt aacaacgccg cgtttagaaa cggccacaac  60
ttcatggtcc ggaacttcag atgtggccag ccgcttcaag tcagggtcca gctgaagggc  120
cgggatcttc tgaccctgaa gaactttact ggcgaagaga tcaagtacat gctctggctc  180
tccgcggact tgaagttccg cattaagcag aagggggaat accttccgct gcttcaagga  240
aagagcctcg gcatgatctt tgagaagcgc tcaaccagga cccgcctttc tactgaaact  300
gggttcgcgc tgctcggtgg ccacccctgc ttcctgacga cccaggacat ccacctcgga  360
gtgaacgaat ccctcaccga taccgcccgg gtgttatcga gcatggcaga tgccgtgctg  420
gccagggtgt acaaacagtc cgatctggac actctggcca aggaggcgtc aattcctatt  480
atcaacggcc ttagtgacct ctaccatccg attcagatcc tggccgatta cctcaccctg  540
caagaacact acagctccct gaagggtctg acattgtcct ggatcggcga cggcaacaac  600
attctccatt ccatcatgat gtccgccgca aaattcggca tgcatcttca agccgccacg  660
ccgaagggtt acgagcccga cgcttccgtg actaagctcg ccgagcagta cgctaaggag  720
aacggaacca agcttctgct gactaacgac ccactagaag cagcccacgg gggcaacgtg  780
cttattactg acacctggat ctccatgggc caggaagaag agaaaaagaa gcggctgcag  840
gcgttccagg gatatcaggt caccatgaaa accgccaagg tcgctgcctc cgactggacc  900
ttcctgcact gcctgcctcg caagcctgaa gaagtggacg acgaggtgtt ctactcgcca  960
cggagcctcg tgttccccga ggccgagaat agaaagtgga ccatcatggc cgtgatggtg  1020
tcactgctca ccgactacag cccgcagctt cagaagccca agttctagat aagtgaa     1077
```

```
SEQ ID NO: 215          moltype = DNA  length = 1065
FEATURE                 Location/Qualifiers
misc_feature            1..1065
                        note = Synthetic construct
source                  1..1065
                        mol_type = other DNA
                        organism = synthetic construct
SEQUENCE: 215
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                1065

SEQ ID NO: 216          moltype = DNA  length = 1068
FEATURE                 Location/Qualifiers
misc_feature            1..1068
                        note = Synthetic construct
source                  1..1068
                        mol_type = other DNA
                        organism = synthetic construct
SEQUENCE: 216
atgggagtat tcaacctgcg catcctgctg aacaacgccg ccttccgcaa cggccacaac  60
ttcatggtgc gcaacttccg ctgcggccag cccctgcaga acaaggtgca gctgaagggc  120
cgcgacctgc tgaccctgaa gaacttcacc ggcgaggaga tcaagtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga             1068

SEQ ID NO: 217          moltype = DNA  length = 1068
FEATURE                 Location/Qualifiers
misc_feature            1..1068
                        note = Synthetic construct
source                  1..1068
                        mol_type = other DNA
                        organism = synthetic construct
SEQUENCE: 217
atgggagtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
```

```
cgcagcctgg tgttccccga ggccgagaac cgcaagtgga ccatcatggc cgtgatggtg  1020
agcctgctga ccgactacag cccccagctg cagaagccca agttctga               1068

SEQ ID NO: 218          moltype = DNA  length = 1068
FEATURE                 Location/Qualifiers
misc_feature            1..1068
                        note = Synthetic construct
source                  1..1068
                        mol_type = other DNA
                        organism = synthetic construct
SEQUENCE: 218
atgctggtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga               1068

SEQ ID NO: 219          moltype = DNA  length = 1068
FEATURE                 Location/Qualifiers
misc_feature            1..1068
                        note = Synthetic construct
source                  1..1068
                        mol_type = other DNA
                        organism = synthetic construct
SEQUENCE: 219
atgggagtat tcaacctgcg catcctgctg aacaacgccg ccttccgcaa cggccacaac  60
ttcatggtgc gcaacttccg ctgcggccag cccctgcaga acaaggtgca gctgaagggc  120
cgcgacctgc tgaccctgaa gaacttcacc ggcgaggaga tcaagtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga               1068

SEQ ID NO: 220          moltype = DNA  length = 1068
FEATURE                 Location/Qualifiers
misc_feature            1..1068
                        note = Synthetic construct
source                  1..1068
                        mol_type = other DNA
                        organism = synthetic construct
SEQUENCE: 220
atgggagtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
```

-continued

```
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga              1068

SEQ ID NO: 221         moltype = DNA  length = 1068
FEATURE                Location/Qualifiers
misc_feature           1..1068
                       note = Synthetic construct
source                 1..1068
                       mol_type = other DNA
                       organism = synthetic construct
SEQUENCE: 221
atgctggtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga              1068

SEQ ID NO: 222         moltype = DNA  length = 1073
FEATURE                Location/Qualifiers
misc_feature           1..1073
                       note = Synthetic construct
source                 1..1073
                       mol_type = other DNA
                       organism = synthetic construct
SEQUENCE: 222
atgttgttca acttgaggat cttgttgaac aacgccgcct tcaggaacgg acacaacttc  60
atggtaagga acttcaggtg cggacagccc ttgcagaaca aagtacagtt gaaaggaagg  120
gacttgttga cattgaaaaa cttcacagga gaagaaatca aatacatgtt gtggttgtcg  180
gccgacttga aattcaggat caaacagaaa ggagaatact tgcccttgtt gcagggaaaa  240
tcgttgggaa tgatcttcga aaaaaggtcg acaaggacaa ggttgtcgac agaaacagga  300
ttcgccttgt tgggaggaca cccctgcttc ttgacaacac aggacatcca cttgggagta  360
aacgaatcgt tgacagacac agccagggta ttgtcgtcga tggccgacgc cgtattggcc  420
agggtataca aacagtcgga cttggacaca ttggccaaag aagcctcgat ccccatcatc  480
aacggattgt cggacttgta ccaccccatc cagatcttgg ccgactactt gacattgcag  540
gaacactact cgtcgttgaa aggattgaca ttgtcgtgga tcggagacgg aaacaacatc  600
ttgcactcga tcatgatgtc ggccgccaaa ttcggaatgc acttgcaggc cgccacaccc  660
aaaggatacg aacccgacgc ctcggtaaca aaattggccg aacagtacgc caaagaaaac  720
ggaacaaaat tgttgttgac aaacgacccc ttggaagccg cccacggagg aaacgtattg  780
atcacagaca catggatctc gatgggacag gaagaagaaa aaaaaaaaag gttgcaggcc  840
ttccagggat accaggtaac aatgaaaaca gccaaagtag ccgcctcgga ctggacattc  900
ttgcactgct tgcccaggaa acccgaagaa gtagacgacg aagtattcta ctcgcccagg  960
tcgttggtat tccccgaagc cgaaaacagg aaatggacaa tcatggccgt aatggtatcg  1020
ttgttgacag actactcgcc ccagttgcag aaacccaaat tctgaatagt gaa         1073

SEQ ID NO: 223         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 223
atgctgttca acctgcgcat cctgctgaac aacgccgcct tccgcaacgg ccacaacttc  60
atggtgcgca acttccgctg cggccagccc ctgcagggca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
```

```
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                 1065

SEQ ID NO: 224         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 224
atgctgttca acctgcgcat cctgctgaac aacgccgcct tccgcaacgg ccacaacttc  60
atggtgcgca acttccgctg cggccagccc ctgcagggcc gggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                 1065

SEQ ID NO: 225         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 225
atgctgttca acctgcgcat cctgctgaac aacgccgcct tccgcaacgg ccacaacttc  60
atggtgcgca acttccgctg cggccagccc ctgcagggcc gggtgcagct gaagggccgc  120
gacctgctga ccctgaagaa cttcaccggc gaggagatcc ggtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                 1065

SEQ ID NO: 226         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 226
atgctgttca acctgcgcat cctgctgaac aacgccgcct tccgcaacgg ccacaacttc  60
atggtgcgca acttccgctg cggccagccc ctgcagggca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
```

```
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                1065
```

```
SEQ ID NO: 227         moltype = DNA  length = 1065
FEATURE                Location/Qualifiers
misc_feature           1..1065
                       note = Synthetic construct
source                 1..1065
                       mol_type = other DNA
                       organism = synthetic construct
SEQUENCE: 227
atgctgttca acctgcgcat cctgctgaac aacgccgcct tccgcaacgg ccacaacttc  60
atggtgcgca acttccgctg cggccagccc ctgcagaaca aggtgcagct gaagggccgc  120
gacctgctga ccctgaagaa cttcaccggc gaggagatca agtacatgct gtggctgagc  180
gccgacctga agttccgcat caagcagaag ggcgagtacc tgcccctgct gcagggcaag  240
agcctgggca tgatcttcga gaagcgcagc acccgcaccc gcctgagcac cgagacaggc  300
ttcgccctgc tgggcggcca cccctgcttc ctgaccaccc aggacatcca cctgggcgtg  360
aacgagagcc tgaccgacac cgcccgcgtg ctgagcagca tggccgacgc cgtgctggcc  420
cgcgtgtaca agcagagcga cctggacacc ctggccaagg aggccagcat ccccatcatc  480
aacggcctga gcgacctgta ccaccccatc cagatcctgg ccgactacct gaccctgcag  540
gagcactaca gcagcctgaa gggcctgacc ctgagctgga tcggcgacgg caacaacatc  600
ctgcacagca tcatgatgag cgccgccaag ttcggcatgc acctgcaggc cgccaccccc  660
aagggctacg agcccgacgc cagcgtgacc aagctggccg agcagtacgc caaggagaac  720
ggcaccaagc tgctgctgac caacgacccc ctggaggccg cccacggcgg caacgtgctg  780
atcaccgaca cctggatcag catgggccag gaggaggaga agaagaagcg cctgcaggcc  840
ttccagggct accaggtgac catgaagacc gccaaggtgg ccgccagcga ctggaccttc  900
ctgcactgcc tgccccgcaa gcccgaggag gtggacgacg aggtgttcta cagcccccgc  960
agcctggtgt tccccgaggc cgagaaccgc aagtggacca tcatggccgt gatggtgagc  1020
ctgctgaccg actacagccc ccagctgcag aagcccaagt tctga                1065
```

```
SEQ ID NO: 228         moltype = DNA  length = 1068
FEATURE                Location/Qualifiers
misc_feature           1..1068
                       note = Synthetic construct
source                 1..1068
                       mol_type = other DNA
                       organism = synthetic construct
SEQUENCE: 228
atgctggtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga             1068
```

```
SEQ ID NO: 229         moltype = DNA  length = 1068
FEATURE                Location/Qualifiers
misc_feature           1..1068
                       note = Synthetic construct
source                 1..1068
                       mol_type = other DNA
                       organism = synthetic construct
SEQUENCE: 229
atgctggtat tcaacctgcg catcctgctg aacaacgccg ccttccgcaa cggccacaac  60
ttcatggtgc gcaacttccg ctgcggccag cccctgcaga accgggtgca gctgaagggc  120
cgcgacctgc tgaccctgaa gaacttcacc ggcgaggaga tccggtacat gctgtggctg  180
agcgccgacc tgaagttccg catcaagcag aagggcgagt acctgcccct gctgcagggc  240
aagagcctgg gcatgatctt cgagaagcgc agcacccgca cccgcctgag caccgagaca  300
ggcttcgccc tgctgggcgg ccacccctgc ttcctgacca cccaggacat ccacctgggc  360
gtgaacgaga gcctgaccga caccgcccgc gtgctgagca gcatggccga cgccgtgctg  420
gcccgcgtgt acaagcagag cgacctggac accctggcca aggaggccag catccccatc  480
```

```
atcaacggcc tgagcgacct gtaccacccc atccagatcc tggccgacta cctgaccctg  540
caggagcact acagcagcct gaagggcctg accctgagct ggatcggcga cggcaacaac  600
atcctgcaca gcatcatgat gagcgccgcc aagttcggca tgcacctgca ggccgccacc  660
cccaagggct acgagcccga cgccagcgtg accaagctgg ccgagcagta cgccaaggag  720
aacggcacca agctgctgct gaccaacgac cccctggagg ccgcccacgg cggcaacgtg  780
ctgatcaccg acacctggat cagcatgggc caggaggagg agaagaagaa gcgcctgcag  840
gccttccagg gctaccaggt gaccatgaag accgccaagg tggccgccag cgactggacc  900
ttcctgcact gcctgccccg caagcccgag gaggtggacg acgaggtgtt ctacagcccc  960
cgcagcctgg tgttccccga ggccgagaac cgcaagtgga ccatcatggc cgtgatggtg  1020
agcctgctga ccgactacag cccccagctg cagaagccca agttctga          1068

SEQ ID NO: 230         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 230
aaccaatcga aagaaaccaa a                                       21

SEQ ID NO: 231         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 231
ctctaatcac caggagtaaa a                                       21

SEQ ID NO: 232         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 232
gagagagatc ttaacaaaaa a                                       21

SEQ ID NO: 233         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 233
tgtgtaacaa caacaacaac a                                       21

SEQ ID NO: 234         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 234
ccgcagtagg aagagaaagc c                                       21

SEQ ID NO: 235         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 235
aaaaaaaaaa gaaatcataa a                                       21

SEQ ID NO: 236         moltype = RNA  length = 21
FEATURE                Location/Qualifiers
misc_feature           1..21
                       note = Synthetic construct
source                 1..21
                       mol_type = other RNA
                       organism = synthetic construct
```

```
SEQUENCE: 236
gagagaagaa agaagaagac g                                              21

SEQ ID NO: 237         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 237
caattaaaaa tacttaccaa a                                              21

SEQ ID NO: 238         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 238
gcaaacagag taagcgaaac g                                              21

SEQ ID NO: 239         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 239
gcgaagaaga cgaacgcaaa g                                              21

SEQ ID NO: 240         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 240
ttaggactgt attgactggc c                                              21

SEQ ID NO: 241         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 241
atcatcggaa ttcggaaaaa g                                              21

SEQ ID NO: 242         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 242
aaaacaaaag ttaaagcaga c                                              21

SEQ ID NO: 243         moltype = RNA  length = 21
FEATURE                Location/Qualifiers
misc_feature           1..21
                       note = Synthetic construct
source                 1..21
                       mol_type = other RNA
                       organism = synthetic construct
SEQUENCE: 243
tttatctcaa ataagaaggc a                                              21

SEQ ID NO: 244         moltype = RNA  length = 21
FEATURE                Location/Qualifiers
misc_feature           1..21
                       note = Synthetic construct
```

-continued

```
source                  1..21
                        mol_type = other RNA
                        organism = synthetic construct
SEQUENCE: 244
ggtggggagg tgagatttct t                                              21

SEQ ID NO: 245          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 245
tgattaggaa actacaaagc c                                              21

SEQ ID NO: 246          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 246
catttttcaa tttcataaaa c                                              21

SEQ ID NO: 247          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 247
ttacttttaa gcccaacaaa a                                              21

SEQ ID NO: 248          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 248
ggcgtgtgtg tgtgttgttg a                                              21

SEQ ID NO: 249          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 249
gtggtgaagg ggaaggttta g                                              21

SEQ ID NO: 250          moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 250
ttgttttttt ttggtttggt t                                              21

SEQ ID NO: 251          moltype = RNA  length = 1331
FEATURE                 Location/Qualifiers
misc_feature            1..1331
                        note = Synthetic construct
source                  1..1331
                        mol_type = other RNA
                        organism = synthetic construct
SEQUENCE: 251
aggattatta catcaaaaca aaaagccgcc accatgctgg tattcaacct gcgcatcctg  60
ctgaacaacg ccgccttccg caacggccac aacttcatgg tgcgcaactt ccgctgcggc  120
cagcccctgc agaaccgggt gcagctgaag ggccgcgacc tgctgaccct gaagaacttc  180
accggcgagg agatccggta catgctgtgg ctgagcgccg acctgaagtt ccgcatcaag  240
cagaagggcg agtacctgcc cctgctgcag ggcaagagcc tgggcatgat cttcgagaag  300
```

```
cgcagcaccc gcacccgcct gagcaccgag acaggcttcg ccctgctggg cggccacccc  360
tgcttcctga ccacccagga catccacctg ggcgtgaacg agagcctgac cgacaccgcc  420
cgcgtgctga gcagcatggc cgacgccgtg ctggcccgcg tgtacaagca gagcgacctg  480
gacaccctgg ccaaggaggc cagcatcccc atcatcaacg gcctgagcga cctgtaccac  540
cccatccaga tcctggccga ctacctgacc ctgcaggagc actacagcag cctgaagggc  600
ctgaccctga gctggatcgg cgacggcaac aacatcctgc acagcatcat gatgagcgcc  660
gccaagttcg gcatgcacct gcaggccgcc acccccaagg gctacgagcc cgacgccagc  720
gtgaccaagc tggccgagca gtacgccaag gagaacggca ccaagctgct gctgaccaac  780
gacccccctgg aggccgccca cggcggcaac gtgctgatca ccgacacctg gatcagcatg  840
ggccaggagg aggagaagaa gaagcgcctg caggccttcc agggctacca ggtgaccatg  900
aagaccgcca aggtggccgc cagcgactgg accttcctgc actgcctgcc ccgcaagccc  960
gaggaggtgg acgacgaggt gttctacagc cccgcagcc tggtgttccc cgaggccgag  1020
aaccgcaagt ggaccatcat ggccgtgatg gtgagcctgc tgaccgacta cagcccccag  1080
ctgcagaagc ccaagttctg aggtctctag taatgagctg gagcctcggt agccgttcct  1140
cctgcccgct gggcctccca acgggccctc ctcccctcct tgcaccggcc cttcctggtc  1200
tttgaataaa gtctgagtgg gcagcatcta gaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa a                                                       1331

SEQ ID NO: 252          moltype = RNA  length = 1334
FEATURE                 Location/Qualifiers
misc_feature            1..1334
                        note = Synthetic construct
source                  1..1334
                        mol_type = other RNA
                        organism = synthetic construct
SEQUENCE: 252
aggattatta catcaaaaca aaaagccgcc accatgctgg tattcaacct gcgcatcctg  60
ctgaacaacg ccgccttccg caacggccac aacttcatgg tgcgcaactt ccgctgcggc  120
cagcccctgc agaaccgggt gcagctgaag ggccgcgacc tgctgaccct gaagaacttc  180
accggcgagg agatccggta catgctgtgg ctgagcgccg acctgaagtt ccgcatcaag  240
cagaagggcg agtacctgcc cctgctgcag ggcaagagcc tgggcatgat cttcgagaag  300
cgcagcaccc gcacccgcct gagcaccgag acaggcttcg ccctgctggg cggccacccc  360
tgcttcctga ccacccagga catccacctg ggcgtgaacg agagcctgac cgacaccgcc  420
cgcgtgctga gcagcatggc cgacgccgtg ctggcccgcg tgtacaagca gagcgacctg  480
gacaccctgg ccaaggaggc cagcatcccc atcatcaacg gcctgagcga cctgtaccac  540
cccatccaga tcctggccga ctacctgacc ctgcaggagc actacagcag cctgaagggc  600
ctgaccctga gctggatcgg cgacggcaac aacatcctgc acagcatcat gatgagcgcc  660
gccaagttcg gcatgcacct gcaggccgcc acccccaagg gctacgagcc cgacgccagc  720
gtgaccaagc tggccgagca gtacgccaag gagaacggca ccaagctgct gctgaccaac  780
gacccccctgg aggccgccca cggcggcaac gtgctgatca ccgacacctg gatcagcatg  840
ggccaggagg aggagaagaa gaagcgcctg caggccttcc agggctacca ggtgaccatg  900
aagaccgcca aggtggccgc cagcgactgg accttcctgc actgcctgcc ccgcaagccc  960
gaggaggtgg acgacgaggt gttctacagc cccgcagcc tggtgttccc cgaggccgag  1020
aaccgcaagt ggaccatcat ggccgtgatg gtgagcctgc tgaccgacta cagcccccag  1080
ctgcagaagc ccaagttctg aggtctctag taatgagctg gagcctcggt agccgttcct  1140
cctgcccgct gggcctccca acgggccctc ctcccctcct tgcaccggcc cttcctggtc  1200
tttgaataaa gtctgagtgg gcagcatcta gaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa agct                                                    1334

SEQ ID NO: 253          moltype = RNA  length = 1328
FEATURE                 Location/Qualifiers
misc_feature            1..1328
                        note = Synthetic construct
source                  1..1328
                        mol_type = other RNA
                        organism = synthetic construct
SEQUENCE: 253
aggattatta catcaaaaca aaaagccgcc accatgctgt tcaacctgcg catcctgctg  60
aacaacgccg ccttccgcaa cggccacaac ttcatggtgc gcaacttccg ctgcggccag  120
cccctgcaga acaaggtgca gctgaagggc cgcgacctgc tgaccctgaa gaacttcacc  180
ggcgaggaga tcaagtacat gctgtggctg agcgccgacc tgaagttccg catcaagcag  240
aagggcgagt acctgcccct gctgcagggc aagagcctgg gcatgatctt cgagaagcgc  300
agcacccgca cccgcctgag caccgagaca ggcttcgccc tgctgggcgg ccacccctgc  360
ttcctgacca cccaggacat ccacctgggc gtgaacgaga gcctgaccga caccgcccgc  420
gtgctgagca gcatggccga cgccgtgctg gcccgcgtgt acaagcagag cgacctggac  480
accctggcca aggaggccag catccccatc atcaacggcc tgagcgacct gtaccacccc  540
atccagatcc tggccgacta cctgaccctg caggagcact acagcagcct gaagggcctg  600
accctgagct ggatcggcga cggcaacaac atcctgcaca gcatcatgat gagcgccgcc  660
aagttcggca tgcacctgca ggccgccacc cccaagggct acgagcccga cgccagcgtg  720
accaagctgg ccgagcagta cgccaaggag aacggcacca agctgctgct gaccaacgac  780
cccctggagg ccgcccacgg cggcaacgtg ctgatcaccg acacctggat cagcatgggc  840
caggaggagg agaagaagaa gcgcctgcag gccttccagg gctaccaggt gaccatgaag  900
accgccaagg tggccgccag cgactggacc ttcctgcact gcctgccccg caagcccgag  960
gaggtggacg acgaggtgtt ctacagcccc cgcagcctgg tgttccccga ggccgagaac  1020
cgcaagtgga ccatcatggc cgtgatggtg agcctgctga ccgactacag cccccagctg  1080
cagaagccca agttctgagg tctctagtaa tgagctggag cctcggtagc cgttcctcct  1140
gcccgctggg cctcccaacg ggccctcctc ccctccttgc accggccctt cctggtcttt  1200
```

-continued

```
gaataaagtc tgagtgggca gcatctagaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaa                                                           1328
```

COMPOSITIONS AND METHODS FOR TREATING ORNITHINE TRANSCARBAMYLASE DEFICIENCY

CROSS-REFERENCE TO RELATED APPLICATIONS

This application is a continuation of U.S. application Ser. No. 16/705,102, filed Dec. 5, 2019, which claims the benefit of and priority to U.S. Provisional Application No. 62/776,302, filed Dec. 6, 2018. The contents of each application are incorporated herein by reference in their entirety.

SEQUENCE LISTING

The instant application contains a Sequence Listing which has been submitted electronically in ASCII format and is hereby incorporated by reference in its entirety. Said ASCII copy, created on May 11, 2023 is named 049386-523C01US_SL_ST26.xml and is 568,374 bytes in size.

BACKGROUND

Ornithine transcarbamylase (OTC) is a mitochondrial enzyme present in mammals which plays an essential role in detoxifying the organism from toxic ammonia. OTC mRNA has a mitochondrial signaling peptide (MSP) that is critical to redirect the nascent pre-peptide from the cytosol into the mitochondria. OTC protein exist as a precursor in the cytosol, the presence of the MSP redirects the pro-peptide into the mitochondria, where it undergoes excision of the signaling peptide and delivery of the functional protein into the mitochondrial matrix. OTC is one of six enzymes that play a role in the breakdown of proteins and removal of ammonia from the body, a process known as the urea cycle, a metabolic process that occurs in hepatocytes. OTC is responsible for converting carbamoyl phosphate and ornithine into citrulline.

Deficiency of the OTC enzyme results in excessive accumulation of nitrogen, in the form of ammonia (hyperammonemia), in the blood. Excess ammonia, which is a neurotoxin, travels to the central nervous system through the blood, resulting in the symptoms and physical findings associated with OTC deficiency. These symptoms can include vomiting, refusal to eat, progressive lethargy, or coma. If left untreated a hyperammonemic episode may progress to coma and life-threatening complications.

The severity and age of onset of OTC deficiency vary from person to person, even within the same family. A severe form of the disorder affects some infants, typically males, shortly after birth (neonatal period). A milder form of the disorder affects some children later in infancy. Both males and females may develop symptoms of OTC deficiency during childhood. Presently, the treatment of OTC deficiency is aimed at preventing excessive ammonia from being formed or from removing excessive ammonia during a hyperammonemic episode. Long-term therapy for OTC deficiency combines dietary restrictions and the stimulation of alternative methods of converting and excreting nitrogen from the body (alternative pathways therapy).

Dietary restrictions in individuals with OTC deficiency are aimed at limiting the amount of protein intake to avoid the development of excess ammonia. However, enough protein must be taken in by an affected infant to ensure proper growth. Infants with OTC deficiency are placed on a low protein, high calorie diet supplemented by essential amino acids.

In addition to dietary restrictions, individuals with OTC deficiency are treated by medications that stimulate the removal of nitrogen from the body. These medications provide an alternative method to the urea cycle in converting and removing nitrogen waste. These medications are unpalatable to many patients and are often administered via a tube that is placed in the stomach through the abdominal wall (gastrostomy tube) or a narrow tube that reaches the stomach via the nose (nasogastric tube).

In cases where there is no improvement or in cases where hyperammonemic coma develops, the removal of wastes by filtering an affected individual's blood through a machine (hemodialysis) may be necessary. Hemodialysis is also used to treat infants, children, and adults who are first diagnosed with OTC deficiency during hyperammonemic coma.

In some cases, liver transplantation, may be an appropriate treatment option. Liver transplantation can cure the hyperammonemia in OTC deficiency. However, this operation is risky and may result in post-operative complications. Also, after liver transplantation, patients will need to follow a medication regimen throughout their lives for immunosuppression.

Novel approaches and therapies are still needed for the treatment of OTC enzyme deficiency. Strategies are needed which overcome the challenges and limitations associated with, for example, gene therapy. Poor stability, getting enough OTC in the mitochondria and efficient delivery to the target cells are still challenges.

SUMMARY

The present disclosure provides a modified human OTC protein of SEQ ID NO: 4 having improved properties for the treatment of OTC deficiency in a patient. SEQ ID NO: 4 has been modified from wild-type OTC to remove one or more predicted ubiquitination sites resulting in a protein that is less susceptible to ubiquitination and degradation by ubiquitin ligases. However, the modified OTC protein of SEQ ID NO: 4 maintains the catalytic enzyme activity of human wild type OTC. The removal of predicted ubiquitination sites preferably comprises replacing N-terminus residues that have been found to support ubiquitination such as asparagine, arginine, leucine, lysine or phenylalanine with N-terminus residues that have been found to be stabilizing against ubiquitination such as alanine, glycine, methionine, serine, threonine, valine and proline. Stabilization of the modified OTC protein of SEQ ID NO: 4 in this manner is particularly advantageous for preserving the stability of the modified OTC protein during its transport from the cytosol to the mitochondria wherein it exerts its enzymatic activity.

Preferably, the protein of SEQ ID NO: 4 described herein is produced from a nucleic acid encoding the protein of SEQ ID NO: 4. The nucleic acid may be RNA or DNA that encodes the protein of SEQ ID NO: 4. Preferably the nucleic acid is a heterologous mRNA construct comprising an open reading frame encoding for the modified protein of SEQ ID NO: 4. Preferably, the open reading frame is a codon-optimized open reading frame. Preferably, the open reading frame sequence is optimized to have a theoretical minimum of uridines possible to encode for the modified protein. Preferably, the heterologous mRNA construct comprises a 5' cap, a 5'UTR, a 3'UTR, an open reading frame encoding a modified protein of SEQ ID NO: 4 and a 3' poly A tail. Preferably, the 5'UTR derived from a gene expressed by *Arabidopsis thaliana*. Preferably the 5" UTR derived from a gene expressed by *Arabidopsis thaliana* is found in Table 2.

The present disclosure also provides mRNA (also referred to herein as mRNA constructs or mRNA sequences) comprising an optimized coding region encoding wild type human ornithine transcarbamylase (OTC) protein of SEQ ID NO: 3 or an OTC protein sequence that is at least 95% identical over the full length of SEQ ID NO: 3 and having OTC protein enzymatic activity wherein the mRNA sequences comprise a 5'UTR derived from a gene expressed by *Arabidopsis thaliana*.

The mRNA constructs described herein provide high-efficiency expression of the OTC proteins described herein. The expression can be in vitro, ex vivo, or in vivo.

The present disclosure also provides pharmaceutical compositions comprising the mRNA sequences described herein and methods of treating ornithine transcarbamylase (OTC) deficiency by administering the pharmaceutical compositions comprising the mRNA sequences described herein to a patient in need thereof wherein the OTC protein of SEQ ID NO: 3 or SEQ ID NO: 4 is expressed in the patient.

DETAILED DESCRIPTION

Definitions

Figure 1:
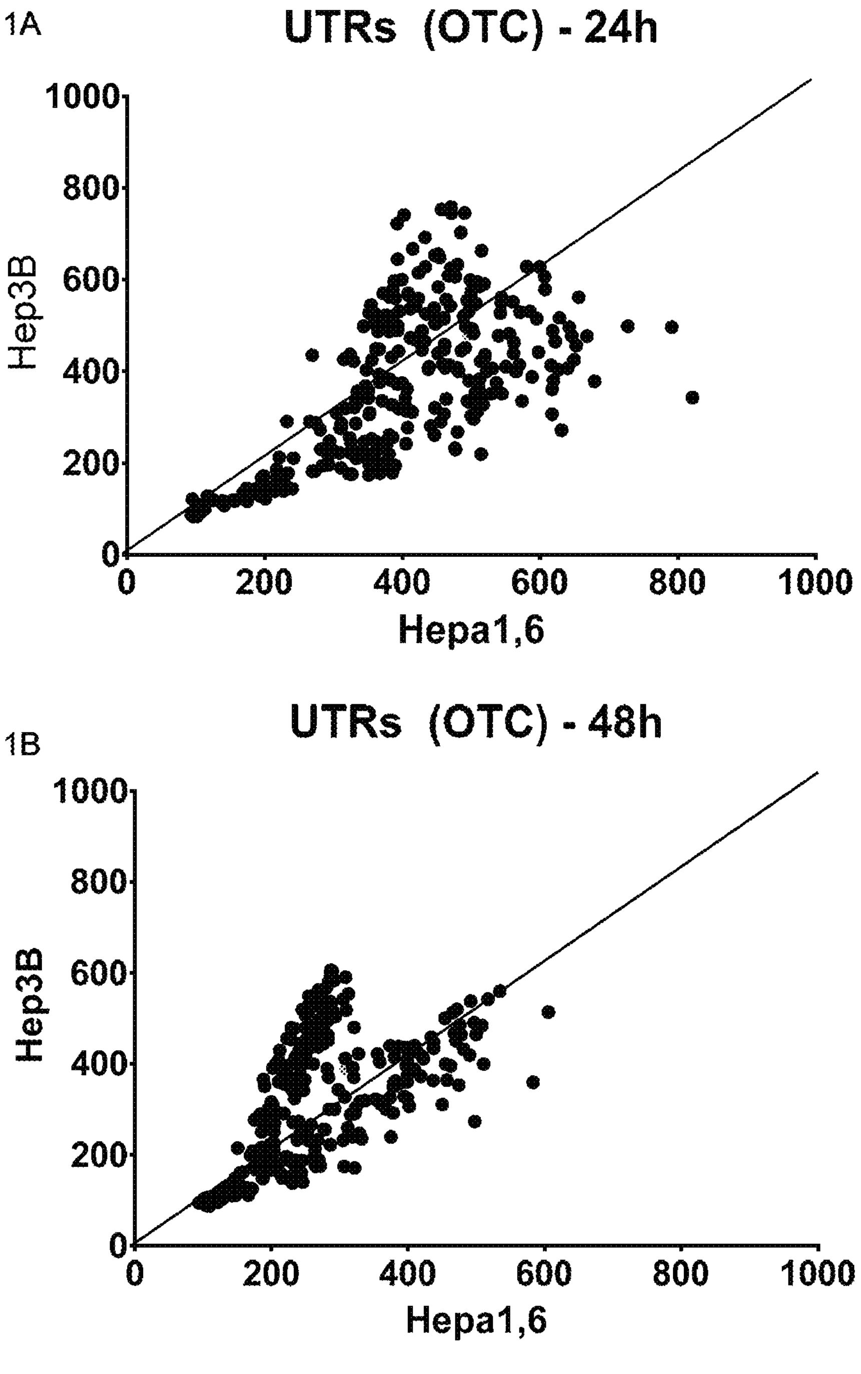
FIGS. 1A-1B show scatter plots illustrating ornithine transcarbamylase (OTC) protein expression in hepatocyte cell lines Hepa1,6 (mouse) and Hep3B (human) at 24 hours (FIG. 1A) and 48 hours (FIG. 1B) using In-Cell Western (ICW) assays.

The term "ornithine transcarbamylase" as used interchangeably herein with "OTC" or "hOTC", or "OTC_HUMAN" generally refers to the human protein associated with UniPRotKB-P00480. The amino acid sequence for the wild type human OTC protein is represented herein by SEQ ID NO: 3.

The term "nucleic acid," in its broadest sense, includes any compound and/or substance that comprise a polymer of nucleotides. These polymers are often referred to as polynucleotides. Exemplary nucleic acids or polynucleotides described herein include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

As used herein, the term "polynucleotide" is generally used to refer to a nucleic acid (e.g., DNA or RNA). When RNA, such as mRNA, is specifically being referred to, the term polyribonucleotide may be used. The terms polynucleotide, polyribonucleotide, nucleic acid, ribo nucleic acid, DNA, RNA, mRNA, and the like include such molecules that may be comprised of standard or unmodified residues; nonstandard or modified residues (e.g., analogs); and mixtures of standard and nonstandard (e.g., analogs) residues. In certain embodiments a polynucleotide or a polyribonucleotide is a modified polynucleotide or a polyribonucleotide. In the context of the present disclosure, for each RNA (polyribonucleotide) sequence listed herein, the corresponding DNA (polydeoxyribonucleotide or polynucleotide) sequence is contemplated and vice versa. "Polynucleotide" may be used interchangeably with the "oligomer". Polynucleotide sequences shown herein are from left to right, 5' to 3', unless stated otherwise.

As used herein, the term "messenger RNA" (mRNA) refers to any polynucleotide which encodes a protein or polypeptide of interest and which is capable of being translated to produce the encoded protein or polypeptide of interest in vitro, in vivo, in situ or ex vivo.

As used herein, the term "translation" is the process in which ribosomes create polypeptides. In translation, messenger RNA (mRNA) is decoded by transfer RNAS (tRNAs)

in a ribosome complex to produce a specific amino acid chain, or polypeptide. The coding region of a polynucleotide sequence (DNA or RNA), also known as the coding sequence or CDS, is capable of being converted to a protein or a fragment thereof by the process of translation.

As used herein, the term "codon-optimized" means a natural (or purposefully designed variant of a natural) coding sequence which has been redesigned by choosing different codons without altering the encoded protein amino acid sequence. Codon optimized sequence can increase the protein expression levels (Gustafsson et al., *Codon bias and heterologous protein expression.* 2004, Trends Biotechnol 22: 346-53) of the encoded proteins amongst providing other advantages. Variables such as high codon adaptation index (CAI), LowU method, mRNA secondary structures, cis-regulatory sequences, GC content and many other similar variables have been shown to somewhat correlate with protein expression levels (Villalobos et al., *Gene Designer: a synthetic biology tool for constructing artificial DNA segments.* 2006, BMC Bioinformatics 7:285). High CAI (codon adaptation index) method picks a most frequently used synonymous codon for an entire protein coding sequence. The most frequently used codon for each amino acid is deduced from 74,218 protein-coding genes from a human genome. The Low U method targets only U-containing codons that can be replaced with a synonymous codon with fewer U moieties. If there are a few choices for the replacement, the more frequently used codon will be selected. The remaining codons in the sequence are not changed by the Low U method. This method may be used in conjunction with the disclosed mRNAs to design coding sequences that are to be synthesized with, for example, 5-methoxyuridine or $N^1$-methylpseudouridine.

As used herein, "modified" refers to a change in the state or structure of a molecule disclosed herein. The molecule may be changed in many ways including chemically, structurally or functionally. Preferably a polynucleotide or polypeptide of the disclosure are modified as compared to the native form of the polynucleotide or polypeptide or as compared to a reference polypeptide sequence or polynucleotide sequence. For example, mRNA disclosed herein may be modified by codon optimization, or by the insertion of non-natural nucleosides or nucleotides. Polypeptides may be modified, for example, by site specific amino acid deletions or substitutions to alter the properties of the polypeptide.

As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the present disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the present disclosure, two protein sequences are considered to be homologous if the proteins are at least about 50%, 60%, 70%, 80%, or 90% identical for at least one stretch of at least about 20 amino acids.

As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes. In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. Methods commonly employed to determine percent identity between sequences include, but are not limited to those disclosed in Carillo, H., and Lipman, D., SIAM J *Applied Math.*, 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984), BLASTP, BLASTN, and FASTA Altschul, S. F. et al., *J. Molec. Biol.,* 215, 403 (1990).

An "effective amount" of the mRNA sequence encoding an open reading frame (ORF) protein or a corresponding composition thereof is generally that amount of mRNA that provides efficient ORF protein production in a cell. Preferably protein production using an mRNA composition described herein is more efficient than a composition containing a corresponding wild type mRNA encoding an ORF protein. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell. When referring to an ORF protein described herein, an effective amount is that amount of ORF protein that overcomes an ORF protein deficiency in a cell.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound described herein. Substantial separation can include compositions containing at least about 50%, at least about 60%, at least about 70%, at least about 80%, at least about 90%, at least about 95%, at least about 97%, or at least about 99% by weight of the compound described herein, or salt thereof. Methods for isolating compounds and their salts are routine in the art.

As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants. Preferably "patient" refers to a human subject who may seek or be in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "therapeutically effective amount" means an amount of an agent to be delivered (e.g., nucleic acid, protein or peptide, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, a "total daily dose" is an amount given or prescribed in a 24 hr period. It may be administered as a single unit dose.

As used herein, the term "treating" refers to partially or completely alleviating, ameliorating, improving, relieving, delaying onset of, inhibiting progression of, reducing severity of, and/or reducing incidence of one or more symptoms or features of OTC deficiency. Treatment may be administered to a subject who does not exhibit signs of OTC deficiency and/or to a subject who exhibits only early signs of OTC deficiency for the purpose of decreasing the risk of developing pathology associated with the disease, disorder, and/or condition.

As used herein, the terms "transfect" or "transfection" mean the intracellular introduction of a nucleic acid into a cell, or preferably into a target cell. The introduced nucleic acid may be stably or transiently maintained in the target cell. The term "transfection efficiency" refers to the relative amount of nucleic acid up-taken by the target cell which is subject to transfection. In practice, transfection efficiency is estimated by the amount of a reporter nucleic acid product expressed by the target cells following transfection. Preferred are compositions with high transfection efficacies and in particular those compositions that minimize adverse effects which are mediated by transfection of non-target cells and tissues.

As used herein, the term "target cell" refers to a cell or tissue to which a composition of the disclosure is to be directed or targeted. In some embodiments, the target cells are deficient in a protein or enzyme of interest. For example, where it is desired to deliver a nucleic acid to a hepatocyte, the hepatocyte represents the target cell. In some embodiments, the nucleic acids and compositions of the present disclosure transfect the target cells on a discriminatory basis (i.e., do not transfect non-target cells). The compositions and methods of the present disclosure may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior hom motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by the compositions and nucleic acids described herein, expression of the protein encoded by such nucleic acid may be preferably stimulated and the capability of such target cells to express the protein of interest is enhanced. For example, transfection of a target cell with an OTC mRNA will allow expression of the OTC protein product following translation of the nucleic acid. The nucleic acids of the compositions and/or methods provided herein preferably encode a product (e.g., a protein, enzyme, polypeptide, peptide, functional RNA, and/or antisense molecule), and preferably encode a product whose in vivo production is desired.

As used herein "an OTC protein enzymatic activity" refers to enzyme activity that catalyzes the reaction between carbamoyl phosphate and ornithine to form citrulline as part of the urea cycle in mammals.

As used herein, the term "about" or "approximately" as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Polynucleotide Sequences

The present disclosure provides improved methods and compositions for the treatment of Ornithine transcarbamylase (OTC) deficiency using, for example, mRNA therapy. The present disclosure provides methods of treating ornithine transcarbamylase (OTC) deficiency, comprising administering to a subject in need of treatment a composition comprising an mRNA sequence described herein encoding a human ornithine transcarbamylase (OTC) protein, modified forms of human OTC protein or active fragments of OTC protein at an effective dose and an administration interval such that at least one symptom or feature of the OTC deficiency is reduced in intensity, severity, or frequency or has delayed onset. The present disclosure also provides modified OTC proteins encoded by the mRNA sequences wherein the modified OTC proteins have improved properties such as enhanced stability and resistance to protein degradation and increased half-life as compared to wild type human OTC proteins.

Preferably, the administration of an mRNA composition described herein results in an increased OTC protein expression or activity of the subject as compared to a control level. Preferably, the control level is a baseline serum OTC protein expression or activity level in the subject prior to the treatment and/or the control level is indicative of the average serum OTC protein expression or activity level in OTC patients without treatment.

Preferably, administration of a mRNA described herein composition results in a reduced urinary orotic acid level in the subject as compared to a control orotic acid level. Preferably, the control orotic acid level is a baseline urinary orotic acid level in the subject prior to the treatment and/or the control orotic acid level is a reference level indicative of the average urinary orotic acid level in OTC patients without treatment.

Preferably, the OTC proteins encoded by the mRNA described herein are produced from a heterologous mRNA construct comprising an open reading frame (ORF) also referred to herein as a "coding sequence" (CDS) encoding for an OTC protein. Preferably, the coding sequence is codon-optimized. Preferably, coding sequence is optimized to have a theoretical minimum of uridines possible to encode for an OTC protein. Preferably, the mRNA constructs described herein comprise one or more of the following features: a 5' cap; a 5'UTR, a 5'UTR enhancer sequence, a Kozak sequence or a partial Kozak sequence, a 3'UTR, an open reading frame encoding an OTC protein and a poly A tail. Preferably, the mRNA constructs described herein can provide high-efficiency expression of an OTC protein. The expression can be in vitro, ex vivo, or in vivo.

Preferably, a human OTC protein encoded by an mRNA described herein comprises a modified human OTC protein of SEQ ID NO: 4 shown in Table 1. SEQ ID NO: 4 has been modified from wild-type OTC of SEQ ID NO: 3 (Table 1) to remove one or more predicted ubiquitination sites resulting in a protein that is less susceptible to ubiquitination and degradation by ubiquitin ligases. The removal of predicted ubiquitination sites preferably comprises replacing N-terminus residues that have been found to support ubiquitination such as asparagine, arginine, leucine, lysine or phenylalanine with N-terminus residues that have been found to be stabilizing against ubiquitination such as alanine, glycine, methionine, serine, threonine, valine and proline. Stabilization of the modified OTC protein of SEQ ID NO: 4 in this manner is particularly advantageous for preserving the stability of the modified OTC protein during its transport from the cytosol to the mitochondria wherein it exerts its enzymatic activity.

Preferably, an OTC protein encoded by an mRNA described herein comprises a protein sequence that is at least 70%, 75%, 80%, 85%, 90%, 95%, 96%, 97%, 98%, 99%, or 10000 identical to human wild type OTC protein of SEQ ID NO: 3 as shown in Table 1, while retaining the OTC protein activity of catalyzing the synthesis of citrulline (in the liver and small intestine) from carbamyl phosphate and ornithine.

TABLE 1

| Selected OTC Nucleotide and Peptide Sequences | |
|---|---|
| mRNA coding sequence for wild type human OTC | **AUGCUGUUUAAUCUGAGGAU**<br>**CCUGUUAAACAAUGCAGCUU**<br>**UUAGAAAUGGUCACAACUUC**<br>**AUGGUUCGAAAUUUUCGGUG**<br>**UGGACAACCACUACAA**AAUA<br>AAGUGCAGCUGAAGGGCCGU<br>GACCUUCUCACUCUAAAAAA<br>CUUUACCGGAGAAGAAAUUA<br>AAUAUAUGCUAUGGCUAUCA<br>GCAGAUCUGAAAUUUAGGAU<br>AAAACAGAAAGGAGAGUAUU<br>UGCCUUUAUUGCAAGGGAAG<br>UCCUUAGGCAUGAUUUUUGA<br>GAAAAGAAGUACUCGAACAA<br>GAUUGUCUACAGAAACAGGC<br>UUUGCACUUCUGGGAGGACA<br>UCCUUGUUUUCUUACCACAC<br>AAGAUAUUCAUUUGGGUGUG<br>AAUGAAAGUCUCACGGACAC<br>GGCCCGUGUAUUGUCUAGCA<br>UGGCAGAUGCAGUAUUGGCU<br>CGAGUGUAUAAACAAUCAGA<br>UUUGGACACCCUGGCUAAAG<br>AAGCAUCCAUCCCAAUUAUC<br>AAUGGGCUGUCAGAUUUGUA<br>CCAUCCUAUCCAGAUCCUGG<br>CUGAUUACCUCACGCUCCAG<br>GAACACUAUAGCUCUCUGAA<br>AGGUCUUACCCUCAGCUGGA<br>UCGGGGAUGGGAACAAUAUC<br>CUGCACUCCAUCAUGAUGAG<br>CGCAGCGAAAUUCGGAAUGC<br>ACCUUCAGGCAGCUACUCCA<br>AAGGGUUAUGAGCCGGAUGC<br>UAGUGUAACCAAGUUGGCAG<br>AGCAGUAUGCCAAAGAGAAU<br>GGUACCAAGCUGUUGCUGAC<br>AAAUGAUCCAUUGGAAGCAG<br>CGCAUGGAGGCAAUGUAUUA<br>AUUACAGACACUUGGAUAAG<br>CAUGGGACAAGAAGAGGAGA<br>AGAAAAAGCGGCUCCAGGCU<br>UUCCAAGGUUACCAGGUUAC<br>AAUGAAGACUGCUAAAGUUG<br>CUGCCUCUGACUGGACAUUU<br>UUACACUGCUUGCCCAGAAA<br>GCCAGAAGAAGUGGAUGAUG<br>AAGUCUUUUAUUCUCCUCGA<br>UCACUAGUGUUCCCAGAGGC<br>AGAAAACAGAAAGUGGACAA<br>UCAUGGCUGUCAUGGUGUCC<br>CUGCUGACAGAUUACUCACC<br>UCAGCUCCAGAAGCCUAAAU<br>UUUGA<br>(SEQ ID NO: 1) |
| DNA coding sequence for wild type human OTC | **ATGCTGTTTAATCTGAGGAT**<br>**CCTGTTAAACAATGCAGCTT**<br>**TTAGAAATGG** |

TABLE 1-continued

| Selected OTC Nucleotide and Peptide Sequences | |
|---|---|
| | **TCACAACTTCATGGTTCGAA**<br>**ATTTTCGGTGTGGACAACCA**<br>**CTACAA**AATA<br>AAGTGCAGCTGAAGGGCCGT<br>GACCTTCTCACTCTAAAAAA<br>CTTTACCGG<br>AGAAGAAATTAAATATATGC<br>TATGGCTATCAGCAGATCTG<br>AAATTTAGG<br>ATAAAACAGAAAGGAGAGTA<br>TTTGCCTTTATTGCAAGGGA<br>AGTCCTTAG<br>GCATGATTTTTGAGAAAAGA<br>AGTACTCGAACAAGATTGTC<br>TACAGAAAC<br>AGGCTTTGCACTTCTGGGAG<br>GACATCCTTGTTTTCTTACC<br>ACACAAGATA<br>TTCATTTGGGTGTGAATGAA<br>AGTCTCACGGACACGGCCCG<br>TGTATTGTCT<br>AGCATGGCAGATGCAGTATT<br>GGCTCGAGTGTATAAACAAT<br>CAGATTTGG<br>ACACCCTGGCTAAAGAAGCA<br>TCCATCCCAATTATCAATGG<br>GCTGTCAGA<br>TTTGTACCATCCTATCCAGA<br>TCCTGGCTGATTACCTCACG<br>CTCCAGGAAC<br>ACTATAGCTCTCTGAAAGGT<br>CTTACCCTCAGCTGGATCGG<br>GGATGGGAA<br>CAATATCCTGCACTCCATCA<br>TGATGAGCGCAGCGAAATTC<br>GGAATGCAC<br>CTTCAGGCAGCTACTCCAAA<br>GGGTTATGAGCCGGATGCTA<br>GTGTAACCA<br>AGTTGGCAGAGCAGTATGCC<br>AAAGAGAATGGTACCAAGCT<br>GTTGCTGAC<br>AAATGATCCATTGGAAGCAG<br>CGCATGGAGGCAATGTATTA<br>ATTACAGAC<br>ACTTGGATAAGCATGGGACA<br>AGAAGAGGAGAAGAAAAAGC<br>GGCTCCAG<br>GCTTTCCAAGGTTACCAGGT<br>TACAATGAAGACTGCTAAAG<br>TTGCTGCCTC<br>TGACTGGACATTTTTACACT<br>GCTTGCCCAGAAAGCCAGAA<br>GAAGTGGAT<br>GATGAAGTCTTTTATTCTCC<br>TCGATCACTAGTGTTCCCAG<br>AGGCAGAAAA<br>CAGAAAGTGGACAATCATGG<br>CTGTCATGGTGTCCCTGCTG<br>ACAGATTACTCACCTCAGCT<br>CCAGAAGCCTAAATTTTGA<br>(SEQ ID NO: 2) |
| Human wild type OTC amino acid sequence (The signal peptide for mitochondrial import is underlined*) | **MLFNLRILLNNAAFRNGHNF**<br>**MVRNFRCGQPLQ**NKVQLKGR<br>DLLTLKNFTGEEIKYMLWLS<br>ADLKFRIKQKGEYLPLLQGK<br>SLGMIFEKRSTRTRLSTETG<br>FALLGGHPCFLTTQDIHLGV<br>NESLTDTARVLSSMADAVLA<br>RVYKQSDLDTLAKEASIPIF<br>GLSDLYHPIQILADYLTLQ<br>EHYSSLKGLTLSWIGDGNNI<br>LHSIMMSAAKFGMHLQAATP<br>KGYEPDASVTKLAEQYAKEN<br>GTKLLLTNDPLEAAHGGNVL<br>ITDTWISMGQEEEKKKRLQA<br>FQGYQVTMKTAKVAASDWTF<br>LHCLPRKPEEVDDEVFYSPR<br>SLVFPEAENRKWTIMAVMVS<br>LLTDYSPQLQKPKF<br>(SEQ ID NO: 3) |
| Modified OTC amino acid sequence (The signal peptide for mitochondrial import is underlined*) | **MLVFNLRILLNNAAFRNGHN**<br>**FMVRNFRCGQPLQ**NRVQLKG<br>RDLLTLKNFTGEEIRYMLWL<br>SADLKFRIKQKGEYLPLLQG<br>KSLGMIFEKRSTRTRLSTET<br>GFALLGGHPCFLTTQDIHLG<br>VNESLTDTARVLSSMADAVL<br>ARVYKQSDLDTLAKEASIPI<br>INGLSDLYHPIQILADYLTL<br>QEHYSSLKGLTLSWIGDGNN<br>ILHSIMMSAAKFGMHLQAAT<br>PKGYEPDASVTKLAEQYAKE<br>NGTKLLLTNDPLEAAHGGNV<br>LITDTWISMGQEEEKKKRLQ<br>AFQGYQVTMKTAKVAASDWT<br>FLHCLPRKPEEVDDEVFYSP<br>RSLVFPEAENRKWTIMAVMV<br>SLLTDYSPQLQKPKF<br>(SEQ ID NO: 4) |

*The OTC protein comprises a signal peptide which is translated and which is responsible for translocation to the mitochondria. This signal peptide is represented by the first 32 amino acids as underlined in SEQ ID NO: 3 and SEQ ID NO: 4.
The signal sequence of SEQ ID NO: 4 has also been modified as compared to SEQ ID NO: 3.
An amino acid, valine is inserted at position 3 of SEQ ID NO: 4.
This modification provides better mitochondrial localization of the modified OTC of SEQ ID NO: 4 as compared to wild type human OTC of SEQ ID NO: 3.

Preferably, the open reading frame (ORF) or coding sequence (CDS) of an mRNA sequence described herein encodes an amino acid sequence that is substantially identical to the modified OTC protein of SEQ ID NO: 4.

Preferably, the open reading frame (ORF) or coding sequence (CDS) of an mRNA sequence described herein encodes an amino acid sequence that is substantially identical to wild type human OTC protein of SEQ ID NO: 3. Preferably, an OTC protein encoded by an mRNA described herein comprises a protein sequence that is at least 70%, 75%, 80%, 85%, 90%, 95% 96%, 97%, 98%, 99%, or 100% identical to a modified human OTC protein of SEQ ID NO: 3 shown in Table 1 while retaining the OTC protein activity of catalyzing the synthesis of citrulline (in the liver and small intestine) from carbamyl phosphate and ornithine.

Preferably, the ORF or CDS of an mRNA described herein encodes an amino acid sequence that is substantially identical to modified human OTC protein of SEQ ID NO: 4.

Preferably, the ORF or CDS of an mRNA described herein encoding a human OTC protein comprises a codon optimized polynucleotide sequence at least 70%, 75%, 80%, 85%, 90%, 95%, 96%, 97%, 98%, 99%, or 100% identical to the mRNA coding sequence of SEQ ID NO: 1 of Table 1.

Preferably an mRNA described herein further comprises a sequence immediately downstream (i.e., in the 3' direction from) of the CDS that creates a triple stop codon. The triple stop codon may be incorporated to enhance the efficiency of translation. In some embodiments, the translatable oligomer may comprise the sequence AUAAGUGAA (SEQ ID NO: 25) immediately downstream of an OTC CDS of an mRNA sequence described herein.

Preferably, an mRNA described herein further comprises a 5' untranslated region (UTR) sequence. As is understood in the art, the 5' and/or 3' UTR may affect an mRNA's stability or efficiency of translation. The 5' UTR may be derived from an mRNA molecule known in the art to be relatively stable (e.g., histone, tubulin, globin, glyceraldehyde 1-phosphate dehydrogenase (GAPDH), actin, or citric acid cycle enzymes) to increase the stability of the translatable oligomer. In other embodiments, a 5' UTR sequence may include a partial sequence of a cytomegalovirus (CMV) immediate-early 1 (IE1) gene.

Preferably, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Preferred 5' UTR sequences comprise SEQ ID NOS: 5-10, 125-127 and 230-250: as shown in Table 2.

TABLE 2

5'UTR sequences

| Name | Sequence | Seq ID No.: |
|---|---|---|
| EV | UCAACACAACAUAUACAAAACAAACGAAUCUCAAGCAAUCAAGC AUUCUACUUCUAUUGCAGCAAUUUAAAUCAUUUCUUUUAAAGCA AAAGCAAUUUUCUGAAAAUUUUCACCAUUUACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGGCGCUGCCUACGGAGGUGGCAGCCAUCUCCUUCU CGGCAUCAAGCUUACCAUGGUGCCCCAGGCCCUGCUCUUGGUCC CGCUGCUGGUGUUCCCCCUCUGCUUCGGCAAGUUCCCCAUCUAC ACCAUCCCCGACAAGCUGGGGCCGUGGAGCCCCAUCGACAUCCA CCACCUGUCCUGCCCCAACAACCUCGUGGUCGAGGACGAGGGCU GCACCAACCUGAGCGGGUUCUCCUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO: 8 |
| HUMAN ALBUMIN | AAUUAUUGGUUAAAGAAGUAUAUUAGUGCUAAUUUCCCUCCG UUUGUCCUAGCUUUUCUCUUCUGUCAACCCCACACGCCUUUGG CACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 125 |
| AT1G35720 | AACACUAAAAGUAGAAGAAAA | SEQ ID NO: 126 |
| AT5G45900 | CUCAGAAAGAUAAGAUCAGCC | SEQ ID NO: 127 |
| AT5G61250 | AACCAAUCGAAAGAAACCAAA | SEQ ID NO: 230 |
| AT5G46430 | CUCUAAUCACCAGGAGUAAAA | SEQ ID NO: 231 |
| AT5G47110 | GAGAGAGAUCUUAACAAAAAA | SEQ ID NO: 232 |
| AT1G03110 | UGUGUAACAACAACAACAACA | SEQ ID NO: 233 |

TABLE 2-continued

| 5'UTR sequences | | |
|---|---|---|
| Name | Sequence | Seq ID No.: |
| AT3G12380 | CCGCAGUAGGAAGAGAAAGCC | SEQ ID NO: 234 |
| AT5G45910 | AAAAAAAAAAGAAAUCAUAAA | SEQ ID NO: 235 |
| AT1G07260 | GAGAGAAGAAAGAAGAAGACG | SEQ ID NO: 236 |
| AT3G55500 | CAAUUAAAAAUACUUACCAAA | SEQ ID NO: 237 |
| AT3G46230 | GCAAACAGAGUAAGCGAAACG | SEQ ID NO: 238 |
| AT2G36170 | GCGAAGAAGACGAACGCAAAG | SEQ ID NO: 239 |
| AT1G10660 | UUAGGACUGUAUUGACUGGCC | SEQ ID NO: 240 |
| AT4G14340 | AUCAUCGGAAUUCGGAAAAAG | SEQ ID NO: 241 |
| AT1G49310 | AAAACAAAAGUUAAAGCAGAC | SEQ ID NO: 242 |
| AT4G14360 | UUUAUCUCAAAUAAGAAGGCA | SEQ ID NO: 243 |
| AT1G28520 | GGUGGGGAGGUGAGAUUUCUU | SEQ ID NO: 244 |
| AT1G20160 | UGAUUAGGAAACUACAAAGCC | SEQ ID NO: 245 |
| AT5G37370 | CAUUUUUCAAUUUCAUAAAAC | SEQ ID NO: 246 |
| AT4G11320 | UUACUUUUAAGCCCAACAAAA | SEQ ID NO: 247 |
| AT5G40850 | GGCGUGUGUGUGUGUUGUUGA | SEQ ID NO: 248 |
| AT1G06150 | GUGGUGAAGGGGAAGGUUUAG | SEQ ID NO: 249 |
| AT2G26080 | UUGUUUUUUUUUUGGUUUGGUU | SEQ ID NO: 250 |

Preferably the 5'UTR sequence comprises SEQ ID NO: 6 (AT1G58420).

Preferably, an mRNA described herein comprises a translation enhancer sequence. Translation enhancer sequences enhance the translation efficiency of a mRNA described herein and thereby provide increased production of the protein encoded by the mRNA. The translation enhancer region may be located in the 5' or 3' UTR of an mRNA sequence. Examples of translation enhancer regions include naturally-occurring enhancer regions from TEV 5'UTR and *Xenopus* beta-globin 3'UTR. Preferred 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID NOS 11-15 as shown in Table 3.

TABLE 3

| 5'UTR enhancers | | |
|---|---|---|
| Name | Sequence | Seq ID No.: |
| HSP70-P2 | GUCAGCUUUCAAACUCUUUGUUUCUUGUUUGUUGAUUGAGAAUA | SEQ ID NO: 11 |
| HSP70-M1 | CUCUCGCCUGAGAAAAAAAAUCCACGAACCAAUUUCUCAGCAACCAGCAGCACG | SEQ ID NO: 12 |
| HSP72-M2 | ACCUGUGAGGGUUCGAAGGAAGUAGCAGUGUUUUUUGUUCCUAGAGGAAGAG | SEQ ID NO: 13 |

TABLE 3-continued

5'UTR enhancers

| Name | Sequence | Seq ID No.: |
|---|---|---|
| HSP17.9 | ACACAGAAACAUU CGCAAAAACAAAA UCCCAGUAUCAAA AUUCUUCUCUUUU UUUCAUAUUUCGC AAAGAC | SEQ ID NO: 14 |
| HSP70-P1 | CAGAAAAAUUUGC UACAUUGUUUCAC AAACUUCAAAUAU UAUUCAUUUAUUU | SEQ ID NO: 15 |

Preferably, an mRNA described herein comprises a Kozak sequence. As is understood in the art, a Kozak sequence is a short consensus sequence centered around the translational initiation site of eukaryotic mRNAs that allows for efficient initiation of translation of the mRNA. The ribosomal translation machinery recognizes the AUG initiation codon in the context of the Kozak sequence. A Kozak sequence, may be inserted upstream of the coding sequence for OTC, downstream of a 5' UTR or inserted upstream of the coding sequence for OTC and downstream of a 5' UTR. Preferably, an mRNA described herein comprises a Kozak sequence having the amino acid sequence GCCACC (SEQ ID NO: 23). Preferably an mRNA described herein comprises a partial Kozak sequence "p" having the amino acid sequence GCCA (SEQ ID NO: 24).

Preferably an mRNA described herein comprises a 3'UTR. Preferably, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *Xenopus* beta globin, or fragments of any of the foregoing. Preferably, the 3' UTR is derived from *Xenopus* beta globin. Preferred 3' UTR sequences include SEQ ID NOS 16-22 as shown in Table 4.

TABLE 4

3'UTR sequences

| Name | Sequence | Seq ID No.: |
|---|---|---|
| XBG | CUAGUGACUGACUAG GAUCUGGUUACCACU AAACCAGCCUCAAGA ACACCCGAAUGGAGU CUCUAAGCUACAUAA UACCAACUUACACUU ACAAAAUGUUGUCCC CCAAAAUGUAGCCAU UCGUAUCUGCUCCUA AUAAAAAGAAAGUUU CUUCACAU | SEQ ID NO: 16 |
| HUMAN HAPTOGLOBIN | UGCAAGGCUGGCCGG AAGCCCUUGCCUGAA AGCAAGAUUUCAGCC UGGAAGAGGGCAAAG UGGACGGGAGUGGAC AGGAGUGGAUGCGAU AAGAUGUGGUUUGAA GCUGAUGGGUGCCAG CCCUGCAUUGCUGAG UCAAUCAAUAAAGAG CUUUCUUUUGACCCA U | SEQ ID NO: 17 |
| HUMAN APOLIPOPROTEIN E | ACGCCGAAGCCUGCA GCCAUGCGACCCCAC GCCACCCCGUGCCUC CUGCCUCCGCGCAGC CUGCAGCGGGAGACC CUGUCCCCGCCCCAG CCGUCCUCCUGGGGU GGACCCUAGUUUAAU AAAGAUUCACCAAGU UUCACGCA | SEQ ID NO: 18 |
| HCV | UAGAGCGGCAAACCC UAGCUACACUCCAUA GCUAGUUUCUUUUUU UUUUGUUUUUUUUUU UUUUUUUUUUUUUUU UUUUUUUUUUUUUUC CUUUUUUUCCUUUUU UUUUCCUCUUUUCUU GGUGGCUCCAUCUUA GCCCUAGUCACGGCU AGCUGUGAAAGGUCC GUGAGCCGCAUGACU GCAGAGAGUGCCGUA ACUGGUCUCUCUGCA GAUCAUGU | SEQ ID NO: 19 |
| MOUSE ALBUMIN | ACACAUCACAACCAC AACCUUCUCAGGCUA CCCUGAGAAAA AAAGACAUGAAGACU CAGGACUCAUCUUUU CUGUUGGUGU AAAAUCAACACCCUA AGGAACACAAAUUUC UUUAAACAUUU GACUUCUUGUCUCUG UGCUGCAAUUAAUAA AAAAUGGAAA GAAUCUAC | SEQ ID NO: 20 |
| HUMAN ALPHA GLOBIN | GCUGGAGCCUCGGUA GCCGUUCCUCCUGCC CGCUGGGCCUCCCAA CGGGCCCUCCUCCCC UCCUUGCACCGGCCC UUCCUGGUCUUUGAA UAAAGUCUGAGUGGG CAGCA | SEQ ID NO: 21 |
| EMCV | UAGUGCAGUCAC UGGCACAACG CGUUGCCCGG UAAGCCAAUC GGGUAUACAC GGUCGUCAUA CUGCAGACAG GGUUCUUCUA CUUUGCAAGA UAGUCUAGAG UAGUAAAAUA AAUAGUAUAAG | SEQ ID NO: 22 |

Preferably, an mRNA described herein comprises a 3' tail region, which can serve to protect the mRNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; sequential adenine nucleotides, 112-121 sequential adenine nucleotides; 114-121 adenine sequential nucleotides; and 115 to 121 sequential adenine nucleotides. Preferably a 3' poly A tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein poly(A) may be ligated to the 3' end of a sense RNA. Preferably, a combination of any of the above methods is utilized.

Preferably, an mRNA described herein comprises a 5' cap. 5'-ends capped with various groups and their analogues are known in the art. The 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7, 2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003). The 5' cap may be an ARCA cap (3'-OMe-m7G(5')pppG). The 5' cap may be an mCAP (m7G(5')ppp(5')G, $N^7$-Methyl-Guanosine-5'-Triphosphate-5'-Guanosine). The 5' cap may be resistant to hydrolysis. A preferred 5' cap is referred to herein as "m7GpppGm cap" also referred to herein as "Cap1" and has the following core structure:

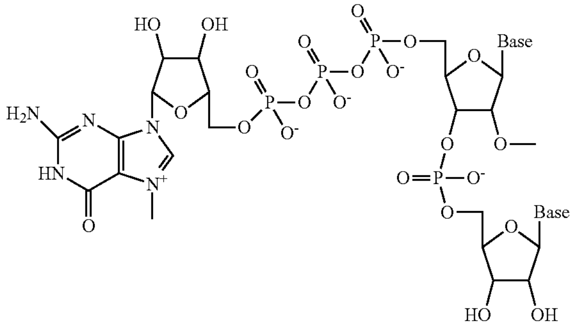

Preferably an mRNA described herein comprises one or more chemically modified nucleotides. Examples of nucleic acid monomers include non-natural, modified, and chemically-modified nucleotides, including any such nucleotides known in the art. mRNA sequences comprising chemically modified nucleotides have been shown to improve mRNA expression, expression rates, half-life and/or expressed protein concentrations. mRNA sequences comprising chemically modified nucleotides have also been useful to optimize protein localization thereby avoiding deleterious bio-responses such as the immune response and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4$,$N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4$,$N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyl-adenosine, $N^6$,$N^6$-dimethyladenosine, N6-hydroxynorvalylcarbamoyladenosine, 2-methylthio-$N^6$-hydroxynorvalylcarbamoyl-adenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6$,$N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Examples of modified or chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Examples of modified or chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine (also referred to herein as "N1MPU"), $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-0,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include $N^1$-methylpseudouridine and 5-methoxyuridine.

The constructs for preferred mRNA sequences are provided in Table 5.

TABLE 5

Exemplary mRNA Constructs

| mRNA Construct No. | Cap | 5'UTR | Kozak* | OTC Protein Encoded | 3'UTR | 3' Poly A Tail | mRNA Construct SEQ ID NO: |
|---|---|---|---|---|---|---|---|
| 563 | Cap1 | TEV | Yes | SEQ ID NO: 3 | XBG | Yes | 26 |
| 564 | Cap1 | TEV | Yes | SEQ ID NO: 3 | XBG | Yes | 27 |
| 565 | Cap1 | TEV | Yes | SEQ ID NO: 3 | XBG | Yes | 28 |
| 566 | Cap1 | TEV | Yes | SEQ ID NO: 3 | XBG | Yes | 29 |
| 567 | Cap1 | TEV | Yes | SEQ ID NO: 3 | XBG | Yes | 30 |
| 568 | Cap1 | TEV | Yes | SEQ ID NO: 3 | XBG | Yes | 31 |
| 569 | Cap1 | TEV | Yes | SEQ ID NO: 3 | XBG | Yes | 32 |
| 570 | Cap1 | TEV | Yes | SEQ ID NO: 3 | XBG | Yes | 33 |
| 571 | Cap1 | TEV | Yes | SEQ ID NO: 3 | XBG | Yes | 34 |
| 572 | Cap1 | TEV | Yes | SEQ ID NO: 3 | XBG | Yes | 35 |
| 573 | Cap1 | TEV | Yes | SEQ ID NO: 3 | XBG | Yes | 36 |
| 574 | Cap1 | TEV | Yes | SEQ ID NO: 3 | XBG | Yes | 37 |
| 575 | Cap1 | TEV | P | SEQ ID NO: 3 | XBG | Yes | 38 |
| 708 | Cap1 | TEV | P | SEQ ID NO: 3 | XBG | Yes | 39 |
| 709 | Cap1 | TEV | P | SEQ ID NO: 3 | XBG | Yes | 40 |
| 710 | Cap1 | TEV | P | SEQ ID NO: 3 | XBG | Yes | 41 |
| 711 | Cap1 | TEV | P | SEQ ID NO: 3 | XBG | Yes | 42 |
| 712 | Cap1 | TEV | Yes | SEQ ID NO: 3 | XBG | Yes | 43 |
| 713 | Cap1 | TEV | Yes | SEQ ID NO: 3 | XBG | Yes | 44 |
| 714 | Cap1 | TEV | Yes | SEQ ID NO: 3 | XBG | Yes | 45 |
| 715 | Cap1 | TEV | Yes | SEQ ID NO: 3 | XBG | Yes | 46 |
| 716 | Cap1 | TEV | Yes | SEQ ID NO: 3 | XBG | Yes | 47 |
| 717 | Cap1 | TEV | Yes | SEQ ID NO: 3 | XBG | Yes | 48 |
| 718 | Cap1 | TEV | Yes | SEQ ID NO: 3 | XBG | Yes | 49 |
| 719 | Cap1 | TEV | Yes | SEQ ID NO: 3 | XBG | Yes | 50 |
| 720 | Cap1 | TEV | Yes | SEQ ID NO: 3 | XBG | Yes | 51 |
| 721 | Cap1 | TEV | Yes | SEQ ID NO: 3 | XBG | Yes | 52 |
| 722 | Cap1 | TEV | Yes | SEQ ID NO: 3 | XBG | Yes | 53 |

TABLE 5-continued

| Exemplary mRNA Constructs | | | | | | | |
|---|---|---|---|---|---|---|---|
| mRNA Construct No. | Cap | 5'UTR | Kozak* | OTC Protein Encoded | 3'UTR | 3' Poly A Tail | mRNA Construct SEQ ID NO: |
| 723 | Cap1 | TEV | Yes | SEQ ID NO: 3 | XBG | Yes | 54 |
| 724 | Cap1 | TEV | Yes | SEQ ID NO: 3 | XBG | Yes | 55 |
| 725 | Cap1 | TEV | Yes | SEQ ID NO: 3 | XBG | Yes | 56 |
| 726 | Cap1 | TEV | Yes | SEQ ID NO: 3 | XBG | Yes | 57 |
| 727 | Cap1 | TEV | Yes | SEQ ID NO: 3 | XBG | Yes | 58 |
| 728 | Cap1 | TEV | Yes | SEQ ID NO: 3 | XBG | Yes | 59 |
| 729 | Cap1 | TEV | Yes | SEQ ID NO: 3 | XBG | Yes | 60 |
| 1787 | Cap1 | ARC5-2 | No | SEQ ID NO: 3 | Hu haptoglob | Yes | 61 |
| 1788 | Cap1 | AT1G58420 | P | SEQ ID NO: 3 | Hu ApoE | Yes | 62 |
| 1789 | Cap1 | ARC5-2 | No | SEQ ID NO: 3 | Hu haptoglob | Yes | 63 |
| 1790 | Cap1 | AT1G58420 | P | SEQ ID NO: 3 | Hu ApoE | Yes | 64 |
| 1791 | Cap1 | ARC5-2 | No | SEQ ID NO: 3 | Hu haptoglob | Yes | 65 |
| 1792 | Cap1 | HCV5' | P | SEQ ID NO: 3 | HCV3' | Yes | 66 |
| 1793 | Cap1 | AT1G58420 | P | SEQ ID NO: 3 | Hu a-glob | Yes | 67 |
| 1794 | Cap1 | AT1G58420 | P | SEQ ID NO: 3 | Hu a-glob | Yes | 68 |
| 1795 | Cap1 | AT1G58420 | P | SEQ ID NO: 3 | Hu a-glob | Yes | 69 |
| 1796 | Cap1 | Hu alb | No | SEQ ID NO: 3 | Ms Alb | Yes | 70 |
| 1797 | Cap1 | Hu alb | No | SEQ ID NO: 3 | Ms Alb | Yes | 71 |
| 1798 | Cap1 | Hu alb | No | SEQ ID NO: 3 | Ms Alb | Yes | 72 |
| 1799 | Cap1 | AT1G58420 | Yes | SEQ ID NO: 3 | Hu a-glob | Yes | 73 |
| 1800 | Cap1 | Hu alb | No | SEQ ID NO: 3 | Ms Alb | Yes | 74 |
| 1801 | Cap1 | AT1G58420 | P | SEQ ID NO: 3 | Hu ApoE | Yes | 75 |
| 1802 | Cap1 | ARC5-2 | No | SEQ ID NO: 3 | Hu haptoglob | Yes | 76 |
| 1803 | Cap1 | TEV | Yes | SEQ ID NO: 3 | XBG | Yes | 77 |
| 1804 | Cap1 | TEV | Yes | SEQ ID NO: 3 | XBG | Yes | 78 |
| 1805 | Cap1 | TEV | Yes | SEQ ID NO: 3 | XBG | Yes | 79 |
| 1806 | Cap1 | TEV | Yes | SEQ ID NO: 3 | XBG | Yes | 80 |
| 1808 | Cap1 | TEV | Yes | SEQ ID NO: 3 | XBG | Yes | 81 |
| 1809 | Cap1 | TEV | Yes | SEQ ID NO: 3 | XBG | Yes | 82 |
| 1816 | Cap1 | TEV | P | SEQ ID NO: 3 | XBG | Yes | 83 |
| 1822 | Cap1 | TEV | Yes | SEQ ID NO: 3 | XBG | Yes | 84 |
| 1823 | Cap1 | TEV | Yes | SEQ ID NO: 3 | XBG | Yes | 85 |
| 1840 | Cap1 | EMCV | No | SEQ ID NO: 3 | EMCV | Yes | 86 |
| 1841 | Cap1 | EMCV | No | SEQ ID NO: 3 | EMCV | Yes | 87 |
| 1842 | Cap1 | EMCV | No | SEQ ID NO: 3 | EMCV | Yes | 88 |
| 1843 | Cap1 | HSP70-P2-TEV | Yes | SEQ ID NO: 3 | XBG | Yes | 89 |
| 1844 | Cap1 | HSP70-M1-TEV | Yes | SEQ ID NO: 3 | XBG | Yes | 90 |
| 1845 | Cap1 | HSP70-M2-TEV | Yes | SEQ ID NO: 3 | XBG | Yes | 91 |
| 1846 | Cap1 | HSP17.9-TEV | Yes | SEQ ID NO: 3 | XBG | Yes | 92 |
| 1847 | Cap1 | HSP70-P1-TEV | Yes | SEQ ID NO: 3 | XBG | Yes | 93 |
| 1882 | Cap1 | TEV | Yes | SEQ ID NO: 3 | XBG | Yes | 94 |
| 1883 | Cap1 | TEV | Yes | SEQ ID NO: 3 | XBG | Yes | 95 |
| 1884 | Cap1 | TEV | Yes | SEQ ID NO: 3 | XBG | Yes | 96 |
| 1885 | Cap1 | TEV | Yes | SEQ ID NO: 3 | XBG | Yes | 97 |
| 1886 | Cap1 | TEV | Yes | SEQ ID NO: 3 | XBG | Yes | 98 |
| 1887 | Cap1 | TEV | Yes | SEQ ID NO: 3 | XBG | Yes | 99 |
| 1888 | Cap1 | TEV | Yes | SEQ ID NO: 3 | XBG | Yes | 100 |
| 1889 | Cap1 | TEV | Yes | SEQ ID NO: 3 | XBG | Yes | 101 |
| 1890 | Cap1 | TEV | Yes | SEQ ID NO: 3 | XBG | Yes | 102 |
| 1891 | Cap1 | TEV | Yes | SEQ ID NO: 3 | XBG | Yes | 103 |
| 1898 | Cap1 | TEV | Yes | SEQ ID NO: 3 | XBG | Yes | 104 |
| 1899 | Cap1 | TEV | Yes | SEQ ID NO: 3 | XBG | Yes | 105 |
| 1900 | Cap1 | TEV | Yes | SEQ ID NO: 3 | XBG | Yes | 106 |
| 1903 | Cap1 | TEV | P | SEQ ID NO: 3 | XBG | Yes | 107 |
| 1904 | Cap1 | TEV | P | SEQ ID NO: 3 | XBG | Yes | 108 |
| 1905 | Cap1 | TEV | P | SEQ ID NO: 3 | XBG | Yes | 109 |
| 1906 | Cap1 | TEV | P | SEQ ID NO: 3 | XBG | Yes | 110 |
| 1907 | Cap1 | TEV | P | SEQ ID NO: 3 | XBG | Yes | 111 |
| 1908 | Cap1 | TEV | P | SEQ ID NO: 3 | XBG | Yes | 112 |
| 1915 | Cap1 | HSP70-P1-AT1G58420 | Yes | SEQ ID NO: 3 | Hu a-glob | Yes | 113 |
| 1916 | Cap1 | HSP70-P1-AT1G58420 | Yes | SEQ ID NO: 3 | Hu a-glob | Yes | 114 |
| 1917 | Cap1 | HSP70-P1-AT1G58420 | Yes | SEQ ID NO: 3 | Hu a-glob | Yes | 115 |
| 1918 | Cap1 | HSP70-P1-AT1G58420 | Yes | SEQ ID NO: 3 | Hu a-glob | Yes | 116 |
| 1919 | Cap1 | AT1G58420 | Yes | SEQ ID NO: 3 | Hu a-glob | Yes | 117 |
| 1920 | Cap1 | AT1G58420 | Yes | SEQ ID NO: 3 | Hu a-glob | Yes | 118 |

TABLE 5-continued

| Exemplary mRNA Constructs | | | | | | | |
|---|---|---|---|---|---|---|---|
| mRNA Construct No. | Cap | 5'UTR | Kozak* | OTC Protein Encoded | 3'UTR | 3' Poly A Tail | mRNA Construct SEQ ID NO: |
| 1921 | Cap1 | AT1G58420 | Yes | SEQ ID NO: 4** | Hu a-glob | Yes | 119 |
| 1925 | Cap1 | TEV | Yes | SEQ ID NO: 3 | XBG | Yes | 120 |
| 1926 | Cap1 | AT1G58420 | Yes | SEQ ID NO: 3 | Hu a-glob | Yes | 121 |
| 1927 | Cap1 | AT1G58420 | Yes | SEQ ID NO: 3 | Hu a-glob | Yes | 122 |
| 1928 | Cap1 | AT1G58420 | Yes | SEQ ID NO: 3 | Hu a-glob | Yes | 123 |
| 1929 | Cap1 | HSP70-P1-AT1G58420 | Yes | SEQ ID NO: 3 | Hu a-glob | Yes | 124 |
| 2016 | Cap1 | AT1G58420 | Yes | SEQ ID NO: 3 | Hu a-glob | Yes | 253 |
| 2260 | Cap1 | AT1G58420 | Yes | SEQ ID NO: 4** | Hu a-glob | Yes | 251 |
| 2262 | Cap1 | AT1G58420 | Yes | SEQ IS NO: 4** | Hu a-glob | Yes | 252 |

*Kozak sequence defined as GCCACC (SEQ ID NO: 23). Partial (P) Kozak defined as GCCA (SEQ ID NO: 24).
**Construct encodes modified human OTC protein of SEQ ID NO: 4.

Preferred mRNA sequences include all of the mRNA sequences listed in Table 5. Preferred mRNA sequences include all of the mRNA sequences listed wherein, 0% to 100%, preferably 1% to 100%, preferably 25% to 100%, preferably 50% to 100% and preferably 75% to 100% of the uracil nucleotides of the mRNA sequences are modified. Preferably, 1% to 100% of the uracil nucleotides are $N^1$-methylpseudouridine or 5-methoxyuridine. Preferably 100% of the uracil nucleotides are $N^1$-methylpseudouridine. Preferably 100% of the uracil nucleotides are 5-methoxyuridine.

Preferred mRNA sequences comprise a 5' cap, a 5'UTR that is derived from a gene expressed by *Arabidopsis thaliana*, an optional translation enhancer sequence, an optional Kozak sequence or partial Kozak sequence, a codon optimized coding sequence (CDS/ORF) coding for an OTC protein, a 3' UTR and a poly A tail. Preferably the codon optimized CDS encodes a protein of SEQ ID NO: 3 or SEQ ID NO: 4. Preferably, the 5' UTR that is derived from a gene expressed by *Arabidopsis thaliana* is selected from found in Table 5. Preferably, the 5' UTR that is derived from a gene expressed by *Arabidopsis thaliana* is selected from the group consisting of: SEQ ID NO: 6, SEQ ID NOS: 125-127 and SEQ ID NOS: 227-247. Preferably the 5' UTR sequence is AT1G58420 having the sequence of SEQ ID NO: 6. Preferably, the uracil content of the codon optimized sequence has been reduced with respect to the percentages of uracil content of SEQ ID NO: 1. Preferably, 0% to 100% of the uracil nucleotides of the mRNA sequences are modified. Preferably, 0% to 100% of the uracil nucleotides are $N^1$-methylpseudouridine or 5-methoxyuridine. Preferably 100% of the uracil nucleotides are $N^1$-methylpseudouridine. Preferably 100% of the uracil nucleotides are 5-methoxyuridine.

Preferred mRNA constructs comprise codon optimized coding sequences and a 5' UTR from a gene expressed by *Arabidopsis thaliana* and are selected from: SEQ ID NOS: 62, 67, 68, 69, 73, 113-119, 121-127.

A preferred mRNA construct of the disclosure comprises mRNA construct 1921 (SEQ ID NO: 119) having an optimized ORF encoding the modified human OTC protein of SEQ ID NO: 4 and comprising a 3' Poly A tail of 121 nucleotides. Another preferred mRNA construct comprises construct 2260 (SEQ ID NO: 251) encoding the modified human OTC protein of SEQ ID NO: 4 and comprising a 3' Poly A tail of 100 nucleotides. Another preferred mRNA construct comprises construct 2262 (SEQ ID NO: 252) encoding the modified human OTC protein of SEQ ID NO: 4 and comprising a 3' Poly A tail of 100 nucleotides.

A preferred mRNA sequence of the disclosure includes the mRNA construct 1799 (SEQ ID NO: 73) having a codon optimized ORF encoding wild type human OTC of SEQ ID NO: 3 and having a 3' Poly A tail of 121 nucleotides. Another preferred mRNA construct of the disclosure includes the mRNA construct 2016 (SEQ ID NO: 253) having a codon optimized ORF encoding wild type human OTC of SEQ ID NO: 3 and comprising a 3' Poly A tail of 100 nucleotides.

Preferably 100% of the uridine nucleotides of mRNA constructs 1799, 2016, 1921, 2260 and 2262, are N1-methylpseudouridine. Preferably 100% of the uracil nucleotides of mRNA constructs 1799, 2016, 1921, 2260 and 2262, are 5-methoxyuridine.

The mRNA for use in accordance with this disclosure can exhibit increased translation efficiency. As used herein, translation efficiency refers to a measure of the production of a protein or polypeptide by translation of an mRNA in accordance with the disclosure. Preferably, an mRNA of the disclosure can exhibit at least 2-fold, 3-fold, 5-fold, or 10-fold increased translation efficiency in vivo as compared to mRNA encoding SEQ ID NO: 3 or SEQ ID NO: 4 that is not codon optimized in accordance with the disclosure and/or that does not comprise the preferred UTRs of the disclosure. Preferably an mRNA of the disclosure can provide at least a 2-fold, 3-fold, 5-fold, or 10-fold increased polypeptide or protein level in vivo as compared to mRNA encoding SEQ ID NO: 3 or SEQ ID NO: 4 that is not codon optimized and/or does not comprise the preferred UTRs of the disclosure. Preferably, an mRNA of the disclosure can provide increased levels of a polypeptide or protein in vivo as compared to mRNA encoding SEQ ID NO: 3 or SEQ ID NO: 4 that is not codon optimized in accordance with the disclosure and/or that does not comprise the preferred UTRs of the disclosure. For example, the level of a polypeptide or protein can be increased by 10%, or 20%, or 30%, or 40%, or 50%, or more.

Preferably the mRNA of the disclosure can provide increased functional half-life in the cytoplasm of mammalian cells over mRNA encoding SEQ ID NO: 3 or SEQ ID NO: 4 that is not codon optimized in accordance with the disclosure and/or that does not comprise the preferred UTRs of the disclosure. The inventive translatable molecules can have increased half-life of activity as compared to mRNA encoding SEQ ID NO: 3 or SEQ ID NO: 4 that is not codon optimized in accordance with the disclosure and/or that does not comprise the preferred UTRs of the disclosure.

Preferably, the mRNA of the disclosure can reduce cellular innate immune response as compared to mRNA encoding SEQ ID NO: 3 or SEQ ID NO: 4 that is not codon optimized in accordance with the disclosure and/or that does not comprise the preferred UTRs of the disclosure.

Preferably, the mRNA of the disclosure can reduce the dose levels required for efficacious therapy as compared to mRNA encoding SEQ ID NO: 3 or SEQ ID NO: 4 that is not codon optimized in accordance with the disclosure and/or that does not comprise the preferred UTRs of the disclosure.

Design and Synthesis of the mRNA Sequences mRNA for use in accordance with the disclosure may be prepared according to any available technique including, but not limited to chemical synthesis, in vitro transcription (IVT) or enzymatic or chemical cleavage of a longer precursor, etc. Methods of synthesizing RNAs are known in the art.

In some embodiments, mRNA is produced from a primary complementary DNA (cDNA) construct. The process of design and synthesis of the primary cDNA constructs described herein generally includes the steps of gene construction, mRNA production (either with or without modifications) and purification. In the IVT method, a target polynucleotide sequence encoding an OTC protein is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a human OTC protein (e.g. SEQ ID NO: 3 or SEQ ID NO: 4) is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

Further, nucleotide sequence of any region of the mRNA or DNA template may be codon optimized. Codon optimization methods are known in the art and may be useful in efforts to achieve one or more of several goals. These goals include to match codon frequencies in target and host organisms to ensure proper folding, to bias GC content to increase mRNA stability or reduce secondary structures, to minimize tandem repeat codons or base runs that may impair gene construction or expression, to customize transcriptional and translational control regions, to insert or remove protein trafficking sequences, to remove/add post translation modification sites in encoded protein (e.g. glycosylation sites), to add, remove or shuffle protein domains, to insert or delete restriction sites, to modify ribosome binding sites and mRNA degradation sites, to adjust translational rates to allow the various domains of the protein to fold properly, or to reduce or eliminate problematic secondary structures within the mRNA. Suitable codon optimization tools, algorithms and services are known in the art.

Preferably, the primary cDNA template may include reducing the occurrence or frequency of appearance of certain nucleotides in the template strand. For example, the occurrence of a nucleotide in a template may be reduced to a level below 25% of nucleotides in the template. In further examples, the occurrence of a nucleotide in a template may be reduced to a level below 20% of nucleotides in the template. In some examples, the occurrence of a nucleotide in a template may be reduced to a level below 16% of nucleotides in the template. Preferably, the occurrence of a nucleotide in a template may be reduced to a level below 15%, and preferably may be reduced to a level below 12% of nucleotides in the template.

For example, the present disclosure provides nucleic acids wherein with altered uracil content at least one codon in the wild-type sequence has been replaced with an alternative codon to generate a uracil-altered sequence. Altered uracil sequences can have at least one of the following properties:

(i) an increase or decrease in global uracil content (i.e., the percentage of uracil of the total nucleotide content in the nucleic acid of a section of the nucleic acid, e.g., the open reading frame); or,
(ii) an increase or decrease in local uracil content (i.e., changes in uracil content are limited to specific subsequences); or,
(iii) a change in uracil distribution without a change in the global uracil content; or,
(iv) a change in uracil clustering (e.g., number of clusters, location of clusters, or distance between clusters); or,
(v) combinations thereof.

Preferably, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the in the nucleic acid sequences of the disclosure. The percentage uracil content can be determined by dividing the number of uracil in a sequence by the total number of nucleotides and multiplying by 100.

Preferably, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure.

Preferably, codons in the nucleic acid sequence of the invention reduce or modify, for example, the number, size, location, or distribution of uracil clusters that could have deleterious effects on protein translation. Although lower uracil content is desirable, in certain aspects, the uracil content, and in particular the local uracil content, of some subsequences of the wild-type sequence can be greater than the wild-type sequence and still maintain beneficial features (e.g., increased expression).

Preferably, the uracil-modified sequence induces a lower Toll-Like Receptor (TLR) response when compared to the wild-type sequence. Several TLRs recognize and respond to nucleic acids. Double-stranded (ds)RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. Preferably, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Preferably, the uracil content of polynucleotides disclosed herein and preferably polynucleotides encoding the modified OTC protein of SEQ ID NO: 4 is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 90%, 80%, 70%, 60%, 5%, 4%, 3%, 2% or 1% of the total nucleobases in the sequence in the reference sequence. Preferably, the uracil content of polynucleotides disclosed herein and preferably polynucleotides encoding the modified OTC protein of SEQ ID NO: 4, is between about 5% and about 25%. Preferably, the uracil content of polynucleotides disclosed herein and preferably polynucleotides encoding the modified OTC protein of SEQ ID NO: 4 is about 15% and about 25%.

The cDNA templates may be transcribed to produce an mRNA sequence described herein using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed mRNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or CLEANCAP® technology (TriLink Biotechnologies). A poly-A tailing reaction may be performed by methods known in the art, such as, but not limited to, 2' O-methyltransferase and by methods as described herein. If the primary construct generated from cDNA does not include a poly-T, it may be beneficial to perform the poly-A-tailing reaction before the primary construct is cleaned.

Codon optimized cDNA constructs encoding an ornithine transcarbamylase (OTC) protein are particularly suitable for generating mRNA sequences described herein. For example, such cDNA constructs may be used as the basis to transcribe, in vitro, a polyribonucleotide encoding an ornithine transcarbamylase (OTC) protein. Table 6 provides a listing of exemplary cDNA ORF templates used for in vitro transcription of the mRNA sequences listed in Table 5.

TABLE 6

Exemplary cDNA Templates

| DNA Construct No***: | SEQ ID NO: | Protein encoded by cDNA template SEQ ID NO: |
|---|---|---|
| p563 | 128 | SEQ ID NO: 3* |
| p564 | 129 | SEQ ID NO: 3* |
| p565 | 130 | SEQ ID NO: 3* |
| p566 | 131 | SEQ ID NO: 3* |
| p567 | 132 | SEQ ID NO: 3* |
| p568 | 133 | SEQ ID NO: 3* |
| p569 | 134 | SEQ ID NO: 3* |
| p570 | 135 | SEQ ID NO: 3* |
| p571 | 136 | SEQ ID NO: 3* |
| p572 | 137 | SEQ ID NO: 3* |
| p573 | 138 | SEQ ID NO: 3* |
| p574 | 139 | SEQ ID NO: 3* |
| p575 | 140 | SEQ ID NO: 3* |
| p708 | 141 | SEQ ID NO: 3* |
| p709 | 142 | SEQ ID NO: 3* |
| p710 | 143 | SEQ ID NO: 3* |
| p711 | 144 | SEQ ID NO: 3* |
| p712 | 145 | SEQ ID NO: 3* |
| p713 | 146 | SEQ ID NO: 3* |
| p714 | 147 | SEQ ID NO: 3* |
| p715 | 148 | SEQ ID NO: 3* |
| p716 | 149 | SEQ ID NO: 3* |
| p717 | 150 | SEQ ID NO: 3* |
| p718 | 151 | SEQ ID NO: 3* |
| p719 | 152 | SEQ ID NO: 3* |
| p720 | 153 | SEQ ID NO: 3* |
| p721 | 154 | SEQ ID NO: 3* |
| p722 | 155 | SEQ ID NO: 3* |
| p723 | 156 | SEQ ID NO: 3* |
| p724 | 157 | SEQ ID NO: 3* |
| p725 | 158 | SEQ ID NO: 3* |
| p726 | 159 | SEQ ID NO: 3* |
| p727 | 160 | SEQ ID NO: 3* |
| p728 | 161 | SEQ ID NO: 3* |
| p729 | 162 | SEQ ID NO: 3* |
| p1787 | 163 | SEQ ID NO: 3* |
| p1788 | 164 | SEQ ID NO: 3* |
| p1789 | 165 | SEQ ID NO: 3* |
| p1790 | 166 | SEQ ID NO: 3* |
| p1791 | 167 | SEQ ID NO: 3* |
| p1792 | 168 | SEQ ID NO: 3* |
| p1793 | 169 | SEQ ID NO: 3* |
| p1794 | 170 | SEQ ID NO: 3* |
| p1795 | 171 | SEQ ID NO: 3* |
| p1796 | 172 | SEQ ID NO: 3* |
| p1797 | 173 | SEQ ID NO: 3* |
| p1798 | 174 | SEQ ID NO: 3* |
| p1799 | 175 | SEQ ID NO: 3* |
| p1800 | 176 | SEQ ID NO: 3* |
| p1801 | 177 | SEQ ID NO: 3* |
| p1802 | 178 | SEQ ID NO: 3* |
| p1803 | 179 | SEQ ID NO: 3* |
| p1804 | 180 | SEQ ID NO: 3* |
| p1805 | 181 | SEQ ID NO: 3* |
| p1806 | 182 | SEQ ID NO: 3* |
| p1808 | 183 | SEQ ID NO: 3* |
| p1809 | 184 | SEQ ID NO: 3* |
| p1816 | 185 | SEQ ID NO: 3* |
| p1822 | 186 | SEQ ID NO: 3* |
| p1823 | 187 | SEQ ID NO: 3* |
| p1840 | 188 | SEQ ID NO: 3* |
| p1841 | 189 | SEQ ID NO: 3* |
| p1842 | 190 | SEQ ID NO: 3* |
| p1843 | 191 | SEQ ID NO: 3* |
| p1844 | 192 | SEQ ID NO: 3* |

TABLE 6-continued

Exemplary cDNA Templates

| DNA Construct No***: | SEQ ID NO: | Protein encoded by cDNA template SEQ ID NO: |
|---|---|---|
| p1845 | 193 | SEQ ID NO: 3* |
| p1846 | 194 | SEQ ID NO: 3* |
| p1847 | 195 | SEQ ID NO: 3* |
| p1882 | 196 | SEQ ID NO: 3* |
| p1883 | 197 | SEQ ID NO: 3* |
| p1884 | 198 | SEQ ID NO: 3* |
| p1885 | 199 | SEQ ID NO: 3* |
| p1886 | 200 | SEQ ID NO: 3* |
| p1887 | 201 | SEQ ID NO: 3* |
| p1888 | 202 | SEQ ID NO: 3* |
| p1889 | 203 | SEQ ID NO: 3* |
| p1890 | 204 | SEQ ID NO: 3* |
| p1891 | 205 | SEQ ID NO: 3* |
| p1898 | 206 | SEQ ID NO: 3* |
| p1899 | 207 | SEQ ID NO: 3* |
| p1900 | 208 | SEQ ID NO: 3* |
| p1903 | 209 | SEQ ID NO: 3* |
| p1904 | 210 | SEQ ID NO: 3* |
| p1905 | 211 | SEQ ID NO: 3* |
| p1906 | 212 | SEQ ID NO: 3* |
| p1907 | 213 | SEQ ID NO: 3* |
| p1908 | 214 | SEQ ID NO: 3* |
| p1915 | 215 | SEQ ID NO: 3* |
| p1916 | 216 | SEQ ID NO: 3* |
| p1917 | 217 | SEQ ID NO: 3* |
| p1918 | 218 | SEQ ID NO: 3* |
| p1919 | 219 | SEQ ID NO: 3* |
| p1920 | 220 | SEQ ID NO: 3* |
| p1921 | 221 | SEQ ID NO: 4** |
| p1925 | 222 | SEQ ID NO: 3* |
| p1926 | 223 | SEQ ID NO: 3* |
| p1927 | 224 | SEQ ID NO: 3* |
| p1928 | 225 | SEQ ID NO: 3* |
| p1929 | 226 | SEQ ID NO: 3* |
| p2016 | 175 | SEQ ID NO: 3* |
| p2260 | 221 | SEQ ID NO: 4** |
| p2262 | 221 | SEQ ID NO: 4** |

*SEQ ID NO: 3 is the amino acid sequence for wild type human OTC.
**SEQ ID NO: 4 is the amino acid sequence for modified human OTC.
***The entire plasmid sequence is not included.

Preferred cDNA template sequences include the DNA sequence of SEQ ID NO: 175 (p1779) having an optimized coding sequence encoding wild type human OTC of SEQ ID NO: 3. Preferred cDNA template sequences also include cDNA sequence of SEQ ID NO: 221 (p1921), having an optimized coding sequence encoding a modified OTC protein of SEQ ID NO: 4.

The present disclosure also provides polynucleotides (e.g. DNA, RNA, cDNA, mRNA) encoding a human OTC protein that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. Preferably, the expression vector contains a selectable marker gene to allow the selection of transformed host cells. Selectable marker genes are well known in the art and will vary with the host cell used.

The present disclosure also provides expression vectors comprising a nucleotide sequence encoding an ornithine transcarbamylase (OTC) protein that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides a host cell transfected with an mRNA or DNA described herein which encodes an omithine transcarbamylase (OTC) polypeptide described herein. Preferably, the human OTC polypeptide has the sequence of SEQ ID NO: 4. The host cell may be any prokaryotic or eukaryotic cell. For example, an ornithine transcarbamylase (OTC) polypeptide may be expressed in bacterial cells such as *E. coli*, insect cells (e.g., using a baculovirus expression system), yeast, or mammalian cells. Other suitable host cells are known to those skilled in the art.

The present disclosure also provides a host cell comprising a vector comprising a polynucleotide which encodes an mRNA sequence of any one of SEQ ID NOs: 26-229.

The present disclosure also provides methods of producing a human wild type OTC protein of SEQ ID NO: 3 or a modified human OTC protein SEQ ID NO: 4. Preferably, the OTC protein is SEQ ID NO: 4 and is encoded by mRNA of SEQ ID NO 119. For example, a host cell transfected with an expression vector encoding an OTC protein can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed OTC proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the OTC polypeptide.

Lipid-Based Formulations

Lipid-based formulations have been increasingly recognized as one of the most promising delivery systems (also referred to herein as a delivery vehicle or carrier) for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behavior in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin R A-shRNA). Cationic lipids, such as DOTAP, (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv. Rev. 2014 February; 66: 110-116.)

Preferably, the mRNA constructs described herein are lipid formulated. The lipid formulation is preferably selected from, but not limited to, liposomes, lipoplexes, copolymers, such as PLGA, and lipid nanoparticles. Preferably a lipid nanoparticle (LNP) comprises:

(a) a nucleic acid,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

Preferably, the lipid nanoparticle formulation consists of (i) at least one cationic lipid; (ii) a neutral lipid; (iii) a sterol, e.g., cholesterol; and (iv) a PEG-lipid, in a molar ratio of about 20-60% cationic lipid: 5-25% neutral lipid: 25-55% sterol; 0.5-15% PEG-lipid.

Some examples of lipids and lipid compositions for delivery of an active molecule of this disclosure are given in WO 2015/074085, U.S. 2018/0169268, WO 2018/119163, WO 20185/118102, U.S. 2018/0222863, WO 2016/081029, WO 2017/023817, WO 2017/117530, each of which is hereby incorporated by reference in its entirety. In certain embodiments, the lipid is a compound of the following Formula I:

Formula I

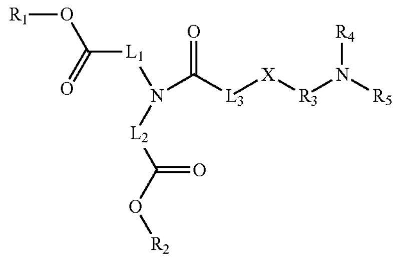

wherein $R_1$ and $R_2$ both consist of a linear alkyl consisting of 1 to 14 carbons, or an alkenyl or alkynyl consisting of 2 to 14 carbons;

$L_1$ and $L_2$ both consist of a linear alkylene or alkenylene consisting of 5 to 18 carbons, or forming a heterocycle with N;

X is S;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, each consisting of a hydrogen or a linear or branched alkyl consisting of 1 to 6 carbons;

or a pharmaceutically acceptable salt thereof.

The lipid formulation of may contain one or more ionizable cationic lipids selected from among the following (also referred to herein as "ATX lipids"):

ATX-001

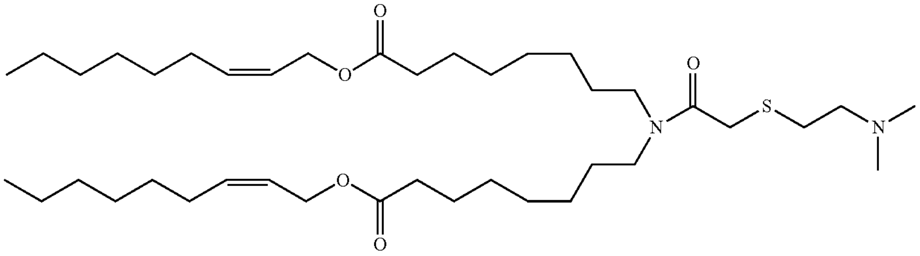

-continued
ATX-002
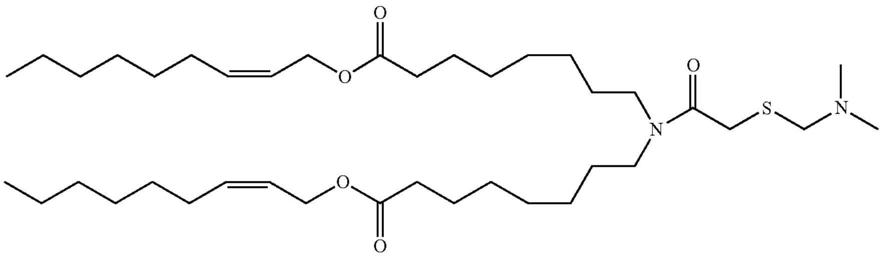
ATX-003
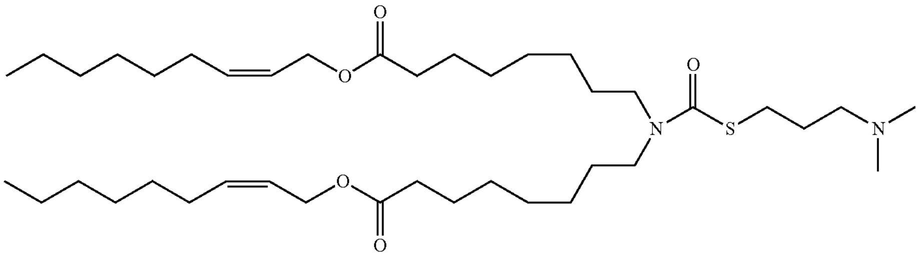
ATX-004
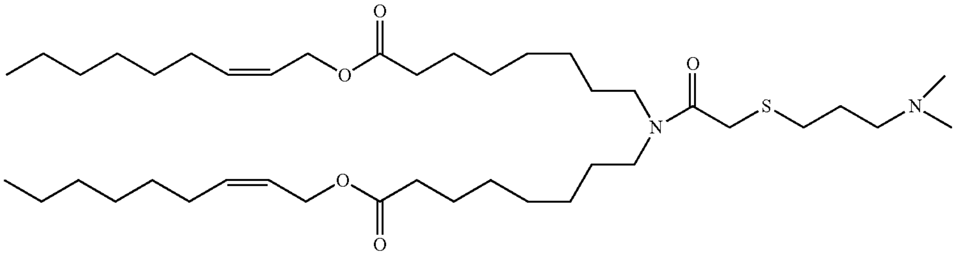
ATX-005
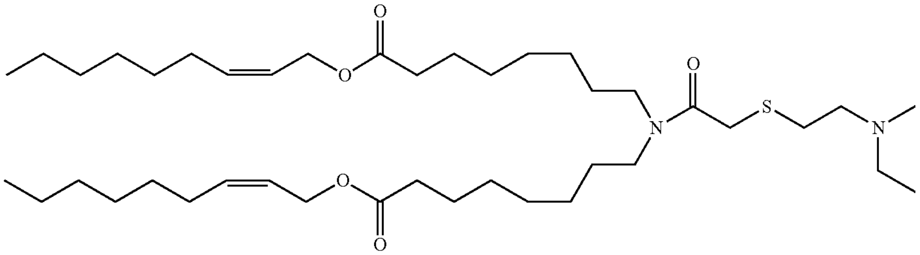
ATX-006
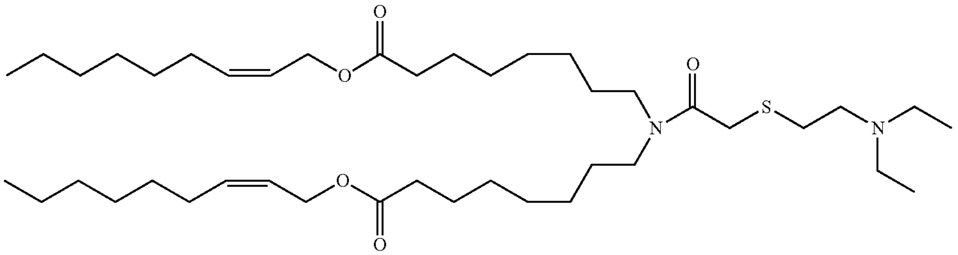
ATX-007
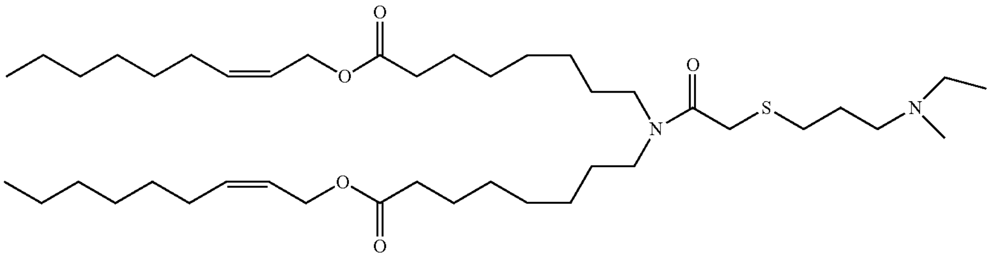

-continued
ATX-008
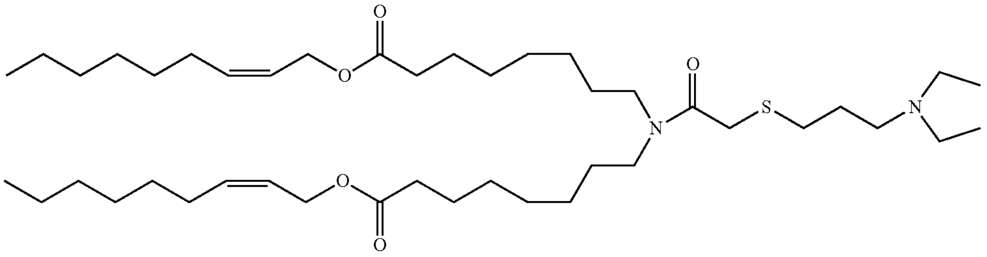
ATX-009
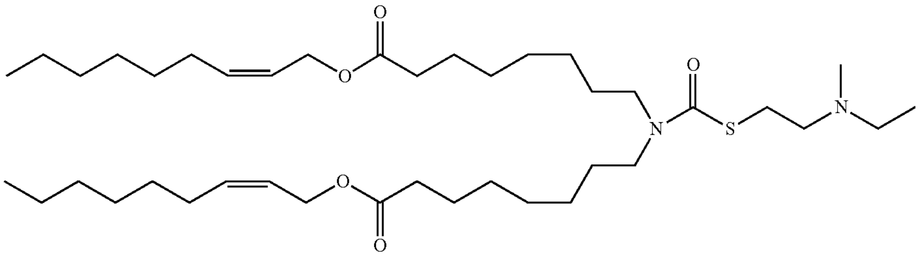
ATX-010
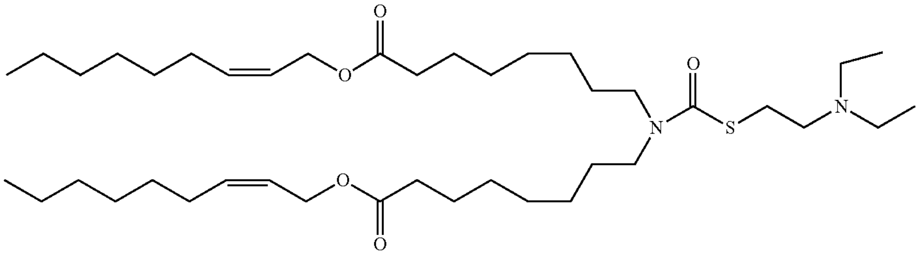
ATX-011
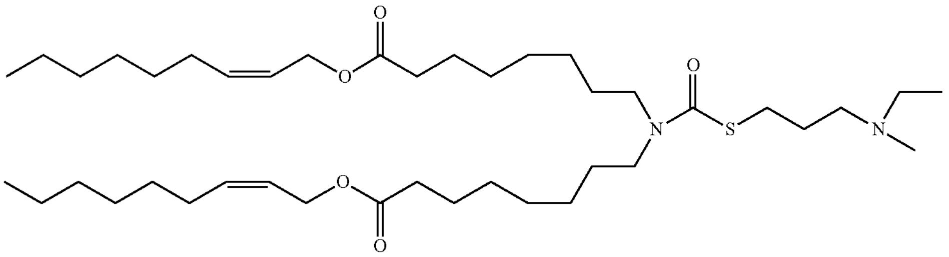
ATX-012
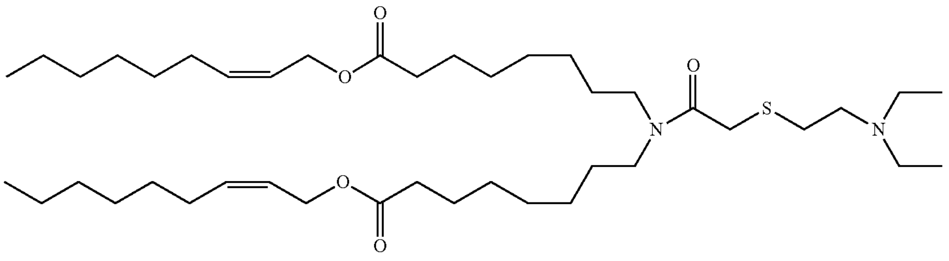
ATX-013
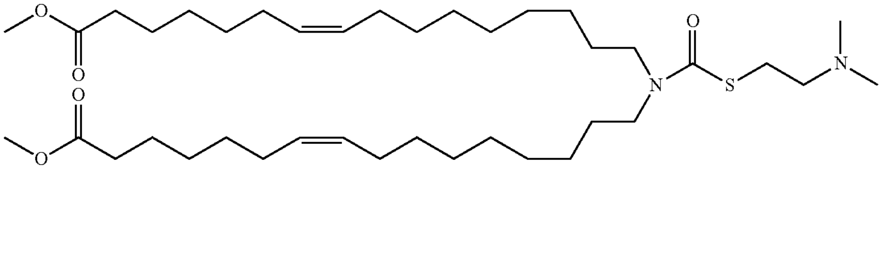

-continued
ATX-014
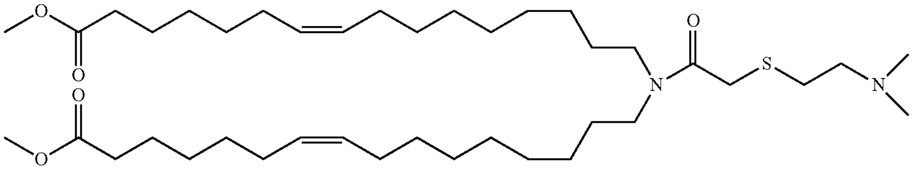
ATX-015
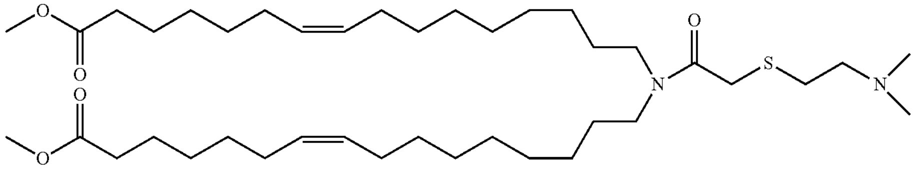
ATX-016
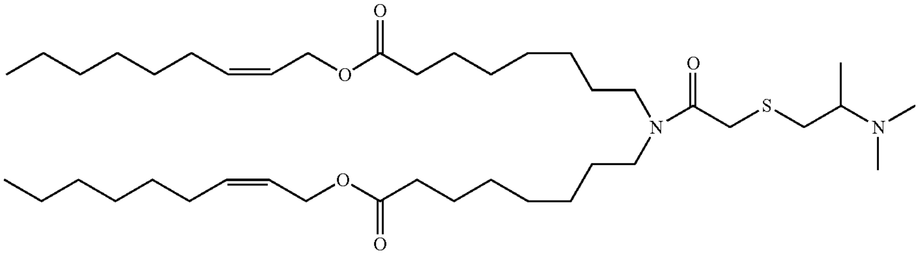
ATX-017
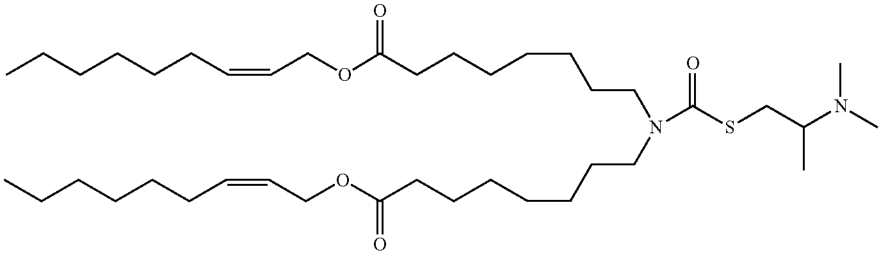
ATX-018
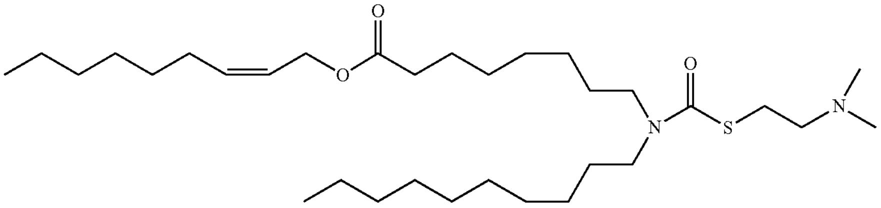
ATX-019
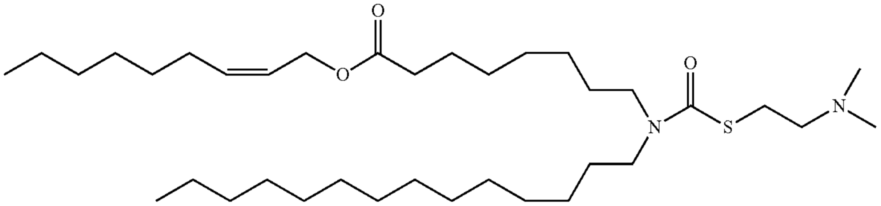
ATX-020
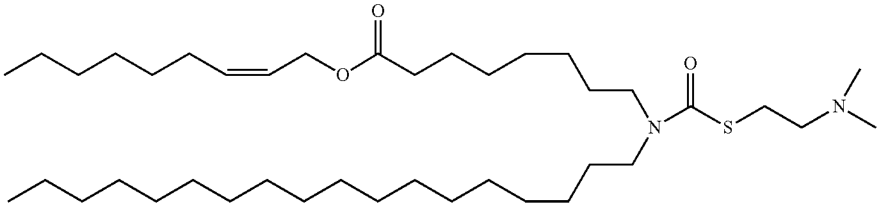

-continued
ATX-021
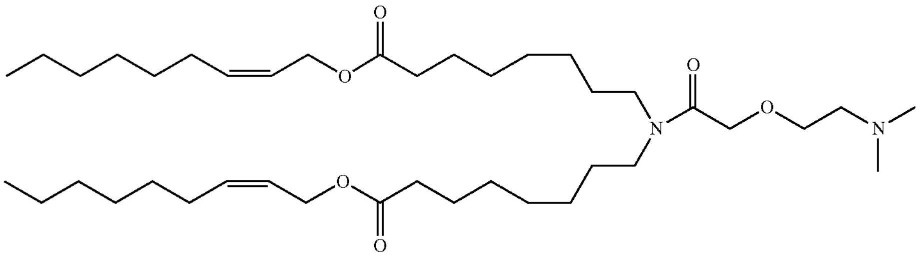
ATX-022
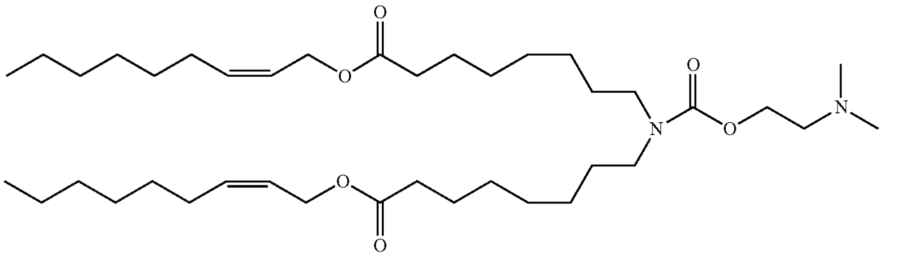
ATX-023
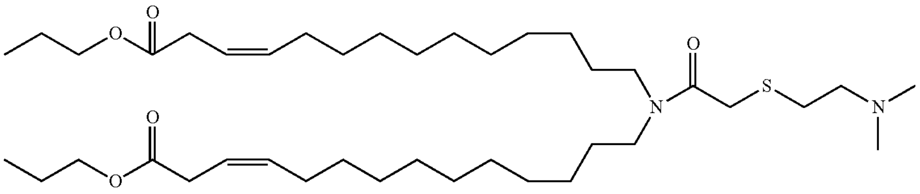
ATX-023
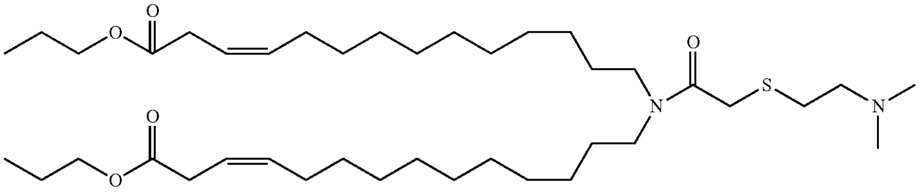
ATX-024
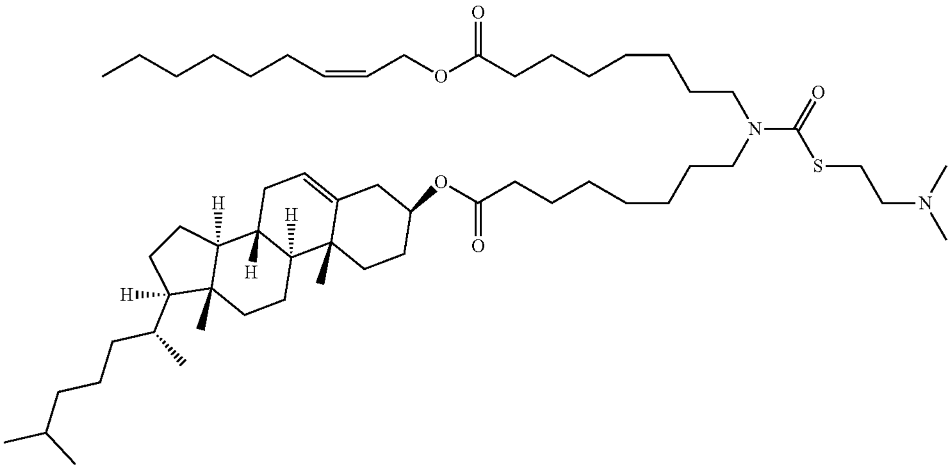

-continued
ATX-025
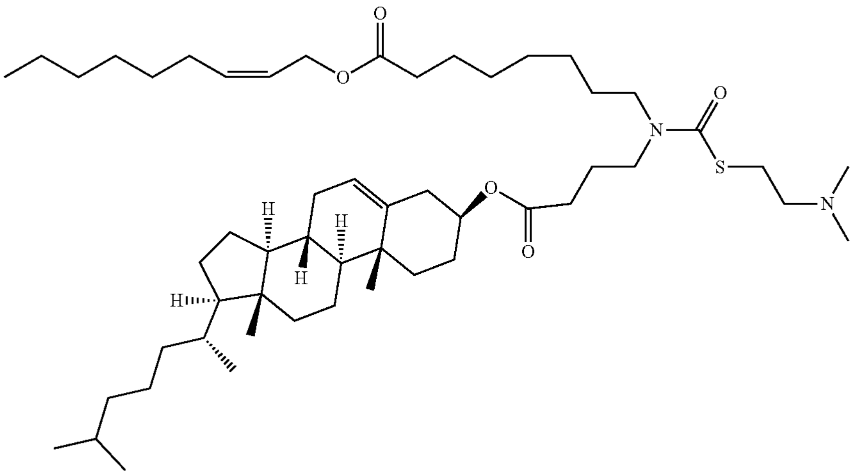
ATX-026
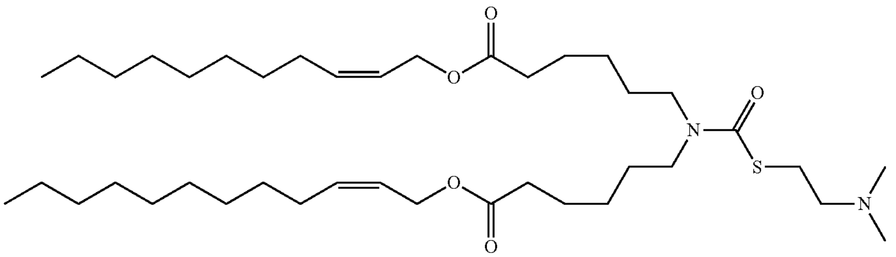
ATX-027
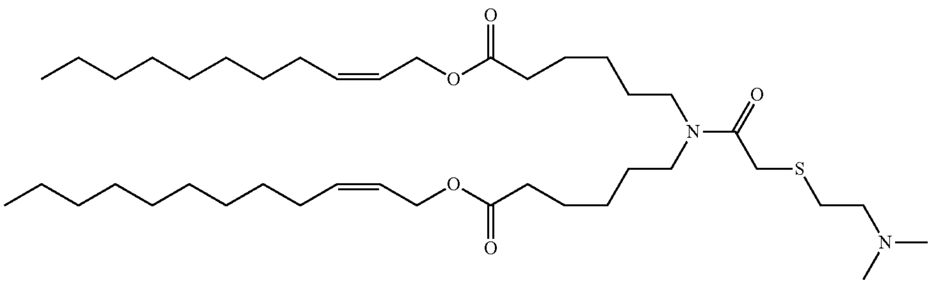
ATX-028
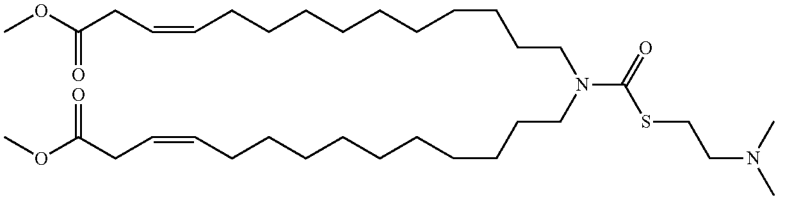
ATX-031
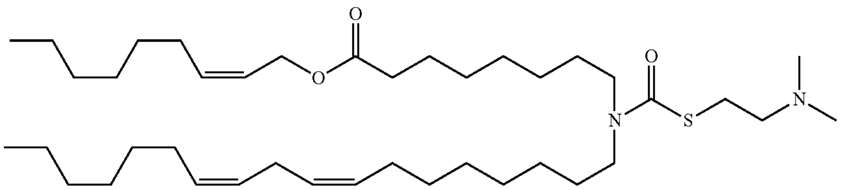
ATX-032
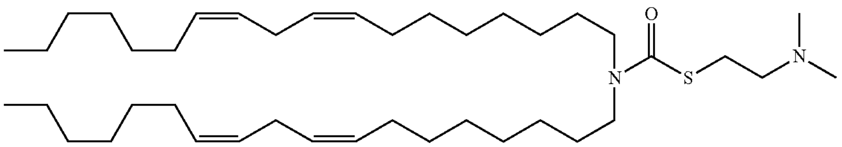

-continued

ATX-081

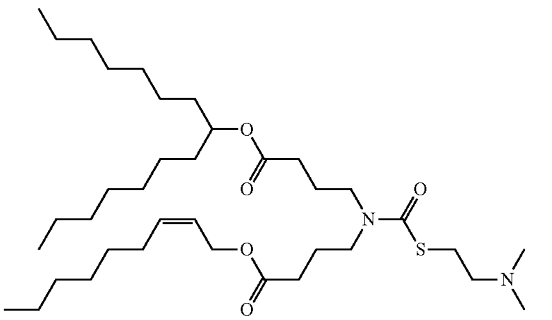

ATX-095

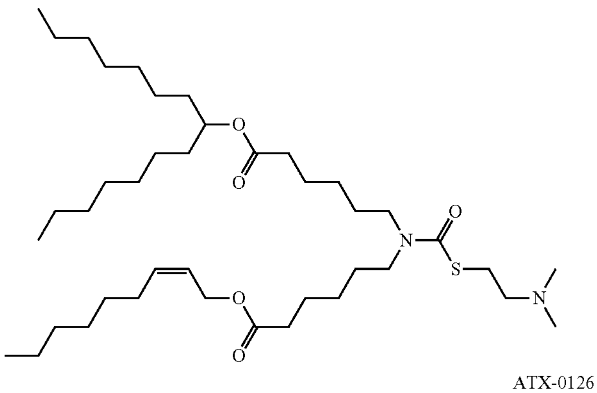

ATX-0126

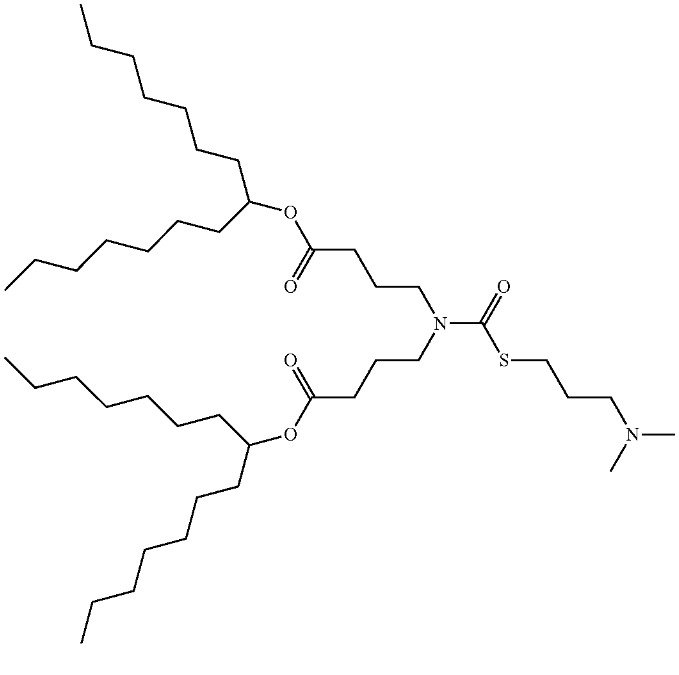

The lipid nanoparticle preferably includes a cationic lipid suitable for forming a lipid nanoparticle. Preferably, the cationic lipid carries a net positive charge at about physiological pH. The cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-y-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination of any of the foregoing.

Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(spermine-carboxamido)ethyl)-N,N-dimethylammonium trifluoroacetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010.

Other suitable amino lipids include those having alternative fatty acid groups and other dialkylamino groups, including those, in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

Preferably, the LNP comprises the cationic lipid with formula (III) according to the patent application PCT/EP2017/064066. In this context, the disclosure of PCT/EP2017/064066 is also incorporated herein by reference.

Preferably, amino or cationic lipids of the disclosure have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11, e.g., a pKa of about 5 to about 7.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.10%, about 50% or about 40% on a molar basis (based upon 100% total moles of lipid in the lipid nanoparticle). In one embodiment, the ratio of cationic lipid to nucleic acid is from about 3 to about 15, such as from about 5 to about 13 or from about 7 to about 11.

Pharmaceutical Compositions

Preferably, the disclosure provides pharmaceutical compositions containing a codon optimized mRNA encoding a human OTC protein of SEQ ID NO: 3 or SEQ ID NO: 4, preferably formulated in a lipid delivery system or lipid carrier and preferably comprising pharmaceutically acceptable excipients. Pharmaceutical compositions disclosed herein preferably facilitate expression of mRNA in vivo.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

Preferably, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Preferably, mRNAs and lipid formulations thereof may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present disclosure can be inhaled (for nasal, tracheal, or bronchial delivery); can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Pharmaceutical compositions may be administered to any desired tissue. In some embodiments, the OTC mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

Preferably, a pharmaceutical composition can contain a polynucleotide described herein such as a primary DNA construct or mRNA described herein within a viral or bacterial vector.

Preferably, the primary DNA construct for an mRNA described herein or an mRNA described herein can be formulated using one or more excipients to: (1) increase stability; (2) increase cell transfection; (3) permit a sustained or delayed release (e.g., from a depot formulation of the polynucleotide, primary construct, or mRNA); (4) alter the biodistribution (e.g., target the polynucleotide, primary construct, or mRNA to specific tissues or cell types); (5) increase the translation of encoded protein in vivo; and/or (6) alter the release profile of encoded protein in vivo.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or mRNA (e.g., for transplantation into a subject), hyaluronidase, nanoparticle mimics and combinations thereof.

Accordingly, the formulations described herein can include one or more excipients, each in an amount that together increases the stability of the primary DNA construct, or mRNA, increases cell transfection by the primary construct, or mRNA, increases the expression of polynucleotide, primary construct, or mRNA encoded protein, and/or alters the release profile of polynucleotide, primary construct, or mRNA encoded proteins. Further, the primary construct and mRNA of the present disclosure may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Therapeutic Uses

The mRNA sequences, primary DNA constructs that transcribe the mRNA sequences described herein and pharmaceutical compositions thereof provide numerous in vivo and in vitro methods and are useful to treat OTC deficiency. The treatment may comprise treating a human patient with OTC deficiency. Similarly, compositions described herein, may be used in vitro or ex vivo to study OTC deficiency in cell or animal-based models. For example, cells deficient for OTC expression can be used to analyze the ability to restore OTC expression and/or activity, as well as the time period over which expression and/or activity persists. Such cells and animal models are also suitable to identify other factors involved in the pathway, whether binding partners or factors in the same biochemical pathway. In other embodiments, compositions described herein can be used to study or track mitochondrial delivery.

Polynucleotides described herein, such as a DNA construct or template or an mRNA sequence described herein can be delivered to patients or cells experiencing OTC deficiency. Preferably the mRNA sequence comprises SEQ ID NO: 119 encoding a modified OTC protein of SEQ ID NO: 4. Preferably the DNA sequence comprises SEQ ID NO: 221 encoding a modified OTC protein of SEQ ID NO: 4.

Following administration, OTC is expressed in the cells or subject. Preferably, compositions described herein are delivered to mitochondria. Preferably compositions described herein are delivered to liver cells.

Preferably the therapeutic methods described herein decrease ammonia levels in plasma and/or urine in a subject in need thereof or in cells in culture, such as a subject having an OTC deficiency. Preferably, the therapeutic methods described herein decrease orotic acid levels in plasma and/or urine in a subject in need thereof or in cells in culture. Preferably, the therapeutic methods described herein increase citrulline in plasma and/or urine in a subject in need thereof or in cells in culture. Preferably, ammonia levels, orotic acid levels and/or citrulline levels are used as biomarkers to (i) identify subjects in need of treatment and/or (ii) to evaluate efficacy of treatment using the mRNA or DNA templates described herein.

Examples of mRNA sequences for use with these methods include those listed in Table 5. Preferably cDNA templates used to transcribe the mRNA sequences described herein are listed in Table 6. Preferred mRNA sequences for administering to patients for treatment of OTC deficiency are SEQ ID NOS: 1799 and SEQ ID NOS: 1921. Preferably the preferred mRNA sequences of SEQ ID NO: 1799 and SEQ ID NO: 1921.

Dosing

An effective dose of a mRNA, a protein or pharmaceutical formulations thereof of the present disclosure can be an amount that is sufficient to treat ORF protein deficiency in a cell and/or in a patient. A therapeutically effective dose can be an amount of an agent or formulation that is sufficient to cause a therapeutic effect. A therapeutically effective dose can be administered in one or more separate administrations, and by different routes. Generally, a therapeutically effective amount is sufficient to achieve a meaningful benefit to the subject (e.g., treating, modulating, curing, preventing and/or ameliorating phenylketonuria). For example, a therapeutically effective amount may be an amount sufficient to achieve a desired therapeutic and/or prophylactic effect. Generally, the amount of a therapeutic agent administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

Methods provided herein contemplate single as well as multiple administrations of a therapeutically effective amount of an mRNA sequence described herein. Pharmaceutical compositions comprising an mRNA sequence encoding an ORF protein described herein can be administered at regular intervals, depending on the nature, severity and extent of the subject's condition. Preferably, a therapeutically effective amount an mRNA sequence of the present disclosure may be administered periodically at regular intervals (e.g., once every year, once every six months, once every four months, once every three months, once every two months, once a month), biweekly, weekly, daily, twice a day, three times a day, four times a day, five times a day, six times a day, or continuously.

Preferably, the pharmaceutical compositions of the mRNA of the present disclosure are formulated such that they are suitable for extended-release of the translatable compound encoding a modified protein described herein contained therein. Such extended-release compositions may be conveniently administered to a subject at extended dosing intervals. For instance, in one embodiment, the pharmaceutical compositions of the present disclosure are administered to a subject twice a day, daily or every other day. In some embodiments, the pharmaceutical compositions of the present disclosure are administered to a subject twice a week, once a week, every 10 days, every two weeks, every 28 days, every month, every six weeks, every eight weeks, every other month, every three months, every four months, every six months, every nine months or once a year. Also contemplated herein are pharmaceutical compositions which are formulated for depot administration (e.g., subcutaneously, intramuscularly) to either deliver or release an mRNA sequence encoding an OTC protein described herein over extended periods of time. Preferably, the extended-release means employed are combined with modifications made to the translatable compound encoding an OTC protein described herein to enhance stability.

A therapeutically effective dose, upon administration, can result in serum or plasma levels of OTC of 1-1000 pg/ml, or 1-1000 ng/ml, or 1-1000 μg/ml, or more. In some embodiments, administering a therapeutically effective dose of a composition comprising an mRNA sequence described herein can result in increased liver modified protein levels in a treated subject. Preferably, administering a composition comprising a mRNA described herein results in a 5%, 10%, 20%, 30%, 40%, 50%, 60%, 70%, 80%, 90%, or 95% increase in liver modified protein levels relative to a baseline modified protein level in the subject prior to treatment. Preferably, administering a therapeutically effective dose of a composition comprising an mRNA described herein will result an increase in liver OTC levels relative to baseline liver OTC levels in the subject prior to treatment. In some embodiments, the increase in liver OTC levels relative to baseline liver OTC levels will be at least 5%, 10%, 20%, 30%, 40%, 50%, 100%, 200%, or more.

Preferably, a therapeutically effective dose, when administered regularly, results in increased expression of OTC in the liver as compared to baseline levels prior to treatment. Preferably, administering a therapeutically effective dose of a composition comprising an mRNA sequence described herein results in the expression of a modified protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

Preferably, a therapeutically effective dose, when administered regularly, results in a reduction of orotic acid levels in a biological sample. In some embodiments, administering a therapeutically effective dose of a composition comprising an mRNA described herein results in a reduction of orotic acid levels in a biological sample (e.g., urine, plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline orotic acid levels before treatment. Preferably, the biological sample is selected from plasma, serum, whole blood, urine, or cerebrospinal fluid. Preferably, administering a therapeutically effective dose of a composition comprising an mRNA described herein results in reduction of orotic acid levels to about 1000 μmol/L or less, about 900 μmol/L or less, about 800 μmol/L or less, about μmol/L or less, about 600 μmol/L or less, about 500 μmol/L or less, about 400 μmol/L or less, about 300 μmol/L or less, about 200 μmol/L or less, about 100 μmol/L or less or about 50 μmol/L or less in serum or plasma. Preferably, a therapeutically effective dose, when administered regularly results in reduction of orotic acid levels to about 600 μmol/L or less in serum or plasma. In another exemplary embodiment, a therapeutically effective dose, when administered regularly results in reduction of orotic acid levels to about 360 μmol/L or less in serum or plasma. Preferably, a therapeutically effective dose, when administered regularly results in reduction of orotic acid levels to about 120 μmol/L or less in serum or plasma.

A therapeutically effective dose of an mRNA described herein in vivo can be a dose of about 0.001 to about 500 mg/kg body weight. For instance, the therapeutically effective dose may be about 0.001-0.01 mg/kg body weight, or 0.01-0.1 mg/kg, or 0.1-1 mg/kg, or 1-10 mg/kg, or 10-100 mg/kg. Preferably, a Lipid-enabled and Unlocked Nucleomonomer Agent modified RNA (LUNAR)-mRNA (see WO 2015/074085 and U.S. 2018/0169268), encoding an OTC protein described herein, is provided at a dose ranging from about 0.1 to about 10 mg/kg body weight.

Combinations

The cDNA primary constructs, mRNA or encoded OTC proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, mRNA disclosed herein and preferably an mRNA sequence comprising SEQ ID NO: 119, encoding a modified OTC protein of SEQ ID NO: 4 may be used in combination with a pharmaceutical agent for the treatment of OTC deficiency. The pharmaceutical agent includes, but is not limited to one or more of: sodium phenylbutyrate, glycerol phenylbutyrate, sodium phenylacetate, sodium benzoate, arginine, citrulline, Multiple vitamins, calcium supplements or combined with low protein/high caloric diet. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

EXAMPLES

Example 1: Material and Methods

In Vitro Transcription Protocol

The mRNAs were synthesized in vitro using T7RNA polymerase-mediated DNA-dependent RNA transcription where uridine triphosphate (UTP) was substituted and unsubstituted with modified UTPs such as 5 methoxy UTP (5MeOU), N1-methoxy methyl pseudo UTP (N1-MOM), 5-hydroxy methyl UTP, 5-carboxy UTP, and mixture of modifications using linearized template for each UTR combination. The mRNA was purified using column chromatography, the DNA and double stranded mRNA contamination of all mRNAs was removed using an enzymatic reaction, and the mRNA was concentrated, and buffer exchanged.

Preparation of Lipid Encapsulated mRNA

Lipid encapsulated mRNA particles were prepared by mixing lipids (ATX lipid: DSPC: Cholesterol: PEG-DMG) in ethanol with OTC mRNA dissolved in Citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 50 mM NaCl and 9% sucrose, pH 7.3. The formulation was concentrated followed by 0.2 μm filtration using PES filters. The mRNA concentration in the formulation was then measured by Ribogreen fluorimetric assay following which the concentration was adjusted to a final desired concentration by diluting with HEPES buffer containing 50 mM NaCl, 9% sucrose, pH 7.3 containing glycerol. The final formulation was then filtered through a 0.2 μm filter and filled into glass vials, stoppered, capped and placed at −70±5° C. The frozen formulations were characterized for their mRNA content and percent encapsulation by Ribogreen assay, mRNA integrity by fragment analyzer, lipid content by high performance liquid chromatography (HPLC), particle size by dynamic light scattering on a Malvern Zetasizer Nano ZS, pH and Osmolality.

In-Cell Western (ICW)

96-well collagen plates were used to seed the cells at the appropriate density in Dulbecco's Modified Eagle Media (DMEM)/Fetal Bovine Serum (FBS) culture media. At the optimal confluence, cells were transfected with the targeted mRNAs diluted in the transfection reagent mix (MessengerMax and Opti-MEM). Cells were placed in the $CO_2$ incubator and allowed to grow. At the desire timepoint, media was removed, and cells were fixed in 4% fresh paraformaldehyde (PFA) for 20 min. After that, fixative was removed, and cells were permeabilize in tris buffered saline with TWEEN (TBST) for 5 min several times. When permeabilization washes were complete, cells were incubated with a blocking buffer (ODYSSEY® Blocking Buffer (PBS) (Li-Cor, Lincoln, NE)) for 45 min. Primary antibody was then added and incubated for 1 h at room temperature. Cells were then washed several times in TBST and incubated for 1 h with a secondary antibody diluted in blocking buffer and containing a CellTag 700 stain. To finalize, cells were washed several times in TBST followed by a last wash in tris-buffered saline (TBS). The plate was imaged using the Licor detection system and data was normalized to the total number of cells labeled by the CellTag 700.

Example 2: UTRs Screening in Hepa1,6 and Hep3B—Correlation at 24 h and 48 h

A UTR library was screened in vitro using mRNA construct #571 comprising the sequence of SEQ ID NO: 34 as CDS (coding sequence). In-Cell Western assays as described in Example 1 were used to transfect the different mRNAs into Hepa1,6 and Hep3B using commercially available transfection reagents. OTC protein expression levels were measured by near-infrared fluorescent imaging systems. Commercially available antibodies for OTC were used for detection. Untransfected and reference sequences were used as internal controls. FIG. 1, Panel A is a scatter plot of OTC protein expression levels found in Hepa1,6 and Hep3B cells at 24 hours. FIG. 1, Panel B is a scatter plot of OTC protein expression levels found in Hepa1,6 and Hep3B cells at 48 hours. The aim of the screening was to determine an UTR-specific impact on OTC expression levels in a human (Hep3B) and a mouse (Hepa1,6) liver cell line that will be beneficial to determine which UTRs would work best in both models, in particular, its translatability from mouse-to-human. Top expressing UTRs were used in further profiling studies.

Figure 2:
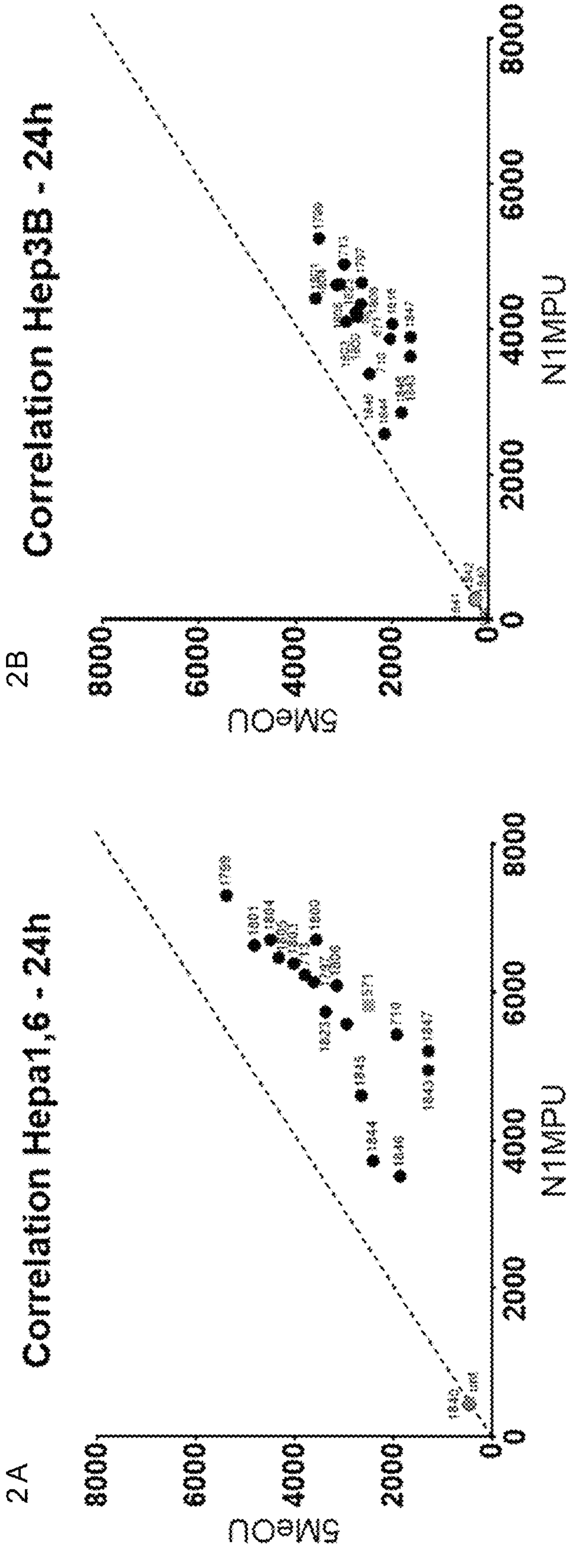
FIGS. 2A-2B show scatter plots illustrating the correlation of protein stability compounds screened in Hepa1,6 cells (FIG. 2A) and Hep3B cells (FIG. 2B) at 24 h in Round 1.

Example 3: Round 1 of Protein Stability Compounds Screened in Hepa1,6 and Hep3B at 24 h—Correlation In vitro screening of certain mRNA constructs of Table 5 that were designed based on a protein-stability approach was performed. The mRNA constructs were tested in two different chemistries $N^1$-methylpseudouridine (N1MPU) and 5-methoxyuridine (5MeOU) meaning that 100% of the uridines in each mRNA were N1MPU only or 5MeOU only (not a combination of 5MeOU or N1MPU). In-Cell Western (ICW) assays as described in Example 1 were used to transfect the different mRNAs into Hepa1,6 and Hep3B using commercially available transfection reagents. OTC protein expression levels were measured by near-infrared fluorescent imaging systems. Commercially available antibodies for OTC were used for detection. Untransfected and reference sequences were used as internal controls. FIG. 2, panel A is a scatter plot showing the correlation of OTC protein expression levels in Hepa1,6 cells at 24 hours as a function of mRNAs tested in N1MPU and 5MeOU chemistries. FIG. 2, panel B is a scatter plot showing the correlation of OTC protein expression levels in Hep3B cells at 24 hours as a function of mRNAs tested in N1MPU and 5MeOU chemistries. These figures exhibit the degree of variability in expression levels when mRNAs from two different chemistries are tested in a mouse and a human liver cell line. It can be seen that that in this experiment, most of the compounds express better when an N1MPU chemistry is used in the mRNA.

Figure 3:
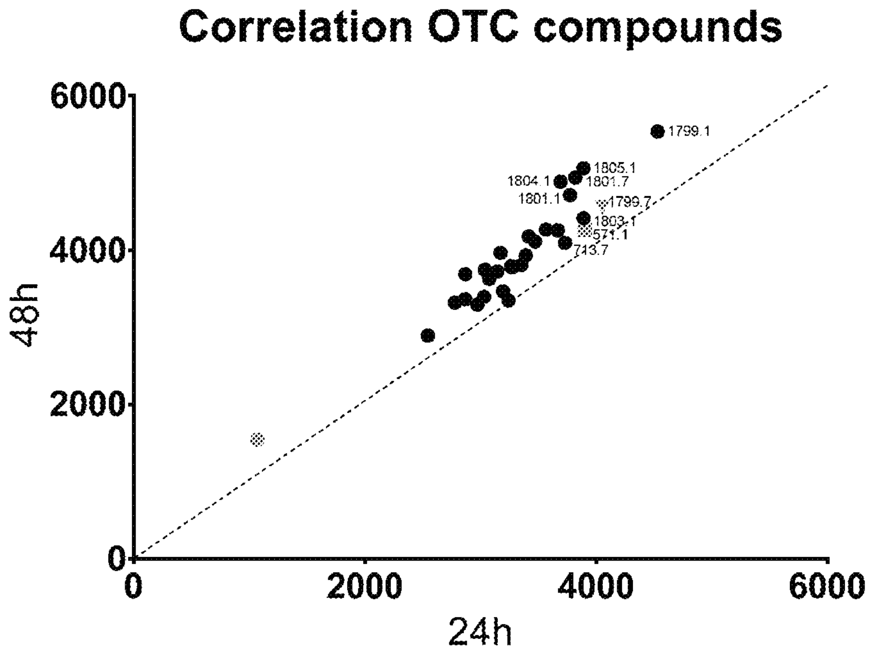
FIGS. 3A-3B show scatter plots illustrating the correlation of protein stability compounds screened in human primary hepatocytes at 24 h and 48 h in Round 2 (newly optimized compounds based on Round 1) as shown with FIG. 3A and FIG. 3B.
Figure 3:
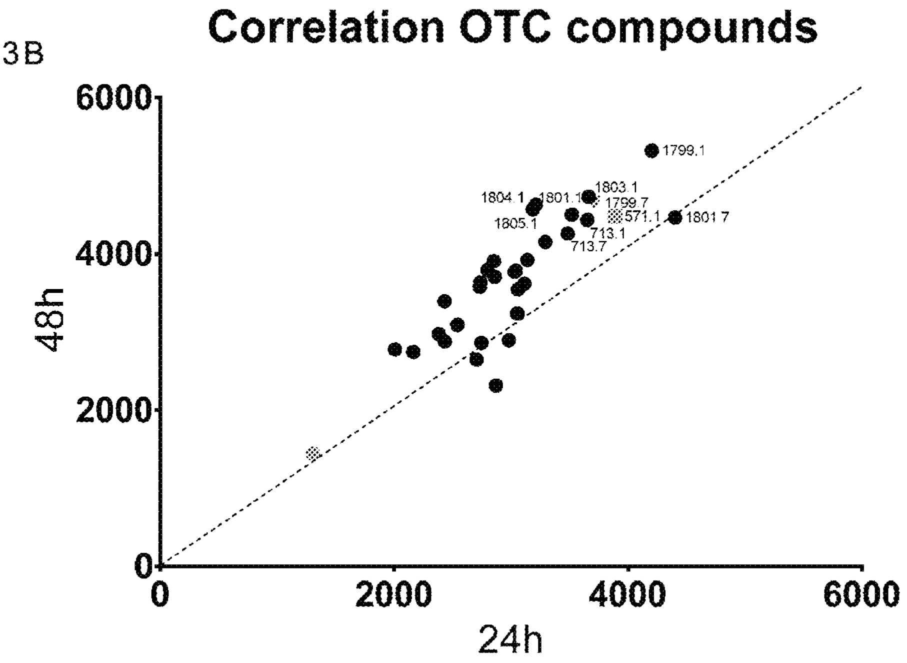

Example 4: Round 2 of Protein Stability Compounds Screened in Human Primary Hepatocytes at 24 h and 48 h—Correlation In vitro screening of certain mRNA constructs of Table 5 that were designed based on a protein stability approach was performed. The mRNAs were tested in two different chemistries, 100% of the Uridines are N1MPU indicated by the name of mRNA constructs followed by "0.1" and 100% of the uridines are 5MeOU indicated by the name of mRNA constructs followed by "0.7". In-Cell Western (ICW) assays as described in Example 1 were used to transfect the different mRNAs into human primary hepatocytes using commercially available transfection reagents. OTC protein expression levels were measured by near-infrared fluorescent imaging systems. Commercially available antibodies for OTC were used for detection. Untransfected and reference sequences were used as internal controls. (FIG. 3, Panels A and B). The results indicate that, in contrast to the experiments conducted in cancer cell lines (Hepa1,6; Hep3B; Example 3, both chemistries express similarly in human primary hepatocytes.

Figure 4:
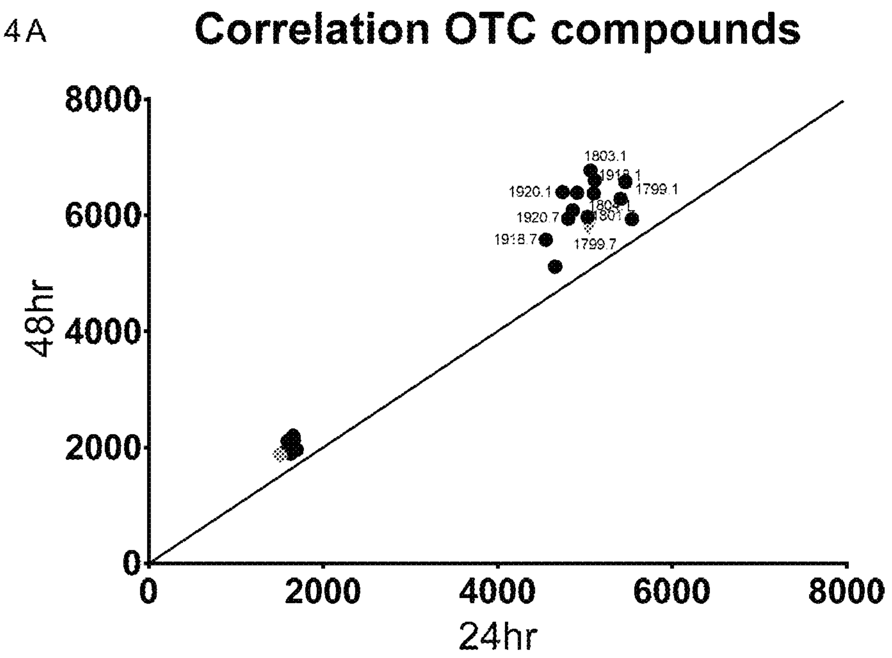
FIGS. 4A-4B show scatter plots illustrating the correlation of protein stability compounds screened in human primary hepatocytes at 24 h and 48 h in Round 3 (newly optimized compounds based on rounds 1 and 2) as shown with FIG. 4A and FIG. 4B.
Figure 4:
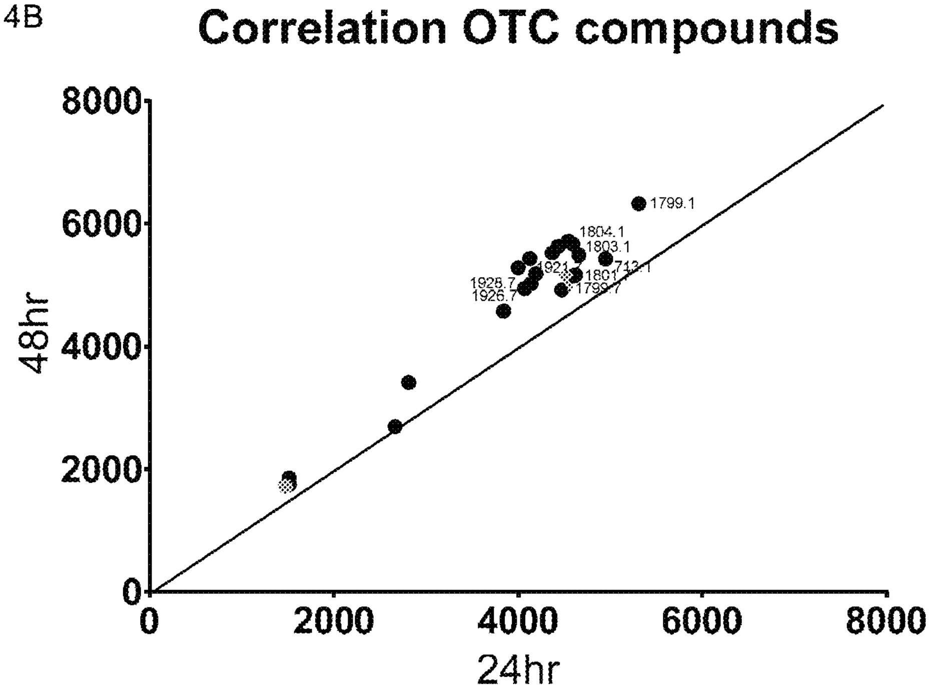

Example 5: Round 3 of Protein Stability Compounds Screening in Human Primary Hepatocytes at 24 h and 48 h—Correlation In vitro screening of novel compounds designed based on a protein stability approach was performed. mRNAs were tested in two different chemistries, N1MPU indicated by the name of mRNA constructs followed by "0.1" and 5MeOU indicated by the name of mRNA constructs followed by "0.7". In-Cell Western (ICW) assays as described in Example 1 were used to transfect the different mRNAs into human primary hepatocytes using commercially-available transfection reagents. OTC protein expression levels were measured by near-infrared fluorescent imaging systems. Commercially available antibodies for OTC protein were used for detection. Untransfected and reference sequences were used as internal controls. (FIG. 4, Panels A and B). The results indicate that, in contrast to the experiments conducted in cancer cell lines (Hepa1,6; Hep3B; Example 3), both chemistries express similarly in human primary hepatocyte.

Example 6: OTC Protein-Expression Levels in Human Primary Cells Transfected with OTC mRNA Constructs 1799.7 (5MeOU Chemistry) Encoding the OTC Protein of SEQ ID NO: 3 and 1921.7 (5MeOU Chemistry) Encoding the Modified OTC Protein of SEQ ID NO: 4

Figure 5:
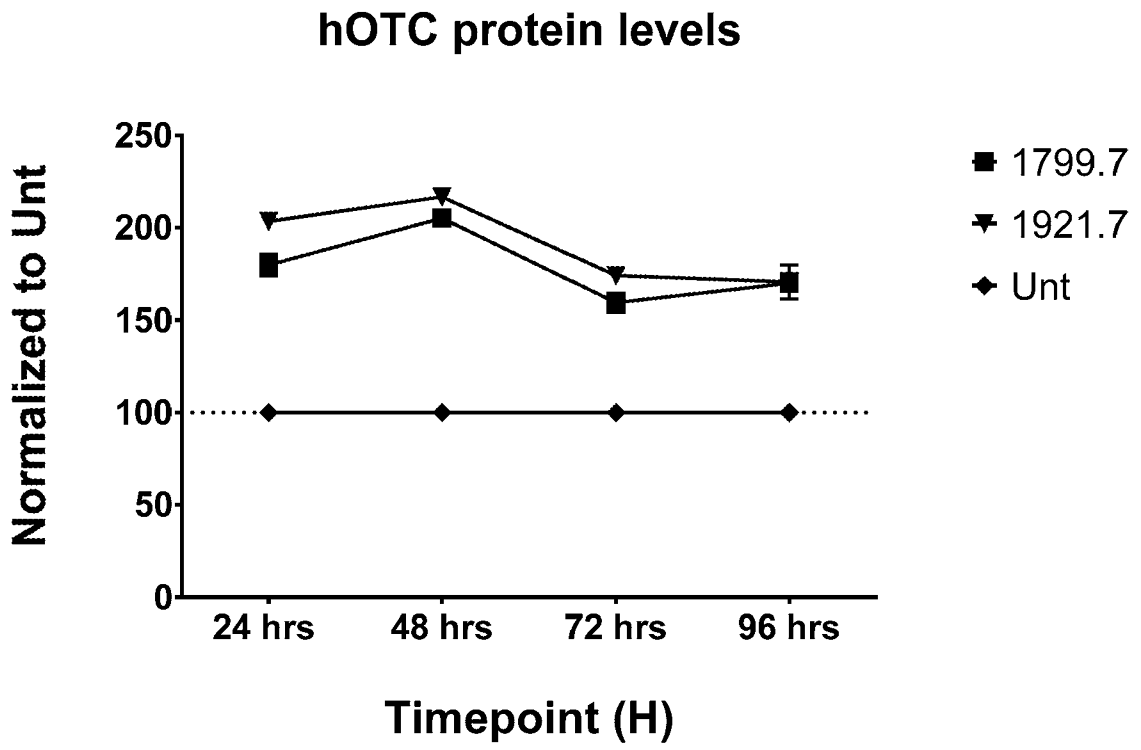
FIG. 5 is a plot illustrating OTC protein expression levels in human primary hepatocytes transfected with lead OTC mRNAs. 1799.7 is an mRNA having the sequence of SEQ ID NO: 175 wherein 100% of the uridines in SEQ ID NO: 175 are $N^1$-methylpseudouridine (N1MPU).

In-Cell Western (ICW) assays as described in Example 1 were used to transfect OTC mRNAs into human primary hepatocytes using commercially available transfection reagents. OTC protein expression levels were measured by near-infrared fluorescent imaging systems during a time course study up to 96 h. Commercially available OTC antibodies were used for detection. Untransfected cells were used as internal control. Plot shows OTC protein levels normalized to untransfected controls. (FIG. 5). The purpose of this study was to evaluate the half-life of the unmodified versus the modified protein sequence (encoded by constructs 1799.7, 1921.7, respectively) under in vitro conditions in transfected human primary hepatocytes. The results indicate that 1921.7 demonstrated more stable expression than 1799.7

Figure 6:
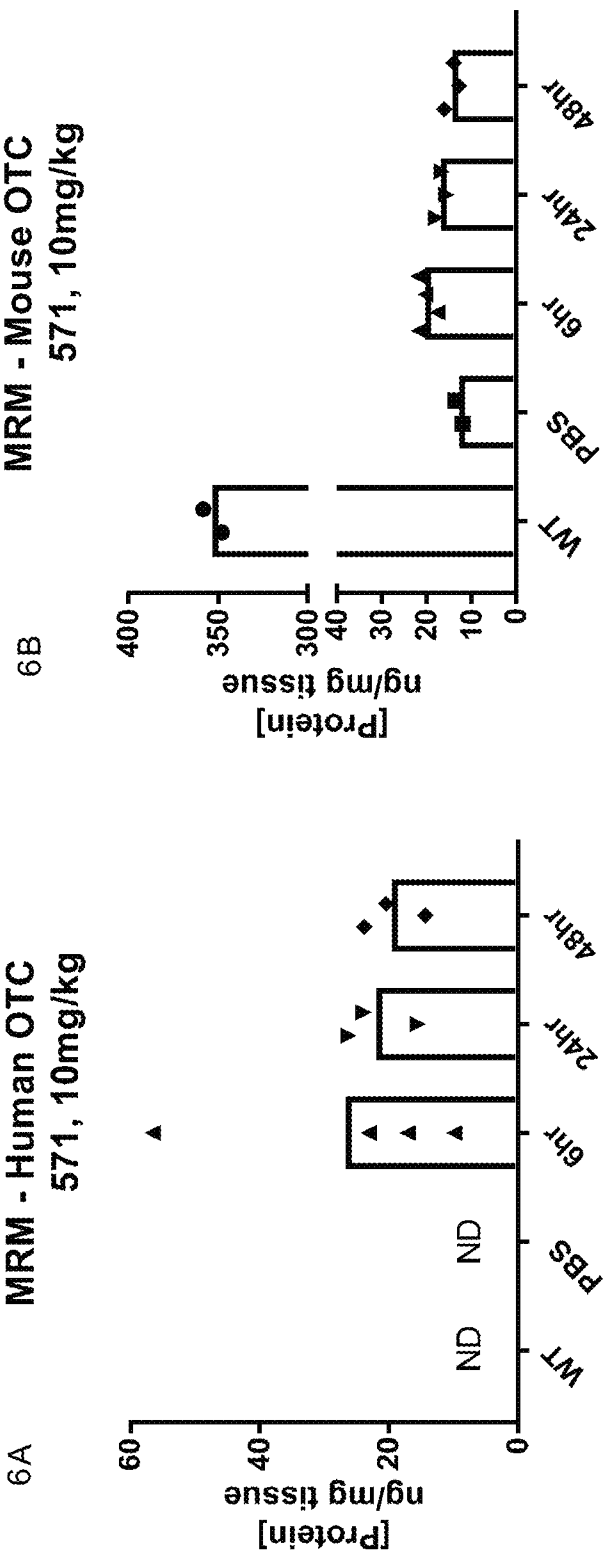
FIGS. 6A-6B show bar graphs depicting time course OTC expression levels in spf/ash mice dosed at 10 mg/kg with human-specific OTC-mRNA epitopes (FIG. 6A) or mouse-specific OTC-mRNA epitopes (FIG. 6B).

Example 7: OTC expression levels measured by multiple reaction monitoring (MRM) mass spectrometry in spf/ash mice dosed at 10 mg/kg. Spf/ash mice received an IV injection with either PBS or lipid-formulated (as described in Example 1) OTC-mRNAs at a 10 mg/kg dosing. WT mice were used as internal controls to determine endogenous levels. A time course (6 h, 24 h and 48 h) was performed, and expression levels were measured by MRM using human and mouse specific epitopes for OTC. Graphs were made that represent the amount of protein (ng/mg tissue) detected by MRM specific for human OTC (FIG. 6, Panel A) or mouse (FIG. 6, Panel B). Human- and mouse-specific heavy peptides were designed to measure total levels of OTC in both species. This data set shows quantitative levels of human-specific OTC derived from translation of delivered mRNAs are detected. This expression maintains a high level of stability up to 48 h.

Figure 7:
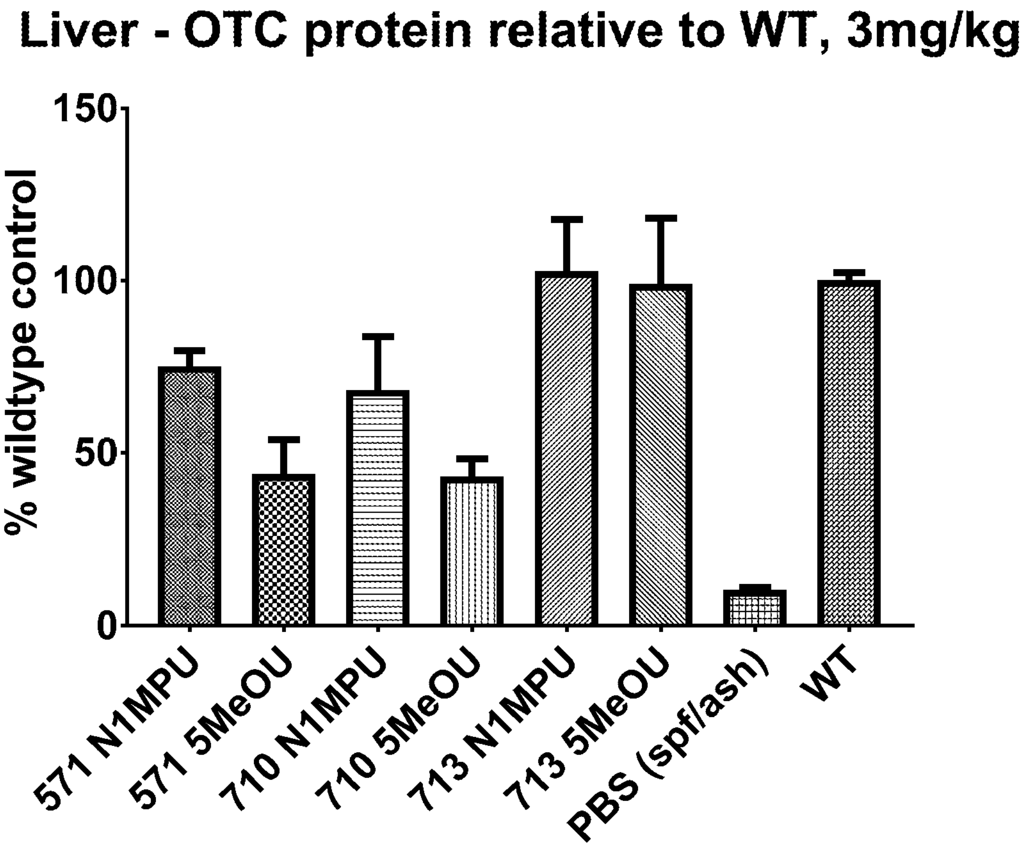
FIG. 7 is a bar graph depicting OTC expression levels in spf/ash mice dosed at 3 mg/kg with OTC-mRNAs using two different chemistries wherein 100% of the uridines are $N^1$-methylpseudouridine (N1MPU) and 100% of the uridines are 5-methoxyuridine (5MeOU).

Example 8: OTC Expression Levels Measured by Western Blot in WT Mice Dosed at 3 mg/kg Spf/ash mice received an IV injection with either phosphate buffered saline (PBS) or lipid-formulated OTC-mRNAs at a 3 mg/kg dosing using two different chemistries (N1MPU and 5MeOU). WT mice were used as internal controls to determine endogenous levels. Animals were sacrificed 24 h post-dose. OTC expression levels were measured by Western Blot (WB) using an OTC specific antibody. In the results provided in FIG. 7, the bars represent the percentage of expression relative to WT levels (100%). The data generated in this figure shows that WT levels of total OTC in a mouse background were achieved for several codon-optimized sequences.

Example 9: OTC Expression Levels Measured by MRM in a Dose Range Finding Study

Figure 8:
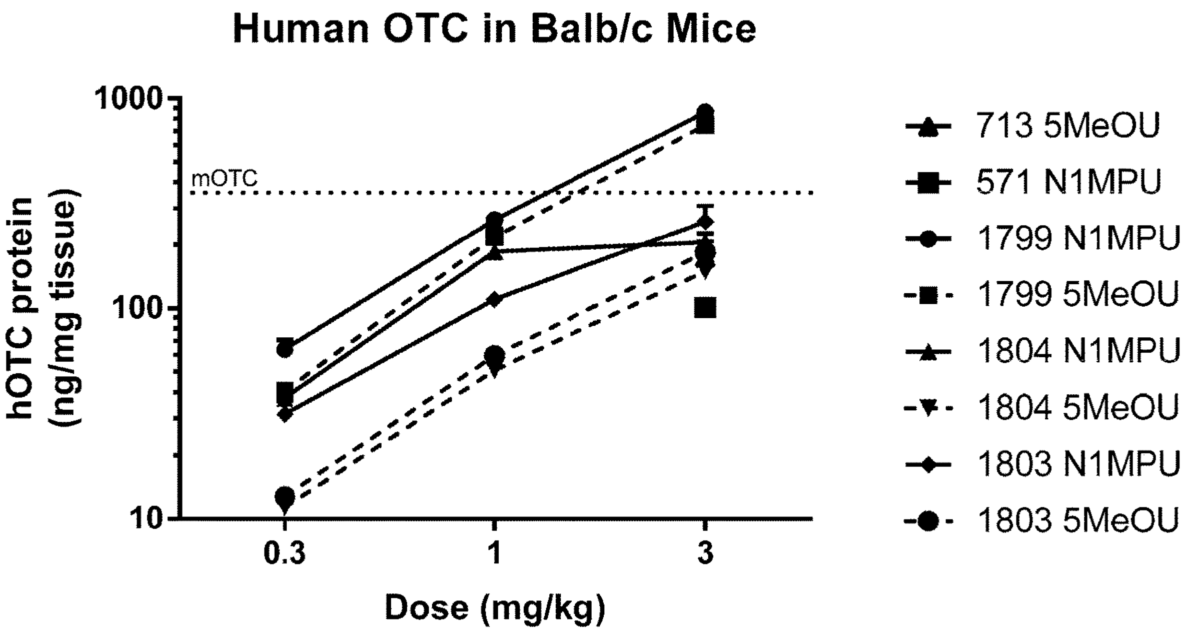
FIG. 8 is a graph depicting OTC expression levels in Balb/c mice dosed with OTC-mRNAs at three different doses and using two different chemistries (N1MPU and 5MeOU).

Balb/c mice received an IV injection with either PBS or lipid-formulated OTC-mRNAs at three different doses: 0.3 mg/kg, 1 mg/kg and 3 mg/kg and using two different chemistries (N1MPU and 5MeOU). Animals were sacrificed 24 h post-dose and expression levels were measured by MRM using human and mouse specific epitopes for OTC. The graph in FIG. 8 represents the percentage of expression of human OTC (ng) per mg of liver tissue in Balb/c mice. The horizontal dotted line represents the relative mouse OTC levels in Balb/c mice. (FIG. 8). Expression levels of hOTC protein for mRNA construct 713 5MeOU and mRNA construct 571 N1MPU are indicated by arrows in FIG. 8. In this figure, the MRM was used to quantitatively determine human-selective and mouse-selective OTC protein levels. The data generated in this figure shows, in a dose dependent manner, that WT levels of human OTC in a mouse background are achieved with the codon-optimized sequences disclosed herein.

Example 10: Urinary Orotate Levels Measured in PBS and Treated Spf/Ash Mice

Figure 9:
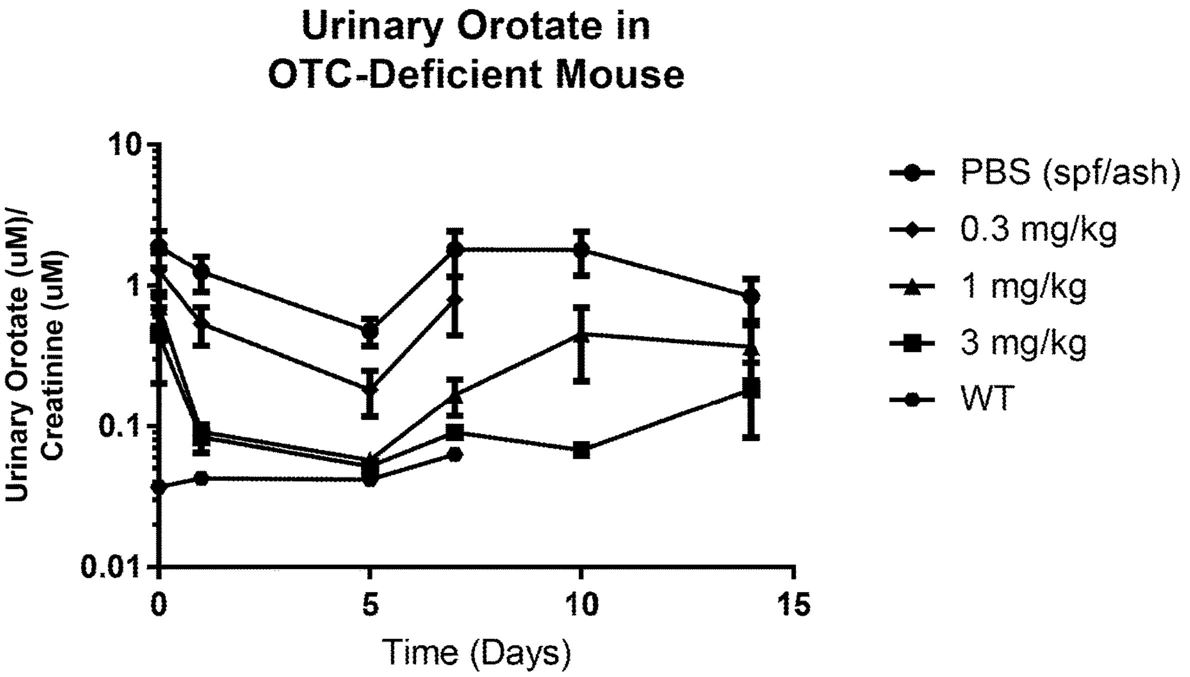
FIG. 9 is a graph depicting urinary orotate levels measured in spf/ash mice dosed with OTC-mRNA 1799.7 at three different doses: 0.3 mg/kg, 1 mg/kg and 3 mg/kg. 1799.7 is an mRNA having the sequence of SEQ ID NO: 175 wherein 100% of the uridines in SEQ ID NO: 175 are 5MeOU.

Spf/ash mice received an IV injection with either PBS or lipid-formulated OTC-mRNA construct 1799.7 (5MeOU chemistry) at three different doses: 0.3 mg/kg, 1 mg/kg and 3 mg/kg. WT and spf/ash mice were used to determine baseline and high urinary orotate levels, respectively. A spf/ash time course was determined, and urinary orotate levels were measured at each timepoint. The results can be seen in FIG. 9. Urinary orotate was normalized to creatinine, which is represented in the graph in the Y axis throughout the time course and serve as a proof-of-concept of functional restoration of OTC activity post-injection. At 3 mg/kg, a sustainable reduction of urinary orotate levels up to 14 days was observed.

Figure 10:
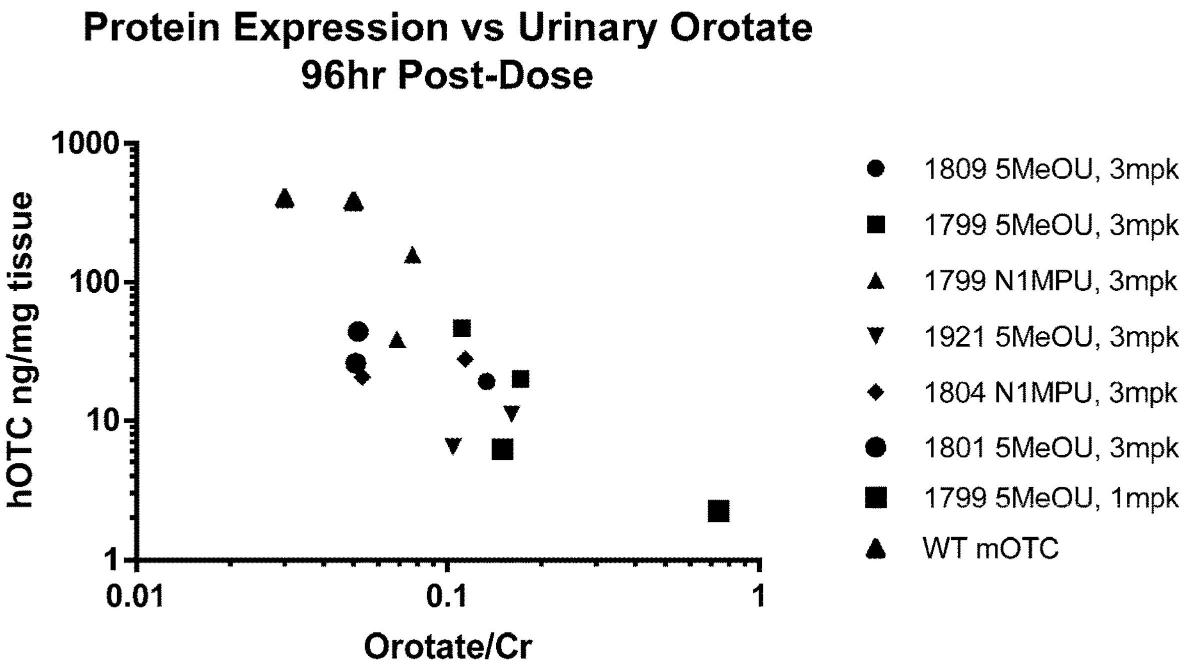
FIG. 10 is a scatter plot comparing human OTC expression levels and Urinary Orotate at 96 h in spf/ash mice dosed with OTC-mRNAs at 1 mg/kg and 3 mg/kg using two different chemistries (N1MPU and 5MeOU).

Example 11: Pharmacokinetic/Pharmacodynamic (PK/PD) Analysis Comparing Human OTC Expression Levels and Urinary Orotate at 96 h Spf/ash mice received an IV injection with either PBS or certain lipid-formulated OTC-mRNAs from Table 5 at 1 mg/kg and 3 mg/kg using two different chemistries (N1MPU and 5MeOU). WT mice were used as internal controls. Human-specific OTC levels were measured by MRM whereas urinary orotate was determined in each sample and normalized to creatinine. PK/PD is plotted in FIG. 10. PK/PD analysis shows the correlation between protein expression levels and reduction of urinary orotate in a compound-specific manner. Construct 1799.7 shows a high PK/PD correlation.

Figure 11:
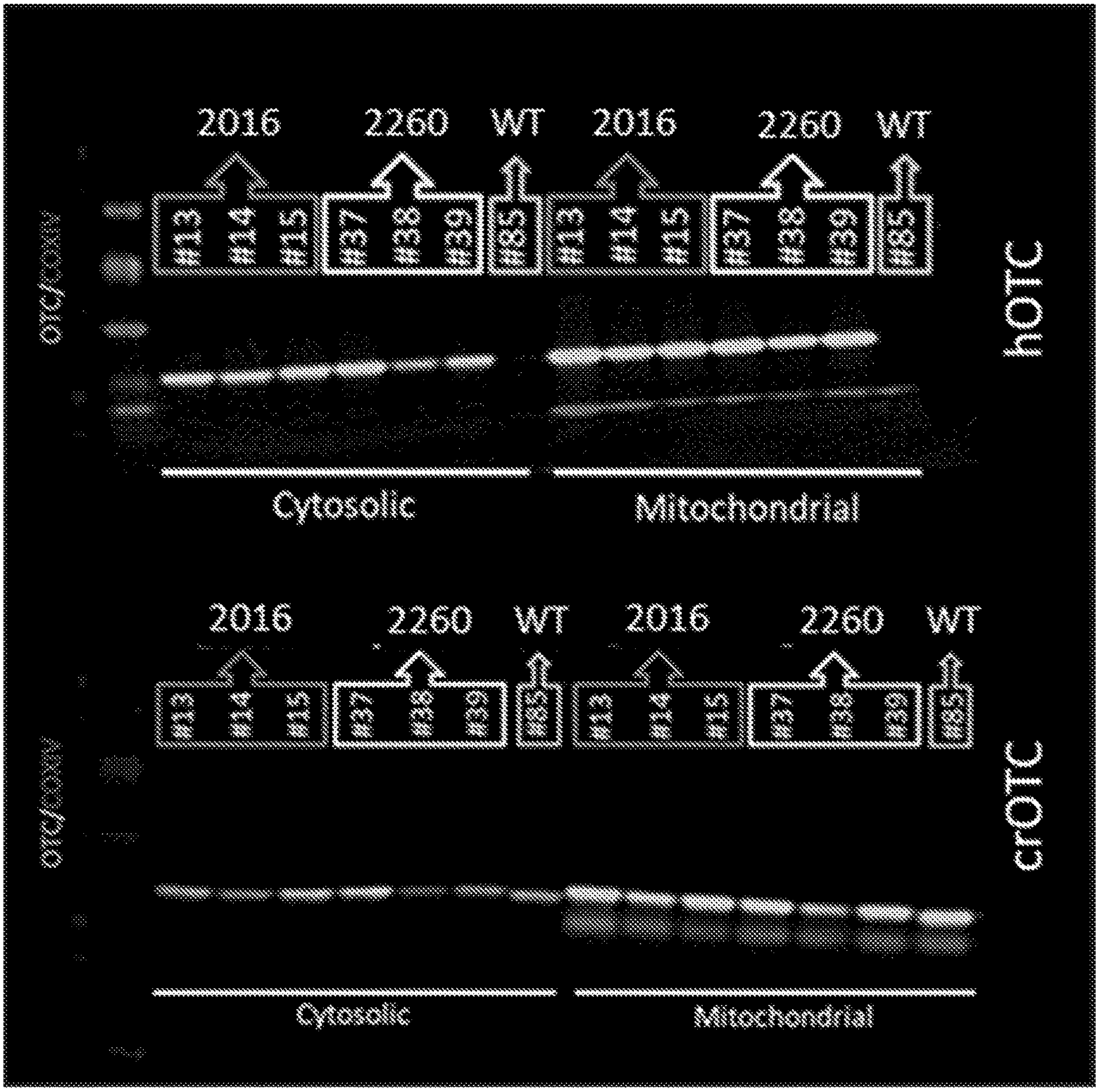
FIG. 11 is a western blot illustrating the protein expression levels of OTC-mRNAs in spf/ash mice dosed at 1 mg/kg and 3 mg/kg with lead OTC-mRNAs.

Example 12: Fractioning of Spf/Ash Mice In Vivo Samples Treated with Selected mRNAs Spf/ash mice received an IV injection with either PBS or lipid-formulated (as described in Example 1) OTC-mRNAs at 1 mg/kg and 3 mg/kg. WT mice were used as internal controls. Sample fractioning was performed on the liver samples, separating a cytosolic and a mitochondrial fraction. OTC levels were measured by WB using human specific (hOTC) and crossreactive (crOTC) antibodies (FIG. 11). Cyclooxygenase IV (CoxIV) was used as a mitochondrial control. OTC protein expression levels were measured by near-infrared fluorescent imaging systems and normalized to total protein. WB indicates differences in OTC expression levels within mitochondrial and cytosolic fractions when 2016 and 2260 mRNAs were delivered in the spf/ash mice. These results indicate that both compounds can efficiently target the mitochondria.

Example 13: Plot of the Mitochondrial vs Cytosolic Fractions of Spf/Ash Mice Samples Treated with mRNA Constructs 2016 and 2260

Figure 12:
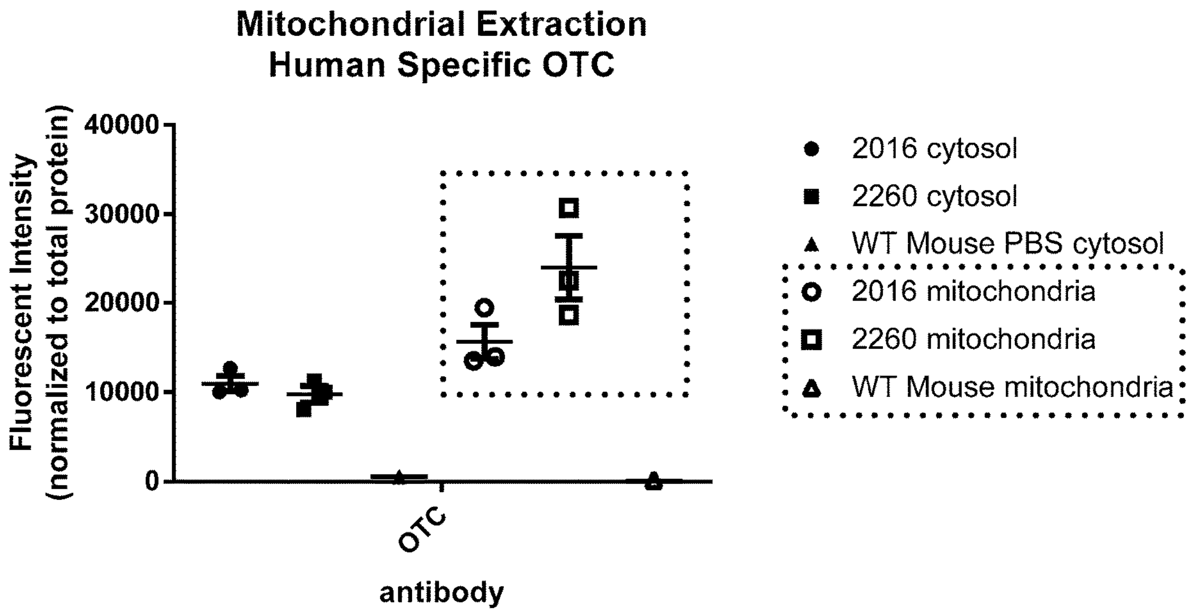
FIG. 12 is a western blot illustrating the protein expression levels in mitochondrial vs cytosolic fractions of spf/ash mice treated with lead OTC-mRNAs.

Spf/ash mice received an IV injection with either PBS or lipid-formulated OTC-mRNAs at 3 mg/kg. WT mice were used as internal controls. Sample fractioning was performed on the liver samples, separating a cytosolic and a mitochondrial fraction. OTC levels were measured by western blot using a human specific antibody. OTC protein expression levels were measured by near-infrared fluorescent imaging systems and both fractions normalized to total protein were plotted (FIG. 12). The plot of protein expression levels shown in FIG. 11 (Example 12), indicate that even though both compounds, 2016 and 2260, deliver similar protein levels in the cytosol, it is in the mitochondria where 2260 delivers more human OTC than 2016. The 2260 includes a modified mitochondrial signaling peptide sequence of the invention.

Example 14: Urinary Orotate Levels in Spf/Ash Mice Treated with mRNA Construct 2260

Figure 13:
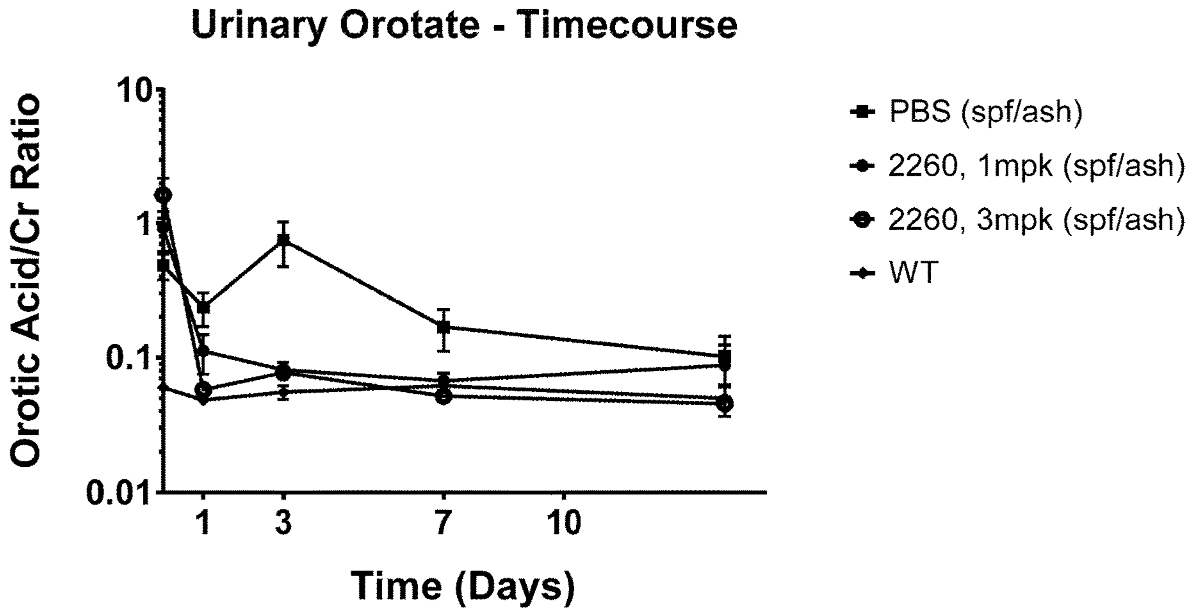
FIG. 13 is a plot illustrating the time course of expression of urinary orotate levels in spf/ash mice treated with lead OTC-mRNA.

Spf/ash mice received an IV injection with either PBS or lipid-formulated (as described in Example 1) OTC-mRNA at 1 mg/kg and 3 mg/kg. WT mice were included as an internal control. Urinary orotate levels were measured at 0, 1, 3, 7 and 14 days, and levels were normalized to creatinine (FIG. 13). The functional read-out of this assay shows that urinary orotate levels are reduced for up to 14 days with compound 2260, in a dose dependent manner.

Example 15: Survival of Spf/Ash Mice on a High Protein Diet During Treatment with OTC-mRNA Construct 1799.7 (5MeOU Chemistry)

Figure 14:
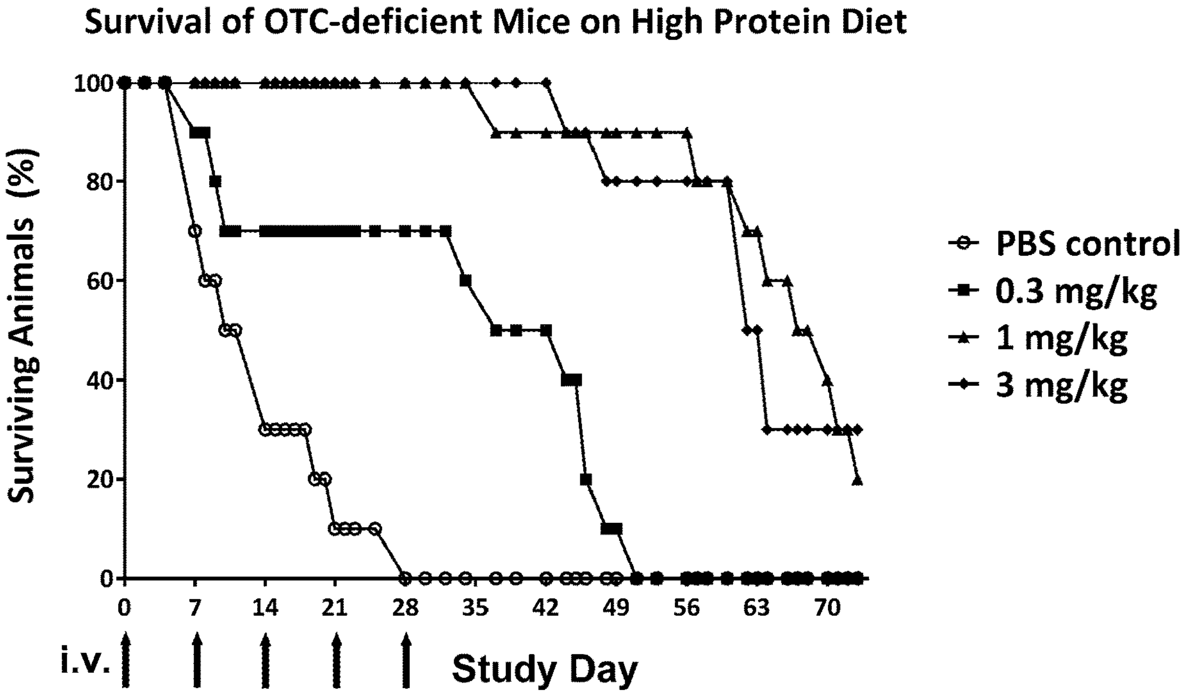
FIG. 14 is a plot illustrating the survival of OTC-deficient mice (spf/ash) on a high protein diet during treatment with three different doses of OTC-mRNA 1799.7.

Spf/ash mice received an IV injection with either PBS or lipid-formulated OTC-mRNA (1799.7) at three doses: 0.3 mg/kg, 1 mg/kg and 3 mg/kg. Mice were under a high protein diet since day 0 to the end of the study. Treated animals were injected by IV on days 0, 7, 14, 21 and 28 (arrows). Survival rates were determined every week. The plot in FIG. 14 summarizes the entire study timeline and the survival rates observed for the different groups. The results show that animals treated with human OTC mRNAs described herein have a higher chance to survive during a hyperammonemic crisis, suggesting the protective role of OTC mRNAs described herein in detoxifying the animals from toxic ammonia. This survival rate was dose-dependent, and animals treated with a 3 mg/kg dose have a higher survival rate than animals treated at 1 mg/kg or 0.3 mg/kg.

Example 16: Comparison of hOTC Expression Levels with Different Modifications

Figure 15:
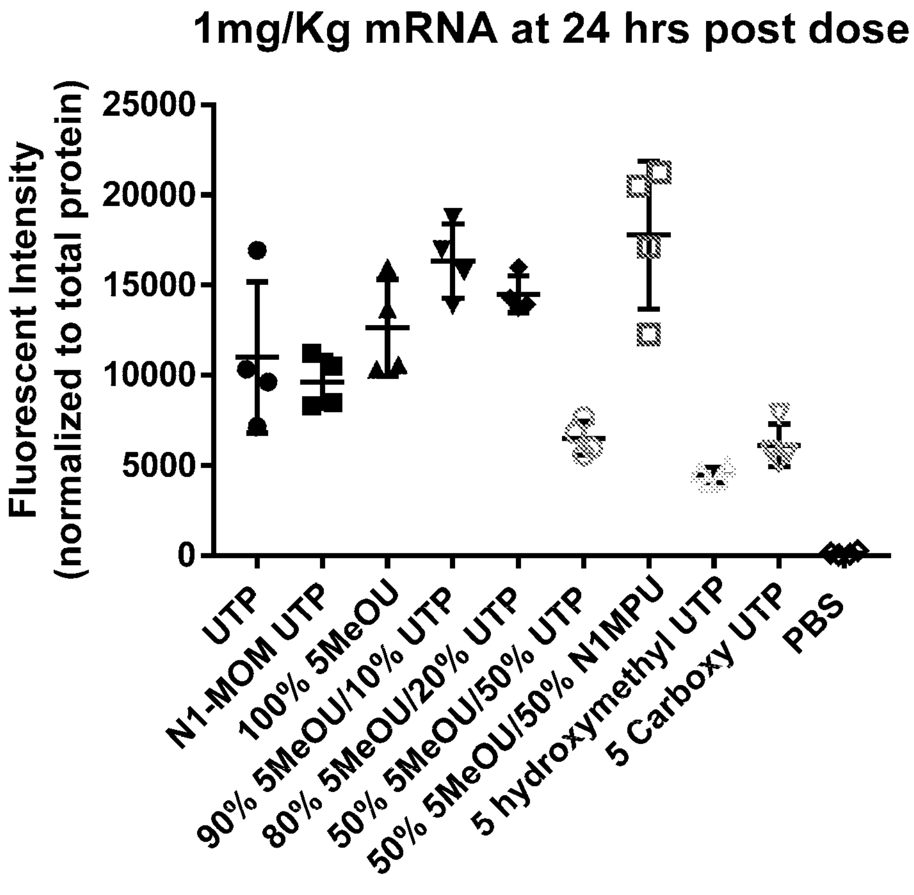
FIG. 15 is a plot illustrating hOTC expression levels in male C57BL/6 mice dosed with OTC-mRNAs (2262) having different modifications.

Lipid-formulated OTC-mRNA construct 2262 doses were injected by IV in 8 week-old male C57BL/6 mice at a dose of 1 mg/kg. Different chemistries were used in this study as indicated in the bottom axis of the chart provided in FIG. 15. The mice livers were harvested at 24 hours post IV-administration, and western blot was performed using a hOTC specific antibody. Levels were normalized to total protein (FIG. 15). Each construct was formulated as a lipid nanoparticle comprising an ATX lipid as described in Example 1. This dataset indicates the impact of different uridine chemistries on the expression levels of our codon-optimized mRNAs.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims. It should also be understood that the embodiments described herein are not mutually exclusive and that features from the various embodiments may be combined in whole or in part in accordance with the disclosure.

SEQUENCE LISTING
mRNA coding sequence for wild type human OTC
(SEQ ID NO: 1)
AUGCUGUUUAAUCUGAGGAUCCUGUUAAACAAUGCAGCUUUUAGAAAU
GGUCACAACUUCAUGGUUCGAAAUUUUCGGUGUGGACAACCACUACAA
AAUAAAGUGCAGCUGAAGGGCCGUGACCUUCUCACUCUAAAAAACUUU
ACCGGAGAAGAAAUUAAAUAUAUGCUAUGGCUAUCAGCAGAUCUGAAA
UUUAGGAUAAAACAGAAAGGAGAGUAUUUGCCUUUAUUGCAAGGGAAG
UCCUUAGGCAUGAUUUUUGAGAAAAGAAGUACUCGAACAAGAUUGUCU
ACAGAAACAGGCUUUGCACUUCUGGGAGGACAUCCUUGUUUUCUUACC
ACACAAGAUAUUCAUUUGGGUGUGAAUGAAAGUCUCACGGACACGGCC
CGUGUAUUGUCUAGCAUGGCAGAUGCAGUAUUGGCUCGAGUGUAUAAA
CAAUCAGAUUUGGACACCCUGGCUAAAGAAGCAUCCAUCCCAAUUAUC
AAUGGGCUGUCAGAUUUGUACCAUCCUAUCCAGAUCCUGGCUGAUUAC
CUCACGCUCCAGGAACACUAUAGCUCUCUGAAAGGUCUUACCCUCAGC
UGGAUCGGGGAUGGGAACAAUAUCCUGCACUCCAUCAUGAUGAGCGCA
GCGAAAUUCGGAAUGCACCUUCAGGCAGCUACUCCAAAGGGUUAUGAG
CCGGAUGCUAGUGUAACCAAGUUGGCAGAGCAGUAUGCCAAAGAGAAU
GGUACCAAGCUGUUGCUGACAAAUGAUCCAUUGGAAGCAGCGCAUGGA
GGCAAUGUAUUAAUUACAGACACUUGGAUAAGCAUGGGACAAGAAGAG
GAGAAGAAAAAGCGGCUCCAGGCUUUCCAAGGUUACCAGGUUACAAUG
AAGACUGCUAAAGUUGCUGCCUCUGACUGGACAUUUUUACACUGCUUG
CCCAGAAAGCCAGAAGAAGUGGAUGAUGAAGUCUUUUAUUCUCCUCGA
UCACUAGUGUUCCCAGAGGCAGAAAACAGAAAGUGGACAAUCAUGGCU
GUCAUGGUGUCCCUGCUGACAGAUUACUCACCUCAGCUCCAGAAGCCU
AAAUUUUGA DNA coding sequence for wild type human OTC
(SEQ ID NO: 2)
ATGCTGTTTAATCTGAGGATCCTGTTAAACAATGCAGCTTTTAGAAAT
GGTCACAACTTCATGGTTCGAAATTTTCGGTGTGGACAACCACTACAA
AATAAAGTGCAGCTGAAGGGCCGTGACCTTCTCACTCTAAAAAACTTT
ACCGGAGAAGAAATTAAATATATGCTATGGCTATCAGCAGATCTGAAA
TTTAGGATAAAACAGAAAGGAGAGTATTTGCCTTTATTGCAAGGGAAG
TCCTTAGGCATGATTTTTGAGAAAAGAAGTACTCGAACAAGATTGTCT
ACAGAAACAGGCTTTGCACTTCTGGGAGGACATCCTTGTTTTCTTACC
ACACAAGATATTCATTTGGGTGTGAATGAAAGTCTCACGGACACGGCC
CGTGTATTGTCTAGCATGGCAGATGCAGTATTGGCTCGAGTGTATAAA
CAATCAGATTTGGACACCCTGGCTAAAGAAGCATCCATCCCAATTATC
AATGGGCTGTCAGATTTGTACCATCCTATCCAGATCCTGGCTGATTAC
CTCACGCTCCAGGAACACTATAGCTCTCTGAAAGGTCTTACCCTCAGC
TGGATCGGGGATGGGAACAATATCCTGCACTCCATCATGATGAGCGCA
GCGAAATTCGGAATGCACCTTCAGGCAGCTACTCCAAAGGGTTATGAG
CCGGATGCTAGTGTAACCAAGTTGGCAGAGCAGTATGCCAAAGAGAAT -continued GGTACCAAGCTGTTGCTGACAAATGATCCATTGGAAGCAGCGCATGGA
GGCAATGTATTAATTACAGACACTTGGATAAGCATGGGACAAGAAGAG
GAGAAGAAAAAGCGGCTCCAGGCTTTCCAAGGTTACCAGGTTACAATG
AAGACTGCTAAAGTTGCTGCCTCTGACTGGACATTTTTACACTGCTTG
CCCAGAAAGCCAGAAGAAGTGGATGATGAAGTCTTTTATTCTCCTCGA
TCACTAGTGTTCCCAGAGGCAGAAAACAGAAAGTGGACAATCATGGCT
GTCATGGTGTCCCTGCTGACAGATTACTCACCTCAGCTCCAGAAGCCT
AAATTTTGA Human wild type OTC amino acid sequence
(The signal peptide for mitochondrial
import is underlined*)
(SEQ ID NO: 3)
<u>MLFNLRILLNNAAFRNGHNFMVRNFRCGQPLQ</u>NKVQLKGRDLLTLKNF
TGEEIKYMLWLSADLKFRIKQKGEYLPLLQGKSLGMIFEKRSTRTRLS
TETGFALLGGHPCFLTTQDIHLGVNESLTDTARVLSSMADAVLARVYK
QSDLDTLAKEASIPIFGLSDLYHPIQILADYLTLQEHYSSLKGLTLSW
IGDGNNILHSIMMSAAKFGMHLQAATPKGYEPDASVTKLAEQYAKENG
TKLLLTNDPLEAAHGGNVLITDTWISMGQEEEKKKRLQAFQGYQVTMK
TAKVAASDWTFLHCLPRKPEEVDDEVFYSPRSLVFPEAENRKWTIMAV
MVSLLTDYSPQLQKPKF Modified OTC amino acid sequence
(The signal peptide for mitochondrial
import is underlined*)
(SEQ ID NO: 4)
<u>MLVFNLRILLNNAAFRNGHNFMVRNFRCGQPLQ</u>NRVQLKGRDLLTLKN
FTGEEIRYMLWLSADLKFRIKQKGEYLPLLQGKSLGMIFEKRSTRTRL
STETGFALLGGHPCFLTTQDIHLGVNESLTDTARVLSSMADAVLARVY
KQSDLDTLAKEASIPIINGLSDLYHPIQILADYLTLQEHYSSLKGLTL
SWIGDGNNILHSIMMSAAKFGMHLQAATPKGYEPDASVTKLAEQYAKE
NGTKLLLTNDPLEAAHGGNVLITDTWISMGQEEEKKKRLQAFQGYQVT
MKTAKVAASDWTFLHCLPRKPEEVDDEVFYSPRSLVFPEAENRKWTIM
AVMVSLLTDYSPQLQKPKF TEV
(SEQ ID NO: 5)
TCAACACAACATATACAAAACAAACGAATCTCAAGCAATCAAGCATTC
TACTTCTATTGCAGCAATTTAAATCATTTCTTTTAAAGCAAAAGCAAT
TTTCTGAAAATTTTCACCATTTACGAACGATAG

AT1G58420
(SEQ ID NO: 6)
ATTATTACATCAAAACAAAAAGCCGCCA

ARC5-2
(SEQ ID NO: 7)
CTTAAGGGGGCGCTGCCTACGGAGGTGGCAGCCATCTCCTTCTCGGCA
TCAAGCTTACCATGGTGCCCCAGGCCCTGCTCTTgGTCCCGCTGCTGG
TGTTCCCCCTCTGCTTCGGCAAGTTCCCCATCTACACCATCCCCGACA
AGCTGGGGCCGTGGAGCCCCATCGACATCCACCACCTGTCCTGCCCCA
ACAACCTCGTGGTCGAGGACGAGGGCTGCACCAACCTGAGCGGGTTCT
CCTAC

-continued

HCV (SEQ ID NO: 8)

TGAGTGTCGT ACAGCCTCCA GGCCCCCCCC TCCCGGGAGA
GCCATAGTGG TCTGCGGAACCGGTGAGTAC ACCGGAATTG
CCGGGAAGAC TGGGTCCTTT CTTGGATAAA CCCACTCTATGC
CCGGCCAT TTGGGCGTGC CCCCGCAAGA CTGCTAGCCG
AGTAGTGTTG GGTTGCG

HUMAN ALBUMIN (SEQ ID NO: 9)

AATTATTGGTTAAAGAAGTATATTAGTGCTAATTTCCCTCCGTTT
GTCCTAGCTTTTCTCTTCTGTCAACCCCACACGCCTTTGGCACA

EMCV (SEQ ID NO: 10)

CTCCCTCCCC CCCCCCTAAC GTTACTGGCC GAAGCCGCTT
GGAATAAGGC CGGTGTGCGT TTGTCTATAT GTTATTTTCC
ACCATATTGC CGTCTTTTGG CAATGTGAGG GCCCGGAAAC
CTGGCCCTGT CTTCTTGACG AGCATTCCTA GGGGTCTTTC
CCCTCTCGCC AAAGGAATGC AAGGTCTGTT GAATGTCGTG
AAGGAAGCAG TTCCTCTGGA AGCTTCTTGA AGACAAACAA
CGTCTGTAGC GACCCTTTGC AGGCAGCGGA ACCCCCCACC
TGGCGACAGG TGCCTCTGCG GCCAAAAGCC ACGTGTATAA
GATACACCTG CAAAGGCGGC ACAACCCCAG TGCCACGTTG
TGAGTTGGAT AGTTGTGGAA AGAGTCAAAT GGCTCTCCTC
AAGCGTATTC AACAAGGGGC TGAAGGATGC CCAGAAGGTA
CCCCATTGTA TGGGATCTGA TCTGGGGCCT CGGTGCACAT
GCTTTACGTG TGTTTAGTCG AGGTTAAAAA ACGTCTAGGC
CCCCCGAACC ACGGGGACGT GGTTTTCCTT TGAAAAACAC
GATGATAAT

HSP70-P2

(SEQ ID NO: 11)

GTCAGCTTTCAAACTCTTTGTTTCTTGTTTGTTGATTGAGAATA

HSP70-M1

(SEQ ID NO: 12)

CTCTCGCCTGAGAAAAAAAATCCACGAACCAATTTCTCAGCAACCAGC
AGCACG

HSP72-M2

(SEQ ID NO: 13)

ACCTGTGAGGGTTCGAAGGAAGTAGCAGTGTTTTTTGTTCCTAGAGGA
AGAG

HSP17.9

(SEQ ID NO: 14)

ACACAGAAACATTCGCAAAAACAAAATCCCAGTATCAAAATTCTTCTC
TTTTTTTCATATTTCGCAAAGAC

HSP70-P1

(SEQ ID NO: 15)

CAGAAAAATTTGCTACATTGTTTCACAAACTTCAAATATTATTCATTT
ATTT

-continued

XBG (SEQ ID NO: 16)

CTAGTGACTGACTAGGATCTGGTTACCACTAAACCAGCCTCAAGAACA
CCCGAATGGAGTCTCTAAGCTACATAATACCAACTTACACTTACAAAA
TGTTGTCCCCCAAAATGTAGCCATTCGTATCTGCTCCTAATAAAAAGA
AAGTTTCTTCACAT

HUMAN HAPTOGLOBIN (SEQ ID NO: 17)

TGCAAGGCTGGCCGGAAGCCCTTGCCTGAAAGCAAGATTTCAGCCTGG
AAGAGGGCAAAGTGGACGGGAGTGGACAGGAGTGGATGCGATAAGATG
TGGTTTGAAGCTGATGGGTGCCAGCCCTGCATTGCTGAGTCAATCAAT
AAAGAGCTTTCTTTTGACCCAT

HUMAN APOLIPOPROTEIN E (SEQ ID NO: 18)

ACGCCGAAGCCTGCAGCCATGCGACCCCACGCCACCCCGTGCCTCCTG
CCTCCGCGCAGCCTGCAGCGGGAGACCCTGTCCCCGCCCCAGCCGTCC
TCCTGGGGTGGACCCTAGTTTAATAAAGATTCACCAAGTTTCACGCA

HCV (SEQ ID NO: 19)

TAGAGCGGCAAACCCTAGCTACACTCCATAGCTAGTTTCTTTTTTTTT
TGTTTTTTTTTTTTTTTTTTTTTTTTTTTTTTTTTTTTTTTCCTTTCT
TTTCCTTCTTTTTTTCCTCTTTTCTTGGTGGCTCCATCTTAGCCCTAG
TCACGGCTAGCTGTGAAAGGTCCGTGAGCCGCATGACTGCAGAGAGTG
CCGTAACTGGTCTCTCTGCAGATCATGT

MOUSE ALBUMIN (SEQ ID NO: 20)

ACACATCACAACCACAACCTTCTCAGGCTACCCTGAGAAAAAAAGACA
TGAAGACTCAGGACTCATCTTTTCTGTTGGTGTAAAATCAACACCCTA
AGGAACACAAATTTCTTTAAACATTTGACTTCTTGTCTCTGTGCTGCA
ATTAATAAAAAATGGAAAGAATCTAC

HUMAN ALPHA GLOBIN (SEQ ID NO: 21)

GCTGGAGCCTCGGTAGCCGTTCCTCCTGCCCGCTGGGCCTCCCAACGG
GCCCTCCTCCCCTCCTTGCACCGGCCCTTCCTGGTCTTTGAATAAAGT
CTGAGTGGGCAGCA

EMCV (SEQ ID NO: 22)

TAGTGCAGTCAC TGGCACAACG CGTTGCCCGG TAAGCCAATC
GGGTATACAC GGTCGTCATACTGCAGACAG GGTTCTTCTA
CTTTGCAAGA TAGTCTAGAG TAGTAAAATA AATAGTATAAG (SEQ ID NO: 23)

GCCACC (SEQ ID NO: 24)

GCCA (SEQ ID NO: 25)

AUAAGUGAA

-continued

>mARM563

(SEQ ID NO: 26)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUUA
AUCUGAGGAUCCUGUUAAACAAUGCAGCUUUUAGAAAUGGUCACAACU
UCAUGGUUCGAAAUUUUCGGUGUGGACAACCACUACAAAAUAAAGUGC
AGCUGAAGGGCCGUGACCUUCUCACUCUAAAAAACUUUACCGGAGAAG
AAAUUAAAUAUAUGCUAUGGCUAUCAGCAGAUCUGAAAUUUAGGAUAA
AACAGAAAGGAGAGUAUUUGCCUUUAUUGCAAGGGAAGUCCUUAGGCA
UGAUUUUUGAGAAAAGAAGUACUCGAACAAGAUUGUCUACAGAAACAG
GCUUUGCACUUCUGGGAGGACAUCCUUGUUUUCUUACCACACAAGAUA
UUCAUUUGGGUGUGAAUGAAAGUCUCACGGACACGGCCCGUGUAUUGU
CUAGCAUGGCAGAUGCAGUAUUGGCUCGAGUGUAUAAACAAUCAGAUU
UGGACACCCUGGCUAAAGAAGCAUCCAUCCCAAUUAUCAAUGGGCUGU
CAGAUUUGUACCAUCCUAUCCAGAUCCUGGCUGAUUACCUCACGCUCC
AGGAACACUAUAGCUCUCUGAAAGGUCUUACCCUCAGCUGGAUCGGGG
AUGGGAACAAUAUCCUGCACUCCAUCAUGAUGAGCGCAGCGAAAUUCG
GAAUGCACCUUCAGGCAGCUACUCCAAAGGGUUAUGAGCCGGAUGCUA
GUGUAACCAAGUUGGCAGAGCAGUAUGCCAAAGAGAAUGGUACCAAGC
UGUUGCUGACAAAUGAUCCAUUGGAAGCAGCGCAUGGAGGCAAUGUAU
UAAUUACAGACACUUGGAUAAGCAUGGGACAAGAAGAGGAGAAGAAAA
AGCGGCUCCAGGCUUUCCAAGGUUACCAGGUUACAAUGAAGACUGCUA
AAGUUGCUGCCUCUGACUGGACAUUUUUACACUGCUUGCCCAGAAAGC
CAGAAGAAGUGGAUGAUGAAGUCUUUUAUUCUCCUCGAUCACUAGUGU
UCCCAGAGGCAGAAAACAGAAAGUGGACAAUCAUGGCUGUCAUGGUGU
CCCUGCUGACAGAUUACUCACCUCAGCUCCAGAAGCCUAAAUUUUGAC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM564

(SEQ ID NO: 27)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUCUUUA
AUCUGCGCAUCUUACUGAACAACGCCGCAUUCCGGAACGGUCACAACU
UCAUGGUCCGCAAUUUCCGCUGUGGCCAGCCGCUUCAAAACAAGGUCC
AGCUGAAGGGACGGGAUCUGCUGACACUGAAGAACUUCACCGGAGAAG
AGAUCAAGUACAUGCUGUGGCUCAGCGCAGACUUGAAGUUCCGGAUCA
AGCAGAAGGGAGAAUACUUGCCCCUGCUGCAAGGAAAGUCGCUGGGAA
UGAUUUUUGAGAAGCGGUCAACUCGCACCAGACUCUCCACCGAAACUG

-continued

GUUUCGCACUGCUUGGCGGGCACCCUUGCUUCCUGACGACUCAGGACA
UCCACCUCGGCGUGAACGAAUCGCUAACCGAUACCGCCAGAGUGCUUU
CUUCCAUGGCCGACGCGGUGCUGGCCAGGGUGUACAAGCAGUCCGACC
UCGAUACCUUGGCAAAGGAGGCUUCCAUUCCCAUCAUCAACGGCCUGA
GCGACCUGUACCACCCAAUCCAAAUCCUGGCUGACUACCUGACCCUGC
AAGAGCACUACAGCAGCCUGAAGGGUCUGACCCUGUCAUGGAUUGGCG
AUGGAAACAAUAUUCUGCACUCCAUCAUGAUGUCCGCCGCGAAGUUCG
GAAUGCAUCUGCAAGCCGCCACUCCAAAAGGAUACGAACCGGAUGCGU
CCGUGACCAAGUUGGCGGAACAGUACGCGAAGGAGAACGGAACCAAGC
UUCUGCUGACUAACGACCCCCUCGAGGCUGCGCAUGGGGGCAACGUGC
UGAUUACCGACACCUGGAUCUCCAUGGGGCAGGAGGAAGAGAAGAAGA
AGAGACUGCAGGCAUUCCAGGGGUACCAGGUCACCAUGAAAACCGCAA
AAGUGGCAGCUUCGGACUGGACUUUCCUGCAUUGCCUGCCGAGGAAGC
CGGAGGAAGUCGACGACGAAGUGUUCUACUCGCCUCGGUCCCUGGUGU
UCCCCGAGGCCGAAAACCGGAAGUGGACCAUCAUGGCCGUGAUGGUGU
CCUUGCUGACUGACUAUAGCCCGCAGCUGCAGAAGCCUAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM565

(SEQ ID NO: 28)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUUA
ACCUACGUAUUUUGCUCAACAAUGCAGCCUUUAGAAACGGACAUAACU
UUAUGGUUCGAAACUUUCGCUGCGGGCAGCCACUGCAGAACAAGGUCC
AGCUGAAAGGGAGAGAUUUGCUCACGCUGAAGAACUUUACUGGCGAAG
AAAUCAAGUAUAUGCUGUGGUUGUCCGCGGACCUCAAGUUUCGGAUUA
AGCAGAAAGGGGAGUAUCUGCCACUGCUGCAAGGAAAGAGCCUCGGCA
UGAUCUUCGAGAAGCGGAGCACUCGGACCAGGCUGAGUACCGAAACUG
GCUUCGCAUUGUUGGGUGGACAUCCAUGUUUUCUGACAACGCAGGACA
UUCAUCUGGGCGUGAACGAGAGUCUGACGGACACAGCUCGCGUUCUGU
CCUCUAUGGCUGAUGCGGUGUUGGCCCGGGUCUAUAAGCAGUCCGAUU
UGGACACCUUGGCUAAGGAAGCUAGCAUACCGAUUAUCAAUGGGCUGU
CCGACCUGUAUCACCCUAUUCAAAUCCUGGCCGACUACCUCACACUGC
AAGAACACUAUAGCUCAUUGAAGGGACUGACCCUGAGCUGGAUAGGGG
ACGGAAACAACAUCCUACAUAGCAUUAUGAUGUCCGCUGCCAAGUUUG
GCAUGCAUCUUCAAGCCGCCACGCCAAAGGGUUAUGAGCCCGACGCGU
CAGUGACAAAGCUGGCCGAGCAGUACGCUAAGGAGAAUGGUACCAAAU
UACUGCUGACUAAUGAUCCACUGGAGGCUGCACAUGGCGGCAAUGUAC
UGAUCACCGACACAUGGAUCUCGAUGGGCCAGGAGGAAGAAAAGAAGA

-continued

AGAGGCUUCAGGCCUUCCAAGGCUACCAGGUCACCAUGAAAACAGCUA
AGGUUGCAGCAUCUGAUUGGACCUUUCUGCACUGUCUGCCAAGGAAGC
CCGAAGAGGUGGACGAUGAAGUAUUCUAUAGCCCACGGAGUUUGGUGU
UCCCUGAGGCUGAAAAUAGGAAGUGGACAAUUAUGGCCGUAAUGGUGU
CCCUGUUAACCGACUACUCUCCGCAACUGCAGAAACCUAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM566
(SEQ ID NO: 29)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUUA
ACUUAAGGAUCCUGCUGAACAACGCCGCUUUUCGUAACGGUCAUAACU
UUAUGGUCCGGAACUUUAGAUGUGGCCAGCCGCUGCAGAACAAGGUUC
AGCUGAAGGGGAGGGAUCUGCUGACCUUGAAGAACUUUACCGGCGAAG
AGAUCAAGUACAUGUUGUGGCUGAGCGCCGAUCUGAAGUUUAGGAUUA
AGCAGAAGGGGGAGUAUUUGCCACUGCUGCAAGGAAAAUCCUUGGGGA
UGAUCUUCGAGAAGCGCUCCACUAGAACCCGGCUAAGCACAGAAACCG
GCUUCGCACUUCUGGGUGGACAUCCCUGUUUUCUGACGACGCAGGAUA
UACACCUGGGCGUGAAUGAGAGUCUGACGGACACAGCUAGGGUGUUGA
GCAGCAUGGCCGAUGCAGUACUGGCCCGCGUUUAUAAGCAGAGCGACU
UGGACACACUGGCCAAGGAAGCGUCAAUUCCGAUUAUCAAUGGGCUGU
CAGACCUGUAUCAUCCCAUUCAAAUCUUGGCUGACUAUCUGACCCUGC
AAGAACAUUACAGCUCCCUGAAGGGCCUCACGUUGUCCUGGAUUGGCG
ACGGAAACAACAUUCUGCAUUCGAUCAUGAUGAGCGCUGCUAAGUUUG
GCAUGCACCUCCAAGCCGCUACACCUAAGGGAUAUGAGCCUGAUGCCA
GCGUAACCAAGCUGGCCGAACAGUACGCGAAGGAGAAUGGCACGAAAC
UGCUGUUGACAAAUGACCCACUGGAGGCAGCUCACGGUGGCAACGUGC
UGAUCACCGACACGUGGAUAUCUAUGGGACAGGAAGAAGAGAAGAAGA
AGCGGCUGCAGGCAUUCCAAGGGUAUCAGGUCACCAUGAAAACGGCCA
AGGUUGCUGCAUCCGACUGGACAUUUCUGCAUUGCUUGCCCCGCAAAC
CAGAAGAAGUAGACGACGAAGUCUUUUAUUCCCCACGGUCGCUGGUGU
UCCCCGAGGCGGAGAAUCGAAAGUGGACGAUUAUGGCCGUGAUGGUGU
CCCUGCUGACUGAUUACUCUCCCCAACUGCAAAAGCCUAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

-continued

>mARM567
(SEQ ID NO: 30)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACCUGAGGAUCCUCCUGAACAACGCCGCCUUUCGCAAUGGUCACAACU
UUAUGGUCCGGAACUUCAGAUGCGGCCAGCCGCUGCAGAACAAGGUCC
AGCUGAAGGGACGGGAUCUGCUGACUCUGAAGAACUUCACCGGAGAAG
AGAUCAAGUACAUGCUGUGGCUGUCGGCCGACCUGAAGUUCAGGAUCA
AGCAGAAGGGAGAAUACCUCCCGCUGCUGCAAGGAAAGUCCCUGGGCA
UGAUUUUCGAGAAGCGCUCGACCAGAACUCGGUUGUCCACCGAAACCG
GGUUUGCGCUGCUGGGCGGACAUCCUUGCUUCCUGACGACUCAGGAUA
UUCACCUGGGAGUGAACGAGUCGCUGACCGACACCGCCAGAGUGCUGA
GCUCGAUGGCCGACGCCGUGUUGGCACGCGUGUACAAGCAGUCCGAUC
UGGAUACCCUGGCCAAAGAAGCUUCCAUCCCGAUCAUUAACGGGCUGA
GCGACCUCUACCACCCCAUUCAAAUCCUGGCCGACUACCUGACUCUGC
AAGAACACUACAGCUCGCUGAAGGGGUUGACUCUGUCCUGGAUCGGCG
ACGGAAACAACAUCCUGCACUCCAUCAUGAUGUCGGCCGCAAAGUUCG
GCAUGCAUUUGCAAGCCGCCACCCCAAAGGGCUACGAACCAGACGCGA
GCGUCACCAAGCUGGCCGAACAGUACGCGAAGGAAAAUGGUACUAAGC
UGCUGCUGACCAACGACCCAUUGGAAGCUGCCCAUGGUGGAAACGUGC
UGAUCACCGACACCUGGAUCUCGAUGGGCCAGGAAGAGGAGAAGAAGA
AGCGGCUGCAGGCGUUCCAGGGGUAUCAGGUCACCAUGAAAACAGCCA
AAGUGGCAGCGUCAGACUGGACCUUCCUCCACUGUCUGCCUCGCAAGC
CAGAGGAGGUGGACGACGAGGUGUUCUACUCCCCUCGGUCCCUCGUGU
UCCCUGAGGCUGAGAACCGGAAGUGGACCAUUAUGGCCGUGAUGGUGU
CACUCCUGACUGAUUACUCCCCGCAACUGCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM568
(SEQ ID NO: 31)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUUA
ACCUGAGGAUCCUAUUGAACAAUGCUGCUUUUCGUAAUGGCCAUAACU
UUAUGGUUCGGAACUUUAGAUGCGGGCAGCCACUGCAGAACAAGGUCC
AGUUGAAAGGCCGCGAUCUGUUGACAUUGAAGAACUUUACCGGCGAAG
AGAUUAAGUAUAUGCUGUGGCUGUCUGCUGACCUCAAGUUUCGAAUCA
AGCAGAAGGGCGAAUAUCUCCCCCUGCUGCAAGGAAAGUCUCUCGGCA
UGAUCUUUGAGAAGCGGAGUACCCGAACACGGCUGAGCACCGAAACGG

-continued

GCUUCGCACUGCUGGGGGGCCAUCCCUGUUUUCUGACAACGCAGGACA
UCCACUUGGGGGUUAACGAAUCAUUGACUGAUACCGCCCGCGUACUGU
CAUCCAUGGCCGACGCUGUGCUGGCUAGGGUGUACAAGCAGUCAGAUC
UGGAUACACUGGCCAAGGAAGCUAGCAUACCAAUCAUCAAUGGACUGA
GUGACCUUUAUCACCCGAUUCAAAUACUAGCCGAUUAUCUGACCCUGC
AAGAGCAUUACUCCUCGCUGAAAGGCCUCACGCUGUCCUGGAUCGGCG
ACGGCAACAACAUUCUGCAUAGUAUUAUGAUGUCUGCUGCCAAAUUCG
GCAUGCAUCUGCAAGCUGCUACGCCGAAGGGUUAUGAACCCGACGCGU
CAGUUACGAAGCUCGCUGAGCAGUAUGCAAAGGAGAAUGGCACAAAGC
UGUUGCUUACCAACGAUCCCCUGGAAGCUGCUCAUGGCGGCAAUGUGC
UGAUUACUGACACCUGGAUUUCAAUGGGCCAGGAGGAGGAGAAGAAGA
AGAGGUUACAGGCUUUUCAAGGUUACCAAGUCACGAUGAAAACCGCUA
AGGUCGCAGCCAGCGACUGGACAUUCCUGCACUGUCUGCCAAGAAAGC
CGGAAGAAGUGGACGACGAGGUGUUCUAUUCCCCGCGGUCUUUGGUGU
UUCCGGAGGCCGAAAACAGGAAAUGGACCAUUAUGGCCGUGAUGGUAU
CGUUGCUGACGGACUACAGCCCUCAGUUGCAAAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM569

(SEQ ID NO: 32)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUCUUUA
ACCUCCGCAUCCUCCUCAACAACGCCGCCUUCCGGAAUGGGCAUAACU
UCAUGGUCCGGAACUUCAGAUGCGGCCAGCCCCUGCAAAACAAGGUCC
AGUUGAAGGGACGGGACCUCCUUACGCUGAAGAACUUUACCGGAGAAG
AGAUUAAGUACAUGCUGUGGUUGUCCGCUGACCUCAAGUUCCGCAUUA
AGCAGAAGGGAGAAUAUCUGCCGCUGCUGCAAGGAAAGAGCCUGGGCA
UGAUCUUCGAAAAGCGCUCCACUAGAACCCGGCUGUCGACUGAGACUG
GAUUCGCCUUGCUCGGUGGACACCCGUGCUUCCUGACGACCCAGGACA
UCCACCUGGGAGUGAACGAGUCACUUACGGAUACCGCGAGGGUGCUGU
CCUCAAUGGCCGACGCAGUGCUCGCGCGCGUGUACAAGCAGUCAGAUC
UGGAUACCCUGGCCAAGGAAGCCAGCAUUCCCAUCAUCAACGGACUGA
GCGACCUUUACCACCCAAUCCAGAUCCUCGCCGACUACUUAACCCUGC
AAGAGCACUACAGCUCCCUGAAGGGACUGACUCUGUCCUGGAUCGGGG
AUGGAAACAACAUCCUGCACUCCAUCAUGAUGUCUGCCGCUAAGUUUG
GGAUGCAUCUGCAAGCCGCAACCCCUAAGGGAUACGAGCCCGACGCCU
CGGUGACCAAACUUGCGGAACAGUACGCCAAGGAAAACGGUACCAAGC
UGCUGCUGACCAACGACCCUCUGGAAGCGGCCCACGGAGGAAAUGUGC
UGAUUACCGACACCUGGAUUUCGAUGGGCCAGGAGGAGGAGAAGAAGA

-continued

AGAGACUGCAGGCGUUCCAGGGAUAUCAGGUCACCAUGAAAACCGCCA
AGGUCGCCGCCAGCGACUGGACCUUCCUGCACUGUCUCCCUCGGAAAC
CGGAAGAAGUGGAUGACGAGGUGUUCUACUCCCCGCGCUCGCUGGUGU
UCCCGGAGGCUGAAAACAGGAAGUGGACAAUCAUGGCCGUGAUGGUGU
CCCUGUUGACCGACUACUCCCCACAACUGCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM570

(SEQ ID NO: 33)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUGCGCAUCCUCCUGAACAACGCCGCCUUCCGCAAUGGACACAACU
UUAUGGUCCGCAACUUCCGCUGUGGGCAGCCGCUGCAGAACAAGGUCC
AGCUCAAGGGGAGAGAUCUCCUGACCCUGAAGAACUUCACUGGAGAGG
AGAUCAAGUACAUGCUGUGGCUGUCCGCCGACCUGAAAUUUCGGAUUA
AGCAGAAGGGCGAAUACCUCCCACUGCUGCAAGGAAAGUCUUUGGGCA
UGAUCUUCGAAAAGAGAAGCACCCGGACCCGGUUGAGCACCGAAACUG
GGUUCGCGCUCCUCGGUGGACACCCGUGCUUCCUGACCACCCAAGAUA
UUCAUCUGGGUGUCAACGAAAGCCUGACCGACACCGCCAGGGUGCUGU
CAUCCAUGGCUGACGCAGUGCUCGCCCGGGUGUACAAGCAGUCAGACC
UGGACACCCUCGCCAAGGAAGCUUCGAUCCCUAUCAUCAACGGACUUU
CCGACCUGUACCACCCCAUCCAAAUUCUGGCCGACUACCUGACUCUGC
AAGAACACUAUAGCUCGCUGAAAGGACUUACUCUGUCCUGGAUCGGGG
ACGGCAACAACAUUCUCCAUUCCAUCAUGAUGUCCGCUGCCAAGUUCG
GAAUGCACCUUCAAGCAGCGACUCCCAAGGGAUACGAACCUGAUGCCU
CCGUGACUAAGCUGGCAGAGCAGUACGCCAAGGAGAACGGUACAAAGC
UGCUGCUCACGAACGACCCCCUGGAGGCGGCCCACGGCGGAAACGUGC
UGAUUACCGAUACCUGGAUCUCAAUGGGCCAGGAAGAGGAGAAGAAGA
AGCGGCUCCAGGCGUUUCAAGGCUACCAGGUCACCAUGAAAACCGCGA
AGGUCGCCGCCUCCGACUGGACUUUCUUGCACUGCCUGCCGCGGAAGC
CCGAGGAAGUGGAUGACGAAGUGUUCUACUCGCCGAGAUCGUUGGUGU
UCCCUGAGGCCGAAAACAGGAAGUGGACCAUCAUGGCCGUGAUGGUGU
CCCUGCUGACUGAUUACAGCCCACAGCUGCAGAAGCCUAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

-continued

>mARM571

(SEQ ID NO: 34)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM572

(SEQ ID NO: 35)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACCUGAGAAUCCUCCUGAACAACGCCGCCUUCCGCAAUGGUCAUAACU
UCAUGGUCCGCAACUUUCGCUGCGGACAGCCUCUCCAAAACAAGGUCC
AGCUCAAGGGGCGCGACCUCCUCACACUGAAGAACUUCACUGGAGAAG
AAAUCAAGUACAUGCUGUGGCUGAGCGCCGAUCUGAAGUUCCGGAUCA
AGCAGAAGGGAGAGUACCUUCCUCUGCUGCAAGGGAAGUCCUUGGGAA
UGAUUUUCGAGAAGCGGUCCACCCGGACCAGGCUGAGCACUGAAACUG

-continued

GCUUCGCCCUGCUGGGAGGCCACCCUUGUUUCCUGACCACUCAGGACA
UCCACCUGGGCGUGAACGAGUCCCUGACCGAUACUGCCAGAGUGCUGU
CCUCCAUGGCCGACGCCGUGCUCGCCCGGGUGUACAAGCAGUCAGACC
UCGAUACGCUGGCCAAGGAAGCCUCCAUUCCCAUUAUCAAUGGUCUGU
CGGACCUCUACCAUCCAAUCCAAAUCCUCGCCGACUACCUGACUCUGC
AAGAACACUACAGCUCACUCAAGGGCCUCACCCUCUCCUGGAUCGGCG
ACGGAAACAACAUCCUUCACUCGAUUAUGAUGUCGGCCGCGAAGUUCG
GGAUGCACCUCCAAGCUGCCACUCCAAAAGGCUACGAGCCGGAUGCCU
CAGUGACUAAGUUGGCGGAACAGUAUGCGAAGGAGAACGGUACCAAGC
UCCUGCUGACUAACGACCCGCUGGAGGCCGCCCACGGGGGAAACGUGC
UCAUCACCGAUACUUGGAUUUCCAUGGGACAGGAGGAAGAGAAGAAGA
AGCGGUUGCAGGCAUUUCAGGGCUACCAGGUCACCAUGAAAACUGCCA
AAGUCGCCGCCAGCGACUGGACCUUCCUGCACUGCCUGCCCCGCAAGC
CUGAAGAAGUGGACGACGAGGUGUUCUACUCUCCCCGGUCCCUCGUGU
UCCCUGAGGCCGAAAACAGGAAGUGGACCAUCAUGGCUGUGAUGGUGU
CCCUCCUGACCGACUACAGCCCUCAGCUCCAAAAACCCAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM573

(SEQ ID NO: 36)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACCUGAGAAUCCUCUUGAACAAUGCUGCUUUUCGGAAUGGCCACAACU
UUAUGGUUCGGAACUUCCGUUGCGGCCAGCCUUUACAAAACAAGGUCC
AGCUGAAGGGCCGGGAUUUGCUCACACUGAAGAACUUUACUGGGGAGG
AGAUUAAGUAUAUGCUGUGGCUGUCCGCUGACCUGAAGUUUAGGAUCA
AGCAGAAGGGCGAAUAUCUGCCGCUGCUGCAAGGGAAAAGUCUGGGCA
UGAUUUUUGAAAAGCGCUCUACCCGGACCAGACUGUCUACGGAAACAG
GCUUUGCCCUGCUGGGCGGCCACCCCUGUUUUCUGACAACGCAGGACA
UCCAUCUGGGCGUGAACGAAUCACUGACCGAUACUGCUCGGGUACUCA
GUUCUAUGGCUGACGCAGUGCUGGCUAGGGUGUACAAGCAGAGCGACU
UGGACACACUGGCUAAGGAGGCCAGCAUCCCCAUUAUCAAUGGCCUGU
CUGAUUUGUACCAUCCCAUUCAAAUCCUGGCUGAUUAUCUGACACUAC
AAGAGCAUUACUCAAGUCUGAAGGGUUUGACUCUCUCCUGGAUCGGCG
ACGGCAACAACAUUUUACAUUCCAUUAUGAUGAGUGCUGCUAAGUUUG
GCAUGCAUUUGCAAGCUGCUACCCCAAAGGGCUAUGAACCUGACGCUA
GCGUAACCAAGUUGGCCGAACAGUAUGCUAAAGAGAAUGGCACCAAGC
UGCUCCUGACGAAUGACCCCCUGGAAGCUGCUCAUGGCGGAAACGUAC
UUAUAACUGAUACAUGGAUUAGCAUGGGCCAGGAAGAGGAGAAGAAGA

AGAGACUGCAGGCCUUCCAAGGCUAUCAGGUCACCAUGAAAACUGCCA
AGGUUGCAGCUAGCGACUGGACCUUCCUGCACUGUUUGCCGAGGAAAC
CCGAGGAGGUGGACGAUGAAGUCUUUUAUUCUCCCCGCUCCUUGGUGU
UUCCCGAGGCUGAAAAUCGAAAGUGGACGAUAAUGGCAGUGAUGGUGU
CCCUACUGACCGACUAUUCUCCACAACUGCAGAAGCCUAAAUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM574

(SEQ ID NO: 37)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUGAGGAUCCUGCUGAACAACGCUGCUUUUCGCAACGGUCAUAACU
UUAUGGUUCGCAAUUUUCGUUGUGGCCAGCCGCUGCAGAACAAGGUUC
AGCUGAAGGGCAGAGAUCUGCUGACUCUGAAGAACUUCACUGGGGAAG
AAAUCAAGUAUAUGUUAUGGCUGUCCGCGGAUCUGAAAUUUCGAAUCA
AGCAGAAGGGCGAAUAUCUUCCCCUGCUGCAAGGGAAAUCCUUGGGCA
UGAUUUUUGAGAAGAGGAGCACUAGGACUAGAUUGUCAACAGAAACAG
GCUUUGCUUUGUUGGGCGGACAUCCCUGCUUUCUGACGACACAGGAUA
UCCACCUCGGCGUAAACGAGUCCCUCACCGACACUGCUAGGGUACUGA
GCAGCAUGGCCGACGCUGUGCUAGCCCGGGUUUACAAGCAGUCAGACC
UGGACACCCUUGCCAAGGAAGCUUCUAUUCCAAUUAUCAACGGCCUGA
GUGACCUGUAUCACCCUAUUCAAAUACUCGCCGACUAUUUGACGCUUC
AAGAACAUUACAGCAGCCUCAAGGGCUUAACCUUGAGUUGGAUAGGCG
ACGGCAACAAUAUCCUGCAUUCCAUUAUGAUGUCUGCCGCUAAGUUUG
GCAUGCAUCUACAAGCCGCAACACCCAAGGGCUAUGAACCCGACGCUA
GCGUGACCAAGCUGGCCGAGCAGUAUGCUAAGGAAAAUGGCACAAAGC
UCCUUCUUACCAACGAUCCCCUGGAGGCUGCUCACGGCGGCAACGUGC
UGAUUACCGAUACAUGGAUUAGCAUGGGCCAGGAGGAGGAGAAAAAGA
AGCGGCUCCAGGCUUUUCAAGGCUAUCAGGUCACCAUGAAAACUGCAA
AGGUCGCUGCCUCCGACUGGACUUUCCUGCAUUGUCUACCCCGCAAGC
CUGAGGAAGUGGACGAUGAGGUGUUCUACUCCCCACGGAGUCUGGUGU
UCCCGGAAGCAGAGAAUCGGAAGUGGACCAUCAUGGCUGUCAUGGUGU
CGCUCUUGACUGACUAUUCUCCCCAACUGCAAAAACCCAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM575

(SEQ ID NO: 38)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGUUAUUCA
ACCUUCGUAUCCUGCUAAACAAUGCUGCUUUUCGCAAUGGCCAUAACU
UUAUGGUUCGCAACUUUAGAUGCGGCCAGCCGCUGCAGAACAAGGUUC
AGCUGAAGGGCCGGGACUUGCUGACGCUGAAAAACUUUACCGGGGAAG
AGAUUAAGUAUAUGCUGUGGCUAAGCGCUGAUCUGAAGUUUAGGAUCA
AGCAGAAGGGCGAAUAUCUGCCACUGCUGCAAGGGAAGAGUCUUGGCA
UGAUUUUUGAAAAGCGGUCUACCAGAACCCGGCUGUCGACCGAGACAG
GUUUUGCUCUGCUGGGGGGCCAUCCCUGUUUUCUGACAACUCAGGACA
UUCACCUGGGCGUGAAUGAGUCCCUGACCGAUACUGCUAGGGUGUUGA
GUAGCAUGGCCGACGCUGUACUCGCUCGAGUGUAUAAGCAGUCUGAUC
UGGACACUCUGGCUAAGGAAGCUUCCAUUCCUAUUAUCAACGGCUUGA
GCGACCUGUACCACCCCAUUCAAAUCCUCGCUGAUUACUUGACUUUGC
AAGAACAUUACAGCAGCUUGAAGGGCUUAACACUGAGCUGGAUAGGCG
ACGGAAACAACAUCUUGCAUUCCAUAAUGAUGUCCGCCGCUAAGUUCG
GGAUGCACCUCCAAGCAGCCACACCCAAGGGCUAUGAACCGGAUGCUU
CCGUGACAAAACUGGCUGAGCAGUAUGCUAAGGAGAAUGGCACGAAAC
UGCUGCUCACCAACGACCCAUUGGAAGCUGCACAUGGUGGCAACGUAC
UGAUCACUGACACUUGGAUCUCAAUGGGCCAGGAGGAAGAGAAGAAGA
AAAGGCUGCAGGCAUUUCAGGGAUACCAAGUCACUAUGAAAACUGCCA
AGGUCGCUGCCUCCGACUGGACAUUCCUGCAUUGUCUGCCACGGAAGC
CUGAGGAAGUCGAUGACGAAGUGUUCUAUAGCCCACGAAGCUUGGUGU
UUCCCGAGGCUGAGAAUAGGAAGUGGACCAUUAUGGCUGUUAUGGUGU
CCCUGCUCACCGACUAUUCCCCUCAACUGCAAAAACCCAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM708

(SEQ ID NO: 39)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGCUUUUUAAUC
UCCGCAUCCUCCUUAACAACGCCGCGUUUAGAAACGGCCACAACUUCA
UGGUCCGGAACUUCAGAUGUGGCCAGCCGCUUCAAAACAAGGUCCAGC
UGAAGGGCCGGGAUCUUCUGACCCUGAAGAACUUUACUGGCGAAGAGA
UCAAGUACAUGCUCUGGCUCUCCGCGGACUUGAAGUUCCGCAUUAAGC
AGAAGGGGGAAUACCUUCCGCUGCUUCAAGGAAAGAGCCUCGGCAUGA
UCUUUGAGAAGCGCUCAACCAGGACCCGCCUUUCUACUGAAACUGGGU

-continued

UCGCGCUGCUCGGUGGCCACCCCUGCUUCCUGACGACCCAGGACAUCC
ACCUCGGAGUGAACGAAUCCCUCACCGAUACCGCCCGGGUGUUAUCGA
GCAUGGCAGAUGCCGUGCUGGCCAGGGUGUACAAACAGUCCGAUCUGG
ACACUCUGGCCAAGGAGGCGUCAAUUCCCAUCAUCAACGGCCUGAGCG
ACCUGUACCACCCAAUCCAAAUCCUGGCUGACUACCUGACCCUGCAAG
AGCACUACAGCAGCCUGAAGGGUCUGACCCUGUCAUGGAUUGGCGAUG
GAAACAAUAUUCUGCACUCCAUCAUGAUGUCCGCCGCGAAGUUCGGAA
UGCAUCUGCAAGCCGCCACGCCAAAAGGAUACGAACCGGAUGCGUCCG
UGACGAAGUUGGCGGAACAGUACGCGAAGGAGAACGGAACCAAGCUUC
UGCUGACUAACGACCCCCUCGAGGCUGCGCAUGGGGGCAACGUGCUGA
UUACCGACACCUGGAUCUCCAUGGGGCAGGAGGAAGAGAAGAAGAAGA
GACUGCAGGCAUUCCAGGGGUACCAGGUCACCAUGAAAACCGCAAAAG
UGGCAGCUUCGGACUGGACUUUCCUGCAUUGCCUGCCGAGGAAGCCGG
AGGAAGUCGACGACGAAGUGUUCUACUCGCCUCGGUCCCUGGUGUUCC
CCGAGGCCGAAAACCGGAAGUGGACCAUCAUGGCCGUGAUGGUGUCCU
UGCUGACUGACUAUAGCCCGCAGCUGCAGAAGCCUAAGUUCUAGCUCG
AGCUAGUGACUGACUAGGAUCUGGUUACCACUAAACCAGCCUCAAGAA
CACCCGAAUGGAGUCUCUAAGCUACAUAAUACCAACUUACACUUACAA
AAUGUUGUCCCCCAAAAUGUAGCCAUUCGUAUCUGCUCCUAAUAAAAA
GAAAGUUUCUUCACAUUCUAG

>mARM709

(SEQ ID NO: 40)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGCUUUUCAACC
UGAGAAUCCUCUUGAACAAUGCUGCUUUUCGGAAUGGCCACAACUUUA
UGGUUCGGAACUUCCGUUGCGGCCAGCCUUUACAAAACAAGGUCCAGC
UGAAGGGCCGGGAUUUGCUCACACUGAAGAACUUUACUGGAGAAGAGA
UCAAGUACAUGCUGUGGCUGUCGGCCGACCUGAAGUUCAGGAUCAAGC
AGAAGGGAGAAUACCUUCCGCUGCUUCAAGGAAAGAGCCUCGGCAUGA
UCUUUGAGAAGCGCUCAACCAGGACCCGCCUUUCUACUGAAACUGGGU
UCGCGCUGCUCGGUGGCCACCCCUGCUUCCUGACGACCCAGGACAUCC
ACCUCGGAGUGAACGAAUCCCUCACCGAUACCGCCCGGGUGUUAUCGA
GCAUGGCAGAUGCCGUGCUGGCCAGGGUGUACAAACAGUCCGAUCUCG
AUACCUUGGCAAAGGAGGCUUCCAUUCCCAUCAUCAACGGCCUGAGCG
ACCUGUACCACCCAAUCCAAAUCCUGGCUGACUACCUGACCCUGCAAG
AGCACUACAGCAGCCUGAAGGGUCUGACCCUGUCAUGGAUUGGCGAUG
GAAACAAUAUUCUGCACUCCAUCAUGAUGUCCGCCGCGAAGUUCGGAA
UGCAUCUGCAAGCCGCCACUCCAAAAGGAUACGAACCGGAUGCGUCCG
UGACCAAGUUGGCGGAACAGUACGCGAAGGAGAACGGAACCAAGCUUC
UGCUGACUAACGACCCCCUCGAGGCUGCGCAUGGGGGCAACGUGCUGA
UUACCGACACCUGGAUCUCCAUGGGGCAGGAGGAAGAGAAGAAGAAGA

-continued

GACUGCAGGCAUUCCAGGGGUACCAGGUCACCAUGAAAACCGCAAAAG
UGGCAGCUUCGGACUGGACUUUCCUGCAUUGCCUGCCGAGGAAGCCGG
AGGAAGUCGACGACGAAGUGUUCUACUCGCCUCGGUCCCUGGUGUUCC
CCGAGGCCGAAAACCGGAAGUGGACCAUCAUGGCCGUGAUGGUGUCCU
UGCUGACUGACUAUAGCCCGCAGCUGCAGAAGCCUAAGUUCUAGCUCG
AGCUAGUGACUGACUAGGAUCUGGUUACCACUAAACCAGCCUCAAGAA
CACCCGAAUGGAGUCUCUAAGCUACAUAAUACCAACUUACACUUACAA
AAUGUUGUCCCCCAAAAUGUAGCCAUUCGUAUCUGCUCCUAAUAAAAA
GAAAGUUUCUUCACAUUCUAG

>mARM710

(SEQ ID NO: 41)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGCUUUUCAACC
UGAGAAUCCUCUUGAACAAUGCUGCUUUUCGGAAUGGCCACAACUUUA
UGGUUCGGAACUUCCGUUGCGGCCAGCCUUUACAAAACAAGGUCCAGC
UGAAGGGCCGGGAUUUGCUCACACUAAAGAACUUUACUGGAGAAGAGA
UCAAGUACAUGCUAUGGCUGUCGGCCGACCUGAAGUUCCGUAUCAAGC
AGAAGGGAGAAUACCUUCCGCUGCUUCAAGGAAAGAGCCUCGGCAUGA
UCUUUGAGAAGCGCUCAACCAGGACCCGCCUUUCUACUGAAACUGGGU
UCGCGCUGCUCGGUGGCCACCCCUGCUUCCUGACGACCCAGGACAUCC
ACCUCGGAGUGAACGAAUCCCUCACCGAUACCGCCCGGGUGUUAUCGA
GCAUGGCAGAUGCCGUGCUGGCCAGGGUGUACAAACAGUCCGAUCUCG
AUACCUUGGCAAAGGAGGCUUCCAUUCCCAUCAUCAACGGCCUGAGCG
ACCUGUACCACCCAAUCCAAAUCCUGGCUGACUACCUGACCCUGCAAG
AGCACUACAGCAGCCUGAAGGGUCUGACCCUGUCAUGGAUUGGCGAUG
GAAACAAUAUUCUGCACUCCAUCAUGAUGUCCGCCGCGAAGUUCGGAA
UGCAUCUGCAAGCCGCCACUCCAAAAGGAUACGAACCGGAUGCAUCCG
UGACCAAGUUGGCGGAACAGUACGCGAAGGAGAACGGAACCAAGCUCC
UGCUGACUAACGACCCGCUCGAGGCUGCGCAUGGGGGUAACGUGCUGA
UUACGGACACCUGGAUCUCCAUGGGGCAGGAGGAAGAGAAGAAGAAGA
GACUGCAGGCAUUCCAGGGGUACCAGGUCACCAUGAAAACCGCAAAAG
UGGCAGCUUCGGACUGGACUUUCCUGCAUUGCCUGCCGAGGAAGCCGG
AGGAAGUCGACGACGAAGUGUUCUACUCGCCUCGGUCCCUGGUGUUCC
CCGAGGCCGAAAACCGGAAGUGGACCAUCAUGGCCGUGAUGGUGUCCU
UGCUGACUGACUAUAGCCCGCAGCUGCAGAAGCCUAAGUUCUAGCUCG
AGCUAGUGACUGACUAGGAUCUGGUUACCACUAAACCAGCCUCAAGAA
CACCCGAAUGGAGUCUCUAAGCUACAUAAUACCAACUUACACUUACAA
AAUGUUGUCCCCCAAAAUGUAGCCAUUCGUAUCUGCUCCUAAUAAAAA
GAAAGUUUCUUCACAUUCUAG

-continued

>mARM711

(SEQ ID NO: 42)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGCUUUUCAACC
UGAGAAUCCUCUUGAACAAUGCUGCUUUUCGGAAUGGCCACAACUUUA
UGGUUCGGAACUUCCGUUGCGGCCAGCCUUUACAAAACAAGGUCCAGC
UGAAGGGCCGGGAUUUGCUCACACUAAAGAACUUUACUGGAGAAGAGA
UCAAGUACAUGCUAUGGCUGUCGGCCGACCUGAAGUUCCGUAUCAAGC
AGAAGGGAGAAUACCUUCCGCUGCUUCAAGGAAAGAGCCUCGGCAUGA
UCUUUGAGAAGCGCUCAACCAGGACCCGCCUUUCUACUGAAACUGGGU
UCGCGCUGCUCGGUGGCCACCCCUGCUUCCUGACGACCCAGGACAUCC
ACCUCGGAGUGAACGAAUCCCUCACCGAUACCGCCCGGGUGUUAUCGA
GCAUGGCAGAUGCCGUGCUGGCCAGGGUGUACAAACAGUCCGAUCUCG
AUACCUUGGCAAAGGAGGCUUCCAUUCCCAUCAUCAACGGCCUGAGCG
ACCUGUACCACCCAAUCCAAAUCCUGGCUGACUACCUGACCCUGCAAG
AGCACUACAGCAGCCUGAAGGGUCUGACCCUGUCAUGGAUUGGCGAUG
GAAACAAUAUUCUGCACUCCAUCAUGAUGUCCGCCGCGAAGUUCGGAA
UGCAUCUGCAAGCCGCCACUCCAAAAGGAUACGAACCGGAUGCGUCCG
UGACCAAGUUGGCGGAACAGUACGCGAAGGAGAACGGAACCAAGCUUC
UGCUGACUAACGACCCCCUCGAGGCUGCGCAUGGGGGCAACGUGCUGA
UUACCGACACCUGGAUCUCCAUGGGGCAGGAGGAAGAGAAGAAGAAGA
GACUGCAGGCAUUCCAGGGGUACCAGGUCACCAUGAAAACCGCAAAAG
UGGCAGCUUCGGACUGGACUUUCCUGCAUUGCCUGCCGAGGAAGCCGG
AGGAAGUCGACGACGAAGUGUUCUACUCGCCUCGGUCCCUGGUGUUCC
CCGAGGCCGAAAACCGGAAGUGGACCAUCAUGGCCGUGAUGGUGUCCU
UGCUGACUGACUAUAGCCCGCAGCUGCAGAAGCCUAAGUUCUAGCUCG
AGCUAGUGACUGACUAGGAUCUGGUUACCACUAAACCAGCCUCAAGAA
CACCCGAAUGGAGUCUCUAAGCUACAUAAUACCAACUUACACUUACAA
AAUGUUGUCCCCCAAAAUGUAGCCAUUCGUAUCUGCUCCUAAUAAAAA
GAAAGUUUCUUCACAUUCUAG

>mARM712

(SEQ ID NO: 43)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGCGAAUCCUGCUGAACAACGCCGCUUUUCGGAACGGGCACAACU
UUAUGGUGAGGAACUUUCGCUGCGGACAGCCCCUCCAGAAUAAGGUCC
AGCUGAAGGGCAGGGACCUGCUGACCCUGAAAAAUUUCACAGGGGAGG
AAAUCAAGUAUAUGCUGUGGCUGUCAGCUGAUCUGAAGUUCCGGAUCA
AGCAGAAGGGCGAAUAUCUGCCUCUGCUCCAGGGCAAAAGCCUGGGGA
UGAUCUUCGAAAAGCGCAGUACUCGGACCAGACUGUCAACCGAGACUG
GAUUCGCUCUGCUGGGAGGACACCCUUGUUUUCUGACCACUCAGGACA
UUCACCUGGGAGUGAACGAGUCCCUGACCGACACUGCUCGCGUCCUGA
GCUCUAUGGCCGACGCUGUGCUGGCUCGAGUCUACAAACAGUCCGACC
UGGAUACCCUGGCCAAGGAAGCUUCUAUCCCAAUUAUUAACGGCCUGU
CAGACCUGUAUCACCCCAUCCAGAUUCUGGCCGAUUACCUGACCCUCC
AGGAGCACUAUUCUAGUCUGAAAGGGCUGACACUGAGUUGGAUUGGGG
ACGGAAACAAUAUCCUGCACUCUAUUAUGAUGUCAGCCGCCAAGUUUG
GAAUGCACCUCCAGGCUGCAACCCCAAAAGGCUACGAACCCGAUGCCU
CAGUGACAAAGCUGGCUGAACAGUACGCCAAAGAGAACGGCACUAAGC
UGCUGCUGACCAACGACCCUCUGGAGGCCGCUCACGGAGGCAACGUGC
UGAUCACCGAUACCUGGAUUAGUAUGGGACAGGAGGAAGAGAAGAAGA
AGCGGCUCCAGGCCUUCCAGGGCUACCAGGUGACAAUGAAAACCGCUA
AGGUCGCAGCCAGCGAUUGGACCUUUCUGCACUGCCUGCCCAGAAAGC
CCGAAGAGGUGGACGACGAGGUCUUCUACUCUCCCAGAAGCCUGGUGU
UUCCCGAAGCUGAGAAUAGGAAGUGGACAAUUAUGGCAGUGAUGGUCA
GCCUGCUGACUGAUUAUUCACCUCAGCUCCAGAAACCAAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM713

(SEQ ID NO: 44)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGCGCAUCCUGCUGAACAACGCCGCCUUCCGCAACGGCCACAACU
UCAUGGUGCGCAACUUCCGCUGCGGCCAGCCCCUGCAGAACAAGGUGC
AGCUGAAGGGCCGCGACCUGCUGACCCUGAAGAACUUCACCGGCGAGG
AGAUCAAGUACAUGCUGUGGCUGAGCGCCGACCUGAAGUUCCGCAUCA
AGCAGAAGGGCGAGUACCUGCCCCUGCUGCAGGGCAAGAGCCUGGGCA
UGAUCUUCGAGAAGCGCAGCACCCGCACCCGCCUGAGCACCGAGACAG
GCCUGGCCCUGCUGGGCGGCCACCCCUGCUUCCUGACCACCCAGGACA
UCCACCUGGGCGUGAACGAGAGCCUGACCGACACCGCCCGCGUGCUGA
GCAGCAUGGCCGACGCCGUGCUGGCCCGCGUGUACAAGCAGAGCGACC
UGGACACCCUGGCCAAGGAGGCCAGCAUCCCCAUCAUCAACGGCCUGA
GCGACCUGUACCACCCCAUCCAGAUCCUGGCCGACUACCUGACCCUGC
AGGAGCACUACAGCAGCCUGAAGGGCCUGACCCUGAGCUGGAUCGGCG
ACGGCAACAACAUCCUGCACAGCAUCAUGAUGAGCGCCGCCAAGUUCG
GCAUGCACCUGCAGGCCGCCACCCCCAAGGGCUACGAGCCCGACGCCA
GCGUGACCAAGCUGGCCGAGCAGUACGCCAAGGAGAACGGCACCAAGC
UGCUGCUGACCAACGACCCCCUGGAGGCCGCCCACGGCGGCAACGUGC
UGAUCACCGACACCUGGAUCAGCAUGGGCCAGGAGGAGGAGAAGAAGA

-continued

AGCGCCUGCAGGCCUUCCAGGGCUACCAGGUGACCAUGAAGACCGCCA
AGGUGGCCGCCAGCGACUGGACCUUCCUGCACUGCCUGCCCCGCAAGC
CCGAGGAGGUGGACGACGAGGUGUUCUACAGCCCCCGCAGCCUGGUGU
UCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM714
(SEQ ID NO: 45)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGCGAAUCCUGCUGAACAACGCCGCUUUUCGGAACGGGCACAACU
UUAUGGUGAGGAACUUUCGCUGCGGACAGCCCCUCCAGAAUAAGGUCC
AGCUGAAGGGCAGGGACCUGCUGACCCUGAAAAAUUUCACAGGGGAGG
AAAUCAAGUAUAUGCUGUGGCUGUCAGCUGAUCUGAAGUUCCGGAUCA
AGCAGAAGGGCGAAUAUCUGCCUCUGCUCCAGGGCAAAAGCCUGGGGA
UGAUCUUCGAAAAGCGCAGUACUCGGACCAGACUGUCAACCGAGACUG
GAUUCGCUCUGCUGGGAGGACACCCUUGUUUUCUGACCACUCAGGACA
UUCACCUGGGAGUGAACGAGUCCCUGACCGACACUGCUCGCGUCCUGA
GCUCUAUGGCCGACGCUGUGCUAGCUCGAGUCUACAAACAGUCCGACC
UGGAUACCCUGGCCAAGGAAGCUUCUAUCCCAAUUAUUAACGGCCUGU
CAGACCUGUAUCACCCCAUCCAGAUUCUGGCCGAUUACCUGACCCUCC
AGGAGCACUAUUCUAGUCUGAAAGGGCUGACACUGAGUUGGAUUGGGG
ACGGAAACAAUAUCCUGCACUCUAUUAUGAUGUCAGCCGCCAAGUUUG
GAAUGCACCUCCAGGCUGCAACCCCAAAAGGCUACGAACCCGAUGCCU
CAGUGACAAAGCUGGCUGAACAGUACGCCAAAGAGAACGGCACUAAGC
UGCUGCUGACCAACGACCCUCUGGAGGCCGCUCACGGAGGCAACGUGC
UGAUCACCGAUACCUGGAUUAGUAUGGGACAGGAGGAAGAGAAGAAGA
AGCGGCUCCAGGCCUUCCAGGGCUACCAGGUGACAAUGAAAACCGCUA
AGGUCGCAGCCAGCGAUUGGACCUUUCUGCACUGCCUGCCCAGAAAGC
CCGAAGAGGUGGACGACGAGGUCUUCUACUCUCCCAGAAGCCUGGUGU
UUCCCGAAGCUGAGAAUAGGAAGUGGACAAUUAUGGCAGUGAUGGUCA
GCCUGCUGACUGAUUAUUCACCUCAGCUCCAGAAACCAAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

-continued

>mARM715
(SEQ ID NO: 46)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGCGAAUCCUGCUGAACAAUGCCGCUUUUCGGAACGGGCACAAUU
UCAUGGUGAGGAACUUUCGCUGCGGACAGCCCCUCCAGAACAAGGUCC
AGCUGAAGGGCAGGGACCUGCUGACCCUGAAAAAUUUCACAGGGGAGG
AAAUCAAGUACAUGCUGUGGCUGUCAGCCGAUCUGAAGUUCCGGAUCA
AGCAGAAGGGCGAAUAUCUGCCUCUGCUCCAGGGCAAAAGCCUGGGGA
UGAUCUUCGAAAAGCGCAGUACUCGGACCAGACUGUCAACAGAGACUG
GAUUCGCACUGCUGGGAGGACACCCAUGUUUUCUGACCACACAGGACA
UUCAUCUGGGAGUGAACGAGUCCCUGACCGACACAGCACGCGUCCUGA
GCUCCAUGGCUGAUGCAGUGCUGGCUCGAGUCUACAAACAGUCUGACC
UGGAUACCCUGGCCAAGGAAGCUUCUAUCCCAAUCAUUAAUGGCCUGA
GUGACCUGUAUCACCCCAUCCAGAUUCUGGCCGAUUACCUGACCCUCC
AGGAGCAUUAUUCUAGUCUGAAAGGGCUGACACUGAGCUGGAUUGGGG
ACGGAAACAAUAUCCUGCACUCCAUUAUGAUGAGCGCCGCCAAGUUUG
GAAUGCACCUCCAGGCUGCAACCCCAAAAGGCUACGAACCCGAUGCCU
CCGUGACAAAGCUGGCAGAACAGUAUGCCAAAGAGAACGGCACUAAGC
UGCUGCUGACCAAUGACCCUCUGGAGGCCGCUCACGGAGGCAACGUGC
UGAUCACUGAUACCUGGAUUAGUAUGGGACAGGAGGAAGAGAAGAAGA
AGCGGCUCCAGGCCUUCCAGGGCUACCAGGUGACAAUGAAAACUGCUA
AGGUCGCAGCCAGCGACUGGACCUUUCUGCAUUGCCUGCCCAGAAAGC
CUGAAGAGGUGGACGAUGAGGUCUUCUACUCACCCAGAAGCCUGGUGU
UUCCUGAAGCUGAGAAUAGGAAGUGGACAAUCAUGGCAGUGAUGGUCA
GCCUGCUGACUGAUUAUUCCCCUCAGCUCCAGAAACCAAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM716
(SEQ ID NO: 47)
UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACCUUCGCAUUCUCCUCAACAACGCCGCGUUUAGAAACGGACACAACU
UCAUGGUCCGCAACUUCCGCUGCGGACAGCCGCUGCAGAACAAGGUCC
AGCUCAAGGGUCGGGAUCUCCUGACGCUGAAGAACUUUACCGGCGAAG
AGAUUAAGUACAUGCUGUGGCUGUCCGCCGACCUUAAGUUCCGGAUCA
AGCAGAAGGGCGAAUACCUUCCCCUGCUGCAAGGAAAGUCCCUGGGCA
UGAUCUUCGAGAAGCGCAGUACCAGAACCAGACUCUCCACUGAAACCG

-continued

GGUUCGCGCUGCUUGGCGGCCACCCGUGUUUCCUCACUACGCAAGACA
UCCAUCUUGGCGUGAACGAGUCCCUUACCGACACCGCCAGGGUGCUGU
CAAGCAUGGCCGACGCCGUCCUUGCGCGCGUGUACAAGCAGUCAGACC
UUGAUACUCUGGCCAAGGAAGCCUCCAUCCCUAUUAUCAACGGCCUAU
CCGACCUUUACCACCCGAUCCAGAUCCUCGCUGACUACCUGACCCUGC
AAGAACACUACAGCAGCCUCAAGGGACUGACUCUGUCCUGGAUCGGCG
ACGGGAACAACAUCCUGCACUCAAUCAUGAUGAGCGCAGCCAAGUUCG
GCAUGCAUCUCCAAGCCGCUACACCCAAGGGUUAUGAACCGGACGCCU
CUGUGACCAAGUUGGCAGAACAGUACGCCAAGGAGAACGGUACUAAGC
UCCUUUUAACCAACGACCCCCUCGAAGCAGCCCAUGGCGGGAAUGUGC
UCAUUACCGAUACCUGGAUUUCGAUGGGCCAGGAGGAGGAGAAGAAGA
AGCGGCUGCAGGCGUUCCAGGGCUACCAGGUCACCAUGAAAACUGCCA
AAGUGGCCGCCUCGGAUUGGACCUUUCUCCACUGCCUGCCUCGGAAGC
CUGAGGAGGUGGACGACGAAGUGUUCUACUCCCCACGGUCCCUCGUGU
UCCCCGAGGCCGAAAAUAGGAAGUGGACCAUCAUGGCCGUGAUGGUGU
CCCUCUUGACCGAUUACAGCCCGCAGCUUCAGAAGCCUAAAUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM717

(SEQ ID NO: 48)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUUCGCAUCCUGUUGAACAACGCCGCCUUCCGCAAUGGUCACAACU
UCAUGGUCCGGAACUUCAGAUGUGGACAGCCUCUCCAAAACAAGGUCC
AGCUGAAGGGAAGGGACCUCUUAACCCUCAAAAACUUUACUGGAGAGG
AGAUCAAGUACAUGCUGUGGCUUAGCGCCGACCUUAAGUUCCGGAUCA
AGCAGAAGGGAGAGUACCUCCCGCUGCUGCAAGGAAAGAGUCUUGGAA
UGAUCUUCGAGAAGCGGUCCACCAGAACUCGCCUCUCCACUGAAACCG
GAUUCGCACUCCUGGGUGGACACCCGUGCUUUCUGACCACCCAAGACA
UCCACCUCGGAGUGAACGAGAGCCUCACGGACACCGCGAGAGUGCUGU
CAUCCAUGGCCGACGCCGUGCUUGCACGGGUCUACAAGCAGUCCGAUC
UGGACACUCUUGCCAAGGAAGCCUCCAUUCCUAUCAUUAACGGUCUGU
CGGAUCUGUACCACCCGAUUCAGAUCCUUGCGGACUACCUCACACUUC
AAGAACACUAUUCAAGCCUAAAGGGUCUGACCCUGUCCUGGAUCGGAG
AUGGAAACAACAUUCUCCAUUCCAUCAUGAUGAGCGCUGCCAAGUUCG
GAAUGCAUCUCCAAGCAGCGACUCCUAAGGGUUACGAGCCGGACGCCU
CAGUGACUAAGCUGGCCGAGCAGUACGCCAAGGAGAACGGUACCAAAC
UGUUGCUUACUAACGACCCGCUUGAAGCGGCCCAUGGAGGAAACGUGC
UGAUUACCGACACCUGGAUUUCGAUGGGACAGGAAGAGGAGAAGAAGA

-continued

AGCGGCUCCAGGCGUUCCAGGGAUACCAGGUCACCAUGAAAACGGCCA
AAGUGGCCGCUAGCGAUUGGACCUUUCUGCACUGCCUCCCGCGCAAGC
CUGAAGAAGUGGACGACGAAGUGUUCUACUCCCCUCGCUCUCUUGUGU
UCCCGGAAGCCGAAAACAGGAAGUGGACCAUCAUGGCCGUGAUGGUGU
CCCUCCUGACCGAUUACAGCCCGCAGCUGCAGAAGCCUAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM718

(SEQ ID NO: 49)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUCAACAACGCCGCGUUUAGAAACGGCCACAACU
UCAUGGUCCGGAACUUCAGAUGUGGCCAGCCGCUUCAGAACAAGGUCC
AGCUCAAGGGCCGGGAUCUUCUGACCCUGAAGAACUUUACUGGCGAAG
AAAUCAAGUACAUGCUCUGGCUCUCCGCCGACUUGAAGUUCCGCAUUA
AGCAGAAGGGGGAAUACCUUCCGCUGCUGCAAGGAAAGUCGCUCGGCA
UGAUCUUUGAGAAGCGCUCAACCCGCACCAGGCUGUCCACUGAAACCG
GGUUCGCGCUGCUUGGUGGCCACCCCUGCUUCCUGACCACCCAAGACA
UUCACCUCGGAGUGAACGAAUCGCUCACUGAUACUGCCCGGGUGCUGU
CGUCGAUGGCCGAUGCAGUGCUGGCCAGGGUGUACAAACAGUCCGAUC
UGGACACUCUGGCCAAGGAGGCGUCCAUCCCUAUUAUCAACGGCCUUU
CCGACCUCUACCACCCGAUUCAGAUCCUUGCCGAUUACCUCACCCUGC
AAGAACACUACUCGUCACUGAAGGGUCUGACCUUGUCCUGGAUCGGCG
ACGGCAACAACAUCCUCCAUUCCAUUAUGAUGUCCGCCGCCAAAUUCG
GCAUGCAUCUUCAAGCCGCAACCCCUAAGGGUUACGAGCCGGACGCUU
CCGUGACCAAGCUCGCCGAGCAGUACGCUAAGGAGAACGGAACCAAGC
UUCUGCUGACUAACGACCCCCUAGAGGCAGCCCACGGGGGCAACGUGC
UUAUUACUGACACCUGGAUCUCCAUGGGACAGGAAGAAGAGAAGAAGA
AGCGGUUACAGGCGUUCCAGGGCUAUCAGGUCACCAUGAAAACCGCCA
AGGUCGCUGCCUCGGACUGGACCUUCCUGCAUUGCCUGCCUCGCAAGC
CCGAAGAAGUGGACGACGAGGUGUUCUACUCGCCACGGUCCCUUGUGU
UCCCUGAGGCCGAGAAUAGAAAGUGGACCAUUAUGGCCGUGAUGGUGU
CCCUUCUCACCGACUACUCGCCGCAACUGCAGAAACCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

-continued

>mARM719

(SEQ ID NO: 50)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUUCGCAUCCUCCUCAACAACGCCGCCUUCCGGAACGGUCACAACU
UCAUGGUCCGGAACUUCCGCUGCGGCCAGCCGCUCCAAAACAAAGUGC
AGCUUAAGGGCCGCGAUCUCCUGACCCUGAAGAACUUCACCGGAGAGG
AAAUCAAGUACAUGCUGUGGCUCUCGGCGGACCUGAAGUUUAGGAUUA
AGCAGAAGGGGGAGUAUCUGCCGCUGCUCCAAGGGAAGUCCCUUGGCA
UGAUCUUCGAAAAGAGGUCCACCCGGACUCGGCUCAGCACCGAAACAG
GUUUUGCACUUCUGGGGGGCCACCCGUGCUUCCUGACGACCCAGGACA
UCCAUCUGGGUGUCAACGAGAGUUUGACCGACACUGCCAGAGUGCUGU
CAUCCAUGGCGGACGCGGUGCUCGCGAGAGUGUACAAGCAGUCCGAUC
UUGACACCCUGGCAAAAGAGGCUUCAAUCCCGAUCAUUAACGGACUCU
CGGAUCUGUACCACCCUAUCCAAAUCUUGGCCGACUACCUGACCCUGC
AAGAACACUACAGCUCCCUGAAGGGCCUGACUCUUUCCUGGAUUGGCG
AUGGAAACAACAUUCUCCAUUCUAUUAUGAUGUCCGCCGCCAAGUUCG
GCAUGCACCUUCAAGCCGCCACCCCGAAGGGCUACGAACCUGACGCCU
CCGUGACUAAGCUAGCCGAACAGUACGCUAAGGAGAACGGCACUAAGC
UUCUCCUUACCAACGAUCCGCUGGAGGCGGCCCAUGGCGGAAAUGUGC
UUAUCACCGACACCUGGAUUAGCAUGGGGCAGGAAGAAGAGAAGAAGA
AACGGCUCCAGGCAUUCCAGGGCUACCAGGUCACCAUGAAAACUGCCA
AGGUCGCCGCUAGCGACUGGACCUUCCUCCACUGUCUGCCUCGCAAGC
CUGAAGAAGUGGACGACGAGGUGUUCUACUCCCCGCGCUCCCUCGUGU
UUCCUGAGGCCGAGAACAGAAAGUGGACCAUCAUGGCCGUGAUGGUGU
CAUUACUUACGGACUACAGCCCGCAGCUGCAGAAGCCGAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM720

(SEQ ID NO: 51)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUUA
ACUUGAGAAUCCUUCUGAACAACGCCGCUUUCCGCAACGGUCAUAACU
UCAUGGUCCGGAACUUCAGAUGUGGCCAGCCCCUCCAAAACAAAGUGC
AGCUGAAGGGCCGGGACCUUCUUACGCUGAAGAAUUUCACCGGCGAAG
AAAUCAAGUACAUGCUCUGGCUGUCCGCCGAUCUUAAGUUCCGCAUUA
AGCAGAAGGGGGAAUACCUCCCGCUGCUGCAAGGGAAGUCGCUGGGCA
UGAUUUUUGAGAAGCGGUCAACUCGCACCCGCCUGUCCACUGAAACUG
GAUUCGCACUGCUCGGUGGCCAUCCCUGCUUCCUGACCACCCAAGACA
UCCACCUCGGCGUGAACGAGUCCCUGACUGACACCGCCCGGGUCUUAU
CCUCGAUGGCCGAUGCUGUGCUUGCGAGGGUGUACAAGCAGUCCGACC
UCGACACACUCGCGAAGGAGGCCUCCAUCCCCAUCAUCAACGGCCUGU
CCGACCUUUACCACCCAAUUCAGAUCCUCGCCGAUUACCUGACCCUGC
AAGAGCACUACUCGUCGCUCAAGGGGCUUACCCUCUCGUGGAUUGGCG
ACGGCAACAACAUCCUUCACUCCAUCAUGAUGUCGGCAGCGAAGUUCG
GCAUGCAUCUGCAAGCCGCCACGCCUAAGGGUUAUGAACCGGAUGCCU
CAGUGACCAAGCUCGCCGAACAGUACGCGAAAGAGAAUGGAACCAAGC
UACUUCUGACCAACGACCCCCUGGAGGCCGCUCACGGCGGCAACGUCC
UCAUUACCGAUACUUGGAUUUCGAUGGGACAGGAAGAGGAAAAGAAGA
AGAGACUGCAGGCGUUCCAGGGAUACCAGGUCACCAUGAAAACUGCCA
AAGUGGCAGCCUCCGACUGGACCUUCCUUCACUGCCUGCCGAGGAAGC
CUGAAGAGGUGGACGACGAGGUGUUCUACUCCCCGCGCUCCUUGGUGU
UUCCUGAGGCCGAAAACCGGAAGUGGACUAUCAUGGCCGUGAUGGUGU
CCCUCCUCACCGACUACUCGCCGCAACUGCAGAAGCCUAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM721

(SEQ ID NO: 52)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGUUAUUCA
ACCUUAGAAUUCUCCUUAACAACGCCGCCUUCCGGAAUGGGCAUAACU
UUAUGGUCCGCAAUUUCCGCUGUGGACAGCCUCUGCAAAACAAGGUCC
AGCUCAAGGGCCGGGAUCUGCUGACUCUCAAGAACUUCACUGGGGAAG
AAAUCAAGUACAUGCUCUGGCUGAGCGCCGACCUCAAGUUCCGCAUCA
AGCAGAAGGGAGAGUACCUCCCGCUGCUCCAAGGGAAGUCCCUGGGCA
UGAUCUUCGAGAAGAGAUCCACCCGCACCAGACUUUCCACUGAGACUG
GCUUCGCCUUGCUGGGAGGCCACCCAUGCUUCCUGACGACCCAGGACA
UUCACCUUGGCGUGAACGAGUCCCUGACUGACACCGCAAGGGUGUUGU
CCUCGAUGGCCGACGCCGUGCUUGCCCGGGUGUACAAGCAGAGCGAUC
UUGACACCCUGGCUAAGGAAGCUUCCAUUCCCAUCAUCAACGGUCUGA
GCGACCUGUACCACCCGAUUCAGAUCCUGGCGGACUACCUAACCCUGC
AAGAGCACUAUAGCUCCCUGAAGGGCCUCACACUUUCAUGGAUCGGCG
ACGGCAACAACAUCCUGCACUCUAUUAUGAUGAGCGCUGCCAAAUUCG
GCAUGCACCUCCAAGCCGCCACGCCUAAAGGCUACGAGCCCGACGCCU
CGGUGACCAAGCUUGCGGAGCAGUACGCGAAGGAAAACGGCACCAAGC
UGCUUCUCACCAACGAUCCUCUGGAAGCGGCCCAUGGUGGCAACGUGC
UCAUUACCGACACUUGGAUCUCCAUGGGACAGGAGGAGGAAAAGAAGA

AGCGGCUCCAGGCGUUUCAGGGUUACCAGGUCACCAUGAAAACCGCCA
AGGUCGCAGCCUCCGACUGGACCUUCCUUCAUUGCCUUCCGCGCAAGC
CCGAAGAAGUGGACGAUGAAGUGUUUUACUCACCUCGGUCACUCGUGU
UCCCGGAAGCAGAGAACAGGAAAUGGACCAUUAUGGCCGUGAUGGUGU
CCCUGCUCACCGAUUACAGUCCGCAACUGCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM722

(SEQ ID NO: 53)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAAAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCUAAGGGUUACGAACCCGACGCUU
CCGUGACUAAGCUCGCCGAGCAGUACGCUAAGGAGAACGGAACCAAGC
UGCUGCUGACUAACGACCCGCUAGAAGCAGCCCACGGGGGCAACGUGC
UUAUUACUGACACCUGGAUCUCCAUGGGCCAGGAGGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUUCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM723

(SEQ ID NO: 54)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUUAAGGGCCGGGAUCUCCUCACCCUUAAAAACUUCACCGGCGAAG
AGAUCAAGUACAUGCUCUGGCUCUCCGCGGACCUUAAGUUCCGCAUUA
AGCAGAAGGGGGAAUACCUUCCGCUGCUUCAAGGAAAGAGCCUCGGCA
UGAUCUUUGAGAAGCGCUCAACCAGGACCAGGCUUUCUACUGAAACUG
GGUUCGCGCUUCUCGGCGGUCAUCCCUGCUUCCUCACGACCCAAGACA
UCCACCUCGGAGUGAACGAAUCCCUCACGGAUACUGCCCGCGUGCUUU
CGAGCAUGGCAGACGCCGUGCUCGCCCGGGUGUACAAACAGUCCGAUC
UCGACACUCUCGCCAAGGAGGCGUCAAUUCCUAUUAUCAACGGUCUUA
GUGACCUUUACCACCCGAUCCAGAUCCUCGCCGAUUACCUCACACUCC
AAGAACACUACAGCUCCCUUAAGGGUCUUACCCUCUCCUGGAUCGGCG
ACGGCAACAACAUUCUCCACUCCAUCAUGAUGUCCGCCGCAAAGUUCG
GCAUGCAUCUUCAAGCCGCCACCCCGAAGGGCUACGAGCCUGAUGCUU
CCGUGACUAAGCUCGCCGAGCAGUACGCUAAGGAGAACGGAACCAAGC
UUCUUCUCACUAACGACCCACUCGAAGCAGCCCAUGGGGGCAACGUGC
UUAUCACUGACACCUGGAUCUCCAUGGGCCAGGAAGAAGAGAAGAAGA
AGCGGCUCCAGGCGUUCCAGGGAUAUCAGGUCACCAUGAAAACCGCCA
AGGUCGCUGCCUCCGACUGGACCUUUCUCCACUGCCUCCCUCGCAAAC
CUGAAGAAGUGGACGACGAGGUGUUCUACUCGCCCCGGAGCCUCGUGU
UCCCCGAGGCCGAGAAUAGAAAGUGGACCAUUAUGGCCGUGAUGGUGU
CACUCCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM724

(SEQ ID NO: 55)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGACAUAACU
UCAUGGUCCGGAACUUCAGAUGUGGACAGCCGCUUCAAAACAAGGUCC
AGCUGAAGGGUCGGGAUCUUCUGACCCUGAAGAACUUUACCGGAGAAG
AGAUCAAGUACAUGCUCUGGCUCUCCGCGGACUUGAAGUUCCGCAUUA
AGCAGAAGGGAGAAUACCUCCCGCUGCUUCAAGGAAAGAGCCUCGGAA
UGAUUUUUGAGAAGCGCUCAACCAGGACCCGCCUUUCUACUGAAACUG

-continued

GAUUCGCGCUGCUGGGUGGACACCCCUGCUUCCUGACGACCCAGGACA

UCCACCUCGGAGUGAACGAAUCCCUCACUGAUACCGCCCGGGUGUUAU

CGAGCAUGGCAGAUGCCGUGCUGGCCAGGGUGUACAAACAGUCCGAUC

UGGACACUCUGGCCAAGGAGGCGUCAAUUCCUAUCAUCAACGGACUUA

GUGACCUCUACCAUCCGAUUCAAAUCCUGGCCGACUACCUCACCCUGC

AAGAACACUACAGCUCCCUGAAGGGUCUGACAUUGUCCUGGAUCGGAG

AUGGAAACAACAUUCUCCACUCCAUCAUGAUGUCCGCCGCAAAAUUCG

GAAUGCAUCUUCAAGCCGCCACGCCUAAGGGUUACGAACCCGACGCUU

CCGUGACUAAGCUCGCCGAGCAGUACGCUAAGGAGAACGGUACCAAGC

UUCUCCUGACCAACGACCCACUAGAAGCAGCCCACGGUGGAAACGUGC

UUAUUACUGACACUUGGAUCUCCAUGGGACAGGAGGAAGAGAAAAAGA

AGCGGCUGCAGGCGUUCCAGGGAUAUCAGGUCACCAUGAAAACCGCCA

AGGUCGCUGCCUCCGACUGGACCUUCCUGCACUGCCUGCCUCGCAAGC

CUGAAGAAGUGGACGACGAGGUGUUCUACUCGCCGCGGAGCCUCGUGU

UCCCCGAGGCCGAGAAUAGAAAGUGGACCAUCAUGGCCGUGAUGGUGU

CACUGCUCACCGACUACAGCCCGCAGCUUCAGAAGCCCAAGUUCUAGC

UCGAGCUAGUGACUGACUAGGAUCUGGUUACCACUAAACCAGCCUCAA

GAACACCCGAAUGGAGUCUCUAAGCUACAUAAUACCAACUUACACUUA

CAAAAUGUUGUCCCCCAAAAUGUAGCCAUUCGUAUCUGCUCCUAAUAA

AAAGAAAGUUUCUUCACAUUCUAG

>mARM725

(SEQ ID NO: 56)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCACCAUGCUUUUCA

ACCUCCGCAUUCUCCUCAACAACGCUGCCUUCCGGAAUGGACAUAACU

UCAUGGUCCGGAACUUCAGAUGCGGACAGCCGCUUCAGAACAAGGUCC

AGCUUAAGGGGAGAGAUCUCCUUACCCUCAAAAACUUCACUGGCGAAG

AAAUCAAGUACAUGCUCUGGCUUAGUGCGGAUCUCAAGUUCCGCAUCA

AGCAGAAGGGAGAAUACCUCCCGCUCCUUCAAGGAAAGAGCCUCGGCA

UGAUUUUUGAGAAGAGGUCCACCAGAACUCGCCUUUCAACCGAGACUG

GGUUCGCCCUGCUUGGCGGUCACCCCUGCUUCCUCACUACCCAAGACA

UCCACCUCGGCGUGAACGAGAGCCUUACCGACACCGCCCGCGUGCUCU

CCUCAAUGGCCGACGCUGUGCUCGCCCGGGUGUACAAGCAGUCCGACC

UUGAUACUCUCGCCAAGGAGGCCUCCAUCCCAAUUAUCAACGGGCUCU

CUGAUCUCUACCACCCUAUCCAAAUCCUCGCGGACUACCUCACCCUCC

AAGAGCACUAUAGCUCGCUCAAGGGCCUCACCCUUUCCUGGAUUGGCG

ACGGCAACAACAUUCUUCACUCGAUCAUGAUGUCCGCCGCCAAGUUCG

GCAUGCAUCUCCAAGCCGCGACCCCCAAGGGCUACGAGCCUGACGCAU

CCGUGACCAAGCUCGCCGAGCAGUACGCGAAGGAAAAUGGCACCAAGC

UUCUUCUCACCAACGACCCCCUUGAGGCCGCUCAUGGCGGCAACGUGC

UCAUCACUGACACUUGGAUCAGCAUGGGCCAGGAGGAGGAAAAGAAGA

-continued

AGCGCCUUCAGGCAUUCCAGGGUUACCAGGUCACCAUGAAAACCGCCA

AAGUGGCCGCCUCCGACUGGACCUUUCUUCACUGUCUCCCGCGGAAGC

CUGAAGAAGUGGAUGACGAAGUGUUUUACUCCCCUCGGUCACUCGUGU

UCCCGGAAGCAGAAAACAGGAAGUGGACCAUUAUGGCGGUCAUGGUGU

CCCUCCUCACCGACUACAGCCCGCAGCUUCAGAAACCCAAGUUCUAGC

UCGAGCUAGUGACUGACUAGGAUCUGGUUACCACUAAACCAGCCUCAA

GAACACCCGAAUGGAGUCUCUAAGCUACAUAAUACCAACUUACACUUA

CAAAAUGUUGUCCCCCAAAAUGUAGCCAUUCGUAUCUGCUCCUAAUAA

AAAGAAAGUUUCUUCACAUUCUAG

>mARM726

(SEQ ID NO: 57)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCACCAUGCUUUUCA

AUCUCCGCAUCCUCCUUAACAACGCAGCGUUUAGAAACGGUCACAACU

UCAUGGUCCGGAACUUCCGCUGUGGACAGCCGCUUCAAAACAAGGUCC

AGCUGAAGGGUCGGGACCUUCUGACCCUGAAGAACUUUACUGGAGAAG

AGAUCAAGUACAUGCUUUGGCUGUCCGCGGACUUGAAGUUCCGCAUUA

AGCAGAAGGGAGAAUACCUUCCGCUGCUCCAAGGAAAGAGCCUGGGAA

UGAUCUUUGAGAAGCGCUCAACCAGGACCCGCCUUUCUACUGAAACUG

GAUUCGCGCUGCUGGGUGGUCACCCUUGCUUCCUGACGACCCAGGACA

UUCACCUCGGAGUGAACGAGUCCCUCACUGAUACCGCCAGAGUGUUAU

CGAGCAUGGCAGAUGCCGUGCUGGCUAGGGUGUACAAACAGUCCGAUC

UGGACACCCUGGCCAAGGAGGCAUCAAUUCCUAUUAUCAACGGACUUA

GUGACCUCUACCAUCCGAUUCAAAUCCUGGCCGAUUACCUCACCCUGC

AAGAACACUACAGCUCCCUGAAGGGUCUGACAUUGUCCUGGAUCGGAG

AUGGAAACAACAUUCUCCAUUCCAUCAUGAUGUCCGCGGCCAAGUUCG

GAAUGCAUCUCCAAGCCGCCACGCCGAAAGGAUACGAGCCGGACGCUU

CCGUGACUAAGCUCGCCGAGCAGUACGCUAAGGAGAACGGAACCAAGC

UUCUGCUGACUAACGACCCGCUAGAAGCCGCCCACGGUGGAAACGUGC

UUAUUACUGACACCUGGAUCUCCAUGGGACAGGAAGAAGAGAAAAAGA

AGCGGCUGCAGGCGUUCCAGGGAUAUCAGGUCACCAUGAAAACCGCCA

AGGUCGCCGCCUCCGACUGGACCUUCCUUCACUGCCUGCCUCGGAAGC

CUGAAGAAGUGGACGACGAGGUGUUCUACUCGCCGCGGAGCCUCGUGU

UCCCUGAGGCCGAGAAUAGAAAGUGGACCAUCAUGGCCGUGAUGGUGU

CACUCCUCACCGACUACAGCCCGCAGCUUCAGAAGCCUAAGUUCUAGC

UCGAGCUAGUGACUGACUAGGAUCUGGUUACCACUAAACCAGCCUCAA

GAACACCCGAAUGGAGUCUCUAAGCUACAUAAUACCAACUUACACUUA

CAAAAUGUUGUCCCCCAAAAUGUAGCCAUUCGUAUCUGCUCCUAAUAA

AAAGAAAGUUUCUUCACAUUCUAG

-continued

>mARM727

(SEQ ID NO: 58)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUUCUCCUCAACAACGCAGCCUUUAGAAACGGCCACAACU
UCAUGGUCCGGAACUUCAGAUGUGGCCAGCCGCUUCAGAACAAGGUCC
AGCUCAAGGGCCGGGACCUCCUCACCCUCAAAAACUUUACCGGCGAAG
AGAUCAAGUACAUGCUCUGGCUUUCGGCCGACCUUAAGUUCCGCAUCA
AGCAGAAGGGGGAAUACCUUCCGCUGCUUCAAGGAAAGUCCCUCGGCA
UGAUCUUUGAAAAGCGCUCGACCAGGACCCGCCUUUCCACUGAAACCG
GGUUCGCGCUUCUCGGUGGCCACCCCUGCUUCCUCACCACCCAAGACA
UUCACCUCGGAGUGAACGAAUCCCUUACCGAUACCGCAAGAGUGCUUU
CGUCGAUGGCCGAUGCCGUGCUUGCGCGGGUGUACAAGCAGUCAGAUC
UCGACACUCUCGCCAAGGAGGCGUCCAUUCCUAUUAUCAACGGCCUUU
CCGACCUUUACCACCCGAUUCAGAUCCUCGCCGAUUACCUCACCCUGC
AAGAGCACUACUCGUCACUCAAGGGUCUUACCCUCUCCUGGAUCGGCG
ACGGAAACAACAUCCUCCAUUCGAUCAUGAUGUCCGCCGCCAAAUUCG
GCAUGCACCUCCAAGCCGCGACCCCGAAGGGUUACGAGCCCGACGCUU
CCGUGACCAAGCUCGCCGAACAGUACGCUAAGGAAAACGGCACCAAGC
UCCUCCUCACUAACGACCCUCUCGAAGCAGCCCAUGGGGGCAACGUGC
UCAUUACUGACACUUGGAUCUCGAUGGGCCAGGAAGAGGAGAAAAAGA
AGCGGCUUCAGGCGUUCCAGGGAUAUCAGGUCACCAUGAAAACCGCCA
AGGUCGCUGCCUCGGACUGGACCUUCCUUCACUGCCUUCCGCGCAAGC
CUGAAGAGGUGGACGAUGAGGUGUUCUACUCCCCACGGUCCCUUGUGU
UCCCCGAGGCCGAGAAUAGGAAGUGGACCAUCAUGGCCGUGAUGGUGU
CGCUCCUCACUGACUACUCCCCGCAACUUCAGAAGCCUAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM728

(SEQ ID NO: 59)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUUA
AUCUGAGAAUACUUCUAAACAACGCCGCCUUCCGGAAUGGCCAUAACU
UUAUGGUUCGGAAUUUCCGCUGCGGCCAGCCGCUGCAGAACAAGGUCC
AGCUGAAGGGAAGAGACUUGCUGACCCUCAAGAACUUCACCGGAGAAG
AAAUCAAGUAUAUGCUGUGGCUGUCCGCCGACCUGAAAUUCCGCAUCA
AGCAGAAGGGCGAAUAUCUGCCGCUGUUGCAAGGGAAGUCCCUGGGGA
UGAUCUUCGAGAAGAGGUCCACCAGAACACGGCUUUCAACCGAAACCG
GGUUUGCACUGCUGGGUGGACACCCCUGUUUUCUGACCACUCAAGAUA
UCCACCUGGGCGUGAACGAGUCCCUUACCGACACUGCUAGGGUGUUGU
CCAGCAUGGCCGAUGCCGUCCUGGCUCGCGUGUACAAGCAGUCCGACC
UGGAUACCCUGGCAAAGGAAGCGUCCAUUCCCAUUAUCAACGGGCUGU
CCGACCUGUACCAUCCGAUUCAAAUCCUGGCGGACUACCUGACUCUGC
AAGAGCAUUACAGCAGCUUGAAGGGGCUUACUCUCUCGUGGAUCGGCG
ACGGGAACAACAUCCUGCACUCCAUCAUGAUGUCCGCCGCCAAGUUCG
GGAUGCAUUUGCAAGCUGCGACCCCGAAAGGUUACGAGCCCGAUGCUA
GCGUAACUAAGCUUGCCGAACAGUACGCCAAAGAGAAUGGUACAAAAC
UGCUUCUGACUAACGACCCGCUGGAAGCAGCCCACGGCGGGAACGUGC
UGAUAACCGACACCUGGAUUUCAAUGGGGCAGGAGGAAGAGAAGAAGA
AGCGACUGCAGGCGUUCCAAGGCUAUCAGGUUACCAUGAAAACCGCCA
AAGUGGCAGCCAGCGAUUGGACUUUCCUGCACUGUCUGCCGCGGAAGC
CCGAGGAAGUUGAUGACGAAGUAUUCUACUCACCCCGGAGCCUCGUGU
UCCCCGAGGCCGAAAACCGGAAGUGGACUAUUAUGGCCGUGAUGGUGU
CGCUGUUGACCGACUACAGCCCGCAACUGCAGAAGCCGAAGUUUUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM729

(SEQ ID NO: 60)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACCUGAGGAUCCUUUUGAACAACGCCGCCUUUCGCAACGGCCACAACU
UUAUGGUCCGCAAUUUCCGCUGCGGGCAGCCGCUGCAGAACAAGGUCC
AGCUGAAGGGCCGGGAUCUGCUGACCCUGAAGAACUUCACCGGGGAGG
AAAUCAAGUACAUGCUUUGGCUCUCCGCCGAUCUGAAGUUCAGAAUCA
AGCAGAAGGGAGAGUACCUCCCGUUGCUGCAAGGAAAGUCACUCGGAA
UGAUUUUCGAAAAGAGAAGCACUAGGACCCGCCUCUCAACUGAAACCG
GGUUCGCGCUGCUCGGGGGCCAUCCGUGUUUCCUGACUACCCAAGACA
UCCACCUGGGAGUGAACGAGUCGCUGACCGACACCGCACGCGUGCUGU
CAUCCAUGGCGGACGCAGUGCUUGCCCGGGUGUACAAGCAGUCGGACC
UGGACACUCUUGCCAAGGAGGCAUCAAUCCCCAUCAUUAACGGACUGU
CCGAUCUCUACCACCCGAUUCAGAUCCUGGCUGACUACCUAACCCUGC
AAGAGCACUACUCAAGCCUGAAGGGGCUGACCCUGUCGUGGAUCGGGG
ACGGCAACAACAUUCUGCACUCCAUCAUGAUGUCGGCGGCUAAGUUCG
GGAUGCAUUUGCAAGCGGCAACUCCGAAGGGUUAUGAACCCGACGCCU
CCGUGACCAAGCUGGCCGAACAGUACGCCAAGGAAAACGGAACCAAGU
UGCUGCUGACUAAUGAUCCCCUGGAGGCGGCCCACGGGGGGAACGUGC
UGAUAACCGAUACCUGGAUCUCCAUGGGGCAGGAAGAAGAGAAGAAAA

-continued

AGCGGCUGCAGGCAUUCCAGGGAUACCAGGUCACCAUGAAAACCGCAA
AAGUGGCAGCCAGCGACUGGACUUUCCUCCAUUGCCUGCCGCGAAAGC
CGGAGGAGGUCGAUGACGAGGUGUUCUACUCCCCGCGGUCGCUGGUGU
UCCCGGAGGCGGAAAACCGGAAGUGGACCAUUAUGGCCGUGAUGGUGU
CACUCCUGACUGACUACAGCCCGCAACUGCAGAAGCCGAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1787

(SEQ ID NO: 61)

CUUAAGGGGGCGCUGCCUACGGAGGUGGCAGCCAUCUCCUUCUCGGCA
UCAAGCUUACCAUGGUGCCCCAGGCCCUGCUCUUGGUCCCGCUGCUGG
UGUUCCCCCUCUGCUUCGGCAAGUUCCCCAUCUACACCAUCCCCGACA
AGCUGGGGCCGUGGAGCCCCAUCGACAUCCACCACCUGUCCUGCCCCA
ACAACCUCGUGGUCGAGGACGAGGGCUGCACCAACCUGAGCGGGUUCU
CCUACAUGCUUUUCAAUCUCCGCAUCCUCCUUAACAACGCCGCGUUUA
GAAACGGCCACAACUUCAUGGUCCGGAACUUCAGAUGUGGCCAGCCGC
UUCAAAACAAGGUCCAGCUGAAGGGCCGGGAUCUUCUGACCCUGAAGA
ACUUUACUGGCGAAGAGAUCAAGUACAUGCUCUGGCUCUCCGCGGACU
UGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCC
UUUCUACUGAAACUGGGUUCGCGCUGCUCGGUGGCCACCCCUGCUUCC
UGACGACCCAGGACAUCCACCUCGGAGUGAACGAAUCCCUCACCGAUA
CCGCCCGGGUGUUAUCGAGCAUGGCAGAUGCCGUGCUGGCCAGGGUGU
ACAAACAGUCCGAUCUGGACACUCUGGCCAAGGAGGCGUCAAUUCCUA
UUAUCAACGGCCUUAGUGACCUCUACCAUCCGAUUCAGAUCCUGGCCG
AUUACCUCACCCUGCAAGAACACUACAGCUCCCUGAAGGGUCUGACAU
UGUCCUGGAUCGGCGACGGCAACAACAUUCUCCAUUCCAUCAUGAUGU
CCGCCGCAAAAUUCGGCAUGCAUCUUCAAGCCGCCACGCCGAAGGGUU
ACGAGCCCGACGCUUCCGUGACUAAGCUCGCCGAGCAGUACGCUAAGG
AGAACGGAACCAAGCUUCUGCUGACUAACGACCCACUAGAAGCAGCCC
ACGGGGGCAACGUGCUUAUUACUGACACCUGGAUCUCCAUGGGCCAGG
AAGAAGAGAAAAAGAAGCGGCUGCAGGCGUUCCAGGGAUAUCAGGUCA
CCAUGAAAACCGCCAAGGUCGCUGCCUCCGACUGGACCUUCCUGCACU
GCCUGCCUCGCAAGCCUGAAGAAGUGGACGACGAGGUGUUCUACUCGC
CACGGAGCCUCGUGUUCCCCGAGGCCGAGAAUAGAAAGUGGACCAUCA
UGGCCGUGAUGGUGUCACUGCUCACCGACUACAGCCCGCAGCUUCAGA
AGCCCAAGUUCUAGAUAAGUGAAUGCAAGGCUGGCCGGAAGCCCUUGC
CUGAAAGCAAGAUUUCAGCCUGGAAGAGGGCAAAGUGGACGGGAGUGG
ACAGGAGUGGAUGCGAUAAGAUGUGGUUUGAAGCUGAUGGGUGCCAGC

-continued

CCUGCAUUGCUGAGUCAAUCAAUAAAGAGCUUUCUUUUGACCCAUUCU
AGAUCUAG

>mARM1788

(SEQ ID NO: 62)

AGGAAACUUAAGAUUAUUACAUCAAAACAAAAAGCCGCCAAUGCUGUU
CAACCUGCGCAUCCUGCUGAACAACGCCGCCUUCCGCAACGGCCACAA
CUUCAUGGUGCGCAACUUCCGCUGCGGCCAGCCCCUGCAGAACAAGGU
GCAGCUGAAGGGCCGCGACCUGCUGACCCUGAAGAACUUCACCGGCGA
GGAGAUCAAGUACAUGCUGUGGCUGAGCGCCGACCUGAAGUUCCGCAU
CAAGCAGAAGGGCGAGUACCUGCCCCUGCUGCAGGGCAAGAGCCUGGG
CAUGAUCUUCGAGAAGCGCAGCACCCGCACCCGCCUGAGCACCGAGAC
AGGCCUGGCCCUGCUGGGCGGCCACCCCUGCUUCCUGACCACCCAGGA
CAUCCACCUGGGCGUGAACGAGAGCCUGACCGACACCGCCCGCGUGCU
GAGCAGCAUGGCCGACGCCGUGCUGGCCCGCGUGUACAAGCAGAGCGA
CCUGGACACCCUGGCCAAGGAGGCCAGCAUCCCCAUCAUCAACGGCCU
GAGCGACCUGUACCACCCCAUCCAGAUCCUGGCCGACUACCUGACCCU
GCAGGAGCACUACAGCAGCCUGAAGGGCCUGACCCUGAGCUGGAUCGG
CGACGGCAACAACAUCCUGCACAGCAUCAUGAUGAGCGCCGCCAAGUU
CGGCAUGCACCUGCAGGCCGCCACCCCCAAGGGCUACGAGCCCGACGC
CAGCGUGACCAAGCUGGCCGAGCAGUACGCCAAGGAGAACGGCACCAA
GCUGCUGCUGACCAACGACCCCCUGGAGGCCGCCCACGGCGGCAACGU
GCUGAUCACCGACACCUGGAUCAGCAUGGGCCAGGAGGAGGAGAAGAA
GAAGCGCCUGCAGGCCUUCCAGGGCUACCAGGUGACCAUGAAGACCGC
CAAGGUGGCCGCCAGCGACUGGACCUUCCUGCACUGCCUGCCCCGCAA
GCCCGAGGAGGUGGACGACGAGGUGUUCUACAGCCCCCGCAGCCUGGU
GUUCCCCGAGGCCGAGAACCGCAAGUGGACCAUCAUGGCCGUGAUGGU
GAGCCUGCUGACCGACUACAGCCCCCAGCUGCAGAAGCCCAAGUUCUG
AACGCCGAAGCCUGCAGCCAUGCGACCCCACGCCACCCCGUGCCUCCU
GCCUCCGCGCAGCCUGCAGCGGGAGACCCUGUCCCCGCCCCAGCCGUC
CUCCUGGGGUGGACCCUAGUUUAAUAAAGAUUCACCAAGUUUCACGCA
AAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAA

>mARM1789

(SEQ ID NO: 63)

CUUAAGGGGGCGCUGCCUACGGAGGUGGCAGCCAUCUCCUUCUCGGCA
UCAAGCUUACCAUGGUGCCCCAGGCCCUGCUCUUGGUCCCGCUGCUGG
UGUUCCCCCUCUGCUUCGGCAAGUUCCCCAUCUACACCAUCCCCGACA
AGCUGGGGCCGUGGAGCCCCAUCGACAUCCACCACCUGUCCUGCCCCA
ACAACCUCGUGGUCGAGGACGAGGGCUGCACCAACCUGAGCGGGUUCU
CCUACAUGCUGUUCAACCUGCGCAUCCUGCUGAACAACGCCGCCUUCC
GCAACGGCCACAACUUCAUGGUGCGCAACUUCCGCUGCGGCCAGCCCC
UGCAGAACAAGGUGCAGCUGAAGGGCCGCGACCUGCUGACCCUGAAGA

-continued

ACUUCACCGGCGAGGAGAUCAAGUACAUGCUGUGGCUGAGCGCCGACC
UGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCC
UGAGCACCGAGACAGGCCUGGCCCUGCUGGGCGGCCACCCCUGCUUCC
UGACCACCCAGGACAUCCACCUGGGCGUGAACGAGAGCCUGACCGACA
CCGCCCGCGUGCUGAGCAGCAUGGCCGACGCCGUGCUGGCCCGCGUGU
ACAAGCAGAGCGACCUGGACACCCUGGCCAAGGAGGCCAGCAUCCCCA
UCAUCAACGGCCUGAGCGACCUGUACCACCCCAUCCAGAUCCUGGCCG
ACUACCUGACCCUGCAGGAGCACUACAGCAGCCUGAAGGGCCUGACCC
UGAGCUGGAUCGGCGACGGCAACAACAUCCUGCACAGCAUCAUGAUGA
GCGCCGCCAAGUUCGGCAUGCACCUGCAGGCCGCCACCCCCAAGGGCU
ACGAGCCCGACGCCAGCGUGACCAAGCUGGCCGAGCAGUACGCCAAGG
AGAACGGCACCAAGCUGCUGCUGACCAACGACCCCCUGGAGGCCGCCC
ACGGCGGCAACGUGCUGAUCACCGACACCUGGAUCAGCAUGGGCCAGG
AGGAGGAGAAGAAGAAGCGCCUGCAGGCCUUCCAGGGCUACCAGGUGA
CCAUGAAGACCGCCAAGGUGGCCGCCAGCGACUGGACCUUCCUGCACU
GCCUGCCCCGCAAGCCCGAGGAGGUGGACGACGAGGUGUUCUACAGCC
CCCGCAGCCUGGUGUUCCCCGAGGCCGAGAACCGCAAGUGGACCAUCA
UGGCCGUGAUGGUGAGCCUGCUGACCGACUACAGCCCCCAGCUGCAGA
AGCCCAAGUUCUGAAUAAGUGAUGCAAGGCUGGCCGGAAGCCCUUGCC
UGAAAGCAAGAUUUCAGCCUGGAAGAGGGCAAAGUGGACGGGAGUGGA
CAGGAGUGGAUGCGAUAAGAUGUGGUUUGAAGCUGAUGGGUGCCAGCC
CUGCAUUGCUGAGUCAAUCAAUAAAGAGCUUUCUUUUGACCCAUUCUA
GAUCUAG

>mARM1790

(SEQ ID NO: 64)

AGGAAACUUAAGAUUAUUACAUCAAAACAAAAAGCCGCCAAUGCUUUU
CAAUCUCCGCAUCCUCCUUAACAACGCCGCGUUUAGAAACGGCCACAA
CUUCAUGGUCCGGAACUUCAGAUGUGGCCAGCCGCUUCAAAACAAGGU
CCAGCUGAAGGGCCGGGAUCUUCUGACCCUGAAGAACUUUACUGGCGA
AGAGAUCAAGUACAUGCUCUGGCUCUCCGCGGACUUGAAGUUCCGCAU
UAAGCAGAAGGGGGAAUACCUUCCGCUGCUUCAAGGAAAGAGCCUCGG
CAUGAUCUUUGAGAAGCGCUCAACCAGGACCCGCCUUUCUACUGAAAC
UGGGUUCGCGCUGCUCGGUGGCCACCCCUGCUUCCUGACGACCCAGGA
CAUCCACCUCGGAGUGAACGAAUCCCUCACCGAUACCGCCCGGGUGUU
AUCGAGCAUGGCAGAUGCCGUGCUGGCCAGGGUGUACAAACAGUCCGA
UCUGGACACUCUGGCCAAGGAGGCGUCAAUUCCUAUUAUCAACGGCCU
UAGUGACCUCUACCAUCCGAUUCAGAUCCUGGCCGAUUACCUCACCCU
GCAAGAACACUACAGCUCCCUGAAGGGUCUGACAUUGUCCUGGAUCGG
CGACGGCAACAACAUUCUCCAUUCCAUCAUGAUGUCCGCCGCAAAAUU
CGGCAUGCAUCUUCAAGCCGCCACGCCGAAGGGUUACGAGCCCGACGC

-continued

UUCCGUGACUAAGCUCGCCGAGCAGUACGCUAAGGAGAACGGAACCAA
GCUUCUGCUGACUAACGACCCACUAGAAGCAGCCCACGGGGGCAACGU
GCUUAUUACUGACACCUGGAUCUCCAUGGGCCAGGAAGAAGAGAAAAA
GAAGCGGCUGCAGGCGUUCCAGGGAUAUCAGGUCACCAUGAAAACCGC
CAAGGUCGCUGCCUCCGACUGGACCUUCCUGCACUGCCUGCCUCGCAA
GCCUGAAGAAGUGGACGACGAGGUGUUCUACUCGCCACGGAGCCUCGU
GUUCCCCGAGGCCGAGAAUAGAAAGUGGACCAUCAUGGCCGUGAUGGU
GUCACUGCUCACCGACUACAGCCCGCAGCUUCAGAAGCCCAAGUUCUA
GACGCCGAAGCCUGCAGCCAUGCGACCCCACGCCACCCCGUGCCUCCU
GCCUCCGCGCAGCCUGCAGCGGGAGACCCUGUCCCCGCCCCAGCCGUC
CUCCUGGGGUGGACCCUAGUUUAAUAAAGAUUCACCAAGUUUCACGCA
AAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAA

>mARM1791

(SEQ ID NO: 65)

CUUAAGGGGGCGCUGCCUACGGAGGUGGCAGCCAUCUCCUUCUCGGCA
UCAAGCUUACCAUGGUGCCCCAGGCCCUGCUCUUGGUCCCGCUGCUGG
UGUUCCCCCUCUGCUUCGGCAAGUUCCCCAUCUACACCAUCCCCGACA
AGCUGGGGCCGUGGAGCCCCAUCGACAUCCACCACCUGUCCUGCCCCA
ACAACCUCGUGGUCGAGGACGAGGGCUGCACCAACCUGAGCGGGUUCU
CCUACAUGCUUUUCAACCUGAGAAUCCUCUUGAACAAUGCUGCUUUUC
GGAAUGGCCACAACUUUAUGGUUCGGAACUUCCGUUGCGGCCAGCCUU
UACAAAACAAGGUCCAGCUGAAGGGCCGGGAUUUGCUCACACUAAAGA
ACUUUACUGGAGAAGAGAUCAAGUACAUGCUAUGGCUGUCGGCCGACC
UGAAGUUCCGUAUCAAGCAGAAGGGAGAAUACCUUCCGCUGCUUCAAG
GAAAGAGCCUCGGCAUGAUCUUUGAGAAGCGCUCAACCAGGACCCGCC
UUUCUACUGAAACUGGGUUCGCGCUGCUCGGUGGCCACCCCUGCUUCC
UGACGACCCAGGACAUCCACCUCGGAGUGAACGAAUCCCUCACCGAUA
CCGCCCGGGUGUUAUCGAGCAUGGCAGAUGCCGUGCUGGCCAGGGUGU
ACAAACAGUCCGAUCUCGAUACCUUGGCAAAGGAGGCUUCCAUUCCCA
UCAUCAACGGCCUGAGCGACCUGUACCACCCAAUCCAAAUCCUGGCUG
ACUACCUGACCCUGCAAGAGCACUACAGCAGCCUGAAGGGUCUGACCC
UGUCAUGGAUUGGCGAUGGAAACAAUAUUCUGCACUCCAUCAUGAUGU
CCGCCGCGAAGUUCGGAAUGCAUCUGCAAGCCGCCACUCCAAAAGGAU
ACGAACCGGAUGCAUCCGUGACCAAGUUGGCGGAACAGUACGCGAAGG
AGAACGGAACCAAGCUCCUGCUGACUAACGACCCGCUCGAGGCUGCGC
AUGGGGGUAACGUGCUGAUUACGGACACCUGGAUCUCCAUGGGGCAGG
AGGAAGAGAAGAAGAAGAGACUGCAGGCAUUCCAGGGGUACCAGGUCA
CCAUGAAAACCGCAAAAGUGGCAGCUUCGGACUGGACUUUCCUGCAUU
GCCUGCCGAGGAAGCCGGAGGAAGUCGACGACGAAGUGUUCUACUCGC
CUCGGUCCCUGGUGUUCCCCGAGGCCGAAAACCGGAAGUGGACCAUCA

-continued

UGGCCGUGAUGGUGUCCUUGCUGACUGACUAUAGCCCGCAGCUGCAGA
AGCCUAAGUUCUAGAUAAGUGAUGCAAGGCUGGCCGGAAGCCCUUGCC
UGAAAGCAAGAUUUCAGCCUGGAAGAGGGCAAAGUGGACGGGAGUGGA
CAGGAGUGGAUGCGAUAAGAUGUGGUUUGAAGCUGAUGGGUGCCAGCC
CUGCAUUGCUGAGUCAAUCAAUAAAGAGCUUUCUUUUGACCCAUUCUA
GAUCUAG

>mARM1792
(SEQ ID NO: 66)
UGAGUGUCGUACAGCCUCCAGGCCCCCCCCUCCCGGGAGAGCCAUAGU
GGUCUGCGGAACCGGUGAGUACACCGGAAUUGCCGGGAAGACUGGGUC
CUUUCUUGGAUAAACCCACUCUAUGCCCGGCCAUUUGGGCGUGCCCCC
GCAAGACUGCUAGCCGAGUAGUGUUGGGUUGCGAUGCUGUUCAACCUG
CGCAUCCUGCUGAACAACGCCGCCUUCCGCAACGGCCACAACUUCAUG
GUGCGCAACUUCCGCUGCGGCCAGCCCCUGCAGAACAAGGUGCAGCUG
AAGGGCCGCGACCUGCUGACCCUGAAGAACUUCACCGGCGAGGAGAUC
AAGUACAUGCUGUGGCUGAGCGCCGACCUGAAGUUCCGCAUCAAGCAG
AAGGGCGAGUACCUGCCCCUGCUGCAGGGCAAGAGCCUGGGCAUGAUC
UUCGAGAAGCGCAGCACCCGCACCCGCCUGAGCACCGAGACAGGCCUG
GCCCUGCUGGGCGGCCACCCCUGCUUCCUGACCACCCAGGACAUCCAC
CUGGGCGUGAACGAGAGCCUGACCGACACCGCCCGCGUGCUGAGCAGC
AUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGAC
CUGUACCACCCCAUCCAGAUCCUGGCCGACUACCUGACCCUGCAGGAG
CACUACAGCAGCCUGAAGGGCCUGACCCUGAGCUGGAUCGGCGACGGC
AACAACAUCCUGCACAGCAUCAUGAUGAGCGCCGCCAAGUUCGGCAUG
CACCUGCAGGCCGCCACCCCCAAGGGCUACGAGCCCGACGCCAGCGUG
ACCAAGCUGGCCGAGCAGUACGCCAAGGAGAACGGCACCAAGCUGCUG
CUGACCAACGACCCCCUGGAGGCCGCCCACGGCGGCAACGUGCUGAUC
ACCGACACCUGGAUCAGCAUGGGCCAGGAGGAGGAGAAGAAGAAGCGC
CUGCAGGCCUUCCAGGGCUACCAGGUGACCAUGAAGACCGCCAAGGUG
GCCGCCAGCGACUGGACCUUCCUGCACUGCCUGCCCCGCAAGCCCGAG
GAGGUGGACGACGAGGUGUUCUACAGCCCCCGCAGCCUGGUGUUCCCC
GAGGCCGAGAACCGCAAGUGGACCAUCAUGGCCGUGAUGGUGAGCCUG
CUGACCGACUACAGCCCCCAGCUGCAGAAGCCCAAGUUCUGAAUAAGU
GAUAGAGCGGCAAACCCUAGCUACACUCCAUAGCUAGUUUCUUUUUUU
UUUGUUUUUUUUUUUUUUUUUUUUUUUUUUUUUUUUUUUUUUUCCUUU
CUUUUCCUUCUUUUUUUCCUCUUUUCUUGGUGGCUCCAUCUUAGCCCU
AGUCACGGCUAGCUGUGAAAGGUCCGUGAGCCGCAUGACUGCAGAGAG
UGCCGUAACUGGCCUCUCUGCAGAUCAUGUUCUAG

-continued

>mARM1793
(SEQ ID NO: 67)
AGGAAACUUAAGAUUAUUACAUCAAAACAAAAAGCCGCCAAUGCUUUU
CAAUCUCCGCAUCCUCCUUAACAACGCCGCGUUUAGAAACGGCCACAA
CUUCAUGGUCCGGAACUUCAGAUGUGGCCAGCCGCUUCAAAACAAGGU
CCAGCUGAAGGGCCGGGAUCUUCUGACCCUGAAGAACUUUACUGGCGA
AGAGAUCAAGUACAUGCUCUGGCUCUCCGCGGACUUGAAGUUCCGCAU
UAAGCAGAAGGGGGAAUACCUUCCGCUGCUUCAAGGAAAGAGCCUCGG
CAUGAUCUUUGAGAAGCGCUCAACCAGGACCCGCCUUUCUACUGAAAC
UGGGUUCGCGCUGCUCGGUGGCCACCCCUGCUUCCUGACGACCCAGGA
CAUCCACCUCGGAGUGAACGAAUCCCUCACCGAUACCGCCCGGGUGUU
AUCGAGCAUGGCAGAUGCCGUGCUGGCCAGGGUGUACAAACAGUCCGA
UCUGGACACUCUGGCCAAGGAGGCGUCAAUUCCUAUUAUCAACGGCCU
UAGUGACCUCUACCAUCCGAUUCAGAUCCUGGCCGAUUACCUCACCCU
GCAAGAACACUACAGCUCCCUGAAGGGUCUGACAUUGUCCUGGAUCGG
CGACGGCAACAACAUUCUCCAUUCCAUCAUGAUGUCCGCCGCAAAAUU
CGGCAUGCAUCUUCAAGCCGCCACGCCGAAGGGUUACGAGCCCGACGC
UUCCGUGACUAAGCUCGCCGAGCAGUACGCUAAGGAGAACGGAACCAA
GCUUCUGCUGACUAACGACCCACUAGAAGCAGCCCACGGGGGCAACGU
GCUUAUUACUGACACCUGGAUCUCCAUGGGCCAGGAAGAAGAGAAAAA
GAAGCGGCUGCAGGCGUUCCAGGGAUAUCAGGUCACCAUGAAAACCGC
CAAGGUCGCUGCCUCCGACUGGACCUUCCUGCACUGCCUGCCUCGCAA
GCCUGAAGAAGUGGACGACGAGGUGUUCUACUCGCCACGGAGCCUCGU
GUUCCCCGAGGCCGAGAAUAGAAAGUGGACCAUCAUGGCCGUGAUGGU
GUCACUGCUCACCGACUACAGCCCGCAGCUUCAGAAGCCCAAGUUCUA
GGCUGGAGCCUCGGUAGCCGUUCCUCCUGCCCGCUGGGCCUCCCAACG
GGCCCUCCUCCCCUCCUUGCACCGGCCCUUCCUGGUCUUUGAAUAAAG
UCUGAGUGGGCAGCAAAAAAAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAAAAAAAAAAAAAAA

>mARM1794
(SEQ ID NO: 68)
AGGAAACUUAAGAUUAUUACAUCAAAACAAAAAGCCGCCAAUGCUGUU
CAACCUGCGCAUCCUGCUGAACAACGCCGCCUUCCGCAACGGCCACAA
CUUCAUGGUGCGCAACUUCCGCUGCGGCCAGCCCCUGCAGAACAAGGU
GCAGCUGAAGGGCCGCGACCUGCUGACCCUGAAGAACUUCACCGGCGA
GGAGAUCAAGUACAUGCUGUGGCUGAGCGCCGACCUGAAGUUCCGCAU
CAAGCAGAAGGGCGAGUACCUGCCCCUGCUGCAGGGCAAGAGCCUGGG
CAUGAUCUUCGAGAAGCGCAGCACCCGCACCCGCCUGAGCACCGAGAC
AGGCCUGGCCCUGCUGGGCGGCCACCCCUGCUUCCUGACCACCCAGGA
CAUCCACCUGGGCGUGAACGAGAGCCUGACCGACACCGCCCGCGUGCU
GAGCAGCAUGGCCGACGCCGUGCUGGCCCGCGUGUACAAGCAGAGCGA

-continued

CCUGGACACCCUGGCCAAGGAGGCCAGCAUCCCCAUCAUCAACGGCCU

GAGCGACCUGUACCACCCCAUCCAGAUCCUGGCCGACUACCUGACCCU

GCAGGAGCACUACAGCAGCCUGAAGGGCCUGACCCUGAGCUGGAUCGG

CGACGGCAACAACAUCCUGCACAGCAUCAUGAUGAGCGCCGCCAAGUU

CGGCAUGCACCUGCAGGCCGCCACCCCCAAGGGCUACGAGCCCGACGC

CAGCGUGACCAAGCUGGCCGAGCAGUACGCCAAGGAGAACGGCACCAA

GCUGCUGCUGACCAACGACCCCCUGGAGGCCGCCCACGGCGGCAACGU

GCUGAUCACCGACACCUGGAUCAGCAUGGGCCAGGAGGAGGAGAAGAA

GAAGCGCCUGCAGGCCUUCCAGGGCUACCAGGUGACCAUGAAGACCGC

CAAGGUGGCCGCCAGCGACUGGACCUUCCUGCACUGCCUGCCCCGCAA

GCCCGAGGAGGUGGACGACGAGGUGUUCUACAGCCCCCGCAGCCUGGU

GUUCCCCGAGGCCGAGAACCGCAAGUGGACCAUCAUGGCCGUGAUGGU

GAGCCUGCUGACCGACUACAGCCCCCAGCUGCAGAAGCCCAAGUUCUG

AGCUGGAGCCUCGGUAGCCGUUCCUCCUGCCCGCUGGGCCUCCCAACG

GGCCCUCCUCCCCUCCUUGCACCGGCCCUUCCUGGUCUUUGAAUAAAG

UCUGAGUGGGCAGCAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAA

>mARM1795

(SEQ ID NO: 69)

AGGAAACUUAAGAUUAUUACAUCAAAACAAAAAGCCGCCAAUGCUUUU

CAACCUGAGAAUCCUCUUGAACAAUGCUGCUUUUCGGAAUGGCCACAA

CUUUAUGGUUCGGAACUUCCGUUGCGGCCAGCCUUUACAAAACAAGGU

CCAGCUGAAGGGCCGGGAUUUGCUCACACUAAAGAACUUUACUGGAGA

AGAGAUCAAGUACAUGCUAUGGCUGUCGGCCGACCUGAAGUUCCGUAU

CAAGCAGAAGGGAGAAUACCUUCCGCUGCUUCAAGGAAAGAGCCUCGG

CAUGAUCUUUGAGAAGCGCUCAACCAGGACCCGCCUUUCUACUGAAAC

UGGGUUCGCGCUGCUCGGUGGCCACCCCUGCUUCCUGACGACCCAGGA

CAUCCACCUCGGAGUGAACGAAUCCCUCACCGAUACCGCCCGGGUGUU

AUCGAGCAUGGCAGAUGCCGUGCUGGCCAGGGUGUACAAACAGUCCGA

UCUCGAUACCUUGGCAAAGGAGGCUUCCAUUCCCAUCAUCAACGGCCU

GAGCGACCUGUACCACCCAAUCCAAAUCCUGGCUGACUACCUGACCCU

GCAAGAGCACUACAGCAGCCUGAAGGGUCUGACCCUGUCAUGGAUUGG

CGAUGGAAACAAUAUUCUGCACUCCAUCAUGAUGUCCGCCGCGAAGUU

CGGAAUGCAUCUGCAAGCCGCCACUCCAAAAGGAUACGAACCGGAUGC

AUCCGUGACCAAGUUGGCGGAACAGUACGCGAAGGAGAACGGAACCAA

GCUCCUGCUGACUAACGACCCGCUCGAGGCUGCGCAUGGGGGUAACGU

GCUGAUUACGGACACCUGGAUCUCCAUGGGGCAGGAGGAAGAGAAGAA

GAAGAGACUGCAGGCAUUCCAGGGGUACCAGGUCACCAUGAAAACCGC

AAAAGUGGCAGCUUCGGACUGGACUUUCCUGCAUUGCCUGCCGAGGAA

GCCGGAGGAAGUCGACGACGAAGUGUUCUACUCGCCUCGGUCCCUGGU

GUUCCCCGAGGCCGAAAACCGGAAGUGGACCAUCAUGGCCGUGAUGGU

GUCCUUGCUGACUGACUAUAGCCCGCAGCUGCAGAAGCCUAAGUUCUA

GGCUGGAGCCUCGGUAGCCGUUCCUCCUGCCCGCUGGGCCUCCCAACG

GGCCCUCCUCCCCUCCUUGCACCGGCCCUUCCUGGUCUUUGAAUAAAG

UCUGAGUGGGCAGCAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAA

>mARM1796

(SEQ ID NO: 70)

AGGAAACUUAAGAAUUAUUGGUUAAAGAAGUAUAUUAGUGCUAAUUUC

CCUCCGUUUGUCCUAGCUUUUCUCUUCUGUCAACCCCACACGCCUUUG

GCACAAUGCUUUUCAAUCUCCGCAUCCUCCUUAACAACGCCGCGUUUA

GAAACGGCCACAACUUCAUGGUCCGGAACUUCAGAUGUGGCCAGCCGC

UUCAAAACAAGGUCCAGCUGAAGGGCCGGGAUCUUCUGACCCUGAAGA

ACUUUACUGGCGAAGAGAUCAAGUACAUGCUCUGGCUCUCCGCGGACU

UGAAGUUCCGCAUUAAGCAGAAGGGGGAAUACCUUCCGCUGCUUCAAG

GAAAGAGCCUCGGCAUGAUCUUUGAGAAGCGCUCAACCAGGACCCGCC

UUUCUACUGAAACUGGGUUCGCGCUGCUCGGUGGCCACCCCUGCUUCC

UGACGACCCAGGACAUCCACCUCGGAGUGAACGAAUCCCUCACCGAUA

CCGCCCGGGUGUUAUCGAGCAUGGCAGAUGCCGUGCUGGCCAGGGUGU

ACAAACAGUCCGAUCUGGACACUCUGGCCAAGGAGGCGUCAAUUCCUA

UUAUCAACGGCCUUAGUGACCUCUACCAUCCGAUUCAGAUCCUGGCCG

AUUACCUCACCCUGCAAGAACACUACAGCUCCCUGAAGGGUCUGACAU

UGUCCUGGAUCGGCGACGGCAACAACAUUCUCCAUUCCAUCAUGAUGU

CCGCCGCAAAAUUCGGCAUGCAUCUUCAAGCCGCCACGCCGAAGGGUU

ACGAGCCCGACGCUUCCGUGACUAAGCUCGCCGAGCAGUACGCUAAGG

AGAACGGAACCAAGCUUCUGCUGACUAACGACCCACUAGAAGCAGCCC

ACGGGGGCAACGUGCUUAUUACUGACACCUGGAUCUCCAUGGGCCAGG

AAGAAGAGAAAAAGAAGCGGCUGCAGGCGUUCCAGGGAUAUCAGGUCA

CCAUGAAAACCGCCAAGGUCGCUGCCUCCGACUGGACCUUCCUGCACU

GCCUGCCUCGCAAGCCUGAAGAAGUGGACGACGAGGUGUUCUACUCGC

CACGGAGCCUCGUGUUCCCCGAGGCCGAGAAUAGAAAGUGGACCAUCA

UGGCCGUGAUGGUGUCACUGCUCACCGACUACAGCCCGCAGCUUCAGA

AGCCCAAGUUCUAGCUCGAGACACAUCACAACCACAACCUUCUCAGGC

UACCCUGAGAAAAAAAGACAUGAAGACUCAGGACUCAUCUUUUCUGUU

GGUGUAAAAUCAACACCCUAAGGAACACAAAUUUCUUUAAACAUUUGA

CUUCUUGUCUCUGUGCUGCAAUUAAUAAAAAAUGGAAAGAAUCUAUCU

AG

>mARM1797

(SEQ ID NO: 71)

AGGAAACUUAAGAAUUAUUGGUUAAAGAAGUAUAUUAGUGCUAAUUUC

CCUCCGUUUGUCCUAGCUUUUCUCUUCUGUCAACCCCACACGCCUUUG

GCACAAUGCUGUUCAACCUGCGCAUCCUGCUGAACAACGCCGCCUUCC

-continued

GCAACGGCCACAACUUCAUGGUGCGCAACUUCCGCUGCGGCCAGCCCC
UGCAGAACAAGGUGCAGCUGAAGGGCCGCGACCUGCUGACCCUGAAGA
ACUUCACCGGCGAGGAGAUCAAGUACAUGCUGUGGCUGAGCGCCGACC
UGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCC
UGAGCACCGAGACAGGCCUGGCCCUGCUGGGCGGCCACCCCCUGCUUCC
UGACCACCCAGGACAUCCACCUGGGCGUGAACGAGAGCCUGACCGACA
CCGCCCGCGUGCUGAGCAGCAUGGCCGACGCCGUGCUGGCCCGCGUGU
ACAAGCAGAGCGACCUGGACACCCUGGCCAAGGAGGCCAGCAUCCCCA
UCAUCAACGGCCUGAGCGACCUGUACCACCCCAUCCAGAUCCUGGCCG
ACUACCUGACCCUGCAGGAGCACUACAGCAGCCUGAAGGGCCUGACCC
UGAGCUGGAUCGGCGACGGCAACAACAUCCUGCACAGCAUCAUGAUGA
GCGCCGCCAAGUUCGGCAUGCACCUGCAGGCCGCCACCCCCAAGGGCU
ACGAGCCCGACGCCAGCGUGACCAAGCUGGCCGAGCAGUACGCCAAGG
AGAACGGCACCAAGCUGCUGCUGACCAACGACCCCCUGGAGGCCGCCC
ACGGCGGCAACGUGCUGAUCACCGACACCUGGAUCAGCAUGGGCCAGG
AGGAGGAGAAGAAGAAGCGCCUGCAGGCCUUCCAGGGCUACCAGGUGA
CCAUGAAGACCGCCAAGGUGGCCGCCAGCGACUGGACCUUCCUGCACU
GCCUGCCCCGCAAGCCCGAGGAGGUGGACGACGAGGUGUUCUACAGCC
CCCGCAGCCUGGUGUUCCCCGAGGCCGAGAACCGCAAGUGGACCAUCA
UGGCCGUGAUGGUGAGCCUGCUGACCGACUACAGCCCCCAGCUGCAGA
AGCCCAAGUUCUGACUCGAGACACAUCACAACCACAACCUUCUCAGGC
UACCCUGAGAAAAAAAGACAUGAAGACUCAGGACUCAUCUUUUCUGUU
GGUGUAAAAUCAACACCCUAAGGAACACAAAUUUCUUUAAACAUUUGA
CUUCUUGUCUCUGUGCUGCAAUUAAUAAAAAAUGGAAAGAAUCUAUCU
AG

>mARM1798

(SEQ ID NO: 72)

AGGAAACUUAAGAAUUAUUGGUUAAAGAAGUAUAUUAGUGCUAAUUUC
CCUCCGUUUGUCCUAGCUUUUCUCUUCUGUCAACCCCACACGCCUUUG
GCACAAUGCUUUUCAACCUGAGAAUCCUCUUGAACAAUGCUGCUUUUC
GGAAUGGCCACAACUUUAUGGUUCGGAACUUCCGUUGCGGCCAGCCUU
UACAAAACAAGGUCCAGCUGAAGGGCCGGGAUUUGCUCACACUAAAGA
ACUUUACUGGAGAAGAGAUCAAGUACAUGCUAUGGCUGUCGGCCGACC
UGAAGUUCCGUAUCAAGCAGAAGGGAGAAUACCUUCCGCUGCUUCAAG
GAAAGAGCCUCGGCAUGAUCUUUGAGAAGCGCUCAACCAGGACCCGCC
UUUCUACUGAAACUGGGUUCGCGCUGCUCGGUGGCCACCCCUGCUUCC
UGACGACCCAGGACAUCCACCUCGGAGUGAACGAAUCCCUCACCGAUA
CCGCCCGGGUGUUAUCGAGCAUGGCAGAUGCCGUGCUGGCCAGGGUGU
ACAAACAGUCCGAUCUCGAUACCUUGGCAAAGGAGGCUUCCAUUCCCA
UCAUCAACGGCCUGAGCGACCUGUACCACCCAAUCCAAAUCCUGGCUG
ACUACCUGACCCUGCAAGAGCACUACAGCAGCCUGAAGGGUCUGACCC

-continued

UGUCAUGGAUUGGCGAUGGAAACAAUAUUCUGCACUCCAUCAUGAUGU
CCGCCGCGAAGUUCGGAAUGCAUCUGCAAGCCGCCACUCCAAAAGGAU
ACGAACCGGAUGCAUCCGUGACCAAGUUGGCGGAACAGUACGCGAAGG
AGAACGGAACCAAGCUCCUGCUGACUAACGACCCGCUCGAGGCUGCGC
AUGGGGGUAACGUGCUGAUUACGGACACCUGGAUCUCCAUGGGGCAGG
AGGAAGAGAAGAAGAAGAGACUGCAGGCAUUCCAGGGGUACCAGGUCA
CCAUGAAAACCGCAAAAGUGGCAGCUUCGGACUGGACUUUCCUGCAUU
GCCUGCCGAGGAAGCCGGAGGAAGUCGACGACGAAGUGUUCUACUCGC
CUCGGUCCCUGGUGUUCCCCGAGGCCGAAAACCGGAAGUGGACCAUCA
UGGCCGUGAUGGUGUCCUUGCUGACUGACUAUAGCCCGCAGCUGCAGA
AGCCUAAGUUCUAGCUCGAGACACAUCACAACCACAACCUUCUCAGGC
UACCCUGAGAAAAAAAGACAUGAAGACUCAGGACUCAUCUUUUCUGUU
GGUGUAAAAUCAACACCCUAAGGAACACAAAUUUCUUUAAACAUUUGA
CUUCUUGUCUCUGUGCUGCAAUUAAUAAAAAAUGGAAAGAAUCUAUCU
AG

>mARM1799

(SEQ ID NO: 73)

AUUAUUACAUCAAAACAAAAAGCCGCCACCAUGCUGUUCAACCUGCGC
AUCCUGCUGAACAACGCCGCCUUCCGCAACGGCCACAACUUCAUGGUG
CGCAACUUCCGCUGCGGCCAGCCCCUGCAGAACAAGGUGCAGCUGAAG
GGCCGCGACCUGCUGACCCUGAAGAACUUCACCGGCGAGGAGAUCAAG
UACAUGCUGUGGCUGAGCGCCGACCUGAAGUUCCGCAUCAAGCAGAAG
GGCGAGUACCUGCCCCUGCUGCAGGGCAAGAGCCUGGGCAUGAUCUUC
GAGAAGCGCAGCACCCGCACCCGCCUGAGCACCGAGACAGGCUUCGCC
CUGCUGGGCGGCCACCCCUGCUUCCUGACCACCCAGGACAUCCACCUG
GGCGUGAACGAGAGCCUGACCGACACCGCCCGCGUGCUGAGCAGCAUG
GCCGACGCCGUGCUGGCCCGCGUGUACAAGCAGAGCGACCUGGACACC
CUGGCCAAGGAGGCCAGCAUCCCCAUCAUCAACGGCCUGAGCGACCUG
UACCACCCCAUCCAGAUCCUGGCCGACUACCUGACCCUGCAGGAGCAC
UACAGCAGCCUGAAGGGCCUGACCCUGAGCUGGAUCGGCGACGGCAAC
AACAUCCUGCACAGCAUCAUGAUGAGCGCCGCCAAGUUCGGCAUGCAC
CUGCAGGCCGCCACCCCCAAGGGCUACGAGCCCGACGCCAGCGUGACC
AAGCUGGCCGAGCAGUACGCCAAGGAGAACGGCACCAAGCUGCUGCUG
ACCAACGACCCCCUGGAGGCCGCCCACGGCGGCAACGUGCUGAUCACC
GACACCUGGAUCAGCAUGGGCCAGGAGGAGGAGAAGAAGAAGCGCCUG
CAGGCCUUCCAGGGCUACCAGGUGACCAUGAAGACCGCCAAGGUGGCC
GCCAGCGACUGGACCUUCCUGCACUGCCUGCCCCGCAAGCCCGAGGAG
GUGGACGACGAGGUGUUCUACAGCCCCCGCAGCCUGGUGUUCCCCGAG
GCCGAGAACCGCAAGUGGACCAUCAUGGCCGUGAUGGUGAGCCUGCUG
ACCGACUACAGCCCCCAGCUGCAGAAGCCCAAGUUCUGAGGUCUCUAG
UAAUGAGCUGGAGCCUCGGUAGCCGUUCCUCCUGCCCGCUGGGCCUCC

-continued

CAACGGGCCCUCCUCCCCUCCUUGCACCGGCCCUUCCUGGUCUUUGAA
UAAAGUCUGAGUGGGCAUCUAG

>mARM1800

(SEQ ID NO: 74)

AGGAAACUUAAGAAUUAUUGGUUAAAGAAGUAUAUUAGUGCUAAUUUC
CCUCCGUUUGUCCUAGCUUUUCUCUUCUGUCAACCCCACACGCCUUUG
GCACAAUGCUGUUCAACCUGCGCAUCCUGCUGAACAACGCCGCCUUCC
GCAACGGCCACAACUUCAUGGUGCGCAACUUCCGCUGCGGCCAGCCCC
UGCAGAACAAGGUGCAGCUGAAGGGCCGCGACCUGCUGACCCUGAAGA
ACUUCACCGGCGAGGAGAUCAAGUACAUGCUGUGGCUGAGCGCCGACC
UGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCC
UGAGCACCGAGACAGGCUUCGCCCUGCUGGGCGGCCACCCCUGCUUCC
UGACCACCCAGGACAUCCACCUGGGCGUGAACGAGAGCCUGACCGACA
CCGCCCGCGUGCUGAGCAGCAUGGCCGACGCCGUGCUGGCCCGCGUGU
ACAAGCAGAGCGACCUGGACACCCUGGCCAAGGAGGCCAGCAUCCCCA
UCAUCAACGGCCUGAGCGACCUGUACCACCCCAUCCAGAUCCUGGCCG
ACUACCUGACCCUGCAGGAGCACUACAGCAGCCUGAAGGGCCUGACCC
UGAGCUGGAUCGGCGACGGCAACAACAUCCUGCACAGCAUCAUGAUGA
GCGCCGCCAAGUUCGGCAUGCACCUGCAGGCCGCCACCCCCAAGGGCU
ACGAGCCCGACGCCAGCGUGACCAAGCUGGCCGAGCAGUACGCCAAGG
AGAACGGCACCAAGCUGCUGCUGACCAACGACCCCCUGGAGGCCGCCC
ACGGCGGCAACGUGCUGAUCACCGACACCUGGAUCAGCAUGGGCCAGG
AGGAGGAGAAGAAGAAGCGCCUGCAGGCCUUCCAGGGCUACCAGGUGA
CCAUGAAGACCGCCAAGGUGGCCGCCAGCGACUGGACCUUCCUGCACU
GCCUGCCCCGCAAGCCCGAGGAGGUGGACGACGAGGUGUUCUACAGCC
CCCGCAGCCUGGUGUUCCCCGAGGCCGAGAACCGCAAGUGGACCAUCA
UGGCCGUGAUGGUGAGCCUGCUGACCGACUACAGCCCCCAGCUGCAGA
AGCCCAAGUUCUGACUCGAGACACAUCACAACCACAACCUUCUCAGGC
UACCCUGAGAAAAAAAGACAUGAAGACUCAGGACUCAUCUUUUCUGUU
GGUGUAAAAUCAACACCCUAAGGAACACAAAUUUCUUUAAACAUUUGA
CUUCUUGUCUCUGUGCUGCAAUUAAUAAAAAAUGGAAAGAAUCUAUCU
AG

>mARM1801

(SEQ ID NO: 75)

AGGAAACUUAAGAUUAUUACAUCAAAACAAAAAGCCGCCAAUGCUGUU
CAACCUGCGCAUCCUGCUGAACAACGCCGCCUUCCGCAACGGCCACAA
CUUCAUGGUGCGCAACUUCCGCUGCGGCCAGCCCCUGCAGAACAAGGU
GCAGCUGAAGGGCCGCGACCUGCUGACCCUGAAGAACUUCACCGGCGA
GGAGAUCAAGUACAUGCUGUGGCUGAGCGCCGACCUGAAGUUCCGCAU
CAAGCAGAAGGGCGAGUACCUGCCCCUGCUGCAGGGCAAGAGCCUGGG
CAUGAUCUUCGAGAAGCGCAGCACCCGCACCCGCCUGAGCACCGAGAC
AGGCUUCGCCCUGCUGGGCGGCCACCCCUGCUUCCUGACCACCCAGGA

-continued

CAUCCACCUGGGCGUGAACGAGAGCCUGACCGACACCGCCCGCGUGCU
GAGCAGCAUGGCCGACGCCGUGCUGGCCCGCGUGUACAAGCAGAGCGA
CCUGGACACCCUGGCCAAGGAGGCCAGCAUCCCCAUCAUCAACGGCCU
GAGCGACCUGUACCACCCCAUCCAGAUCCUGGCCGACUACCUGACCCU
GCAGGAGCACUACAGCAGCCUGAAGGGCCUGACCCUGAGCUGGAUCGG
CGACGGCAACAACAUCCUGCACAGCAUCAUGAUGAGCGCCGCCAAGUU
CGGCAUGCACCUGCAGGCCGCCACCCCCAAGGGCUACGAGCCCGACGC
CAGCGUGACCAAGCUGGCCGAGCAGUACGCCAAGGAGAACGGCACCAA
GCUGCUGCUGACCAACGACCCCCUGGAGGCCGCCCACGGCGGCAACGU
GCUGAUCACCGACACCUGGAUCAGCAUGGGCCAGGAGGAGGAGAAGAA
GAAGCGCCUGCAGGCCUUCCAGGGCUACCAGGUGACCAUGAAGACCGC
CAAGGUGGCCGCCAGCGACUGGACCUUCCUGCACUGCCUGCCCCGCAA
GCCCGAGGAGGUGGACGACGAGGUGUUCUACAGCCCCCGCAGCCUGGU
GUUCCCCGAGGCCGAGAACCGCAAGUGGACCAUCAUGGCCGUGAUGGU
GAGCCUGCUGACCGACUACAGCCCCCAGCUGCAGAAGCCCAAGUUCUG
AACGCCGAAGCCUGCAGCCAUGCGACCCCACGCCACCCCGUGCCUCCU
GCCUCCGCGCAGCCUGCAGCGGGAGACCCUGUCCCCGCCCCAGCCGUC
CUCCUGGGGUGGACCCUAGUUUAAUAAAGAUUCACCAAGUUUCACGCA
AAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAA

>mARM1802

(SEQ ID NO: 76)

CUUAAGGGGGCGCUGCCUACGGAGGUGGCAGCCAUCUCCUUCUCGGCA
UCAAGCUUACCAUGGUGCCCCAGGCCCUGCUCUUGGUCCCGCUGCUGG
UGUUCCCCCUCUGCUUCGGCAAGUUCCCCAUCUACACCAUCCCCGACA
AGCUGGGGCCGUGGAGCCCCAUCGACAUCCACCACCUGUCCUGCCCCA
ACAACCUCGUGGUCGAGGACGAGGGCUGCACCAACCUGAGCGGGUUCU
CCUACAUGCUGUUCAACCUGCGCAUCCUGCUGAACAACGCCGCCUUCC
GCAACGGCCACAACUUCAUGGUGCGCAACUUCCGCUGCGGCCAGCCCC
UGCAGAACAAGGUGCAGCUGAAGGGCCGCGACCUGCUGACCCUGAAGA
ACUUCACCGGCGAGGAGAUCAAGUACAUGCUGUGGCUGAGCGCCGACC
UGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCC
UGAGCACCGAGACAGGCUUCGCCCUGCUGGGCGGCCACCCCUGCUUCC
UGACCACCCAGGACAUCCACCUGGGCGUGAACGAGAGCCUGACCGACA
CCGCCCGCGUGCUGAGCAGCAUGGCCGACGCCGUGCUGGCCCGCGUGU
ACAAGCAGAGCGACCUGGACACCCUGGCCAAGGAGGCCAGCAUCCCCA
UCAUCAACGGCCUGAGCGACCUGUACCACCCCAUCCAGAUCCUGGCCG
ACUACCUGACCCUGCAGGAGCACUACAGCAGCCUGAAGGGCCUGACCC
UGAGCUGGAUCGGCGACGGCAACAACAUCCUGCACAGCAUCAUGAUGA

-continued

GCGCCGCCAAGUUCGGCAUGCACCUGCAGGCCGCCACCCCCAAGGGCU

ACGAGCCCGACGCCAGCGUGACCAAGCUGGCCGAGCAGUACGCCAAGG

AGAACGGCACCAAGCUGCUGCUGACCAACGACCCCCUGGAGGCCGCCC

ACGGCGGCAACGUGCUGAUCACCGACACCUGGAUCAGCAUGGGCCAGG

AGGAGGAGAAGAAGAAGCGCCUGCAGGCCUUCCAGGGCUACCAGGUGA

CCAUGAAGACCGCCAAGGUGGCCGCCAGCGACUGGACCUUCCUGCACU

GCCUGCCCCGCAAGCCCGAGGAGGUGGACGACGAGGUGUUCUACAGCC

CCCGCAGCCUGGUGUUCCCCGAGGCCGAGAACCGCAAGUGGACCAUCA

UGGCCGUGAUGGUGAGCCUGCUGACCGACUACAGCCCCCAGCUGCAGA

AGCCCAAGUUCUGAAUAAGUGAAUGCAAGGCUGGCCGGAAGCCCUUGC

CUGAAAGCAAGAUUUCAGCCUGGAAGAGGGCAAAGUGGACGGGAGUGG

ACAGGAGUGGAUGCGAUAAGAUGUGGUUUGAAGCUGAUGGGUGCCAGC

CCUGCAUUGCUGAGUCAAUCAAUAAAGAGCUUUCUUUUGACCCAUUCU

AGAUCUAG

>mARM1803

(SEQ ID NO: 77)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCACCAUGGGCGUCU

UCAACCUGCGGAUCCUGCUGAACAACGCCGCCUUCCGGAACGGCCACA

ACUUCAUGGUCCGCAACUUCAGAUGCGGCCAGCCCCUGCAGAACAAGG

UGCAGCUGAAGGGCCGGGACCUGCUGACCCUGAAGAACUUCACCGGCG

AAGAGAUCAAGUACAUGCUGUGGCUGAGCGCCGACCUGAAGUUCCGGA

UCAAGCAGAAGGGCGAGUACCUGCCCCUGCUGCAAGGCAAGAGCCUGG

GCAUGAUCUUCGAGAAGCGGAGCACCCGGACCCGGCUGAGCACCGAGA

CAGGCUUUGCCCUGCUGGGAGGCCACCCCUGCUUUCUGACCACCCAGG

ACAUCCACCUGGGCGUGAACGAGAGCCUGACCGACACCGCCAGAGUGC

UGAGCAGCAUGGCCGACGCCGUGCUGGCCCGGGUGUACAAGCAGAGCG

ACCUGGACACCCUGGCCAAAGAGGCCAGCAUCCCCAUCAUCAACGGCC

UGAGCGACCUGUACCACCCCAUCCAGAUCCUGGCCGACUACCUGACCC

UGCAGGAACACUACAGCUCCCUGAAGGGCCUGACCCUGAGCUGGAUCG

GCGACGGCAACAACAUCCUGCACAGCAUCAUGAUGAGCGCCGCCAAGU

UCGGCAUGCAUCUGCAGGCCGCCACCCCCAAGGGCUACGAGCCUGAUG

CCAGCGUGACCAAGCUGGCCGAGCAGUACGCCAAAGAGAACGGCACCA

AGCUGCUGCUGACCAACGACCCCCUGGAAGCCGCCCACGGCGGCAACG

UGCUGAUCACCGACACCUGGAUCAGCAUGGGCCAGGAAGAGGAAAAGA

AGAAGCGGCUGCAGGCCUUCCAGGGCUACCAGGUCACAAUGAAGACCG

CCAAGGUGGCCGCCAGCGACUGGACCUUCCUGCACUGCCUGCCCCGGA

AGCCCGAAGAGGUGGACGACGAGGUGUUCUACAGCCCCCGGUCCCUGG

UGUUCCCCGAGGCCGAGAACCGGAAGUGGACCAUUAUGGCCGUGAUGG

UGUCCCUGCUGACCGACUACUCCCCCCAGCUGCAGAAGCCCAAGUUCU

AGAUAAGUGAACUCGAGCUAGUGACUGACUAGGAUCUGGUUACCACUA

-continued

AACCAGCCUCAAGAACACCCGAAUGGAGUCUCUAAGCUACAUAAUACC

AACUUACACUUACAAAAUGUUGUCCCCCAAAAUGUAGCCAUUCGUAUC

UGCUCCUAAUAAAAAGAAAGUUUCUUCACAUUCUAG

>mARM1804

(SEQ ID NO: 78)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCACCAUGGGCGUCU

UCAACCUGCGGAUCCUGCUGAACAACGCCGCCUUCCGGAACGGCCACA

ACUUCAUGGUCCGCAACUUCAGAUGCGGCCAGCCCCUGCAGAACAGGG

UGCAGCUGAAGGGCCGGGACCUGCUGACCCUGAAGAACUUCACCGGCG

AAGAGAUCAGGUACAUGCUGUGGCUGAGCGCCGACCUGAAGUUCCGGA

UCAAGCAGAAGGGCGAGUACCUGCCCCUGCUGCAAGGCAAGAGCCUGG

GCAUGAUCUUCGAGAAGCGGAGCACCCGGACCCGGCUGAGCACCGAGA

CAGGCUUUGCCCUGCUGGGAGGCCACCCCUGCUUUCUGACCACCCAGG

ACAUCCACCUGGGCGUGAACGAGAGCCUGACCGACACCGCCAGAGUGC

UGAGCAGCAUGGCCGACGCCGUGCUGGCCCGGGUGUACAAGCAGAGCG

ACCUGGACACCCUGGCCAAAGAGGCCAGCAUCCCCAUCAUCAACGGCC

UGAGCGACCUGUACCACCCCAUCCAGAUCCUGGCCGACUACCUGACCC

UGCAGGAACACUACAGCUCCCUGAAGGGCCUGACCCUGAGCUGGAUCG

GCGACGGCAACAACAUCCUGCACAGCAUCAUGAUGAGCGCCGCCAAGU

UCGGCAUGCAUCUGCAGGCCGCCACCCCCAAGGGCUACGAGCCUGAUG

CCAGCGUGACCAAGCUGGCCGAGCAGUACGCCAAAGAGAACGGCACCA

AGCUGCUGCUGACCAACGACCCCCUGGAAGCCGCCCACGGCGGCAACG

UGCUGAUCACCGACACCUGGAUCAGCAUGGGCCAGGAAGAGGAAAAGA

AGAAGCGGCUGCAGGCCUUCCAGGGCUACCAGGUCACAAUGAAGACCG

CCAAGGUGGCCGCCAGCGACUGGACCUUCCUGCACUGCCUGCCCCGGA

AGCCCGAAGAGGUGGACGACGAGGUGUUCUACAGCCCCCGGUCCCUGG

UGUUCCCCGAGGCCGAGAACCGGAAGUGGACCAUUAUGGCCGUGAUGG

UGUCCCUGCUGACCGACUACUCCCCCCAGCUGCAGAAGCCCAAGUUCU

AGAUAAGUGAACUCGAGCUAGUGACUGACUAGGAUCUGGUUACCACUA

AACCAGCCUCAAGAACACCCGAAUGGAGUCUCUAAGCUACAUAAUACC

AACUUACACUUACAAAAUGUUGUCCCCCAAAAUGUAGCCAUUCGUAUC

UGCUCCUAAUAAAAAGAAAGUUUCUUCACAUUCUAG

>mARM1805

(SEQ ID NO: 79)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCACCAUGCUGGUCU

UCAACCUGCGGAUCCUGCUGAACAACGCCGCCUUCCGGAACGGCCACA

ACUUCAUGGUCCGCAACUUCAGAUGCGGCCAGCCCCUGCAGAACAGGG

UGCAGCUGAAGGGCCGGGACCUGCUGACCCUGAAGAACUUCACCGGCG

-continued

AAGAGAUCAGGUACAUGCUGUGGCUGAGCGCCGACCUGAAGUUCCGGA
UCAAGCAGAAGGGCGAGUACCUGCCCCUGCUGCAAGGCAAGAGCCUGG
GCAUGAUCUUCGAGAAGCGGAGCACCCGGACCCGGCUGAGCACCGAGA
CAGGCUUUGCCCUGCUGGGAGGCCACCCCUGCUUUCUGACCACCCAGG
ACAUCCACCUGGGCGUGAACGAGAGCCUGACCGACACCGCCAGAGUGC
UGAGCAGCAUGGCCGACGCCGUGCUGGCCCGGGUGUACAAGCAGAGCG
ACCUGGACACCCUGGCCAAAGAGGCCAGCAUCCCCAUCAUCAACGGCC
UGAGCGACCUGUACCACCCCAUCCAGAUCCUGGCCGACUACCUGACCC
UGCAGGAACACUACAGCUCCCUGAAGGGCCUGACCCUGAGCUGGAUCG
GCGACGGCAACAACAUCCUGCACAGCAUCAUGAUGAGCGCCGCCAAGU
UCGGCAUGCAUCUGCAGGCCGCCACCCCCAAGGGCUACGAGCCUGAUG
CCAGCGUGACCAAGCUGGCCGAGCAGUACGCCAAAGAGAACGGCACCA
AGCUGCUGCUGACCAACGACCCCUGGAAGCCGCCCACGGCGGCAACG
UGCUGAUCACCGACACCUGGAUCAGCAUGGGCCAGGAAGAGGAAAAGA
AGAAGCGGCUGCAGGCCUUCCAGGGCUACCAGGUCACAAUGAAGACCG
CCAAGGUGGCCGCCAGCGACUGGACCUUCCUGCACUGCCUGCCCCGGA
AGCCCGAAGAGGUGGACGACGAGGUGUUCUACAGCCCCCGGUCCCUGG
UGUUCCCCGAGGCCGAGAACCGGAAGUGGACCAUUAUGGCCGUGAUGG
UGUCCCUGCUGACCGACUACUCCCCCCAGCUGCAGAAGCCCAAGUUCU
AGAUAAGUGAACUCGAGCUAGUGACUGACUAGGAUCUGGUUACCACUA
AACCAGCCUCAAGAACACCCGAAUGGAGUCUCUAAGCUACAUAAUACC
AACUUACACUUACAAAAUGUUGUCCCCCAAAAUGUAGCCAUUCGUAUC
UGCUCCUAAUAAAAAGAAAGUUUCUUCACAUUCUAG

>mARM1806

(SEQ ID NO: 80)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGAGGAUCCUGCUGAACAACGCAGCUUUCAGGAACGGCCACAACU
UCAUGGUGAGGAACUUCCGGUGCGGCCAGCCCCUGCAGAACAAGGUGC
AGCUGAAGGGCAGGGACCUGCUGACCCUGAAGAACUUCACCGGAGAGG
AGAUCAAGUACAUGCUGUGGCUGAGCGCAGACCUGAAGUUCAGGAUCA
AGCAGAAGGGAGAGUACCUGCCCCUGCUGCAGGGGAAGUCCCUGGGCA
UGAUCUUCGAGAAGAGGAGUACCAGGACCAGGCUGAGCACCGAAACCG
GCUUCGCCCUGCUGGGAGGACACCCCUGCUUCCUGACCACCCAGGACA
UCCACCUGGGCGUGAACGAGAGUCUGACCGACACCGCCAGGGUGCUGU
CUAGCAUGGCCGACGCCGUGCUGGCCAGGGUGUACAAGCAGUCAGACC
UGGACACCCUGGCUAAGGAGGCCAGCAUCCCCAUCAUCAACGGCCUGA
GCGACCUGUACCACCCCAUCCAGAUCCUGGCUGACUACCUGACCCUGC
AGGAGCACUACAGCUCUCUGAAGGGCCUGACCCUGAGCUGGAUCGGCG
ACGGGAACAACAUCCUGCACAGCAUCAUGAUGAGCGCCGCCAAGUUCG
GCAUGCACCUGCAGGCCGCUACCCCCAAGGGUUACGAGCCCGACGCCA
GCGUGACCAAGCUGGCAGAGCAGUACGCCAAGGAGAACGGCACCAAGC
UGCUGCUGACCAACGACCCCCUGGAGGCCGCCCACGGAGGCAACGUGC
UGAUCACCGACACCUGGAUCAGCAUGGGACAGGAGGAGGAGAAGAAGA
AGCGGCUGCAGGCUUUCCAGGGUUACCAGGUGACCAUGAAGACCGCCA
AGGUGGCUGCCAGCGACUGGACCUUCCUGCACUGCCUGCCCAGGAAGC
CCGAGGAGGUGGACGACGAGGUGUUCUACUCUCCCAGGAGCCUGGUGU
UCCCCGAGGCCGAGAACAGGAAGUGGACCAUCAUGGCUGUGAUGGUGU
CCCUGCUGACCGACUACAGCCCCCAGCUGCAGAAGCCCAAGUUCUGAA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC
UUACACUUACAAAAUGUUGUCCCCCAAAAUGUAGCCAUUCGUAUCUGC
UCCUAAUAAAAAGAAAGUUUCUUCACAUUCUAG

>mARM1808

(SEQ ID NO: 81)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGAGGAUCCUGCUGAACAACGCAGCUUUCAGGAACGGCCACAACU
UCAUGGUGAGGAACUUCCGGUGCGGCCAGCCCCUGCAGAACAAGGUGC
AGCUGAAGGGCAGGGACCUGCUGACCCUGAAGAACUUCACCGGAGAGG
AGAUCAAGUACAUGCUGUGGCUGAGCGCAGACCUGAAGUUCAGGAUCA
AGCAGAAGGGAGAGUACCUGCCCCUGCUGCAGGGGAAGUCCCUGGGCA
UGAUCUUCGAGAAGAGGAGUACCAGGACCAGGCUGAGCACCGAAACCG
GCUUCGCCCUGCUGGGAGGACACCCCUGCUUCCUGACGACCCAGGACA
UCCACCUCGGAGUGAACGAAUCCCUCACCGAUACCGCCCGGGUGUUAU
CAAGCAUGGCAGAUGCCGUGCUGGCCAGGGUGUACAAACAGUCCGAUC
UGGACACUCUGGCUAAGGAGGCCAGCAUCCCCAUCAUCAACGGCCUGA
GCGACCUGUACCACCCCAUCCAGAUCCUGGCUGACUACCUGACCCUGC
AGGAGCACUACAGCUCUCUGAAGGGCCUGACCCUGAGCUGGAUCGGCG
ACGGGAACAACAUCCUGCACUCCAUCAUGAUGUCCGCCGCGAAGUUCG
GAAUGCAUCUGCAAGCCGCCACGCCAAAAGGAUACGAACCGGAUGCGC
CCGUGACAAAGUUGGCGGAACAGUACGCUAAGGAGAACGGAACCAAGC
UGCUGCUGACCAACGACCCCCUGGAGGCCGCCCACGGAGGCAACGUGC
UGAUCACCGACACCUGGAUCAGCAUGGGACAGGAGGAGGAGAAGAAGA
AGCGGCUGCAGGCUUUCCAGGGUUACCAGGUGACCAUGAAGACCGCCA
AGGUGGCUGCCAGCGACUGGACCUUCCUGCACUGCCUGCCCAGGAAGC
CCGAGGAGGUGGACGACGAGGUGUUCUACUCUCCCAGGAGCCUGGUGU
UCCCCGAGGCCGAGAACAGGAAGUGGACCAUCAUGGCUGUGAUGGUGU
CCCUGCUGACCGACUACAGCCCCCAGCUGCAGAAGCCCAAGUUCUGAA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC

-continued

UUACACUUACAAAAUGUUGUCCCCCAAAAUGUAGCCAUUCGUAUCUGC
UCCUAAUAAAAAGAAAGUUUCUUCACAUUCUAG

>mARM1809

(SEQ ID NO: 82)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUGCGCAUCCUGCUGAACAACGCCGCCUUCCGCAACGGCCACAACU
UCAUGGUGCGCAACUUCCGCUGCGGCCAGCCCCUGCAGAACAAGGUGC
AGCUGAAGGGCCGCGACCUGCUGACCCUGAAGAACUUCACCGGCGAGG
AGAUCAAGUACAUGCUGUGGCUGAGCGCCGACCUGAAGUUCCGCAUCA
AGCAGAAGGGCGAGUACCUGCCCCUGCUGCAGGGCAAGAGCCUGGGCA
UGAUCUUCGAGAAGCGCAGCACCCGCACCCGCCUGAGCACCGAGACAG
GCUUCGCCCUGCUGGGCGGCCACCCCUGCUUCCUGACCACCCAGGACA
UCCACCUGGGCGUGAACGAGAGCCUGACCGACACCGCCCGCGUGCUGA
GCAGCAUGGCCGACGCCGUGCUGGCCCGCGUGUACAAGCAGAGCGACC
UGGACACCCUGGCCAAGGAGGCCAGCAUCCCCAUCAUCAACGGCCUGA
GCGACCUGUACCACCCCAUCCAGAUCCUGGCCGACUACCUGACCCUGC
AGGAGCACUACAGCAGCCUGAAGGGCCUGACCCUGAGCUGGAUCGGCG
ACGGCAACAACAUCCUGCACAGCAUCAUGAUGAGCGCCGCCAAGUUCG
GCAUGCACCUGCAGGCCGCCACCCCCAAGGGCUACGAGCCCGACGCCA
GCGUGACCAAGCUGGCCGAGCAGUACGCCAAGGAGAACGGCACCAAGC
UGCUGCUGACCAACGACCCCCUGGAGGCCGCCCACGGCGGCAACGUGC
UGAUCACCGACACCUGGAUCAGCAUGGGCCAGGAGGAGGAGAAGAAGA
AGCGCCUGCAGGCCUUCCAGGGCUACCAGGUGACCAUGAAGACCGCCA
AGGUGGCCGCCAGCGACUGGACCUUCCUGCACUGCCUGCCCCGCAAGC
CCGAGGAGGUGGACGACGAGGUGUUCUACAGCCCCCGCAGCCUGGUGU
UCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC
UUACACUUACAAAAUGUUGUCCCCCAAAAUGUAGCCAUUCGUAUCUGC
UCCUAAUAAAAAGAAAGUUUCUUCACAUUCUAGAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAAAAAAAAAAAA

>mARM1816

(SEQ ID NO: 83)

AGGAAACUUAAGUCAACACAACAUAUACAAAACAAACGAAUCUCAAGC
AAUCAAGCAUUCUACUUCUAUUGCAGCAAUUUAAAUCAUUUCUUUUAA
AGCAAAAGCAAUUUUCUGAAAAUUUUCACCAUUUACGAACGAUAGCCA
UGCUGUUCAACCUGCGCAUCCUGCUGAACAACGCCGCCUUCCGCAACG
GCCACAACUUCAUGGUGCGCAACUUCCGCUGCGGCCAGCCCCUGCAGA
ACAAGGUGCAGCUGAAGGGCCGCGACCUGCUGACCCUGAAGAACUUCA

-continued

CCGGCGAGGAGAUCAAGUACAUGCUGUGGCUGAGCGCCGACCUGAAGU
UCCGCAUCAAGCAGAAGGGCGAGUACCUGCCCCUGCUGCAGGGCAAGA
GCCUGGGCAUGAUCUUCGAGAAGCGCAGCACCCGCACCCGCCUGAGCA
CCGAGACAGGCUUCGCCCUGCUGGGCGGCCACCCCUGCUUCCUGACCA
CCCAGGACAUCCACCUGGGCGUGAACGAGAGCCUGACCGACACCGCCC
GCGUGCUGAGCAGCAUGGCCGACGCCGUGCUGGCCCGCGUGUACAAGC
AGAGCGACCUGGACACCCUGGCCAAGGAGGCCAGCAUCCCCAUCAUCA
ACGGCCUGAGCGACCUGUACCACCCCAUCCAGAUCCUGGCCGACUACC
UGACCCUGCAGGAGCACUACAGCAGCCUGAAGGGCCUGACCCUGAGCU
GGAUCGGCGACGGCAACAACAUCCUGCACAGCAUCAUGAUGAGCGCCG
CCAAGUUCGGCAUGCACCUGCAGGCCGCCACCCCCAAGGGCUACGAGC
CCGACGCCAGCGUGACCAAGCUGGCCGAGCAGUACGCCAAGGAGAACG
GCACCAAGCUGCUGCUGACCAACGACCCCCUGGAGGCCGCCCACGGCG
GCAACGUGCUGAUCACCGACACCUGGAUCAGCAUGGGCCAGGAGGAGG
AGAAGAAGAAGCGCCUGCAGGCCUUCCAGGGCUACCAGGUGACCAUGA
AGACCGCCAAGGUGGCCGCCAGCGACUGGACCUUCCUGCACUGCCUGC
CCCGCAAGCCCGAGGAGGUGGACGACGAGGUGUUCUACAGCCCCCGCA
GCCUGGUGUUCCCCGAGGCCGAGAACCGCAAGUGGACCAUCAUGGCCG
UGAUGGUGAGCCUGCUGACCGACUACAGCCCCCAGCUGCAGAAGCCCA
AGUUCUGACUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1822

(SEQ ID NO: 84)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
ACUUGAGAAUCCUGCUGAACAACGCCGCCUUUCGCAACGGUCACAAUU
UUAUGGUCAGAAACUUCAGAUGCGGACAGCCCCUCCAAAACAAGGUCC
AGCUGAAGGGCCGCGAUCUCCUCACCCUGAAGAACUUCACGGGGGAGG
AGAUCAAGUACAUGCUGUGGCUCUCCGCUGACCUGAAGUUCAGGAUCA
AGCAGAAGGGAGAAUAUCUGCCGCUGCUGCAAGGGAAGUCCCUGGGGA
UGAUUUUCGAGAAGCGGAGCACCCGGACUCGGCUCUCCACUGAAACUG
GUUUCGCCCUUCUGGGCGGUCACCCCUGCUUCCUGACCACUCAAGACA
UUCACCUCGGAGUGAACGAGUCCUUGACUGACACCGCCCGGGUGCUGU
CGAGCAUGGCAGACGCCGUGCUAGCCCGCGUGUACAAGCAGUCAGACC
UCGAUACCCUGGCCAAGGAGGCUUCGAUCCCGAUCAUCAACGGGUUGU
CCGACCUGUACCACCCGAUUCAGAUUCUCGCCGACUACCUCACCCUGC
AAGAGCAUUACAGCUCCCUGAAGGGGCUUACCCUGUCCUGGAUUGGCG
ACGGAAACAACAUCCUGCACUCCAUUAUGAUGUCGGCGGCCAAGUUCG

-continued

GCAUGCACCUCCAAGCCGCGACCCCUAAGGGUUACGAACCAGACGCGU
CAGUGACUAAGCUGGCCGAACAGUACGCAAAGGAAAAUGGCACGAAGC
UGCUCCUGACCAACGAUCCGUUGGAAGCCGCCCAUGGCGGAAAUGUGC
UCAUCACCGACACCUGGAUCUCGAUGGGACAGGAGGAAGAGAAGAAGA
AGCGGCUGCAGGCGUUCCAGGGCUACCAGGUCACCAUGAAAACUGCCA
AGGUGGCCGCCAGCGACUGGACCUUCCUGCACUGCCUUCCGCGCAAGC
CUGAGGAGGUGGACGAUGAAGUGUUCUACUCUCCACGGUCCCUGGUGU
UCCCCGAGGCGGAGAACCGCAAAUGGACCAUCAUGGCUGUGAUGGUCA
GCCUGCUGACCGAUUACAGCCCUCAGUUGCAAAAGCCGAAGUUUUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1823

(SEQ ID NO: 85)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGUUCA
ACCUCCGCAUCCUCCUCAACAACGCCGCAUUCAGAAACGGGCACAACU
UCAUGGUCAGAAACUUCCGCUGCGGGCAACCCCUACAAAACAAGGUCC
AGCUCAAGGGGCGGGACCUCCUGACCCUGAAGAACUUCACCGGCGAAG
AGAUCAAGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC

-continued

UUACAAAAUGUUGUCCCCCAAAAUGUAGCCAUUCGUAUCUGCUCCUAA
UAAAAAGAAAGUUUCUUCACAUUCUAGAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAAAAAAA

>mARM1840

(SEQ ID NO: 86)

CUCCCUCCCCCCCCCCUAACGUUACUGGCCGAAGCCGCUUGGAAUAAG
GCCGGUGUGCGUUUGUCUAUAUGUUAUUUUCCACCAUAUUGCCGUCUU
UUGGCAAUGUGAGGGCCCGGAAACCUGGCCCUGUCUUCUUGACGAGCA
UUCCUAGGGGUCUUUCCCCUCUCGCCAAAGGAAUGCAAGGUCUGUUGA
AUGUCGUGAAGGAAGCAGUUCCUCUGGAAGCUUCUUGAAGACAAACAA
CGUCUGUAGCGACCCUUUGCAGGCAGCGGAACCCCCCACCUGGCGACA
GGUGCCUCUGCGGCCAAAAGCCACGUGUAUAAGAUACACCUGCAAAGG
CGGCACAACCCCAGUGCCACGUUGUGAGUUGGAUAGUUGUGGAAAGAG
UCAAAUGGCUCUCCUCAAGCGUAUUCAACAAGGGGCUGAAGGAUGCCC
AGAAGGUACCCCAUUGUAUGGGAUCUGAUCUGGGGCCUCGGUGCACAU
GCUUUACGUGUGUUUAGUCGAGGUUAAAAAACGUCUAGGCCCCCCGAA
CCACGGGGACGUGGUUUUCCUUUGAAAAACACGAUGAUAAUAUGCUUU
UCAAUCUCCGCAUCCUCCUUAACAACGCCGCGUUUAGAAACGGCCACA
ACUUCAUGGUCCGGAACUUCAGAUGUGGCCAGCCGCUUCAAAACAAGG
UCCAGCUGAAGGGCCGGGAUCUUCUGACCCUGAAGAACUUUACUGGCG
AAGAGAUCAAGUACAUGCUCUGGCUCUCCGCGGACUUGAAGUUCCGCA
UUAAGCAGAAGGGGGAAUACCUUCCGCUGCUUCAAGGAAAGAGCCUCG
GCAUGAUCUUUGAGAAGCGCUCAACCAGGACCCGCCUUUCUACUGAAA
CUGGGUUCGCGCUGCUCGGUGGCCACCCCUGCUUCCUGACGACCCAGG
ACAUCCACCUCGGAGUGAACGAAUCCCUCACCGAUACCGCCCGGGUGU
UAUCGAGCAUGGCAGAUGCCGUGCUGGCCAGGGUGUACAAACAGUCCG
AUCUGGACACUCUGGCCAAGGAGGCGUCAAUUCCUAUUAUCAACGGCC
UUAGUGACCUCUACCAUCCGAUUCAGAUCCUGGCCGAUUACCUCACCC
UGCAAGAACACUACAGCUCCCUGAAGGGUCUGACAUUGUCCUGGAUCG
GCGACGGCAACAACAUUCUCCAUUCCAUCAUGAUGUCCGCCGCAAAAU
UCGGCAUGCAUCUUCAAGCCGCCACGCCGAAGGGUUACGAGCCCGACG
CUUCCGUGACUAAGCUCGCCGAGCAGUACGCUAAGGAGAACGGAACCA
AGCUUCUGCUGACUAACGACCCACUAGAAGCAGCCCACGGGGGCAACG
UGCUUAUUACUGACACCUGGAUCUCCAUGGGCCAGGAAGAAGAGAAAA
AGAAGCGGCUGCAGGCGUUCCAGGGAUAUCAGGUCACCAUGAAAACCG
CCAAGGUCGCUGCCUCCGACUGGACCUUCCUGCACUGCCUGCCUCGCA
AGCCUGAAGAAGUGGACGACGAGGUGUUCUACUCGCCACGGAGCCUCG
UGUUCCCCGAGGCCGAGAAUAGAAAGUGGACCAUCAUGGCCGUGAUGG
UGUCACUGCUCACCGACUACAGCCCGCAGCUUCAGAAGCCCAAGUUCU
GAAUAAGUAGAUAGUGCAGUCACUGGCACAACGCGUUGCCCGGUAAGC

-continued

CAAUCGGGUAUACACGGUCGUCAUACUGCAGACAGGGUUCUUCUACUU

UGCAAGAUAGUCUAGAGUAGUAAAAUAAAUAGUAUAAGUCUAG

>mARM1841

(SEQ ID NO: 87)

CUCCCUCCCCCCCCCCUAACGUUACUGGCCGAAGCCGCUUGGAAUAAG

GCCGGUGUGCGUUUGUCUAUAUGUUAUUUUCCACCAUAUUGCCGUCUU

UUGGCAAUGUGAGGGCCCGGAAACCUGGCCCUGUCUUCUUGACGAGCA

UUCCUAGGGGUCUUUCCCCUCUCGCCAAAGGAAUGCAAGGUCUGUUGA

AUGUCGUGAAGGAAGCAGUUCCUCUGGAAGCUUCUUGAAGACAAACAA

CGUCUGUAGCGACCCUUUGCAGGCAGCGGAACCCCCCACCUGGCGACA

GGUGCCUCUGCGGCCAAAAGCCACGUGUAUAAGAUACACCUGCAAAGG

CGGCACAACCCCAGUGCCACGUUGUGAGUUGGAUAGUUGUGGAAAGAG

UCAAAUGGCUCUCCUCAAGCGUAUUCAACAAGGGGCUGAAGGAUGCCC

AGAAGGUACCCCAUUGUAUGGGAUCUGAUCUGGGGCCUCGGUGCACAU

GCUUUACGUGUGUUUAGUCGAGGUUAAAAAACGUCUAGGCCCCCCGAA

CCACGGGGACGUGGUUUUCCUUUGAAAAACACGAUGAUAAUAUGCUUU

UCAACCUGAGAAUCCUCUUGAACAAUGCUGCUUUUCGGAAUGGCCACA

ACUUUAUGGUUCGGAACUUCCGUUGCGGCCAGCCUUUACAAAACAAGG

UCCAGCUGAAGGGCCGGGAUUUGCUCACACUAAAGAACUUUACUGGAG

AAGAGAUCAAGUACAUGCUAUGGCUGUCGGCCGACCUGAAGUUCCGUA

UCAAGCAGAAGGGAGAAUACCUUCCGCUGCUUCAAGGAAAGAGCCUCG

GCAUGAUCUUUGAGAAGCGCUCAACCAGGACCCGCCUUUCUACUGAAA

CUGGGUUCGCGCUGCUCGGUGGCCACCCCUGCUUCCUGACGACCCAGG

ACAUCCACCUCGGAGUGAACGAAUCCCUCACCGAUACCGCCCGGGUGU

UAUCGAGCAUGGCAGAUGCCGUGCUGGCCAGGGUGUACAAACAGUCCG

AUCUCGAUACCUUGGCAAAGGAGGCUUCCAUUCCCAUCAUCAACGGCC

UGAGCGACCUGUACCACCCAAUCCAAAUCCUGGCUGACUACCUGACCC

UGCAAGAGCACUACAGCAGCCUGAAGGGUCUGACCCUGUCAUGGAUUG

GCGAUGGAAACAAUAUUCUGCACUCCAUCAUGAUGUCCGCCGCGAAGU

UCGGAAUGCAUCUGCAAGCCGCCACUCCAAAAGGAUACGAACCGGAUG

CAUCCGUGACCAAGUUGGCGGAACAGUACGCGAAGGAGAACGGAACCA

AGCUCCUGCUGACUAACGACCCGCUCGAGGCUGCGCAUGGGGGUAACG

UGCUGAUUACGGACACCUGGAUCUCCAUGGGGCAGGAGGAAGAGAAGA

AGAAGAGACUGCAGGCAUUCCAGGGGUACCAGGUCACCAUGAAAACCG

CAAAAGUGGCAGCUUCGGACUGGACUUUCCUGCAUUGCCUGCCGAGGA

AGCCGGAGGAAGUCGACGACGAAGUGUUCUACUCGCCUCGGUCCCUGG

UGUUCCCCGAGGCCGAAAACCGGAAGUGGACCAUCAUGGCCGUGAUGG

UGUCCUUGCUGACUGACUAUAGCCCGCAGCUGCAGAAGCCUAAGUUCU

GAAUAAGUAGAUAGUGCAGUCACUGGCACAACGCGUUGCCCGGUAAGC

CAAUCGGGUAUACACGGUCGUCAUACUGCAGACAGGGUUCUUCUACUU

UGCAAGAUAGUCUAGAGUAGUAAAAUAAAUAGUAUAAGUCUAG

-continued

>mARM1842

(SEQ ID NO: 88)

CUCCCUCCCCCCCCCCUAACGUUACUGGCCGAAGCCGCUUGGAAUAAG

GCCGGUGUGCGUUUGUCUAUAUGUUAUUUUCCACCAUAUUGCCGUCUU

UUGGCAAUGUGAGGGCCCGGAAACCUGGCCCUGUCUUCUUGACGAGCA

UUCCUAGGGGUCUUUCCCCUCUCGCCAAAGGAAUGCAAGGUCUGUUGA

AUGUCGUGAAGGAAGCAGUUCCUCUGGAAGCUUCUUGAAGACAAACAA

CGUCUGUAGCGACCCUUUGCAGGCAGCGGAACCCCCCACCUGGCGACA

GGUGCCUCUGCGGCCAAAAGCCACGUGUAUAAGAUACACCUGCAAAGG

CGGCACAACCCCAGUGCCACGUUGUGAGUUGGAUAGUUGUGGAAAGAG

UCAAAUGGCUCUCCUCAAGCGUAUUCAACAAGGGGCUGAAGGAUGCCC

AGAAGGUACCCCAUUGUAUGGGAUCUGAUCUGGGGCCUCGGUGCACAU

GCUUUACGUGUGUUUAGUCGAGGUUAAAAAACGUCUAGGCCCCCCGAA

CCACGGGGACGUGGUUUUCCUUUGAAAAACACGAUGAUAAUAUGCUGU

UCAACCUGCGCAUCCUGCUGAACAACGCCGCCUUCCGCAACGGCCACA

ACUUCAUGGUGCGCAACUUCCGCUGCGGCCAGCCCCUGCAGAACAAGG

UGCAGCUGAAGGGCCGCGACCUGCUGACCCUGAAGAACUUCACCGGCG

AGGAGAUCAAGUACAUGCUGUGGCUGAGCGCCGACCUGAAGUUCCGCA

UCAAGCAGAAGGGCGAGUACCUGCCCCUGCUGCAGGGCAAGAGCCUGG

GCAUGAUCUUCGAGAAGCGCAGCACCCGCACCCGCCUGAGCACCGAGA

CAGGCCUGGCCCUGCUGGGCGGCCACCCCUGCUUCCUGACCACCCAGG

ACAUCCACCUGGGCGUGAACGAGAGCCUGACCGACACCGCCCGCGUGC

UGAGCAGCAUGGCCGACGCCGUGCUGGCCCGCGUGUACAAGCAGAGCG

ACCUGGACACCCUGGCCAAGGAGGCCAGCAUCCCCAUCAUCAACGGCC

UGAGCGACCUGUACCACCCCAUCCAGAUCCUGGCCGACUACCUGACCC

UGCAGGAGCACUACAGCAGCCUGAAGGGCCUGACCCUGAGCUGGAUCG

GCGACGGCAACAACAUCCUGCACAGCAUCAUGAUGAGCGCCGCCAAGU

UCGGCAUGCACCUGCAGGCCGCCACCCCCAAGGGCUACGAGCCCGACG

CCAGCGUGACCAAGCUGGCCGAGCAGUACGCCAAGGAGAACGGCACCA

AGCUGCUGCUGACCAACGACCCCCUGGAGGCCGCCCACGGCGGCAACG

UGCUGAUCACCGACACCUGGAUCAGCAUGGGCCAGGAGGAGGAGAAGA

AGAAGCGCCUGCAGGCCUUCCAGGGCUACCAGGUGACCAUGAAGACCG

CCAAGGUGGCCGCCAGCGACUGGACCUUCCUGCACUGCCUGCCCCGCA

AGCCCGAGGAGGUGGACGACGAGGUGUUCUACAGCCCCCGCAGCCUGG

UGUUCCCCGAGGCCGAGAACCGCAAGUGGACCAUCAUGGCCGUGAUGG

UGAGCCUGCUGACCGACUACAGCCCCCAGCUGCAGAAGCCCAAGUUCU

GAAUAAGUAGAUAGUGCAGUCACUGGCACAACGCGUUGCCCGGUAAGC

CAAUCGGGUAUACACGGUCGUCAUACUGCAGACAGGGUUCUUCUACUU

UGCAAGAUAGUCUAGAGUAGUAAAAUAAAUAGUAUAAGUCUAG

-continued

>mARM1843

(SEQ ID NO: 89)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1844

(SEQ ID NO: 90)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG

-continued

GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1845

(SEQ ID NO: 91)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA

-continued

AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1846

(SEQ ID NO: 92)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

-continued

>mARM1847

(SEQ ID NO: 93)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUUUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1882

(SEQ ID NO: 94)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGUGUUCA
ACCUCCGCAUCCUCCUCAACAACGCCGCAUUCAGAAACGGGCACAACU
UCAUGGUCAGAAACUUCCGCUGCGGGCAACCCCUACAAAACAAGGUCC
AGCUCAAGGGGCGGGACCUCCUGACCCUGAAGAACUUCACCGGCGAAG
AGAUCAAGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG

-continued

GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1883

(SEQ ID NO: 95)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGUGUUCA
ACCUCCGCAUCCUCCUCAACAACGCCGCAUUCAGAAACGGGCACAACU
UCAUGGUCAGAAACUUCCGCUGCGGGCAACCCCUACAAAACCGGGUCC
AGCUCAAGGGGCGGGACCUCCUGACCCUGAAGAACUUCACCGGCGAAG
AGAUCAAGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA

-continued

AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1884

(SEQ ID NO: 96)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGUGUUCA
ACCUCCGCAUCCUCCUCAACAACGCCGCAUUCAGAAACGGGCACAACU
UCAUGGUCAGAAACUUCCGCUGCGGGCAACCCCUACAAAACCGGGUCC
AGCUCAAGGGGCGGGACCUCCUGACCCUGAAGAACUUCACCGGCGAAG
AGAUCCGGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

-continued

>mARM1885

(SEQ ID NO: 97)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGGUCA
ACCUCCGCAUCCUCCUCAACAACGCCGCAUUCAGAAACGGGCACAACU
UCAUGGUCAGAAACUUCCGCUGCGGGCAACCCCUACAAAACAAGGUCC
AGCUCAAGGGGCGGGACCUCCUGACCCUGAAGAACUUCACCGGCGAAG
AGAUCAAGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1886

(SEQ ID NO: 98)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGGUCA
ACCUCCGCAUCCUCCUCAACAACGCCGCAUUCAGAAACGGGCACAACU
UCAUGGUCAGAAACUUCCGCUGCGGGCAACCCCUACAAAACCGGGUCC
AGCUCAAGGGGCGGGACCUCCUGACCCUGAAGAACUUCACCGGCGAAG
AGAUCAAGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC
UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAGAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAAAAAA

>mARM1887

(SEQ ID NO: 99)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGGUCA
ACCUCCGCAUCCUCCUCAACAACGCCGCAUUCAGAAACGGGCACAACU
UCAUGGUCAGAAACUUCCGCUGCGGGCAACCCCUACAAAACCGGGUCC
AGCUCAAGGGGCGGGACCUCCUGACCCUGAAGAACUUCACCGGCGAAG
AGAUCCGGUACAUGCUGUGGCUCUCCGCCGACCUGAAGUUCCGCAUCA
AGCAGAAGGGAGAGUACCUCCCGCUGCUGCAAGGGAAGUCGCUGGGGA
UGAUCUUCGAGAAGCGGUCAACCAGAACCCGGCUGUCAACCGAAACCG
GGUUCGCACUGCUGGGGGGACACCCGUGCUUCCUGACCACCCAAGACA
UCCACCUGGGAGUGAACGAAUCGCUGACCGACACCGCCCGCGUGCUGA
GCUCAAUGGCGGACGCCGUGCUGGCCCGCGUGUACAAGCAGUCCGACC
UGGACACCCUGGCCAAGGAAGCGUCCAUCCCGAUCAUCAACGGACUGU
CCGACCUGUACCACCCGAUCCAGAUCCUGGCAGACUACCUGACCCUGC
AAGAACACUACAGCUCCCUGAAGGGCCUGACCCUGUCAUGGAUCGGGG
ACGGGAACAACAUCCUGCACUCCAUAAUGAUGUCAGCCGCCAAGUUCG
GAAUGCACCUCCAAGCCGCAACCCCGAAGGGCUACGAACCGGACGCAU
CAGUGACCAAACUGGCCGAGCAGUACGCCAAGGAAAACGGCACCAAGC

-continued

UCCUGCUGACCAACGACCCGCUGGAGGCCGCACACGGGGGGAACGUGC
UGAUCACCGACACCUGGAUCUCCAUGGGACAGGAGGAGGAAAAGAAGA
AGCGGCUGCAGGCGUUCCAGGGGUACCAGGUCACCAUGAAAACCGCGA
AGGUCGCGGCAUCAGACUGGACCUUCCUGCACUGCCUGCCCCGGAAGC
CGGAAGAGGUGGACGACGAGGUGUUCUACUCGCCGCGCUCGCUGGUGU
UCCCCGAGGCGGAGAACAGGAAGUGGACCAUCAUGGCGGUGAUGGUCA
GCCUCCUGACCGACUACUCGCCGCAGCUGCAGAAGCCGAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1888

(SEQ ID NO: 100)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGGUCA
ACCUGCGCAUCCUGCUGAACAACGCCGCCUUCCGCAACGGCCACAACU
UCAUGGUGCGCAACUUCCGCUGCGGCCAGCCCCUGCAGAACAAGGUGC
AGCUGAAGGGCCGCGACCUGCUGACCCUGAAGAACUUCACCGGCGAGG
AGAUCAAGUACAUGCUGUGGCUGAGCGCCGACCUGAAGUUCCGCAUCA
AGCAGAAGGGCGAGUACCUGCCCCUGCUGCAGGGCAAGAGCCUGGGCA
UGAUCUUCGAGAAGCGCAGCACCCGCACCCGCCUGAGCACCGAGACAG
GCUUCGCCCUGCUGGGCGGCCACCCCUGCUUCCUGACCACCCAGGACA
UCCACCUGGGCGUGAACGAGAGCCUGACCGACACCGCCCGCGUGCUGA
GCAGCAUGGCCGACGCCGUGCUGGCCCGCGUGUACAAGCAGAGCGACC
UGGACACCCUGGCCAAGGAGGCCAGCAUCCCCAUCAUCAACGGCCUGA
GCGACCUGUACCACCCCAUCCAGAUCCUGGCCGACUACCUGACCCUGC
AGGAGCACUACAGCAGCCUGAAGGGCCUGACCCUGAGCUGGAUCGGCG
ACGGCAACAACAUCCUGCACAGCAUCAUGAUGAGCGCCGCCAAGUUCG
GCAUGCACCUGCAGGCCGCCACCCCCAAGGGCUACGAGCCCGACGCCA
GCGUGACCAAGCUGGCCGAGCAGUACGCCAAGGAGAACGGCACCAAGC
UGCUGCUGACCAACGACCCCCUGGAGGCCGCCCACGGCGGCAACGUGC
UGAUCACCGACACCUGGAUCAGCAUGGGCCAGGAGGAGGAGAAGAAGA
AGCGCCUGCAGGCCUUCCAGGGCUACCAGGUGACCAUGAAGACCGCCA
AGGUGGCCGCCAGCGACUGGACCUUCCUGCACUGCCUGCCCCGCAAGC
CCGAGGAGGUGGACGACGAGGUGUUCUACAGCCCCCGCAGCCUGGUGU
UCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAGAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAAAAAA

>mARM1889

(SEQ ID NO: 101)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUGGUCA
ACCUGCGCAUCCUGCUGAACAACGCCGCCUUCCGCAACGGCCACAACU
UCAUGGUGCGCAACUUCCGCUGCGGCCAGCCCCUGCAGAACCGGGUGC
AGCUGAAGGGCCGCGACCUGCUGACCCUGAAGAACUUCACCGGCGAGG
AGAUCAAGUACAUGCUGUGGCUGAGCGCCGACCUGAAGUUCCGCAUCA
AGCAGAAGGGCGAGUACCUGCCCCUGCUGCAGGGCAAGAGCCUGGGCA
UGAUCUUCGAGAAGCGCAGCACCCGCACCCGCCUGAGCACCGAGACAG
GCUUCGCCCUGCUGGGCGGCCACCCCUGCUUCCUGACCACCCAGGACA
UCCACCUGGGCGUGAACGAGAGCCUGACCGACACCGCCCGCGUGCUGA
GCAGCAUGGCCGACGCCGUGCUGGCCCGCGUGUACAAGCAGAGCGACC
UGGACACCCUGGCCAAGGAGGCCAGCAUCCCCAUCAUCAACGGCCUGA
GCGACCUGUACCACCCCAUCCAGAUCCUGGCCGACUACCUGACCCUGC
AGGAGCACUACAGCAGCCUGAAGGGCCUGACCCUGAGCUGGAUCGGCG
ACGGCAACAACAUCCUGCACAGCAUCAUGAUGAGCGCCGCCAAGUUCG
GCAUGCACCUGCAGGCCGCCACCCCCAAGGGCUACGAGCCCGACGCCA
GCGUGACCAAGCUGGCCGAGCAGUACGCCAAGGAGAACGGCACCAAGC
UGCUGCUGACCAACGACCCCCUGGAGGCCGCCCACGGCGGCAACGUGC
UGAUCACCGACACCUGGAUCAGCAUGGGCCAGGAGGAGGAGAAGAAGA
AGCGCCUGCAGGCCUUCCAGGGCUACCAGGUGACCAUGAAGACCGCCA
AGGUGGCCGCCAGCGACUGGACCUUCCUGCACUGCCUGCCCCGCAAGC
CCGAGGAGGUGGACGACGAGGUGUUCUACAGCCCCCGCAGCCUGGUGU
UCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAU
AACUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAG

>mARM1890

(SEQ ID NO: 102)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUGUCA
AUCUCCGCAUCCUCCUUAACAACGCCGCGUUUAGAAACGGCCACAACU
UCAUGGUCCGGAACUUCAGAUGUGGCCAGCCGCUUCAAAACAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA

-continued

AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1891

(SEQ ID NO: 103)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGCUUGUCA
AUCUCCGCAUCCUCCUUAACAACGCCGCGUUUAGAAACGGCCACAACU
UCAUGGUCCGGAACUUCAGAUGUGGCCAGCCGCUUCAAAACCGGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU

-continued

CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGC
UCGAGCUAGUGACUGACUAGGAUCUGGUUACCACUAAACCAGCCUCAA
GAACACCCGAAUGGAGUCUCUAAGCUACAUAAUACCAACUUACACUUA
CAAAAUGUUGUCCCCCAAAAUGUAGCCAUUCGUAUCUGCUCCUAAUAA
AAAGAAAGUUUCUUCACAUUCUAG

>mARM1898

(SEQ ID NO: 104)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGGCCUUG
UCAAUCUCCGCAUCCUCCUUAACAACGCCGCGUUUAGAAACGGCCACA
ACUUCAUGGUCCGGAACUUCAGAUGUGGCCAGCCGCUUCAAAACAAGG
UCCAGCUGAAGGGCCGGGAUCUUCUGACCCUGAAGAACUUUACUGGCG
AAGAGAUCAAGUACAUGCUCUGGCUCUCCGCGGACUUGAAGUUCCGCA
UUAAGCAGAAGGGGGAAUACCUUCCGCUGCUUCAAGGAAAGAGCCUCG
GCAUGAUCUUUGAGAAGCGCUCAACCAGGACCCGCCUUUCUACUGAAA
CUGGGUUCGCGCUGCUCGGUGGCCACCCCUGCUUCCUGACGACCCAGG
ACAUCCACCUCGGAGUGAACGAAUCCCUCACCGAUACCGCCCGGGUGU
UAUCGAGCAUGGCAGAUGCCGUGCUGGCCAGGGUGUACAAACAGUCCG
AUCUGGACACUCUGGCCAAGGAGGCGUCAAUUCCUAUUAUCAACGGCC
UUAGUGACCUCUACCAUCCGAUUCAGAUCCUGGCCGAUUACCUCACCC
UGCAAGAACACUACAGCUCCCUGAAGGGUCUGACAUUGUCCUGGAUCG
GCGACGGCAACAACAUUCUCCAUUCCAUCAUGAUGUCCGCCGCAAAAU
UCGGCAUGCAUCUUCAAGCCGCCACGCCGAAGGGUUACGAGCCCGACG
CUUCCGUGACUAAGCUCGCCGAGCAGUACGCUAAGGAGAACGGAACCA
AGCUUCUGCUGACUAACGACCCACUAGAAGCAGCCCACGGGGGCAACG
UGCUUAUUACUGACACCUGGAUCUCCAUGGGCCAGGAAGAAGAGAAAA
AGAAGCGGCUGCAGGCGUUCCAGGGAUAUCAGGUCACCAUGAAAACCG
CCAAGGUCGCUGCCUCCGACUGGACCUUCCUGCACUGCCUGCCUCGCA
AGCCUGAAGAAGUGGACGACGAGGUGUUCUACUCGCCACGGAGCCUCG
UGUUCCCCGAGGCCGAGAAUAGAAAGUGGACCAUCAUGGCCGUGAUGG
UGUCACUGCUCACCGACUACAGCCCGCAGCUUCAGAAGCCCAAGUUCU
AGCUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA

-continued

UAAAAAGAAAGUUUCUUCACAUUCUAG

>mARM1899

(SEQ ID NO: 105)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGGCCUUG
UCAAUCUCCGCAUCCUCCUUAACAACGCCGCGUUUAGAAACGGCCACA
ACUUCAUGGUCCGGAACUUCAGAUGUGGCCAGCCGCUUCAAAACCGGG
UCCAGCUGAAGGGCCGGGAUCUUCUGACCCUGAAGAACUUUACUGGCG
AAGAGAUCAAGUACAUGCUCUGGCUCUCCGCGGACUUGAAGUUCCGCA
UUAAGCAGAAGGGGGAAUACCUUCCGCUGCUUCAAGGAAAGAGCCUCG
GCAUGAUCUUUGAGAAGCGCUCAACCAGGACCCGCCUUUCUACUGAAA
CUGGGUUCGCGCUGCUCGGUGGCCACCCCUGCUUCCUGACGACCCAGG
ACAUCCACCUCGGAGUGAACGAAUCCCUCACCGAUACCGCCCGGGUGU
UAUCGAGCAUGGCAGAUGCCGUGCUGGCCAGGGUGUACAAACAGUCCG
AUCUGGACACUCUGGCCAAGGAGGCGUCAAUUCCUAUUAUCAACGGCC
UUAGUGACCUCUACCAUCCGAUUCAGAUCCUGGCCGAUUACCUCACCC
UGCAAGAACACUACAGCUCCCUGAAGGGUCUGACAUUGUCCUGGAUCG
GCGACGGCAACAACAUUCUCCAUUCCAUCAUGAUGUCCGCCGCAAAAU
UCGGCAUGCAUCUUCAAGCCGCCACGCCGAAGGGUUACGAGCCCGACG
CUUCCGUGACUAAGCUCGCCGAGCAGUACGCUAAGGAGAACGGAACCA
AGCUUCUGCUGACUAACGACCCACUAGAAGCAGCCCACGGGGGCAACG
UGCUUAUUACUGACACCUGGAUCUCCAUGGGCCAGGAAGAAGAGAAAA
AGAAGCGGCUGCAGGCGUUCCAGGGAUAUCAGGUCACCAUGAAAACCG
CCAAGGUCGCUGCCUCCGACUGGACCUUCCUGCACUGCCUGCCUCGCA
AGCCUGAAGAAGUGGACGACGAGGUGUUCUACUCGCCACGGAGCCUCG
UGUUCCCCGAGGCCGAGAAUAGAAAGUGGACCAUCAUGGCCGUGAUGG
UGUCACUGCUCACCGACUACAGCCCGCAGCUUCAGAAGCCCAAGUUCU
AGCUCGAGCUAGUGACUGACUAGGAUCUGGUUACCACUAAACCAGCCU
CAAGAACACCCGAAUGGAGUCUCUAAGCUACAUAAUACCAACUUACAC
UUACAAAAUGUUGUCCCCCAAAAUGUAGCCAUUCGUAUCUGCUCCUAA
UAAAAAGAAAGUUUCUUCACAUUCUAGAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

>mARM1900

(SEQ ID NO: 106)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGGGCGGAC
UUGUCAAUCUCCGCAUCCUCCUUAACAACGCCGCGUUUAGAAACGGCC
ACAACUUCAUGGUCCGGAACUUCAGAUGUGGCCAGCCGCUUCAAAACA
AGGUCCAGCUGAAGGGCCGGGAUCUUCUGACCCUGAAGAACUUUACUG

-continued

GCGAAGAGAUCAAGUACAUGCUCUGGCUCUCCGCGGACUUGAAGUUCC
GCAUUAAGCAGAAGGGGGAAUACCUUCCGCUGCUUCAAGGAAAGAGCC
UCGGCAUGAUCUUUGAGAAGCGCUCAACCAGGACCCGCCUUUCUACUG
AAACUGGGUUCGCGCUGCUCGGUGGCCACCCCUGCUUCCUGACGACCC
AGGACAUCCACCUCGGAGUGAACGAAUCCCUCACCGAUACCGCCCGGG
UGUUAUCGAGCAUGGCAGAUGCCGUGCUGGCCAGGGUGUACAAACAGU
CCGAUCUGGACACUCUGGCCAAGGAGGCGUCAAUUCCUAUUAUCAACG
GCCUUAGUGACCUCUACCAUCCGAUUCAGAUCCUGGCCGAUUACCUCA
CCCUGCAAGAACACUACAGCUCCCUGAAGGGUCUGACAUUGUCCUGGA
UCGGCGACGGCAACAACAUUCUCCAUUCCAUCAUGAUGUCCGCCGCAA
AAUUCGGCAUGCAUCUUCAAGCCGCCACGCCGAAGGGUUACGAGCCCG
ACGCUUCCGUGACUAAGCUCGCCGAGCAGUACGCUAAGGAGAACGGAA
CCAAGCUUCUGCUGACUAACGACCCACUAGAAGCAGCCCACGGGGGCA
ACGUGCUUAUUACUGACACCUGGAUCUCCAUGGGCCAGGAAGAAGAGA
AAAAGAAGCGGCUGCAGGCGUUCCAGGGAUAUCAGGUCACCAUGAAAA
CCGCCAAGGUCGCUGCCUCCGACUGGACCUUCCUGCACUGCCUGCCUC
GCAAGCCUGAAGAAGUGGACGACGAGGUGUUCUACUCGCCACGGAGCC
UCGUGUUCCCCGAGGCCGAGAAUAGAAAGUGGACCAUCAUGGCCGUGA
UGGUGUCACUGCUCACCGACUACAGCCCGCAGCUUCAGAAGCCCAAGU
UCUAGCUCGAGCUAGUGACUGACUAGGAUCUGGUUACCACUAAACCAG
CCUCAAGAACACCCGAAUGGAGUCUCUAAGCUACAUAAUACCAACUUA
CACUUACAAAAUGUUGUCCCCCAAAAUGUAGCCAUUCGUAUCUGCUCC
UAAUAAAAAGAAAGUUUCUUCACAUUCUAG

>mARM1903

(SEQ ID NO: 107)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGGCCCUUUUCA
AUCUCCGCAUCCUCCUUAACAACGCCGCGUUUAGAAACGGCCACAACU
UCAUGGUCCGGAACUUCAGAUGUGGCCAGCCGCUUCAAGGCAAGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU

-continued

CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC
UUACACUUACAAAAUGUUGUCCCCCAAAAUGUAGCCAUUCGUAUCUGC
UCCUAAUAAAAAGAAAGUUUCUUCACAUUCUAG

>mARM1904
(SEQ ID NO: 108)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGGCCCUUUUCA
AUCUCCGCAUCCUCCUUAACAACGCCGCGUUUAGAAACGGCCACAACU
UCAUGGUCCGGAACUUCAGAUGUGGCCAGCCGCUUCAAGGCCGGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC

-continued

UUACACUUACAAAAUGUUGUCCCCCAAAAUGUAGCCAUUCGUAUCUGC
UCCUAAUAAAAAGAAAGUUUCUUCACAUUCUAG

>mARM1905
(SEQ ID NO: 109)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGGCCCUUUUCA
AUCUCCGCAUCCUCCUUAACAACGCCGCGUUUAGAAACGGCCACAACU
UCAUGGUCCGGAACUUCAGAUGUGGCCAGCCGCUUCAAGGCCGGGUCC
AGCUGAAGGGCCGGGAUCUUCUGACCCUGAAGAACUUUACUGGCGAAG
AGAUCAGGUACAUGCUCUGGCUCUCCGCGGACUUGAAGUUCCGCAUUA
AGCAGAAGGGGGAAUACCUUCCGCUGCUUCAAGGAAAGAGCCUCGGCA
UGAUCUUUGAGAAGCGCUCAACCAGGACCCGCCUUUCUACUGAAACUG
GGUUCGCGCUGCUCGGUGGCCACCCCUGCUUCCUGACGACCCAGGACA
UCCACCUCGGAGUGAACGAAUCCCUCACCGAUACCGCCCGGGUGUUAU
CGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUA
GUGACCUCUACCAUCCGAUUCAGAUCCUGGCCGAUUACCUCACCCUGC
AAGAACACUACAGCUCCCUGAAGGGUCUGACAUUGUCCUGGAUCGGCG
ACGGCAACAACAUUCUCCAUUCCAUCAUGAUGUCCGCCGCAAAAUUCG
GCAUGCAUCUUCAAGCCGCCACGCCGAAGGGUUACGAGCCCGACGCUU
CCGUGACUAAGCUCGCCGAGCAGUACGCUAAGGAGAACGGAACCAAGC
UUCUGCUGACUAACGACCCACUAGAAGCAGCCCACGGGGGCAACGUGC
UUAUUACUGACACCUGGAUCUCCAUGGGCCAGGAAGAAGAGAAAAAGA
AGCGGCUGCAGGCGUUCCAGGGAUAUCAGGUCACCAUGAAAACCGCCA
AGGUCGCUGCCUCCGACUGGACCUUCCUGCACUGCCUGCCUCGCAAGC
CUGAAGAAGUGGACGACGAGGUGUUCUACUCGCCACGGAGCCUCGUGU
UCCCCGAGGCCGAGAAUAGAAAGUGGACCAUCAUGGCCGUGAUGGUGU
CACUGCUCACCGACUACAGCCCGCAGCUUCAGAAGCCCAAGUUCUAGA
UAAGUGAACUCGAGCUAGUGACUGACUAGGAUCUGGUUACCACUAAAC
CAGCCUCAAGAACACCCGAAUGGAGUCUCUAAGCUACAUAAUACCAAC
UUACACUUACAAAAUGUUGUCCCCCAAAAUGUAGCCAUUCGUAUCUGC
UCCUAAUAAAAAGAAAGUUUCUUCACAUUCUAG

>mARM1906
(SEQ ID NO: 110)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCAUGGCCCUUGUCA
AUCUCCGCAUCCUCCUUAACAACGCCGCGUUUAGAAACGGCCACAACU
UCAUGGUCCGGAACUUCAGAUGUGGCCAGCCGCUUCAAGGCAGGGUCC
AGCUGAAGGGCCGGGAUCUUCUGACCCUGAAGAACUUUACUGGCGAAG
AGAUCAAGUACAUGCUCUGGCUCUCCGCGGACUUGAAGUUCCGCAUUA
AGCAGAAGGGGGAAUACCUUCCGCUGCUUCAAGGAAAGAGCCUCGGCA

-continued

UGAUCUUUGAGAAGCGCUCAACCAGGACCCGCCUUUCUACUGAAACUG

GGUUCGCGCUGCUCGGUGGCCACCCCUGCUUCCUGACGACCCAGGACA

UCCACCUCGGAGUGAACGAAUCCCUCACCGAUACCGCCCGGGUGUUAU

CGAGCAUGGCAGAUGCCGUGCUGGCCAGGGUGUACAAACAGUCCGAUC

UGGACACUCUGGCCAAGGAGGCGUCAAUUCCUAUUAUCAACGGCCUUA

GUGACCUCUACCAUCCGAUUCAGAUCCUGGCCGAUUACCUCACCCUGC

AAGAACACUACAGCUCCCUGAAGGGUCUGACAUUGUCCUGGAUCGGCG

ACGGCAACAACAUUCUCCAUUCCAUCAUGAUGUCCGCCGCAAAAUUCG

GCAUGCAUCUUCAAGCCGCCACGCCGAAGGGUUACGAGCCCGACGCUU

CCGUGACUAAGCUCGCCGAGCAGUACGCUAAGGAGAACGGAACCAAGC

UUCUGCUGACUAACGACCCACUAGAAGCAGCCCACGGGGGCAACGUGC

UUAUUACUGACACCUGGAUCUCCAUGGGCCAGGAAGAAGAGAAAAAGA

AGCGGCUGCAGGCGUUCCAGGGAUAUCAGGUCACCAUGAAAACCGCCA

AGGUCGCUGCCUCCGACUGGACCUUCCUGCACUGCCUGCCUCGCAAGC

CUGAAGAAGUGGACGACGAGGUGUUCUACUCGCCACGGAGCCUCGUGU

UCCCCGAGGCCGAGAAUAGAAAGUGGACCAUCAUGGCCGUGAUGGUGU

CACUGCUCACCGACUACAGCCCGCAGCUUCAGAAGCCCAAGUUCUAAG

UGAAUAGACUCGAGCUAGUGACUGACUAGGAUCUGGUUACCACUAAAC

CAGCCUCAAGAACACCCGAAUGGAGUCUCUAAGCUACAUAAUACCAAC

UUACACUUACAAAAUGUUGUCCCCCAAAAUGUAGCCAUUCGUAUCUGC

UCCUAAUAAAAAGAAAGUUUCUUCACAUUCUAG

>mARM1907

(SEQ ID NO: 111)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCAUGGCCCUUUUCA

AUCUCCGCAUCCUCCUUAACAACGCCGCGUUUAGAAACGGCCACAACU

UCAUGGUCCGGAACUUCAGAUGUGGCCAGCCGCUUCAAGUCAAGGUCC

AGCUGAAGGGCCGGGAUCUUCUGACCCUGAAGAACUUUACUGGCGAAG

AGAUCAAGUACAUGCUCUGGCUCUCCGCGGACUUGAAGUUCCGCAUUA

AGCAGAAGGGGGAAUACCUUCCGCUGCUUCAAGGAAAGAGCCUCGGCA

UGAUCUUUGAGAAGCGCUCAACCAGGACCCGCCUUUCUACUGAAACUG

GGUUCGCGCUGCUCGGUGGCCACCCCUGCUUCCUGACGACCCAGGACA

UCCACCUCGGAGUGAACGAAUCCCUCACCGAUACCGCCCGGGUGUUAU

CGAGCAUGGCAGAUGCCGUGCUGGCCAGGGUGUACAAACAGUCCGAUC

UGGACACUCUGGCCAAGGAGGCGUCAAUUCCUAUUAUCAACGGCCUUA

GUGACCUCUACCAUCCGAUUCAGAUCCUGGCCGAUUACCUCACCCUGC

AAGAACACUACAGCUCCCUGAAGGGUCUGACAUUGUCCUGGAUCGGCG

ACGGCAACAACAUUCUCCAUUCCAUCAUGAUGUCCGCCGCAAAAUUCG

GCAUGCAUCUUCAAGCCGCCACGCCGAAGGGUUACGAGCCCGACGCUU

CCGUGACUAAGCUCGCCGAGCAGUACGCUAAGGAGAACGGAACCAAGC

UUCUGCUGACUAACGACCCACUAGAAGCAGCCCACGGGGGCAACGUGC

UUAUUACUGACACCUGGAUCUCCAUGGGCCAGGAAGAAGAGAAAAAGA

AGCGGCUGCAGGCGUUCCAGGGAUAUCAGGUCACCAUGAAAACCGCCA

AGGUCGCUGCCUCCGACUGGACCUUCCUGCACUGCCUGCCUCGCAAGC

CUGAAGAAGUGGACGACGAGGUGUUCUACUCGCCACGGAGCCUCGUGU

UCCCCGAGGCCGAGAAUAGAAAGUGGACCAUCAUGGCCGUGAUGGUGU

CACUGCUCACCGACUACAGCCCGCAGCUUCAGAAGCCCAAGUUCUAGA

UAAGUGAACUCGAGCUAGUGACUGACUAGGAUCUGGUUACCACUAAAC

CAGCCUCAAGAACACCCGAAUGGAGUCUCUAAGCUACAUAAUACCAAC

UUACACUUACAAAAUGUUGUCCCCCAAAAUGUAGCCAUUCGUAUCUGC

UCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAA

>mARM1908

(SEQ ID NO: 112)

UCAACACAACAUAUACAAAACAAACGAAUCUCAAGCAAUCAAGCAUUC

UACUUCUAUUGCAGCAAUUUAAAUCAUUUCUUUUAAAGCAAAAGCAAU

UUUCUGAAAAUUUUCACCAUUUACGAACGAUAGCCAUGGCCCUUUUCA

AUCUCCGCAUCCUCCUUAACAACGCCGCGUUUAGAAACGGCCACAACU

UCAUGGUCCGGAACUUCAGAUGUGGCCAGCCGCUUCAAGUCAGGGUCC

AGCUGAAGGGCCGGGAUCUUCUGACCCUGAAGAACUUUACUGGCGAAG

AGAUCAAGUACAUGCUCUGGCUCUCCGCGGACUUGAAGUUCCGCAUUA

AGCAGAAGGGGGAAUACCUUCCGCUGCUUCAAGGAAAGAGCCUCGGCA

UGAUCUUUGAGAAGCGCUCAACCAGGACCCGCCUUUCUACUGAAACUG

GGUUCGCGCUGCUCGGUGGCCACCCCUGCUUCCUGACGACCCAGGACA

UCCACCUCGGAGUGAACGAAUCCCUCACCGAUACCGCCCGGGUGUUAU

CGAGCAUGGCAGAUGCCGUGCUGGCCAGGGUGUACAAACAGUCCGAUC

UGGACACUCUGGCCAAGGAGGCGUCAAUUCCUAUUAUCAACGGCCUUA

GUGACCUCUACCAUCCGAUUCAGAUCCUGGCCGAUUACCUCACCCUGC

AAGAACACUACAGCUCCCUGAAGGGUCUGACAUUGUCCUGGAUCGGCG

ACGGCAACAACAUUCUCCAUUCCAUCAUGAUGUCCGCCGCAAAAUUCG

GCAUGCAUCUUCAAGCCGCCACGCCGAAGGGUUACGAGCCCGACGCUU

CCGUGACUAAGCUCGCCGAGCAGUACGCUAAGGAGAACGGAACCAAGC

UUCUGCUGACUAACGACCCACUAGAAGCAGCCCACGGGGGCAACGUGC

UUAUUACUGACACCUGGAUCUCCAUGGGCCAGGAAGAAGAGAAAAAGA

AGCGGCUGCAGGCGUUCCAGGGAUAUCAGGUCACCAUGAAAACCGCCA

AGGUCGCUGCCUCCGACUGGACCUUCCUGCACUGCCUGCCUCGCAAGC

CUGAAGAAGUGGACGACGAGGUGUUCUACUCGCCACGGAGCCUCGUGU

UCCCCGAGGCCGAGAAUAGAAAGUGGACCAUCAUGGCCGUGAUGGUGU

CACUGCUCACCGACUACAGCCCGCAGCUUCAGAAGCCCAAGUUCUAGA

UAAGUGAACUCGAGCUAGUGACUGACUAGGAUCUGGUUACCACUAAAC

-continued

CAGCCUCAAGAACACCCGAAUGGAGUCUCUAAGCUACAUAAUACCAAC
UUACACUUACAAAAUGUUGUCCCCCAAAAUGUAGCCAUUCGUAUCUGC
UCCUAAUAAAAAGAAAGUUUCUUCACAUUCUAG

>mARM1915
(SEQ ID NO: 113)
GGCAGAAAAAUUUGCUACAUUGUUUCACAAACUUCAAAUAUUAUUCAU
UUAUUUAGAUCUAUUAUUACAUCAAAACAAAAAGCCGCCACCAUGCUG
UUCAACCUGCGCAUCCUGCUGAACAACGCCGCCUUCCGCAACGGCCAC
AACUUCAUGGUGCGCAACUUCCGCUGCGGCCAGCCCCUGCAGAACAAG
GUGCAGCUGAAGGGCCGCGACCUGCUGACCCUGAAGAACUUCACCGGC
GAGGAGAUCAAGUACAUGCUGUGGCUGAGCGCCGACCUGAAGUUCCGC
AUCAAGCAGAAGGGCGAGUACCUGCCCCUGCUGCAGGGCAAGAGCCUG
GGCAUGAUCUUCGAGAAGCGCAGCACCCGCACCCGCCUGAGCACCGAG
ACAGGCUUCGCCCUGCUGGGCGGCCACCCCUGCUUCCUGACCACCCAG
GACAUCCACCUGGGCGUGAACGAGAGCCUGACCGACACCGCCCGCGUG
CUGAGCAGCAUGGCCGACGCCGUGCUGGCCCGCGUGUACAAGCAGAGC
GACCUGGACACCCUGGCCAAGGAGGCCAGCAUCCCCAUCAUCAACGGC
CUGAGCGACCUGUACCACCCCAUCCAGAUCCUGGCCGACUACCUGACC
CUGCAGGAGCACUACAGCAGCCUGAAGGGCCUGACCCUGAGCUGGAUC
GGCGACGGCAACAACAUCCUGCACAGCAUCAUGAUGAGCGCCGCCAAG
UUCGGCAUGCACCUGCAGGCCGCCACCCCCAAGGGCUACGAGCCCGAC
GCCAGCGUGACCAAGCUGGCCGAGCAGUACGCCAAGGAGAACGGCACC
AAGCUGCUGCUGACCAACGACCCCCUGGAGGCCGCCCACGGCGGCAAC
GUGCUGAUCACCGACACCUGGAUCAGCAUGGGCCAGGAGGAGGAGAAG
AAGAAGCGCCUGCAGGCCUUCCAGGGCUACCAGGUGACCAUGAAGACC
GCCAAGGUGGCCGCCAGCGACUGGACCUUCCUGCACUGCCUGCCCCGC
AAGCCCGAGGAGGUGGACGACGAGGUGUUCUACAGCCCCCGCAGCCUG
GUGUUCCCCGAGGCCGAGAACCGCAAGUGGACCAUCAUGGCCGUGAUG
GUGAGCCUGCUGACCGACUACAGCCCCCAGCUGCAGAAGCCCAAGUUC
UGAGGUCUCUAGUAAUGAGCUGGAGCCUCGGUAGCCGUUCCUCCUGCC
CGCUGGGCCUCCCAACGGGCCCUCCUCCCCUCCUUGCACCGGCCCUUC
CUGGUCUUUGAAUAAAGUCUGAGUGGGCAUCUAG

>mARM1916
(SEQ ID NO: 114)
GGCAGAAAAAUUUGCUACAUUGUUUCACAAACUUCAAAUAUUAUUCAU
UUAUUUAGAUCUAUUAUUACAUCAAAACAAAAAGCCGCCACCAUGGGA
GUAUUCAACCUGCGCAUCCUGCUGAACAACGCCGCCUUCCGCAACGGC
CACAACUUCAUGGUGCGCAACUUCCGCUGCGGCCAGCCCCUGCAGAAC
AAGGUGCAGCUGAAGGGCCGCGACCUGCUGACCCUGAAGAACUUCACC
GGCGAGGAGAUCAAGUACAUGCUGUGGCUGAGCGCCGACCUGAAGUUC
CGCAUCAAGCAGAAGGGCGAGUACCUGCCCCUGCUGCAGGGCAAGAGC
CUGGGCAUGAUCUUCGAGAAGCGCAGCACCCGCACCCGCCUGAGCACC
GAGACAGGCUUCGCCCUGCUGGGCGGCCACCCCUGCUUCCUGACCACC
CAGGACAUCCACCUGGGCGUGAACGAGAGCCUGACCGACACCGCCCGC
GUGCUGAGCAGCAUGGCCGACGCCGUGCUGGCCCGCGUGUACAAGCAG
AGCGACCUGGACACCCUGGCCAAGGAGGCCAGCAUCCCCAUCAUCAAC
GGCCUGAGCGACCUGUACCACCCCAUCCAGAUCCUGGCCGACUACCUG
ACCCUGCAGGAGCACUACAGCAGCCUGAAGGGCCUGACCCUGAGCUGG
AUCGGCGACGGCAACAACAUCCUGCACAGCAUCAUGAUGAGCGCCGCC
AAGUUCGGCAUGCACCUGCAGGCCGCCACCCCCAAGGGCUACGAGCCC
GACGCCAGCGUGACCAAGCUGGCCGAGCAGUACGCCAAGGAGAACGGC
ACCAAGCUGCUGCUGACCAACGACCCCCUGGAGGCCGCCCACGGCGGC
AACGUGCUGAUCACCGACACCUGGAUCAGCAUGGGCCAGGAGGAGGAG
AAGAAGAAGCGCCUGCAGGCCUUCCAGGGCUACCAGGUGACCAUGAAG
ACCGCCAAGGUGGCCGCCAGCGACUGGACCUUCCUGCACUGCCUGCCC
CGCAAGCCCGAGGAGGUGGACGACGAGGUGUUCUACAGCCCCCGCAGC
CUGGUGUUCCCCGAGGCCGAGAACCGCAAGUGGACCAUCAUGGCCGUG
AUGGUGAGCCUGCUGACCGACUACAGCCCCCAGCUGCAGAAGCCCAAG
UUCUGAGGUCUCUAGUAAUGAGCUGGAGCCUCGGUAGCCGUUCCUCCU
GCCCGCUGGGCCUCCCAACGGGCCCUCCUCCCCUCCUUGCACCGGCCC
UUCCUGGUCUUUGAAUAAAGUCUGAGUGGGCAUCUAG

>mARM1917
(SEQ ID NO: 115)
GGCAGAAAAAUUUGCUACAUUGUUUCACAAACUUCAAAUAUUAUUCAU
UUAUUUAGAUCUAUUAUUACAUCAAAACAAAAAGCCGCCACCAUGGGA
GUAUUCAACCUGCGCAUCCUGCUGAACAACGCCGCCUUCCGCAACGGC
CACAACUUCAUGGUGCGCAACUUCCGCUGCGGCCAGCCCCUGCAGAAC
CGGGUGCAGCUGAAGGGCCGCGACCUGCUGACCCUGAAGAACUUCACC
GGCGAGGAGAUCCGGUACAUGCUGUGGCUGAGCGCCGACCUGAAGUUC
CGCAUCAAGCAGAAGGGCGAGUACCUGCCCCUGCUGCAGGGCAAGAGC
CUGGGCAUGAUCUUCGAGAAGCGCAGCACCCGCACCCGCCUGAGCACC
GAGACAGGCUUCGCCCUGCUGGGCGGCCACCCCUGCUUCCUGACCACC
CAGGACAUCCACCUGGGCGUGAACGAGAGCCUGACCGACACCGCCCGC
GUGCUGAGCAGCAUGGCCGACGCCGUGCUGGCCCGCGUGUACAAGCAG
AGCGACCUGGACACCCUGGCCAAGGAGGCCAGCAUCCCCAUCAUCAAC
GGCCUGAGCGACCUGUACCACCCCAUCCAGAUCCUGGCCGACUACCUG
ACCCUGCAGGAGCACUACAGCAGCCUGAAGGGCCUGACCCUGAGCUGG
AUCGGCGACGGCAACAACAUCCUGCACAGCAUCAUGAUGAGCGCCGCC
AAGUUCGGCAUGCACCUGCAGGCCGCCACCCCCAAGGGCUACGAGCCC
GACGCCAGCGUGACCAAGCUGGCCGAGCAGUACGCCAAGGAGAACGGC
ACCAAGCUGCUGCUGACCAACGACCCCCUGGAGGCCGCCCACGGCGGC
AACGUGCUGAUCACCGACACCUGGAUCAGCAUGGGCCAGGAGGAGGAG
AAGAAGAAGCGCCUGCAGGCCUUCCAGGGCUACCAGGUGACCAUGAAG
ACCGCCAAGGUGGCCGCCAGCGACUGGACCUUCCUGCACUGCCUGCCC

-continued

CGCAAGCCCGAGGAGGUGGACGACGAGGUGUUCUACAGCCCCCGCAGC
CUGGUGUUCCCCGAGGCCGAGAACCGCAAGUGGACCAUCAUGGCCGUG
AUGGUGAGCCUGCUGACCGACUACAGCCCCCAGCUGCAGAAGCCCAAG
UUCUGAGGUCUCUAGUAAUGAGCUGGAGCCUCGGUAGCCGUUCCUCCU
GCCCGCUGGGCCUCCCAACGGGCCCUCCUCCCCUCCUUGCACCGGCCC
UUCCUGGUCUUUGAAUAAAGUCUGAGUGGGCAUCUAG

>mARM1918

(SEQ ID NO: 116)

GGCAGAAAAAUUUGCUACAUUGUUUCACAAACUUCAAAUAUUAUUCAU
UUAUUUAGAUCUAUUAUUACAUCAAAACAAAAAGCCGCCACCAUGCUG
GUAUUCAACCUGCGCAUCCUGCUGAACAACGCCGCCUUCCGCAACGGC
CACAACUUCAUGGUGCGCAACUUCCGCUGCGGCCAGCCCCUGCAGAAC
CGGGUGCAGCUGAAGGGCCGCGACCUGCUGACCCUGAAGAACUUCACC
GGCGAGGAGAUCCGGUACAUGCUGUGGCUGAGCGCCGACCUGAAGUUC
CGCAUCAAGCAGAAGGGCGAGUACCUGCCCCUGCUGCAGGGCAAGAGC
CUGGGCAUGAUCUUCGAGAAGCGCAGCACCCGCACCCGCCUGAGCACC
GAGACAGGCUUCGCCCUGCUGGGCGGCCACCCCUGCUUCCUGACCACC
CAGGACAUCCACCUGGGCGUGAACGAGAGCCUGACCGACACCGCCCGC
GUGCUGAGCAGCAUGGCCGACGCCGUGCUGGCCCGCGUGUACAAGCAG
AGCGACCUGGACACCCUGGCCAAGGAGGCCAGCAUCCCCAUCAUCAAC
GGCCUGAGCGACCUGUACCACCCCAUCCAGAUCCUGGCCGACUACCUG
ACCCUGCAGGAGCACUACAGCAGCCUGAAGGGCCUGACCCUGAGCUGG
AUCGGCGACGGCAACAACAUCCUGCACAGCAUCAUGAUGAGCGCCGCC
AAGUUCGGCAUGCACCUGCAGGCCGCCACCCCCAAGGGCUACGAGCCC
GACGCCAGCGUGACCAAGCUGGCCGAGCAGUACGCCAAGGAGAACGGC
ACCAAGCUGCUGCUGACCAACGACCCCCUGGAGGCCGCCCACGGCGGC
AACGUGCUGAUCACCGACACCUGGAUCAGCAUGGGCCAGGAGGAGGAG
AAGAAGAAGCGCCUGCAGGCCUUCCAGGGCUACCAGGUGACCAUGAAG
ACCGCCAAGGUGGCCGCCAGCGACUGGACCUUCCUGCACUGCCUGCCC
CGCAAGCCCGAGGAGGUGGACGACGAGGUGUUCUACAGCCCCCGCAGC
CUGGUGUUCCCCGAGGCCGAGAACCGCAAGUGGACCAUCAUGGCCGUG
AUGGUGAGCCUGCUGACCGACUACAGCCCCCAGCUGCAGAAGCCCAAG
UUCUGAGGUCUCUAGUAAUGAGCUGGAGCCUCGGUAGCCGUUCCUCCU
GCCCGCUGGGCCUCCCAACGGGCCCUCCUCCCCUCCUUGCACCGGCCC
UUCCUGGUCUUUGAAUAAAGUCUGAGUGGGCAUCUAG

>mARM1919

(SEQ ID NO: 117)

AUUAUUACAUCAAAACAAAAAGCCGCCACCAUGGGAGUAUUCAACCUG
CGCAUCCUGCUGAACAACGCCGCCUUCCGCAACGGCCACAACUUCAUG
GUGCGCAACUUCCGCUGCGGCCAGCCCCUGCAGAACAAGGUGCAGCUG
AAGGGCCGCGACCUGCUGACCCUGAAGAACUUCACCGGCGAGGAGAUC
AAGUACAUGCUGUGGCUGAGCGCCGACCUGAAGUUCCGCAUCAAGCAG

-continued

AAGGGCGAGUACCUGCCCCUGCUGCAGGGCAAGAGCCUGGGCAUGAUC
UUCGAGAAGCGCAGCACCCGCACCCGCCUGAGCACCGAGACAGGCUUC
GCCCUGCUGGGCGGCCACCCCUGCUUCCUGACCACCCAGGACAUCCAC
CUGGGCGUGAACGAGAGCCUGACCGACACCGCCCGCGUGCUGAGCAGC
AUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGAC
CUGUACCACCCCAUCCAGAUCCUGGCCGACUACCUGACCCUGCAGGAG
CACUACAGCAGCCUGAAGGGCCUGACCCUGAGCUGGAUCGGCGACGGC
AACAACAUCCUGCACAGCAUCAUGAUGAGCGCCGCCAAGUUCGGCAUG
CACCUGCAGGCCGCCACCCCCAAGGGCUACGAGCCCGACGCCAGCGUG
ACCAAGCUGGCCGAGCAGUACGCCAAGGAGAACGGCACCAAGCUGCUG
CUGACCAACGACCCCCUGGAGGCCGCCCACGGCGGCAACGUGCUGAUC
ACCGACACCUGGAUCAGCAUGGGCCAGGAGGAGGAGAAGAAGAAGCGC
CUGCAGGCCUUCCAGGGCUACCAGGUGACCAUGAAGACCGCCAAGGUG
GCCGCCAGCGACUGGACCUUCCUGCACUGCCUGCCCCGCAAGCCCGAG
GAGGUGGACGACGAGGUGUUCUACAGCCCCCGCAGCCUGGUGUUCCCC
GAGGCCGAGAACCGCAAGUGGACCAUCAUGGCCGUGAUGGUGAGCCUG
CUGACCGACUACAGCCCCCAGCUGCAGAAGCCCAAGUUCUGAGGUCUC
UAGUAAUGAGCUGGAGCCUCGGUAGCCGUUCCUCCUGCCCGCUGGGCC
UCCCAACGGGCCCUCCUCCCCUCCUUGCACCGGCCCUUCCUGGUCUUU
GAAUAAAGUCUGAGUGGGCAUCUAG

>mARM1920

(SEQ ID NO: 118)

AUUAUUACAUCAAAACAAAAAGCCGCCACCAUGGGAGUAUUCAACCUG
CGCAUCCUGCUGAACAACGCCGCCUUCCGCAACGGCCACAACUUCAUG
GUGCGCAACUUCCGCUGCGGCCAGCCCCUGCAGAACCGGGUGCAGCUG
AAGGGCCGCGACCUGCUGACCCUGAAGAACUUCACCGGCGAGGAGAUC
CGGUACAUGCUGUGGCUGAGCGCCGACCUGAAGUUCCGCAUCAAGCAG
AAGGGCGAGUACCUGCCCCUGCUGCAGGGCAAGAGCCUGGGCAUGAUC
UUCGAGAAGCGCAGCACCCGCACCCGCCUGAGCACCGAGACAGGCUUC
GCCCUGCUGGGCGGCCACCCCUGCUUCCUGACCACCCAGGACAUCCAC
CUGGGCGUGAACGAGAGCCUGACCGACACCGCCCGCGUGCUGAGCAGC
AUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGAC
CUGUACCACCCCAUCCAGAUCCUGGCCGACUACCUGACCCUGCAGGAG
CACUACAGCAGCCUGAAGGGCCUGACCCUGAGCUGGAUCGGCGACGGC
AACAACAUCCUGCACAGCAUCAUGAUGAGCGCCGCCAAGUUCGGCAUG
CACCUGCAGGCCGCCACCCCCAAGGGCUACGAGCCCGACGCCAGCGUG
ACCAAGCUGGCCGAGCAGUACGCCAAGGAGAACGGCACCAAGCUGCUG
CUGACCAACGACCCCCUGGAGGCCGCCCACGGCGGCAACGUGCUGAUC
ACCGACACCUGGAUCAGCAUGGGCCAGGAGGAGGAGAAGAAGAAGCGC
CUGCAGGCCUUCCAGGGCUACCAGGUGACCAUGAAGACCGCCAAGGUG

-continued

GCCGCCAGCGACUGGACCUUCCUGCACUGCCUGCCCCGCAAGCCCGAG
GAGGUGGACGACGAGGUGUUCUACAGCCCCCGCAGCCUGGUGUUCCCC
GAGGCCGAGAACCGCAAGUGGACCAUCAUGGCCGUGAUGGUGAGCCUG
CUGACCGACUACAGCCCCCAGCUGCAGAAGCCCAAGUUCUGAGGUCUC
UAGUAAUGAGCUGGAGCCUCGGUAGCCGUUCCUCCUGCCCGCUGGGCC
UCCCAACGGGCCCUCCUCCCCUCCUUGCACCGGCCCUUCCUGGUCUUU
GAAUAAAGUCUGAGUGGGCAUCUAG

>mARM1921

(SEQ ID NO: 119)

AUUAUUACAUCAAAACAAAAAGCCGCCACCAUGCUGGUAUUCAACCUG
CGCAUCCUGCUGAACAACGCCGCCUUCCGCAACGGCCACAACUUCAUG
GUGCGCAACUUCCGCUGCGGCCAGCCCCUGCAGAACCGGGUGCAGCUG
AAGGGCCGCGACCUGCUGACCCUGAAGAACUUCACCGGCGAGGAGAUC
CGGUACAUGCUGUGGCUGAGCGCCGACCUGAAGUUCCGCAUCAAGCAG
AAGGGCGAGUACCUGCCCCUGCUGCAGGGCAAGAGCCUGGGCAUGAUC
UUCGAGAAGCGCAGCACCCGCACCCGCCUGAGCACCGAGACAGGCUUC
GCCCUGCUGGGCGGCCACCCCUGCUUCCUGACCACCCAGGACAUCCAC
CUGGGCGUGAACGAGAGCCUGACCGACACCGCCCGCGUGCUGAGCAGC
AUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGAC
CUGUACCACCCCAUCCAGAUCCUGGCCGACUACCUGACCCUGCAGGAG
CACUACAGCAGCCUGAAGGGCCUGACCCUGAGCUGGAUCGGCGACGGC
AACAACAUCCUGCACAGCAUCAUGAUGAGCGCCGCCAAGUUCGGCAUG
CACCUGCAGGCCGCCACCCCCAAGGGCUACGAGCCCGACGCCAGCGUG
ACCAAGCUGGCCGAGCAGUACGCCAAGGAGAACGGCACCAAGCUGCUG
CUGACCAACGACCCCCUGGAGGCCGCCCACGGCGGCAACGUGCUGAUC
ACCGACACCUGGAUCAGCAUGGGCCAGGAGGAGGAGAAGAAGAAGCGC
CUGCAGGCCUUCCAGGGCUACCAGGUGACCAUGAAGACCGCCAAGGUG
GCCGCCAGCGACUGGACCUUCCUGCACUGCCUGCCCCGCAAGCCCGAG
GAGGUGGACGACGAGGUGUUCUACAGCCCCCGCAGCCUGGUGUUCCCC
GAGGCCGAGAACCGCAAGUGGACCAUCAUGGCCGUGAUGGUGAGCCUG
CUGACCGACUACAGCCCCCAGCUGCAGAAGCCCAAGUUCUGAGGUCUC
UAGUAAUGAGCUGGAGCCUCGGUAGCCGUUCCUCCUGCCCGCUGGGCC
UCCCAACGGGCCCUCCUCCCCUCCUUGCACCGGCCCUUCCUGGUCUUU
GAAUAAAGUCUGAGUGGGCAGCAUCUAG

>mARM1925

(SEQ ID NO: 120)

UCAACACAACAUAUACAAAACAAACGAAUCUCAAGCAAUCAAGCAUUC
UACUUCUAUUGCAGCAAUUUAAAUCAUUUCUUUUAAAGCAAAAGCAAU
UUUCUGAAAAUUUUCACCAUUUACGAACGAUAGCCACCAUGUUGUUCA
ACUUGAGGAUCUUGUUGAACAACGCCGCCUUCAGGAACGGACACAACU
UCAUGGUAAGGAACUUCAGGUGCGGACAGCCCUUGCAGAACAAAGUAC

-continued

AGUUGAAAGGAAGGGACUUGUUGACAUUGAAAAACUUCACAGGAGAAG
AAAUCAAAUACAUGUUGUGGUUGUCGGCCGACUUGAAAUUCAGGAUCA
AACAGAAAGGAGAAUACUUGCCCUUGUUGCAGGGAAAAUCGUUGGGAA
UGAUCUUCGAAAAAAGGUCGACAAGGACAAGGUUGUCGACAGAAACAG
GAUUCGCCUUGUUGGGAGGACACCCCUGCUUCUUGACAACACAGGACA
UCCACUUGGGAGUAAACGAAUCGUUGACAGACACAGCCAGGGUAUUGU
CGUCGAUGGCCGACGCCGUAUUGGCCAGGGUAUACAAACAGUCGGACU
UGGACACAUUGGCCAAAGAAGCCUCGAUCCCCAUCAUCAACGGAUUGU
CGGACUUGUACCACCCCAUCCAGAUCUUGGCCGACUACUUGACAUUGC
AGGAACACUACUCGUCGUUGAAAGGAUUGACAUUGUCGUGGAUCGGAG
ACGGAAACAACAUCUUGCACUCGAUCAUGAUGUCGGCCGCCAAAUUCG
GAAUGCACUUGCAGGCCGCCACACCCAAAGGAUACGAACCCGACGCCU
CGGUAACAAAAUUGGCCGAACAGUACGCCAAAGAAAACGGAACAAAAU
UGUUGUUGACAAACGACCCCUUGGAAGCCGCCCACGGAGGAAACGUAU
UGAUCACAGACACAUGGAUCUCGAUGGGACAGGAAGAAGAAAAAAAAA
AAAGGUUGCAGGCCUUCCAGGGAUACCAGGUAACAAUGAAAACAGCCA
AAGUAGCCGCCUCGGACUGGACAUUCUUGCACUGCUUGCCCAGGAAAC
CCGAAGAAGUAGACGACGAAGUAUUCUACUCGCCCAGGUCGUUGGUAU
UCCCCGAAGCCGAAAACAGGAAAUGGACAAUCAUGGCCGUAAUGGUAU
CGUUGUUGACAGACUACUCGCCCCAGUUGCAGAAACCCAAAUUCUGAA
UAGUGAACUCGAGCUAGUGACUGACUAGGAUCUGGUUACCACUAAACC
AGCCUCAAGAACACCCGAAUGGAGUCUCUAAGCUACAUAAUACCAACU
UACACUUACAAAAUGUUGUCCCCCAAAAUGUAGCCAUUCGUAUCUGCU
CCUAAUAAAAAGAAAGUUUCUUCACAUUCUAG

>mARM1926

(SEQ ID NO: 121)

AUUAUUACAUCAAAACAAAAAGCCGCCACCAUGCUGUUCAACCUGCGC
AUCCUGCUGAACAACGCCGCCUUCCGCAACGGCCACAACUUCAUGGUG
CGCAACUUCCGCUGCGGCCAGCCCCUGCAGGGCAAGGUGCAGCUGAAG
GGCCGCGACCUGCUGACCCUGAAGAACUUCACCGGCGAGGAGAUCAAG
UACAUGCUGUGGCUGAGCGCCGACCUGAAGUUCCGCAUCAAGCAGAAG
GGCGAGUACCUGCCCCUGCUGCAGGGCAAGAGCCUGGGCAUGAUCUUC
GAGAAGCGCAGCACCCGCACCCGCCUGAGCACCGAGACAGGCUUCGCC
CUGCUGGGCGGCCACCCCUGCUUCCUGACCACCCAGGACAUCCACCUG
GGCGUGAACGAGAGCCUGACCGACACCGCCCGCGUGCUGAGCAGCAUG
GCCGACGCCGUGCUGGCCCGCGUGUACAAGCAGAGCGACCUGGACACC
CUGGCCAAGGAGGCCAGCAUCCCCAUCAUCAACGGCCUGAGCGACCUG
UACCACCCCAUCCAGAUCCUGGCCGACUACCUGACCCUGCAGGAGCAC
UACAGCAGCCUGAAGGGCCUGACCCUGAGCUGGAUCGGCGACGGCAAC
AACAUCCUGCACAGCAUCAUGAUGAGCGCCGCCAAGUUCGGCAUGCAC
CUGCAGGCCGCCACCCCCAAGGGCUACGAGCCCGACGCCAGCGUGACC
AAGCUGGCCGAGCAGUACGCCAAGGAGAACGGCACCAAGCUGCUGCUG

ACCAACGACCCCCUGGAGGCCGCCCACGGCGGCAACGUGCUGAUCACC

GACACCUGGAUCAGCAUGGGCCAGGAGGAGGAGAAGAAGAAGCGCCUG

CAGGCCUUCCAGGGCUACCAGGUGACCAUGAAGACCGCCAAGGUGGCC

GCCAGCGACUGGACCUUCCUGCACUGCCUGCCCCGCAAGCCCGAGGAG

GUGGACGACGAGGUGUUCUACAGCCCCCGCAGCCUGGUGUUCCCCGAG

GCCGAGAACCGCAAGUGGACCAUCAUGGCCGUGAUGGUGAGCCUGCUG

ACCGACUACAGCCCCCAGCUGCAGAAGCCCAAGUUCUGAGGUCUCUAG

UAAUGAGCUGGAGCCUCGGUAGCCGUUCCUCCUGCCCGCUGGGCCUCC

CAACGGGCCCUCCUCCCCUCCUUGCACCGGCCCUUCCUGGUCUUUGAA

UAAAGUCUGAGUGGGCAUCUAG

>mARM1927

(SEQ ID NO: 122)

AUUAUUACAUCAAAACAAAAAGCCGCCACCAUGCUGUUCAACCUGCGC

AUCCUGCUGAACAACGCCGCCUUCCGCAACGGCCACAACUUCAUGGUG

CGCAACUUCCGCUGCGGCCAGCCCCUGCAGGGCCGGGUGCAGCUGAAG

GGCCGCGACCUGCUGACCCUGAAGAACUUCACCGGCGAGGAGAUCAAG

UACAUGCUGUGGCUGAGCGCCGACCUGAAGUUCCGCAUCAAGCAGAAG

GGCGAGUACCUGCCCCUGCUGCAGGGCAAGAGCCUGGGCAUGAUCUUC

GAGAAGCGCAGCACCCGCACCCGCCUGAGCACCGAGACAGGCUUCGCC

CUGCUGGGCGGCCACCCCUGCUUCCUGACCACCCAGGACAUCCACCUG

GGCGUGAACGAGAGCCUGACCGACACCGCCCGCGUGCUGAGCAGCAUG

GCCGACGCCGUGCUGGCCCGCGUGUACAAGCAGAGCGACCUGGACACC

CUGGCCAAGGAGGCCAGCAUCCCCAUCAUCAACGGCCUGAGCGACCUG

UACCACCCCAUCCAGAUCCUGGCCGACUACCUGACCCUGCAGGAGCAC

UACAGCAGCCUGAAGGGCCUGACCCUGAGCUGGAUCGGCGACGGCAAC

AACAUCCUGCACAGCAUCAUGAUGAGCGCCGCCAAGUUCGGCAUGCAC

CUGCAGGCCGCCACCCCCAAGGGCUACGAGCCCGACGCCAGCGUGACC

AAGCUGGCCGAGCAGUACGCCAAGGAGAACGGCACCAAGCUGCUGCUG

ACCAACGACCCCCUGGAGGCCGCCCACGGCGGCAACGUGCUGAUCACC

GACACCUGGAUCAGCAUGGGCCAGGAGGAGGAGAAGAAGAAGCGCCUG

CAGGCCUUCCAGGGCUACCAGGUGACCAUGAAGACCGCCAAGGUGGCC

GCCAGCGACUGGACCUUCCUGCACUGCCUGCCCCGCAAGCCCGAGGAG

GUGGACGACGAGGUGUUCUACAGCCCCCGCAGCCUGGUGUUCCCCGAG

GCCGAGAACCGCAAGUGGACCAUCAUGGCCGUGAUGGUGAGCCUGCUG

ACCGACUACAGCCCCCAGCUGCAGAAGCCCAAGUUCUGAGGUCUCUAG

UAAUGAGCUGGAGCCUCGGUAGCCGUUCCUCCUGCCCGCUGGGCCUCC

CAACGGGCCCUCCUCCCCUCCUUGCACCGGCCCUUCCUGGUCUUUGAA

UAAAGUCUGAGUGGGCAUCUAG

>mARM1928

(SEQ ID NO: 123)

AUUAUUACAUCAAAACAAAAAGCCGCCACCAUGCUGUUCAACCUGCGC

AUCCUGCUGAACAACGCCGCCUUCCGCAACGGCCACAACUUCAUGGUG

CGCAACUUCCGCUGCGGCCAGCCCCUGCAGGGCCGGGUGCAGCUGAAG

GGCCGCGACCUGCUGACCCUGAAGAACUUCACCGGCGAGGAGAUCCGG

UACAUGCUGUGGCUGAGCGCCGACCUGAAGUUCCGCAUCAAGCAGAAG

GGCGAGUACCUGCCCCUGCUGCAGGGCAAGAGCCUGGGCAUGAUCUUC

GAGAAGCGCAGCACCCGCACCCGCCUGAGCACCGAGACAGGCUUCGCC

CUGCUGGGCGGCCACCCCUGCUUCCUGACCACCCAGGACAUCCACCUG

GGCGUGAACGAGAGCCUGACCGACACCGCCCGCGUGCUGAGCAGCAUG

GCCGACGCCGUGCUGGCCCGCGUGUACAAGCAGAGCGACCUGGACACC

CUGGCCAAGGAGGCCAGCAUCCCCAUCAUCAACGGCCUGAGCGACCUG

UACCACCCCAUCCAGAUCCUGGCCGACUACCUGACCCUGCAGGAGCAC

UACAGCAGCCUGAAGGGCCUGACCCUGAGCUGGAUCGGCGACGGCAAC

AACAUCCUGCACAGCAUCAUGAUGAGCGCCGCCAAGUUCGGCAUGCAC

CUGCAGGCCGCCACCCCCAAGGGCUACGAGCCCGACGCCAGCGUGACC

AAGCUGGCCGAGCAGUACGCCAAGGAGAACGGCACCAAGCUGCUGCUG

ACCAACGACCCCCUGGAGGCCGCCCACGGCGGCAACGUGCUGAUCACC

GACACCUGGAUCAGCAUGGGCCAGGAGGAGGAGAAGAAGAAGCGCCUG

CAGGCCUUCCAGGGCUACCAGGUGACCAUGAAGACCGCCAAGGUGGCC

GCCAGCGACUGGACCUUCCUGCACUGCCUGCCCCGCAAGCCCGAGGAG

GUGGACGACGAGGUGUUCUACAGCCCCCGCAGCCUGGUGUUCCCCGAG

GCCGAGAACCGCAAGUGGACCAUCAUGGCCGUGAUGGUGAGCCUGCUG

ACCGACUACAGCCCCCAGCUGCAGAAGCCCAAGUUCUGAGGUCUCUAG

UAAUGAGCUGGAGCCUCGGUAGCCGUUCCUCCUGCCCGCUGGGCCUCC

CAACGGGCCCUCCUCCCCUCCUUGCACCGGCCCUUCCUGGUCUUUGAA

UAAAGUCUGAGUGGGCAUCUAG

>mARM1929

(SEQ ID NO: 124)

GGCAGAAAAAUUUGCUACAUUGUUUCACAAACUUCAAAUAUUAUUCAU

UUAUUUAGAUCUAUUAUUACAUCAAAACAAAAAGCCGCCACCAUGCUG

UUCAACCUGCGCAUCCUGCUGAACAACGCCGCCUUCCGCAACGGCCAC

AACUUCAUGGUGCGCAACUUCCGCUGCGGCCAGCCCCUGCAGGGCAAG

GUGCAGCUGAAGGGCCGCGACCUGCUGACCCUGAAGAACUUCACCGGC

GAGGAGAUCAAGUACAUGCUGUGGCUGAGCGCCGACCUGAAGUUCCGC

AUCAAGCAGAAGGGCGAGUACCUGCCCCUGCUGCAGGGCAAGAGCCUG

GGCAUGAUCUUCGAGAAGCGCAGCACCCGCACCCGCCUGAGCACCGAG

ACAGGCUUCGCCCUGCUGGGCGGCCACCCCUGCUUCCUGACCACCCAG

GACAUCCACCUGGGCGUGAACGAGAGCCUGACCGACACCGCCCGCGUG

CUGAGCAGCAUGGCCGACGCCGUGCUGGCCCGCGUGUACAAGCAGAGC

GACCUGGACACCCUGGCCAAGGAGGCCAGCAUCCCCAUCAUCAACGGC

CUGAGCGACCUGUACCACCCCAUCCAGAUCCUGGCCGACUACCUGACC

CUGCAGGAGCACUACAGCAGCCUGAAGGGCCUGACCCUGAGCUGGAUC

GGCGACGGCAACAACAUCCUGCACAGCAUCAUGAUGAGCGCCGCCAAG

UUCGGCAUGCACCUGCAGGCCGCCACCCCCAAGGGCUACGAGCCCGAC

-continued

GCCAGCGUGACCAAGCUGGCCGAGCAGUACGCCAAGGAGAACGGCACC

AAGCUGCUGCUGACCAACGACCCCCUGGAGGCCGCCCACGGCGGCAAC

GUGCUGAUCACCGACACCUGGAUCAGCAUGGGCCAGGAGGAGGAGAAG

AAGAAGCGCCUGCAGGCCUUCCAGGGCUACCAGGUGACCAUGAAGACC

GCCAAGGUGGCCGCCAGCGACUGGACCUUCCUGCACUGCCUGCCCCGC

AAGCCCGAGGAGGUGGACGACGAGGUGUUCUACAGCCCCCGCAGCCUG

GUGUUCCCCGAGGCCGAGAACCGCAAGUGGACCAUCAUGGCCGUGAUG

GUGAGCCUGCUGACCGACUACAGCCCCCAGCUGCAGAAGCCCAAGUUC

UGAGGUCUCUAGUAAUGAGCUGGAGCCUCGGUAGCCGUUCCUCCUGCC

CGCUGGGCCUCCCAACGGGCCCUCCUCCCCUCCUUGCACCGGCCCUUC

CUGGUCUUUGAAUAAAGUCUGAGUGGGCAUCUAG

AT1G67090>

(SEQ ID NO: 125)

CACAAAGAGUAAAGAAGAACA

AT1G35720>

(SEQ ID NO: 126)

AACACUAAAAGUAGAAGAAAA

AT5G45900>

(SEQ ID NO: 127)

CUCAGAAAGAUAAGAUCAGCC

>pARM563

(SEQ ID NO: 128)

ATGCTGTTTAATCTGAGGATCCTGTTAAACAATGCAGCTTTTAGAAAT

GGTCACAACTTCATGGTTCGAAATTTTCGGTGTGGACAACCACTACAA

AATAAAGTGCAGCTGAAGGGCCGTGACCTTCTCACTCTAAAAAACTTT

ACCGGAGAAGAAATTAAATATATGCTATGGCTATCAGCAGATCTGAAA

TTTAGGATAAAACAGAAAGGAGAGTATTTGCCTTTATTGCAAGGGAAG

TCCTTAGGCATGATTTTTGAGAAAAGAAGTACTCGAACAAGATTGTCT

ACAGAAACAGGCTTTGCACTTCTGGGAGGACATCCTTGTTTTCTTACC

ACACAAGATATTCATTTGGGTGTGAATGAAAGTCTCACGGACACGGCC

CGTGTATTGTCTAGCATGGCAGATGCAGTATTGGCTCGAGTGTATAAA

CAATCAGATTTGGACACCCTGGCTAAAGAAGCATCCATCCCAATTATC

AATGGGCTGTCAGATTTGTACCATCCTATCCAGATCCTGGCTGATTAC

CTCACGCTCCAGGAACACTATAGCTCTCTGAAAGGTCTTACCCTCAGC

TGGATCGGGGATGGGAACAATATCCTGCACTCCATCATGATGAGCGCA

GCGAAATTCGGAATGCACCTTCAGGCAGCTACTCCAAAGGGTTATGAG

CCGGATGCTAGTGTAACCAAGTTGGCAGAGCAGTATGCCAAAGAGAAT

GGTACCAAGCTGTTGCTGACAAATGATCCATTGGAAGCAGCGCATGGA

GGCAATGTATTAATTACAGACACTTGGATAAGCATGGGACAAGAAGAG

GAGAAGAAAAAGCGGCTCCAGGCTTTCCAAGGTTACCAGGTTACAATG

AAGACTGCTAAAGTTGCTGCCTCTGACTGGACATTTTTACACTGCTTG

CCCAGAAAGCCAGAAGAAGTGGATGATGAAGTCTTTTATTCTCCTCGA

TCACTAGTGTTCCCAGAGGCAGAAAACAGAAAGTGGACAATCATGGCT

GTCATGGTGTCCCTGCTGACAGATTACTCACCTCAGCTCCAGAAGCCT

AAATTTTGA

>pARM564

(SEQ ID NO: 129)

ATGCTCTTTAATCTGCGCATCTTACTGAACAACGCCGCATTCCGGAAC

GGTCACAACTTCATGGTCCGCAATTTCCGCTGTGGCCAGCCGCTTCAA

AACAAGGTCCAGCTGAAGGGACGGGATCTGCTGACACTGAAGAACTTC

ACCGGAGAAGAGATCAAGTACATGCTGTGGCTCAGCGCAGACTTGAAG

TTCCGGATCAAGCAGAAGGGAGAATACTTGCCCCTGCTGCAAGGAAAG

TCGCTGGGAATGATTTTTGAGAAGCGGTCAACTCGCACCAGACTCTCC

ACCGAAACTGGTTTCGCACTGCTTGGCGGGCACCCTTGCTTCCTGACG

ACTCAGGACATCCACCTCGGCGTGAACGAATCGCTAACCGATACCGCC

AGAGTGCTTTCTTCCATGGCCGACGCGGTGCTGGCCAGGGTGTACAAG

CAGTCCGACCTCGATACCTTGGCAAAGGAGGCTTCCATTCCCATCATC

AACGGCCTGAGCGACCTGTACCACCCAATCCAAATCCTGGCTGACTAC

CTGACCCTGCAAGAGCACTACAGCAGCCTGAAGGGTCTGACCCTGTCA

TGGATTGGCGATGGAAACAATATTCTGCACTCCATCATGATGTCCGCC

GCGAAGTTCGGAATGCATCTGCAAGCCGCCACTCCAAAAGGATACGAA

CCGGATGCGTCCGTGACCAAGTTGGCGGAACAGTACGCGAAGGAGAAC

GGAACCAAGCTTCTGCTGACTAACGACCCCCTCGAGGCTGCGCATGGG

GGCAACGTGCTGATTACCGACACCTGGATCTCCATGGGGCAGGAGGAA

GAGAAGAAGAAGAGACTGCAGGCATTCCAGGGGTACCAGGTCACCATG

AAAACCGCAAAAGTGGCAGCTTCGGACTGGACTTTCCTGCATTGCCTG

CCGAGGAAGCCGGAGGAAGTCGACGACGAAGTGTTCTACTCGCCTCGG

TCCCTGGTGTTCCCCGAGGCCGAAAACCGGAAGTGGACCATCATGGCC

GTGATGGTGTCCTTGCTGACTGACTATAGCCCGCAGCTGCAGAAGCCT

AAGTTCTAG

>pARM565

(SEQ ID NO: 130)

ATGCTGTTTAACCTACGTATTTTGCTCAACAATGCAGCCTTTAGAAAC

GGACATAACTTTATGGTTCGAAACTTTCGCTGCGGGCAGCCACTGCAG

AACAAGGTCCAGCTGAAAGGGAGAGATTTGCTCACGCTGAAGAACTTT

ACTGGCGAAGAAATCAAGTATATGCTGTGGTTGTCCGCGGACCTCAAG

TTTCGGATTAAGCAGAAAGGGGAGTATCTGCCACTGCTGCAAGGAAAG

AGCCTCGGCATGATCTTCGAGAAGCGGAGCACTCGGACCAGGCTGAGT

ACCGAAACTGGCTTCGCATTGTTGGGTGGACATCCATGTTTTCTGACA

ACGCAGGACATTCATCTGGGCGTGAACGAGAGTCTGACGGACACAGCT

CGCGTTCTGTCCTCTATGGCTGATGCGGTGTTGGCCCGGGTCTATAAG

CAGTCCGATTTGGACACCTTGGCTAAGGAAGCTAGCATACCGATTATC

AATGGGCTGTCCGACCTGTATCACCCTATTCAAATCCTGGCCGACTAC

CTCACACTGCAAGAACACTATAGCTCATTGAAGGGACTGACCCTGAGC

TGGATAGGGGACGGAAACAACATCCTACATAGCATTATGATGTCCGCT

-continued

GCCAAGTTTGGCATGCATCTTCAAGCCGCCACGCCAAAGGGTTATGAG

CCCGACGCGTCAGTGACAAAGCTGGCCGAGCAGTACGCTAAGGAGAAT

GGTACCAAATTACTGCTGACTAATGATCCACTGGAGGCTGCACATGGC

GGCAATGTACTGATCACCGACACATGGATCTCGATGGGCCAGGAGGAA

GAAAAGAAGAAGAGGCTTCAGGCCTTCCAAGGCTACCAGGTCACCATG

AAAACAGCTAAGGTTGCAGCATCTGATTGGACCTTTCTGCACTGTCTG

CCAAGGAAGCCCGAAGAGGTGGACGATGAAGTATTCTATAGCCCACGG

AGTTTGGTGTTCCCTGAGGCTGAAAATAGGAAGTGGACAATTATGGCC

GTAATGGTGTCCCTGTTAACCGACTACTCTCCGCAACTGCAGAAACCT

AAGTTTTAG

>pARM566

(SEQ ID NO: 131)

ATGCTGTTTAACTTAAGGATCCTGCTGAACAACGCCGCTTTTCGTAAC

GGTCATAACTTTATGGTCCGGAACTTTAGATGTGGCCAGCCGCTGCAG

AACAAGGTTCAGCTGAAGGGGAGGGATCTGCTGACCTTGAAGAACTTT

ACCGGCGAAGAGATCAAGTACATGTTGTGGCTGAGCGCCGATCTGAAG

TTTAGGATTAAGCAGAAGGGGGAGTATTTGCCACTGCTGCAAGGAAAA

TCCTTGGGGATGATCTTCGAGAAGCGCTCCACTAGAACCCGGCTAAGC

ACAGAAACCGGCTTCGCACTTCTGGGTGGACATCCCTGTTTTCTGACG

ACGCAGGATATACACCTGGGCGTGAATGAGAGTCTGACGGACACAGCT

AGGGTGTTGAGCAGCATGGCCGATGCAGTACTGGCCCGCGTTTATAAG

CAGAGCGACTTGGACACACTGGCCAAGGAAGCGTCAATTCCGATTATC

AATGGGCTGTCAGACCTGTATCATCCCATTCAAATCTTGGCTGACTAT

CTGACCCTGCAAGAACATTACAGCTCCCTGAAGGGCCTCACGTTGTCC

TGGATTGGCGACGGAAACAACATTCTGCATTCGATCATGATGAGCGCT

GCTAAGTTTGGCATGCACCTCCAAGCCGCTACACCTAAGGGATATGAG

CCTGATGCCAGCGTAACCAAGCTGGCCGAACAGTACGCGAAGGAGAAT

GGCACGAAACTGCTGTTGACAAATGACCCCACTGGAGGCAGCTCACGGT

GGCAACGTGCTGATCACCGACACGTGGATATCTATGGGACAGGAAGAA

GAGAAGAAGAAGCGGCTGCAGGCATTCCAAGGGTATCAGGTCACCATG

AAAACGGCCAAGGTTGCTGCATCCGACTGGACATTTCTGCATTGCTTG

CCCCGCAAACCAGAAGAAGTAGACGACGAAGTCTTTTATTCCCCACGG

TCGCTGGTGTTCCCCGAGGCGGAGAATCGAAAGTGGACGATTATGGCC

GTGATGGTGTCCCTGCTGACTGATTACTCTCCCCAACTGCAAAAGCCT

AAGTTTTAG

>pARM567

(SEQ ID NO: 132)

ATGCTTTTCAACCTGAGGATCCTCCTGAACAACGCCGCCTTTCGCAAT

GGTCACAACTTTATGGTCCGGAACTTCAGATGCGGCCAGCCGCTGCAG

AACAAGGTCCAGCTGAAGGGACGGGATCTGCTGACTCTGAAGAACTTC

ACCGGAGAAGAGATCAAGTACATGCTGTGGCTGTCGGCCGACCTGAAG

TTCAGGATCAAGCAGAAGGGAGAATACCTCCCGCTGCTGCAAGGAAAG

TCCCTGGGCATGATTTTCGAGAAGCGCTCGACCAGAACTCGGTTGTCC

ACCGAAACCGGGTTTGCGCTGCTGGGCGGACATCCTTGCTTCCTGACG

ACTCAGGATATTCACCTGGGAGTGAACGAGTCGCTGACCGACACCGCC

AGAGTGCTGAGCTCGATGGCCGACGCCGTGTTGGCACGCGTGTACAAG

CAGTCCGATCTGGATACCCTGGCCAAAGAAGCTTCCATCCCGATCATT

AACGGGCTGAGCGACCTCTACCACCCCATTCAAATCCTGGCCGACTAC

CTGACTCTGCAAGAACACTACAGCTCGCTGAAGGGGTTGACTCTGTCC

TGGATCGGCGACGGAAACAACATCCTGCACTCCATCATGATGTCGGCC

GCAAAGTTCGGCATGCATTTGCAAGCCGCCACCCCAAAGGGCTACGAA

CCAGACGCGAGCGTCACCAAGCTGGCCGAACAGTACGCGAAGGAAAAT

GGTACTAAGCTGCTGCTGACCAACGACCCATTGGAAGCTGCCCATGGT

GGAAACGTGCTGATCACCGACACCTGGATCTCGATGGGCCAGGAAGAG

GAGAAGAAGAAGCGGCTGCAGGCGTTCCAGGGGTATCAGGTCACCATG

AAAACAGCCAAAGTGGCAGCGTCAGACTGGACCTTCCTCCACTGTCTG

CCTCGCAAGCCAGAGGAGGTGGACGACGAGGTGTTCTACTCCCCTCGG

TCCCTCGTGTTCCCTGAGGCTGAGAACCGGAAGTGGACCATTATGGCC

GTGATGGTGTCACTCCTGACTGATTACTCCCCGCAACTGCAGAAGCCC

AAGTTCTAG

>pARM568

(SEQ ID NO: 133)

ATGCTGTTTAACCTGAGGATCCTATTGAACAATGCTGCTTTTCGTAAT

GGCCATAACTTTATGGTTCGGAACTTTAGATGCGGGCAGCCACTGCAG

AACAAGGTCCAGTTGAAAGGCCGCGATCTGTTGACATTGAAGAACTTT

ACCGGCGAAGAGATTAAGTATATGCTGTGGCTGTCTGCTGACCTCAAG

TTTCGAATCAAGCAGAAGGGCGAATATCTCCCCCTGCTGCAAGGAAAG

TCTCTCGGCATGATCTTTGAGAAGCGGAGTACCCGAACACGGCTGAGC

ACCGAAACGGGCTTCGCACTGCTGGGGGGCCATCCCTGTTTTCTGACA

ACGCAGGACATCCACTTGGGGGTTAACGAATCATTGACTGATACCGCC

CGCGTACTGTCATCCATGGCCGACGCTGTGCTGGCTAGGGTGTACAAG

CAGTCAGATCTGGATACACTGGCCAAGGAAGCTAGCATACCAATCATC

AATGGACTGAGTGACCTTTATCACCCGATTCAAATACTAGCCGATTAT

CTGACCCTGCAAGAGCATTACTCCTCGCTGAAAGGCCTCACGCTGTCC

TGGATCGGCGACGGCAACAACATTCTGCATAGTATTATGATGTCTGCT

GCCAAATTCGGCATGCATCTGCAAGCTGCTACGCCGAAGGGTTATGAA

CCCGACGCGTCAGTTACGAAGCTCGCTGAGCAGTATGCAAAGGAGAAT

GGCACAAAGCTGTTGCTTACCAACGATCCCCTGGAAGCTGCTCATGGC

GGCAATGTGCTGATTACTGACACCTGGATTTCAATGGGCCAGGAGGAG

GAGAAGAAGAAGAGGTTACAGGCTTTTCAAGGTTACCAAGTCACGATG

AAAACCGCTAAGGTCGCAGCCAGCGACTGGACATTCCTGCACTGTCTG

CCAAGAAAGCCGGAAGAAGTGGACGACGAGGTGTTCTATTCCCCGCGG

TCTTTGGTGTTTCCGGAGGCCGAAAACAGGAAATGGACCATTATGGCC

-continued

GTGATGGTATCGTTGCTGACGGACTACAGCCCTCAGTTGCAAAAGCCC

AAGTTCTAG

>pARM569

(SEQ ID NO: 134)

ATGCTCTTTAACCTCCGCATCCTCCTCAACAACGCCGCCTTCCGGAAT

GGGCATAACTTCATGGTCCGGAACTTCAGATGCGGCCAGCCCCTGCAA

AACAAGGTCCAGTTGAAGGGACGGACCTCCTTACGCTGAAGAACTTT

ACCGGAGAAGAGATTAAGTACATGCTGTGGTTGTCCGCTGACCTCAAG

TTCCGCATTAAGCAGAAGGGAGAATATCTGCCGCTGCTGCAAGGAAAG

AGCCTGGGCATGATCTTCGAAAAGCGCTCCACTAGAACCCGGCTGTCG

ACTGAGACTGGATTCGCCTTGCTCGGTGGACACCCGTGCTTCCTGACG

ACCCAGGACATCCACCTGGGAGTGAACGAGTCACTTACGGATACCGCG

AGGGTGCTGTCCTCAATGGCCGACGCAGTGCTCGCGCGCGTGTACAAG

CAGTCAGATCTGGATACCCTGGCCAAGGAAGCCAGCATTCCCATCATC

AACGGACTGAGCGACCTTTACCACCCAATCCAGATCCTCGCCGACTAC

TTAACCCTGCAAGAGCACTACAGCTCCCTGAAGGGACTGACTCTGTCC

TGGATCGGGGATGGAAACAACATCCTGCACTCCATCATGATGTCTGCC

GCTAAGTTTGGGATGCATCTGCAAGCCGCAACCCCTAAGGGATACGAG

CCCGACGCCTCGGTGACCAAACTTGCGGAACAGTACGCCAAGGAAAAC

GGTACCAAGCTGCTGCTGACCAACGACCCTCTGGAAGCGGCCCACGGA

GGAAATGTGCTGATTACCGACACCTGGATTTCGATGGGCCAGGAGGAG

GAGAAGAAGAAGAGACTGCAGGCGTTCCAGGGATATCAGGTCACCATG

AAAACCGCCAAGGTCGCCGCCAGCGACTGGACCTTCCTGCACTGTCTC

CCTCGGAAACCGGAAGAAGTGGATGACGAGGTGTTCTACTCCCCGCGC

TCGCTGGTGTTCCCGGAGGCTGAAAACAGGAAGTGGACAATCATGGCC

GTGATGGTGTCCCTGTTGACCGACTACTCCCCACAACTGCAGAAGCCC

AAGTTCTAG

>pARM570

(SEQ ID NO: 135)

ATGCTTTTCAATCTGCGCATCCTCCTGAACAACGCCGCCTTCCGCAAT

GGACACAACTTTATGGTCCGCAACTTCCGCTGTGGGCAGCCGCTGCAG

AACAAGGTCCAGCTCAAGGGGAGAGATCTCCTGACCCTGAAGAACTTC

ACTGGAGAGGAGATCAAGTACATGCTGTGGCTGTCCGCCGACCTGAAA

TTTCGGATTAAGCAGAAGGGCGAATACCTCCCACTGCTGCAAGGAAAG

TCTTTGGGCATGATCTTCGAAAAGAGAAGCACCCGGACCCGGTTGAGC

ACCGAAACTGGGTTCGCGCTCCTCGGTGGACACCCGTGCTTCCTGACC

ACCCAAGATATTCATCTGGGTGTCAACGAAAGCCTGACCGACACCGCC

AGGGTGCTGTCATCCATGGCTGACGCAGTGCTCGCCCGGGTGTACAAG

CAGTCAGACCTGGACACCCTCGCCAAGGAAGCTTCGATCCCTATCATC

AACGGACTTTCCGACCTGTACCACCCCATCCAAATTCTGGCCGACTAC

CTGACTCTGCAAGAACACTATAGCTCGCTGAAAGGACTTACTCTGTCC

TGGATCGGGGACGGCAACAACATTCTCCATTCCATCATGATGTCCGCT

GCCAAGTTCGGAATGCACCTTCAAGCAGCGACTCCCAAGGGATACGAA

CCTGATGCCTCCGTGACTAAGCTGGCAGAGCAGTACGCCAAGGAGAAC

GGTACAAAGCTGCTGCTCACGAACGACCCCCTGGAGGCGGCCCACGGC

GGAAACGTGCTGATTACCGATACCTGGATCTCAATGGGCCAGGAAGAG

GAGAAGAAGAAGCGGCTCCAGGCGTTTCAAGGCTACCAGGTCACCATG

AAAACCGCGAAGGTCGCCGCCTCCGACTGGACTTTCTTGCACTGCCTG

CCGCGGAAGCCCGAGGAAGTGGATGACGAAGTGTTCTACTCGCCGAGA

TCGTTGGTGTTCCCTGAGGCCGAAAACAGGAAGTGGACCATCATGGCC

GTGATGGTGTCCCTGCTGACTGATTACAGCCCACAGCTGCAGAAGCCT

AAGTTCTAG

>pARM571

(SEQ ID NO: 136)

ATGCTTTTCAATCTCCGCATCCTCCTTAACAACGCCGCGTTTAGAAAC

GGCCACAACTTCATGGTCCGGAACTTCAGATGTGGCCAGCCGCTTCAA

AACAAGGTCCAGCTGAAGGGCCGGGATCTTCTGACCCTGAAGAACTTT

ACTGGCGAAGAGATCAAGTACATGCTCTGGCTCTCCGCGGACTTGAAG

TTCCGCATTAAGCAGAAGGGGGAATACCTTCCGCTGCTTCAAGGAAAG

AGCCTCGGCATGATCTTTGAGAAGCGCTCAACCAGGACCCGCCTTTCT

ACTGAAACTGGGTTCGCGCTGCTCGGTGGCCACCCCTGCTTCCTGACG

ACCCAGGACATCCACCTCGGAGTGAACGAATCCCTCACCGATACCGCC

CGGGTGTTATCGAGCATGGCAGATGCCGTGCTGGCCAGGGTGTACAAA

CAGTCCGATCTGGACACTCTGGCCAAGGAGGCGTCAATTCCTATTATC

AACGGCCTTAGTGACCTCTACCATCCGATTCAGATCCTGGCCGATTAC

CTCACCCTGCAAGAACACTACAGCTCCCTGAAGGGTCTGACATTGTCC

TGGATCGGCGACGGCAACAACATTCTCCATTCCATCATGATGTCCGCC

GCAAAATTCGGCATGCATCTTCAAGCCGCCACGCCGAAGGGTTACGAG

CCCGACGCTTCCGTGACTAAGCTCGCCGAGCAGTACGCTAAGGAGAAC

GGAACCAAGCTTCTGCTGACTAACGACCCACTAGAAGCAGCCCACGGG

GGCAACGTGCTTATTACTGACACCTGGATCTCCATGGGCCAGGAAGAA

GAGAAAAAGAAGCGGCTGCAGGCGTTCCAGGGATATCAGGTCACCATG

AAAACCGCCAAGGTCGCTGCCTCCGACTGGACCTTCCTGCACTGCCTG

CCTCGCAAGCCTGAAGAAGTGGACGACGAGGTGTTCTACTCGCCACGG

AGCCTCGTGTTCCCCGAGGCCGAGAATAGAAAGTGGACCATCATGGCC

GTGATGGTGTCACTGCTCACCGACTACAGCCCGCAGCTTCAGAAGCCC

AAGTTCTAG

>pARM572

(SEQ ID NO: 137)

ATGCTTTTCAACCTGAGAATCCTCCTGAACAACGCCGCCTTCCGCAAT

GGTCATAACTTCATGGTCCGCAACTTTCGCTGCGGACAGCCTCTCCAA

AACAAGGTCCAGCTCAAGGGGCGCGACCTCCTCACACTGAAGAACTTC

ACTGGAGAAGAAATCAAGTACATGCTGTGGCTGAGCGCCGATCTGAAG

TTCCGGATCAAGCAGAAGGGAGAGTACCTTCCTCTGCTGCAAGGGAAG

TCCTTGGGAATGATTTTCGAGAAGCGGTCCACCCGGACCAGGCTGAGC

-continued

ACTGAAACTGGCTTCGCCCTGCTGGGAGGCCACCCTTGTTTCCTGACC

ACTCAGGACATCCACCTGGGCGTGAACGAGTCCCTGACCGATACTGCC

AGAGTGCTGTCCTCCATGGCCGACGCCGTGCTCGCCCGGGTGTACAAG

CAGTCAGACCTCGATACGCTGGCCAAGGAAGCCTCCATTCCCATTATC

AATGGTCTGTCGGACCTCTACCATCCAATCCAAATCCTCGCCGACTAC

CTGACTCTGCAAGAACACTACAGCTCACTCAAGGGCCTCACCCTCTCC

TGGATCGGCGACGGAAACAACATCCTTCACTCGATTATGATGTCGGCC

GCGAAGTTCGGGATGCACCTCCAAGCTGCCACTCCAAAAGGCTACGAG

CCGGATGCCTCAGTGACTAAGTTGGCGGAACAGTATGCGAAGGAGAAC

GGTACCAAGCTCCTGCTGACTAACGACCCGCTGGAGGCCGCCCACGGG

GGAAACGTGCTCATCACCGATACTTGGATTTCCATGGGACAGGAGGAA

GAGAAGAAGAAGCGGTTGCAGGCATTTCAGGGCTACCAGGTCACCATG

AAAACTGCCAAAGTCGCCGCCAGCGACTGGACCTTCCTGCACTGCCTG

CCCCGCAAGCCTGAAGAAGTGGACGACGAGGTGTTCTACTCTCCCCGG

TCCCTCGTGTTCCCTGAGGCCGAAAACAGGAAGTGGACCATCATGGCT

GTGATGGTGTCCCTCCTGACCGACTACAGCCCTCAGCTCCAAAAACCC

AAGTTTTAG

>pARM573

(SEQ ID NO: 138)

ATGCTTTTCAACCTGAGAATCCTCTTGAACAATGCTGCTTTTCGGAAT

GGCCACAACTTTATGGTTCGGAACTTCCGTTGCGGCCAGCCTTTACAA

AACAAGGTCCAGCTGAAGGGCCGGGATTTGCTCACACTGAAGAACTTT

ACTGGGGAGGAGATTAAGTATATGCTGTGGCTGTCCGCTGACCTGAAG

TTTAGGATCAAGCAGAAGGGCGAATATCTGCCGCTGCTGCAAGGGAAA

AGTCTGGGCATGATTTTTGAAAAGCGCTCTACCCGGACCAGACTGTCT

ACGGAAACAGGCTTTGCCCTGCTGGGCGGCCACCCCTGTTTTCTGACA

ACGCAGGACATCCATCTGGGCGTGAACGAATCACTGACCGATACTGCT

CGGGTACTCAGTTCTATGGCTGACGCAGTGCTGGCTAGGGTGTACAAG

CAGAGCGACTTGGACACACTGGCTAAGGAGGCCAGCATCCCCATTATC

AATGGCCTGTCTGATTTGTACCATCCCATTCAAATCCTGGCTGATTAT

CTGACACTACAAGAGCATTACTCAAGTCTGAAGGGTTTGACTCTCTCC

TGGATCGGCGACGGCAACAACATTTTACATTCCATTATGATGAGTGCT

GCTAAGTTTGGCATGCATTTGCAAGCTGCTACCCCAAAGGGCTATGAA

CCTGACGCTAGCGTAACCAAGTTGGCCGAACAGTATGCTAAAGAGAAT

GGCACCAAGCTGCTCCTGACGAATGACCCCCTGGAAGCTGCTCATGGC

GGAAACGTACTTATAACTGATACATGGATTAGCATGGGCCAGGAAGAG

GAGAAGAAGAAGAGACTGCAGGCCTTCCAAGGCTATCAGGTCACCATG

AAAACTGCCAAGGTTGCAGCTAGCGACTGGACCTTCCTGCACTGTTTG

CCGAGGAAACCCGAGGAGGTGGACGATGAAGTCTTTTATTCTCCCCGC

TCCTTGGTGTTTCCCGAGGCTGAAAATCGAAAGTGGACGATAATGGCA

-continued

GTGATGGTGTCCCTACTGACCGACTATTCTCCACAACTGCAGAAGCCT

AAATTCTAG

>pARM574

(SEQ ID NO: 139)

ATGCTTTTCAATCTGAGGATCCTGCTGAACAACGCTGCTTTTCGCAAC

GGTCATAACTTTATGGTTCGCAATTTTCGTTGTGGCCAGCCGCTGCAG

AACAAGGTTCAGCTGAAGGGCAGAGATCTGCTGACTCTGAAGAACTTC

ACTGGGGAAGAAATCAAGTATATGTTATGGCTGTCCGCGGATCTGAAA

TTTCGAATCAAGCAGAAGGGCGAATATCTTCCCCTGCTGCAAGGGAAA

TCCTTGGGCATGATTTTTGAGAAGAGGAGCACTAGGACTAGATTGTCA

ACAGAAACAGGCTTTGCTTTGTTGGGCGGACATCCCTGCTTTCTGACG

ACACAGGATATCCACCTCGGCGTAAACGAGTCCCTCACCGACACTGCT

AGGGTACTGAGCAGCATGGCCGACGCTGTGCTAGCCCGGGTTTACAAG

CAGTCAGACCTGGACACCCTTGCCAAGGAAGCTTCTATTCCAATTATC

AACGGCCTGAGTGACCTGTATCACCCTATTCAAATACTCGCCGACTAT

TTGACGCTTCAAGAACATTACAGCAGCCTCAAGGGCTTAACCTTGAGT

TGGATAGGCGACGGCAACAATATCCTGCATTCCATTATGATGTCTGCC

GCTAAGTTTGGCATGCATCTACAAGCCGCAACACCCAAGGGCTATGAA

CCCGACGCTAGCGTGACCAAGCTGGCCGAGCAGTATGCTAAGGAAAAT

GGCACAAAGCTCCTTCTTACCAACGATCCCCTGGAGGCTGCTCACGGC

GGCAACGTGCTGATTACCGATACATGGATTAGCATGGGCCAGGAGGAG

GAGAAAAAGAAGCGGCTCCAGGCTTTTCAAGGCTATCAGGTCACCATG

AAAACTGCAAAGGTCGCTGCCTCCGACTGGACTTTCCTGCATTGTCTA

CCCCGCAAGCCTGAGGAAGTGGACGATGAGGTGTTCTACTCCCCACGG

AGTCTGGTGTTCCCGGAAGCAGAGAATCGGAAGTGGACCATCATGGCT

GTCATGGTGTCGCTCTTGACTGACTATTCTCCCCAACTGCAAAAACCC

AAGTTTTAG

>pARM575

(SEQ ID NO: 140)

ATGCTTTTCAATCTGAGGATCCTGCTGAACAACGCTGCTTTTCGCAAC

GGTCATAACTTTATGGTTCGCAATTTTCGTTGTGGCCAGCCGCTGCAG

AACAAGGTTCAGCTGAAGGGCAGAGATCTGCTGACTCTGAAGAACTTC

ACTGGGGAAGAAATCAAGTATATGTTATGGCTGTCCGCGGATCTGAAA

TTTCGAATCAAGCAGAAGGGCGAATATCTTCCCCTGCTGCAAGGGAAA

TCCTTGGGCATGATTTTTGAGAAGAGGAGCACTAGGACTAGATTGTCA

ACAGAAACAGGCTTTGCTTTGTTGGGCGGACATCCCTGCTTTCTGACG

ACACAGGATATCCACCTCGGCGTAAACGAGTCCCTCACCGACACTGCT

AGGGTACTGAGCAGCATGGCCGACGCTGTGCTAGCCCGGGTTTACAAG

CAGTCAGACCTGGACACCCTTGCCAAGGAAGCTTCTATTCCAATTATC

AACGGCCTGAGTGACCTGTATCACCCTATTCAAATACTCGCCGACTAT

TTGACGCTTCAAGAACATTACAGCAGCCTCAAGGGCTTAACCTTGAGT

TGGATAGGCGACGGCAACAATATCCTGCATTCCATTATGATGTCTGCC

-continued

GCTAAGTTTGGCATGCATCTACAAGCCGCAACACCCAAGGGCTATGAA
CCCGACGCTAGCGTGACCAAGCTGGCCGAGCAGTATGCTAAGGAAAAT
GGCACAAAGCTCCTTCTTACCAACGATCCCCTGGAGGCTGCTCACGGC
GGCAACGTGCTGATTACCGATACATGGATTAGCATGGGCCAGGAGGAG
GAGAAAAAGAAGCGGCTCCAGGCTTTTCAAGGCTATCAGGTCACCATG
AAAACTGCAAAGGTCGCTGCCTCCGACTGGACTTTCCTGCATTGTCTA
CCCCGCAAGCCTGAGGAAGTGGACGATGAGGTGTTCTACTCCCCACGG
AGTCTGGTGTTCCCGGAAGCAGAGAATCGGAAGTGGACCATCATGGCT
GTCATGGTGTCGCTCTTGACTGACTATTCTCCCCAACTGCAAAAACCC
AAGTTTTAG

>pARM708

(SEQ ID NO: 141)

ATGCTTTTTAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACGCCAAAAGGATACGAA
CCGGATGCGTCCGTGACGAAGTTGGCGGAACAGTACGCGAAGGAGAAC
GGAACCAAGCTTCTGCTGACTAACGACCCCCTCGAGGCTGCGCATGGG
GGCAACGTGCTGATTACCGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAG

>pARM709

(SEQ ID NO: 142)

ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTGAAGAACTTT
ACTGGAGAAGAGATCAAGTACATGCTGTGGCTGTCGGCCGACCTGAAG
TTCAGGATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCGTCCGTGACCAAGTTGGCGGAACAGTACGCGAAGGAGAAC
GGAACCAAGCTTCTGCTGACTAACGACCCCCTCGAGGCTGCGCATGGG
GGCAACGTGCTGATTACCGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAG

>pARM710

(SEQ ID NO: 143)

ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTAAAGAACTTT
ACTGGAGAAGAGATCAAGTACATGCTATGGCTGTCGGCCGACCTGAAG
TTCCGTATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCATCCGTGACCAAGTTGGCGGAACAGTACGCGAAGGAGAAC
GGAACCAAGCTCCTGCTGACTAACGACCCGCTCGAGGCTGCGCATGGG
GGTAACGTGCTGATTACGGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC

-continued

GTGATGGTGTCCTTGCTGACTGACTATAGCCCGCAGCTGCAGAAGCCT
AAGTTCTAG

>pARM711

(SEQ ID NO: 144)

ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTAAAGAACTTT
ACTGGAGAAGAGATCAAGTACATGCTATGGCTGTCGGCCGACCTGAAG
TTCCGTATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCGTCCGTGACCAAGTTGGCGGAACAGTACGCGAAGGAGAAC
GGAACCAAGCTTCTGCTGACTAACGACCCCCTCGAGGCTGCGCATGGG
GGCAACGTGCTGATTACCGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAG

>pARM712

(SEQ ID NO: 145)

ATGCTGTTCAACCTGCGAATCCTGCTGAACAACGCCGCTTTTCGGAAC
GGGCACAACTTTATGGTGAGGAACTTTCGCTGCGGACAGCCCCTCCAG
AATAAGGTCCAGCTGAAGGGCAGGGACCTGCTGACCCTGAAAAATTTC
ACAGGGGAGGAAATCAAGTATATGCTGTGGCTGTCAGCTGATCTGAAG
TTCCGGATCAAGCAGAAGGGCGAATATCTGCCTCTGCTCCAGGGCAAA
AGCCTGGGGATGATCTTCGAAAAGCGCAGTACTCGGACCAGACTGTCA
ACCGAGACTGGATTCGCTCTGCTGGGAGGACACCCTTGTTTTCTGACC
ACTCAGGACATTCACCTGGGAGTGAACGAGTCCCTGACCGACACTGCT
CGCGTCCTGAGCTCTATGGCCGACGCTGTGCTGGCTCGAGTCTACAAA
CAGTCCGACCTGGATACCCTGGCCAAGGAAGCTTCTATCCCAATTATT
AACGGCCTGTCAGACCTGTATCACCCCATCCAGATTCTGGCCGATTAC
CTGACCCTCCAGGAGCACTATTCTAGTCTGAAAGGGCTGACACTGAGT
TGGATTGGGGACGGAAACAATATCCTGCACTCTATTATGATGTCAGCC
GCCAAGTTTGGAATGCACCTCCAGGCTGCAACCCCAAAAGGCTACGAA
CCCGATGCCTCAGTGACAAAGCTGGCTGAACAGTACGCCAAAGAGAAC
GGCACTAAGCTGCTGCTGACCAACGACCCTCTGGAGGCCGCTCACGGA
GGCAACGTGCTGATCACCGATACCTGGATTAGTATGGGACAGGAGGAA
GAGAAGAAGAAGCGGCTCCAGGCCTTCCAGGGCTACCAGGTGACAATG
AAAACCGCTAAGGTCGCAGCCAGCGATTGGACCTTTCTGCACTGCCTG
CCCAGAAAGCCCGAAGAGGTGGACGACGAGGTCTTCTACTCTCCCAGA
AGCCTGGTGTTTCCCGAAGCTGAGAATAGGAAGTGGACAATTATGGCA
GTGATGGTCAGCCTGCTGACTGATTATTCACCTCAGCTCCAGAAACCA
AAGTTCTGA

>pARM713

(SEQ ID NO: 146)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCCTGGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM714

(SEQ ID NO: 147)

ATGCTGTTCAACCTGCGAATCCTGCTGAACAACGCCGCTTTTCGGAAC
GGGCACAACTTTATGGTGAGGAACTTTCGCTGCGGACAGCCCCTCCAG
AATAAGGTCCAGCTGAAGGGCAGGGACCTGCTGACCCTGAAAAATTTC
ACAGGGGAGGAAATCAAGTATATGCTGTGGCTGTCAGCTGATCTGAAG
TTCCGGATCAAGCAGAAGGGCGAATATCTGCCTCTGCTCCAGGGCAAA
AGCCTGGGGATGATCTTCGAAAAGCGCAGTACTCGGACCAGACTGTCA

-continued

ACCGAGACTGGATTCGCTCTGCTGGGAGGACACCCTTGTTTTCTGACC
ACTCAGGACATTCACCTGGGAGTGAACGAGTCCCTGACCGACACTGCT
CGCGTCCTGAGCTCTATGGCCGACGCTGTGCTAGCTCGAGTCTACAAA
CAGTCCGACCTGGATACCCTGGCCAAGGAAGCTTCTATCCCAATTATT
AACGGCCTGTCAGACCTGTATCACCCCATCCAGATTCTGGCCGATTAC
CTGACCCTCCAGGAGCACTATTCTAGTCTGAAAGGGCTGACACTGAGT
TGGATTGGGGACGGAAACAATATCCTGCACTCTATTATGATGTCAGCC
GCCAAGTTTGGAATGCACCTCCAGGCTGCAACCCCAAAAGGCTACGAA
CCCGATGCCTCAGTGACAAAGCTGGCTGAACAGTACGCCAAAGAGAAC
GGCACTAAGCTGCTGCTGACCAACGACCCTCTGGAGGCCGCTCACGGA
GGCAACGTGCTGATCACCGATACCTGGATTAGTATGGGACAGGAGGAA
GAGAAGAAGAAGCGGCTCCAGGCCTTCCAGGGCTACCAGGTGACAATG
AAAACCGCTAAGGTCGCAGCCAGCGATTGGACCTTTCTGCACTGCCTG
CCCAGAAAGCCCGAAGAGGTGGACGACGAGGTCTTCTACTCTCCCAGA
AGCCTGGTGTTTCCCGAAGCTGAGAATAGGAAGTGGACAATTATGGCA
GTGATGGTCAGCCTGCTGACTGATTATTCACCTCAGCTCCAGAAACCA
AAGTTCTGA

>pARM715

(SEQ ID NO: 148)

ATGCTGTTCAACCTGCGAATCCTGCTGAACAATGCCGCTTTTCGGAAC
GGGCACAATTTCATGGTGAGGAACTTTCGCTGCGGACAGCCCCTCCAG
AACAAGGTCCAGCTGAAGGGCAGGGACCTGCTGACCCTGAAAAATTTC
ACAGGGGAGGAAATCAAGTACATGCTGTGGCTGTCAGCCGATCTGAAG
TTCCGGATCAAGCAGAAGGGCGAATATCTGCCTCTGCTCCAGGGCAAA
AGCCTGGGGATGATCTTCGAAAAGCGCAGTACTCGGACCAGACTGTCA
ACAGAGACTGGATTCGCACTGCTGGGAGGACACCCATGTTTTCTGACC
ACACAGGACATTCATCTGGGAGTGAACGAGTCCCTGACCGACACAGCA
CGCGTCCTGAGCTCCATGGCTGATGCAGTGCTGGCTCGAGTCTACAAA
CAGTCTGACCTGGATACCCTGGCCAAGGAAGCTTCTATCCCAATCATT
AATGGCCTGAGTGACCTGTATCACCCCATCCAGATTCTGGCCGATTAC
CTGACCCTCCAGGAGCATTATTCTAGTCTGAAAGGGCTGACACTGAGC
TGGATTGGGGACGGAAACAATATCCTGCACTCCATTATGATGAGCGCC
GCCAAGTTTGGAATGCACCTCCAGGCTGCAACCCCAAAAGGCTACGAA
CCCGATGCCTCCGTGACAAAGCTGGCAGAACAGTATGCCAAAGAGAAC
GGCACTAAGCTGCTGCTGACCAATGACCCTCTGGAGGCCGCTCACGGA
GGCAACGTGCTGATCACTGATACCTGGATTAGTATGGGACAGGAGGAA
GAGAAGAAGAAGCGGCTCCAGGCCTTCCAGGGCTACCAGGTGACAATG
AAAACTGCTAAGGTCGCAGCCAGCGACTGGACCTTTCTGCATTGCCTG
CCCAGAAAGCCTGAAGAGGTGGACGATGAGGTCTTCTACTCACCCAGA
AGCCTGGTGTTTCCTGAAGCTGAGAATAGGAAGTGGACAATCATGGCA

-continued

GTGATGGTCAGCCTGCTGACTGATTATTCCCCTCAGCTCCAGAAACCA
AAGTTCTGA

>pARM716

(SEQ ID NO: 149)

ATGCTTTTCAACCTTCGCATTCTCCTCAACAACGCCGCGTTTAGAAAC
GGACACAACTTCATGGTCCGCAACTTCCGCTGCGGACAGCCGCTGCAG
AACAAGGTCCAGCTCAAGGGTCGGGATCTCCTGACGCTGAAGAACTTT
ACCGGCGAAGAGATTAAGTACATGCTGTGGCTGTCCGCCGACCTTAAG
TTCCGGATCAAGCAGAAGGGCGAATACCTTCCCCTGCTGCAAGGAAAG
TCCCTGGGCATGATCTTCGAGAAGCGCAGTACCAGAACCAGACTCTCC
ACTGAAACCGGGTTCGCGCTGCTTGGCGGCCACCCGTGTTTCCTCACT
ACGCAAGACATCCATCTTGGCGTGAACGAGTCCCTTACCGACACCGCC
AGGGTGCTGTCAAGCATGGCCGACGCCGTCCTTGCGCGCGTGTACAAG
CAGTCAGACCTTGATACTCTGGCCAAGGAAGCCTCCATCCCTATTATC
AACGGCCTATCCGACCTTTACCACCCGATCCAGATCCTCGCTGACTAC
CTGACCCTGCAAGAACACTACAGCAGCCTCAAGGGACTGACTCTGTCC
TGGATCGGCGACGGGAACAACATCCTGCACTCAATCATGATGAGCGCA
GCCAAGTTCGGCATGCATCTCCAAGCCGCTACACCCAAGGGTTATGAA
CCGGACGCCTCTGTGACCAAGTTGGCAGAACAGTACGCCAAGGAGAAC
GGTACTAAGCTCCTTTTAACCAACGACCCCCTCGAAGCAGCCCATGGC
GGGAATGTGCTCATTACCGATACCTGGATTTCGATGGGCCAGGAGGAG
GAGAAGAAGAAGCGGCTGCAGGCGTTCCAGGGCTACCAGGTCACCATG
AAAACTGCCAAAGTGGCCGCCTCGGATTGGACCTTTCTCCACTGCCTG
CCTCGGAAGCCTGAGGAGGTGGACGACGAAGTGTTCTACTCCCCACGG
TCCCTCGTGTTCCCCGAGGCCGAAAATAGGAAGTGGACCATCATGGCC
GTGATGGTGTCCCTCTTGACCGATTACAGCCCGCAGCTTCAGAAGCCT
AAATTCTAG

>pARM717

(SEQ ID NO: 150)

ATGCTTTTCAATCTTCGCATCCTGTTGAACAACGCCGCCTTCCGCAAT
GGTCACAACTTCATGGTCCGGAACTTCAGATGTGGACAGCCTCTCCAA
AACAAGGTCCAGCTGAAGGGAAGGGACCTCTTAACCCTCAAAAACTTT
ACTGGAGAGGAGATCAAGTACATGCTGTGGCTTAGCGCCGACCTTAAG
TTCCGGATCAAGCAGAAGGGAGAGTACCTCCCGCTGCTGCAAGGAAAG
AGTCTTGGAATGATCTTCGAGAAGCGGTCCACCAGAACTCGCCTCTCC
ACTGAAACCGGATTCGCACTCCTGGGTGGACACCCGTGCTTTCTGACC
ACCCAAGACATCCACCTCGGAGTGAACGAGAGCCTCACGGACACCGCG
AGAGTGCTGTCATCCATGGCCGACGCCGTGCTTGCACGGGTCTACAAG
CAGTCCGATCTGGACACTCTTGCCAAGGAAGCCTCCATTCCTATCATT
AACGGTCTGTCGGATCTGTACCACCCGATTCAGATCCTTGCGGACTAC
CTCACACTTCAAGAACACTATTCAAGCCTAAAGGGTCTGACCCTGTCC
TGGATCGGAGATGGAAACAACATTCTCCATTCCATCATGATGAGCGCT

-continued

GCCAAGTTCGGAATGCATCTCCAAGCAGCGACTCCTAAGGGTTACGAG
CCGGACGCCTCAGTGACTAAGCTGGCCGAGCAGTACGCCAAGGAGAAC
GGTACCAAACTGTTGCTTACTAACGACCCGCTTGAAGCGGCCCATGGA
GGAAACGTGCTGATTACCGACACCTGGATTTCGATGGGACAGGAAGAG
GAGAAGAAGAAGCGGCTCCAGGCGTTCCAGGGATACCAGGTCACCATG
AAAACGGCCAAAGTGGCCGCTAGCGATTGGACCTTTCTGCACTGCCTC
CCGCGCAAGCCTGAAGAAGTGGACGACGAAGTGTTCTACTCCCCTCGC
TCTCTTGTGTTCCCGGAAGCCGAAAACAGGAAGTGGACCATCATGGCC
GTGATGGTGTCCCTCCTGACCGATTACAGCCCGCAGCTGCAGAAGCCT
AAGTTCTAG

>pARM718

(SEQ ID NO: 151)

ATGCTTTTCAATCTCCGCATCCTCCTCAACAACGCCGCGTTTAGAAAC
GGCCACAACTTCATGGTCCGGAACTTCAGATGTGGCCAGCCGCTTCAG
AACAAGGTCCAGCTCAAGGGCCGGGATCTTCTGACCCTGAAGAACTTT
ACTGGCGAAGAAATCAAGTACATGCTCTGGCTCTCCGCCGACTTGAAG
TTCCGCATTAAGCAGAAGGGGGAATACCTTCCGCTGCTGCAAGGAAAG
TCGCTCGGCATGATCTTTGAGAAGCGCTCAACCCGCACCAGGCTGTCC
ACTGAAACCGGGTTCGCGCTGCTTGGTGGCCACCCCTGCTTCCTGACC
ACCCAAGACATTCACCTCGGAGTGAACGAATCGCTCACTGATACTGCC
CGGGTGCTGTCGTCGATGGCCGATGCAGTGCTGGCCAGGGTGTACAAA
CAGTCCGATCTGGACACTCTGGCCAAGGAGGCGTCCATCCCTATTATC
AACGGCCTTTCCGACCTCTACCACCCGATTCAGATCCTTGCCGATTAC
CTCACCCTGCAAGAACACTACTCGTCACTGAAGGGTCTGACCTTGTCC
TGGATCGGCGACGGCAACAACATCCTCCATTCCATTATGATGTCCGCC
GCCAAATTCGGCATGCATCTTCAAGCCGCAACCCCTAAGGGTTACGAG
CCGGACGCTTCCGTGACCAAGCTCGCCGAGCAGTACGCTAAGGAGAAC
GGAACCAAGCTTCTGCTGACTAACGACCCCCTAGAGGCAGCCCACGGG
GGCAACGTGCTTATTACTGACACCTGGATCTCCATGGGACAGGAAGAA
GAGAAGAAGAAGCGGTTACAGGCGTTCCAGGGCTATCAGGTCACCATG
AAAACCGCCAAGGTCGCTGCCTCGGACTGGACCTTCCTGCATTGCCTG
CCTCGCAAGCCCGAAGAAGTGGACGACGAGGTGTTCTACTCGCCACGG
TCCCTTGTGTTCCCTGAGGCCGAGAATAGAAAGTGGACCATTATGGCC
GTGATGGTGTCCCTTCTCACCGACTACTCGCCGCAACTGCAGAAACCC
AAGTTCTAG

>pARM719

(SEQ ID NO: 152)

ATGCTTTTCAATCTTCGCATCCTCCTCAACAACGCCGCCTTCCGGAAC
GGTCACAACTTCATGGTCCGGAACTTCCGCTGCGGCCAGCCGCTCCAA
AACAAAGTGCAGCTTAAGGGCCGCGATCTCCTGACCCTGAAGAACTTC
ACCGGAGAGGAAATCAAGTACATGCTGTGGCTCTCGGCGGACCTGAAG
TTTAGGATTAAGCAGAAGGGGGAGTATCTGCCGCTGCTCCAAGGGAAG
TCCCTTGGCATGATCTTCGAAAAGAGGTCCACCCGGACTCGGCTCAGC

-continued

ACCGAAACAGGTTTTGCACTTCTGGGGGGCCACCCGTGCTTCCTGACG
ACCCAGGACATCCATCTGGGTGTCAACGAGAGTTTGACCGACACTGCC
AGAGTGCTGTCATCCATGGCGGACGCGGTGCTCGCGAGAGTGTACAAG
CAGTCCGATCTTGACACCCTGGCAAAAGAGGCTTCAATCCCGATCATT
AACGGACTCTCGGATCTGTACCACCCTATCCAAATCTTGGCCGACTAC
CTGACCCTGCAAGAACACTACAGCTCCCTGAAGGGCCTGACTCTTTCC
TGGATTGGCGATGGAAACAACATTCTCCATTCTATTATGATGTCCGCC
GCCAAGTTCGGCATGCACCTTCAAGCCGCCACCCCGAAGGGCTACGAA
CCTGACGCCTCCGTGACTAAGCTAGCCGAACAGTACGCTAAGGAGAAC
GGCACTAAGCTTCTCCTTACCAACGATCCGCTGGAGGCGGCCCATGGC
GGAAATGTGCTTATCACCGACACCTGGATTAGCATGGGGCAGGAAGAA
GAGAAGAAGAAACGGCTCCAGGCATTCCAGGGCTACCAGGTCACCATG
AAAACTGCCAAGGTCGCCGCTAGCGACTGGACCTTCCTCCACTGTCTG
CCTCGCAAGCCTGAAGAAGTGGACGACGAGGTGTTCTACTCCCCGCGC
TCCCTCGTGTTTCCTGAGGCCGAGAACAGAAAGTGGACCATCATGGCC
GTGATGGTGTCATTACTTACGGACTACAGCCCGCAGCTGCAGAAGCCG
AAGTTCTAG

>pARM720

(SEQ ID NO: 153)

ATGCTTTTTAACTTGAGAATCCTTCTGAACAACGCCGCTTTCCGCAAC
GGTCATAACTTCATGGTCCGGAACTTCAGATGTGGCCAGCCCCTCCAA
AACAAAGTGCAGCTGAAGGGCCGGGACCTTCTTACGCTGAAGAATTTC
ACCGGCGAAGAAATCAAGTACATGCTCTGGCTGTCCGCCGATCTTAAG
TTCCGCATTAAGCAGAAGGGGGAATACCTCCCGCTGCTGCAAGGGAAG
TCGCTGGGCATGATTTTTGAGAAGCGGTCAACTCGCACCCGCCTGTCC
ACTGAAACTGGATTCGCACTGCTCGGTGGCCATCCCTGCTTCCTGACC
ACCCAAGACATCCACCTCGGCGTGAACGAGTCCCTGACTGACACCGCC
CGGGTCTTATCCTCGATGGCCGATGCTGTGCTTGCGAGGGTGTACAAG
CAGTCCGACCTCGACACACTCGCGAAGGAGGCCTCCATCCCCATCATC
AACGGCCTGTCCGACCTTTACCACCCAATTCAGATCCTCGCCGATTAC
CTGACCCTGCAAGAGCACTACTCGTCGCTCAAGGGGCTTACCCTCTCG
TGGATTGGCGACGGCAACAACATCCTTCACTCCATCATGATGTCGGCA
GCGAAGTTCGGCATGCATCTGCAAGCCGCCACGCCTAAGGGTTATGAA
CCGGATGCCTCAGTGACCAAGCTCGCCGAACAGTACGCGAAAGAGAAT
GGAACCAAGCTACTTCTGACCAACGACCCCCTGGAGGCCGCTCACGGC
GGCAACGTCCTCATTACCGATACTTGGATTTCGATGGGACAGGAAGAG
GAAAAGAAGAAGAGACTGCAGGCGTTCCAGGGATACCAGGTCACCATG
AAAACTGCCAAAGTGGCAGCCTCCGACTGGACCTTCCTTCACTGCCTG
CCGAGGAAGCCTGAAGAGGTGGACGACGAGGTGTTCTACTCCCCGCGC
TCCTTGGTGTTTCCTGAGGCCGAAAACCGGAAGTGGACTATCATGGCC

-continued

GTGATGGTGTCCCTCCTCACCGACTACTCGCCGCAACTGCAGAAGCCT

AAGTTCTAG

>pARM721

(SEQ ID NO: 154)

ATGTTATTCAACCTTAGAATTCTCCTTAACAACGCCGCCTTCCGGAAT

GGGCATAACTTTATGGTCCGCAATTTCCGCTGTGGACAGCCTCTGCAA

AACAAGGTCCAGCTCAAGGGCCGGGATCTGCTGACTCTCAAGAACTTC

ACTGGGGAAGAAATCAAGTACATGCTCTGGCTGAGCGCCGACCTCAAG

TTCCGCATCAAGCAGAAGGGAGAGTACCTCCCGCTGCTCCAAGGGAAG

TCCCTGGGCATGATCTTCGAGAAGAGATCCACCCGCACCAGACTTTCC

ACTGAGACTGGCTTCGCCTTGCTGGGAGGCCACCCATGCTTCCTGACG

ACCCAGGACATTCACCTTGGCGTGAACGAGTCCCTGACTGACACCGCA

AGGGTGTTGTCCTCGATGGCCGACGCCGTGCTTGCCCGGGTGTACAAG

CAGAGCGATCTTGACACCCTGGCTAAGGAAGCTTCCATTCCCATCATC

AACGGTCTGAGCGACCTGTACCACCCGATTCAGATCCTGGCGGACTAC

CTAACCCTGCAAGAGCACTATAGCTCCCTGAAGGGCCTCACACTTTCA

TGGATCGGCGACGGCAACAACATCCTGCACTCTATTATGATGAGCGCT

GCCAAATTCGGCATGCACCTCCAAGCCGCCACGCCTAAAGGCTACGAG

CCCGACGCCTCGGTGACCAAGCTTGCGGAGCAGTACGCGAAGGAAAAC

GGCACCAAGCTGCTTCTCACCAACGATCCTCTGGAAGCGGCCCATGGT

GGCAACGTGCTCATTACCGACACTTGGATCTCCATGGGACAGGAGGAG

GAAAAGAAGAAGCGGCTCCAGGCGTTTCAGGGTTACCAGGTCACCATG

AAAACCGCCAAGGTCGCAGCCTCCGACTGGACCTTCCTTCATTGCCTT

CCGCGCAAGCCCGAAGAAGTGGACGATGAAGTGTTTTACTCACCTCGG

TCACTCGTGTTCCCGGAAGCAGAGAACAGGAAATGGACCATTATGGCC

GTGATGGTGTCCCTGCTCACCGATTACAGTCCGCAACTGCAGAAGCCC

AAGTTCTAG

>pARM722

(SEQ ID NO: 155)

ATGCTTTTCAATCTCCGCATCCTCCTTAACAACGCCGCGTTTAGAAAC

GGCCACAACTTCATGGTCCGGAACTTCAGATGTGGCCAGCCGCTTCAA

AACAAGGTCCAGCTGAAGGGCCGGGATCTTCTGACCCTGAAGAACTTT

ACTGGCGAAGAGATCAAGTACATGCTCTGGCTCTCCGCGGACTTGAAG

TTCCGCATTAAGCAGAAGGGGGAATACCTTCCGCTGCTTCAAGGAAAG

AGCCTCGGCATGATCTTTGAGAAGCGCTCAACCAGGACCCGCCTTTCT

ACTGAAACTGGGTTCGCGCTGCTCGGTGGCCACCCCTGCTTCCTGACG

ACCCAGGACATCCACCTCGGAGTGAACGAATCCCTCACCGATACCGCC

CGGGTGTTATCGAGCATGGCAGATGCCGTGCTGGCCAGGGTGTACAAA

CAGTCCGATCTGGACACTCTGGCCAAGGAGGCGTCAATTCCTATTATC

AACGGCCTTAGTGACCTCTACCATCCGATTCAAATCCTGGCCGATTAC

CTCACCCTGCAAGAACACTACAGCTCCCTGAAGGGTCTGACATTGTCC

TGGATCGGCGACGGCAACAACATTCTCCATTCCATCATGATGTCCGCC

GCAAAATTCGGCATGCATCTTCAAGCCGCCACGCCTAAGGGTTACGAA

CCCGACGCTTCCGTGACTAAGCTCGCCGAGCAGTACGCTAAGGAGAAC

GGAACCAAGCTGCTGCTGACTAACGACCCGCTAGAAGCAGCCCACGGG

GGCAACGTGCTTATTACTGACACCTGGATCTCCATGGGCCAGGAGGAA

GAGAAAAAGAAGCGGCTGCAGGCGTTCCAGGGATATCAGGTCACCATG

AAAACCGCCAAGGTCGCTGCCTCCGACTGGACCTTCCTGCACTGCCTG

CCTCGCAAGCCTGAAGAAGTGGACGACGAGGTGTTCTACTCGCCACGG

AGCCTCGTGTTCCCCGAGGCCGAGAATAGAAAGTGGACCATCATGGCC

GTGATGGTGTCACTTCTCACCGACTACAGCCCGCAGCTTCAGAAGCCC

AAGTTCTAG

>pARM723

(SEQ ID NO: 156)

ATGCTTTTCAATCTCCGCATCCTCCTTAACAACGCCGCGTTTAGAAAC

GGCCACAACTTCATGGTCCGGAACTTCAGATGTGGCCAGCCGCTTCAA

AACAAGGTCCAGCTTAAGGGCCGGGATCTCCTCACCCTTAAAAACTTC

ACCGGCGAAGAGATCAAGTACATGCTCTGGCTCTCCGCGGACCTTAAG

TTCCGCATTAAGCAGAAGGGGGAATACCTTCCGCTGCTTCAAGGAAAG

AGCCTCGGCATGATCTTTGAGAAGCGCTCAACCAGGACCAGGCTTTCT

ACTGAAACTGGGTTCGCGCTTCTCGGCGGTCATCCCTGCTTCCTCACG

ACCCAAGACATCCACCTCGGAGTGAACGAATCCCTCACGGATACTGCC

CGCGTGCTTTCGAGCATGGCAGACGCCGTGCTCGCCCGGGTGTACAAA

CAGTCCGATCTCGACACTCTCGCCAAGGAGGCGTCAATTCCTATTATC

AACGGTCTTAGTGACCTTTACCACCCGATCCAGATCCTCGCCGATTAC

CTCACACTCCAAGAACACTACAGCTCCCTTAAGGGTCTTACCCTCTCC

TGGATCGGCGACGGCAACAACATTCTCCACTCCATCATGATGTCCGCC

GCAAAGTTCGGCATGCATCTTCAAGCCGCCACCCCGAAGGGCTACGAG

CCTGATGCTTCCGTGACTAAGCTCGCCGAGCAGTACGCTAAGGAGAAC

GGAACCAAGCTTCTTCTCACTAACGACCCACTCGAAGCAGCCCATGGG

GGCAACGTGCTTATCACTGACACCTGGATCTCCATGGGCCAGGAAGAA

GAGAAGAAGAAGCGGCTCCAGGCGTTCCAGGGATATCAGGTCACCATG

AAAACCGCCAAGGTCGCTGCCTCCGACTGGACCTTTCTCCACTGCCTC

CCTCGCAAACCTGAAGAAGTGGACGACGAGGTGTTCTACTCGCCCCGG

AGCCTCGTGTTCCCCGAGGCCGAGAATAGAAAGTGGACCATTATGGCC

GTGATGGTGTCACTCCTCACCGACTACAGCCCGCAGCTTCAGAAGCCC

AAGTTCTAG

>pARM724

(SEQ ID NO: 157)

ATGCTTTTCAATCTCCGCATCCTCCTTAACAACGCCGCGTTTAGAAAC

GGACATAACTTCATGGTCCGGAACTTCAGATGTGGACAGCCGCTTCAA

AACAAGGTCCAGCTGAAGGGTCGGGATCTTCTGACCCTGAAGAACTTT

ACCGGAGAAGAGATCAAGTACATGCTCTGGCTCTCCGCGGACTTGAAG

TTCCGCATTAAGCAGAAGGGAGAATACCTCCCGCTGCTTCAAGGAAAG

AGCCTCGGAATGATTTTTGAGAAGCGCTCAACCAGGACCCGCCTTTCT

-continued

ACTGAAACTGGATTCGCGCTGCTGGGTGGACACCCCTGCTTCCTGACG
ACCCAGGACATCCACCTCGGAGTGAACGAATCCCTCACTGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATCATC
AACGGACTTAGTGACCTCTACCATCCGATTCAAATCCTGGCCGACTAC
CTCACCCTGCAAGAACACTACAGCTCCCTGAAGGGTCTGACATTGTCC
TGGATCGGAGATGGAAACAACATTCTCCACTCCATCATGATGTCCGCC
GCAAAATTCGGAATGCATCTTCAAGCCGCCACGCCTAAGGGTTACGAA
CCCGACGCTTCCGTGACTAAGCTCGCCGAGCAGTACGCTAAGGAGAAC
GGTACCAAGCTTCTCCTGACCAACGACCCACTAGAAGCAGCCCACGGT
GGAAACGTGCTTATTACTGACACTTGGATCTCCATGGGACAGGAGGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCGCGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM725

(SEQ ID NO: 158)

ATGCTTTTCAACCTCCGCATTCTCCTCAACAACGCTGCCTTCCGGAAT
GGACATAACTTCATGGTCCGGAACTTCAGATGCGGACAGCCGCTTCAG
AACAAGGTCCAGCTTAAGGGGAGAGATCTCCTTACCCTCAAAAACTTC
ACTGGCGAAGAAATCAAGTACATGCTCTGGCTTAGTGCGGATCTCAAG
TTCCGCATCAAGCAGAAGGGAGAATACCTCCCGCTCCTTCAAGGAAAG
AGCCTCGGCATGATTTTTGAGAAGAGGTCCACCAGAACTCGCCTTTCA
ACCGAGACTGGGTTCGCCCTGCTTGGCGGTCACCCCTGCTTCCTCACT
ACCCAAGACATCCACCTCGGCGTGAACGAGAGCCTTACCGACACCGCC
CGCGTGCTCTCCTCAATGGCCGACGCTGTGCTCGCCCGGGTGTACAAG
CAGTCCGACCTTGATACTCTCGCCAAGGAGGCCTCCATCCCAATTATC
AACGGGCTCTCTGATCTCTACCACCCTATCCAAATCCTCGCGGACTAC
CTCACCCTCCAAGAGCACTATAGCTCGCTCAAGGGCCTCACCCTTTCC
TGGATTGGCGACGGCAACAACATTCTTCACTCGATCATGATGTCCGCC
GCCAAGTTCGGCATGCATCTCCAAGCCGCGACCCCCAAGGGCTACGAG
CCTGACGCATCCGTGACCAAGCTCGCCGAGCAGTACGCGAAGGAAAAT
GGCACCAAGCTTCTTCTCACCAACGACCCCCTTGAGGCCGCTCATGGC
GGCAACGTGCTCATCACTGACACTTGGATCAGCATGGGCCAGGAGGAG
GAAAAGAAGAAGCGCCTTCAGGCATTCCAGGGTTACCAGGTCACCATG
AAAACCGCCAAAGTGGCCGCCTCCGACTGGACCTTTCTTCACTGTCTC
CCGCGGAAGCCTGAAGAAGTGGATGACGAAGTGTTTTACTCCCCTCGG
TCACTCGTGTTCCCGGAAGCAGAAAACAGGAAGTGGACCATTATGGCG
GTCATGGTGTCCCTCCTCACCGACTACAGCCCGCAGCTTCAGAAACCC
AAGTTCTAG

>pARM726

(SEQ ID NO: 159)

ATGCTTTTCAATCTCCGCATCCTCCTTAACAACGCAGCGTTTAGAAAC
GGTCACAACTTCATGGTCCGGAACTTCCGCTGTGGACAGCCGCTTCAA
AACAAGGTCCAGCTGAAGGGTCGGGACCTTCTGACCCTGAAGAACTTT
ACTGGAGAAGAGATCAAGTACATGCTTTGGCTGTCCGCGGACTTGAAG
TTCCGCATTAAGCAGAAGGGAGAATACCTTCCGCTGCTCCAAGGAAAG
AGCCTGGGAATGATCTTTGAGAAGCGCTCAACCAGGACCCGCCTTTCT
ACTGAAACTGGATTCGCGCTGCTGGGTGGTCACCCTTGCTTCCTGACG
ACCCAGGACATTCACCTCGGAGTGAACGAGTCCCTCACTGATACCGCC
AGAGTGTTATCGAGCATGGCAGATGCCGTGCTGGCTAGGGTGTACAAA
CAGTCCGATCTGGACACCCTGGCCAAGGAGGCATCAATTCCTATTATC
AACGGACTTAGTGACCTCTACCATCCGATTCAAATCCTGGCCGATTAC
CTCACCCTGCAAGAACACTACAGCTCCCTGAAGGGTCTGACATTGTCC
TGGATCGGAGATGGAAACAACATTCTCCATTCCATCATGATGTCCGCG
GCCAAGTTCGGAATGCATCTCCAAGCCGCCACGCCGAAAGGATACGAG
CCGGACGCTTCCGTGACTAAGCTCGCCGAGCAGTACGCTAAGGAGAAC
GGAACCAAGCTTCTGCTGACTAACGACCCGCTAGAAGCCGCCCACGGT
GGAAACGTGCTTATTACTGACACCTGGATCTCCATGGGACAGGAAGAA
GAGAAAAAGAAGCGGCTGCAGGCGTTCCAGGGATATCAGGTCACCATG
AAAACCGCCAAGGTCGCCGCCTCCGACTGGACCTTCCTTCACTGCCTG
CCTCGGAAGCCTGAAGAAGTGGACGACGAGGTGTTCTACTCGCCGCGG
AGCCTCGTGTTCCCTGAGGCCGAGAATAGAAAGTGGACCATCATGGCC
GTGATGGTGTCACTCCTCACCGACTACAGCCCGCAGCTTCAGAAGCCT
AAGTTCTAG

>pARM727

(SEQ ID NO: 160)

ATGCTTTTCAATCTCCGCATTCTCCTCAACAACGCAGCCTTTAGAAAC
GGCCACAACTTCATGGTCCGGAACTTCAGATGTGGCCAGCCGCTTCAG
AACAAGGTCCAGCTCAAGGGCCGGGACCTCCTCACCCTCAAAAACTTT
ACCGGCGAAGAGATCAAGTACATGCTCTGGCTTTCGGCCGACCTTAAG
TTCCGCATCAAGCAGAAGGGGGAATACCTTCCGCTGCTTCAAGGAAAG
TCCCTCGGCATGATCTTTGAAAAGCGCTCGACCAGGACCCGCCTTTCC
ACTGAAACCGGGTTCGCGCTTCTCGGTGGCCACCCCTGCTTCCTCACC
ACCCAAGACATTCACCTCGGAGTGAACGAATCCCTTACCGATACCGCA
AGAGTGCTTTCGTCGATGGCCGATGCCGTGCTTGCGCGGGTGTACAAG
CAGTCAGATCTCGACACTCTCGCCAAGGAGGCGTCCATTCCTATTATC
AACGGCCTTTCCGACCTTTACCACCCGATTCAGATCCTCGCCGATTAC
CTCACCCTGCAAGAGCACTACTCGTCACTCAAGGGTCTTACCCTCTCC

-continued

TGGATCGGCGACGGAAACAACATCCTCCATTCGATCATGATGTCCGCC

GCCAAATTCGGCATGCACCTCCAAGCCGCGACCCCGAAGGGTTACGAG

CCCGACGCTTCCGTGACCAAGCTCGCCGAACAGTACGCTAAGGAAAAC

GGCACCAAGCTCCTCCTCACTAACGACCCTCTCGAAGCAGCCCATGGG

GGCAACGTGCTCATTACTGACACTTGGATCTCGATGGGCCAGGAAGAG

GAGAAAAAGAAGCGGCTTCAGGCGTTCCAGGGATATCAGGTCACCATG

AAAACCGCCAAGGTCGCTGCCTCGGACTGGACCTTCCTTCACTGCCTT

CCGCGCAAGCCTGAAGAGGTGGACGATGAGGTGTTCTACTCCCCACGG

TCCCTTGTGTTCCCCGAGGCCGAGAATAGGAAGTGGACCATCATGGCC

GTGATGGTGTCGCTCCTCACTGACTACTCCCCGCAACTTCAGAAGCCT

AAGTTCTAG

>pARM728

(SEQ ID NO: 161)

ATGCTGTTTAATCTGAGAATACTTCTAAACAACGCCGCCTTCCGGAAT

GGCCATAACTTTATGGTTCGGAATTTCCGCTGCGGCCAGCCGCTGCAG

AACAAGGTCCAGCTGAAGGGAAGAGACTTGCTGACCCTCAAGAACTTC

ACCGGAGAAGAAATCAAGTATATGCTGTGGCTGTCCGCCGACCTGAAA

TTCCGCATCAAGCAGAAGGGCGAATATCTGCCGCTGTTGCAAGGGAAG

TCCCTGGGGATGATCTTCGAGAAGAGGTCCACCAGAACACGGCTTTCA

ACCGAAACCGGGTTTGCACTGCTGGGTGGACACCCCTGTTTTCTGACC

ACTCAAGATATCCACCTGGGCGTGAACGAGTCCCTTACCGACACTGCT

AGGGTGTTGTCCAGCATGGCCGATGCCGTCCTGGCTCGCGTGTACAAG

CAGTCCGACCTGGATACCCTGGCAAAGGAAGCGTCCATTCCCATTATC

AACGGGCTGTCCGACCTGTACCATCCGATTCAAATCCTGGCGGACTAC

CTGACTCTGCAAGAGCATTACAGCAGCTTGAAGGGGCTTACTCTCTCG

TGGATCGGCGACGGGAACAACATCCTGCACTCCATCATGATGTCCGCC

GCCAAGTTCGGGATGCATTTGCAAGCTGCGACCCCGAAAGGTTACGAG

CCCGATGCTAGCGTAACTAAGCTTGCCGAACAGTACGCCAAAGAGAAT

GGTACAAAACTGCTTCTGACTAACGACCCGCTGGAAGCAGCCCACGGC

GGGAACGTGCTGATAACCGACACCTGGATTTCAATGGGGCAGGAGGAA

GAGAAGAAGAAGCGACTGCAGGCGTTCCAAGGCTATCAGGTTACCATG

AAAACCGCCAAAGTGGCAGCCAGCGATTGGACTTTCCTGCACTGTCTG

CCGCGGAAGCCCGAGGAAGTTGATGACGAAGTATTCTACTCACCCCGG

AGCCTCGTGTTCCCCGAGGCCGAAAACCGGAAGTGGACTATTATGGCC

GTGATGGTGTCGCTGTTGACCGACTACAGCCCGCAACTGCAGAAGCCG

AAGTTTTAG

>pARM729

(SEQ ID NO: 162)

ATGCTTTTCAACCTGAGGATCCTTTTGAACAACGCCGCCTTTCGCAAC

GGCCACAACTTTATGGTCCGCAATTTCCGCTGCGGGCAGCCGCTGCAG

AACAAGGTCCAGCTGAAGGGCCGGGATCTGCTGACCCTGAAGAACTTC

ACCGGGGAGGAAATCAAGTACATGCTTTGGCTCTCCGCCGATCTGAAG

TTCAGAATCAAGCAGAAGGGAGAGTACCTCCCGTTGCTGCAAGGAAAG

TCACTCGGAATGATTTTCGAAAAGAGAAGCACTAGGACCCGCCTCTCA

ACTGAAACCGGGTTCGCGCTGCTCGGGGGCCATCCGTGTTTCCTGACT

ACCCAAGACATCCACCTGGGAGTGAACGAGTCGCTGACCGACACCGCA

CGCGTGCTGTCATCCATGGCGGACGCAGTGCTTGCCCGGGTGTACAAG

CAGTCGGACCTGGACACTCTTGCCAAGGAGGCATCAATCCCCATCATT

AACGGACTGTCCGATCTCTACCACCCGATTCAGATCCTGGCTGACTAC

CTAACCCTGCAAGAGCACTACTCAAGCCTGAAGGGGCTGACCCTGTCG

TGGATCGGGGACGGCAACAACATTCTGCACTCCATCATGATGTCGGCG

GCTAAGTTCGGGATGCATTTGCAAGCGGCAACTCCGAAGGGTTATGAA

CCCGACGCCTCCGTGACCAAGCTGGCCGAACAGTACGCCAAGGAAAAC

GGAACCAAGTTGCTGCTGACTAATGATCCCCTGGAGGCGGCCCACGGG

GGGAACGTGCTGATAACCGATACCTGGATCTCCATGGGGCAGGAAGAA

GAGAAGAAAAAGCGGCTGCAGGCATTCCAGGGATACCAGGTCACCATG

AAAACCGCAAAAGTGGCAGCCAGCGACTGGACTTTCCTCCATTGCCTG

CCGCGAAAGCCGGAGGAGGTCGATGACGAGGTGTTCTACTCCCCGCGG

TCGCTGGTGTTCCCGGAGGCGGAAAACCGGAAGTGGACCATTATGGCC

GTGATGGTGTCACTCCTGACTGACTACAGCCCGCAACTGCAGAAGCCG

AAGTTCTAG

>pARM1787

(SEQ ID NO: 163)

ATGCTTTTCAATCTCCGCATCCTCCTTAACAACGCCGCGTTTAGAAAC

GGCCACAACTTCATGGTCCGGAACTTCAGATGTGGCCAGCCGCTTCAA

AACAAGGTCCAGCTGAAGGGCCGGGATCTTCTGACCCTGAAGAACTTT

ACTGGCGAAGAGATCAAGTACATGCTCTGGCTCTCCGCGGACTTGAAG

TTCCGCATTAAGCAGAAGGGGGAATACCTTCCGCTGCTTCAAGGAAAG

AGCCTCGGCATGATCTTTGAGAAGCGCTCAACCAGGACCCGCCTTTCT

ACTGAAACTGGGTTCGCGCTGCTCGGTGGCCACCCCTGCTTCCTGACG

ACCCAGGACATCCACCTCGGAGTGAACGAATCCCTCACCGATACCGCC

CGGGTGTTATCGAGCATGGCAGATGCCGTGCTGGCCAGGGTGTACAAA

CAGTCCGATCTGGACACTCTGGCCAAGGAGGCGTCAATTCCTATTATC

AACGGCCTTAGTGACCTCTACCATCCGATTCAGATCCTGGCCGATTAC

CTCACCCTGCAAGAACACTACAGCTCCCTGAAGGGTCTGACATTGTCC

TGGATCGGCGACGGCAACAACATTCTCCATTCCATCATGATGTCCGCC

GCAAAATTCGGCATGCATCTTCAAGCCGCCACGCCGAAGGGTTACGAG

CCCGACGCTTCCGTGACTAAGCTCGCCGAGCAGTACGCTAAGGAGAAC

GGAACCAAGCTTCTGCTGACTAACGACCCACTAGAAGCAGCCCACGGG

GGCAACGTGCTTATTACTGACACCTGGATCTCCATGGGCCAGGAAGAA

GAGAAAAAGAAGCGGCTGCAGGCGTTCCAGGGATATCAGGTCACCATG

AAAACCGCCAAGGTCGCTGCCTCCGACTGGACCTTCCTGCACTGCCTG

CCTCGCAAGCCTGAAGAAGTGGACGACGAGGTGTTCTACTCGCCACGG

AGCCTCGTGTTCCCCGAGGCCGAGAATAGAAAGTGGACCATCATGGCC

GTGATGGTGTCACTGCTCACCGACTACAGCCCGCAGCTTCAGAAGCCC

AAGTTCTAGATAAGTGAA

>pARM1788 (SEQ ID NO: 164)
ATGCTGTTCAACCTGCGCATCCTGCTGAACAACGCCGCCTTCCGCAAC

GGCCACAACTTCATGGTGCGCAACTTCCGCTGCGGCCAGCCCCTGCAG

AACAAGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCCTGGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGAATAAGTGA

>pARM1789 (SEQ ID NO: 165)
ATGCTGTTCAACCTGCGCATCCTGCTGAACAACGCCGCCTTCCGCAAC

GGCCACAACTTCATGGTGCGCAACTTCCGCTGCGGCCAGCCCCTGCAG

AACAAGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCCTGGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGAATAAGTGA

>pARM1790 (SEQ ID NO: 166)
ATGCTTTTCAATCTCCGCATCCTCCTTAACAACGCCGCGTTTAGAAAC

GGCCACAACTTCATGGTCCGGAACTTCAGATGTGGCCAGCCGCTTCAA

AACAAGGTCCAGCTGAAGGGCCGGGATCTTCTGACCCTGAAGAACTTT

ACTGGCGAAGAGATCAAGTACATGCTCTGGCTCTCCGCGGACTTGAAG

TTCCGCATTAAGCAGAAGGGGGAATACCTTCCGCTGCTTCAAGGAAAG

AGCCTCGGCATGATCTTTGAGAAGCGCTCAACCAGGACCCGCCTTTCT

ACTGAAACTGGGTTCGCGCTGCTCGGTGGCCACCCCTGCTTCCTGACG

ACCCAGGACATCCACCTCGGAGTGAACGAATCCCTCACCGATACCGCC

CGGGTGTTATCGAGCATGGCAGATGCCGTGCTGGCCAGGGTGTACAAA

CAGTCCGATCTGGACACTCTGGCCAAGGAGGCGTCAATTCCTATTATC

AACGGCCTTAGTGACCTCTACCATCCGATTCAGATCCTGGCCGATTAC

CTCACCCTGCAAGAACACTACAGCTCCCTGAAGGGTCTGACATTGTCC

TGGATCGGCGACGGCAACAACATTCTCCATTCCATCATGATGTCCGCC

GCAAAATTCGGCATGCATCTTCAAGCCGCCACGCCGAAGGGTTACGAG

CCCGACGCTTCCGTGACTAAGCTCGCCGAGCAGTACGCTAAGGAGAAC

GGAACCAAGCTTCTGCTGACTAACGACCCACTAGAAGCAGCCCACGGG

GGCAACGTGCTTATTACTGACACCTGGATCTCCATGGGCCAGGAAGAA

GAGAAAAAGAAGCGGCTGCAGGCGTTCCAGGGATATCAGGTCACCATG

AAAACCGCCAAGGTCGCTGCCTCCGACTGGACCTTCCTGCACTGCCTG

CCTCGCAAGCCTGAAGAAGTGGACGACGAGGTGTTCTACTCGCCACGG

AGCCTCGTGTTCCCCGAGGCCGAGAATAGAAAGTGGACCATCATGGCC

GTGATGGTGTCACTGCTCACCGACTACAGCCCGCAGCTTCAGAAGCCC

AAGTTCTAGATAAGTGAA

>pARM1791 (SEQ ID NO: 167)
ATGCTTTTCAACCTGAGAATCCTCTTGAACAATGCTGCTTTTCGGAAT

GGCCACAACTTTATGGTTCGGAACTTCCGTTGCGGCCAGCCTTTACAA

AACAAGGTCCAGCTGAAGGGCCGGGATTTGCTCACACTAAAGAACTTT

ACTGGAGAAGAGATCAAGTACATGCTATGGCTGTCGGCCGACCTGAAG

TTCCGTATCAAGCAGAAGGGAGAATACCTTCCGCTGCTTCAAGGAAAG

AGCCTCGGCATGATCTTTGAGAAGCGCTCAACCAGGACCCGCCTTTCT

-continued

ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCATCCGTGACCAAGTTGGCGGAACAGTACGCGAAGGAGAAC
GGAACCAAGCTCCTGCTGACTAACGACCCGCTCGAGGCTGCGCATGGG
GGTAACGTGCTGATTACGGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAGATAAGTGA

>pARM1792

(SEQ ID NO: 168)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCCTGGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGAATAAGTGA

-continued

>pARM1793

(SEQ ID NO: 169)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAGATAAGTGAA

>pARM1794

(SEQ ID NO: 170)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCCTGGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC

-continued

GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGAATAAGTGA

>pARM1795

(SEQ ID NO: 171)

ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTAAAGAACTTT
ACTGGAGAAGAGATCAAGTACATGCTATGGCTGTCGGCCGACCTGAAG
TTCCGTATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCATCCGTGACCAAGTTGGCGGAACAGTACGCGAAGGAGAAC
GGAACCAAGCTCCTGCTGACTAACGACCCGCTCGAGGCTGCGCATGGG
GGTAACGTGCTGATTACGGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAGATAAGTGA

>pARM1796

(SEQ ID NO: 172)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAGATAAGTGAA

>pARM1797

(SEQ ID NO: 173)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCCTGGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGAATAAGTGA

-continued

>pARM1798
(SEQ ID NO: 174)
ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTAAAGAACTTT
ACTGGAGAAGAGATCAAGTACATGCTATGGCTGTCGGCCGACCTGAAG
TTCCGTATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCATCCGTGACCAAGTTGGCGGAACAGTACGCGAAGGAGAAC
GGAACCAAGCTCCTGCTGACTAACGACCCGCTCGAGGCTGCGCATGGG
GGTAACGTGCTGATTACGGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTAGATAAGTGA

>pARM1799
(SEQ ID NO: 175)
ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1800
(SEQ ID NO: 176)
ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1801
(SEQ ID NO: 177)
ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC

-continued

CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1802

(SEQ ID NO: 178)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGAATAAGTGAA

>pARM1803

(SEQ ID NO: 179)

ATGGGCGTCTTCAACCTGCGGATCCTGCTGAACAACGCCGCCTTCCGG
AACGGCCACAACTTCATGGTCCGCAACTTCAGATGCGGCCAGCCCCTG
CAGAACAAGGTGCAGCTGAAGGGCCGGGACCTGCTGACCCTGAAGAAC
TTCACCGGCGAAGAGATCAAGTACATGCTGTGGCTGAGCGCCGACCTG
AAGTTCCGGATCAAGCAGAAGGGCGAGTACCTGCCCCTGCTGCAAGGC
AAGAGCCTGGGCATGATCTTCGAGAAGCGGAGCACCCGGACCCGGCTG
AGCACCGAGACAGGCTTTGCCCTGCTGGGAGGCCACCCCTGCTTTCTG
ACCACCCAGGACATCCACCTGGGCGTGAACGAGAGCCTGACCGACACC
GCCAGAGTGCTGAGCAGCATGGCCGACGCCGTGCTGGCCCGGGTGTAC
AAGCAGAGCGACCTGGACACCCTGGCCAAAGAGGCCAGCATCCCCATC
ATCAACGGCCTGAGCGACCTGTACCACCCCATCCAGATCCTGGCCGAC
TACCTGACCCTGCAGGAACACTACAGCTCCCTGAAGGGCCTGACCCTG
AGCTGGATCGGCGACGGCAACAACATCCTGCACAGCATCATGATGAGC
GCCGCCAAGTTCGGCATGCATCTGCAGGCCGCCACCCCCAAGGGCTAC
GAGCCTGATGCCAGCGTGACCAAGCTGGCCGAGCAGTACGCCAAAGAG
AACGGCACCAAGCTGCTGCTGACCAACGACCCCCTGGAAGCCGCCCAC
GGCGGCAACGTGCTGATCACCGACACCTGGATCAGCATGGGCCAGGAA
GAGGAAAAGAAGAAGCGGCTGCAGGCCTTCCAGGGCTACCAGGTCACA
ATGAAGACCGCCAAGGTGGCCGCCAGCGACTGGACCTTCCTGCACTGC
CTGCCCCGGAAGCCCGAAGAGGTGGACGACGAGGTGTTCTACAGCCCC
CGGTCCCTGGTGTTCCCCGAGGCCGAGAACCGGAAGTGGACCATTATG
GCCGTGATGGTGTCCCTGCTGACCGACTACTCCCCCCAGCTGCAGAAG
CCCAAGTTCTAGATAAGTGAA

>pARM1804

(SEQ ID NO: 180)

ATGGGCGTCTTCAACCTGCGGATCCTGCTGAACAACGCCGCCTTCCGG
AACGGCCACAACTTCATGGTCCGCAACTTCAGATGCGGCCAGCCCCTG
CAGAACAGGGTGCAGCTGAAGGGCCGGGACCTGCTGACCCTGAAGAAC
TTCACCGGCGAAGAGATCAGGTACATGCTGTGGCTGAGCGCCGACCTG
AAGTTCCGGATCAAGCAGAAGGGCGAGTACCTGCCCCTGCTGCAAGGC
AAGAGCCTGGGCATGATCTTCGAGAAGCGGAGCACCCGGACCCGGCTG
AGCACCGAGACAGGCTTTGCCCTGCTGGGAGGCCACCCCTGCTTTCTG
ACCACCCAGGACATCCACCTGGGCGTGAACGAGAGCCTGACCGACACC
GCCAGAGTGCTGAGCAGCATGGCCGACGCCGTGCTGGCCCGGGTGTAC
AAGCAGAGCGACCTGGACACCCTGGCCAAAGAGGCCAGCATCCCCATC
ATCAACGGCCTGAGCGACCTGTACCACCCCATCCAGATCCTGGCCGAC
TACCTGACCCTGCAGGAACACTACAGCTCCCTGAAGGGCCTGACCCTG
AGCTGGATCGGCGACGGCAACAACATCCTGCACAGCATCATGATGAGC
GCCGCCAAGTTCGGCATGCATCTGCAGGCCGCCACCCCCAAGGGCTAC
GAGCCTGATGCCAGCGTGACCAAGCTGGCCGAGCAGTACGCCAAAGAG

-continued

AACGGCACCAAGCTGCTGCTGACCAACGACCCCCTGGAAGCCGCCCAC
GGCGGCAACGTGCTGATCACCGACACCTGGATCAGCATGGGCCAGGAA
GAGGAAAAGAAGAAGCGGCTGCAGGCCTTCCAGGGCTACCAGGTCACA
ATGAAGACCGCCAAGGTGGCCGCCAGCGACTGGACCTTCCTGCACTGC
CTGCCCCGGAAGCCCGAAGAGGTGGACGACGAGGTGTTCTACAGCCCC
CGGTCCCTGGTGTTCCCCGAGGCCGAGAACCGGAAGTGGACCATTATG
GCCGTGATGGTGTCCCTGCTGACCGACTACTCCCCCCAGCTGCAGAAG
CCCAAGTTCTAGATAAGTGAA

>pARM1805

(SEQ ID NO: 181)

ATGCTGGTCTTCAACCTGCGGATCCTGCTGAACAACGCCGCCTTCCGG
AACGGCCACAACTTCATGGTCCGCAACTTCAGATGCGGCCAGCCCCTG
CAGAACAGGGTGCAGCTGAAGGGCCGGGACCTGCTGACCCTGAAGAAC
TTCACCGGCGAAGAGATCAGGTACATGCTGTGGCTGAGCGCCGACCTG
AAGTTCCGGATCAAGCAGAAGGGCGAGTACCTGCCCCTGCTGCAAGGC
AAGAGCCTGGGCATGATCTTCGAGAAGCGGAGCACCCGGACCCGGCTG
AGCACCGAGACAGGCTTTGCCCTGCTGGGAGGCCACCCCTGCTTTCTG
ACCACCCAGGACATCCACCTGGGCGTGAACGAGAGCCTGACCGACACC
GCCAGAGTGCTGAGCAGCATGGCCGACGCCGTGCTGGCCCGGGTGTAC
AAGCAGAGCGACCTGGACACCCTGGCCAAAGAGGCCAGCATCCCCATC
ATCAACGGCCTGAGCGACCTGTACCACCCCATCCAGATCCTGGCCGAC
TACCTGACCCTGCAGGAACACTACAGCTCCCTGAAGGGCCTGACCCTG
AGCTGGATCGGCGACGGCAACAACATCCTGCACAGCATCATGATGAGC
GCCGCCAAGTTCGGCATGCATCTGCAGGCCGCCACCCCCAAGGGCTAC
GAGCCTGATGCCAGCGTGACCAAGCTGGCCGAGCAGTACGCCAAAGAG
AACGGCACCAAGCTGCTGCTGACCAACGACCCCCTGGAAGCCGCCCAC
GGCGGCAACGTGCTGATCACCGACACCTGGATCAGCATGGGCCAGGAA
GAGGAAAAGAAGAAGCGGCTGCAGGCCTTCCAGGGCTACCAGGTCACA
ATGAAGACCGCCAAGGTGGCCGCCAGCGACTGGACCTTCCTGCACTGC
CTGCCCCGGAAGCCCGAAGAGGTGGACGACGAGGTGTTCTACAGCCCC
CGGTCCCTGGTGTTCCCCGAGGCCGAGAACCGGAAGTGGACCATTATG
GCCGTGATGGTGTCCCTGCTGACCGACTACTCCCCCCAGCTGCAGAAG
CCCAAGTTCTAGATAAGTGAA

>pARM1806

(SEQ ID NO: 182)

ATGCTGTTCAACCTGAGGATCCTGCTGAACAACGCAGCTTTCAGGAAC
GGCCACAACTTCATGGTGAGGAACTTCCGGTGCGGCCAGCCCCTGCAG
AACAAGGTGCAGCTGAAGGGCAGGGACCTGCTGACCCTGAAGAACTTC
ACCGGAGAGGAGATCAAGTACATGCTGTGGCTGAGCGCAGACCTGAAG
TTCAGGATCAAGCAGAAGGGAGAGTACCTGCCCCTGCTGCAGGGGAAG
TCCCTGGGCATGATCTTCGAGAAGAGGAGTACCAGGACCAGGCTGAGC
ACCGAAACCGGCTTCGCCCTGCTGGGAGGACACCCCTGCTTCCTGACC
ACCCAGGACATCCACCTGGGCGTGAACGAGAGTCTGACCGACACCGCC

-continued

AGGGTGCTGTCTAGCATGGCCGACGCCGTGCTGGCCAGGGTGTACAAG
CAGTCAGACCTGGACACCCTGGCTAAGGAGGCCAGCATCCCCATCATC
AACGGCCTGAGCGACCTGTACCACCCCATCCAGATCCTGGCTGACTAC
CTGACCCTGCAGGAGCACTACAGCTCTCTGAAGGGCCTGACCCTGAGC
TGGATCGGCGACGGGAACAACATCCTGCACAGCATCATGATGAGCGCC
GCCAAGTTCGGCATGCACCTGCAGGCCGCTACCCCCAAGGGTTACGAG
CCCGACGCCAGCGTGACCAAGCTGGCAGAGCAGTACGCCAAGGAGAAC
GGCACCAAGCTGCTGCTGACCAACGACCCCCTGGAGGCCGCCCACGGA
GGCAACGTGCTGATCACCGACACCTGGATCAGCATGGGACAGGAGGAG
GAGAAGAAGAAGCGGCTGCAGGCTTTCCAGGGTTACCAGGTGACCATG
AAGACCGCCAAGGTGGCTGCCAGCGACTGGACCTTCCTGCACTGCCTG
CCCAGGAAGCCCGAGGAGGTGGACGACGAGGTGTTCTACTCTCCCAGG
AGCCTGGTGTTCCCCGAGGCCGAGAACAGGAAGTGGACCATCATGGCT
GTGATGGTGTCCCTGCTGACCGACTACAGCCCCCAGCTGCAGAAGCCC
AAGTTCTGAATAAGTGAA

>pARM1808

(SEQ ID NO: 183)

ATGCTGTTCAACCTGAGGATCCTGCTGAACAACGCAGCTTTCAGGAAC
GGCCACAACTTCATGGTGAGGAACTTCCGGTGCGGCCAGCCCCTGCAG
AACAAGGTGCAGCTGAAGGGCAGGGACCTGCTGACCCTGAAGAACTTC
ACCGGAGAGGAGATCAAGTACATGCTGTGGCTGAGCGCAGACCTGAAG
TTCAGGATCAAGCAGAAGGGAGAGTACCTGCCCCTGCTGCAGGGGAAG
TCCCTGGGCATGATCTTCGAGAAGAGGAGTACCAGGACCAGGCTGAGC
ACCGAAACCGGCTTCGCCCTGCTGGGAGGACACCCCTGCTTCCTGACG
ACCCAGGACATCCACCTCGGAGTGAACGAATCCCTCACCGATACCGCC
CGGGTGTTATCAAGCATGGCAGATGCCGTGCTGGCCAGGGTGTACAAA
CAGTCCGATCTGGACACTCTGGCTAAGGAGGCCAGCATCCCCATCATC
AACGGCCTGAGCGACCTGTACCACCCCATCCAGATCCTGGCTGACTAC
CTGACCCTGCAGGAGCACTACAGCTCTCTGAAGGGCCTGACCCTGAGC
TGGATCGGCGACGGGAACAACATCCTGCACTCCATCATGATGTCCGCC
GCGAAGTTCGGAATGCATCTGCAAGCCGCCACGCCAAAAGGATACGAA
CCGGATGCGCCCGTGACAAAGTTGGCGGAACAGTACGCTAAGGAGAAC
GGAACCAAGCTGCTGCTGACCAACGACCCCCTGGAGGCCGCCCACGGA
GGCAACGTGCTGATCACCGACACCTGGATCAGCATGGGACAGGAGGAG
GAGAAGAAGAAGCGGCTGCAGGCTTTCCAGGGTTACCAGGTGACCATG
AAGACCGCCAAGGTGGCTGCCAGCGACTGGACCTTCCTGCACTGCCTG
CCCAGGAAGCCCGAGGAGGTGGACGACGAGGTGTTCTACTCTCCCAGG
AGCCTGGTGTTCCCCGAGGCCGAGAACAGGAAGTGGACCATCATGGCT
GTGATGGTGTCCCTGCTGACCGACTACAGCCCCCAGCTGCAGAAGCCC
AAGTTCTGAATAAGTGAA

>pARM1809
(SEQ ID NO: 184)
ATGCTGTTCAACCTGCGCATCCTGCTGAACAACGCCGCCTTCCGCAAC

GGCCACAACTTCATGGTGCGCAACTTCCGCTGCGGCCAGCCCCTGCAG

AACAAGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCTTCGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGAATAAGTGAA

>pARM1816
(SEQ ID NO: 185)
ATGCTGTTCAACCTGCGCATCCTGCTGAACAACGCCGCCTTCCGCAAC

GGCCACAACTTCATGGTGCGCAACTTCCGCTGCGGCCAGCCCCTGCAG

AACAAGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCTTCGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGAATAAGTGAA

>pARM1822
(SEQ ID NO: 186)
ATGCTTTTCAACTTGAGAATCCTGCTGAACAACGCCGCCTTTCGCAAC

GGTCACAATTTTATGGTCAGAAACTTCAGATGCGGACAGCCCCTCCAA

AACAAGGTCCAGCTGAAGGGCCGCGATCTCCTCACCCTGAAGAACTTC

ACGGGGGAGGAGATCAAGTACATGCTGTGGCTCTCCGCTGACCTGAAG

TTCAGGATCAAGCAGAAGGGAGAATATCTGCCGCTGCTGCAAGGGAAG

TCCCTGGGGATGATTTTCGAGAAGCGGAGCACCCGGACTCGGCTCTCC

ACTGAAACTGGTTTCGCCCTTCTGGGCGGTCACCCCTGCTTCCTGACC

ACTCAAGACATTCACCTCGGAGTGAACGAGTCCTTGACTGACACCGCC

CGGGTGCTGTCGAGCATGGCAGACGCCGTGCTAGCCCGCGTGTACAAG

CAGTCAGACCTCGATACCCTGGCCAAGGAGGCTTCGATCCCGATCATC

AACGGGTTGTCCGACCTGTACCACCCGATTCAGATTCTCGCCGACTAC

CTCACCCTGCAAGAGCATTACAGCTCCCTGAAGGGGCTTACCCTGTCC

TGGATTGGCGACGGAAACAACATCCTGCACTCCATTATGATGTCGGCG

GCCAAGTTCGGCATGCACCTCCAAGCCGCGACCCCTAAGGGTTACGAA

CCAGACGCGTCAGTGACTAAGCTGGCCGAACAGTACGCAAAGGAAAAT

GGCACGAAGCTGCTCCTGACCAACGATCCGTTGGAAGCCGCCCATGGC

GGAAATGTGCTCATCACCGACACCTGGATCTCGATGGGACAGGAGGAA

GAGAAGAAGAAGCGGCTGCAGGCGTTCCAGGGCTACCAGGTCACCATG

AAAACTGCCAAGGTGGCCGCCAGCGACTGGACCTTCCTGCACTGCCTT

CCGCGCAAGCCTGAGGAGGTGGACGATGAAGTGTTCTACTCTCCACGG

TCCCTGGTGTTCCCCGAGGCGGAGAACCGCAAATGGACCATCATGGCT

GTGATGGTCAGCCTGCTGACCGATTACAGCCCTCAGTTGCAAAAGCCG

AAGTTTTGA

>pARM1823
(SEQ ID NO: 187)
ATGCTGTTCAACCTCCGCATCCTCCTCAACAACGCCGCATTCAGAAAC

GGGCACAACTTCATGGTCAGAAACTTCCGCTGCGGGCAACCCCTACAA

AACAAGGTCCAGCTCAAGGGGGGGGACCTCCTGACCCTGAAGAACTTC

ACCGGCGAAGAGATCAAGTACATGCTGTGGCTCTCCGCCGACCTGAAG

TTCCGCATCAAGCAGAAGGGAGAGTACCTCCCGCTGCTGCAAGGGAAG

TCGCTGGGGATGATCTTCGAGAAGCGGTCAACCAGAACCCGGCTGTCA

ACCGAAACCGGGTTCGCACTGCTGGGGGGACACCCGTGCTTCCTGACC

ACCCAAGACATCCACCTGGGAGTGAACGAATCGCTGACCGACACCGCC

-continued

CGCGTGCTGAGCTCAATGGCGGACGCCGTGCTGGCCCGCGTGTACAAG
CAGTCCGACCTGGACACCCTGGCCAAGGAAGCGTCCATCCCGATCATC
AACGGACTGTCCGACCTGTACCACCCGATCCAGATCCTGGCAGACTAC
CTGACCCTGCAAGAACACTACAGCTCCCTGAAGGGCCTGACCCTGTCA
TGGATCGGGGACGGGAACAACATCCTGCACTCCATAATGATGTCAGCC
GCCAAGTTCGGAATGCACCTCCAAGCCGCAACCCCGAAGGGCTACGAA
CCGGACGCATCAGTGACCAAACTGGCCGAGCAGTACGCCAAGGAAAAC
GGCACCAAGCTCCTGCTGACCAACGACCCGCTGGAGGCCGCACACGGG
GGGAACGTGCTGATCACCGACACCTGGATCTCCATGGGACAGGAGGAG
GAAAAGAAGAAGCGGCTGCAGGCGTTCCAGGGGTACCAGGTCACCATG
AAAACCGCGAAGGTCGCGGCATCAGACTGGACCTTCCTGCACTGCCTG
CCCCGGAAGCCGGAAGAGGTGGACGACGAGGTGTTCTACTCGCCGCGC
TCGCTGGTGTTCCCCGAGGCGGAGAACAGGAAGTGGACCATCATGGCG
GTGATGGTCAGCCTCCTGACCGACTACTCGCCGCAGCTGCAGAAGCCG
AAGTTCTGA

>pARM1840

(SEQ ID NO: 188)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTGAATAAGTAGA

-continued

>pARM1841

(SEQ ID NO: 189)

ATGCTTTTCAACCTGAGAATCCTCTTGAACAATGCTGCTTTTCGGAAT
GGCCACAACTTTATGGTTCGGAACTTCCGTTGCGGCCAGCCTTTACAA
AACAAGGTCCAGCTGAAGGGCCGGGATTTGCTCACACTAAAGAACTTT
ACTGGAGAAGAGATCAAGTACATGCTATGGCTGTCGGCCGACCTGAAG
TTCCGTATCAAGCAGAAGGGAGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTCGATACCTTGGCAAAGGAGGCTTCCATTCCCATCATC
AACGGCCTGAGCGACCTGTACCACCCAATCCAAATCCTGGCTGACTAC
CTGACCCTGCAAGAGCACTACAGCAGCCTGAAGGGTCTGACCCTGTCA
TGGATTGGCGATGGAAACAATATTCTGCACTCCATCATGATGTCCGCC
GCGAAGTTCGGAATGCATCTGCAAGCCGCCACTCCAAAAGGATACGAA
CCGGATGCATCCGTGACCAAGTTGGCGGAACAGTACGCGAAGGAGAAC
GGAACCAAGCTCCTGCTGACTAACGACCCGCTCGAGGCTGCGCATGGG
GGTAACGTGCTGATTACGGACACCTGGATCTCCATGGGGCAGGAGGAA
GAGAAGAAGAAGAGACTGCAGGCATTCCAGGGGTACCAGGTCACCATG
AAAACCGCAAAAGTGGCAGCTTCGGACTGGACTTTCCTGCATTGCCTG
CCGAGGAAGCCGGAGGAAGTCGACGACGAAGTGTTCTACTCGCCTCGG
TCCCTGGTGTTCCCCGAGGCCGAAAACCGGAAGTGGACCATCATGGCC
GTGATGGTGTCCTTGCTGACTGACTATAGCCCGCAGCTGCAGAAGCCT
AAGTTCTGAATAAGTAGA

>pARM1842

(SEQ ID NO: 190)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCCTGGCCCTGCTGGGCGGCCACCCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC

-continued

GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGAATAAGTAGA

>pARM1843

(SEQ ID NO: 191)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1844

(SEQ ID NO: 192)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC

-continued

CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1845

(SEQ ID NO: 193)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

-continued

>pARM1846

(SEQ ID NO: 194)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1847

(SEQ ID NO: 195)

ATGCTTTTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC

-continued

GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1882

(SEQ ID NO: 196)

ATGGTGTTCAACCTCCGCATCCTCCTCAACAACGCCGCATTCAGAAAC
GGGCACAACTTCATGGTCAGAAACTTCCGCTGCGGGCAACCCCTACAA
AACAAGGTCCAGCTCAAGGGGGGGGACCTCCTGACCCTGAAGAACTTC
ACCGGCGAAGAGATCAAGTACATGCTGTGGCTCTCCGCCGACCTGAAG
TTCCGCATCAAGCAGAAGGGAGAGTACCTCCCGCTGCTGCAAGGGAAG
TCGCTGGGGATGATCTTCGAGAAGCGGTCAACCAGAACCCGGCTGTCA
ACCGAAACCGGGTTCGCACTGCTGGGGGGACACCCGTGCTTCCTGACC
ACCCAAGACATCCACCTGGGAGTGAACGAATCGCTGACCGACACCGCC
CGCGTGCTGAGCTCAATGGCGGACGCCGTGCTGGCCCGCGTGTACAAG
CAGTCCGACCTGGACACCCTGGCCAAGGAAGCGTCCATCCCGATCATC
AACGGACTGTCCGACCTGTACCACCCGATCCAGATCCTGGCAGACTAC
CTGACCCTGCAAGAACACTACAGCTCCCTGAAGGGCCTGACCCTGTCA
TGGATCGGGGACGGGAACAACATCCTGCACTCCATAATGATGTCAGCC
GCCAAGTTCGGAATGCACCTCCAAGCCGCAACCCCGAAGGGCTACGAA
CCGGACGCATCAGTGACCAAACTGGCCGAGCAGTACGCCAAGGAAAAC
GGCACCAAGCTCCTGCTGACCAACGACCCGCTGGAGGCCGCACACGGG
GGGAACGTGCTGATCACCGACACCTGGATCTCCATGGGACAGGAGGAG
GAAAAGAAGAAGCGGCTGCAGGCGTTCCAGGGGTACCAGGTCACCATG
AAAACCGCGAAGGTCGCGGCATCAGACTGGACCTTCCTGCACTGCCTG
CCCCGGAAGCCGGAAGAGGTGGACGACGAGGTGTTCTACTCGCCGCGC
TCGCTGGTGTTCCCCGAGGCGGAGAACAGGAAGTGGACCATCATGGCG
GTGATGGTCAGCCTCCTGACCGACTACTCGCCGCAGCTGCAGAAGCCG
AAGTTCTGA

>pARM1883

(SEQ ID NO: 197)

ATGGTGTTCAACCTCCGCATCCTCCTCAACAACGCCGCATTCAGAAAC
GGGCACAACTTCATGGTCAGAAACTTCCGCTGCGGGCAACCCCTACAA
AACCGGGTCCAGCTCAAGGGGGGGGACCTCCTGACCCTGAAGAACTTC
ACCGGCGAAGAGATCAAGTACATGCTGTGGCTCTCCGCCGACCTGAAG
TTCCGCATCAAGCAGAAGGGAGAGTACCTCCCGCTGCTGCAAGGGAAG
TCGCTGGGGATGATCTTCGAGAAGCGGTCAACCAGAACCCGGCTGTCA
ACCGAAACCGGGTTCGCACTGCTGGGGGGACACCCGTGCTTCCTGACC
ACCCAAGACATCCACCTGGGAGTGAACGAATCGCTGACCGACACCGCC

-continued

CGCGTGCTGAGCTCAATGGCGGACGCCGTGCTGGCCCGCGTGTACAAG

CAGTCCGACCTGGACACCCTGGCCAAGGAAGCGTCCATCCCGATCATC

AACGGACTGTCCGACCTGTACCACCCGATCCAGATCCTGGCAGACTAC

CTGACCCTGCAAGAACACTACAGCTCCCTGAAGGGCCTGACCCTGTCA

TGGATCGGGGACGGGAACAACATCCTGCACTCCATAATGATGTCAGCC

GCCAAGTTCGGAATGCACCTCCAAGCCGCAACCCCGAAGGGCTACGAA

CCGGACGCATCAGTGACCAAACTGGCCGAGCAGTACGCCAAGGAAAAC

GGCACCAAGCTCCTGCTGACCAACGACCCGCTGGAGGCCGCACACGGG

GGGAACGTGCTGATCACCGACACCTGGATCTCCATGGGACAGGAGGAG

GAAAAGAAGAAGCGGCTGCAGGCGTTCCAGGGGTACCAGGTCACCATG

AAAACCGCGAAGGTCGCGGCATCAGACTGGACCTTCCTGCACTGCCTG

CCCCGGAAGCCGGAAGAGGTGGACGACGAGGTGTTCTACTCGCCGCGC

TCGCTGGTGTTCCCCGAGGCGGAGAACAGGAAGTGGACCATCATGGCG

GTGATGGTCAGCCTCCTGACCGACTACTCGCCGCAGCTGCAGAAGCCG

AAGTTCTGA

>pARM1884

(SEQ ID NO: 198)

ATGGTGTTCAACCTCCGCATCCTCCTCAACAACGCCGCATTCAGAAAC

GGGCACAACTTCATGGTCAGAAACTTCCGCTGCGGGCAACCCCTACAA

AACCGGGTCCAGCTCAAGGGGCGGGACCTCCTGACCCTGAAGAACTTC

ACCGGCGAAGAGATCCGGTACATGCTGTGGCTCTCCGCCGACCTGAAG

TTCCGCATCAAGCAGAAGGGAGAGTACCTCCCGCTGCTGCAAGGGAAG

TCGCTGGGGATGATCTTCGAGAAGCGGTCAACCAGAACCCGGCTGTCA

ACCGAAACCGGGTTCGCACTGCTGGGGGGACACCCGTGCTTCCTGACC

ACCCAAGACATCCACCTGGGAGTGAACGAATCGCTGACCGACACCGCC

CGCGTGCTGAGCTCAATGGCGGACGCCGTGCTGGCCCGCGTGTACAAG

CAGTCCGACCTGGACACCCTGGCCAAGGAAGCGTCCATCCCGATCATC

AACGGACTGTCCGACCTGTACCACCCGATCCAGATCCTGGCAGACTAC

CTGACCCTGCAAGAACACTACAGCTCCCTGAAGGGCCTGACCCTGTCA

TGGATCGGGGACGGGAACAACATCCTGCACTCCATAATGATGTCAGCC

GCCAAGTTCGGAATGCACCTCCAAGCCGCAACCCCGAAGGGCTACGAA

CCGGACGCATCAGTGACCAAACTGGCCGAGCAGTACGCCAAGGAAAAC

GGCACCAAGCTCCTGCTGACCAACGACCCGCTGGAGGCCGCACACGGG

GGGAACGTGCTGATCACCGACACCTGGATCTCCATGGGACAGGAGGAG

GAAAAGAAGAAGCGGCTGCAGGCGTTCCAGGGGTACCAGGTCACCATG

AAAACCGCGAAGGTCGCGGCATCAGACTGGACCTTCCTGCACTGCCTG

CCCCGGAAGCCGGAAGAGGTGGACGACGAGGTGTTCTACTCGCCGCGC

TCGCTGGTGTTCCCCGAGGCGGAGAACAGGAAGTGGACCATCATGGCG

GTGATGGTCAGCCTCCTGACCGACTACTCGCCGCAGCTGCAGAAGCCG

AAGTTCTGA

-continued

>pARM1885

(SEQ ID NO: 199)

ATGCTGGTCAACCTCCGCATCCTCCTCAACAACGCCGCATTCAGAAAC

GGGCACAACTTCATGGTCAGAAACTTCCGCTGCGGGCAACCCCTACAA

AACAAGGTCCAGCTCAAGGGGGGGGACCTCCTGACCCTGAAGAACTTC

ACCGGCGAAGAGATCAAGTACATGCTGTGGCTCTCCGCCGACCTGAAG

TTCCGCATCAAGCAGAAGGGAGAGTACCTCCCGCTGCTGCAAGGGAAG

TCGCTGGGGATGATCTTCGAGAAGCGGTCAACCAGAACCCGGCTGTCA

ACCGAAACCGGGTTCGCACTGCTGGGGGGACACCCGTGCTTCCTGACC

ACCCAAGACATCCACCTGGGAGTGAACGAATCGCTGACCGACACCGCC

CGCGTGCTGAGCTCAATGGCGGACGCCGTGCTGGCCCGCGTGTACAAG

CAGTCCGACCTGGACACCCTGGCCAAGGAAGCGTCCATCCCGATCATC

AACGGACTGTCCGACCTGTACCACCCGATCCAGATCCTGGCAGACTAC

CTGACCCTGCAAGAACACTACAGCTCCCTGAAGGGCCTGACCCTGTCA

TGGATCGGGGACGGGAACAACATCCTGCACTCCATAATGATGTCAGCC

GCCAAGTTCGGAATGCACCTCCAAGCCGCAACCCCGAAGGGCTACGAA

CCGGACGCATCAGTGACCAAACTGGCCGAGCAGTACGCCAAGGAAAAC

GGCACCAAGCTCCTGCTGACCAACGACCCGCTGGAGGCCGCACACGGG

GGGAACGTGCTGATCACCGACACCTGGATCTCCATGGGACAGGAGGAG

GAAAAGAAGAAGCGGCTGCAGGCGTTCCAGGGGTACCAGGTCACCATG

AAAACCGCGAAGGTCGCGGCATCAGACTGGACCTTCCTGCACTGCCTG

CCCCGGAAGCCGGAAGAGGTGGACGACGAGGTGTTCTACTCGCCGCGC

TCGCTGGTGTTCCCCGAGGCGGAGAACAGGAAGTGGACCATCATGGCG

GTGATGGTCAGCCTCCTGACCGACTACTCGCCGCAGCTGCAGAAGCCG

AAGTTCTGA

>pARM1886

(SEQ ID NO: 200)

ATGCTGGTCAACCTCCGCATCCTCCTCAACAACGCCGCATTCAGAAAC

GGGCACAACTTCATGGTCAGAAACTTCCGCTGCGGGCAACCCCTACAA

AACCGGGTCCAGCTCAAGGGGGGGGACCTCCTGACCCTGAAGAACTTC

ACCGGCGAAGAGATCAAGTACATGCTGTGGCTCTCCGCCGACCTGAAG

TTCCGCATCAAGCAGAAGGGAGAGTACCTCCCGCTGCTGCAAGGGAAG

TCGCTGGGGATGATCTTCGAGAAGCGGTCAACCAGAACCCGGCTGTCA

ACCGAAACCGGGTTCGCACTGCTGGGGGGACACCCGTGCTTCCTGACC

ACCCAAGACATCCACCTGGGAGTGAACGAATCGCTGACCGACACCGCC

CGCGTGCTGAGCTCAATGGCGGACGCCGTGCTGGCCCGCGTGTACAAG

CAGTCCGACCTGGACACCCTGGCCAAGGAAGCGTCCATCCCGATCATC

AACGGACTGTCCGACCTGTACCACCCGATCCAGATCCTGGCAGACTAC

CTGACCCTGCAAGAACACTACAGCTCCCTGAAGGGCCTGACCCTGTCA

TGGATCGGGGACGGGAACAACATCCTGCACTCCATAATGATGTCAGCC

GCCAAGTTCGGAATGCACCTCCAAGCCGCAACCCCGAAGGGCTACGAA

CCGGACGCATCAGTGACCAAACTGGCCGAGCAGTACGCCAAGGAAAAC

GGCACCAAGCTCCTGCTGACCAACGACCCGCTGGAGGCCGCACACGGG

GGGAACGTGCTGATCACCGACACCTGGATCTCCATGGGACAGGAGGAG

GAAAAGAAGAAGCGGCTGCAGGCGTTCCAGGGGTACCAGGTCACCATG

AAAACCGCGAAGGTCGCGGCATCAGACTGGACCTTCCTGCACTGCCTG

CCCCGGAAGCCGGAAGAGGTGGACGACGAGGTGTTCTACTCGCCGCGC

TCGCTGGTGTTCCCCGAGGCGGAGAACAGGAAGTGGACCATCATGGCG

GTGATGGTCAGCCTCCTGACCGACTACTCGCCGCAGCTGCAGAAGCCG

AAGTTCTGA

>pARM1887

(SEQ ID NO: 201)

ATGCTGGTCAACCTCCGCATCCTCCTCAACAACGCCGCATTCAGAAAC

GGGCACAACTTCATGGTCAGAAACTTCCGCTGCGGGCAACCCCTACAA

AACCGGGTCCAGCTCAAGGGGGGGGACCTCCTGACCCTGAAGAACTTC

ACCGGCGAAGAGATCCGGTACATGCTGTGGCTCTCCGCCGACCTGAAG

TTCCGCATCAAGCAGAAGGGAGAGTACCTCCCGCTGCTGCAAGGGAAG

TCGCTGGGGATGATCTTCGAGAAGCGGTCAACCAGAACCCGGCTGTCA

ACCGAAACCGGGTTCGCACTGCTGGGGGGACACCCGTGCTTCCTGACC

ACCCAAGACATCCACCTGGGAGTGAACGAATCGCTGACCGACACCGCC

CGCGTGCTGAGCTCAATGGCGGACGCCGTGCTGGCCCGCGTGTACAAG

CAGTCCGACCTGGACACCCTGGCCAAGGAAGCGTCCATCCCGATCATC

AACGGACTGTCCGACCTGTACCACCCGATCCAGATCCTGGCAGACTAC

CTGACCCTGCAAGAACACTACAGCTCCCTGAAGGGCCTGACCCTGTCA

TGGATCGGGGACGGGAACAACATCCTGCACTCCATAATGATGTCAGCC

GCCAAGTTCGGAATGCACCTCCAAGCCGCAACCCCGAAGGGCTACGAA

CCGGACGCATCAGTGACCAAACTGGCCGAGCAGTACGCCAAGGAAAAC

GGCACCAAGCTCCTGCTGACCAACGACCCGCTGGAGGCCGCACACGGG

GGGAACGTGCTGATCACCGACACCTGGATCTCCATGGGACAGGAGGAG

GAAAAGAAGAAGCGGCTGCAGGCGTTCCAGGGGTACCAGGTCACCATG

AAAACCGCGAAGGTCGCGGCATCAGACTGGACCTTCCTGCACTGCCTG

CCCCGGAAGCCGGAAGAGGTGGACGACGAGGTGTTCTACTCGCCGCGC

TCGCTGGTGTTCCCCGAGGCGGAGAACAGGAAGTGGACCATCATGGCG

GTGATGGTCAGCCTCCTGACCGACTACTCGCCGCAGCTGCAGAAGCCG

AAGTTCTGA

>pARM1888

(SEQ ID NO: 202)

ATGCTGGTCAACCTGCGCATCCTGCTGAACAACGCCGCCTTCCGCAAC

GGCCACAACTTCATGGTGCGCAACTTCCGCTGCGGCCAGCCCCTGCAG

AACAAGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCTTCGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGA

>pARM1889

(SEQ ID NO: 203)

ATGCTGGTCAACCTGCGCATCCTGCTGAACAACGCCGCCTTCCGCAAC

GGCCACAACTTCATGGTGCGCAACTTCCGCTGCGGCCAGCCCCTGCAG

AACCGGGTGCAGCTGAAGGGCCGCGACCTGCTGACCCTGAAGAACTTC

ACCGGCGAGGAGATCAAGTACATGCTGTGGCTGAGCGCCGACCTGAAG

TTCCGCATCAAGCAGAAGGGCGAGTACCTGCCCCTGCTGCAGGGCAAG

AGCCTGGGCATGATCTTCGAGAAGCGCAGCACCCGCACCCGCCTGAGC

ACCGAGACAGGCTTCGCCCTGCTGGGCGGCCACCCCTGCTTCCTGACC

ACCCAGGACATCCACCTGGGCGTGAACGAGAGCCTGACCGACACCGCC

CGCGTGCTGAGCAGCATGGCCGACGCCGTGCTGGCCCGCGTGTACAAG

CAGAGCGACCTGGACACCCTGGCCAAGGAGGCCAGCATCCCCATCATC

AACGGCCTGAGCGACCTGTACCACCCCATCCAGATCCTGGCCGACTAC

CTGACCCTGCAGGAGCACTACAGCAGCCTGAAGGGCCTGACCCTGAGC

TGGATCGGCGACGGCAACAACATCCTGCACAGCATCATGATGAGCGCC

GCCAAGTTCGGCATGCACCTGCAGGCCGCCACCCCCAAGGGCTACGAG

CCCGACGCCAGCGTGACCAAGCTGGCCGAGCAGTACGCCAAGGAGAAC

GGCACCAAGCTGCTGCTGACCAACGACCCCCTGGAGGCCGCCCACGGC

GGCAACGTGCTGATCACCGACACCTGGATCAGCATGGGCCAGGAGGAG

GAGAAGAAGAAGCGCCTGCAGGCCTTCCAGGGCTACCAGGTGACCATG

AAGACCGCCAAGGTGGCCGCCAGCGACTGGACCTTCCTGCACTGCCTG

CCCCGCAAGCCCGAGGAGGTGGACGACGAGGTGTTCTACAGCCCCCGC

AGCCTGGTGTTCCCCGAGGCCGAGAACCGCAAGTGGACCATCATGGCC

GTGATGGTGAGCCTGCTGACCGACTACAGCCCCCAGCTGCAGAAGCCC

AAGTTCTGA

-continued

>pARM1890

(SEQ ID NO: 204)

ATGCTTGTCAATCTCCGCATCCTCCTTAACAACGCCGCGTTTAGAAAC
GGCCACAACTTCATGGTCCGGAACTTCAGATGTGGCCAGCCGCTTCAA
AACAAGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC
GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1891

(SEQ ID NO: 205)

ATGCTTGTCAATCTCCGCATCCTCCTTAACAACGCCGCGTTTAGAAAC
GGCCACAACTTCATGGTCCGGAACTTCAGATGTGGCCAGCCGCTTCAA
AACCGGGTCCAGCTGAAGGGCCGGGATCTTCTGACCCTGAAGAACTTT
ACTGGCGAAGAGATCAAGTACATGCTCTGGCTCTCCGCGGACTTGAAG
TTCCGCATTAAGCAGAAGGGGGAATACCTTCCGCTGCTTCAAGGAAAG
AGCCTCGGCATGATCTTTGAGAAGCGCTCAACCAGGACCCGCCTTTCT
ACTGAAACTGGGTTCGCGCTGCTCGGTGGCCACCCCTGCTTCCTGACG
ACCCAGGACATCCACCTCGGAGTGAACGAATCCCTCACCGATACCGCC
CGGGTGTTATCGAGCATGGCAGATGCCGTGCTGGCCAGGGTGTACAAA
CAGTCCGATCTGGACACTCTGGCCAAGGAGGCGTCAATTCCTATTATC
AACGGCCTTAGTGACCTCTACCATCCGATTCAGATCCTGGCCGATTAC
CTCACCCTGCAAGAACACTACAGCTCCCTGAAGGGTCTGACATTGTCC
TGGATCGGCGACGGCAACAACATTCTCCATTCCATCATGATGTCCGCC
GCAAAATTCGGCATGCATCTTCAAGCCGCCACGCCGAAGGGTTACGAG
CCCGACGCTTCCGTGACTAAGCTCGCCGAGCAGTACGCTAAGGAGAAC

-continued

GGAACCAAGCTTCTGCTGACTAACGACCCACTAGAAGCAGCCCACGGG
GGCAACGTGCTTATTACTGACACCTGGATCTCCATGGGCCAGGAAGAA
GAGAAAAAGAAGCGGCTGCAGGCGTTCCAGGGATATCAGGTCACCATG
AAAACCGCCAAGGTCGCTGCCTCCGACTGGACCTTCCTGCACTGCCTG
CCTCGCAAGCCTGAAGAAGTGGACGACGAGGTGTTCTACTCGCCACGG
AGCCTCGTGTTCCCCGAGGCCGAGAATAGAAAGTGGACCATCATGGCC
GTGATGGTGTCACTGCTCACCGACTACAGCCCGCAGCTTCAGAAGCCC
AAGTTCTAG

>pARM1898

(SEQ ID NO: 206)

ATGGGCCTTGTCAATCTCCGCATCCTCCTTAACAACGCCGCGTTTAGA
AACGGCCACAACTTCATGGTCCGGAACTTCAGATGTGGCCAGCCGCTT
CAAAACAAGGTCCAGCTGAAGGGCCGGGATCTTCTGACCCTGAAGAAC
TTTACTGGCGAAGAGATCAAGTACATGCTCTGGCTCTCCGCGGACTTG
AAGTTCCGCATTAAGCAGAAGGGGGAATACCTTCCGCTGCTTCAAGGA
AAGAGCCTCGGCATGATCTTTGAGAAGCGCTCAACCAGGACCCGCCTT
TCTACTGAAACTGGGTTCGCGCTGCTCGGTGGCCACCCCTGCTTCCTG
ACGACCCAGGACATCCACCTCGGAGTGAACGAATCCCTCACCGATACC
GCCCGGGTGTTATCGAGCATGGCAGATGCCGTGCTGGCCAGGGTGTAC
AAACAGTCCGATCTGGACACTCTGGCCAAGGAGGCGTCAATTCCTATT
ATCAACGGCCTTAGTGACCTCTACCATCCGATTCAGATCCTGGCCGAT
TACCTCACCCTGCAAGAACACTACAGCTCCCTGAAGGGTCTGACATTG
TCCTGGATCGGCGACGGCAACAACATTCTCCATTCCATCATGATGTCC
GCCGCAAAATTCGGCATGCATCTTCAAGCCGCCACGCCGAAGGGTTAC
GAGCCCGACGCTTCCGTGACTAAGCTCGCCGAGCAGTACGCTAAGGAG
AACGGAACCAAGCTTCTGCTGACTAACGACCCACTAGAAGCAGCCCAC
GGGGGCAACGTGCTTATTACTGACACCTGGATCTCCATGGGCCAGGAA
GAAGAGAAAAAGAAGCGGCTGCAGGCGTTCCAGGGATATCAGGTCACC
ATGAAAACCGCCAAGGTCGCTGCCTCCGACTGGACCTTCCTGCACTGC
CTGCCTCGCAAGCCTGAAGAAGTGGACGACGAGGTGTTCTACTCGCCA
CGGAGCCTCGTGTTCCCCGAGGCCGAGAATAGAAAGTGGACCATCATG
GCCGTGATGGTGTCACTGCTCACCGACTACAGCCCGCAGCTTCAGAAG
CCCAAGTTCTAG

>pARM1899

(SEQ ID NO: 207)

ATGGGCCTTGTCAATCTCCGCATCCTCCTTAACAACGCCGCGTTTAGA
AACGGCCACAACTTCATGGTCCGGAACTTCAGATGTGGCCAGCCGCTT
CAAAACCGGGTCCAGCTGAAGGGCCGGGATCTTCTGACCCTGAAGAAC
TTTACTGGCGAAGAGATCAAGTACATGCTCTGGCTCTCCGCGGACTTG
AAGTTCCGCATTAAGCAGAAGGGGGAATACCTTCCGCTGCTTCAAGGA
AAGAGCCTCGGCATGATCTTTGAGAAGCGCTCAACCAGGACCCGCCTT
TCTACTGAAACTGGGTTCGCGCTGCTCGGTGGCCACCCCTGCTTCCTG
ACGACCCAGGACATCCACCTCGGAGTGAACGAATCCCTCACCGATACC

-continued

GCCCGGGTGTTATCGAGCATGGCAGATGCCGTGCTGGCCAGGGTGTAC
AAACAGTCCGATCTGGACACTCTGGCCAAGGAGGCGTCAATTCCTATT
ATCAACGGCCTTAGTGACCTCTACCATCCGATTCAGATCCTGGCCGAT
TACCTCACCCTGCAAGAACACTACAGCTCCCTGAAGGGTCTGACATTG
TCCTGGATCGGCGACGGCAACAACATTCTCCATTCCATCATGATGTCC
GCCGCAAAATTCGGCATGCATCTTCAAGCCGCCACGCCGAAGGGTTAC
GAGCCCGACGCTTCCGTGACTAAGCTCGCCGAGCAGTACGCTAAGGAG
AACGGAACCAAGCTTCTGCTGACTAACGACCCACTAGAAGCAGCCCAC
GGGGGCAACGTGCTTATTACTGACACCTGGATCTCCATGGGCCAGGAA
GAAGAGAAAAAGAAGCGGCTGCAGGCGTTCCAGGGATATCAGGTCACC
ATGAAAACCGCCAAGGTCGCTGCCTCCGACTGGACCTTCCTGCACTGC
CTGCCTCGCAAGCCTGAAGAAGTGGACGACGAGGTGTTCTACTCGCCA
CGGAGCCTCGTGTTCCCCGAGGCCGAGAATAGAAAGTGGACCATCATG
GCCGTGATGGTGTCACTGCTCACCGACTACAGCCCGCAGCTTCAGAAG
CCCAAGTTCTAG

>pARM1900

(SEQ ID NO: 208)

ATGGGCGGACTTGTCAATCTCCGCATCCTCCTTAACAACGCCGCGTTT
AGAAACGGCCACAACTTCATGGTCCGGAACTTCAGATGTGGCCAGCCG
CTTCAAAACAAGGTCCAGCTGAAGGGCCGGGATCTTCTGACCCTGAAG
AACTTTACTGGCGAAGAGATCAAGTACATGCTCTGGCTCTCCGCGGAC
TTGAAGTTCCGCATTAAGCAGAAGGGGGAATACCTTCCGCTGCTTCAA
GGAAAGAGCCTCGGCATGATCTTTGAGAAGCGCTCAACCAGGACCCGC
CTTTCTACTGAAACTGGGTTCGCGCTGCTCGGTGGCCACCCCTGCTTC
CTGACGACCCAGGACATCCACCTCGGAGTGAACGAATCCCTCACCGAT
ACCGCCCGGGTGTTATCGAGCATGGCAGATGCCGTGCTGGCCAGGGTG
TACAAACAGTCCGATCTGGACACTCTGGCCAAGGAGGCGTCAATTCCT
ATTATCAACGGCCTTAGTGACCTCTACCATCCGATTCAGATCCTGGCC
GATTACCTCACCCTGCAAGAACACTACAGCTCCCTGAAGGGTCTGACA
TTGTCCTGGATCGGCGACGGCAACAACATTCTCCATTCCATCATGATG
TCCGCCGCAAAATTCGGCATGCATCTTCAAGCCGCCACGCCGAAGGGT
TACGAGCCCGACGCTTCCGTGACTAAGCTCGCCGAGCAGTACGCTAAG
GAGAACGGAACCAAGCTTCTGCTGACTAACGACCCACTAGAAGCAGCC
CACGGGGGCAACGTGCTTATTACTGACACCTGGATCTCCATGGGCCAG
GAAGAAGAGAAAAAGAAGCGGCTGCAGGCGTTCCAGGGATATCAGGTC
ACCATGAAAACCGCCAAGGTCGCTGCCTCCGACTGGACCTTCCTGCAC
TGCCTGCCTCGCAAGCCTGAAGAAGTGGACGACGAGGTGTTCTACTCG
CCACGGAGCCTCGTGTTCCCCGAGGCCGAGAATAGAAAGTGGACCATC
ATGGCCGTGATGGTGTCACTGCTCACCGACTACAGCCCGCAGCTTCAG
AAGCCCAAGTTCTAG

-continued

>pARM1903

(SEQ ID NO: 209)

ATGGCCCTTTTCAATCTCCGCATCCTCCTTAACAACGCCGCGTTTAGA
AACGGCCACAACTTCATGGTCCGGAACTTCAGATGTGGCCAGCCGCTT
CAAGGCAAGGTCCAGCTGAAGGGCCGGGATCTTCTGACCCTGAAGAAC
TTTACTGGCGAAGAGATCAAGTACATGCTCTGGCTCTCCGCGGACTTG
AAGTTCCGCATTAAGCAGAAGGGGGAATACCTTCCGCTGCTTCAAGGA
AAGAGCCTCGGCATGATCTTTGAGAAGCGCTCAACCAGGACCCGCCTT
TCTACTGAAACTGGGTTCGCGCTGCTCGGTGGCCACCCCTGCTTCCTG
ACGACCCAGGACATCCACCTCGGAGTGAACGAATCCCTCACCGATACC
GCCCGGGTGTTATCGAGCATGGCAGATGCCGTGCTGGCCAGGGTGTAC
AAACAGTCCGATCTGGACACTCTGGCCAAGGAGGCGTCAATTCCTATT
ATCAACGGCCTTAGTGACCTCTACCATCCGATTCAGATCCTGGCCGAT
TACCTCACCCTGCAAGAACACTACAGCTCCCTGAAGGGTCTGACATTG
TCCTGGATCGGCGACGGCAACAACATTCTCCATTCCATCATGATGTCC
GCCGCAAAATTCGGCATGCATCTTCAAGCCGCCACGCCGAAGGGTTAC
GAGCCCGACGCTTCCGTGACTAAGCTCGCCGAGCAGTACGCTAAGGAG
AACGGAACCAAGCTTCTGCTGACTAACGACCCACTAGAAGCAGCCCAC
GGGGGCAACGTGCTTATTACTGACACCTGGATCTCCATGGGCCAGGAA
GAAGAGAAAAAGAAGCGGCTGCAGGCGTTCCAGGGATATCAGGTCACC
ATGAAAACCGCCAAGGTCGCTGCCTCCGACTGGACCTTCCTGCACTGC
CTGCCTCGCAAGCCTGAAGAAGTGGACGACGAGGTGTTCTACTCGCCA
CGGAGCCTCGTGTTCCCCGAGGCCGAGAATAGAAAGTGGACCATCATG
GCCGTGATGGTGTCACTGCTCACCGACTACAGCCCGCAGCTTCAGAAG
CCCAAGTTCTAGATAAGTGAA

>pARM1904

(SEQ ID NO: 210)

ATGGCCCTTTTCAATCTCCGCATCCTCCTTAACAACGCCGCGTTTAGA
AACGGCCACAACTTCATGGTCCGGAACTTCAGATGTGGCCAGCCGCTT
CAAGGCCGGGTCCAGCTGAAGGGCCGGGATCTTCTGACCCTGAAGAAC
TTTACTGGCGAAGAGATCAAGTACATGCTCTGGCTCTCCGCGGACTTG
AAGTTCCGCATTAAGCAGAAGGGGGAATACCTTCCGCTGCTTCAAGGA
AAGAGCCTCGGCATGATCTTTGAGAAGCGCTCAACCAGGACCCGCCTT
TCTACTGAAACTGGGTTCGCGCTGCTCGGTGGCCACCCCTGCTTCCTG
ACGACCCAGGACATCCACCTCGGAGTGAACGAATCCCTCACCGATACC
GCCCGGGTGTTATCGAGCATGGCAGATGCCGTGCTGGCCAGGGTGTAC
AAACAGTCCGATCTGGACACTCTGGCCAAGGAGGCGTCAATTCCTATT
ATCAACGGCCTTAGTGACCTCTACCATCCGATTCAGATCCTGGCCGAT
TACCTCACCCTGCAAGAACACTACAGCTCCCTGAAGGGTCTGACATTG
TCCTGGATCGGCGACGGCAACAACATTCTCCATTCCATCATGATGTCC
GCCGCAAAATTCGGCATGCATCTTCAAGCCGCCACGCCGAAGGGTTAC
GAGCCCGACGCTTCCGTGACTAAGCTCGCCGAGCAGTACGCTAAGGAG

-continued

AACGGAACCAAGCTTCTGCTGACTAACGACCCACTAGAAGCAGCCCAC

GGGGGCAACGTGCTTATTACTGACACCTGGATCTCCATGGGCCAGGAA

GAAGAGAAAAAGAAGCGGCTGCAGGCGTTCCAGGGATATCAGGTCACC

ATGAAAACCGCCAAGGTCGCTGCCTCCGACTGGACCTTCCTGCACTGC

CTGCCTCGCAAGCCTGAAGAAGTGGACGACGAGGTGTTCTACTCGCCA

CGGAGCCTCGTGTTCCCCGAGGCCGAGAATAGAAAGTGGACCATCATG

GCCGTGATGGTGTCACTGCTCACCGACTACAGCCCGCAGCTTCAGAAG

CCCAAGTTCTAGATAAGTGAA

>pARM1905

(SEQ ID NO: 211)

ATGGCCCTTTTCAATCTCCGCATCCTCCTTAACAACGCCGCGTTTAGA

AACGGCCACAACTTCATGGTCCGGAACTTCAGATGTGGCCAGCCGCTT

CAAGGCCGGGTCCAGCTGAAGGGCCGGGATCTTCTGACCCTGAAGAAC

TTTACTGGCGAAGAGATCAGGTACATGCTCTGGCTCTCCGCGGACTTG

AAGTTCCGCATTAAGCAGAAGGGGGAATACCTTCCGCTGCTTCAAGGA

AAGAGCCTCGGCATGATCTTTGAGAAGCGCTCAACCAGGACCCGCCTT

TCTACTGAAACTGGGTTCGCGCTGCTCGGTGGCCACCCCTGCTTCCTG

ACGACCCAGGACATCCACCTCGGAGTGAACGAATCCCTCACCGATACC

GCCCGGGTGTTATCGAGCATGGCAGATGCCGTGCTGGCCAGGGTGTAC

AAACAGTCCGATCTGGACACTCTGGCCAAGGAGGCGTCAATTCCTATT

ATCAACGGCCTTAGTGACCTCTACCATCCGATTCAGATCCTGGCCGAT

TACCTCACCCTGCAAGAACACTACAGCTCCCTGAAGGGTCTGACATTG

TCCTGGATCGGCGACGGCAACAACATTCTCCATTCCATCATGATGTCC

GCCGCAAAATTCGGCATGCATCTTCAAGCCGCCACGCCGAAGGGTTAC

GAGCCCGACGCTTCCGTGACTAAGCTCGCCGAGCAGTACGCTAAGGAG

AACGGAACCAAGCTTCTGCTGACTAACGACCCACTAGAAGCAGCCCAC

GGGGGCAACGTGCTTATTACTGACACCTGGATCTCCATGGGCCAGGAA

GAAGAGAAAAAGAAGCGGCTGCAGGCGTTCCAGGGATATCAGGTCACC

ATGAAAACCGCCAAGGTCGCTGCCTCCGACTGGACCTTCCTGCACTGC

CTGCCTCGCAAGCCTGAAGAAGTGGACGACGAGGTGTTCTACTCGCCA

CGGAGCCTCGTGTTCCCCGAGGCCGAGAATAGAAAGTGGACCATCATG

GCCGTGATGGTGTCACTGCTCACCGACTACAGCCCGCAGCTTCAGAAG

CCCAAGTTCTAGATAAGTGAA

>pARM1906

(SEQ ID NO: 212)

ATGGCCCTTGTCAATCTCCGCATCCTCCTTAACAACGCCGCGTTTAGA

AACGGCCACAACTTCATGGTCCGGAACTTCAGATGTGGCCAGCCGCTT

CAAGGCAGGGTCCAGCTGAAGGGCCGGGATCTTCTGACCCTGAAGAAC

TTTACTGGCGAAGAGATCAAGTACATGCTCTGGCTCTCCGCGGACTTG

AAGTTCCGCATTAAGCAGAAGGGGGAATACCTTCCGCTGCTTCAAGGA

AAGAGCCTCGGCATGATCTTTGAGAAGCGCTCAACCAGGACCCGCCTT

TCTACTGAAACTGGGTTCGCGCTGCTCGGTGGCCACCCCTGCTTCCTG

ACGACCCAGGACATCCACCTCGGAGTGAACGAATCCCTCACCGATACC

GCCCGGGTGTTATCGAGCATGGCAGATGCCGTGCTGGCCAGGGTGTAC

AAACAGTCCGATCTGGACACTCTGGCCAAGGAGGCGTCAATTCCTATT

ATCAACGGCCTTAGTGACCTCTACCATCCGATTCAGATCCTGGCCGAT

TACCTCACCCTGCAAGAACACTACAGCTCCCTGAAGGGTCTGACATTG

TCCTGGATCGGCGACGGCAACAACATTCTCCATTCCATCATGATGTCC

GCCGCAAAATTCGGCATGCATCTTCAAGCCGCCACGCCGAAGGGTTAC

GAGCCCGACGCTTCCGTGACTAAGCTCGCCGAGCAGTACGCTAAGGAG

AACGGAACCAAGCTTCTGCTGACTAACGACCCACTAGAAGCAGCCCAC

GGGGGCAACGTGCTTATTACTGACACCTGGATCTCCATGGGCCAGGAA

GAAGAGAAAAAGAAGCGGCTGCAGGCGTTCCAGGGATATCAGGTCACC

ATGAAAACCGCCAAGGTCGCTGCCTCCGACTGGACCTTCCTGCACTGC

CTGCCTCGCAAGCCTGAAGAAGTGGACGACGAGGTGTTCTACTCGCCA

CGGAGCCTCGTGTTCCCCGAGGCCGAGAATAGAAAGTGGACCATCATG

GCCGTGATGGTGTCACTGCTCACCGACTACAGCCCGCAGCTTCAGAAG

CCCAAGTTCTAAGTGAATAGA

>pARM1907

(SEQ ID NO: 213)

ATGGCCCTTTTCAATCTCCGCATCCTCCTTAACAACGCCGCGTTTAGA

AACGGCCACAACTTCATGGTCCGGAACTTCAGATGTGGCCAGCCGCTT

CAAGTCAAGGTCCAGCTGAAGGGCCGGGATCTTCTGACCCTGAAGAAC

TTTACTGGCGAAGAGATCAAGTACATGCTCTGGCTCTCCGCGGACTTG

AAGTTCCGCATTAAGCAGAAGGGGGAATACCTTCCGCTGCTTCAAGGA

AAGAGCCTCGGCATGATCTTTGAGAAGCGCTCAACCAGGACCCGCCTT

TCTACTGAAACTGGGTTCGCGCTGCTCGGTGGCCACCCCTGCTTCCTG

ACGACCCAGGACATCCACCTCGGAGTGAACGAATCCCTCACCGATACC

GCCCGGGTGTTATCGAGCATGGCAGATGCCGTGCTGGCCAGGGTGTAC

AAACAGTCCGATCTGGACACTCTGGCCAAGGAGGCGTCAATTCCTATT

ATCAACGGCCTTAGTGACCTCTACCATCCGATTCAGATCCTGGCCGAT

TACCTCACCCTGCAAGAACACTACAGCTCCCTGAAGGGTCTGACATTG

TCCTGGATCGGCGACGGCAACAACATTCTCCATTCCATCATGATGTCC

GCCGCAAAATTCGGCATGCATCTTCAAGCCGCCACGCCGAAGGGTTAC

GAGCCCGACGCTTCCGTGACTAAGCTCGCCGAGCAGTACGCTAAGGAG

AACGGAACCAAGCTTCTGCTGACTAACGACCCACTAGAAGCAGCCCAC

GGGGGCAACGTGCTTATTACTGACACCTGGATCTCCATGGGCCAGGAA

GAAGAGAAAAAGAAGCGGCTGCAGGCGTTCCAGGGATATCAGGTCACC

ATGAAAACCGCCAAGGTCGCTGCCTCCGACTGGACCTTCCTGCACTGC

CTGCCTCGCAAGCCTGAAGAAGTGGACGACGAGGTGTTCTACTCGCCA

CGGAGCCTCGTGTTCCCCGAGGCCGAGAATAGAAAGTGGACCATCATG

GCCGTGATGGTGTCACTGCTCACCGACTACAGCCCGCAGCTTCAGAAG

CCCAAGTTCTAGATAAGTGAA

-continued

>pARM1908

(SEQ ID NO: 214)

ATGGCCCTTTTCAATCTCCGCATCCTCCTTAACAACGCCGCGTTTAGA
AACGGCCACAACTTCATGGTCCGGAACTTCAGATGTGGCCAGCCGCTT
CAAGTCAGGGTCCAGCTGAAGGGCCGGGATCTTCTGACCCTGAAGAAC
TTTACTGGCGAAGAGATCAAGTACATGCTCTGGCTCTCCGCGGACTTG
AAGTTCCGCATTAAGCAGAAGGGGGAATACCTTCCGCTGCTTCAAGGA
AAGAGCCTCGGCATGATCTTTGAGAAGCGCTCAACCAGGACCCGCCTT
TCTACTGAAACTGGGTTCGCGCTGCTCGGTGGCCACCCCTGCTTCCTG
ACGACCCAGGACATCCACCTCGGAGTGAACGAATCCCTCACCGATACC
GCCCGGGTGTTATCGAGCATGGCAGATGCCGTGCTGGCCAGGGTGTAC
AAACAGTCCGATCTGGACACTCTGGCCAAGGAGGCGTCAATTCCTATT
ATCAACGGCCTTAGTGACCTCTACCATCCGATTCAGATCCTGGCCGAT
TACCTCACCCTGCAAGAACACTACAGCTCCCTGAAGGGTCTGACATTG
TCCTGGATCGGCGACGGCAACAACATTCTCCATTCCATCATGATGTCC
GCCGCAAAATTCGGCATGCATCTTCAAGCCGCCACGCCGAAGGGTTAC
GAGCCCGACGCTTCCGTGACTAAGCTCGCCGAGCAGTACGCTAAGGAG
AACGGAACCAAGCTTCTGCTGACTAACGACCCACTAGAAGCAGCCCAC
GGGGGCAACGTGCTTATTACTGACACCTGGATCTCCATGGGCCAGGAA
GAAGAGAAAAAGAAGCGGCTGCAGGCGTTCCAGGGATATCAGGTCACC
ATGAAAACCGCCAAGGTCGCTGCCTCCGACTGGACCTTCCTGCACTGC
CTGCCTCGCAAGCCTGAAGAAGTGGACGACGAGGTGTTCTACTCGCCA
CGGAGCCTCGTGTTCCCCGAGGCCGAGAATAGAAAGTGGACCATCATG
GCCGTGATGGTGTCACTGCTCACCGACTACAGCCCGCAGCTTCAGAAG
CCCAAGTTCTAGATAAGTGAA

>pARM1915

(SEQ ID NO: 215)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1916

(SEQ ID NO: 216)

ATGGGAGTATTCAACCTGCGCATCCTGCTGAACAACGCCGCCTTCCGC
AACGGCCACAACTTCATGGTGCGCAACTTCCGCTGCGGCCAGCCCCTG
CAGAACAAGGTGCAGCTGAAGGGCCGCGACCTGCTGACCCTGAAGAAC
TTCACCGGCGAGGAGATCAAGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1917

(SEQ ID NO: 217)

ATGGGAGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC

GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1918

(SEQ ID NO: 218)

ATGCTGGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1919

(SEQ ID NO: 219)

ATGGGAGTATTCAACCTGCGCATCCTGCTGAACAACGCCGCCTTCCGC
AACGGCCACAACTTCATGGTGCGCAACTTCCGCTGCGGCCAGCCCCTG
CAGAACAAGGTGCAGCTGAAGGGCCGCGACCTGCTGACCCTGAAGAAC
TTCACCGGCGAGGAGATCAAGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1920

(SEQ ID NO: 220)

ATGGGAGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG

-continued

AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1921

(SEQ ID NO: 221)

ATGCTGGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

>pARM1925

(SEQ ID NO: 222)

ATGTTGTTCAACTTGAGGATCTTGTTGAACAACGCCGCCTTCAGGAAC
GGACACAACTTCATGGTAAGGAACTTCAGGTGCGGACAGCCCTTGCAG
AACAAAGTACAGTTGAAAGGAAGGGACTTGTTGACATTGAAAAACTTC
ACAGGAGAAGAAATCAAATACATGTTGTGGTTGTCGGCCGACTTGAAA
TTCAGGATCAAACAGAAAGGAGAATACTTGCCCTTGTTGCAGGGAAAA
TCGTTGGGAATGATCTTCGAAAAAAGGTCGACAAGGACAAGGTTGTCG
ACAGAAACAGGATTCGCCTTGTTGGGAGGACACCCCTGCTTCTTGACA
ACACAGGACATCCACTTGGGAGTAAACGAATCGTTGACAGACACAGCC
AGGGTATTGTCGTCGATGGCCGACGCCGTATTGGCCAGGGTATACAAA
CAGTCGGACTTGGACACATTGGCCAAAGAAGCCTCGATCCCCATCATC
AACGGATTGTCGGACTTGTACCACCCCATCCAGATCTTGGCCGACTAC
TTGACATTGCAGGAACACTACTCGTCGTTGAAAGGATTGACATTGTCG
TGGATCGGAGACGGAAACAACATCTTGCACTCGATCATGATGTCGGCC
GCCAAATTCGGAATGCACTTGCAGGCCGCCACACCCAAAGGATACGAA
CCCGACGCCTCGGTAACAAAATTGGCCGAACAGTACGCCAAAGAAAAC
GGAACAAAATTGTTGTTGACAAACGACCCCTTGGAAGCCGCCCACGGA
GGAAACGTATTGATCACAGACACATGGATCTCGATGGGACAGGAAGAA
GAAAAAAAAAAAAGGTTGCAGGCCTTCCAGGGATACCAGGTAACAATG
AAAACAGCCAAAGTAGCCGCCTCGGACTGGACATTCTTGCACTGCTTG
CCCAGGAAACCCGAAGAAGTAGACGACGAAGTATTCTACTCGCCCAGG
TCGTTGGTATTCCCCGAAGCCGAAAACAGGAAATGGACAATCATGGCC
GTAATGGTATCGTTGTTGACAGACTACTCGCCCCAGTTGCAGAAACCC
AAATTCTGAATAGTGAA

>pARM1926

(SEQ ID NO: 223)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
GGCAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

-continued

>pARM1927

(SEQ ID NO: 224)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
GGCCGGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1928

(SEQ ID NO: 225)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
GGCCGGGTGCAGCTGAAGGGCCGCGACCTGCTGACCCTGAAGAACTTC
ACCGGCGAGGAGATCCGGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC

-continued

GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM1929

(SEQ ID NO: 226)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
GGCAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC
CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM2016

(SEQ ID NO: 227)

ATGCTGTTCAACCTGCGCATCCTGCTGAACAACGCCGCCTTCCGCAAC
GGCCACAACTTCATGGTGCGCAACTTCCGCTGCGGCCAGCCCCTGCAG
AACAAGGTGCAGCTGAAGGGCCGCGACCTGCTGACCCTGAAGAACTTC
ACCGGCGAGGAGATCAAGTACATGCTGTGGCTGAGCGCCGACCTGAAG
TTCCGCATCAAGCAGAAGGGCGAGTACCTGCCCCTGCTGCAGGGCAAG
AGCCTGGGCATGATCTTCGAGAAGCGCAGCACCCGCACCCGCCTGAGC
ACCGAGACAGGCTTCGCCCTGCTGGGCGGCCACCCCTGCTTCCTGACC
ACCCAGGACATCCACCTGGGCGTGAACGAGAGCCTGACCGACACCGCC

-continued

CGCGTGCTGAGCAGCATGGCCGACGCCGTGCTGGCCCGCGTGTACAAG
CAGAGCGACCTGGACACCCTGGCCAAGGAGGCCAGCATCCCCATCATC
AACGGCCTGAGCGACCTGTACCACCCCATCCAGATCCTGGCCGACTAC
CTGACCCTGCAGGAGCACTACAGCAGCCTGAAGGGCCTGACCCTGAGC
TGGATCGGCGACGGCAACAACATCCTGCACAGCATCATGATGAGCGCC
GCCAAGTTCGGCATGCACCTGCAGGCCGCCACCCCCAAGGGCTACGAG
CCCGACGCCAGCGTGACCAAGCTGGCCGAGCAGTACGCCAAGGAGAAC
GGCACCAAGCTGCTGCTGACCAACGACCCCCTGGAGGCCGCCCACGGC
GGCAACGTGCTGATCACCGACACCTGGATCAGCATGGGCCAGGAGGAG
GAGAAGAAGAAGCGCCTGCAGGCCTTCCAGGGCTACCAGGTGACCATG
AAGACCGCCAAGGTGGCCGCCAGCGACTGGACCTTCCTGCACTGCCTG
CCCCGCAAGCCCGAGGAGGTGGACGACGAGGTGTTCTACAGCCCCCGC
AGCCTGGTGTTCCCCGAGGCCGAGAACCGCAAGTGGACCATCATGGCC
GTGATGGTGAGCCTGCTGACCGACTACAGCCCCCAGCTGCAGAAGCCC
AAGTTCTGA

>pARM2260
(SEQ ID NO: 228)
ATGCTGGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

-continued

>pARM2262
(SEQ ID NO: 229)
ATGCTGGTATTCAACCTGCGCATCCTGCTGAACAACGCCGCCTTCCGC
AACGGCCACAACTTCATGGTGCGCAACTTCCGCTGCGGCCAGCCCCTG
CAGAACCGGGTGCAGCTGAAGGGCCGCGACCTGCTGACCCTGAAGAAC
TTCACCGGCGAGGAGATCCGGTACATGCTGTGGCTGAGCGCCGACCTG
AAGTTCCGCATCAAGCAGAAGGGCGAGTACCTGCCCCTGCTGCAGGGC
AAGAGCCTGGGCATGATCTTCGAGAAGCGCAGCACCCGCACCCGCCTG
AGCACCGAGACAGGCTTCGCCCTGCTGGGCGGCCACCCCTGCTTCCTG
ACCACCCAGGACATCCACCTGGGCGTGAACGAGAGCCTGACCGACACC
GCCCGCGTGCTGAGCAGCATGGCCGACGCCGTGCTGGCCCGCGTGTAC
AAGCAGAGCGACCTGGACACCCTGGCCAAGGAGGCCAGCATCCCCATC
ATCAACGGCCTGAGCGACCTGTACCACCCCATCCAGATCCTGGCCGAC
TACCTGACCCTGCAGGAGCACTACAGCAGCCTGAAGGGCCTGACCCTG
AGCTGGATCGGCGACGGCAACAACATCCTGCACAGCATCATGATGAGC
GCCGCCAAGTTCGGCATGCACCTGCAGGCCGCCACCCCCAAGGGCTAC
GAGCCCGACGCCAGCGTGACCAAGCTGGCCGAGCAGTACGCCAAGGAG
AACGGCACCAAGCTGCTGCTGACCAACGACCCCCTGGAGGCCGCCCAC
GGCGGCAACGTGCTGATCACCGACACCTGGATCAGCATGGGCCAGGAG
GAGGAGAAGAAGAAGCGCCTGCAGGCCTTCCAGGGCTACCAGGTGACC
ATGAAGACCGCCAAGGTGGCCGCCAGCGACTGGACCTTCCTGCACTGC
CTGCCCCGCAAGCCCGAGGAGGTGGACGACGAGGTGTTCTACAGCCCC
CGCAGCCTGGTGTTCCCCGAGGCCGAGAACCGCAAGTGGACCATCATG
GCCGTGATGGTGAGCCTGCTGACCGACTACAGCCCCCAGCTGCAGAAG
CCCAAGTTCTGA

| | | |
|---|---|---|
| AT5G61250 | AACCAAUCGAAAGAAACCAAA | SEQ ID NO: 230 |
| AT5G46430 | CUCUAAUCACCAGGAGUAAAA | SEQ ID NO: 231 |
| AT5G47110 | GAGAGAGAUCUUAACAAAAAA | SEQ ID NO: 232 |
| AT1G03110 | UGUGUAACAACAACAACAACA | SEQ ID NO: 233 |
| AT3G12380 | CCGCAGUAGGAAGAGAAAGCC | SEQ ID NO: 234 |
| AT5G45910 | AAAAAAAAAAGAAAUCAUAAA | SEQ ID NO: 235 |
| AT1G07260 | GAGAGAAGAAAGAAGAAGACG | SEQ ID NO: 236 |
| AT3G55500 | CAAUUAAAAAUACUUACCAAA | SEQ ID NO: 237 |
| AT3G46230 | GCAAACAGAGUAAGCGAAACG | SEQ ID NO: 238 |
| AT2G36170 | GCGAAGAAGACGAACGCAAAG | SEQ ID NO: 239 |
| AT1G10660 | UUAGGACUGUAUUGACUGGCC | SEQ ID NO: 240 |
| AT4G14340 | AUCAUCGGAAUUCGGAAAAAG | SEQ ID NO: 241 |
| AT1G49310 | AAAACAAAAGUUAAAGCAGAC | SEQ ID NO: 242 |
| AT4G14360 | UUUAUCUCAAAUAAGAAGGCA | SEQ ID NO: 243 |
| AT1G28520 | GGUGGGGAGGUGAGAUUUCUU | SEQ ID NO: 244 |

-continued

| | | |
|---|---|---|
| AT1G20160 | UGAUUAGGAAACUACAAAGCC | SEQ ID NO: 245 |
| AT5G37370 | CAUUUUUCAAUUUCAUAAAAC | SEQ ID NO: 246 |
| AT4G11320 | UUACUUUUAAGCCCAACAAAA | SEQ ID NO: 247 |
| AT5G40850 | GGCGUGUGUGUGUGUUGUUGA | SEQ ID NO: 248 |
| AT1G06150 | GUGGUGAAGGGGAAGGUUUAG | SEQ ID NO: 249 |
| AT2G26080 | UUGUUUUUUUUUGGUUUGGUU | SEQ ID NO:250 |

mARM2260
(SEQ ID NO: 251)
AGGAUUAUUACAUCAAAACAAAAAGCCGCCACCAUGCUGGUAUUCAACC
UGCGCAUCCUGCUGAACAACGCCGCCUUCCGCAACGGCCACAACUUCAU
GGUGCGCAACUUCCGCUGCGGCCAGCCCCUGCAGAACCGGGUGCAGCUG
AAGGGCCGCGACCUGCUGACCCUGAAGAACUUCACCGGCGAGGAGAUCC
GGUACAUGCUGUGGCUGAGCGCCGACCUGAAGUUCCGCAUCAAGCAGAA
GGGCGAGUACCUGCCCCUGCUGCAGGGCAAGAGCCUGGGCAUGAUCUUC
GAGAAGCGCAGCACCCGCACCCGCCUGAGCACCGAGACAGGCUUCGCCC
UGCUGGGCGGCCACCCCUGCUUCCUGACCACCCAGGACAUCCACCUGGG
CGUGAACGAGAGCCUGACCGACACCGCCCGCGUGCUGAGCAGCAUGGCC
GACGCCGUGCUGGCCCGCGUGUACAAGCAGAGCGACCUGGACACCCUGG
CCAAGGAGGCCAGCAUCCCCAUCAUCAACGGCCUGAGCGACCUGUACCA
CCCCAUCCAGAUCCUGGCCGACUACCUGACCCUGCAGGAGCACUACAGC
AGCCUGAAGGGCCUGACCCUGAGCUGGAUCGGCGACGGCAACAACAUCC
UGCACAGCAUCAUGAUGAGCGCCGCCAAGUUCGGCAUGCACCUGCAGGC
CGCCACCCCCAAGGGCUACGAGCCCGACGCCAGCGUGACCAAGCUGGCC
GAGCAGUACGCCAAGGAGAACGGCACCAAGCUGCUGCUGACCAACGACC
CCCUGGAGGCCGCCCACGGCGGCAACGUGCUGAUCACCGACACCUGGAU
CAGCAUGGGCCAGGAGGAGGAGAAGAAGAAGCGCCUGCAGGCCUUCCAG
GGCUACCAGGUGACCAUGAAGACCGCCAAGGUGGCCGCCAGCGACUGGA
CCUUCCUGCACUGCCUGCCCCGCAAGCCCGAGGAGGUGGACGACGAGGU
GUUCUACAGCCCCCGCAGCCUGGUGUUCCCCGAGGCCGAGAACCGCAAG
UGGACCAUCAUGGCCGUGAUGGUGAGCCUGCUGACCGACUACAGCCCCC
AGCUGCAGAAGCCCAAGUUCUGAGGUCUCUAGUAAUGAGCUGGAGCCUC
GGUAGCCGUUCCUCCUGCCCGCUGGGCCUCCCAACGGGCCCUCCUCCCC
UCCUUGCACCGGCCCUUCCUGGUCUUUGAAUAAAGUCUGAGUGGGCAGC
AUCUAGAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAA
AAAAAAAA mARM2262
(SEQ ID NO: 252)
AGGAUUAUUACAUCAAAACAAAAAGCCGCCACCAUGCUGGUAUUCAACC
UGCGCAUCCUGCUGAACAACGCCGCCUUCCGCAACGGCCACAACUUCAU
GGUGCGCAACUUCCGCUGCGGCCAGCCCCUGCAGAACCGGGUGCAGCUG
AAGGGCCGCGACCUGCUGACCCUGAAGAACUUCACCGGCGAGGAGAUCC
GGUACAUGCUGUGGCUGAGCGCCGACCUGAAGUUCCGCAUCAAGCAGAA
GGGCGAGUACCUGCCCCUGCUGCAGGGCAAGAGCCUGGGCAUGAUCUUC
GAGAAGCGCAGCACCCGCACCCGCCUGAGCACCGAGACAGGCUUCGCCC
UGCUGGGCGGCCACCCCUGCUUCCUGACCACCCAGGACAUCCACCUGGG
CGUGAACGAGAGCCUGACCGACACCGCCCGCGUGCUGAGCAGCAUGGCC
GACGCCGUGCUGGCCCGCGUGUACAAGCAGAGCGACCUGGACACCCUGG
CCAAGGAGGCCAGCAUCCCCAUCAUCAACGGCCUGAGCGACCUGUACCA
CCCCAUCCAGAUCCUGGCCGACUACCUGACCCUGCAGGAGCACUACAGC
AGCCUGAAGGGCCUGACCCUGAGCUGGAUCGGCGACGGCAACAACAUCC
UGCACAGCAUCAUGAUGAGCGCCGCCAAGUUCGGCAUGCACCUGCAGGC
CGCCACCCCCAAGGGCUACGAGCCCGACGCCAGCGUGACCAAGCUGGCC
GAGCAGUACGCCAAGGAGAACGGCACCAAGCUGCUGCUGACCAACGACC
CCCUGGAGGCCGCCCACGGCGGCAACGUGCUGAUCACCGACACCUGGAU
CAGCAUGGGCCAGGAGGAGGAGAAGAAGAAGCGCCUGCAGGCCUUCCAG
GGCUACCAGGUGACCAUGAAGACCGCCAAGGUGGCCGCCAGCGACUGGA
CCUUCCUGCACUGCCUGCCCCGCAAGCCCGAGGAGGUGGACGACGAGGU
GUUCUACAGCCCCCGCAGCCUGGUGUUCCCCGAGGCCGAGAACCGCAAG
UGGACCAUCAUGGCCGUGAUGGUGAGCCUGCUGACCGACUACAGCCCCC
AGCUGCAGAAGCCCAAGUUCUGAGGUCUCUAGUAAUGAGCUGGAGCCUC
GGUAGCCGUUCCUCCUGCCCGCUGGGCCUCCCAACGGGCCCUCCUCCCC
UCCUUGCACCGGCCCUUCCUGGUCUUUGAAUAAAGUCUGAGUGGGCAGC
AUCUAGAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAA
AAAAAAAAAGCU mARM2016
(SEQ ID NO: 253)
AGGAUUAUUACAUCAAAACAAAAAGCCGCCACCAUGCUGUUCAACCUGC
GCAUCCUGCUGAACAACGCCGCCUUCCGCAACGGCCACAACUUCAUGGU
GCGCAACUUCCGCUGCGGCCAGCCCCUGCAGAACAAGGUGCAGCUGAAG
GGCCGCGACCUGCUGACCCUGAAGAACUUCACCGGCGAGGAGAUCAAGU
ACAUGCUGUGGCUGAGCGCCGACCUGAAGUUCCGCAUCAAGCAGAAGGG
CGAGUACCUGCCCCUGCUGCAGGGCAAGAGCCUGGGCAUGAUCUUCGAG
AAGCGCAGCACCCGCACCCGCCUGAGCACCGAGACAGGCUUCGCCCUGC
UGGGCGGCCACCCCUGCUUCCUGACCACCCAGGACAUCCACCUGGGCGU
GAACGAGAGCCUGACCGACACCGCCCGCGUGCUGAGCAGCAUGGCCGAC
GCCGUGCUGGCCCGCGUGUACAAGCAGAGCGACCUGGACACCCUGGCCA
AGGAGGCCAGCAUCCCCAUCAUCAACGGCCUGAGCGACCUGUACCACCC
CAUCCAGAUCCUGGCCGACUACCUGACCCUGCAGGAGCACUACAGCAGC
CUGAAGGGCCUGACCCUGAGCUGGAUCGGCGACGGCAACAACAUCCUGC

-continued

ACAGCAUCAUGAUGAGCGCCGCCAAGUUCGGCAUGCACCUGCAGGCCGC

CACCCCCAAGGGCUACGAGCCCGACGCCAGCGUGACCAAGCUGGCCGAG

CAGUACGCCAAGGAGAACGGCACCAAGCUGCUGCUGACCAACGACCCCC

UGGAGGCCGCCCACGGCGGCAACGUGCUGAUCACCGACACCUGGAUCAG

CAUGGGCCAGGAGGAGGAGAAGAAGAAGCGCCUGCAGGCCUUCCAGGGC

UACCAGGUGACCAUGAAGACCGCCAAGGUGGCCGCCAGCGACUGGACCU

UCCUGCACUGCCUGCCCCGCAAGCCCGAGGAGGUGGACGACGAGGUGUU

CUACAGCCCCCGCAGCCUGGUGUUCCCCGAGGCCGAGAACCGCAAGUGG

-continued

ACCAUCAUGGCCGUGAUGGUGAGCCUGCUGACCGACUACAGCCCCCAGC

UGCAGAAGCCCAAGUUCUGAGGUCUCUAGUAAUGAGCUGGAGCCUCGGU

AGCCGUUCCUCCUGCCCGCUGGGCCUCCCAACGGGCCCUCCUCCCCUCC

UUGCACCGGCCCUUCCUGGUCUUUGAAUAAAGUCUGAGUGGGCAGCAUC

UAGAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAA

What is claimed is:

1. A polynucleotide encoding an ornithine transcarbamylase (OTC) protein comprising the amino acid sequence of SEQ ID NO:4 and having OTC enzymatic activity, wherein (i) the polynucleotide comprises a sequence of SEQ ID NO:221; or (ii) the polynucleotide comprises a sequence of SEQ ID NO:221, wherein T is substituted with U.

2. The polynucleotide of claim 1, wherein the polynucleotide is an mRNA comprising a 3'poly A tail.

3. The polynucleotide of claim 1, wherein the polynucleotide is an mRNA comprising a 5' untranslated region (5'UTR).

4. The polynucleotide of claim 3, wherein the 5'UTR is derived from a gene expressed by *Arabidopsis thaliana.*

5. The polynucleotide of claim 4, wherein the 5' UTR comprises a sequence selected from SEQ ID NO: 6, SEQ ID NOS: 125-127, and SEQ ID NOS: 230-250.

6. The polynucleotide of claim 5, wherein the 5'UTR comprises a sequence of SEQ ID NO: 6.

7. The polynucleotide of claim 1, wherein the polynucleotide is an mRNA comprising a 3' UTR.

8. The polynucleotide of claim 7, wherein the 3' UTR comprises a sequence selected from SEQ ID NOS: 16-22.

9. The polynucleotide of claim 1, comprising a Kozak sequence of SEQ ID NO: 23 or a partial Kozak sequence of SEQ ID NO: 24.

10. The polynucleotide of claim 1, wherein the polynucleotide is an mRNA comprising a 5' cap.

11. The polynucleotide of claim 10, wherein the 5' cap is m7GpppGm having the following structure:

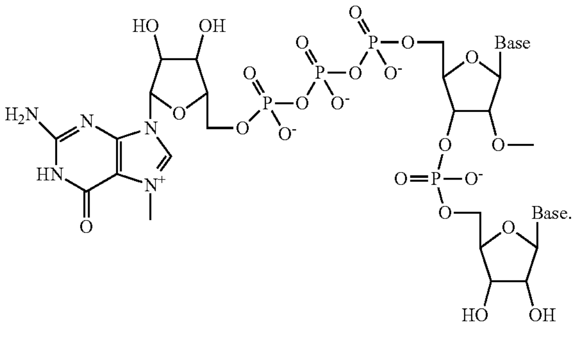

12. The polynucleotide of claim 1, wherein the polynucleotide is an mRNA comprising (a) a sequence of SEQ ID NO: 21; or (b) a sequence of SEQ ID NO: 6 and a sequence of SEQ ID NO: 21.

13. The polynucleotide of claim 1, wherein the polynucleotide is an mRNA, and wherein (a) the percentage of uracil nucleobases in the coding region of the polynucleotide is reduced with respect to the percentage of uracil nucleobases in the wild-type OTC nucleic acid sequence; or (b) 1-100% of the uridines are modified uridine analogs; or (c) 1-100% of the uridine nucleotides are each independently a modified uridine analog selected from the group consisting of 5-methoxyuridine, $N^1$-methylpseudouridine, 5-hydroxyuridine, 5-methyluridine, 5-hydroxymethyluridine, 5-carboxyuridine, 5-carboxymethylesteruridine, 5-formyluridine, 5-propynyluridine, 5-bromouridine, 5-fluorouridine, 5-iodouridine, 2-thiouridine, 6-methyluridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, $N^1$-hydroxymethylpseudouridine, 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy) pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl) uridine, 2'-O-methylpseudouridine, 2-thio-2'O-methyluridine, and 3,2'-O-dimethyluridine; or (d) 100% of the uridine nucleotides are 5-methoxyuridine; or (e) 100% of the uridine nucleotides are $N^1$-methylpseudouridine.

14. A pharmaceutical composition comprising the polynucleotide of claim 1 and pharmaceutically acceptable carrier, wherein the pharmaceutically acceptable carrier is a lipid formulation.

15. A pharmaceutical composition comprising the polynucleotide of claim 13 and pharmaceutically acceptable carrier, wherein the pharmaceutically acceptable carrier is a lipid formulation.

16. A method of treating OTC deficiency in a patient identified as suffering from OTC deficiency, comprising administering to the patient a pharmaceutical composition of claim 15, wherein upon administration of the pharmaceutical composition to the patient, the protein of SEQ ID NO: 4 is expressed in the patient.

17. A method of treating OTC deficiency in a patient identified as suffering from OTC deficiency, comprising administering to the patient a polynucleotide of claim 1, wherein the polynucleotide expresses the protein of SEQ ID NO: 4 in the patient.

18. A vector comprising the polynucleotide of claim 1.

19. An mRNA encoding an OTC protein having the amino acid sequence of SEQ ID NO: 4, wherein the mRNA comprises a polynucleotide sequence of SEQ ID NO: 221, wherein T is substituted with U, and wherein the encoded protein has OTC enzymatic activity.

20. The mRNA of claim 19, wherein (a) 1-100% of the uridines are modified uridine analogs; or (b) 1-100% of the uridine nucleotides are each independently a modified uridine analog selected from the group consisting of 5-methoxyuridine, N1-methylpseudouridine, 5-hydroxyuridine, 5-methyluridine, 5-hydroxymethyluridine, 5-carboxyuridine, 5-carboxymethylesteruridine, 5-formyluridine, 5-propynyluridine, 5-bromouridine, 5-fluorouridine, 5-iodouridine, 2-thiouridine, 6-methyluridine, N1-ethylpseudouridine, N1-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, $N^1$-hydroxymethylpseudouridine, 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy) pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl) uridine, 2'-O-methylpseudouridine, 2-thio-2'O-methyluridine, and 3,2'-O-dimethyluridine; or (c) 100% of the uridine nucleotides are 5-methoxyuridine; or (d) 100% of the uridine nucleotides are $N^1$-methylpseudouridine.

* * * * *